US006573068B1

(12) United States Patent
Milne Edwards et al.

(10) Patent No.: US 6,573,068 B1
(45) Date of Patent: Jun. 3, 2003

(54) CLAUDIN-50 PROTEIN

(75) Inventors: Jean-Baptiste Dumas Milne Edwards, Paris (FR); Aymeric Duclert, Saint-Maur (FR); Lydie Bougueleret, Vanves (FR)

(73) Assignee: Genset, S. A. (FR)

( * ) Notice: Subject to any disclaimer, the term of this patent is extended or adjusted under 35 U.S.C. 154(b) by 0 days.

(21) Appl. No.: 09/663,600

(22) Filed: Sep. 15, 2000

Related U.S. Application Data

(63) Continuation-in-part of application No. 09/191,997, filed on Nov. 13, 1998, now abandoned.
(60) Provisional application No. 60/066,677, filed on Nov. 13, 1997, provisional application No. 60/069,957, filed on Dec. 17, 1997, provisional application No. 60/074,121, filed on Feb. 9, 1998, provisional application No. 60/081,563, filed on Apr. 13, 1998, provisional application No. 60/096,116, filed on Aug. 10, 1998, and provisional application No. 60/099,273, filed on Sep. 4, 1998.

(51) Int. Cl.⁷ ......................... C12P 21/02; C07K 14/705
(52) U.S. Cl. ..................... 435/69.1; 530/350; 536/23.5; 435/320.1; 435/325
(58) Field of Search ........................ 530/350; 536/23.5; 435/69.1, 320.1, 325

(56) References Cited

U.S. PATENT DOCUMENTS 6,022,715 A      2/2000   Merenkova et al.

FOREIGN PATENT DOCUMENTS

| WO | WO 97/07198 A2 | 2/1997 |
|---|---|---|
| WO | WO 98/45436 A2 | 10/1998 |
| WO | WO 99/06548 - A2 A3 | 2/1999 |
| WO | WO 99/25825 A2 | 5/1999 |
| WO | WO 00/12708 A2 | 3/2000 |
| WO | WO 00/18915 A2 | 4/2000 |
| WO | WO 00/26360 A1 | 5/2000 |

OTHER PUBLICATIONS

Furuse, et al.; "Claudin–1 and –2: Novel Integral Membrane Proteins Localizing at Tight Junctions with No Sequence Similarity to Occludin"; The Journal of Cell Biology, vol. 141, No. 7, Jun. 29, 1998, pp. 1539–1550; The Rockefeller University Press, 0021–9525/98/0615391/12.

Furuse, et al.; "Manner of Interaction of Heterogeneous Claudin Species Within and Between Tight Junction Strands"; The Journal of Cell Biology, vol. 147, No. 4, Nov. 15, 1999, pp. 891–903; The Rockefeller University PRess, 0021–9525/99/11/891/13.

Katahira, et al.; "Molecular Cloning and Functional Characterization of the Receptor for Clostridium perfringens Enterotoxin"; The Journal of Cell Biology, vol. 136, No. 6, Mar. 24, 1997, pp. 1239–1247; The Rockefeller University Press, 0021–9525/97/03/1239/9.

Kinugasa, et al.; "Claudins Regulate the Intestinal Barrier inResponse to Immune Mediators"; Gastroenterology 2000, vol. 118; pp. 1001–1011; The American Gastroenterological Association; 0016–5085/00.

Lippoldt, et al.; "Organization of choroid plexus epithelial and endothelial cell tight junctions and regulations of claudin–1, –2 and –5 expression by proein kinase C"; Molecular Neuroscience, NeuroReport, vol. 11, No. 7, pp. 1427–1431, May 15, 2000; Lippincott Williams & Wilkins, 0959–4965.

Lockhart, et al.; "Expression monitoring by hybridizationto high–density oligonucleotide arrays"; Research Article; Nat Biotechnol. 14(13):1675–80; Published Dec. 1996; XP–002074420.

Tashiro, et al.; "Signal Sequence Trap: A Cloning Strategy for Secreted Proteins and Type 1 Membrane Proteins"; Science, vol. 261, Jul. 30, 1993; pp. 600–603; XP–000673204.

Yokoyama–Kobayashi, et al.; "A signal sequence detection system using secreted protease activity as an indicator"; Gene, vol. 163 (1995), pp. 193–196; Elsevier Science B.V.; SSDI 0378–1119(95)00322–3.

Accesson No. AAG17984; Claudin–2; *Homo Sapiens*, Database: Genbank; GU, J.R., et al.; submitted Aug. 1999; "Novel human cDNA–clone with function of Inhibiting cancer cell growth"; Unpublished.

Accession No. AAC27079; Claudin–2, Mus musculus; Database: Genbank; Furuse, et al.; submitted Jun. 15, 1998; "Claudin–1 and –2; Novel Integral Membrane Proteins Localizing at Tight Junctions with No Sequence Similarity to Occuludin"; J. Cell. Biol. 141 (7), 1539–1550 (1998).

Accesion No. T03538; Bento Soares Homo sapiens cDNA clone IB43; Database: EMBL; SIKELA, J.M.; submitted Sep. 21, 1992.

Accession No. AA057573; *Homo sapiens* cDNA clone IMAGE:381523; Database: EMBL; WILSON; submitted Sep. 6, 1996.

Accession No. N57409; Homo sapiens cDNA clone Image:258726; Database: EMBL; Wilson; submitted Feb. 22, 1996.

Accession No. AA057573; *Homo sapiens* cDNA clone IMAGE:381523; Database: EMBL; Wilson; submitted Sep. 6, 1996.

(List continued on next page.)

*Primary Examiner*—Yvonne Eyler
*Assistant Examiner*—Eileen B. O'Hara
(74) *Attorney, Agent, or Firm*—Saliwanchik, Lloyd & Saliwanchik

(57) ABSTRACT

The sequence of a cDNA encoding Claudin-50 and sequence of Claudin-50 protein are disclosed. The cDNA can be used to express the protein or portions thereof or to obtain antibodies capable of specifically binding to the secreted protein. The cDNA may also be used in diagnostic, forensic, gene therapy, and chromosome mapping procedures. The cDNA may also be used to design expression vectors and secretion vectors.

4 Claims, 8 Drawing Sheets

OTHER PUBLICATIONS

Accession No. . N57409; *Homo sapiens* cDNA clone IMAGE:258726; Database: EMBL; Wilson; submitted Feb. 22, 1996.

Carninci, et al., "High–efficiency full–length cDNA cloning by biotinylated CAP trapper"; Genomics, 37(3):327–36; Nov. 1, 1996; PMID:8938445.

Kato, et al.; "Construction of a human full–length cDNA bank"; Gene, 150(2):243–50; Dec. 15, 1994; PMID:7821789.

Von Heijne, G.; "A new method for predicting signal sequence cleavage sites"; Nucleic Acids Res. 14(11):4683–90; published Jun. 11, 1986; PMID:3714490.

Nomura, N., et al.; "Predictionof the coding sequences of unidentified human genes. I. The coding sequences of 40 new genes (KIAA0001–KIAA0040) deduced by analysis of randomly sampled cDNA clones from human immature myeloid cell line KG–1"; DNA Res. 1(1):27–35; published in 1994; PMID:7584026.

Adams, M.D. et al.; "Initial assessment of human gene diversity and expression patterns based upon 83 million nucleotides of cDNA sequence"; Nature 377 (6547 Suppl):3–174; published Sep. 28, 1995; PMID:7566098.

Hillier, L.D., et al; "Generation and analysis of 280,000 human expressed sequence tags"; Genome Res. 6(9):807–28; published Sep. 1996; PMID:8889549.

Introna, M. and Golay, J., "How can oncogenic transcription factors cause cancer: a critical review of the myb story" *Leukemia* (1999), 13:1301–1306; Stockton Press.

Ward, A.C. et al., "Regulation of granulopiesis by transcription factors and cytokine signals" *Leukemia* (2000), 14:973–990; Macmillan Publishers, Ltd.

Stewart, G., "The membrane defect in hereditary stomatocytosis", *Ballière's Clinical Haematology* (1993), 6(2):371–99; Baillière's Tindall.

| Minimum signal peptide score | false positive rate | false negative rate | proba(0.1) | proba(0.2) |
|---|---|---|---|---|
| 3.5 | 0.121 | 0.036 | 0.467 | 0.664 |
| 4 | 0.096 | 0.06 | 0.519 | 0.708 |
| 4.5 | 0.078 | 0.079 | 0.565 | 0.745 |
| 5 | 0.062 | 0.098 | 0.615 | 0.782 |
| 5.5 | 0.05 | 0.127 | 0.659 | 0.813 |
| 6 | 0.04 | 0.163 | 0.694 | 0.836 |
| 6.5 | 0.033 | 0.202 | 0.725 | 0.855 |
| 7 | 0.025 | 0.248 | 0.763 | 0.878 |
| 7.5 | 0.021 | 0.304 | 0.78 | 0.889 |
| 8 | 0.015 | 0.368 | 0.816 | 0.909 |
| 8.5 | 0.012 | 0.418 | 0.836 | 0.92 |
| 9 | 0.009 | 0.512 | 0.856 | 0.93 |
| 9.5 | 0.007 | 0.581 | 0.863 | 0.934 |
| 10 | 0.006 | 0.679 | 0.835 | 0.919 |

Figure 2

| Minimum signal peptide score | All ESTs | New ESTs | ESTs matching public EST closer than 40 bp from beginning | ESTs extending known mRNA more than 40 bp | ESTs extending public EST more than 40 bp |
|---|---|---|---|---|---|
| 3.5 | 2674 | 947 | 599 | 23 | 150 |
| 4 | 2278 | 784 | 499 | 23 | 126 |
| 4.5 | 1943 | 647 | 425 | 22 | 112 |
| 5 | 1657 | 523 | 353 | 21 | 96 |
| 5.5 | 1417 | 419 | 307 | 19 | 80 |
| 6 | 1190 | 340 | 238 | 18 | 68 |
| 6.5 | 1035 | 280 | 186 | 18 | 60 |
| 7 | 893 | 219 | 161 | 15 | 48 |
| 7.5 | 753 | 173 | 132 | 12 | 36 |
| 8 | 636 | 133 | 101 | 11 | 29 |
| 8.5 | 543 | 104 | 83 | 8 | 26 |
| 9 | 456 | 81 | 63 | 6 | 24 |
| 9.5 | 364 | 57 | 48 | 6 | 18 |
| 10 | 303 | 47 | 35 | 6 | 15 |

Figure 4

| Tissue | All ESTs | New ESTs | ESTs matching public EST closer than 40 bp from beginning | ESTs extending known mRNA more than 40 bp | ESTs extending public EST more than 40 bp |
|---|---|---|---|---|---|
| Brain | 329 | 131 | 75 | 3 | 24 |
| Cancerous prostate | 134 | 40 | 37 | 1 | 6 |
| Cerebellum | 17 | 9 | 1 | 0 | 6 |
| Colon | 21 | 11 | 4 | 0 | 0 |
| Dystrophic muscle | 41 | 18 | 8 | 0 | 1 |
| Fetal brain | 70 | 37 | 16 | 0 | 1 |
| Fetal kidney | 227 | 116 | 46 | 1 | 19 |
| Fetal liver | 13 | 7 | 2 | 0 | 0 |
| Heart | 30 | 15 | 7 | 0 | 1 |
| Hypertrophic prostate | 86 | 23 | 22 | 2 | 2 |
| Kidney | 10 | 7 | 3 | 0 | 0 |
| Large intestine | 21 | 8 | 4 | 0 | 1 |
| Liver | 23 | 9 | 6 | 0 | 0 |
| Lung | 24 | 12 | 4 | 0 | 1 |
| Lung (cells) | 57 | 38 | 6 | 0 | 4 |
| Lymph ganglia | 163 | 60 | 23 | 2 | 12 |
| Lymphocytes | 23 | 6 | 4 | 0 | 2 |
| Muscle | 33 | 16 | 6 | 0 | 4 |
| Normal prostate | 181 | 61 | 45 | 7 | 11 |
| Ovary | 90 | 57 | 12 | 1 | 2 |
| Pancreas | 48 | 11 | 6 | 0 | 1 |
| Placenta | 24 | 5 | 1 | 0 | 0 |
| Prostate | 34 | 16 | 4 | 0 | 2 |
| Spleen | 56 | 28 | 10 | 0 | 1 |
| Substantia nigra | 108 | 47 | 27 | 1 | 6 |
| Surrenals | 15 | 3 | 3 | 1 | 0 |
| Testis | 131 | 68 | 25 | 1 | 8 |
| Thyroid | 17 | 8 | 2 | 0 | 2 |
| Umbilical cord | 55 | 17 | 12 | 1 | 3 |
| Uterus | 28 | 15 | 3 | 0 | 2 |
| Non tissue-specific | 568 | 48 | 177 | 2 | 28 |
| Total | 2677 | 947 | 601 | 23 | 150 |

Figure 5

Plasmid name: pED6dpc2
Plasmid size: 5374 bp

Comments/References: pED6dpc2 is derived from pED6dpc1 by insertion of a new polylinker to facilitate cDNA cloning. SST cDNAs are cloned between EcoRI and NotI. pED vectors are described in Kaufman et al. (1991), NAR 19: 4485-4490

Description of Transcription Factor Binding Sites present on promoters
isolated from SignalTag sequences

Promoter sequence P13H2 (546 bp):

| Matrix | Position | Orientation | Score | Length | Sequence |
|---|---|---|---|---|---|
| CMYB_01 | -502 | + | 0.983 | 9 | TGTCAGTTG |
| MYOD_Q6 | -501 | - | 0.961 | 10 | CCCAACTGAC |
| S8_01 | -444 | - | 0.960 | 11 | AATAGAATTAG |
| S8_01 | -425 | + | 0.966 | 11 | AACTAAATTAG |
| DELTAEF1_01 | -390 | - | 0.960 | 11 | GCACACCTCAG |
| GATA_C | -364 | - | 0.964 | 11 | AGATAAATCCA |
| CMYB_01 | -349 | + | 0.958 | 9 | CTTCAGTT |
| GATA1_02 | -343 | + | 0.959 | 14 | TTGTAGATAGGACA |
| GATA_C | -339 | + | 0.953 | 11 | AGATAGGACAT |
| TAL1ALPHAE47_01 | -235 | + | 0.973 | 16 | CATAACAGATGGTAAG |
| TAL1BETAE47_01 | -235 | + | 0.983 | 16 | CATAACAGATGGTAAG |
| TAL1BETAITF2_01 | -235 | + | 0.978 | 16 | CATAACAGATGGTAAG |
| MYOD_Q6 | -232 | - | 0.954 | 10 | ACCATCTGTT |
| GATA1_04 | -217 | - | 0.953 | 13 | TCAAGATAAAGTA |
| IK1_01 | -126 | + | 0.963 | 13 | AGTTGGGAATTCC |
| IK2_01 | -126 | + | 0.985 | 12 | AGTTGGGAATTC |
| CREL_01 | -123 | + | 0.962 | 10 | TGGGAATTCC |
| GATA1_02 | -96 | + | 0.950 | 14 | TCAGTGATATGGCA |
| SRY_02 | -41 | - | 0.951 | 12 | TAAAACAAAACA |
| E2F_02 | -33 | + | 0.957 | 8 | TTTAGCGC |
| MZF1_01 | -5 | - | 0.975 | 8 | TGAGGGGA |

Promoter sequence P15B4 (861bp):

| Matrix | Position | Orientation | Score | Length | Sequence |
|---|---|---|---|---|---|
| NFY_Q6 | -748 | - | 0.956 | 11 | GGACCAATCAT |
| MZF1_01 | -738 | + | 0.962 | 8 | CCTGGGGA |
| CMYB_01 | -684 | + | 0.994 | 9 | TGACCGTTG |
| VMYB_02 | -682 | - | 0.985 | 9 | TCCAACGGT |
| STAT_01 | -673 | + | 0.968 | 9 | TTCCTGGAA |
| STAT_01 | -673 | - | 0.951 | 9 | TTCCAGGAA |
| MZF1_01 | -556 | - | 0.956 | 8 | TTGGGGGA |
| IK2_01 | -451 | + | 0.965 | 12 | GAATGGGATTTC |
| MZF1_01 | -424 | + | 0.986 | 8 | AGAGGGGA |
| SRY_02 | -398 | - | 0.955 | 12 | GAAAACAAAACA |
| MZF1_01 | -216 | + | 0.960 | 8 | GAAGGGGA |
| MYOD_Q6 | -190 | + | 0.981 | 10 | AGCATCTGCC |
| DELTAEF1_01 | -176 | + | 0.958 | 11 | TCCCACCTTCC |
| S8_01 | 5 | - | 0.992 | 11 | GAGGCAATTAT |
| MZF1_01 | 16 | - | 0.986 | 8 | AGAGGGGA |

Promoter sequence P29B6 (555 bp):

| Matrix | Position | Orientation | Score | Length | Sequence |
|---|---|---|---|---|---|
| ARNT_01 | -311 | + | 0.964 | 16 | GGACTCACGTGCTGCT |
| NMYC_01 | -309 | + | 0.965 | 12 | ACTCACGTGCTG |
| USF_01 | -309 | + | 0.985 | 12 | ACTCACGTGCTG |
| USF_01 | -309 | - | 0.985 | 12 | CAGCACGTGAGT |
| NMYC_01 | -309 | - | 0.956 | 12 | CAGCACGTGAGT |
| MYCMAX_02 | -309 | - | 0.972 | 12 | CAGCACGTGAGT |
| USF_C | -307 | + | 0.997 | 8 | TCACGTGC |
| USF_C | -307 | - | 0.991 | 8 | GCACGTGA |
| MZF1_01 | -292 | - | 0.968 | 8 | CATGGGGA |
| ELK1_02 | -105 | + | 0.963 | 14 | CTCTCCGGAAGCCT |
| CETS1P54_01 | -102 | + | 0.974 | 10 | TCCGGAAGCC |
| AP1_Q4 | -42 | - | 0.963 | 11 | AGTGACTGAAC |
| AP1FJ_Q2 | -42 | - | 0.961 | 11 | AGTGACTGAAC |
| PADS_C | 45 | + | 1.000 | 9 | TGTGGTCTC |

Figure 8

SEQUENCE LISTING

```
<160> NUMBER OF SEQ ID NOS: 229

<210> SEQ ID NO 1
<211> LENGTH: 47
<212> TYPE: RNA
<213> ORGANISM: Artificial Sequence
<220> FEATURE:
<223> OTHER INFORMATION: in vitro transcription product
<221> NAME/KEY: modified_base
<222> LOCATION: 1
<223> OTHER INFORMATION: m7g

<400> SEQUENCE: 1
ggcauccuac ucccauccaa uuccacccua acuccuccca ucuccac                47

<210> SEQ ID NO 2
<211> LENGTH: 46
<212> TYPE: RNA
<213> ORGANISM: Artificial Sequence
<220> FEATURE:
<223> OTHER INFORMATION: in vitro transcription product

<400> SEQUENCE: 2
gcauccuacu cccauccaau uccacccuaa cuccucccau cuccac                 46

<210> SEQ ID NO 3
<211> LENGTH: 25
```

-continued

```
<212> TYPE: DNA
<213> ORGANISM: Artificial Sequence
<220> FEATURE:
<223> OTHER INFORMATION: Derivatized oligonucleotide for linking to mRNA

<400> SEQUENCE: 3
atcaagaatt cgcacgagac catta                                              25

<210> SEQ ID NO 4
<211> LENGTH: 25
<212> TYPE: DNA
<213> ORGANISM: Artificial Sequence
<220> FEATURE:
<223> OTHER INFORMATION: Probe complementary to oligonucleotide of SEQ
      ID NO:3

<400> SEQUENCE: 4
taatggtctc gtgcgaattc ttgat                                              25

<210> SEQ ID NO 5
<211> LENGTH: 25
<212> TYPE: DNA
<213> ORGANISM: Artificial Sequence
<220> FEATURE:
<223> OTHER INFORMATION: Alpha globin gene primer GLO-S

<400> SEQUENCE: 5
ccgacaagac caacgtcaag gccgc                                              25

<210> SEQ ID NO 6
<211> LENGTH: 25
<212> TYPE: DNA
<213> ORGANISM: Artificial Sequence
<220> FEATURE:
<223> OTHER INFORMATION: Alpha globin gene primer GLO-As

<400> SEQUENCE: 6
tcaccagcag gcagtggctt aggag                                              25

<210> SEQ ID NO 7
<211> LENGTH: 25
<212> TYPE: DNA
<213> ORGANISM: Artificial Sequence
<220> FEATURE:
<223> OTHER INFORMATION: Dehydrogenase gene primer 3 DH-S

<400> SEQUENCE: 7
agtgattcct gctactttgg atggc                                              25

<210> SEQ ID NO 8
<211> LENGTH: 25
<212> TYPE: DNA
<213> ORGANISM: Artificial Sequence
<220> FEATURE:
<223> OTHER INFORMATION: Dehydrogenase gene primer 3 DH-As

<400> SEQUENCE: 8
gcttggtctt gttctggagt ttaga                                              25

<210> SEQ ID NO 9
<211> LENGTH: 25
<212> TYPE: DNA
<213> ORGANISM: Artificial Sequence
<220> FEATURE:
<223> OTHER INFORMATION: PP15 gene primer PP15-S

<400> SEQUENCE: 9
```

```
tccagaatgg gagacaagcc aattt                                            25

<210> SEQ ID NO 10
<211> LENGTH: 25
<212> TYPE: DNA
<213> ORGANISM: Artificial Sequence
<220> FEATURE:
<223> OTHER INFORMATION: PP15 gene primer PP15-As

<400> SEQUENCE: 10
agggaggagg aaacagcgtg agtcc                                            25

<210> SEQ ID NO 11
<211> LENGTH: 25
<212> TYPE: DNA
<213> ORGANISM: Artificial Sequence
<220> FEATURE:
<223> OTHER INFORMATION: Elongation Factor A4 gene primer EFA1-S

<400> SEQUENCE: 11
atgggaaagg aaaagactca tatca                                            25

<210> SEQ ID NO 12
<211> LENGTH: 25
<212> TYPE: DNA
<213> ORGANISM: Artificial Sequence
<220> FEATURE:
<223> OTHER INFORMATION: Elongation Factor A4 gene primer EF1A-As

<400> SEQUENCE: 12
agcagcaaca atcaggacag cacag                                            25

<210> SEQ ID NO 13
<211> LENGTH: 25
<212> TYPE: DNA
<213> ORGANISM: Artificial Sequence
<220> FEATURE:
<223> OTHER INFORMATION: Primer derived from oligonucleotide of SEQ ID
      NO:3

<400> SEQUENCE: 13
atcaagaatt cgcacgagac catta                                            25

<210> SEQ ID NO 14
<211> LENGTH: 67
<212> TYPE: DNA
<213> ORGANISM: Artificial Sequence
<220> FEATURE:
<223> OTHER INFORMATION: PolydT primer
<221> NAME/KEY: misc_feature
<222> LOCATION: 67
<223> OTHER INFORMATION: n=a, g, c or t

<400> SEQUENCE: 14
atcgttgaga ctcgtaccag cagagtcacg agagagacta cacggtactg gtttttttt      60 tttttvn                                                               67

<210> SEQ ID NO 15
<211> LENGTH: 29
<212> TYPE: DNA
<213> ORGANISM: Artificial Sequence
<220> FEATURE:
<223> OTHER INFORMATION: Nested 3' primer

<400> SEQUENCE: 15
```

-continued ccagcagagt cacgagagag actacacgg                                    29

<210> SEQ ID NO 16
<211> LENGTH: 25
<212> TYPE: DNA
<213> ORGANISM: Artificial Sequence
<220> FEATURE:
<223> OTHER INFORMATION: Nested 3' primer

<400> SEQUENCE: 16
cacgagagag actacacggt actgg                                        25

<210> SEQ ID NO 17
<211> LENGTH: 526
<212> TYPE: DNA
<213> ORGANISM: Homo Sapiens
<220> FEATURE:
<221> NAME/KEY: misc_feature
<222> LOCATION: complement(261..376)
<223> OTHER INFORMATION: blastn
<221> NAME/KEY: misc_feature
<222> LOCATION: complement(380..486)
<223> OTHER INFORMATION: blastn
<221> NAME/KEY: misc_feature
<222> LOCATION: complement(110..145)
<223> OTHER INFORMATION: blastn
<221> NAME/KEY: misc_feature
<222> LOCATION: complement(196..229)
<223> OTHER INFORMATION: blastn
<221> NAME/KEY: sig_peptide
<222> LOCATION: 90..140
<223> OTHER INFORMATION: Von Heijne matrix
<221> NAME/KEY: misc_feature
<222> LOCATION: 290
<223> OTHER INFORMATION: n=a, g, c or t

<400> SEQUENCE: 17
aatatrarac agctacaata ttccagggcc artcacttgc catttctcat aacagcgtca     60
gagagaaaga actgactgar acgtttgag atg aag aaa gtt ctc ctc ctg atc    113
                                Met Lys Lys Val Leu Leu Leu Ile
                                    -15                 -10 aca gcc atc ttg gca gtg gct gtw ggt ttc cca gtc tct caa gac cag    161
Thr Ala Ile Leu Ala Val Ala Val Gly Phe Pro Val Ser Gln Asp Gln
        -5                  1               5 gaa cga gaa aaa aga agt atc agt gac agc gat gaa tta gct tca ggr    209
Glu Arg Glu Lys Arg Ser Ile Ser Asp Ser Asp Glu Leu Ala Ser Gly
        10                  15              20 wtt ttt gtg ttc cct tac cca tat cca ttt cgc cca ctt cca cca att    257
Xaa Phe Val Phe Pro Tyr Pro Tyr Pro Phe Arg Pro Leu Pro Pro Ile
25                  30                  35 cca ttt cca aga ttt cca tgg ttt aga cgt aan ttt cct att cca ata    305
Pro Phe Pro Arg Phe Pro Trp Phe Arg Arg Xaa Phe Pro Ile Pro Ile
40                  45                  50                  55 cct gaa tct gcc cct aca act ccc ctt cct agc gaa aag taaacaaraa     354
Pro Glu Ser Ala Pro Thr Thr Pro Leu Pro Ser Glu Lys
                    60                  65 ggaaaagtca crataaacct ggtcacctga aattgaaatt gagccacttc cttgaaraat   414
caaaattcct gttaataaaa raaaaacaaa tgtaattgaa atagcacaca gcattctcta   474
gtcaatatct ttagtgatct tctttaataa acatgaaagc aaaaaaaaaa aa           526

<210> SEQ ID NO 18
<211> LENGTH: 17
<212> TYPE: PRT
<213> ORGANISM: Homo Sapiens
<220> FEATURE:

-continued

```
<221> NAME/KEY: SIGNAL
<222> LOCATION: 1..17
<223> OTHER INFORMATION: Von Heijne matrix
      score 8.2
      seq LLLITAILAVAVG/FP

<400> SEQUENCE: 18

Met Lys Lys Val Leu Leu Leu Ile Thr Ala Ile Leu Ala Val Ala Val
1               5                   10                  15

Gly

<210> SEQ ID NO 19
<211> LENGTH: 822
<212> TYPE: DNA
<213> ORGANISM: Homo Sapiens
<220> FEATURE:
<221> NAME/KEY: misc_feature
<222> LOCATION: 260..464
<223> OTHER INFORMATION: blastn
<221> NAME/KEY: misc_feature
<222> LOCATION: 118..184
<223> OTHER INFORMATION: blastn
<221> NAME/KEY: misc_feature
<222> LOCATION: 56..113
<223> OTHER INFORMATION: blastn
<221> NAME/KEY: misc_feature
<222> LOCATION: 454..485
<223> OTHER INFORMATION: blastn
<221> NAME/KEY: misc_feature
<222> LOCATION: 118..545
<223> OTHER INFORMATION: blastn
<221> NAME/KEY: misc_feature
<222> LOCATION: 65..369
<223> OTHER INFORMATION: blastn
<221> NAME/KEY: misc_feature
<222> LOCATION: 61..399
<223> OTHER INFORMATION: blastn
<221> NAME/KEY: misc_feature
<222> LOCATION: 408..458
<223> OTHER INFORMATION: blastn
<221> NAME/KEY: misc_feature
<222> LOCATION: 60..399
<223> OTHER INFORMATION: blastn
<221> NAME/KEY: misc_feature
<222> LOCATION: 393..432
<223> OTHER INFORMATION: blastn
<221> NAME/KEY: sig_peptide
<222> LOCATION: 346..408
<223> OTHER INFORMATION: Von Heijne matrix
<221> NAME/KEY: misc_feature
<222> LOCATION: 115
<223> OTHER INFORMATION: n=a, g, c or t

<400> SEQUENCE: 19 actccttta gcatagggc ttcggcgcca gcggccagcg ctagtcggtc tggtaagtgc      60
ctgatgccga gttccgtctc tcgcgtcttt tcctggtccc aggcaaagcg gasgnagatc   120
ctcaaacggc ctagtgcttc gcgcttccgg agaaaatcag cggtctaatt aattcctctg   180
gtttgttgaa gcagttacca agaatcttca acccttccc acaaaagcta attgagtaca    240
cgttcctgtt gagtacacgt tcctgttgat ttacaaaagg tgcaggtatg agcaggtctg   300
aagactaaca ttttgtgaag ttgtaaaaca gaaaacctgt tagaa atg tgg tgg ttt   357
                                                Met Trp Trp Phe
                                                -20 cag caa ggc ctc agt ttc ctt cct tca gcc ctt gta att tgg aca tct    405
Gln Gln Gly Leu Ser Phe Leu Pro Ser Ala Leu Val Ile Trp Thr Ser
    -15                 -10                 -5 gct gct ttc ata ttt tca tac att act gca gta aca ctc cac cat ata    453
Ala Ala Phe Ile Phe Ser Tyr Ile Thr Ala Val Thr Leu His His Ile
 1               5                  10                  15
```

```
gac ccg gct tta cct tat atc agt gac act ggt aca gta gct cca raa    501
Asp Pro Ala Leu Pro Tyr Ile Ser Asp Thr Gly Thr Val Ala Pro Xaa
             20                  25                  30 aaa tgc tta ttt ggg gca atg cta aat att gcg gca gtt tta tgt caa    549
Lys Cys Leu Phe Gly Ala Met Leu Asn Ile Ala Ala Val Leu Cys Gln
         35                  40                  45 aaa tagaaatcag gaarataatt caacttaaag aakttcattt catgaccaaa         602
Lys ctcttcaraa acatgtcttt acaagcatat ctcttgtatt gctttctaca ctgttgaatt  662
gtctggcaat atttctgcag tggaaaattt gatttarmta gttcttgact gataaatatg  722
gtaaggtggg cttttccccc tgtgtaattg gctactatgt cttactgagc caagttgtaw  782
tttgaaataa aatgatatga gagtgacaca aaaaaaaaaa                       822

<210> SEQ ID NO 20
<211> LENGTH: 21
<212> TYPE: PRT
<213> ORGANISM: Homo Sapiens
<220> FEATURE:
<221> NAME/KEY: SIGNAL
<222> LOCATION: 1..21
<223> OTHER INFORMATION: Von Heijne matrix
      score 5.5
      seq SFLPSALVIWTSA/AF

<400> SEQUENCE: 20

Met Trp Trp Phe Gln Gln Gly Leu Ser Phe Leu Pro Ser Ala Leu Val
1               5                   10                  15

Ile Trp Thr Ser Ala
            20

<210> SEQ ID NO 21
<211> LENGTH: 405
<212> TYPE: DNA
<213> ORGANISM: Homo Sapiens
<220> FEATURE:
<221> NAME/KEY: misc_feature
<222> LOCATION: complement(103..398)
<223> OTHER INFORMATION: blastn
<221> NAME/KEY: sig_peptide
<222> LOCATION: 185..295
<223> OTHER INFORMATION: Von Heijne matrix

<400> SEQUENCE: 21
atcaccttct tctccatcct tstctgggcc agtccccarc ccagtccctc tcctgacctg   60
cccagcccaa gtcagccttc agcacgcgct tttctgcaca cagatattcc aggcctacct  120
ggcattccag gacctccgma atgatgctcc agtcccttac aagcgcttcc tggatgaggg  180 tggc atg gtg ctg acc acc ctc ccc ttg ccc tct gcc aac agc cct gtg   229
     Met Val Leu Thr Thr Leu Pro Leu Pro Ser Ala Asn Ser Pro Val
         -35                 -30                 -25 aac atg ccc acc act ggc ccc aac agc ctg agt tat gct agc tct gcc   277
Asn Met Pro Thr Thr Gly Pro Asn Ser Leu Ser Tyr Ala Ser Ser Ala
        -20                 -15                 -10 ctg tcc ccc tgt ctg acc gct cca aak tcc ccc cgg ctt gct atg atg   325
Leu Ser Pro Cys Leu Thr Ala Pro Xaa Ser Pro Arg Leu Ala Met Met
     -5                   1                   5                  10 cct gac aac taaatatcct tatccaaatc aataaarwra raatcctccc            374
Pro Asp Asn tccaraaggg tttctaaaaa caaaaaaaaa a                                 405
```

```
<210> SEQ ID NO 22
<211> LENGTH: 37
<212> TYPE: PRT
<213> ORGANISM: Homo Sapiens
<220> FEATURE:
<221> NAME/KEY: SIGNAL
<222> LOCATION: 1..37
<223> OTHER INFORMATION: Von Heijne matrix
      score 5.9
      seq LSYASSALSPCLT/AP

<400> SEQUENCE: 22

Met Val Leu Thr Thr Leu Pro Leu Pro Ser Ala Asn Ser Pro Val Asn
1               5                   10                  15

Met Pro Thr Thr Gly Pro Asn Ser Leu Ser Tyr Ala Ser Ser Ala Leu
            20                  25                  30

Ser Pro Cys Leu Thr
        35

<210> SEQ ID NO 23
<211> LENGTH: 496
<212> TYPE: DNA
<213> ORGANISM: Homo Sapiens
<220> FEATURE:
<221> NAME/KEY: misc_feature
<222> LOCATION: 149..331
<223> OTHER INFORMATION: blastn
<221> NAME/KEY: misc_feature
<222> LOCATION: 328..485
<223> OTHER INFORMATION: blastn
<221> NAME/KEY: misc_feature
<222> LOCATION: complement(182..496)
<223> OTHER INFORMATION: blastn
<221> NAME/KEY: sig_peptide
<222> LOCATION: 196..240
<223> OTHER INFORMATION: Von Heijne matrix
<221> NAME/KEY: misc_feature
<222> LOCATION: 101
<223> OTHER INFORMATION: n=a, g, c or t

<400> SEQUENCE: 23
aaaaaattgg tcccagtttt caccctgccg cagggctggc tggggagggc agcggtttag      60
attagccgtg gcctaggccg tttaacgggg tgacacgagc ntgcagggcc gagtccaagg     120
cccggagata ggaccaaccg tcaggaatgc gaggaatgtt tttcttcgga ctctatcgag     180
gcacacagac agacc atg ggg att ctg tct aca gtg aca gcc tta aca ttt     231
            Met Gly Ile Leu Ser Thr Val Thr Ala Leu Thr Phe
                -15             -10                 -5 gcc ara gcc ctg gac ggc tgc aga aat ggc att gcc cac cct gca agt     279
Ala Xaa Ala Leu Asp Gly Cys Arg Asn Gly Ile Ala His Pro Ala Ser
        1               5                   10 gag aag cac aga ctc gag aaa tgt agg gaa ctc gag asc asc cac tcg     327
Glu Lys His Arg Leu Glu Lys Cys Arg Glu Leu Glu Xaa Xaa His Ser
    15                  20                  25 gcc cca gga tca acc cas cac cga aga aaa aca acc aga aga aat tat     375
Ala Pro Gly Ser Thr Xaa His Arg Arg Lys Thr Thr Arg Arg Asn Tyr
30              35                  40                  45 tct tca gcc tgaaatgaak ccgggatcaa atggttgctg atcaragccc             424
Ser Ser Ala atatttaaat tggaaaagtc aaattgasca ttattaaata aagcttgttt aatatgtctc     484
aaacaaaaaa aa                                                        496

<210> SEQ ID NO 24
<211> LENGTH: 15
<212> TYPE: PRT
```

```
<213> ORGANISM: Homo Sapiens
<220> FEATURE:
<221> NAME/KEY: SIGNAL
<222> LOCATION: 1..15
<223> OTHER INFORMATION: Von Heijne matrix
      score 5.5
      seq ILSTVTALTFAXA/LD
<221> NAME/KEY: UNSURE
<222> LOCATION: 14
<223> OTHER INFORMATION: Xaa = any one of the twenty amino acids

<400> SEQUENCE: 24

Met Gly Ile Leu Ser Thr Val Thr Ala Leu Thr Phe Ala Xaa Ala
1               5                   10                  15

<210> SEQ ID NO 25
<211> LENGTH: 623
<212> TYPE: DNA
<213> ORGANISM: Homo Sapiens
<220> FEATURE:
<221> NAME/KEY: sig_peptide
<222> LOCATION: 49..96
<223> OTHER INFORMATION: Von Heijne matrix

<400> SEQUENCE: 25
aaagatccct gcagcccggc aggagagaag gctgagcctt ctggcgtc atg gag agg      57
                                                     Met Glu Arg
                                                         -15 ctc gtc cta acc ctg tgc acc ctc ccg ctg gct gtg gcg tct gct ggc     105
Leu Val Leu Thr Leu Cys Thr Leu Pro Leu Ala Val Ala Ser Ala Gly
        -10                 -5                  1 tgc gcc acg acg cca gct cgc aac ctg agc tgc tac cag tgc ttc aag     153
Cys Ala Thr Thr Pro Ala Arg Asn Leu Ser Cys Tyr Gln Cys Phe Lys
    5                   10                  15 gtc agc agc tgg acg gag tgc ccg ccc acc tgg tgc agc ccg ctg gac     201
Val Ser Ser Trp Thr Glu Cys Pro Pro Thr Trp Cys Ser Pro Leu Asp
20                  25                  30                  35 caa gtc tgc atc tcc aac gag gtg gtc gtc tct ttt aaa tgg agt gta     249
Gln Val Cys Ile Ser Asn Glu Val Val Val Ser Phe Lys Trp Ser Val
                40                  45                  50 cgc gtc ctg ctc agc aaa cgc tgt gct ccc aga tgt ccc aac gac aac     297
Arg Val Leu Leu Ser Lys Arg Cys Ala Pro Arg Cys Pro Asn Asp Asn
            55                  60                  65 atg aak ttc gaa tgg tcg ccg gcc ccc atg gtg caa ggc gtg atc acc     345
Met Xaa Phe Glu Trp Ser Pro Ala Pro Met Val Gln Gly Val Ile Thr
        70                  75                  80 agg cgc tgc tgt tcc tgg gct ctc tgc aac agg gca ctg acc cca cag     393
Arg Arg Cys Cys Ser Trp Ala Leu Cys Asn Arg Ala Leu Thr Pro Gln
85                  90                  95 gag ggg cgc tgg gcc ctg cra ggg ggg ctc ctg ctc cag gac cct tcg     441
Glu Gly Arg Trp Ala Leu Xaa Gly Gly Leu Leu Leu Gln Asp Pro Ser
100                 105                 110                 115 agg ggc ara aaa acc tgg gtg cgg cca cag ctg ggg ctc cca ctc tgc     489
Arg Gly Xaa Lys Thr Trp Val Arg Pro Gln Leu Gly Leu Pro Leu Cys
                120                 125                 130 ctt ccc awt tcc aac ccc ctc tgc cca rgg gaa acc cag gaa gga          534
Leu Pro Xaa Ser Asn Pro Leu Cys Pro Xaa Glu Thr Gln Glu Gly
            135                 140                 145 taacactgtg ggtgccccca cctgtgcatt gggaccacra cttcaccctc ttggaracaa    594
taaactctca tgcccccaaa aaaaaaaaa                                      623

<210> SEQ ID NO 26
<211> LENGTH: 16
```

```
<212> TYPE: PRT
<213> ORGANISM: Homo Sapiens
<220> FEATURE:
<221> NAME/KEY: SIGNAL
<222> LOCATION: 1..16
<223> OTHER INFORMATION: Von Heijne matrix
      score 10.1
      seq LVLTLCTLPLAVA/SA

<400> SEQUENCE: 26

Met Glu Arg Leu Val Leu Thr Leu Cys Thr Leu Pro Leu Ala Val Ala
1               5                   10                  15

<210> SEQ ID NO 27
<211> LENGTH: 848
<212> TYPE: DNA
<213> ORGANISM: Homo Sapiens
<220> FEATURE:
<221> NAME/KEY: sig_peptide
<222> LOCATION: 32..73
<223> OTHER INFORMATION: Von Heijne matrix

<400> SEQUENCE: 27
aactttgcct tgtgttttcc accctgaaag a atg ttg tgg ctg ctc ttt ttt        52
                                   Met Leu Trp Leu Leu Phe Phe
                                                       -10
ctg gtg act gcc att cat gct gaa ctc tgt caa cca ggt gca gaa aat      100
Leu Val Thr Ala Ile His Ala Glu Leu Cys Gln Pro Gly Ala Glu Asn
        -5                  1                   5 gct ttt aaa gtg aga ctt agt atc aga aca gct ctg gga gat aaa gca      148
Ala Phe Lys Val Arg Leu Ser Ile Arg Thr Ala Leu Gly Asp Lys Ala
 10              15                  20                  25 tat gcc tgg gat acc aat gaa gaa tac ctc ttc aaa gcg atg gta gct      196
Tyr Ala Trp Asp Thr Asn Glu Glu Tyr Leu Phe Lys Ala Met Val Ala
                 30                  35                  40 ttc tcc atg aga aaa gtt ccc aac aga gaa gca aca gaa att tcc cat      244
Phe Ser Met Arg Lys Val Pro Asn Arg Glu Ala Thr Glu Ile Ser His
             45                  50                  55 gtc cta ctt tgc aat gta acc cag agg gta tca ttc tgg ttt gtg gtt      292
Val Leu Leu Cys Asn Val Thr Gln Arg Val Ser Phe Trp Phe Val Val
         60                  65                  70 aca gac cct tca aaa aat cac acc ctt cct gct gtt gag gtg caa tca      340
Thr Asp Pro Ser Lys Asn His Thr Leu Pro Ala Val Glu Val Gln Ser
     75                  80                  85 gcc ata aga atg aac aag aac cgg atc aac aat gcc ttc ttt cta aat      388
Ala Ile Arg Met Asn Lys Asn Arg Ile Asn Asn Ala Phe Phe Leu Asn
 90                  95                 100                 105 gac caa act ctg gaa ttt tta aaa atc cct tcc aca ctt gca cca ccc      436
Asp Gln Thr Leu Glu Phe Leu Lys Ile Pro Ser Thr Leu Ala Pro Pro
                 110                 115                 120 atg gac cca tct gtg ccc atc tgg att att ata ttt ggt gtg ata ttt      484
Met Asp Pro Ser Val Pro Ile Trp Ile Ile Ile Phe Gly Val Ile Phe
             125                 130                 135 tgc atc atc ata gtt gca att gca cta ctg att tta tca ggg atc tgg      532
Cys Ile Ile Ile Val Ala Ile Ala Leu Leu Ile Leu Ser Gly Ile Trp
         140                 145                 150 caa cgt ada ara aag aac aaa gaa cca tct gaa gtg gat gac gct gaa      580
Gln Arg Xaa Xaa Lys Asn Lys Glu Pro Ser Glu Val Asp Asp Ala Glu
     155                 160                 165 rat aak tgt gaa aac atg atc aca att gaa aat ggc atc ccc tct gat      628
Xaa Xaa Cys Glu Asn Met Ile Thr Ile Glu Asn Gly Ile Pro Ser Asp
 170                 175                 180                 185 ccc ctg gac atg aag gga ggg cat att aat gat gcc ttc atg aca gag      676
Pro Leu Asp Met Lys Gly Gly His Ile Asn Asp Ala Phe Met Thr Glu
```

```
                    190              195             200
gat gag agg ctc acc cct ctc tgaagggctg ttgttctgct tcctcaaraa        727
Asp Glu Arg Leu Thr Pro Leu
            205 attaaacatt tgtttctgtg tgactgctga gcatcctgaa ataccaagag cagatcatat   787 wttttgtttc accattcttc ttttgtaata aattttgaat gtgcttgaaa aaaaaaaaa    847 c                                                                   848

<210> SEQ ID NO 28
<211> LENGTH: 14
<212> TYPE: PRT
<213> ORGANISM: Homo Sapiens
<220> FEATURE:
<221> NAME/KEY: SIGNAL
<222> LOCATION: 1..14
<223> OTHER INFORMATION: Von Heijne matrix
      score 10.7
      seq LWLLFFLVTAIHA/EL

<400> SEQUENCE: 28

Met Leu Trp Leu Leu Phe Phe Leu Val Thr Ala Ile His Ala
1               5                   10

<210> SEQ ID NO 29
<211> LENGTH: 25
<212> TYPE: DNA
<213> ORGANISM: Artificial Sequence
<220> FEATURE:
<223> OTHER INFORMATION: oligonucleotide

<400> SEQUENCE: 29
gggaagatgg agatagtatt gcctg                                         25

<210> SEQ ID NO 30
<211> LENGTH: 26
<212> TYPE: DNA
<213> ORGANISM: Artificial Sequence
<220> FEATURE:
<223> OTHER INFORMATION: oligonucleotide

<400> SEQUENCE: 30
ctgccatgta catgatagag agattc                                        26

<210> SEQ ID NO 31
<211> LENGTH: 546
<212> TYPE: DNA
<213> ORGANISM: Homo Sapiens
<220> FEATURE:
<221> NAME/KEY: promoter
<222> LOCATION: 1..517
<221> NAME/KEY: transcription start site
<222> LOCATION: 518
<221> NAME/KEY: protein_bind
<222> LOCATION: 17..25
<223> OTHER INFORMATION: matinspector prediction
      name CMYB_01
      score 0.983
      sequence tgtcagttg
<221> NAME/KEY: protein_bind
<222> LOCATION: complement(18..27)
<223> OTHER INFORMATION: matinspector prediction
      name MYOD_Q6
      score 0.961
      sequence cccaactgac
<221> NAME/KEY: protein_bind
<222> LOCATION: complement(75..85)
<223> OTHER INFORMATION: matinspector prediction
      name S8_01
```

```
            score 0.960
            sequence aatagaattag
<221> NAME/KEY: protein_bind
<222> LOCATION: 94..104
<223> OTHER INFORMATION: matinspector prediction
      name S8_01
      score 0.966
      sequence aactaaattag
<221> NAME/KEY: protein_bind
<222> LOCATION: complement(129..139)
<223> OTHER INFORMATION: matinspector prediction
      name DELTAEF1_01
      score 0.960
      sequence gcacacctcag
<221> NAME/KEY: protein_bind
<222> LOCATION: complement(155..165)
<223> OTHER INFORMATION: matinspector prediction
      name GATA_C
      score 0.964
      sequence agataaatcca
<221> NAME/KEY: protein_bind
<222> LOCATION: 170..178
<223> OTHER INFORMATION: matinspector prediction
      name CMYB_01
      score 0.958
      sequence cttcagttg
<221> NAME/KEY: protein_bind
<222> LOCATION: 176..189
<223> OTHER INFORMATION: matinspector prediction
      name GATA1_02
      score 0.959
      sequence ttgtagataggaca
<221> NAME/KEY: protein_bind
<222> LOCATION: 180..190
<223> OTHER INFORMATION: matinspector prediction
      name GATA_C
      score 0.953
      sequence agataggacat
<221> NAME/KEY: protein_bind
<222> LOCATION: 284..299
<223> OTHER INFORMATION: matinspector prediction
      name TAL1ALPHAE47_01
      score 0.973
      sequence cataacagatggtaag
<221> NAME/KEY: protein_bind
<222> LOCATION: 284..299
<223> OTHER INFORMATION: matinspector prediction
      name TAL1BETAE47_01
      score 0.983
      sequence cataacagatggtaag
<221> NAME/KEY: protein_bind
<222> LOCATION: 284..299
<223> OTHER INFORMATION: matinspector prediction
      name TAL1BETAITF2_01
      score 0.978
      sequence cataacagatggtaag
<221> NAME/KEY: protein_bind
<222> LOCATION: complement(287..296)
<223> OTHER INFORMATION: matinspector prediction
      name MYOD_Q6
      score 0.954
      sequence accatctgtt
<221> NAME/KEY: protein_bind
<222> LOCATION: complement(302..314)
<223> OTHER INFORMATION: matinspector prediction
      name GATA1_04
      score 0.953
      sequence tcaagataaagta
<221> NAME/KEY: protein_bind
<222> LOCATION: 393..405
<223> OTHER INFORMATION: matinspector prediction
      name IK1_01
      score 0.963
      sequence agttgggaattcc
<221> NAME/KEY: protein_bind
<222> LOCATION: 393..404
<223> OTHER INFORMATION: matinspector prediction
      name IK2_01
      score 0.985
```

```
      sequence agttgggaattc
<221> NAME/KEY: protein_bind
<222> LOCATION: 396..405
<223> OTHER INFORMATION: matinspector prediction
      name CREL_01
      score 0.962
      sequence tgggaattcc
<221> NAME/KEY: protein_bind
<222> LOCATION: 423..436
<223> OTHER INFORMATION: matinspector prediction
      name GATA1_02
      score 0.950
      sequence tcagtgatatggca
<221> NAME/KEY: protein_bind
<222> LOCATION: complement(478..489)
<223> OTHER INFORMATION: matinspector prediction
      name SRY_02
      score 0.951
      sequence taaaacaaaaca
<221> NAME/KEY: protein_bind
<222> LOCATION: 486..493
<223> OTHER INFORMATION: matinspector prediction
      name E2F_02
      score 0.957
      sequence tttagcgc
<221> NAME/KEY: protein_bind
<222> LOCATION: complement(514..521)
<223> OTHER INFORMATION: matinspector prediction
      name MZF1_01
      score 0.975
      sequence tgagggga

<400> SEQUENCE: 31
tgagtgcagt gttacatgtc agttgggtta agtttgttaa tgtcattcaa atcttctatg      60
tcttgatttg cctgctaatt ctattatttc tggaactaaa ttagtttgat ggttctatta     120
gttattgact gaggtgtgct aatctcccat tatgtggatt tatctatttc ttcagttgta     180
gataggacat tgatagatac ataagtacca ggacaaaagc agggagatct ttttttccaaa    240 atcaggagaa aaaaatgaca tctggaaaac ctataggaa aggcataaca gatggtaagg       300
atactttatc ttgagtagga gagccttcct gtggcaacgt ggagaaggga agaggtcgta     360
gaattgagga gtcagctcag ttagaagcag ggagttggga attccgttca tgtgatttag    420
catcagtgat atggcaaatg tgggactaag ggtagtgatc agagggttaa aattgtgtgt    480
tttgttttag cgctgctggg gcatcgcctt gggtcccctc aaacagattc ccatgaatct    540
cttcat                                                               546

<210> SEQ ID NO 32
<211> LENGTH: 23
<212> TYPE: DNA
<213> ORGANISM: Artificial Sequence
<220> FEATURE:
<223> OTHER INFORMATION: oligonucleotide

<400> SEQUENCE: 32
gtaccaggga ctgtgaccat tgc                                             23

<210> SEQ ID NO 33
<211> LENGTH: 24
<212> TYPE: DNA
<213> ORGANISM: Artificial Sequence
<220> FEATURE:
<223> OTHER INFORMATION: oligonucleotide

<400> SEQUENCE: 33
ctgtgaccat tgctcccaag agag                                            24
```

```
<210> SEQ ID NO 34
<211> LENGTH: 861
<212> TYPE: DNA
<213> ORGANISM: Homo Sapiens
<220> FEATURE:
<221> NAME/KEY: promoter
<222> LOCATION: 1..806
<221> NAME/KEY: transcription start site
<222> LOCATION: 807
<221> NAME/KEY: protein_bind
<222> LOCATION: complement(60..70)
<223> OTHER INFORMATION: matinspector prediction
      name NFY_Q6
      score 0.956
      sequence ggaccaatcat
<221> NAME/KEY: protein_bind
<222> LOCATION: 70..77
<223> OTHER INFORMATION: matinspector prediction
      name MZF1_01
      score 0.962
      sequence cctgggga
<221> NAME/KEY: protein_bind
<222> LOCATION: 124..132
<223> OTHER INFORMATION: matinspector prediction
      name CMYB_01
      score 0.994
      sequence tgaccgttg
<221> NAME/KEY: protein_bind
<222> LOCATION: complement(126..134)
<223> OTHER INFORMATION: matinspector prediction
      name VMYB_02
      score 0.985
      sequence tccaacggt
<221> NAME/KEY: protein_bind
<222> LOCATION: 135..143
<223> OTHER INFORMATION: matinspector prediction
      name STAT_01
      score 0.968
      sequence ttcctggaa
<221> NAME/KEY: protein_bind
<222> LOCATION: complement(135..143)
<223> OTHER INFORMATION: matinspector prediction
      name STAT_01
      score 0.951
      sequence ttccaggaa
<221> NAME/KEY: protein_bind
<222> LOCATION: complement(252..259)
<223> OTHER INFORMATION: matinspector prediction
      name MZF1_01
      score 0.956
      sequence ttggggga
<221> NAME/KEY: protein_bind
<222> LOCATION: 357..368
<223> OTHER INFORMATION: matinspector prediction
      name IK2_01
      score 0.965
      sequence gaatgggatttc
<221> NAME/KEY: protein_bind
<222> LOCATION: 384..391
<223> OTHER INFORMATION: matinspector prediction
      name MZF1_01
      score 0.986
      sequence agagggga
<221> NAME/KEY: protein_bind
<222> LOCATION: complement(410..421)
<223> OTHER INFORMATION: matinspector prediction
      name SRY_02
      score 0.955
      sequence gaaaacaaaaca
<221> NAME/KEY: protein_bind
<222> LOCATION: 592..599
<223> OTHER INFORMATION: matinspector prediction
      name MZF1_01
      score 0.960
      sequence gaagggga
<221> NAME/KEY: protein_bind
<222> LOCATION: 618..627
<223> OTHER INFORMATION: matinspector prediction
      name MYOD_Q6
```

```
        score 0.981
        sequence agcatctgcc
<221> NAME/KEY: protein_bind
<222> LOCATION: 632..642
<223> OTHER INFORMATION: matinspector prediction
        name DELTAEF1_01
        score 0.958
        sequence tcccaccttcc
<221> NAME/KEY: protein_bind
<222> LOCATION: complement(813..823)
<223> OTHER INFORMATION: matinspector prediction
        name S8_01
        score 0.992
        sequence gaggcaattat
<221> NAME/KEY: protein_bind
<222> LOCATION: complement(824..831)
<223> OTHER INFORMATION: matinspector prediction
        name MZF1_01
        score 0.986
        sequence agagggga
<221> NAME/KEY: misc_feature
<222> LOCATION: 335,376
<223> OTHER INFORMATION: n=a, g, c or t

<400> SEQUENCE: 34
tactataggg cacgcgtggt cgacggccgg gctgttctgg agcagagggc atgtcagtaa      60
tgattggtcc ctggggaagg tctggctggc tccagcacag tgaggcattt aggtatctct     120
cggtgaccgt tggattcctg gaagcagtag ctgttctgtt tggatctggt agggacaggg     180
ctcagagggc taggcacgag ggaaggtcag aggagaaggs aggsarggcc cagtgagarg     240
ggagcatgcc ttcccccaac cctggcttsc ycttggymam agggcgktty tgggmacttr     300
aaytcagggc ccaascagaa scacaggccc aktcntggct smaagcacaa tagcctgaat     360
gggatttcag gttagncagg gtgagagggg aggctctctg gcttagtttt gttttgtttt     420
ccaaatcaag gtaacttgct cccttctgct acgggccttg gtcttggctt gtcctcaccc     480
agtcggaact ccctaccact ttcaggagag tggttttagg cccgtggggc tgttctgttc     540
caagcagtgt gagaacatgg ctggtagagg ctctagctgt gtgcggggcc tgaaggggag     600
tgggttctcg cccaaagagc atctgcccat ttcccacctt cccttctccc accagaagct     660
tgcctgagct gttttggacaa aaatccaaac cccacttggc tactctggcc tggcttcagc     720
ttggaaccca atacctaggc ttacaggcca tcctgagcca ggggcctctg gaattctct      780 tcctgatggt cctttaggtt tgggcacaaa atataattgc ctctcccctc tcccattttc     840
tctcttggga gcaatggtca c                                                861

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
ctgggatgga aggcacggta                                                  20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
gagaccacac agctagacaa                                                  20
```

```
<210> SEQ ID NO 37
<211> LENGTH: 555
<212> TYPE: DNA
<213> ORGANISM: Homo Sapiens
<220> FEATURE:
<221> NAME/KEY: promoter
<222> LOCATION: 1..500
<221> NAME/KEY: transcription start site
<222> LOCATION: 501
<221> NAME/KEY: protein_bind
<222> LOCATION: 191..206
<223> OTHER INFORMATION: matinspector prediction
      name ARNT_01
      score 0.964
      sequence ggactcacgtgctgct
<221> NAME/KEY: protein_bind
<222> LOCATION: 193..204
<223> OTHER INFORMATION: matinspector prediction
      name NMYC_01
      score 0.965
      sequence actcacgtgctg
<221> NAME/KEY: protein_bind
<222> LOCATION: 193..204
<223> OTHER INFORMATION: matinspector prediction
      name USF_01
      score 0.985
      sequence actcacgtgctg
<221> NAME/KEY: protein_bind
<222> LOCATION: complement(193..204)
<223> OTHER INFORMATION: matinspector prediction
      name USF_01
      score 0.985
      sequence cagcacgtgagt
<221> NAME/KEY: protein_bind
<222> LOCATION: complement(193..204)
<223> OTHER INFORMATION: matinspector prediction
      name NMYC_01
      score 0.956
      sequence cagcacgtgagt
<221> NAME/KEY: protein_bind
<222> LOCATION: complement(193..204)
<223> OTHER INFORMATION: matinspector prediction
      name MYCMAX_02
      score 0.972
      sequence cagcacgtgagt
<221> NAME/KEY: protein_bind
<222> LOCATION: 195..202
<223> OTHER INFORMATION: matinspector prediction
      name USF_C
      score 0.997
      sequence tcacgtgc
<221> NAME/KEY: protein_bind
<222> LOCATION: complement(195..202)
<223> OTHER INFORMATION: matinspector prediction
      name USF_C
      score 0.991
      sequence gcacgtga
<221> NAME/KEY: protein_bind
<222> LOCATION: complement(210..217)
<223> OTHER INFORMATION: matinspector prediction
      name MZF1_01
      score 0.968
      sequence catggga
<221> NAME/KEY: protein_bind
<222> LOCATION: 397..410
<223> OTHER INFORMATION: matinspector prediction
      name ELK1_02
      score 0.963
      sequence ctctccggaagcct
<221> NAME/KEY: protein_bind
<222> LOCATION: 400..409
<223> OTHER INFORMATION: matinspector prediction
      name CETS1P54_01
      score 0.974
      sequence tccggaagcc
<221> NAME/KEY: protein_bind
<222> LOCATION: complement(460..470)
```

```
<223> OTHER INFORMATION: matinspector prediction
     name AP1_Q4
     score 0.963
     sequence agtgactgaac
<221> NAME/KEY: protein_bind
<222> LOCATION: complement(460..470)
<223> OTHER INFORMATION: matinspector prediction
     name AP1FJ_Q2
     score 0.961
     sequence agtgactgaac
<221> NAME/KEY: protein_bind
<222> LOCATION: 547..555
<223> OTHER INFORMATION: matinspector prediction
     name PADS_C
     score 1.000
     sequence tgtggtctc

<400> SEQUENCE: 37
ctatagggca cgcktggtcg acggcccggg ctggtctggt ctgtkgtgga gtcgggttga      60
aggacagcat ttgtkacatc tggtctactg caccttccct ctgccgtgca cttggccttt    120
kawaagctca gcaccggtgc ccatcacagg gccggcagca cacacatccc attactcaga    180
aggaactgac ggactcacgt gctgctccgt ccccatgagc tcagtggacc tgtctatgta    240
gagcagtcag acagtgcctg ggatagagtg agagttcagc cagtaaatcc aagtgattgt    300
cattcctgtc tgcattagta actcccaacc tagatgtgaa aacttagttc tttctcatag    360
gttgctctgc ccatggtccc actgcagacc caggcactct ccggaagcct ggaaatcacc    420
cgtgtcttct gcctgctccc gctcacatcc cacacttgtg ttcagtcact gagttacaga    480
ttttgcctcc tcaatttctc ttgtcttagt cccatcctct gttcccctgg ccagtttgtc    540
tagctgtgtg gtctc                                                     555

<210> SEQ ID NO 38
<211> LENGTH: 19
<212> TYPE: DNA
<213> ORGANISM: Artificial Sequence
<220> FEATURE:
<223> OTHER INFORMATION: oligonucleotide

<400> SEQUENCE: 38
ggccatacac ttgagtgac                                                  19

<210> SEQ ID NO 39
<211> LENGTH: 19
<212> TYPE: DNA
<213> ORGANISM: Artificial Sequence
<220> FEATURE:
<223> OTHER INFORMATION: oligonucleotide

<400> SEQUENCE: 39
atatagacaa acgcacacc                                                  19

<210> SEQ ID NO 40
<211> LENGTH: 1098
<212> TYPE: DNA
<213> ORGANISM: Homo sapiens
<220> FEATURE:
<221> NAME/KEY: sig_peptide
<222> LOCATION: 173..211
<223> OTHER INFORMATION: Von Heijne matrix
     score 4.19999980926514
     seq MLAVSLTVPLLGA/MM
<221> NAME/KEY: polyA_signal
<222> LOCATION: 1063..1068
<221> NAME/KEY: polyA_site
<222> LOCATION: 1087..1098
<221> NAME/KEY: misc_feature
```

```
<222> LOCATION: 144..467
<223> OTHER INFORMATION: homology
      id :AA057573
      est
<221> NAME/KEY: misc_feature
<222> LOCATION: 510..640
<223> OTHER INFORMATION: homology
      id :AA057573
      est
<221> NAME/KEY: misc_feature
<222> LOCATION: 436..523
<223> OTHER INFORMATION: homology
      id :AA057573
      est
<221> NAME/KEY: misc_feature
<222> LOCATION: 708..786
<223> OTHER INFORMATION: homology
      id :AA057573
      est
<221> NAME/KEY: misc_feature
<222> LOCATION: 635..682
<223> OTHER INFORMATION: homology
      id :AA057573
      est
<221> NAME/KEY: misc_feature
<222> LOCATION: 625..1084
<223> OTHER INFORMATION: homology
      id :N57409
      est
<221> NAME/KEY: misc_feature
<222> LOCATION: 779..1084
<223> OTHER INFORMATION: homology
      id :R71351
      est
<221> NAME/KEY: misc_feature
<222> LOCATION: 144..506
<223> OTHER INFORMATION: homology
      id :H12619
      est
<221> NAME/KEY: misc_feature
<222> LOCATION: 90..467
<223> OTHER INFORMATION: homology
      id :T03538
      est
<221> NAME/KEY: misc_feature
<222> LOCATION: 314..523
<223> OTHER INFORMATION: homology
      id :T34150
      est
<221> NAME/KEY: misc_feature
<222> LOCATION: 567..687
<223> OTHER INFORMATION: homology
      id :T34150
      est
<221> NAME/KEY: misc_feature
<222> LOCATION: 686..730
<223> OTHER INFORMATION: homology
      id :T34150
      est
<221> NAME/KEY: misc_feature
<222> LOCATION: 510..553
<223> OTHER INFORMATION: homology
      id :T34150
      est
<221> NAME/KEY: misc_feature
<222> LOCATION: 550..579
<223> OTHER INFORMATION: homology
      id :T34150
      est
<221> NAME/KEY: misc_feature
<222> LOCATION: 144..523
<223> OTHER INFORMATION: homology
      id :N32314
      est
<221> NAME/KEY: misc_feature
<222> LOCATION: 510..553
<223> OTHER INFORMATION: homology
      id :N32314
      est
```

```
<221> NAME/KEY: misc_feature
<222> LOCATION: 352..523
<223> OTHER INFORMATION: homology
      id :T77966
      est
<221> NAME/KEY: misc_feature
<222> LOCATION: 218..351
<223> OTHER INFORMATION: homology
      id :T77966
      est
<221> NAME/KEY: misc_feature
<222> LOCATION: 510..553
<223> OTHER INFORMATION: homology
      id :T77966
      est
<221> NAME/KEY: misc_feature
<222> LOCATION: 550..917
<223> OTHER INFORMATION: homology
      id :AA464128
      est
<221> NAME/KEY: misc_feature
<222> LOCATION: 1083
<223> OTHER INFORMATION: n=a, g, c or t

<400> SEQUENCE: 40
```

| | | |
|---|---|---|
| agtgaggtgg tttctgcggg tgaggctggc gcccgtacca tgagcgaggc ggacgggctg | 60 |
| cgacagcgcc ggccccctgcg gcccgcaagt cgtcacagac gatgatggcc aggccccgga | 120 |
| ggctaaggac ggcagctcct ttagcggcag agttttccga gtgaccttct tg atg ctg | 178 |

```
                                                             Met Leu gct gtt tct ctc acc gtt ccc ctg ctt gga gcc atg atg ctg ctg gaa     226
Ala Val Ser Leu Thr Val Pro Leu Leu Gly Ala Met Met Leu Leu Glu
    -10              -5                   1               5 tct cct ata gat cca cag cct ctc agc ttc aaa gaa ccc ccg ctc ttg     274
Ser Pro Ile Asp Pro Gln Pro Leu Ser Phe Lys Glu Pro Pro Leu Leu
               10                   15                  20 ctt ggt gtt ctg cat cca aat acg aag ctg cga cag gca gaa agg ctg     322
Leu Gly Val Leu His Pro Asn Thr Lys Leu Arg Gln Ala Glu Arg Leu
            25                  30                  35 ttt gaa aat caa ctt gtt gga ccg gag tcc ata gca cat att ggg gat     370
Phe Glu Asn Gln Leu Val Gly Pro Glu Ser Ile Ala His Ile Gly Asp
        40                  45                  50 gtg atg ttt act ggg aca gca gat ggc cgg gtc gta aaa ctt gaa aat     418
Val Met Phe Thr Gly Thr Ala Asp Gly Arg Val Val Lys Leu Glu Asn
    55                  60                  65 ggt gaa ata gag acc att gcc cgg ttt ggt tcg ggc cct tgc aaa acc     466
Gly Glu Ile Glu Thr Ile Ala Arg Phe Gly Ser Gly Pro Cys Lys Thr
70                  75                  80                  85 cga ggt gat gag cct gtg tgt ggg aga ccc ctg ggt atc cgt ggc agg     514
Arg Gly Asp Glu Pro Val Cys Gly Arg Pro Leu Gly Ile Arg Gly Arg
                90                  95                 100 gcc caa tgg gac tct ctt tgt ggc cga tgc ata caa agg gac tat ttg     562
Ala Gln Trp Asp Ser Leu Cys Gly Arg Cys Ile Gln Arg Asp Tyr Leu
            105                 110                 115 aag taaatccctg gaaacgtgaa gtgaaactgc tgctgtcctc cgagacaccc          615
Lys attgagggga agaacatgtc ctttgtgaat gatcttacag tcactcagga tgggaggaag    675
atttatttca ccgattctag cagcaaatgg caaagacgag actacctgct tctggtgatg    735
gagggcacag atgacgggcg cctgctggag tatgatactg tgaccaggga agtaaaagtt    795
ttattggacc agctgcggtt cccgaatgga gtccagctgt ctcctgcaga agactttgtc    855
ctggtggcag aaacaaccat ggccaggata cgaagagtct acgtttctgg cctgatgaag    915
ggcggggctg atctgtttgt ggagaacatg cctggatttc cagacaacat ccggcccagc    975
```

```
agctctgggg ggtactgggt gggcatgtcg accatccgcc ctaaccctgg gtttttccatg   1035 ctggatttct tatctgagag accctggatt aaaaggatga ttttttaangg taaaaaaaaa   1095 aaa                                                                  1098
```

```
<210> SEQ ID NO 41
<211> LENGTH: 855
<212> TYPE: DNA
<213> ORGANISM: Homo sapiens
<220> FEATURE:
<221> NAME/KEY: sig_peptide
<222> LOCATION: 267..371
<223> OTHER INFORMATION: Von Heijne matrix
      score 5.90000009536743
      seq LCGLLHLWLKVFS/LK
<221> NAME/KEY: polyA_signal
<222> LOCATION: 817..822
<221> NAME/KEY: polyA_site
<222> LOCATION: 842..855
<221> NAME/KEY: misc_feature
<222> LOCATION: 608..811
<223> OTHER INFORMATION: homology
      id :M85769
      est
```

<400> SEQUENCE: 41

```
acaatcagtt tgccaatacc tcagaaacaa atacctcgga caaatctttc tctaaagacc    60
tcagtcagat actagtcaat atcaaatcat gtagatggcg gcattttagg cctcggacac   120
catccctaca tgacagtgac aatgatgaac tctcctgtag aaaattatat aggagtataa   180
accgaacagg aacagcacaa cctgggaccc agacatgcag tacctctacg caaagtaaaa   240
gtagcagtgg ttcagcacac tttggt atg ttg act gtt aat gat gta cgt ttc   293
                              Met Leu Thr Val Asn Asp Val Arg Phe
                              -35                 -30
```

| tat | aga | aat | gtc | agg | tcc | aac | cat | ttc | cca | ttt | gtt | cga | cta | tgt | ggt | 341 |
|-----|-----|-----|-----|-----|-----|-----|-----|-----|-----|-----|-----|-----|-----|-----|-----|-----|
| Tyr | Arg | Asn | Val | Arg | Ser | Asn | His | Phe | Pro | Phe | Val | Arg | Leu | Cys | Gly |     |
|     | -25 |     |     |     | -20 |     |     |     |     | -15 |     |     |     |     |     |     |

| ctg | tta | cat | tta | tgg | ctt | aaa | gtc | ttt | tct | ctt | aaa | cag | tta | aaa | aaa | 389 |
|-----|-----|-----|-----|-----|-----|-----|-----|-----|-----|-----|-----|-----|-----|-----|-----|-----|
| Leu | Leu | His | Leu | Trp | Leu | Lys | Val | Phe | Ser | Leu | Lys | Gln | Leu | Lys | Lys |     |
| -10 |     |     |     | -5  |     |     |     |     | 1   |     |     |     | 5   |     |     |     |

| aaa | tct | tgg | tct | aag | tat | tta | ttt | gaa | tcc | tgt | tgc | tat | agg | agt | ttg | 437 |
|-----|-----|-----|-----|-----|-----|-----|-----|-----|-----|-----|-----|-----|-----|-----|-----|-----|
| Lys | Ser | Trp | Ser | Lys | Tyr | Leu | Phe | Glu | Ser | Cys | Cys | Tyr | Arg | Ser | Leu |     |
|     |     |     | 10  |     |     |     |     | 15  |     |     |     |     | 20  |     |     |     |

```
tat gtg tgt gtc ttc att taaacatacc tgcatacaaa gatggtttat              485
Tyr Val Cys Val Phe Ile
            25 ttctatttaa tatgtgacat ttgtttcctg gatatagtcc gtgaaccaca agatttatca    545 tattttcaa taatatgaga agaaaatggg ccgtaaattg ttaaccattt tatgttcaga     605 tatttctcta gttttttacct agtttgcttt aacatagaga ccagcaagtg aatatatatg   665 cataaccta tatgttgaca caataattca gaataatttg ttaaagataa actaattttt    725 cagagaagaa catttaaagg gttaatattt ttgaaacgtt ttcagataat atctatttga    785 ttattgtggc ttctatttga aatgtgtcta aaataaaatg ctgtttattt aaaatgaaaa    845 aaaaaaaaaa                                                            855
```

```
<210> SEQ ID NO 42
<211> LENGTH: 1176
<212> TYPE: DNA
<213> ORGANISM: Homo sapiens
<220> FEATURE:
<221> NAME/KEY: sig_peptide
```

```
<222> LOCATION: 174..266
<223> OTHER INFORMATION: Von Heijne matrix
      score 3.5
      seq WSPLSTRSGGTHA/CS
<221> NAME/KEY: polyA_signal
<222> LOCATION: 1144..1149
<221> NAME/KEY: polyA_site
<222> LOCATION: 1165..1176
<221> NAME/KEY: misc_feature
<222> LOCATION: 886..1134
<223> OTHER INFORMATION: homology
      id :AA595193
      est
<221> NAME/KEY: misc_feature
<222> LOCATION: 756..894
<223> OTHER INFORMATION: homology
      id :AA595193
      est
<221> NAME/KEY: misc_feature
<222> LOCATION: 655..755
<223> OTHER INFORMATION: homology
      id :AA595193
      est
<221> NAME/KEY: misc_feature
<222> LOCATION: 167..367
<223> OTHER INFORMATION: homology
      id :W81213
      est
<221> NAME/KEY: misc_feature
<222> LOCATION: 66..172
<223> OTHER INFORMATION: homology
      id :W81213
      est
<221> NAME/KEY: misc_feature
<222> LOCATION: 429..508
<223> OTHER INFORMATION: homology
      id :W81213
      est
<221> NAME/KEY: misc_feature
<222> LOCATION: 756..894
<223> OTHER INFORMATION: homology
      id :AA150887
      est
<221> NAME/KEY: misc_feature
<222> LOCATION: 536..643
<223> OTHER INFORMATION: homology
      id :AA150887
      est
<221> NAME/KEY: misc_feature
<222> LOCATION: 655..755
<223> OTHER INFORMATION: homology
      id :AA150887
      est
<221> NAME/KEY: misc_feature
<222> LOCATION: 429..643
<223> OTHER INFORMATION: homology
      id :AA493644
      est
<221> NAME/KEY: misc_feature
<222> LOCATION: 655..755
<223> OTHER INFORMATION: homology
      id :AA493644
      est
<221> NAME/KEY: misc_feature
<222> LOCATION: 429..643
<223> OTHER INFORMATION: homology
      id :AA493494
      est
<221> NAME/KEY: misc_feature
<222> LOCATION: 655..755
<223> OTHER INFORMATION: homology
      id :AA493494
      est
<221> NAME/KEY: misc_feature
<222> LOCATION: 500..643
<223> OTHER INFORMATION: homology
      id :AA179182
      est
<221> NAME/KEY: misc_feature
```

```
<222> LOCATION: 655..755
<223> OTHER INFORMATION: homology
      id :AA179182
      est
<221> NAME/KEY: misc_feature
<222> LOCATION: 756..847
<223> OTHER INFORMATION: homology
      id :AA179182
      est
<221> NAME/KEY: misc_feature
<222> LOCATION: 3..338
<223> OTHER INFORMATION: homology
      id :HUM524F05B
      est
<221> NAME/KEY: misc_feature
<222> LOCATION: 334..374
<223> OTHER INFORMATION: homology
      id :HUM524F05B
      est
<221> NAME/KEY: misc_feature
<222> LOCATION: 886..1134
<223> OTHER INFORMATION: homology
      id :AA398156
      est
<221> NAME/KEY: misc_feature
<222> LOCATION: 756..894
<223> OTHER INFORMATION: homology
      id :AA398156
      est
<221> NAME/KEY: misc_feature
<222> LOCATION: 590,601
<223> OTHER INFORMATION: n=a, g, c or t

<400> SEQUENCE: 42
aaaaacaata ggacggaaac gccgaggaac ccggctgagg cggcagagca tcctggccag      60
aacaagccaa ggagccaaga cgagagggac acacggacaa acaacagaca gaagacgtac     120
tggccgctgg actccgctgc ctccccatc tccccgccat ctgcgcccgg agg atg        176
                                                            Met agc cca gcc ttc agg gcc atg gat gtg gag ccc cgc gcc aaa ggc tcc      224
Ser Pro Ala Phe Arg Ala Met Asp Val Glu Pro Arg Ala Lys Gly Ser
-30             -25                 -20                 -15 ttc tgg agc cct ttg tcc acc agg tcg ggg ggc act cat gcg tgc tcc      272
Phe Trp Ser Pro Leu Ser Thr Arg Ser Gly Gly Thr His Ala Cys Ser
            -10                 -5                   1 gct tca atg aga caa ccc tgg gca agc ccc tgg tcc caa ggg aac atc      320
Ala Ser Met Arg Gln Pro Trp Ala Ser Pro Trp Ser Gln Gly Asn Ile
        5                  10                  15 agt tct acg aga ccc tcc ctg ctg aga tgc gca aat tct ctc ccc agt      368
Ser Ser Thr Arg Pro Ser Leu Leu Arg Cys Ala Asn Ser Leu Pro Ser
    20                  25                  30 aca aag gac aaa gcc aaa ggc ccc ttg tta gct ggc cat ccc tgc ccc      416
Thr Lys Asp Lys Ala Lys Gly Pro Leu Leu Ala Gly His Pro Cys Pro
35                  40                  45                  50 att ttt tcc cct ggt cct ttc ccc tgt ggc cac agg gaa gtg tgg cct      464
Ile Phe Ser Pro Gly Pro Phe Pro Cys Gly His Arg Glu Val Trp Pro
                55                  60                  65 gaa tac ccc acc ccg gct cct ctg cac cca gag ctg ggg gcc acc tca      512
Glu Tyr Pro Thr Pro Ala Pro Leu His Pro Glu Leu Gly Ala Thr Ser
            70                  75                  80 gaa gtg tca tct ctc tct gag cac gsa ttc ccc tgc agc agt cga gga      560
Glu Val Ser Ser Leu Ser Glu His Xaa Phe Pro Cys Ser Ser Arg Gly
        85                  90                  95 ctg agc aga ttg agt gat gct ggg gca gan adg cct gag ang aaa ggt      608
Leu Ser Arg Leu Ser Asp Ala Gly Ala Xaa Xaa Pro Glu Xaa Lys Gly
    100                 105                 110 gtt cag cca gtc gtt tgt aag gcg ctc gkc ggm act gct gaa acg ccc      656
```

```
Val Gln Pro Val Val Cys Lys Ala Leu Xaa Gly Thr Ala Glu Thr Pro
115                 120                 125                 130 cca ccc tgacagcccc atcctcaaag actgtcttaa ttactcatgg caggttctag    712
Pro Pro agacttaagg ggaaaagctg ctttcaaggc caccacatgt ctggtgctcc ccmaccagst  772
statctgcct wgtgttcatt ttgytatttt gtgasgtgag acagcaaaga ccaataaaaa  832
catattttat aagaacaaaa ggcytggtg cctacccgkg tgggggcacw gtgggaagcc   892
ttctgmtagg gtgtcttgtg ctgtrtggyt tgttttgttt gccccyttat tttgctttgc  952
ttacccagtc ttcccytamt yttggatgst tyttaaccct caggcaaacc tgtgttcccc  1012
ctgtattcag gstytgcttt aaagcaagcc atgaggctgt tggagtttct gtttagggca  1072
ttaaaaattc ccgcaaacta taaagagcaa tgttttcagt yttttaggat tagaagaatt  1132
acataaaaat taataaacat tttcaatgat ggaaaaaaaa aaaa                  1176

<210> SEQ ID NO 43
<211> LENGTH: 648
<212> TYPE: DNA
<213> ORGANISM: Homo sapiens
<220> FEATURE:
<221> NAME/KEY: sig_peptide
<222> LOCATION: 460..555
<223> OTHER INFORMATION: Von Heijne matrix
      score 4
      seq FSFMLLGMGGCLP/GF
<221> NAME/KEY: polyA_signal
<222> LOCATION: 614..619
<221> NAME/KEY: polyA_site
<222> LOCATION: 635..648

<400> SEQUENCE: 43
aattctggcc cagcttcttc cccagctcta tcctgcttcc ctccatctcc tataggattc    60
tccttagagt tctccctcca ttagtagttg cttagggtc tgtttctggg gagccctgcc   120
taagactcat gctacaagaa gttaaataag tttcccgaag tcacacagct agcctctcat   180
cccttttcta ctgagaggaa gtggaatgca ctccgacaag gataaggttt tattgtgagc   240
tggccttgga attaaaccac caccaacaca cttttggatt atcagaaggt ggaaggagtg   300
caaatgccag ttcggtgat gcgttcaaca tccttatttc cagtctttat gacgcctttc   360
ctgaatcaca ggtgcattgg ggtgcttcct cctccccagg actcccaccc aactttgtga   420
acacaaccca cttagaggag ttatctcagc acattatga atg ttg ggg acc acg     474
                                              Met Leu Gly Thr Thr
                                                           -30 ggc ctc ggg aca cag ggt cct tcc cag cag gct ctg ggc ttt ttc tcc    522
Gly Leu Gly Thr Gln Gly Pro Ser Gln Gln Ala Leu Gly Phe Phe Ser
         -25                 -20                 -15 ttt atg tta ctt gga atg ggc ggg tgc ctg cct gga ttc ctg cta cag    570
Phe Met Leu Leu Gly Met Gly Gly Cys Leu Pro Gly Phe Leu Leu Gln
        -10                  -5                   1               5 cct ccc aat cga tct cct act ttg cct gca tcc acc ttt gcc cat        615
Pro Pro Asn Arg Ser Pro Thr Leu Pro Ala Ser Thr Phe Ala His
                    10                  15                  20 taaagtcaat tctccaccca taaaaaaaaa aaa                               648

<210> SEQ ID NO 44
<211> LENGTH: 1251
<212> TYPE: DNA
<213> ORGANISM: Homo sapiens
<220> FEATURE:
<221> NAME/KEY: sig_peptide
```

```
<222> LOCATION: 79..369
<223> OTHER INFORMATION: Von Heijne matrix
      score 4
      seq RLPLVVSFIASSS/AN
<221> NAME/KEY: polyA_signal
<222> LOCATION: 1217..1222
<221> NAME/KEY: polyA_site
<222> LOCATION: 1240..1251
<221> NAME/KEY: misc_feature
<222> LOCATION: 2..423
<223> OTHER INFORMATION: homology
      id :AA056667
      est
<221> NAME/KEY: misc_feature
<222> LOCATION: 463..520
<223> OTHER INFORMATION: homology
      id :AA056667
      est
<221> NAME/KEY: misc_feature
<222> LOCATION: 418..467
<223> OTHER INFORMATION: homology
      id :AA056667
      est
<221> NAME/KEY: misc_feature
<222> LOCATION: 159..636
<223> OTHER INFORMATION: homology
      id :AA044187
      est
<221> NAME/KEY: misc_feature
<222> LOCATION: 629..684
<223> OTHER INFORMATION: homology
      id :AA044187
      est
<221> NAME/KEY: misc_feature
<222> LOCATION: 5..453
<223> OTHER INFORMATION: homology
      id :AA131958
      est
<221> NAME/KEY: misc_feature
<222> LOCATION: 446..494
<223> OTHER INFORMATION: homology
      id :AA131958
      est
<221> NAME/KEY: misc_feature
<222> LOCATION: 14..343
<223> OTHER INFORMATION: homology
      id :W95957
      est
<221> NAME/KEY: misc_feature
<222> LOCATION: 323..467
<223> OTHER INFORMATION: homology
      id :W95957
      est
<221> NAME/KEY: misc_feature
<222> LOCATION: 463..494
<223> OTHER INFORMATION: homology
      id :W95957
      est
<221> NAME/KEY: misc_feature
<222> LOCATION: 14..475
<223> OTHER INFORMATION: homology
      id :W95790
      est
<221> NAME/KEY: misc_feature
<222> LOCATION: 410..876
<223> OTHER INFORMATION: homology
      id :AA461134
      est
<221> NAME/KEY: misc_feature
<222> LOCATION: 974..1195
<223> OTHER INFORMATION: homology
      id :AA595195
      est
<221> NAME/KEY: misc_feature
<222> LOCATION: 769..982
<223> OTHER INFORMATION: homology
      id :AA595195
      est
<221> NAME/KEY: misc_feature
```

```
<222> LOCATION: 1208..1237
<223> OTHER INFORMATION: homology
      id :AA595195
      est
<221> NAME/KEY: misc_feature
<222> LOCATION: 223..522
<223> OTHER INFORMATION: homology
      id :AA041216
      est
<221> NAME/KEY: misc_feature
<222> LOCATION: 518..636
<223> OTHER INFORMATION: homology
      id :AA041216
      est
<221> NAME/KEY: misc_feature
<222> LOCATION: 774..1127
<223> OTHER INFORMATION: homology
      id :N94607
      est
<221> NAME/KEY: misc_feature
<222> LOCATION: 690..765
<223> OTHER INFORMATION: homology
      id :N94607
      est
<221> NAME/KEY: misc_feature
<222> LOCATION: 833..1195
<223> OTHER INFORMATION: homology
      id :AA076410
      est

<400> SEQUENCE: 44
aaagtgacag cggagagaac caggsagccc agaaacccca ggcgtggaga ttgatcctgc        60
gagagaaggg ggttcatc atg gcg gat gac cta aag cga ttc ttg tat aaa       111
                    Met Ala Asp Asp Leu Lys Arg Phe Leu Tyr Lys
                        -95                 -90 aag tta cca agt gtt gaa ggg ctc cat gcc att gtt gtg tca gat aga       159
Lys Leu Pro Ser Val Glu Gly Leu His Ala Ile Val Val Ser Asp Arg
    -85                 -80                 -75 gat gga gta cct gtt att aaa gtg gca aat gac aat gct cca gag cat       207
Asp Gly Val Pro Val Ile Lys Val Ala Asn Asp Asn Ala Pro Glu His
-70                 -65                 -60                 -55 gct ttg cga cct ggt ttc tta tcc act ttt gcc ctt gca aca gac caa       255
Ala Leu Arg Pro Gly Phe Leu Ser Thr Phe Ala Leu Ala Thr Asp Gln
                -50                 -45                 -40 gga agc aaa ctt gga ctt tcc aaa aat aaa agt atc atc tgt tac tat       303
Gly Ser Lys Leu Gly Leu Ser Lys Asn Lys Ser Ile Ile Cys Tyr Tyr
            -35                 -30                 -25 aac acc tac cag gtg gtt caa ttt aat cgt tta cct ttg gtg gtg agt       351
Asn Thr Tyr Gln Val Val Gln Phe Asn Arg Leu Pro Leu Val Val Ser
        -20                 -15                 -10 ttc ata gcc agc agc agt gcc aat aca gga cta att gtc agc cta gaa       399
Phe Ile Ala Ser Ser Ser Ala Asn Thr Gly Leu Ile Val Ser Leu Glu
    -5                   1                   5                  10 aag gag ctt gct cca ttg ttt gaa gaa ctg aga caa gtt gtg gaa att       447
Lys Glu Leu Ala Pro Leu Phe Glu Glu Leu Arg Gln Val Val Glu Ile
                15                  20                  25 tct taatctgaca gtggtttcag tgtgtacctt atcttcatta taacaacaca            500
Ser atatcaatcc agcaatcttt agactacaat aatgcttta tccatgtgct caagaaggg       560 ccccctttc caacttatac taagaacta gcatatagat gtaatttata gatagatcag       620
ttgctatatt ttctggtgta aggtctttct tatttagtga gatctaggga taccacagaa     680
atggttcagt ctatcacagc tcccatggag ttagtctggt caccagatat ggatgagaga     740
ttctattcag tggattagaa tcaaactggt acattgatcc acttgagccg ttaagtgctg     800
```

-continued

```
ccaattgtac aatatgccca ggcttgcaga ataaagccaa ctttttattg tgaataataa      860
taaggacata ttttcttca gattatgttt tatttctttg cattgagtga ggtacataaa       920
atggcttggt aaaagtaata aaatcagtac aatcactaac tttcctttgt acatattatt      980
ttgcagtata gatgaatatt actaatcagt ttgattattc tcagagggtg ctgctcttta    1040
atgaaaatga aaattatagc taatgttttt tcctcaaact ctgctttctg taaccaatca    1100
gtgttttaat gtttgtgtgt tcttcataaa atttaaatac aattcgttat tctgtttcca    1160
atgttagtat gtatgtaaac atgatagtac agccattttt ttcatatgtg agtaaaaata    1220
aaatagtatt tttaaaagta aaaaaaaaaa a                                    1251
```

<210> SEQ ID NO 45
<211> LENGTH: 1524
<212> TYPE: DNA
<213> ORGANISM: Homo sapiens
<220> FEATURE:
<221> NAME/KEY: sig_peptide
<222> LOCATION: 160..231
<223> OTHER INFORMATION: Von Heijne matrix
      score 5.69999980926514
      seq ILGLLGLLGTLVA/ML
<221> NAME/KEY: polyA_signal
<222> LOCATION: 1510..1515
<221> NAME/KEY: polyA_site
<222> LOCATION: 1506..1519
<221> NAME/KEY: misc_feature
<222> LOCATION: 1048..1504
<223> OTHER INFORMATION: homology
      id :AA552647
      est
<221> NAME/KEY: misc_feature
<222> LOCATION: 597..846
<223> OTHER INFORMATION: homology
      id :AA345449
      est
<221> NAME/KEY: misc_feature
<222> LOCATION: 39..93
<223> OTHER INFORMATION: homology
      id :AA345449
      est
<221> NAME/KEY: misc_feature
<222> LOCATION: 113..149
<223> OTHER INFORMATION: homology
      id :AA345449
      est
<221> NAME/KEY: misc_feature
<222> LOCATION: 98..400
<223> OTHER INFORMATION: homology
      id :T86266
      est
<221> NAME/KEY: misc_feature
<222> LOCATION: 1210..1489
<223> OTHER INFORMATION: homology
      id :T86158
      est
<221> NAME/KEY: misc_feature
<222> LOCATION: 954..983
<223> OTHER INFORMATION: homology
      id :AA116709
      est

<400> SEQUENCE: 45

```
agctgcttgt ggccacccac agacacttgt aaggaggaga gaagtcagcc tggcagagag       60
actctgaaat gassgattag aggtgttcaa ggragcaaag agcttcagcc tgaagacaag      120
ggagcagtcc ctgaagacgc ttctactgag aggtctgcc atg gcc tct ctt ggc        174
                                           Met Ala Ser Leu Gly
                                                           -20 ctc caa ctt gtg ggc tac atc cta ggc ctt ctg ggg ctt ttg ggc aca       222
Leu Gln Leu Val Gly Tyr Ile Leu Gly Leu Leu Gly Leu Leu Gly Thr
```

```
                -15                 -10                 -5
ctg gtt gcc atg ctg ctc ccc agc tgg aaa aca agt tct tat gtc ggt      270
Leu Val Ala Met Leu Leu Pro Ser Trp Lys Thr Ser Ser Tyr Val Gly
             1               5                  10 gcc agc att gtg aca gca gtt ggc ttc tcc aag ggc ctc tgg atg gaa      318
Ala Ser Ile Val Thr Ala Val Gly Phe Ser Lys Gly Leu Trp Met Glu
 15                  20                  25 tgt gcc aca cac agc aca ggc atc acc cag tgt gac atc tat agc acc      366
Cys Ala Thr His Ser Thr Gly Ile Thr Gln Cys Asp Ile Tyr Ser Thr
 30                  35                  40                  45 ctt ctg ggc ctg ccc gct gac atc cak gct gcc cag gcc atg atg gtg      414
Leu Leu Gly Leu Pro Ala Asp Ile Xaa Ala Ala Gln Ala Met Met Val
                 50                  55                  60 aca tcc agt gca atc tcc tcc ctg gcc tgc att atc tct gtg gtg ggc      462
Thr Ser Ser Ala Ile Ser Ser Leu Ala Cys Ile Ile Ser Val Val Gly
                 65                  70                  75 atg ara tgc aca gtc ttc tgc cag gaa tcc cga gcc aaa gac aga gtg      510
Met Xaa Cys Thr Val Phe Cys Gln Glu Ser Arg Ala Lys Asp Arg Val
             80                  85                  90 gcg gta gca ggt gga gtc ttt ttc atc ctt gga ggc ctc ctg gga ttc      558
Ala Val Ala Gly Gly Val Phe Phe Ile Leu Gly Gly Leu Leu Gly Phe
 95                 100                 105 att cct gtt gcc tgg aat ctt cat ggg atc cta cgg gac ttc tac tca      606
Ile Pro Val Ala Trp Asn Leu His Gly Ile Leu Arg Asp Phe Tyr Ser
110                 115                 120                 125 cca ctg gtg cct gac agc atg aaa ttt gag att gga gag gct ctt tac      654
Pro Leu Val Pro Asp Ser Met Lys Phe Glu Ile Gly Glu Ala Leu Tyr
                130                 135                 140 ttg ggc att att tct tcc ctg ttc tcc ctg ata gct gga atc atc ctc      702
Leu Gly Ile Ile Ser Ser Leu Phe Ser Leu Ile Ala Gly Ile Ile Leu
                145                 150                 155 tgc ttt tcc tgc tca tcc cag aga aat cgc tcc aac tac tac gat gcc      750
Cys Phe Ser Cys Ser Ser Gln Arg Asn Arg Ser Asn Tyr Tyr Asp Ala
        160                 165                 170 tac caa gcc caa cct ctt gcc aca agg agc tct cca agg cct ggt caa      798
Tyr Gln Ala Gln Pro Leu Ala Thr Arg Ser Ser Pro Arg Pro Gly Gln
175                 180                 185 cct ccc aaa gtc aag agt gag ttc aat tcc tac agc ctg aca ggg tat      846
Pro Pro Lys Val Lys Ser Glu Phe Asn Ser Tyr Ser Leu Thr Gly Tyr
190                 195                 200                 205 gtg tgaagaacca ggggccagag ctgggggtg gctgggtctg tgaaaaacag            899
Val tggacagcac cccgagggcc acaggtgagg gacactacca ctggatcgtg tcagaaggtg    959
ctgctgaggg tagactgact ttggccattg gattgagcaa aggcagaaat gggggctagt   1019
gtaacagcat gcaggttgaa ttgccaagga tgctcgccat gccagccttt ctgttttcct   1079
caccttgctg ctcccctgcc ctaagtcccc aaccctcaac ttgaaacccc attcccttaa   1139
gccaggamtc agaggatccc tytgccctck ggtttamctg ggactccatc cccaaaccca   1199
ctaatcacat cccactgact gaccctctgt gatcaaagac cctccctctg ctgaggttg    1259 gstyttagct cattgctggg gatgggaagg agaagcagtg gctttystgg gcattgctyt   1319
aacctamtty tcaagcttcc ctccaaagaa amtgattggc cctggaacct ccatcccact   1379
yttgttatga ctccacagtg tccagamtaa tttgtgcatg aactgaaata aaaccatcct   1439
acggtatyca gggaacagaa agcaggatgc aggatgggag acaggaagg cagcctggga    1499 catttaaaaa aataaaaaaa aaaaa                                        1524
```

```
<210> SEQ ID NO 46
<211> LENGTH: 610
<212> TYPE: DNA
<213> ORGANISM: Homo sapiens
<220> FEATURE:
<221> NAME/KEY: sig_peptide
<222> LOCATION: 106..201
<223> OTHER INFORMATION: Von Heijne matrix
      score 8.80000019073486
      seq VPMLLLIVGGSFG/LR
<221> NAME/KEY: polyA_signal
<222> LOCATION: 577..582
<221> NAME/KEY: polyA_site
<222> LOCATION: 598..610
<221> NAME/KEY: misc_feature
<222> LOCATION: 68..167
<223> OTHER INFORMATION: homology
      id :AA531561
      est
<221> NAME/KEY: misc_feature
<222> LOCATION: 166..262
<223> OTHER INFORMATION: homology
      id :AA531561
      est
<221> NAME/KEY: misc_feature
<222> LOCATION: 423..520
<223> OTHER INFORMATION: homology
      id :AA531561
      est
<221> NAME/KEY: misc_feature
<222> LOCATION: 518..564
<223> OTHER INFORMATION: homology
      id :AA531561
      est
<221> NAME/KEY: misc_feature
<222> LOCATION: 276..313
<223> OTHER INFORMATION: homology
      id :AA531561
      est
<221> NAME/KEY: misc_feature
<222> LOCATION: 41..70
<223> OTHER INFORMATION: homology
      id :AA531561
      est
<221> NAME/KEY: misc_feature
<222> LOCATION: 41..262
<223> OTHER INFORMATION: homology
      id :AA535454
      est
<221> NAME/KEY: misc_feature
<222> LOCATION: 423..520
<223> OTHER INFORMATION: homology
      id :AA535454
      est
<221> NAME/KEY: misc_feature
<222> LOCATION: 518..564
<223> OTHER INFORMATION: homology
      id :AA535454
      est
<221> NAME/KEY: misc_feature
<222> LOCATION: 276..313
<223> OTHER INFORMATION: homology
      id :AA535454
      est
<221> NAME/KEY: misc_feature
<222> LOCATION: 46..262
<223> OTHER INFORMATION: homology
      id :H81225
      est
<221> NAME/KEY: misc_feature
<222> LOCATION: 2..39
<223> OTHER INFORMATION: homology
      id :H81225
      est
<221> NAME/KEY: misc_feature
<222> LOCATION: 455..493
<223> OTHER INFORMATION: homology
      id :H81225
``` est
<221> NAME/KEY: misc_feature
<222> LOCATION: 276..313
<223> OTHER INFORMATION: homology
      id :H81225
      est
<221> NAME/KEY: misc_feature
<222> LOCATION: 423..458
<223> OTHER INFORMATION: homology
      id :H81225
      est
<221> NAME/KEY: misc_feature
<222> LOCATION: 53..262
<223> OTHER INFORMATION: homology
      id :AA044291
      est
<221> NAME/KEY: misc_feature
<222> LOCATION: 423..520
<223> OTHER INFORMATION: homology
      id :AA044291
      est
<221> NAME/KEY: misc_feature
<222> LOCATION: 518..564
<223> OTHER INFORMATION: homology
      id :AA044291
      est
<221> NAME/KEY: misc_feature
<222> LOCATION: 276..313
<223> OTHER INFORMATION: homology
      id :AA044291
      est
<221> NAME/KEY: misc_feature
<222> LOCATION: 125..262
<223> OTHER INFORMATION: homology
      id :W47031
      est

<400> SEQUENCE: 46
aaagtgagtt aaggacgtac tcgtcttggt gagagcgtga stgctgagat ttgggagtct      60
gcgctaggcc cgcttggagt tctgagccga tggaagagtt cactc atg ttt gca ccc    117
                                                 Met Phe Ala Pro
                                                     -30 gcg gtg atg cgt gct ttt cgc aag aac aag act ctc ggc tat gga gtc      165
Ala Val Met Arg Ala Phe Arg Lys Asn Lys Thr Leu Gly Tyr Gly Val
        -25                 -20                 -15 ccc atg ttg ttg ctg att gtt gga ggt tct ttt ggt ctt cgt gag ttt      213
Pro Met Leu Leu Leu Ile Val Gly Gly Ser Phe Gly Leu Arg Glu Phe
    -10                  -5                   1 tct caa atc cga tat gat gct gtg aag agt aaa atg gat cct gag ctt      261
Ser Gln Ile Arg Tyr Asp Ala Val Lys Ser Lys Met Asp Pro Glu Leu
5                10                  15                  20 gaa aaa aaa ccg aaa gag aat aaa ata tct tta gag tcg gaa tat gag      309
Glu Lys Lys Pro Lys Glu Asn Lys Ile Ser Leu Glu Ser Glu Tyr Glu
                25                  30                  35 gga agt atc tgt tgaagggcta ctatctttcc ttggcccttc tcccttgttg          361
Gly Ser Ile Cys
            40 ggactcaatc tccagactat ctccccagag aatcttgtca aggcttggct ttaagctttg    421 ttgggaaaat caaagactcc aagtttgatg actggaagaa tattcgagga cccaggcctt    481 gggaagatcc tgacctcctc caaggaagaa atccaggaaa gccttaagac taagacaact    541 tgactctgct gattcttttt tccttttttt ttttaaataa aatactatt aactggaaaa     601 aaaaaaaaa                                                            610

<210> SEQ ID NO 47
<211> LENGTH: 1370
<212> TYPE: DNA

```
<213> ORGANISM: Homo sapiens
<220> FEATURE:
<221> NAME/KEY: sig_peptide
<222> LOCATION: 359..466
<223> OTHER INFORMATION: Von Heijne matrix
      score 7.80000019073486
      seq LTFLFLHLPPSTS/LF
<221> NAME/KEY: polyA_signal
<222> LOCATION: 1334..1339
<221> NAME/KEY: polyA_site
<222> LOCATION: 1357..1370
<221> NAME/KEY: misc_feature
<222> LOCATION: 113..420
<223> OTHER INFORMATION: homology
      id :R79290
      est
<221> NAME/KEY: misc_feature
<222> LOCATION: 406..482
<223> OTHER INFORMATION: homology
      id :R79290
      est
<221> NAME/KEY: misc_feature
<222> LOCATION: 199..420
<223> OTHER INFORMATION: homology
      id :R81173
      est
<221> NAME/KEY: misc_feature
<222> LOCATION: 406..514
<223> OTHER INFORMATION: homology
      id :R81173
      est
<221> NAME/KEY: misc_feature
<222> LOCATION: 2..269
<223> OTHER INFORMATION: homology
      id :R81277
      est
<221> NAME/KEY: misc_feature
<222> LOCATION: 406..646
<223> OTHER INFORMATION: homology
      id :R74123
      est
<221> NAME/KEY: misc_feature
<222> LOCATION: 647..682
<223> OTHER INFORMATION: homology
      id :R74123
      est
<221> NAME/KEY: misc_feature
<222> LOCATION: 439..646
<223> OTHER INFORMATION: homology
      id :AA450228
      est
<221> NAME/KEY: misc_feature
<222> LOCATION: 647..739
<223> OTHER INFORMATION: homology
      id :AA450228
      est
<221> NAME/KEY: misc_feature
<222> LOCATION: 406..646
<223> OTHER INFORMATION: homology
      id :R02473
      est
<221> NAME/KEY: misc_feature
<222> LOCATION: 406..604
<223> OTHER INFORMATION: homology
      id :T71107
      est
<221> NAME/KEY: misc_feature
<222> LOCATION: 71..282
<223> OTHER INFORMATION: homology
      id :C06030
      est
<221> NAME/KEY: misc_feature
<222> LOCATION: 319..365
<223> OTHER INFORMATION: homology
      id :C06030
      est
<221> NAME/KEY: misc_feature
<222> LOCATION: 2..57
<223> OTHER INFORMATION: homology
```

-continued

```
      id :C06030
      est
<221> NAME/KEY: misc_feature
<222> LOCATION: 1173..1277
<223> OTHER INFORMATION: homology
      id :N54909
      est
<221> NAME/KEY: misc_feature
<222> LOCATION: 1080..1177
<223> OTHER INFORMATION: homology
      id :N54909
      est
<221> NAME/KEY: misc_feature
<222> LOCATION: 1273..1356
<223> OTHER INFORMATION: homology
      id :N54909
      est
<221> NAME/KEY: misc_feature
<222> LOCATION: 1173..1277
<223> OTHER INFORMATION: homology
      id :AA196824
      est
<221> NAME/KEY: misc_feature
<222> LOCATION: 1080..1177
<223> OTHER INFORMATION: homology
      id :AA196824
      est
<221> NAME/KEY: misc_feature
<222> LOCATION: 1273..1356
<223> OTHER INFORMATION: homology
      id :AA196824
      est

<400> SEQUENCE: 47
acaaggcaga gcttctgaat ttcaggcctt cattccagag ccctcttgtg gccaggcctt     60
cctttgctgg aggaaggtac acagggtgaa gctgawgstg tacttggggg atctccttgg    120
cctgttccac caagtgagag aagtactta ctcttgtacc tcctgttcag ccaggtgcat     180
taacagacct ccctacagct gtaggaacta ctgtcccaga gctgaggcaa ggggatttct    240
caggtcattt ggagaacaag tgctttagta gtagtttaaa gtagtaactg ctactgtatt    300
tagtggggtg gaattcagaa gaaatttgaa gaccagatca tgggtggtct gcatgtga     358 atg aac ach ttt gag cca gac agc ctg gct gtc att gct ttc ttc ctc    406
Met Asn Thr Phe Glu Pro Asp Ser Leu Ala Val Ile Ala Phe Phe Leu
    -35             -30                 -25 ccc att tgg acc ttc tct gcc ctt aca ttt ttg ttt ctc cat cta cca    454
Pro Ile Trp Thr Phe Ser Ala Leu Thr Phe Leu Phe Leu His Leu Pro
-20             -15                 -10                  -5 cca tcc acc agt cta ttt att aac tta gca aga gga caa ata aag ggc    502
Pro Ser Thr Ser Leu Phe Ile Asn Leu Ala Arg Gly Gln Ile Lys Gly
                 1               5                  10 cct ctt ggc ttg att ttg ctt ctt tct ttc tgt gga gga tat act aag    550
Pro Leu Gly Leu Ile Leu Leu Leu Ser Phe Cys Gly Gly Tyr Thr Lys
         15                  20                  25 tgc gac ttt gcc cta tcc tat ttg gaa atc cct aac aga att gag ttt    598
Cys Asp Phe Ala Leu Ser Tyr Leu Glu Ile Pro Asn Arg Ile Glu Phe
     30                  35                  40 tct att atg gat cca aaa aga aaa aca aaa tgc taatgaagcc atcasgtcaa   651
Ser Ile Met Asp Pro Lys Arg Lys Thr Lys Cys
 45                  50                  55 gggtcacatg ccaataaaca ataaattttc cagaagaaat gaaatccaac tagacaaata   711
aagtagagct tatgaaatgg ttcagtaagg atgagcttgt tgttttttgt tttgttttgt   771
tttgtttttt taaagacgga gtctcgctct gtcactcagg ctggagtgca gtggtatgat   831
cttggctcac tgtaacctcc gcctcccggg ttcaagccat tctcctgcct cagtctcctg   891
```

-continued

```
agtagctggg attgcaggtg cgtgccacca tgcctggcta attttgtgt ttttggtaga    951
gacagggttt caccacgttg gtcgggctgg tctcgggctc ctgacctctt gatccgcctg   1011
ccttggcctc ccaaagtgat gggattacag atgtgagcca ccgtgcctag ccaaggatga   1071
gatttttaaa gtatgttcca gttctgtgtc atggttggaa gacagagtag gaaggatatg   1131
gaaaaggtca tggggaagca gaggtgattc atggctctgt ggaatttgag gtgaatggtt   1191
ccttattgtc taggccactt gtgaagaata tgagtcagtt attgccagcc ttggaattta   1251
cttctctagc ttacaatgga cctttttgaa ctgggaaaca ccttgtctgc attcacttta   1311
aaatgtcaaa actaattttt aataaaatg tttattttca catygaaaaa aaaaaaaaa    1370
```

```
<210> SEQ ID NO 48
<211> LENGTH: 791
<212> TYPE: DNA
<213> ORGANISM: Homo sapiens
<220> FEATURE:
<221> NAME/KEY: sig_peptide
<222> LOCATION: 191..286
<223> OTHER INFORMATION: Von Heijne matrix
      score 8.80000019073486
      seq VPMLLLIVGGSFG/LR
<221> NAME/KEY: polyA_signal
<222> LOCATION: 755..760
<221> NAME/KEY: polyA_site
<222> LOCATION: 780..791
<221> NAME/KEY: misc_feature
<222> LOCATION: 361..531
<223> OTHER INFORMATION: homology
      id :W73841
      est
<221> NAME/KEY: misc_feature
<222> LOCATION: 210..347
<223> OTHER INFORMATION: homology
      id :W73841
      est
<221> NAME/KEY: misc_feature
<222> LOCATION: 548..637
<223> OTHER INFORMATION: homology
      id :W73841
      est
<221> NAME/KEY: misc_feature
<222> LOCATION: 181..210
<223> OTHER INFORMATION: homology
      id :W73841
      est
<221> NAME/KEY: misc_feature
<222> LOCATION: 361..530
<223> OTHER INFORMATION: homology
      id :HSU74317
      est
<221> NAME/KEY: misc_feature
<222> LOCATION: 238..347
<223> OTHER INFORMATION: homology
      id :HSU74317
      est
<221> NAME/KEY: misc_feature
<222> LOCATION: 568..637
<223> OTHER INFORMATION: homology
      id :HSU74317
      est
<221> NAME/KEY: misc_feature
<222> LOCATION: 698..733
<223> OTHER INFORMATION: homology
      id :HSU74317
      est
<221> NAME/KEY: misc_feature
<222> LOCATION: 361..531
<223> OTHER INFORMATION: homology
      id :W47031
      est
<221> NAME/KEY: misc_feature
<222> LOCATION: 210..347
<223> OTHER INFORMATION: homology
```

-continued

```
      id :W47031
      est
<221> NAME/KEY: misc_feature
<222> LOCATION: 148..210
<223> OTHER INFORMATION: homology
      id :W47031
      est
<221> NAME/KEY: misc_feature
<222> LOCATION: 548..600
<223> OTHER INFORMATION: homology
      id :W47031
      est
<221> NAME/KEY: misc_feature
<222> LOCATION: 129..347
<223> OTHER INFORMATION: homology
      id :AA044118
      est
<221> NAME/KEY: misc_feature
<222> LOCATION: 437..531
<223> OTHER INFORMATION: homology
      id :AA044118
      est
<221> NAME/KEY: misc_feature
<222> LOCATION: 361..454
<223> OTHER INFORMATION: homology
      id :AA044118
      est
<221> NAME/KEY: misc_feature
<222> LOCATION: 176..347
<223> OTHER INFORMATION: homology
      id :AA293342
      est
<221> NAME/KEY: misc_feature
<222> LOCATION: 361..531
<223> OTHER INFORMATION: homology
      id :AA293342
      est
<221> NAME/KEY: misc_feature
<222> LOCATION: 548..605
<223> OTHER INFORMATION: homology
      id :AA293342
      est
<221> NAME/KEY: misc_feature
<222> LOCATION: 361..531
<223> OTHER INFORMATION: homology
      id :AA531561
      est
<221> NAME/KEY: misc_feature
<222> LOCATION: 153..252
<223> OTHER INFORMATION: homology
      id :AA531561
      est
<221> NAME/KEY: misc_feature
<222> LOCATION: 750
<223> OTHER INFORMATION: n=a, g, c or t

<400> SEQUENCE: 48
aacaagtatg ttacgatggc tcgattgctt ttgcctagcg gaaaccattc actaaggacc      60
gagcaccaaa taaccaagga aaaggaagtg agttaaggac gtactcgtct tggtgagagc     120
gtgagctgct gagatttggg agtctgcgct aggcccgctt ggagttctga gccgatggaa     180
gagttcactc atg ttt gca ccc gcg gtg atg cgt gct ttt cgc aag aac        229
            Met Phe Ala Pro Ala Val Met Arg Ala Phe Arg Lys Asn
                 -30             -25              -20 aag act ctc ggc tat gga gtc ccc atg ttg ttg ctg att gtt gga ggt        277
Lys Thr Leu Gly Tyr Gly Val Pro Met Leu Leu Leu Ile Val Gly Gly
            -15             -10              -5 tct ttt ggt ctt cgt gag ttt tct caa atc cga tat gat gct gtg aag        325
Ser Phe Gly Leu Arg Glu Phe Ser Gln Ile Arg Tyr Asp Ala Val Lys
 1               5              10 ggt aaa atg gat cct gag ctt gaa aaa aaa ctg aaa gag aat aaa ata        373
Gly Lys Met Asp Pro Glu Leu Glu Lys Lys Leu Lys Glu Asn Lys Ile
    15                  20              25
```

```
tct tta gag tcg gaa tat gag aaa atc aaa gac tcc aag ttt gat gac    421
Ser Leu Glu Ser Glu Tyr Glu Lys Ile Lys Asp Ser Lys Phe Asp Asp
 30              35                  40                  45 tgg aag aat att cga gga ccc agg cct tgg gaa gat cct gac ctc ctc    469
Trp Lys Asn Ile Arg Gly Pro Arg Pro Trp Glu Asp Pro Asp Leu Leu
             50                  55                  60 caa gga aga aat cca gaa agc ctt aag act aag aca act tgactctgct     518
Gln Gly Arg Asn Pro Glu Ser Leu Lys Thr Lys Thr Thr
                 65                  70 gattctcttt ccttttttt ttttaaataa aaatactatt aactggactt cctaatatat   578
acttctatca agtggaaagg aaattccagg cccatggaaa cttggatatg ggtaatttgg  638
atggacaaaa ktaatctktc actaaaggtc atgtaccagg tttttatact tcccagctaa  698
ttccatctgt ggatgaaagt tgcaatgttg gcccccgtat kattttacac cntcgaaata  758
aaaaatgtga ataactgctc caaaaaaaaa aaa                                791

<210> SEQ ID NO 49
<211> LENGTH: 1433
<212> TYPE: DNA
<213> ORGANISM: Homo sapiens
<220> FEATURE:
<221> NAME/KEY: sig_peptide
<222> LOCATION: 346..408
<223> OTHER INFORMATION: Von Heijne matrix
      score 5.5
      seq SFLPSALVIWTSA/AF
<221> NAME/KEY: polyA_signal
<222> LOCATION: 1400..1405
<221> NAME/KEY: polyA_site
<222> LOCATION: 1420..1433
<221> NAME/KEY: misc_feature
<222> LOCATION: 268..634
<223> OTHER INFORMATION: homology
      id :W02860
      est
<221> NAME/KEY: misc_feature
<222> LOCATION: 118..564
<223> OTHER INFORMATION: homology
      id :N27248
      est
<221> NAME/KEY: misc_feature
<222> LOCATION: 268..697
<223> OTHER INFORMATION: homology
      id :N44490
      est
<221> NAME/KEY: misc_feature
<222> LOCATION: 582..687
<223> OTHER INFORMATION: homology
      id :AA274731
      est
<221> NAME/KEY: misc_feature
<222> LOCATION: 65..369
<223> OTHER INFORMATION: homology
      id :H94779
      est
<221> NAME/KEY: misc_feature
<222> LOCATION: 471..519
<223> OTHER INFORMATION: homology
      id :H94779
      est
<221> NAME/KEY: misc_feature
<222> LOCATION: 61..399
<223> OTHER INFORMATION: homology
      id :H09880
      est
<221> NAME/KEY: misc_feature
<222> LOCATION: 408..452
<223> OTHER INFORMATION: homology
      id :H09880
      est
<221> NAME/KEY: misc_feature
```

-continued

```
<222> LOCATION: 484..699
<223> OTHER INFORMATION: homology
      id :H04537
      est
<221> NAME/KEY: misc_feature
<222> LOCATION: 685..772
<223> OTHER INFORMATION: homology
      id :H04537
      est
<221> NAME/KEY: misc_feature
<222> LOCATION: 454..486
<223> OTHER INFORMATION: homology
      id :H04537
      est
<221> NAME/KEY: misc_feature
<222> LOCATION: 410..439
<223> OTHER INFORMATION: homology
      id :H04537
      est
<221> NAME/KEY: misc_feature
<222> LOCATION: 572..687
<223> OTHER INFORMATION: homology
      id :AA466632
      est
<221> NAME/KEY: misc_feature
<222> LOCATION: 260..444
<223> OTHER INFORMATION: homology
      id :AA459511
      est
<221> NAME/KEY: misc_feature
<222> LOCATION: 449..567
<223> OTHER INFORMATION: homology
      id :AA459511
      est
<221> NAME/KEY: misc_feature
<222> LOCATION: 117..184
<223> OTHER INFORMATION: homology
      id :AA459511
      est
<221> NAME/KEY: misc_feature
<222> LOCATION: 260..464
<223> OTHER INFORMATION: homology
      id :H57434
      est
<221> NAME/KEY: misc_feature
<222> LOCATION: 118..184
<223> OTHER INFORMATION: homology
      id :H57434
      est
<221> NAME/KEY: misc_feature
<222> LOCATION: 56..113
<223> OTHER INFORMATION: homology
      id :H57434
      est
<221> NAME/KEY: misc_feature
<222> LOCATION: 454..485
<223> OTHER INFORMATION: homology
      id :H57434
      est
<221> NAME/KEY: misc_feature
<222> LOCATION: 115,1177,1181,1200,1210,1245,1254,1263
<223> OTHER INFORMATION: n=a, g, c or t

<400> SEQUENCE: 49
actcctttta gcatagggc ttcggcgcca gcggccagcg ctagtcggtc tggtaagtgc      60
ctgatgccga gttccgtctc tcgcgtcttt tcctggtccc aggcaaagcg gasgnagatc    120
ctcaaacggc ctagtgcttc gcgcttccgg agaaaatcag cggtctaatt aattcctctg    180
gtttgttgaa gcagttacca agaatcttca acccttccc acaaaagcta attgagtaca     240
cgttcctgtt gagtacacgt tcctgttgat ttacaaaagg tgcaggtatg agcaggtctg    300
aagactaaca ttttgtgaag ttgtaaaaca gaaaacctgt tagaa atg tgg tgg ttt    357
                                                  Met Trp Trp Phe
                                                  -20
```

```
cag caa ggc ctc agt ttc ctt cct tca gcc ctt gta att tgg aca tct      405
Gln Gln Gly Leu Ser Phe Leu Pro Ser Ala Leu Val Ile Trp Thr Ser
        -15                 -10                  -5 gct gct ttc ata ttt tca tac att act gca gta aca ctc cac cat ata      453
Ala Ala Phe Ile Phe Ser Tyr Ile Thr Ala Val Thr Leu His His Ile
 1               5                  10                  15 gac ccg gct tta cct tat atc agt gac act ggt aca gta gct cca gaa      501
Asp Pro Ala Leu Pro Tyr Ile Ser Asp Thr Gly Thr Val Ala Pro Glu
                 20                  25                  30 aaa tgc tta ttt ggg gca atg cta aat att gcg gca gtt tta tgc att      549
Lys Cys Leu Phe Gly Ala Met Leu Asn Ile Ala Ala Val Leu Cys Ile
             35                  40                  45 gct acc att tat gtt cgt tat aag caa gtt cat gct ctg agt cct gaa      597
Ala Thr Ile Tyr Val Arg Tyr Lys Gln Val His Ala Leu Ser Pro Glu
         50                  55                  60 gag aac gtt atc atc aaa tta aac aag gct ggc ctt gta ctt gga ata      645
Glu Asn Val Ile Ile Lys Leu Asn Lys Ala Gly Leu Val Leu Gly Ile
 65                  70                  75 ctg agt tgt tta gga ctt tct att gtg gca aac ttc cag gaa aac aac      693
Leu Ser Cys Leu Gly Leu Ser Ile Val Ala Asn Phe Gln Glu Asn Asn
 80                  85                  90                  95 cct ttt tgc tgc aca tgt aag tgg agc tgt gct tac ctt tgg tat ggg      741
Pro Phe Cys Cys Thr Cys Lys Trp Ser Cys Ala Tyr Leu Trp Tyr Gly
                 100                 105                 110 ctc att ata tat gtt tgt tca gac cat cct ttc cta cca aaa tgc agc      789
Leu Ile Ile Tyr Val Cys Ser Asp His Pro Phe Leu Pro Lys Cys Ser
             115                 120                 125 cca aaa tcc aat ggc aaa aca agt ctt ctg gat cag act gtt gtt ggt      837
Pro Lys Ser Asn Gly Lys Thr Ser Leu Leu Asp Gln Thr Val Val Gly
         130                 135                 140 tat ctg gtg tgg agt aag tgc act tagcatgctg acttgctcat cagttttgca    891
Tyr Leu Val Trp Ser Lys Cys Thr
 145                 150 cagtggcaat tttgggactg atttagaaca gaaactccat tggaacccccg aggacaaagg   951 ttatgcgctt cacatgatca ctactgcagc agaatggtct atgtcatttt ccttctttgg  1011
ttttttcctg acttacattc gtgattttca gaaaatttcc ttacgggtgg aagccaactt  1071
acatggatta accctctatg acactgcacc ttgccctatt aacaatgaac gaacacggct  1131
actttccags aagatattag atgaaaggat aaaatatttc tgtaantgan ttastgastt  1191
ctcagggant tggggaaang gttcacagaa gttgcttavt tcttcatcrt gaanattttc  1251
aanccactta antcaaggct gacagstaac acgtgatgaa tgctgataat caggaaacat  1311
gaaagaagcc atttgcatag attattytaa aggatatcat caagaagamt attaaaaaca  1371
cctatgccta tactttttta tytcagaaaa taaagtcaaa agactatgaa aaaaaaaaaa  1431
aa                                                                 1433

<210> SEQ ID NO 50
<211> LENGTH: 1158
<212> TYPE: DNA
<213> ORGANISM: Homo sapiens
<220> FEATURE:
<221> NAME/KEY: sig_peptide
<222> LOCATION: 214..339
<223> OTHER INFORMATION: Von Heijne matrix
      score 6.09999990463257
      seq AILLLQSQCAYWA/LP
<221> NAME/KEY: polyA_signal
<222> LOCATION: 1133..1138
<221> NAME/KEY: polyA_site
<222> LOCATION: 1146..1158
```

```
<221> NAME/KEY: misc_feature
<222> LOCATION: 840..968
<223> OTHER INFORMATION: homology
      id :H64717
      est
<221> NAME/KEY: misc_feature
<222> LOCATION: 858..968
<223> OTHER INFORMATION: homology
      id :H65208
      est
<221> NAME/KEY: misc_feature
<222> LOCATION: 652
<223> OTHER INFORMATION: n=a, g, c or t

<400> SEQUENCE: 50
aarttgagct tggggactgc agctgtgggg agatttcagt gcattgcctc ccctgggtgc     60
tcttcatctt ggatttgaaa gttgagagca gcatgttttg cccactgaaa ctcatcctgs   120
tgrsagtgta mtggattatt ccttgggcct gaatgacttg aatgtttccc cgcctgagct   180
aacagtccat gtgggtgatt cagctctgat ggg atg tgt ttt cca gag cac aga   234
                                  Met Cys Phe Pro Glu His Arg
                                                          -40 aga caa atg tat att caa gat aga ctg gac tct gtc acc agg aga gca   282
Arg Gln Met Tyr Ile Gln Asp Arg Leu Asp Ser Val Thr Arg Arg Ala
-35             -30                 -25                 -20 cgc caa gga cga ata tgt gct ata cta tta ctc caa tct cag tgt gcc   330
Arg Gln Gly Arg Ile Cys Ala Ile Leu Leu Leu Gln Ser Gln Cys Ala
        -15                 -10                  -5 tat tgg gcg ctt cca gaa ccg cgt aca ctt gat ggg gga cat ctt atg   378
Tyr Trp Ala Leu Pro Glu Pro Arg Thr Leu Asp Gly Gly His Leu Met
          1               5                   10 caa tgatggctct ctcctgctcc aagatgtgca agaggctgac cagggaacct          431
Gln atatctgtga atccgcctc aaggggaga gccaggtgtt caagaaggcg gtggtactgc     491
atgtgcttcc agaggagccc aaaggtacgc aaatgcttac ttaaagaggg gccaaggggc   551
aagagctttc atgtgcaaga ggcaaggaaa ctgattatct tgagtaaatg ccagcctttg   611
ggctaagtac ttaccacaga gtgaatcttc aaagaaatga ntcattaaat tatttcagrt   671
cagaataaaa atakgagtta ttttagttaa kaataaaata ttgataatta ttgtattatt   731
actttaaaca cacttccccc tcacaaaagc cctgtgaagg atgttttgtt cacatataat   791
gtccaaatat gttttggaca catatttatt aaatggaata aatagtamtt gaaccctggc   851
accthtgaca acaaagtcya tgttyttttt actatgccct aatacctttts atcagttatc   911 cacattgatg ctacatytgt attttatagg taccctatgt taggtgtttt ggggatatga   971
aaagaaataa gcagkycagg ctcagtggct catgcctgta atcctagcat tttgggaggc   1031
tgaggcagca gaamtgcctg agccccaggg ttcaagactg cagtgagcta tgawggcacc   1091
actgcattyt agcctgggwg acagagcaag actytgttta aaataaaaaa agagaaaaaa   1151
aaaaaaa                                                            1158

<210> SEQ ID NO 51
<211> LENGTH: 850
<212> TYPE: DNA
<213> ORGANISM: Homo sapiens
<220> FEATURE:
<221> NAME/KEY: sig_peptide
<222> LOCATION: 372..437
<223> OTHER INFORMATION: Von Heijne matrix
      score 6.09999990463257
      seq LFLTCLFWPLAAL/NV
<221> NAME/KEY: polyA_signal
```

```
<222> LOCATION: 812..817
<221> NAME/KEY: polyA_site
<222> LOCATION: 838..850
<221> NAME/KEY: misc_feature
<222> LOCATION: 128..424
<223> OTHER INFORMATION: homology
      id :N78012
      est
<221> NAME/KEY: misc_feature
<222> LOCATION: 61..128
<223> OTHER INFORMATION: homology
      id :N78012
      est
<221> NAME/KEY: misc_feature
<222> LOCATION: 483..554
<223> OTHER INFORMATION: homology
      id :N78012
      est
<221> NAME/KEY: misc_feature
<222> LOCATION: 417..464
<223> OTHER INFORMATION: homology
      id :N78012
      est
<221> NAME/KEY: misc_feature
<222> LOCATION: 460..500
<223> OTHER INFORMATION: homology
      id :N78012
      est
<221> NAME/KEY: misc_feature
<222> LOCATION: 577..612
<223> OTHER INFORMATION: homology
      id :N78012
      est
<221> NAME/KEY: misc_feature
<222> LOCATION: 612..649
<223> OTHER INFORMATION: homology
      id :N78012
      est
<221> NAME/KEY: misc_feature
<222> LOCATION: 546..577
<223> OTHER INFORMATION: homology
      id :N78012
      est
<221> NAME/KEY: misc_feature
<222> LOCATION: 29..63
<223> OTHER INFORMATION: homology
      id :N78012
      est
<221> NAME/KEY: misc_feature
<222> LOCATION: 128..294
<223> OTHER INFORMATION: homology
      id :W37233
      est
<221> NAME/KEY: misc_feature
<222> LOCATION: 370..509
<223> OTHER INFORMATION: homology
      id :W37233
      est
<221> NAME/KEY: misc_feature
<222> LOCATION: 505..591
<223> OTHER INFORMATION: homology
      id :W37233
      est
<221> NAME/KEY: misc_feature
<222> LOCATION: 293..330
<223> OTHER INFORMATION: homology
      id :W37233
      est
<221> NAME/KEY: misc_feature
<222> LOCATION: 22..57
<223> OTHER INFORMATION: homology
      id :W37233
      est
<221> NAME/KEY: misc_feature
<222> LOCATION: 95..128
<223> OTHER INFORMATION: homology
      id :W37233
      est
<221> NAME/KEY: misc_feature
```

```
<222> LOCATION: 128..326
<223> OTHER INFORMATION: homology
      id :AA186399
      est
<221> NAME/KEY: misc_feature
<222> LOCATION: 418..605
<223> OTHER INFORMATION: homology
      id :AA186399
      est
<221> NAME/KEY: misc_feature
<222> LOCATION: 326..423
<223> OTHER INFORMATION: homology
      id :AA186399
      est
<221> NAME/KEY: misc_feature
<222> LOCATION: 39..128
<223> OTHER INFORMATION: homology
      id :AA186399
      est
<221> NAME/KEY: misc_feature
<222> LOCATION: 206..640
<223> OTHER INFORMATION: homology
      id :W52489
      est

<400> SEQUENCE: 51
agacacttcc tggtgggatc cgagtgaggc gacggggtag gggttggcgc tcaggcggcg      60
accatggcgt atcacggcct cactgtgcct ctcattgtga tgagcgtgtt ctggggcttc     120
gtcggctttc ttggtgcctt ggttcatccc taagggtcct aaccggggag ttatcattac     180
catgttggtg acctgttcag tttgctgcta tctcttttgg ctgattgcaa ttctggccca     240
actcaaccct ctctttggac cgcaattgaa aaatgaaacc atctggtatc tgaagtatca     300
ttggccttga ggaagaagac atgctctaca gtgctcagtc tttgaggtca cgagaagaga     360
atgccttcta g atg caa aat cac ctc caa acc aga cca ctt ttc ttg act     410
             Met Gln Asn His Leu Gln Thr Arg Pro Leu Phe Leu Thr
                 -20             -15                 -10 tgc ctg ttt tgg cca tta gct gcc tta aac gtt aac agc aca ttt gaa     458
Cys Leu Phe Trp Pro Leu Ala Ala Leu Asn Val Asn Ser Thr Phe Glu
         -5                  1                5 tgc ctt att cta caa tgc agc gtg ttt tcc ttt gcc ttt ttt gca ctt     506
Cys Leu Ile Leu Gln Cys Ser Val Phe Ser Phe Ala Phe Phe Ala Leu
    10                  15                  20 tgg tgaattacgt gcctccataa cctgaactgt gccgactcca caaaacgatt         559
Trp atgtactctt ctgagataga agatgctgtt cttctgagag atacgttact ctctccttgg     619
aatctgtgga tttgaaaatg gctcctgcct tctcacgtgg gaatcagtga agtgtttaga     679
aactgctgca agacaaacaa gactccagtg gggtggtcag taggaaaaca cgttcagagg     739
gaagaaccat ctcaacagaa tcgcaccaaa ctatactttc aggatgaatt tcttctttct     799
gccatctttt ggaataaata ttttcctcct ttytatgtaa aaaaaaaaa a             850

<210> SEQ ID NO 52
<211> LENGTH: 1107
<212> TYPE: DNA
<213> ORGANISM: Homo sapiens
<220> FEATURE:
<221> NAME/KEY: sig_peptide
<222> LOCATION: 132..215
<223> OTHER INFORMATION: Von Heijne matrix
      score 3.59999990463257
      seq PLSDSWALLPASA/GV
<221> NAME/KEY: polyA_signal
<222> LOCATION: 1069..1074
<221> NAME/KEY: polyA_site
<222> LOCATION: 1094..1107
```

```
<221> NAME/KEY: misc_feature
<222> LOCATION: 177..392
<223> OTHER INFORMATION: homology
      id :W80978
      est
<221> NAME/KEY: misc_feature
<222> LOCATION: 425..542
<223> OTHER INFORMATION: homology
      id :W80978
      est
<221> NAME/KEY: misc_feature
<222> LOCATION: 43..114
<223> OTHER INFORMATION: homology
      id :W80978
      est
<221> NAME/KEY: misc_feature
<222> LOCATION: 387..441
<223> OTHER INFORMATION: homology
      id :W80978
      est
<221> NAME/KEY: misc_feature
<222> LOCATION: 113..165
<223> OTHER INFORMATION: homology
      id :W80978
      est
<221> NAME/KEY: misc_feature
<222> LOCATION: 551..590
<223> OTHER INFORMATION: homology
      id :W80978
      est
<221> NAME/KEY: misc_feature
<222> LOCATION: 166..314
<223> OTHER INFORMATION: homology
      id :AA043154
      est
<221> NAME/KEY: misc_feature
<222> LOCATION: 27..181
<223> OTHER INFORMATION: homology
      id :AA043154
      est
<221> NAME/KEY: misc_feature
<222> LOCATION: 425..564
<223> OTHER INFORMATION: homology
      id :AA043154
      est
<221> NAME/KEY: misc_feature
<222> LOCATION: 387..441
<223> OTHER INFORMATION: homology
      id :AA043154
      est
<221> NAME/KEY: misc_feature
<222> LOCATION: 309..352
<223> OTHER INFORMATION: homology
      id :AA043154
      est
<221> NAME/KEY: misc_feature
<222> LOCATION: 549..580
<223> OTHER INFORMATION: homology
      id :AA043154
      est
<221> NAME/KEY: misc_feature
<222> LOCATION: 601..1071
<223> OTHER INFORMATION: homology
      id :AA126732
      est
<221> NAME/KEY: misc_feature
<222> LOCATION: 576..605
<223> OTHER INFORMATION: homology
      id :AA126732
      est
<221> NAME/KEY: misc_feature
<222> LOCATION: 387..477
<223> OTHER INFORMATION: homology
      id :AA161280
      est
<221> NAME/KEY: misc_feature
<222> LOCATION: 292..362
<223> OTHER INFORMATION: homology
      id :AA161280
```

```
        est
<221> NAME/KEY: misc_feature
<222> LOCATION: 46..113
<223> OTHER INFORMATION: homology
      id :AA161280
      est
<221> NAME/KEY: misc_feature
<222> LOCATION: 217..277
<223> OTHER INFORMATION: homology
      id :AA161280
      est
<221> NAME/KEY: misc_feature
<222> LOCATION: 113..160
<223> OTHER INFORMATION: homology
      id :AA161280
      est
<221> NAME/KEY: misc_feature
<222> LOCATION: 173..217
<223> OTHER INFORMATION: homology
      id :AA161280
      est

<400> SEQUENCE: 52
aacaacttcc ggccccactg agcggtgtcc tgagccgatt acagctaggt agtggagcgc      60
cgctgcttac ctgggtgcag gagacagccg gagtcgctgg gggagctccg cgccgccgga     120
cgcccgtgac c atg tgg agg ctg ctg gct cgc gct agt gcg ccg ctc ctg      170
             Met Trp Arg Leu Leu Ala Arg Ala Ser Ala Pro Leu Leu
                 -25                 -20 cgg gtg ccc ttg tca gat tcc tgg gca ctc ctc ccc gcc agt gct ggc       218
Arg Val Pro Leu Ser Asp Ser Trp Ala Leu Leu Pro Ala Ser Ala Gly
-15             -10              -5                   1 gta aag aca ctg ctc cca gta cca agt ttt gaa gat gtt tcc att cct       266
Val Lys Thr Leu Leu Pro Val Pro Ser Phe Glu Asp Val Ser Ile Pro
            5                  10                  15 gaa aaa ccc aag ctt aga ttt att gaa agg gca cca ctt gtg cca aaa       314
Glu Lys Pro Lys Leu Arg Phe Ile Glu Arg Ala Pro Leu Val Pro Lys
         20                 25                  30 gta aga aga gaa cct aaa aat tta agt gac ata cgg gga cct tcc act       362
Val Arg Arg Glu Pro Lys Asn Leu Ser Asp Ile Arg Gly Pro Ser Thr
     35                 40                  45 gaa gct acg gag kkk aca gaa ggc aat ttt gca atc ttg gca ttg ggt       410
Glu Ala Thr Glu Xaa Thr Glu Gly Asn Phe Ala Ile Leu Ala Leu Gly
 50                 55                  60                  65 ggt ggc tac ctg cat tgg ggc cac ttt gaa atg atg cgc ctg aca atc       458
Gly Gly Tyr Leu His Trp Gly His Phe Glu Met Met Arg Leu Thr Ile
                 70                  75                  80 aac cgc tct atg gac ccc aag aac atg ttt gcc ata tgg cga gta cca       506
Asn Arg Ser Met Asp Pro Lys Asn Met Phe Ala Ile Trp Arg Val Pro
             85                  90                  95 gcc cct ttc aag ccc atc act cgc aaa agt gtt ggg cat cgc atg ggg       554
Ala Pro Phe Lys Pro Ile Thr Arg Lys Ser Val Gly His Arg Met Gly
         100                 105                 110 gga ggc aaa ggt gct att gac cac tac gtg aca cct gtg aag gct ggc       602
Gly Gly Lys Gly Ala Ile Asp His Tyr Val Thr Pro Val Lys Ala Gly
     115                 120                 125 cgc mww gww gta gag atg ggt ggg cgt tgt gma ttt gaa gaa gtg caa       650
Arg Xaa Xaa Val Glu Met Gly Gly Arg Cys Xaa Phe Glu Glu Val Gln
130                 135                 140                 145 ggt ttc ctt gac cag gtt gcc cac aag ttg ccc tty gca gca aag gct       698
Gly Phe Leu Asp Gln Val Ala His Lys Leu Pro Phe Ala Ala Lys Ala
                 150                 155                 160 gtg agc cgc ggg act yta gag aag atg cga aaa gat caa gag gaa aga       746
Val Ser Arg Gly Thr Leu Glu Lys Met Arg Lys Asp Gln Glu Glu Arg
             165                 170                 175
```

```
gaa mgt aac aac cag aac ccc tgg aca ttt gag cga ata gcc act gcc      794
Glu Xaa Asn Asn Gln Asn Pro Trp Thr Phe Glu Arg Ile Ala Thr Ala
        180                 185                 190 mac atg ctg ggc ata cgg aaa gta ctg agc cca tat gac ttg acc cac      842
Xaa Met Leu Gly Ile Arg Lys Val Leu Ser Pro Tyr Asp Leu Thr His
195                 200                 205 aag ggg aaa tam tgg ggc aag tty tac atg ccc mam cgt gtg              884
Lys Gly Lys Xaa Trp Gly Lys Phe Tyr Met Pro Xaa Arg Val
210                 215                 220 tagtgagtgt aggagataac tgtatatagg stactgaaag aaggattytg catttytatt    944
cccctcagcc tacccactga agtytttggg tagctyttaa gccataamta aggagcagca   1004
tttgagtaga tttytgaaaa acgatgttat ttgttgattt aaaaagaaaa cwgtatttt    1064 attaaataaa atttaaacat cacttcagga aaaaaaaaaa aaa                     1107

<210> SEQ ID NO 53
<211> LENGTH: 500
<212> TYPE: DNA
<213> ORGANISM: Homo sapiens
<220> FEATURE:
<221> NAME/KEY: sig_peptide
<222> LOCATION: 199..288
<223> OTHER INFORMATION: Von Heijne matrix
      score 5.59999990463257
      seq IVSVLALIPETTT/LT
<221> NAME/KEY: polyA_signal
<222> LOCATION: 464..469
<221> NAME/KEY: polyA_site
<222> LOCATION: 489..500
<221> NAME/KEY: misc_feature
<222> LOCATION: 197..412
<223> OTHER INFORMATION: homology
      id :AA429945
      est
<221> NAME/KEY: misc_feature
<222> LOCATION: 61..195
<223> OTHER INFORMATION: homology
      id :AA429945
      est
<221> NAME/KEY: misc_feature
<222> LOCATION: 425..488
<223> OTHER INFORMATION: homology
      id :AA429945
      est
<221> NAME/KEY: misc_feature
<222> LOCATION: 197..412
<223> OTHER INFORMATION: homology
      id :AA455042
      est
<221> NAME/KEY: misc_feature
<222> LOCATION: 61..195
<223> OTHER INFORMATION: homology
      id :AA455042
      est
<221> NAME/KEY: misc_feature
<222> LOCATION: 425..488
<223> OTHER INFORMATION: homology
      id :AA455042
      est
<221> NAME/KEY: misc_feature
<222> LOCATION: 207..412
<223> OTHER INFORMATION: homology
      id :W93646
      est
<221> NAME/KEY: misc_feature
<222> LOCATION: 58..195
<223> OTHER INFORMATION: homology
      id :W93646
      est
<221> NAME/KEY: misc_feature
<222> LOCATION: 425..488
<223> OTHER INFORMATION: homology
```

```
         id :W93646
         est
<221> NAME/KEY: misc_feature
<222> LOCATION: 197..412
<223> OTHER INFORMATION: homology
         id :AA516431
         est
<221> NAME/KEY: misc_feature
<222> LOCATION: 90..195
<223> OTHER INFORMATION: homology
         id :AA516431
         est
<221> NAME/KEY: misc_feature
<222> LOCATION: 425..488
<223> OTHER INFORMATION: homology
         id :AA516431
         est
<221> NAME/KEY: misc_feature
<222> LOCATION: 52..195
<223> OTHER INFORMATION: homology
         id :W38899
         est
<221> NAME/KEY: misc_feature
<222> LOCATION: 197..324
<223> OTHER INFORMATION: homology
         id :W38899
         est
<221> NAME/KEY: misc_feature
<222> LOCATION: 443..477
<223> OTHER INFORMATION: homology
         id :W38899
         est
<221> NAME/KEY: misc_feature
<222> LOCATION: 197..338
<223> OTHER INFORMATION: homology
         id :W52820
         est
<221> NAME/KEY: misc_feature
<222> LOCATION: 71..195
<223> OTHER INFORMATION: homology
         id :W52820
         est
<221> NAME/KEY: misc_feature
<222> LOCATION: 339..401
<223> OTHER INFORMATION: homology
         id :W52820
         est
<221> NAME/KEY: misc_feature
<222> LOCATION: 425..469
<223> OTHER INFORMATION: homology
         id :W52820
         est
<221> NAME/KEY: misc_feature
<222> LOCATION: 40..195
<223> OTHER INFORMATION: homology
         id :W19506
         est
<221> NAME/KEY: misc_feature
<222> LOCATION: 9..10,12
<223> OTHER INFORMATION: n=a, g, c or t

<400> SEQUENCE: 53
agagctgtnn cnsaagtagg ggagggcggt gctccgcmgm ggtggcggdh tgctatcgct      60
tcgcagaacc tactcaggca gccagctgag aagagttgag ggaaagtgct gctgctgggt     120
ctgcagacgc gatggataac gtgcagccga aaataaaaca tcgccccttc tgcttcagtg     180
tgaaaggcca cgtgayag atg ctg cgg ctg gat att atc aac tca ctg gta      231
                   Met Leu Arg Leu Asp Ile Ile Asn Ser Leu Val
                       -30              -25                 -20 aca aca gta ttc atg ctc atc gta tct gtg ttg gca ctg ata cca gaa      279
Thr Thr Val Phe Met Leu Ile Val Ser Val Leu Ala Leu Ile Pro Glu
            -15                 -10                  -5 acc aca aca ttg aca gtt ggt gga ggg gtg ttt gca ctt gtg aca gca      327
Thr Thr Thr Leu Thr Val Gly Gly Gly Val Phe Ala Leu Val Thr Ala
```

```
              1               5                   10
gta tgc tgt ctt gcc gac ggg gcc ctt att tac cgg aag ctt ctg ttc      375
Val Cys Cys Leu Ala Asp Gly Ala Leu Ile Tyr Arg Lys Leu Leu Phe
     15                  20                  25 aat ccc agc ggt cct tac cag aaa aag cct gtg cat gaa aaa aaa gaa      423
Asn Pro Ser Gly Pro Tyr Gln Lys Lys Pro Val His Glu Lys Lys Glu
30                  35                  40                  45 gtt ttg taattttata ttactttta gtttgatact aagtattaaa catatttctg        479
Val Leu tattcttcca aaaaaaaaa a                                               500

<210> SEQ ID NO 54
<211> LENGTH: 765
<212> TYPE: DNA
<213> ORGANISM: Homo sapiens
<220> FEATURE:
<221> NAME/KEY: sig_peptide
<222> LOCATION: 293..385
<223> OTHER INFORMATION: Von Heijne matrix
      score 4.40000009536743
      seq TCCHLGLPHPVRA/PR
<221> NAME/KEY: polyA_signal
<222> LOCATION: 733..738
<221> NAME/KEY: polyA_site
<222> LOCATION: 752..765
<221> NAME/KEY: misc_feature
<222> LOCATION: 310..576
<223> OTHER INFORMATION: homology
      id :HUM426A07B
      est
<221> NAME/KEY: misc_feature
<222> LOCATION: 119
<223> OTHER INFORMATION: n=a, g, c or t

<400> SEQUENCE: 54
aaaccttgtt gctagggacc gggcggtttg cggcaaccgt gggcactgct gaatttgaat     60 tgagggcga gggaaaagtt ttcctcaggt gtggtgggga gagggaggcg gatgccggng    120
aaaccgtagg kacgcggtca gaaaggcgac gggctgtcgg agttggaaag ggacgcctgg    180
tttcccccca agcgaaccgg gatgggaagt gacttcaatg agattgaact tcagctggat    240
tgaaagagag gctagaagtt ccgcttgcca gcagcctcct tagtagagcg ga atg agt    298
                                                          Met Ser
                                                              -30 aat acc cac acg gtg ctt gtc tca ctt ccc cat ccg cac ccg gcc ctc     346
Asn Thr His Thr Val Leu Val Ser Leu Pro His Pro His Pro Ala Leu
            -25                 -20                 -15 acc tgc tgt cac ctc ggc ctc cca cac ccg gtc cgc gct ccc cgc cct    394
Thr Cys Cys His Leu Gly Leu Pro His Pro Val Arg Ala Pro Arg Pro
            -10                  -5                   1 ctt cct cgc gta gaa ccg tgg gat cct agg tgg cag gac tca gag cta    442
Leu Pro Arg Val Glu Pro Trp Asp Pro Arg Trp Gln Asp Ser Glu Leu
    5                   10                  15 agg tat cca cag gcc atg aat tcc ttc cta aat gag cgg tca tcg ccg    490
Arg Tyr Pro Gln Ala Met Asn Ser Phe Leu Asn Glu Arg Ser Ser Pro
20                  25                  30                  35 tgc agg acc tta agg caa gaa gca tcg gct gac aga tgt gat ctc        535
Cys Arg Thr Leu Arg Gln Glu Ala Ser Ala Asp Arg Cys Asp Leu
                40                  45                  50 tgaacctgat agattgctga ttttatctta ttttatcctt gacttggtac aagttttggg    595
atttctgaaa agaccataca gataaccaca aatatcaaga aagtcgtctt cagtattaag    655
tagaatttag atttaggttt ccttcctgct tcccacctcc ttcgaataag gaaacgtctt    715
```

```
tgggaccaac tttatggaat aaataagctg agctgcaaaa waaaaaaaa                    765
```

```
<210> SEQ ID NO 55
<211> LENGTH: 584
<212> TYPE: DNA
<213> ORGANISM: Homo sapiens
<220> FEATURE:
<221> NAME/KEY: sig_peptide
<222> LOCATION: 130..189
<223> OTHER INFORMATION: Von Heijne matrix
      score 3.5
      seq KFCLICLLTFIFH/HC
<221> NAME/KEY: polyA_signal
<222> LOCATION: 546..551
<221> NAME/KEY: polyA_site
<222> LOCATION: 572..584

<400> SEQUENCE: 55
aagacgcgcc ggtttctgcg acgcagttag cgcagtctgc tttggtgaat acacgatttg       60
gtgcagccgg ggtttggtac cgagcggaga ggagatgcac acggcactcg agtgtgagga      120 aaaatagaa atg aag gta cat atg cac aca aaa ttt tgc ctc att tgt ttg      171
         Met Lys Val His Met His Thr Lys Phe Cys Leu Ile Cys Leu
          -20             -15                 -10 ctg aca ttt att ttt cat cat tgc aac cat tgc cat gaa gaa cat gac        219
Leu Thr Phe Ile Phe His His Cys Asn His Cys His Glu Glu His Asp
    -5                  1               5                   10 cat ggc cct gaa gcg ctt cac aga cag cat cgt gga atg aca gaa ttg        267
His Gly Pro Glu Ala Leu His Arg Gln His Arg Gly Met Thr Glu Leu
                15                  20                  25 gag cca agc aaa ttt tca aag caa gct gct gaa aat gaa aaa aaa tac        315
Glu Pro Ser Lys Phe Ser Lys Gln Ala Ala Glu Asn Glu Lys Lys Tyr
            30                  35                  40 tat att gaa aaa ctt ttt gag cgt tat ggt gaa aat gga aga tta tcc        363
Tyr Ile Glu Lys Leu Phe Glu Arg Tyr Gly Glu Asn Gly Arg Leu Ser
        45                  50                  55 ttt ttt ggt ttg gag aaa ctt tta aca aac ttg ggc ctt gga gag aga        411
Phe Phe Gly Leu Glu Lys Leu Leu Thr Asn Leu Gly Leu Gly Glu Arg
    60                  65                  70 aaa gta gtt gag att aat cat gag gat ctt ggc cac gat cat gtt tct        459
Lys Val Val Glu Ile Asn His Glu Asp Leu Gly His Asp His Val Ser
75                  80                  85                  90 cat tta agg tat ttt ggc agt tca aga ggg aaa gca ttt tca ctc aca        507
His Leu Arg Tyr Phe Gly Ser Ser Arg Gly Lys Ala Phe Ser Leu Thr
                95                  100                 105 taaccaccca gcattcccat aatcatttaa attcagaaaa tcaaaactgt gaccagtgta      567
wtccacaaaa aaaaaaa                                                      584
```

```
<210> SEQ ID NO 56
<211> LENGTH: 1387
<212> TYPE: DNA
<213> ORGANISM: Homo sapiens
<220> FEATURE:
<221> NAME/KEY: sig_peptide
<222> LOCATION: 191..325
<223> OTHER INFORMATION: Von Heijne matrix
      score 4.59999990463257
      seq VLVYLVTAERVWS/DD
<221> NAME/KEY: polyA_signal
<222> LOCATION: 1348..1353
<221> NAME/KEY: polyA_site
<222> LOCATION: 1374..1387
<221> NAME/KEY: misc_feature
<222> LOCATION: 1258..1372
<223> OTHER INFORMATION: homology
      id :AA417826
```

```
            est
<221> NAME/KEY: misc_feature
<222> LOCATION: 791..887
<223> OTHER INFORMATION: homology
      id :AA417826
      est
<221> NAME/KEY: misc_feature
<222> LOCATION: 94..524
<223> OTHER INFORMATION: homology
      id :AA235826
      est
<221> NAME/KEY: misc_feature
<222> LOCATION: 44..94
<223> OTHER INFORMATION: homology
      id :AA235826
      est
<221> NAME/KEY: misc_feature
<222> LOCATION: 1258..1372
<223> OTHER INFORMATION: homology
      id :AA236941
      est
<221> NAME/KEY: misc_feature
<222> LOCATION: 935..1279
<223> OTHER INFORMATION: homology
      id :AA480326
      est
<221> NAME/KEY: misc_feature
<222> LOCATION: 1258..1372
<223> OTHER INFORMATION: homology
      id :AA480326
      est
<221> NAME/KEY: misc_feature
<222> LOCATION: 724..1148
<223> OTHER INFORMATION: homology
      id :AA234245
      est
<221> NAME/KEY: misc_feature
<222> LOCATION: 944..1279
<223> OTHER INFORMATION: homology
      id :AA479344
      est
<221> NAME/KEY: misc_feature
<222> LOCATION: 1258..1372
<223> OTHER INFORMATION: homology
      id :AA479344
      est
<221> NAME/KEY: misc_feature
<222> LOCATION: 1070..1212
<223> OTHER INFORMATION: homology
      id :AA133636
      est
<221> NAME/KEY: misc_feature
<222> LOCATION: 1258..1372
<223> OTHER INFORMATION: homology
      id :AA133636
      est
<221> NAME/KEY: misc_feature
<222> LOCATION: 938..1054
<223> OTHER INFORMATION: homology
      id :AA133636
      est
<221> NAME/KEY: misc_feature
<222> LOCATION: 94..436
<223> OTHER INFORMATION: homology
      id :AA133635
      est
<221> NAME/KEY: misc_feature
<222> LOCATION: 32..94
<223> OTHER INFORMATION: homology
      id :AA133635
      est
<221> NAME/KEY: misc_feature
<222> LOCATION: 895..1273
<223> OTHER INFORMATION: homology
      id :AA479453
      est
<221> NAME/KEY: misc_feature
<222> LOCATION: 1258..1371
<223> OTHER INFORMATION: homology
```

```
        id :AA253214
        est
<221> NAME/KEY: misc_feature
<222> LOCATION: 94..268
<223> OTHER INFORMATION: homology
        id :AA482378
        est
<221> NAME/KEY: misc_feature
<222> LOCATION: 946
<223> OTHER INFORMATION: n=a, g, c or t

<400> SEQUENCE: 56
actcccaggc tgggccagca cacccggcag gctctgtcct ggaaacaggc ttcaacgggc      60
ttccccgaaa accttcccg cttctggata tgaavattca agctgcttgc tgagtcctat     120
tgccggctgc tgggagccag gagagccctg aggagtagtc actcagtagc agctgacgcg    180
tgggtccacc atg aac tgg agt atc ttt gag gga ctc ctg agt ggg gtc       229
            Met Asn Trp Ser Ile Phe Glu Gly Leu Leu Ser Gly Val
                -45             -40                 -35 aac aag tac tcc aca gcc ttt ggg cgc atc tgg ctg tct ctg gtc ttc       277
Asn Lys Tyr Ser Thr Ala Phe Gly Arg Ile Trp Leu Ser Leu Val Phe
        -30             -25                 -20 atc ttc cgc gtg ctg gtg tac ctg gtg acg gcc gag cgt gtg tgg agt       325
Ile Phe Arg Val Leu Val Tyr Leu Val Thr Ala Glu Arg Val Trp Ser
    -15             -10                 -5 gat gac cac aag gac ttc gac tgc aat act cgc cag ccc ggc tgc tcc       373
Asp Asp His Lys Asp Phe Asp Cys Asn Thr Arg Gln Pro Gly Cys Ser
1               5                   10                  15 aac gtc tgc ttt gat gag ttc ttc cct gtg tcc cat gtg cgc ctc tgg       421
Asn Val Cys Phe Asp Glu Phe Phe Pro Val Ser His Val Arg Leu Trp
                20                  25                  30 gcc ctg cag ctt atc ctg gtg aca tgc ccc tca ctg ctc gtg gtc atg       469
Ala Leu Gln Leu Ile Leu Val Thr Cys Pro Ser Leu Leu Val Val Met
            35                  40                  45 cac gtg gcc tac cgg gag gtt cag gag aag agg cac cga gaa gcc cat       517
His Val Ala Tyr Arg Glu Val Gln Glu Lys Arg His Arg Glu Ala His
        50                  55                  60 ggg gag aac agt ggg cgc ctc tac ctg aac ccc ggc aag aar cgg ggt       565
Gly Glu Asn Ser Gly Arg Leu Tyr Leu Asn Pro Gly Lys Lys Arg Gly
65              70                  75                  80 ggg ctc tgg tgg aca tat gtc tgc agc cta gtg ttc aag gcg agc gtg       613
Gly Leu Trp Trp Thr Tyr Val Cys Ser Leu Val Phe Lys Ala Ser Val
                85                  90                  95 gac atc gcc ttt ctc tat gtg ttc cac tca ttc tac ccc aaa tat atc       661
Asp Ile Ala Phe Leu Tyr Val Phe His Ser Phe Tyr Pro Lys Tyr Ile
            100                 105                 110 ctc cct cct gtg gtc aag tgc cac gca gat cca tgt ccc aat ata gtg       709
Leu Pro Pro Val Val Lys Cys His Ala Asp Pro Cys Pro Asn Ile Val
        115                 120                 125 gac tgc ttc atc tcc aag ccc tca gag aag aac att ttc acc ctc ttc       757
Asp Cys Phe Ile Ser Lys Pro Ser Glu Lys Asn Ile Phe Thr Leu Phe
    130                 135                 140 atg gtg gcc aca gct gcc atc tgc atc ctg ctc aac ctc gtg gag ctc       805
Met Val Ala Thr Ala Ala Ile Cys Ile Leu Leu Asn Leu Val Glu Leu
145             150                 155                 160 atc tac ctg gtg agc aag aga tgc cac gag tgc ctg gca gca agg aaa       853
Ile Tyr Leu Val Ser Lys Arg Cys His Glu Cys Leu Ala Ala Arg Lys
                165                 170                 175 gct caa gcc atg kgc aca ggt cat cac ccc cav gat acc acy ttt tcc       901
Ala Gln Ala Met Xaa Thr Gly His His Pro Xaa Asp Thr Thr Phe Ser
            180                 185                 190
```

```
kgc aaa caa gas gac ytc ytt tcg ggk gac ytc atc ttt ctg ggn tca      949
Xaa Lys Gln Xaa Asp Xaa Xaa Ser Gly Asp Xaa Ile Phe Leu Gly Ser
        195                 200                 205 gac agt cat cyt cct ytc tta cca gac cgc ccc cga gac cat gtg aag      997
Asp Ser His Xaa Pro Xaa Leu Pro Asp Arg Pro Arg Asp His Val Lys
        210                 215                 220 aaa acc aty ttg tgaggggctg cctggamtgg tytggcaggt tgggcctgga         1049
Lys Thr Ile Leu
225 tggggaggct ytagcatyty tcataggtgc aacctgagag tgggggagct aagccatgag   1109 gtagggcag gcaagagaga ggattcagac gytytgggag ccagttccta gtcctcaamt    1169 ccagccacct gccccagsth gacggcamtg ggccagttcc ccctytgsty tgcagstcgg   1229 tttccttty tagaatggaa atagtgaggg ccaatgccca gggttggagg gaggagggcg    1289 ttcatagaag aacacacatg cgggcacctt catygtgtgt ggcccactgt cagaacttaa   1349 taaaagtcaa mtcatttgct ggttaaaaaa aaaaaaaa                           1387
```

```
<210> SEQ ID NO 57
<211> LENGTH: 1385
<212> TYPE: DNA
<213> ORGANISM: Homo sapiens
<220> FEATURE:
<221> NAME/KEY: sig_peptide
<222> LOCATION: 141..251
<223> OTHER INFORMATION: Von Heijne matrix
      score 4
      seq PLSLDCGHSLCRA/CI
<221> NAME/KEY: polyA_signal
<222> LOCATION: 1354..1359
<221> NAME/KEY: polyA_site
<222> LOCATION: 1375..1385
<221> NAME/KEY: misc_feature
<222> LOCATION: 1183..1240
<223> OTHER INFORMATION: homology
      id :AA463623
      est
<221> NAME/KEY: misc_feature
<222> LOCATION: 176..239
<223> OTHER INFORMATION: homology
      id :AA258927
      est
<221> NAME/KEY: misc_feature
<222> LOCATION: 803..854
<223> OTHER INFORMATION: homology
      id :AA286417
      est
<221> NAME/KEY: misc_feature
<222> LOCATION: 1183..1213
<223> OTHER INFORMATION: homology
      id :AA608077
      est

<400> SEQUENCE: 57
```

```
aacacccacc ctggcttttc ttcacctctt caaccaggag ccgagatttc tgttgctctg     60
aagccatcca ggggtcttta accagaagag agaggagagc ctcaggagtt aggaccagaa   120
gaagccaggg aagcagtgca atg gct tca aaa atc ttg ctt aac gta caa gag   173
                        Met Ala Ser Lys Ile Leu Leu Asn Val Gln Glu
                                -35                 -30 gag gtg acc tgt ccc atc tgc ctg gag ctg ttg aca gaa ccc ttg agt     221
Glu Val Thr Cys Pro Ile Cys Leu Glu Leu Leu Thr Glu Pro Leu Ser
        -25                 -20                 -15 cta gac tgt ggc cac agc ctc tgc cga gcc tgc atc act gtg agc aac     269
Leu Asp Cys Gly His Ser Leu Cys Arg Ala Cys Ile Thr Val Ser Asn
-10                  -5                  1                   5 aag gag gca gtg acc agc atg gga gga aaa agc agc tgt cct gtg tgt     317
```

```
                Lys Glu Ala Val Thr Ser Met Gly Gly Lys Ser Ser Cys Pro Val Cys
                             10                  15                  20 ggt atc agt tac tca ttt gaa cat cta cag gct aat cag cat cgg gcc              365
Gly Ile Ser Tyr Ser Phe Glu His Leu Gln Ala Asn Gln His Arg Ala
             25                  30                  35 aac ata gtg gag aga ctc aag gag gtc aag ttg agc cca gac aat ggg              413
Asn Ile Val Glu Arg Leu Lys Glu Val Lys Leu Ser Pro Asp Asn Gly
         40                  45                  50 aag aag aga gat ctc tgt gat cat cat gga gag aaa ctc cta ctc ttc              461
Lys Lys Arg Asp Leu Cys Asp His His Gly Glu Lys Leu Leu Leu Phe
55                  60                  65                  70 tgt aag gag gat agg aaa gtc att tgc tgg ctt tgt gag cgg tct cag              509
Cys Lys Glu Asp Arg Lys Val Ile Cys Trp Leu Cys Glu Arg Ser Gln
             75                  80                  85 gag cac cgt ggt cac cac aca ggt cct cac gga gga agt att caa gga              557
Glu His Arg Gly His His Thr Gly Pro His Gly Gly Ser Ile Gln Gly
         90                  95                 100 atg tca gga gaa act cca ggc agt cct caa gag gct gaa gaa gga aga              605
Met Ser Gly Glu Thr Pro Gly Ser Pro Gln Glu Ala Glu Glu Gly Arg
            105                 110                 115 gga gga agc tgagaagctg aagctgaca tcagagaaga gaaaacttcc                       654
Gly Gly Ser
    120 tggaagtatc aggtacaaac tgagagacaa aggatacaaa cagaatttga tcagcttaga            714 agcatcctaa ataatgagga gcagagagag ctgcaaagat tggaagaaga agaaaagaag            774 acgctggata agtttgcaga ggctgaggat gagctagttc agcagaagca gttggtgaga            834 gagctcatct cagatgtgga gtgtcggagt cagtggtcaa caatggagct gctgcaggac            894 atgagtggaa tcatgaaatg gagtgagatc tggaggctga aaaagccaaa aatggtttcc            954 aagaaactga agactgtatt ccatgctcca gatctgagta ggatgctgcr aatgtttaga            1014 ggaactgaca gctgtccggt gctactgggt ggatgtcaca ctgaattcag tcaacctaaa            1074 tttgaatckt gtcctttcag aagatcagag acaagtgata tctgtgccaa tttggccttt           1134 tcagtgttat aattatggtg tkbttgggat cccaatattt btcctsstgg gaaacattac            1194 tgggaagtgg acgtgtccaa gaaaactgcc tggatcctgg gggtatactg tagaacatat            1254 tcccgccata tgaagtatgt tgttagaaga tgtgcaaaty gtcaaaatbt ttacaccaaa            1314 tacagacctc tatttggsta ctgggttata gggttacaga ataaatgtaa gtatggtgcc            1374 aaaaaaaaaa a                                                                 1385

<210> SEQ ID NO 58
<211> LENGTH: 1497
<212> TYPE: DNA
<213> ORGANISM: Homo sapiens
<220> FEATURE:
<221> NAME/KEY: sig_peptide
<222> LOCATION: 212..268
<223> OTHER INFORMATION: Von Heijne matrix
      score 8.60000038146973
      seq LLWLALACSPVHT/TL
<221> NAME/KEY: polyA_signal
<222> LOCATION: 1465..1470
<221> NAME/KEY: polyA_site
<222> LOCATION: 1489..1497
<221> NAME/KEY: misc_feature
<222> LOCATION: 958..1110
<223> OTHER INFORMATION: homology
      id :W72124
      est
<221> NAME/KEY: misc_feature
<222> LOCATION: 1362..1488
```

-continued

```
<223> OTHER INFORMATION: homology
      id :W72124
      est
<221> NAME/KEY: misc_feature
<222> LOCATION: 1202..1312
<223> OTHER INFORMATION: homology
      id :W72124
      est
<221> NAME/KEY: misc_feature
<222> LOCATION: 1115..1190
<223> OTHER INFORMATION: homology
      id :W72124
      est
<221> NAME/KEY: misc_feature
<222> LOCATION: 1312..1370
<223> OTHER INFORMATION: homology
      id :W72124
      est
<221> NAME/KEY: misc_feature
<222> LOCATION: 653..942
<223> OTHER INFORMATION: homology
      id :AA009415
      est
<221> NAME/KEY: misc_feature
<222> LOCATION: 454..605
<223> OTHER INFORMATION: homology
      id :AA009415
      est
<221> NAME/KEY: misc_feature
<222> LOCATION: 598..639
<223> OTHER INFORMATION: homology
      id :AA009415
      est
<221> NAME/KEY: misc_feature
<222> LOCATION: 805..1032
<223> OTHER INFORMATION: homology
      id :AA088502
      est
<221> NAME/KEY: misc_feature
<222> LOCATION: 633..807
<223> OTHER INFORMATION: homology
      id :AA088502
      est
<221> NAME/KEY: misc_feature
<222> LOCATION: 598..639
<223> OTHER INFORMATION: homology
      id :AA088502
      est
<221> NAME/KEY: misc_feature
<222> LOCATION: 564..605
<223> OTHER INFORMATION: homology
      id :AA088502
      est
<221> NAME/KEY: misc_feature
<222> LOCATION: 653..807
<223> OTHER INFORMATION: homology
      id :AA181148
      est
<221> NAME/KEY: misc_feature
<222> LOCATION: 907..1046
<223> OTHER INFORMATION: homology
      id :AA181148
      est
<221> NAME/KEY: misc_feature
<222> LOCATION: 475..605
<223> OTHER INFORMATION: homology
      id :AA181148
      est
<221> NAME/KEY: misc_feature
<222> LOCATION: 598..639
<223> OTHER INFORMATION: homology
      id :AA181148
      est
<221> NAME/KEY: misc_feature
<222> LOCATION: 1069..1190
<223> OTHER INFORMATION: homology
      id :AA181149
      est
<221> NAME/KEY: misc_feature
```

```
<222> LOCATION: 1362..1475
<223> OTHER INFORMATION: homology
      id :AA181149
      est
<221> NAME/KEY: misc_feature
<222> LOCATION: 1202..1312
<223> OTHER INFORMATION: homology
      id :AA181149
      est
<221> NAME/KEY: misc_feature
<222> LOCATION: 1312..1370
<223> OTHER INFORMATION: homology
      id :AA181149
      est
<221> NAME/KEY: misc_feature
<222> LOCATION: 72,93
<223> OTHER INFORMATION: n=a, g, c or t

<400> SEQUENCE: 58
atccggcgcg ctggagcgtt ttccggccgt gcgtttgtgg ccgtccggcc tccctgacat      60
gcagatttcc anssagaaga cagagaagga gcnagtggtc atggaatggg ctggggtcaa     120
agactgggtg cctgggagct gaggcagcca ccgtttcagc ctggccagcc ctctggaccc     180
cgaggttgga ccctactgtg acacacctac c atg cgg aca ctc ttc aac ctc        232
                                  Met Arg Thr Leu Phe Asn Leu
                                                          -15 ctc tgg ctt gcc ctg gcc tgc agc cct gtt cac act acc ctg tca aag       280
Leu Trp Leu Ala Leu Ala Cys Ser Pro Val His Thr Thr Leu Ser Lys
        -10                 -5                   1 tca gat gcc asa aaa ccg cct caa aga cgc tgc tgg aga aga gtc agt       328
Ser Asp Ala Xaa Lys Pro Pro Gln Arg Arg Cys Trp Arg Arg Val Ser
  5              10                  15                  20 ttt cag ata agc cgg tgc aar acc ggg gtt tgg tgg tgacggacct            374
Phe Gln Ile Ser Arg Cys Lys Thr Gly Val Trp Trp
              25                  30 caaagctgag agtgtggttc ttgagcatcg cagctactgc tcggcaaagg cccgggacag     434
acactttgct ggggatgtac tgggctatgt cactccatgg aacagccatg gctacgatgt     494
caccaaggtc tttgggagca agttcacaca gatctcaccc gtctggctgc agttgaagag     554
acgtggccgt gagatgtttg aggtcacggg cctccacgac gtggaccaag ggtggatgcg     614
agctgtcagg aagcatgcca agggcctgca catagtgcct cggctcctgt ttgaggactg     674
gacttacgat gatttccgga acgtcttaga cagtgaggat gagatagagg agctgagcaa     734
gaccgtggtc caggtggcaa agaaccagca tttcgatggc ttcgtggtgg aggtctggaa     794
ccagctgcta agccagaagc gcgtgggcct catccacatg ctcacccact ggccgaggc      854 cctgcaccag gccggctgc tggccctcct ggtcatcccg cctgccatca ccccggac       914 cgaccagctg ggcatgttca cgcacaagga gtttgagcag ctgccccccg tgctggatgg     974
tttcagcctc atgacctacg actactctac agcgcatcag cctggcccta atgcaccct    1034 gtcctgggtt cgagcctgcg tccaggtcct ggacccggaa gtccaagtgg cgaagcaaaa    1094
tcctcctggg gctcaacttc tatggtatgg actacgcgac ctccaaggat gcccgtgagc    1154
ctgttgtcgg ggccaggtac atccagacac tgaadggacc acaggccccg ggaatggtgt    1214
gggacagcca ggcctcagag cacttcttcg agtacaagaa gagccgcagt gggaggcacg    1274
tcgtcttcta cccaaccctg aagtccctgc aggtgcgggc tggagctggc ccgggagctg    1334
ggcgttgggg tctctatytg ggagctgggc cagggcctgg actacttyta cgacctgcty    1394
taggtgggca ttgcggcctc cgcggtggac gtgttytttt ytaagccatg gagtgagtga    1454
gcaggtgtga aatacaggcc tccactccgt ttgcaaaaaa aaa                      1497
```

```
<210> SEQ ID NO 59
<211> LENGTH: 1570
<212> TYPE: DNA
<213> ORGANISM: Homo sapiens
<220> FEATURE:
<221> NAME/KEY: sig_peptide
<222> LOCATION: 147..248
<223> OTHER INFORMATION: Von Heijne matrix
      score 4.30000019073486
      seq QLFAFLNLLPVEA/DI
<221> NAME/KEY: polyA_signal
<222> LOCATION: 1538..1543
<221> NAME/KEY: polyA_site
<222> LOCATION: 1558..1570
<221> NAME/KEY: misc_feature
<222> LOCATION: 466..968
<223> OTHER INFORMATION: homology
      id :AA506103
      est
<221> NAME/KEY: misc_feature
<222> LOCATION: 142..664
<223> OTHER INFORMATION: homology
      id :AA237105
      est
<221> NAME/KEY: misc_feature
<222> LOCATION: 114..269
<223> OTHER INFORMATION: homology
      id :AA317201
      est
<221> NAME/KEY: misc_feature
<222> LOCATION: 2..122
<223> OTHER INFORMATION: homology
      id :AA317201
      est
<221> NAME/KEY: misc_feature
<222> LOCATION: 401..443
<223> OTHER INFORMATION: homology
      id :AA317201
      est
<221> NAME/KEY: misc_feature
<222> LOCATION: 103..385
<223> OTHER INFORMATION: homology
      id :T80259
      est
<221> NAME/KEY: misc_feature
<222> LOCATION: 21..120
<223> OTHER INFORMATION: homology
      id :T80259
      est
<221> NAME/KEY: misc_feature
<222> LOCATION: 109..459
<223> OTHER INFORMATION: homology
      id :N32697
      est
<221> NAME/KEY: misc_feature
<222> LOCATION: 45..87
<223> OTHER INFORMATION: homology
      id :N32697
      est
<221> NAME/KEY: misc_feature
<222> LOCATION: 92..122
<223> OTHER INFORMATION: homology
      id :N32697
      est
<221> NAME/KEY: misc_feature
<222> LOCATION: 1220..1409
<223> OTHER INFORMATION: homology
      id :AA449621
      est
<221> NAME/KEY: misc_feature
<222> LOCATION: 928..1092
<223> OTHER INFORMATION: homology
      id :AA449621
      est
<221> NAME/KEY: misc_feature
<222> LOCATION: 1178..1222
<223> OTHER INFORMATION: homology
```

```
          id :AA449621
          est
<221> NAME/KEY: misc_feature
<222> LOCATION: 1220..1545
<223> OTHER INFORMATION: homology
          id :N34685
          est
<221> NAME/KEY: misc_feature
<222> LOCATION: 1168..1222
<223> OTHER INFORMATION: homology
          id :N34685
          est
<221> NAME/KEY: misc_feature
<222> LOCATION: 1220..1545
<223> OTHER INFORMATION: homology
          id :N22990
          est
<221> NAME/KEY: misc_feature
<222> LOCATION: 1178..1222
<223> OTHER INFORMATION: homology
          id :N22990
          est
<221> NAME/KEY: misc_feature
<222> LOCATION: 114..325
<223> OTHER INFORMATION: homology
          id :AA330462
          est
<221> NAME/KEY: misc_feature
<222> LOCATION: 18..122
<223> OTHER INFORMATION: homology
          id :AA330462
          est
<221> NAME/KEY: misc_feature
<222> LOCATION: 135..475
<223> OTHER INFORMATION: homology
          id :HUMEST5H12
          est
<221> NAME/KEY: misc_feature
<222> LOCATION: 1093,1128,1135,1147
<223> OTHER INFORMATION: n=a, g, c or t

<400> SEQUENCE: 59
agtcgtccct gctagtactc cgggctgtgg gggtcggtgc ggatattcag tcatgaaatc      60
agggtaggga cttctcccgc agcgacgcgg ctggcaagac tgtttgtgtt gcggggccg     120 gaacttcaag gtgattttac aacgag atg ctg ctc tcc ata ggg atg ctc atg     173
                             Met Leu Leu Ser Ile Gly Met Leu Met
                                                              -30 ctg tca gcc aca caa gtc tac acc atc ttg act gtc cag ctc ttt gca     221
Leu Ser Ala Thr Gln Val Tyr Thr Ile Leu Thr Val Gln Leu Phe Ala
-25                 -20                 -15                 -10 ttc tta aac cta ctg cct gta gaa gca gac att tta gca tat aac ttt     269
Phe Leu Asn Leu Leu Pro Val Glu Ala Asp Ile Leu Ala Tyr Asn Phe
                -5                   1                   5 gaa aat gca tct cag aca ttt gat gac ctc ccc gca ara ttt ggt tat     317
Glu Asn Ala Ser Gln Thr Phe Asp Asp Leu Pro Ala Xaa Phe Gly Tyr
            10                  15                  20 aga ctt cca gct gaa ggt tta aag ggt ttt tta att aac tca aaa cca     365
Arg Leu Pro Ala Glu Gly Leu Lys Gly Phe Leu Ile Asn Ser Lys Pro
        25                  30                  35 gag aat gcc tgt gaa ccc ata gtg cct cca cca gta aaa gac aat tca     413
Glu Asn Ala Cys Glu Pro Ile Val Pro Pro Pro Val Lys Asp Asn Ser
 40                  45                  50                  55 tct ggc act ttc atc gtg tta att ara ara ctt gat tgt aat ttt gat     461
Ser Gly Thr Phe Ile Val Leu Ile Xaa Xaa Leu Asp Cys Asn Phe Asp
                 60                  65                  70 ata aag gtt tta aat gca cag aga gca gga tac aag gca gcc ata gtt     509
Ile Lys Val Leu Asn Ala Gln Arg Ala Gly Tyr Lys Ala Ala Ile Val
             75                  80                  85
```

```
cac aat gtt gat tct gat gac ctc att agc atg gga tcc aac gac att        557
His Asn Val Asp Ser Asp Asp Leu Ile Ser Met Gly Ser Asn Asp Ile
             90                  95                 100 gag gta cta aag aaa att gac att cca tct gtc ttt att ggt gaa tca        605
Glu Val Leu Lys Lys Ile Asp Ile Pro Ser Val Phe Ile Gly Glu Ser
        105                 110                 115 tca gct agt tct ctg aaa gat gaa ttc aca tak gaa aaa ggg ggc cac        653
Ser Ala Ser Ser Leu Lys Asp Glu Phe Thr Xaa Glu Lys Gly Gly His
120                 125                 130                 135 ctt atc tta gtt cca gaa ttt agt ctt cct ttg gaa tac tac cta att        701
Leu Ile Leu Val Pro Glu Phe Ser Leu Pro Leu Glu Tyr Tyr Leu Ile
                140                 145                 150 ccc ttc ctt atc atr gtg ggc atc tgt ctc atc ttg ata gtc att ttc        749
Pro Phe Leu Ile Xaa Val Gly Ile Cys Leu Ile Leu Val Ile Phe
            155                 160                 165 atg atc aca aaa ttg tcc agg gat aga cat aga gct aga aga aac aga        797
Met Ile Thr Lys Leu Ser Arg Asp Arg His Arg Ala Arg Arg Asn Arg
        170                 175                 180 ctt cgt aaa gat caa ctt aag aaa ctt cct gta cat aaa ttc aag aaa        845
Leu Arg Lys Asp Gln Leu Lys Lys Leu Pro Val His Lys Phe Lys Lys
185                 190                 195 gga gat gag tat gat gta tgt gcc att tgt ttg gat gag tat gaa gat        893
Gly Asp Glu Tyr Asp Val Cys Ala Ile Cys Leu Asp Glu Tyr Glu Asp
200                 205                 210                 215 gga gac aaa ctc aga atc ctt ccc tgt tcc cat gct tat cat tgc aag        941
Gly Asp Lys Leu Arg Ile Leu Pro Cys Ser His Ala Tyr His Cys Lys
                220                 225                 230 tgt gta gac cct tgg cta act aaa acc aaa aaa acc tgt cca gtg tgc        989
Cys Val Asp Pro Trp Leu Thr Lys Thr Lys Lys Thr Cys Pro Val Cys
            235                 240                 245 agg caa aaa gtt gtt cct tct caa ggc gat tca gac tct gac aca gac       1037
Arg Gln Lys Val Val Pro Ser Gln Gly Asp Ser Asp Ser Asp Thr Asp
        250                 255                 260 agt agt caa gaa gaa aat gaa gtg aca gaa cat acc cct tta ctg aga       1085
Ser Ser Gln Glu Glu Asn Glu Val Thr Glu His Thr Pro Leu Leu Arg
265                 270                 275 cct tta gnc ttc tgt cag tgc cca rgt cam ttt ggg gct tta ntc gga       1133
Pro Leu Xaa Phe Cys Gln Cys Pro Xaa Xaa Phe Gly Ala Leu Xaa Gly
280                 285                 290                 295 ant ccc gct cac ant cag aak cat gac aga atc att cag act ast gag       1181
Xaa Pro Ala His Xaa Gln Xaa His Asp Arg Ile Ile Gln Thr Xaa Glu
                300                 305                 310 gaa gac gac aat gaa gat act gac agt agt gat gca gaa gaa                1223
Glu Asp Asp Asn Glu Asp Thr Asp Ser Ser Asp Ala Glu Glu
            315                 320                 325 tgaaattaat gaacatgatg tcgtggtcca gttgcagcct aatggtgaac gggattacaa     1283
catagcaaat actgtttgac tttcagaaga tgattggttt atttccttt aaaatgatta      1343 ggtatatact gtaatttgat tttttgctcc cttaaaagat ttytgtagaa ataacttatt     1403
ttttagtact ytcagttta atcaaattac tgaaacagga cttttgatyt ggtatttatc      1463
tgccaagaat atacttcatt cactaataat agactggtgc tgtaactcaa gcatcaattc     1523
agctyttytt ttggaatgaa agtatagcca aacaaaaaa aaaaaaa                    1570
```

<210> SEQ ID NO 60
<211> LENGTH: 1022
<212> TYPE: DNA
<213> ORGANISM: Homo sapiens
<220> FEATURE:
<221> NAME/KEY: sig_peptide

```
<222> LOCATION: 112..237
<223> OTHER INFORMATION: Von Heijne matrix
      score 7.19999980926514
      seq ILFSLSFLLVIIT/FP
<221> NAME/KEY: polyA_signal
<222> LOCATION: 976..981
<221> NAME/KEY: polyA_site
<222> LOCATION: 1010..1022

<400> SEQUENCE: 60
```

| | | |
|---|---|---|
| aatactttct cctctcccct ctcccaagca catctgagtt gctgcctgtt cttcacactt | | 60 |
| agctccaaac ccatgaaaaa ttgccaagta taaaagcttc tcaagaatga g atg gat<br>                                                                             Met Asp | | 117 |
| tct agg gtg tct tca cct gag aag caa gat aaa gag aat ttc gtg ggt<br>Ser Arg Val Ser Ser Pro Glu Lys Gln Asp Lys Glu Asn Phe Val Gly<br>-40                  -35                  -30                  -25 | | 165 |
| gtc aac aat aaa cgg ctt ggt gta tgt ggc tgg atc ctg ttt tcc ctc<br>Val Asn Asn Lys Arg Leu Gly Val Cys Gly Trp Ile Leu Phe Ser Leu<br>              -20                  -15                  -10 | | 213 |
| tct ttc ctg ttg gtg atc att acc ttc ccc atc tcc ata tgg atg tgc<br>Ser Phe Leu Leu Val Ile Ile Thr Phe Pro Ile Ser Ile Trp Met Cys<br>        -5                           1                      5 | | 261 |
| ttg aag atc att aag gag tat gaa cgt gct gtt gta ttc cgt ctg gga<br>Leu Lys Ile Ile Lys Glu Tyr Glu Arg Ala Val Val Phe Arg Leu Gly<br>    10                    15                    20 | | 309 |
| cgc atc caa gct gac aaa gcc aag ggg cca ggt ttg atc ctg gtc ctg<br>Arg Ile Gln Ala Asp Lys Ala Lys Gly Pro Gly Leu Ile Leu Val Leu<br>25                30                  35                  40 | | 357 |
| cca tgc ata gat gtg ttt gtc aag gtt gac ctc cga aca gtt act tgc<br>Pro Cys Ile Asp Val Phe Val Lys Val Asp Leu Arg Thr Val Thr Cys<br>            45                  50                  55 | | 405 |
| aac att cct cca caa gag atc ctc acc aga gac tcc gta act act cag<br>Asn Ile Pro Pro Gln Glu Ile Leu Thr Arg Asp Ser Val Thr Thr Gln<br>              60                  65                  70 | | 453 |
| gta gat gga gtt gtc tat tac aga atc tat agt gct gtc tca gca gtg<br>Val Asp Gly Val Val Tyr Tyr Arg Ile Tyr Ser Ala Val Ser Ala Val<br>75                80                  85 | | 501 |
| gct aat gtc aac gat gtc cat caa gca aca ttt ctg ctg gct caa acc<br>Ala Asn Val Asn Asp Val His Gln Ala Thr Phe Leu Leu Ala Gln Thr<br>    90                    95                    100 | | 549 |
| act ctg aga aat gtc tta ggg aca cag acc ttg tcc cag atc tta gct<br>Thr Leu Arg Asn Val Leu Gly Thr Gln Thr Leu Ser Gln Ile Leu Ala<br>105                110                  115              120 | | 597 |
| gga cga gaa gag atc gcc cat agc atc cag act tta ctt gat gat gcc<br>Gly Arg Glu Glu Ile Ala His Ser Ile Gln Thr Leu Leu Asp Asp Ala<br>              125                  130              135 | | 645 |
| acc gaa ctg tgg ggg atc cgg gtg gcc cga gtg gaa atc aaa gat gtt<br>Thr Glu Leu Trp Gly Ile Arg Val Ala Arg Val Glu Ile Lys Asp Val<br>            140                  145                  150 | | 693 |
| cgg att ccc gtg cag ttg cag aga tcc atg gca gcc gag gct gag gcc<br>Arg Ile Pro Val Gln Leu Gln Arg Ser Met Ala Ala Glu Ala Glu Ala<br>              155                  160              165 | | 741 |
| acc cgg gaa gcg aga gcc aag gtc ctt gca gct gaa gga gaa atg agt<br>Thr Arg Glu Ala Arg Ala Lys Val Leu Ala Ala Glu Gly Glu Met Ser<br>        170                  175                  180 | | 789 |
| gct tcc aaa tcc ctg aag tca gcc tcc atg gtg ctg gct gag tct ccc<br>Ala Ser Lys Ser Leu Lys Ser Ala Ser Met Val Leu Ala Glu Ser Pro<br>185                190                  195              200 | | 837 |
| ata gct ctc cag ctg cgc tac ctg cag acc ttg agc acg gta gcc acc<br>Ile Ala Leu Gln Leu Arg Tyr Leu Gln Thr Leu Ser Thr Val Ala Thr<br>              205                  210              215 | | 885 |

```
gag aag aat tct acg att gtg ttt cct ctg ccc atg aat ata cta gag      933
Glu Lys Asn Ser Thr Ile Val Phe Pro Leu Pro Met Asn Ile Leu Glu
            220                 225                 230 ggc att ggt ggc gtc agc tat gat aac cac aag aag ctt cca aat aaa      981
Gly Ile Gly Gly Val Ser Tyr Asp Asn His Lys Lys Leu Pro Asn Lys
            235                 240                 245 gcc tgaggtcctc ttgcggtagt cagctaaaaa aaaaaaaa                       1022
Ala

<210> SEQ ID NO 61
<211> LENGTH: 615
<212> TYPE: DNA
<213> ORGANISM: Homo sapiens
<220> FEATURE:
<221> NAME/KEY: sig_peptide
<222> LOCATION: 239..316
<223> OTHER INFORMATION: Von Heijne matrix
      score 3.90000009536743
      seq ITWVSLFIDCVMT/RK
<221> NAME/KEY: polyA_signal
<222> LOCATION: 586..591
<221> NAME/KEY: polyA_site
<222> LOCATION: 603..615
<221> NAME/KEY: misc_feature
<222> LOCATION: 341..574
<223> OTHER INFORMATION: homology
      id :AA453275
      est
<221> NAME/KEY: misc_feature
<222> LOCATION: 174..332
<223> OTHER INFORMATION: homology
      id :AA453275
      est
<221> NAME/KEY: misc_feature
<222> LOCATION: 85..171
<223> OTHER INFORMATION: homology
      id :AA453275
      est
<221> NAME/KEY: misc_feature
<222> LOCATION: 341..574
<223> OTHER INFORMATION: homology
      id :AA149631
      est
<221> NAME/KEY: misc_feature
<222> LOCATION: 170..339
<223> OTHER INFORMATION: homology
      id :AA149631
      est
<221> NAME/KEY: misc_feature
<222> LOCATION: 43..123
<223> OTHER INFORMATION: homology
      id :AA149631
      est
<221> NAME/KEY: misc_feature
<222> LOCATION: 88..339
<223> OTHER INFORMATION: homology
      id :AA588414
      est
<221> NAME/KEY: misc_feature
<222> LOCATION: 341..574
<223> OTHER INFORMATION: homology
      id :AA588414
      est
<221> NAME/KEY: misc_feature
<222> LOCATION: 1..345
<223> OTHER INFORMATION: homology
      id :AA156847
      est
<221> NAME/KEY: misc_feature
<222> LOCATION: 342..414
<223> OTHER INFORMATION: homology
      id :AA156847
      est
<221> NAME/KEY: misc_feature
<222> LOCATION: 341..574
```

```
<223> OTHER INFORMATION: homology
      id :AA501739
      est
<221> NAME/KEY: misc_feature
<222> LOCATION: 110..339
<223> OTHER INFORMATION: homology
      id :AA501739
      est
<221> NAME/KEY: misc_feature
<222> LOCATION: 341..574
<223> OTHER INFORMATION: homology
      id :AA131792
      est
<221> NAME/KEY: misc_feature
<222> LOCATION: 153..259
<223> OTHER INFORMATION: homology
      id :AA131792
      est
<221> NAME/KEY: misc_feature
<222> LOCATION: 259..339
<223> OTHER INFORMATION: homology
      id :AA131792
      est
<221> NAME/KEY: misc_feature
<222> LOCATION: 59..338
<223> OTHER INFORMATION: homology
      id :AA131842
      est
<221> NAME/KEY: misc_feature
<222> LOCATION: 344..415
<223> OTHER INFORMATION: homology
      id :AA131842
      est
<221> NAME/KEY: misc_feature
<222> LOCATION: 400..434
<223> OTHER INFORMATION: homology
      id :AA131842
      est
<221> NAME/KEY: misc_feature
<222> LOCATION: 341..574
<223> OTHER INFORMATION: homology
      id :AA152042
      est
<221> NAME/KEY: misc_feature
<222> LOCATION: 183..339
<223> OTHER INFORMATION: homology
      id :AA152042
      est

<400> SEQUENCE: 61
atctttgaag aagaagaagt tgaatttatc agtgtgcctg tcccagagtt tgcagatagt      60
gatcctgcca acattgttca tgactttaac aagaaactta cagcctattt agatcttaac     120
ctggataagt gctatgtgat ccctctgaac acttccattg ttatgccacc cagaaaccta     180
ctggagttac ttattaacat caaggctgga acctatttgc ctcagtccta tctgattc       238 atg agc aca tgg tta tta ctg atc gca ttg aaa aca ttg atc acc tgg       286
Met Ser Thr Trp Leu Leu Leu Ile Ala Leu Lys Thr Leu Ile Thr Trp
    -25                 -20                 -15 gtt tct tta ttt atc gac tgt gtc atg aca agg aaa ctt aca aac tgc       334
Val Ser Leu Phe Ile Asp Cys Val Met Thr Arg Lys Leu Thr Asn Cys
-10                  -5                   1                   5 aac gct aga gaa act att aaa ggt att cag aaa cgt gaa gcc agc aat       382
Asn Ala Arg Glu Thr Ile Lys Gly Ile Gln Lys Arg Glu Ala Ser Asn
                10                  15                  20 tgt ttc gca att cgg cat ttt gaa aac aaa ttt gcc gtg gaa act tta       430
Cys Phe Ala Ile Arg His Phe Glu Asn Lys Phe Ala Val Glu Thr Leu
            25                  30                  35 att tgt tct tgaacagtca agaaaaacat tattgaggaa aattaatatc                479
Ile Cys Ser
    40
```

-continued

```
acagcataac cccacccttt acattttgtg cagtgattat tttttaaagt cttctttcat     539
gtaagtagca aacagggctt tactatcttt tcatctcatt aattcaatta aaaccattac     599
cccaaaaaaa aaaaaa                                                     615
```

```
<210> SEQ ID NO 62
<211> LENGTH: 804
<212> TYPE: DNA
<213> ORGANISM: Homo sapiens
<220> FEATURE:
<221> NAME/KEY: sig_peptide
<222> LOCATION: 157..345
<223> OTHER INFORMATION: Von Heijne matrix
      score 3.5
      seq GLVCAGLADMARP/AE
<221> NAME/KEY: polyA_signal
<222> LOCATION: 771..776
<221> NAME/KEY: polyA_site
<222> LOCATION: 791..804
<221> NAME/KEY: misc_feature
<222> LOCATION: 244..789
<223> OTHER INFORMATION: homology
      id :AA576425
      est
<221> NAME/KEY: misc_feature
<222> LOCATION: 286..790
<223> OTHER INFORMATION: homology
      id :AA236527
      est
<221> NAME/KEY: misc_feature
<222> LOCATION: 287..790
<223> OTHER INFORMATION: homology
      id :AA435919
      est
<221> NAME/KEY: misc_feature
<222> LOCATION: 520..790
<223> OTHER INFORMATION: homology
      id :AA165350
      est
<221> NAME/KEY: misc_feature
<222> LOCATION: 389..522
<223> OTHER INFORMATION: homology
      id :AA165350
      est
<221> NAME/KEY: misc_feature
<222> LOCATION: 336..386
<223> OTHER INFORMATION: homology
      id :AA165350
      est
<221> NAME/KEY: misc_feature
<222> LOCATION: 326..790
<223> OTHER INFORMATION: homology
      id :AA490322
      est
<221> NAME/KEY: misc_feature
<222> LOCATION: 326..790
<223> OTHER INFORMATION: homology
      id :AA490310
      est
<221> NAME/KEY: misc_feature
<222> LOCATION: 515..780
<223> OTHER INFORMATION: homology
      id :AA164559
      est
<221> NAME/KEY: misc_feature
<222> LOCATION: 325..522
<223> OTHER INFORMATION: homology
      id :AA164559
      est
<221> NAME/KEY: misc_feature
<222> LOCATION: 350..790
<223> OTHER INFORMATION: homology
      id :AA427895
      est
<221> NAME/KEY: misc_feature
<222> LOCATION: 378..790
<223> OTHER INFORMATION: homology
```

```
         id :AA532390
         est
<221> NAME/KEY: misc_feature
<222> LOCATION: 186..382
<223> OTHER INFORMATION: homology
         id :AA082259
         est
<221> NAME/KEY: misc_feature
<222> LOCATION: 61..141
<223> OTHER INFORMATION: homology
         id :AA082259
         est
<221> NAME/KEY: misc_feature
<222> LOCATION: 426..478
<223> OTHER INFORMATION: homology
         id :AA082259
         est
<221> NAME/KEY: misc_feature
<222> LOCATION: 29..61
<223> OTHER INFORMATION: homology
         id :AA082259
         est
<221> NAME/KEY: misc_feature
<222> LOCATION: 389..790
<223> OTHER INFORMATION: homology
         id :AA157009
         est
<221> NAME/KEY: misc_feature
<222> LOCATION: 425..790
<223> OTHER INFORMATION: homology
         id :AA034912
         est
<221> NAME/KEY: misc_feature
<222> LOCATION: 186..430
<223> OTHER INFORMATION: homology
         id :AA428006
         est
<221> NAME/KEY: misc_feature
<222> LOCATION: 59..132
<223> OTHER INFORMATION: homology
         id :AA428006
         est

<400> SEQUENCE: 62
aacagcgggc agggaaagcc gcgggaaggg tactccaggc gagaggcgga cgcgagtcgt      60
cgtggcagga aaagtgacta gctccccttc gttgtcagcc agggacgaga acacagccac     120
gctcccaccc ggctgcchaa ggatccctcg gcggcg atg tcg gcc gcc ggt gcc      174
                                        Met Ser Ala Ala Gly Ala
                                                           -60 cga ggc ctg cgg gcc acc tac cac cgg ctc ctc gat aaa gtg gag ctg      222
Arg Gly Leu Arg Ala Thr Tyr His Arg Leu Leu Asp Lys Val Glu Leu
        -55                 -50                 -45 atg ctg ccc gag aaa ttg agg ccg ttg tac aac cat cca gca ggt ccc      270
Met Leu Pro Glu Lys Leu Arg Pro Leu Tyr Asn His Pro Ala Gly Pro
-40                 -35                 -30 aga aca gtt ttc ttc tgg gct cca att atg aaa tgg ggg ttg gtg tgt      318
Arg Thr Val Phe Phe Trp Ala Pro Ile Met Lys Trp Gly Leu Val Cys
-25                 -20                 -15                 -10 gct gga ttg gct gat atg gcc aga cct gca gaa aaa ctt agc aca gct      366
Ala Gly Leu Ala Asp Met Ala Arg Pro Ala Glu Lys Leu Ser Thr Ala
                -5                  1               5 caa tct gct gtt ttg atg gct aca ggg ttt att tgg tca aga tac tca      414
Gln Ser Ala Val Leu Met Ala Thr Gly Phe Ile Trp Ser Arg Tyr Ser
        10                  15                  20 ctt gta att att ccg aaa aat tgg agt ctg ttt gct gtt aat ttc ttt      462
Leu Val Ile Ile Pro Lys Asn Trp Ser Leu Phe Ala Val Asn Phe Phe
    25                  30                  35 gtg ggg gca gca gga gcc tct cag ctt ttt cgt att tgg aga tat aac      510
Val Gly Ala Ala Gly Ala Ser Gln Leu Phe Arg Ile Trp Arg Tyr Asn
```

```
                40              45              50              55
caa gaa cta aaa gct aaa gca cac aaa taaaagagtt cctgatcacc          557
Gln Glu Leu Lys Ala Lys Ala His Lys
                                60 tgaacaatct agatgtggac aaaaccattg ggacctagtt tattatttgg ttattgataa   617 agcaaagcta actgtgtgtt tagaaggcac tgtaactggt agctagttct tgattcaata   677 gaaaaatgca gcaaacttt t aataacagtc tctctacatg acttaaggaa cttatctatg  737 gatattagta acatttttct accatttgtc cgtaataaaa catacttgct cgtaaaaaaa   797 aaaaaaa                                                             804
```

<210> SEQ ID NO 63
<211> LENGTH: 792
<212> TYPE: DNA
<213> ORGANISM: Homo sapiens
<220> FEATURE:
<221> NAME/KEY: sig_peptide
<222> LOCATION: 194..253
<223> OTHER INFORMATION: Von Heijne matrix
      score 12.3999996185303
      seq ALLLGALLGTAWA/RR
<221> NAME/KEY: polyA_signal
<222> LOCATION: 768..773
<221> NAME/KEY: polyA_site
<222> LOCATION: 780..792
<221> NAME/KEY: misc_feature
<222> LOCATION: 154..428
<223> OTHER INFORMATION: homology
      id :R22491
      est
<221> NAME/KEY: misc_feature
<222> LOCATION: 104..160
<223> OTHER INFORMATION: homology
      id :R22491
      est
<221> NAME/KEY: misc_feature
<222> LOCATION: 47..218
<223> OTHER INFORMATION: homology
      id :AA136163
      est
<221> NAME/KEY: misc_feature
<222> LOCATION: 265..403
<223> OTHER INFORMATION: homology
      id :AA136163
      est
<221> NAME/KEY: misc_feature
<222> LOCATION: 3..40
<223> OTHER INFORMATION: homology
      id :AA136163
      est
<221> NAME/KEY: misc_feature
<222> LOCATION: 123..265
<223> OTHER INFORMATION: homology
      id :N57089
      est
<221> NAME/KEY: misc_feature
<222> LOCATION: 47..127
<223> OTHER INFORMATION: homology
      id :N57089
      est
<221> NAME/KEY: misc_feature
<222> LOCATION: 282..323
<223> OTHER INFORMATION: homology
      id :N57089
      est
<221> NAME/KEY: misc_feature
<222> LOCATION: 128..403
<223> OTHER INFORMATION: homology
      id :AA314970
      est
<221> NAME/KEY: misc_feature
<222> LOCATION: 138..403
<223> OTHER INFORMATION: homology

```
        id :AA314807
        est
<221> NAME/KEY: misc_feature
<222> LOCATION: 164..403
<223> OTHER INFORMATION: homology
        id :AA271811
        est
<221> NAME/KEY: misc_feature
<222> LOCATION: 163..385
<223> OTHER INFORMATION: homology
        id :AA103053
        est
<221> NAME/KEY: misc_feature
<222> LOCATION: 154..403
<223> OTHER INFORMATION: homology
        id :AA042016
        est
<221> NAME/KEY: misc_feature
<222> LOCATION: 2..250
<223> OTHER INFORMATION: homology
        id :AA315322
        est
<221> NAME/KEY: misc_feature
<222> LOCATION: 154..403
<223> OTHER INFORMATION: homology
        id :AA470189
        est
<221> NAME/KEY: misc_feature
<222> LOCATION: 217..403
<223> OTHER INFORMATION: homology
        id :AA462839
        est
<221> NAME/KEY: misc_feature
<222> LOCATION: 154..403
<223> OTHER INFORMATION: homology
        id :AA120322
        est
<221> NAME/KEY: misc_feature
<222> LOCATION: 163..403
<223> OTHER INFORMATION: homology
        id :W71694
        est
<221> NAME/KEY: misc_feature
<222> LOCATION: 164..385
<223> OTHER INFORMATION: homology
        id :AA250603
        est
<221> NAME/KEY: misc_feature
<222> LOCATION: 266..403
<223> OTHER INFORMATION: homology
        id :AA036242
        est

<400> SEQUENCE: 63
aaggcggtcg ccgggacacc ccgtgtgtgg caggcggcga asgctctgga gaatcccgga      60
cagccctgct ccctgcagcc aggtgtagtt tcgggagcca ctggggccaa agtgagagtc     120
cagcggtctt ccagcgcttg ggccacgcg gcggccctgg gagcagaggt ggagcgaccc      180
cattacgcta aag atg aaa ggc tgg ggt tgg ctg gcc ctg ctt ctg ggg       229
            Met Lys Gly Trp Gly Trp Leu Ala Leu Leu Leu Gly
            -20             -15                 -10 gcc ctg ctg gga acc gcc tgg gct cgg agg agc cgg gat ctc cac tgt       277
Ala Leu Leu Gly Thr Ala Trp Ala Arg Arg Ser Arg Asp Leu His Cys
        -5                  1               5 gga gca tgc agg gct ctg gtg gat gaa cta gaa tgg gaa att gcc cag       325
Gly Ala Cys Arg Ala Leu Val Asp Glu Leu Glu Trp Glu Ile Ala Gln
    10                  15                  20 gtg gac ccc aag aag acc att cag atg gga tcc ttc cgg atc aat cca       373
Val Asp Pro Lys Lys Thr Ile Gln Met Gly Ser Phe Arg Ile Asn Pro
25                  30                  35                  40 gat ggc agc cag tca gtg gtg gag gta act gtt act gkt tcc ccc aaa       421
Asp Gly Ser Gln Ser Val Val Glu Val Thr Val Thr Xaa Ser Pro Lys
```

```
                    45                  50                  55
aca aaa gta gct cac tct ggc ttt tgg atg aaa att cga ctg ctt aaa        469
Thr Lys Val Ala His Ser Gly Phe Trp Met Lys Ile Arg Leu Leu Lys
             60                  65                  70 aaa gga cct tgg tct taatagaaaa tgaagraaaa cagactcaga aaaaagatt         524
Lys Gly Pro Trp Ser
 75 tbggctctgt ctcawtttgg aagaaggctg gcaggcttat tccccaatgc aactttgctt      584 cctggctgca aaccyttaat acytttgttt ctgctgtaga aatttgttag ccaaaacawg      644 ggagtcctga twcagcaacc ccttcttcca caatccacca tgactggttt ttaatgtamc      704 acttggggta tacatgcaaa accatccgtt cmaaaatctg aatycggagc ttaaaaattt      764 aaaaatgaaa aacchaaaaa aaaaaaaa                                         792
```

```
<210> SEQ ID NO 64
<211> LENGTH: 832
<212> TYPE: DNA
<213> ORGANISM: Homo sapiens
<220> FEATURE:
<221> NAME/KEY: sig_peptide
<222> LOCATION: 148..207
<223> OTHER INFORMATION: Von Heijne matrix
      score 12.3999996185303
      seq ALLLGALLGTAWA/RR
<221> NAME/KEY: polyA_signal
<222> LOCATION: 789..794
<221> NAME/KEY: polyA_site
<222> LOCATION: 820..832
<221> NAME/KEY: misc_feature
<222> LOCATION: 258..553
<223> OTHER INFORMATION: homology
      id :AA435303
      est
<221> NAME/KEY: misc_feature
<222> LOCATION: 117..219
<223> OTHER INFORMATION: homology
      id :AA435303
      est
<221> NAME/KEY: misc_feature
<222> LOCATION: 552..645
<223> OTHER INFORMATION: homology
      id :AA435303
      est
<221> NAME/KEY: misc_feature
<222> LOCATION: 217..258
<223> OTHER INFORMATION: homology
      id :AA435303
      est
<221> NAME/KEY: misc_feature
<222> LOCATION: 258..553
<223> OTHER INFORMATION: homology
      id :AA314807
      est
<221> NAME/KEY: misc_feature
<222> LOCATION: 92..258
<223> OTHER INFORMATION: homology
      id :AA314807
      est
<221> NAME/KEY: misc_feature
<222> LOCATION: 258..554
<223> OTHER INFORMATION: homology
      id :AA314970
      est
<221> NAME/KEY: misc_feature
<222> LOCATION: 82..258
<223> OTHER INFORMATION: homology
      id :AA314970
      est
<221> NAME/KEY: misc_feature
<222> LOCATION: 258..553
<223> OTHER INFORMATION: homology
      id :AA547310
```

```
         est
<221> NAME/KEY: misc_feature
<222> LOCATION: 119..258
<223> OTHER INFORMATION: homology
      id :AA547310
         est
<221> NAME/KEY: misc_feature
<222> LOCATION: 359..553
<223> OTHER INFORMATION: homology
      id :AA565602
         est
<221> NAME/KEY: misc_feature
<222> LOCATION: 552..683
<223> OTHER INFORMATION: homology
      id :AA565602
         est
<221> NAME/KEY: misc_feature
<222> LOCATION: 684..751
<223> OTHER INFORMATION: homology
      id :AA565602
         est
<221> NAME/KEY: misc_feature
<222> LOCATION: 742..783
<223> OTHER INFORMATION: homology
      id :AA565602
         est
<221> NAME/KEY: misc_feature
<222> LOCATION: 364..553
<223> OTHER INFORMATION: homology
      id :AA136094
         est
<221> NAME/KEY: misc_feature
<222> LOCATION: 552..683
<223> OTHER INFORMATION: homology
      id :AA136094
         est
<221> NAME/KEY: misc_feature
<222> LOCATION: 684..751
<223> OTHER INFORMATION: homology
      id :AA136094
         est
<221> NAME/KEY: misc_feature
<222> LOCATION: 258..461
<223> OTHER INFORMATION: homology
      id :AA136163
         est
<221> NAME/KEY: misc_feature
<222> LOCATION: 2..172
<223> OTHER INFORMATION: homology
      id :AA136163
         est
<221> NAME/KEY: misc_feature
<222> LOCATION: 216..258
<223> OTHER INFORMATION: homology
      id :AA136163
         est
<221> NAME/KEY: misc_feature
<222> LOCATION: 743
<223> OTHER INFORMATION: n=a, g, c or t

<400> SEQUENCE: 64
aggagaatcc cggacagccc tgctccctgc agccaggtgt agtttcggga gccactgggg      60
ccaaagtgag agtccagcgg tcttccagcg cttgggccac ggcggcggcc ctgggagcag     120
aggtggagcg acccccattac gctaaag atg aaa ggc tgg ggt tgg ctg gcc ctg    174
                                Met Lys Gly Trp Gly Trp Leu Ala Leu
                                 -20                 -15 ctt ctg ggg gcc ctg ctg gga acc gcc tgg gct cgg agg agc cag gat        222
Leu Leu Gly Ala Leu Leu Gly Thr Ala Trp Ala Arg Arg Ser Gln Asp
     -10              -5                   1              5 ctc cac tgt gga gca tgc agg gct ctg gtg gat gaa act aga atg gga        270
Leu His Cys Gly Ala Cys Arg Ala Leu Val Asp Glu Thr Arg Met Gly
                 10                  15                  20 aat tgc cca ggt gga ccc caa gaa gac cat tca gat ggg atc ttt ccg        318
```

```
Asn Cys Pro Gly Gly Pro Gln Glu Asp His Ser Asp Gly Ile Phe Pro
             25                  30                  35 gat caa tcc aga tgg cag cca gtc agt ggt gga ggt gcc tta tgc ccg      366
Asp Gln Ser Arg Trp Gln Pro Val Ser Gly Gly Gly Ala Leu Cys Pro
         40                  45                  50 ctc aga ggc cca cct cac aga gct gct gga gga gat atg tgaccggatg       415
Leu Arg Gly Pro Pro His Arg Ala Ala Gly Gly Asp Met
         55                  60                  65 aaggagtatg gggaacagat tgatccttcc acccatcgca agaactacg acgtgtagtg    475 ggccggaatg gagaatccag tgaactggac ctacaaggca tccgaatcga ctcagatatt   535
agcggcaccc tcaagbtttg cgtgtgggaa cattgtggag gaatacgagg atgaactcat   595
tgaattcttt tcccgagagg ctgacaatgt taaagacaaa ctttgcagta agcgaacaga   655
tctttgtgac catgccctgc acatatcggc atgatgagct atgaaccact ggagcagccc   715
acactggctt gatggatcac ccccaggnaa gggaaaatgg tggcaatgcc ttttatatat   775
tatgttttac tgaaattaac tgaaaaatat gaaaccaaaa gtscaaaaaa aaaaaaa     832

<210> SEQ ID NO 65
<211> LENGTH: 721
<212> TYPE: DNA
<213> ORGANISM: Homo sapiens
<220> FEATURE:
<221> NAME/KEY: sig_peptide
<222> LOCATION: 156..230
<223> OTHER INFORMATION: Von Heijne matrix
      score 5
      seq MFAASLLAMCAGA/EV
<221> NAME/KEY: polyA_signal
<222> LOCATION: 706..711
<221> NAME/KEY: polyA_site
<222> LOCATION: 709..721
<221> NAME/KEY: misc_feature
<222> LOCATION: 351..688
<223> OTHER INFORMATION: homology
      id :H98648
      est
<221> NAME/KEY: misc_feature
<222> LOCATION: 289..353
<223> OTHER INFORMATION: homology
      id :H98648
      est
<221> NAME/KEY: misc_feature
<222> LOCATION: 274..641
<223> OTHER INFORMATION: homology
      id :AA181022
      est
<221> NAME/KEY: misc_feature
<222> LOCATION: 255..286
<223> OTHER INFORMATION: homology
      id :AA181022
      est
<221> NAME/KEY: misc_feature
<222> LOCATION: 242..641
<223> OTHER INFORMATION: homology
      id :AA143192
      est
<221> NAME/KEY: misc_feature
<222> LOCATION: 261..646
<223> OTHER INFORMATION: homology
      id :AA594850
      est
<221> NAME/KEY: misc_feature
<222> LOCATION: 165..474
<223> OTHER INFORMATION: homology
      id :AA563681
      est
<221> NAME/KEY: misc_feature
<222> LOCATION: 1..74
<223> OTHER INFORMATION: homology
      id :AA563681
```

```
            est
<221> NAME/KEY: misc_feature
<222> LOCATION: 261..643
<223> OTHER INFORMATION: homology
      id :AA287457
            est
<221> NAME/KEY: misc_feature
<222> LOCATION: 352..646
<223> OTHER INFORMATION: homology
      id :N22567
            est
<221> NAME/KEY: misc_feature
<222> LOCATION: 299..354
<223> OTHER INFORMATION: homology
      id :N22567
            est
<221> NAME/KEY: misc_feature
<222> LOCATION: 265..303
<223> OTHER INFORMATION: homology
      id :N22567
            est
<221> NAME/KEY: misc_feature
<222> LOCATION: 30..165
<223> OTHER INFORMATION: homology
      id :AA186657
            est
<221> NAME/KEY: misc_feature
<222> LOCATION: 270..349
<223> OTHER INFORMATION: homology
      id :AA186657
            est
<221> NAME/KEY: misc_feature
<222> LOCATION: 213..261
<223> OTHER INFORMATION: homology
      id :AA186657
            est
<221> NAME/KEY: misc_feature
<222> LOCATION: 165..214
<223> OTHER INFORMATION: homology
      id :AA186657
            est
<221> NAME/KEY: misc_feature
<222> LOCATION: 346..387
<223> OTHER INFORMATION: homology
      id :AA186657
            est
<221> NAME/KEY: misc_feature
<222> LOCATION: 52..400
<223> OTHER INFORMATION: homology
      id :HSC1ED081
            est
<221> NAME/KEY: misc_feature
<222> LOCATION: 398..436
<223> OTHER INFORMATION: homology
      id :HSC1ED081
            est
<221> NAME/KEY: misc_feature
<222> LOCATION: 171..316
<223> OTHER INFORMATION: homology
      id :AA143136
            est

<400> SEQUENCE: 65
attttgggtc cggcctgctc gcmgtccgct ccgtccgccc ttagacctgt tgcccagcat      60
ccctgcagtt cgcggwacag tctctattag agcgcgtgta tagaggcaga kaggagtgaa    120
gtccacagtt cctctcctcc tagagcctgc cgacc atg ccc gcg ggc gtg ccc       173
                                        Met Pro Ala Gly Val Pro
                                        -25                 -20 atg tcc acc tac ctg aaa atg ttc gca gcc agt ctc ctg gcc atg tgc      221
Met Ser Thr Tyr Leu Lys Met Phe Ala Ala Ser Leu Leu Ala Met Cys
            -15                 -10                  -5 gca ggg gca gaa gtg gtg cac agg tac tac cga ccg gac ctg aca ata      269
Ala Gly Ala Glu Val Val His Arg Tyr Tyr Arg Pro Asp Leu Thr Ile
            1               5                   10
```

```
cct gaa att cca cca aag cgt gga gaa ctc aaa acg gag ctt ttg gga      317
Pro Glu Ile Pro Pro Lys Arg Gly Glu Leu Lys Thr Glu Leu Leu Gly
    15                  20                  25 ctg aaa gaa aga aaa cac aaa cct caa gtt tct caa cag gag gaa ctt      365
Leu Lys Glu Arg Lys His Lys Pro Gln Val Ser Gln Gln Glu Glu Leu
 30                  35                  40                  45 aaa taactatgcc aagaattctg tgaataatat aagtcttaaa tatgtatttc           418
Lys ttaatttatt gcatcaaact acttgtcctt aagcacttag tctaatgcta actgcaagag    478
gaggtgctca gtggatgttt agccgatacg ttgaaattta attacggttt gattgatatt    538
tcttgaaaac tgccaaagca catatcatca aaccatttca tgaatatggt ttggaagatg    598
tttagtcttg aatataacgc gaaatagaat atttgtaagt ctactatatg ggttgtcttt    658
atttcatata aattaagaaa ttatttaaaa actatgaact aggtttcatt aaaaaaaaaa    718
gaa                                                                  721
```

```
<210> SEQ ID NO 66
<211> LENGTH: 531
<212> TYPE: DNA
<213> ORGANISM: Homo sapiens
<220> FEATURE:
<221> NAME/KEY: sig_peptide
<222> LOCATION: 272..397
<223> OTHER INFORMATION: Von Heijne matrix
      score 4.59999990463257
      seq RIPSLPGSPVCWA/WP
<221> NAME/KEY: polyA_signal
<222> LOCATION: 503..508
<221> NAME/KEY: polyA_site
<222> LOCATION: 518..531
<221> NAME/KEY: misc_feature
<222> LOCATION: 235..517
<223> OTHER INFORMATION: homology
      id :AA524403
      est
<221> NAME/KEY: misc_feature
<222> LOCATION: 52..208
<223> OTHER INFORMATION: homology
      id :AA524403
      est
<221> NAME/KEY: misc_feature
<222> LOCATION: 259..517
<223> OTHER INFORMATION: homology
      id :N93600
      est
<221> NAME/KEY: misc_feature
<222> LOCATION: 85..207
<223> OTHER INFORMATION: homology
      id :N93600
      est
<221> NAME/KEY: misc_feature
<222> LOCATION: 353..517
<223> OTHER INFORMATION: homology
      id :AA594610
      est
<221> NAME/KEY: misc_feature
<222> LOCATION: 258..363
<223> OTHER INFORMATION: homology
      id :AA594610
      est
<221> NAME/KEY: misc_feature
<222> LOCATION: 105..207
<223> OTHER INFORMATION: homology
      id :AA594610
      est
<221> NAME/KEY: misc_feature
<222> LOCATION: 202..517
<223> OTHER INFORMATION: homology
      id :AA074748
      est
```

```
<221> NAME/KEY: misc_feature
<222> LOCATION: 116..153
<223> OTHER INFORMATION: homology
       id :AA074748
       est
<221> NAME/KEY: misc_feature
<222> LOCATION: 167..202
<223> OTHER INFORMATION: homology
       id :AA074748
       est
<221> NAME/KEY: misc_feature
<222> LOCATION: 258..517
<223> OTHER INFORMATION: homology
       id :N93603
       est
<221> NAME/KEY: misc_feature
<222> LOCATION: 208..251
<223> OTHER INFORMATION: homology
       id :N93603
       est
<221> NAME/KEY: misc_feature
<222> LOCATION: 163..202
<223> OTHER INFORMATION: homology
       id :N93603
       est
<221> NAME/KEY: misc_feature
<222> LOCATION: 90..125
<223> OTHER INFORMATION: homology
       id :N93603
       est
<221> NAME/KEY: misc_feature
<222> LOCATION: 125..363
<223> OTHER INFORMATION: homology
       id :HSPD04938
       est
<221> NAME/KEY: misc_feature
<222> LOCATION: 353..517
<223> OTHER INFORMATION: homology
       id :HSPD04938
       est
<221> NAME/KEY: misc_feature
<222> LOCATION: 28..227
<223> OTHER INFORMATION: homology
       id :AA074804
       est
<221> NAME/KEY: misc_feature
<222> LOCATION: 265..310
<223> OTHER INFORMATION: homology
       id :AA074804
       est
<221> NAME/KEY: misc_feature
<222> LOCATION: 227..263
<223> OTHER INFORMATION: homology
       id :AA074804
       est
<221> NAME/KEY: misc_feature
<222> LOCATION: 352..385
<223> OTHER INFORMATION: homology
       id :AA074804
       est

<400> SEQUENCE: 66
aaaaggaaag aggtysggag cgctcgcgag atctcggacc acccaacctg aaaggtgctt        60
aggaagttga aaggcccaga ggaggcctcc gggcaaatgg ccggagctgg accgaccatg       120
ctgctacgag aagagaatgg ctgttgcagt cggcgtcaga gcagctccag tgccggggat       180
tcggacggag agcgcgagga ctcggcggct gagcgcgccc gacagcagct agaggcgctg       240
ctcaacaaga ctatgcgcat tcgcatgaca g atg gac gga cac tgg tcg gct          292
                                  Met Asp Gly His Trp Ser Ala
                                                       -40 gct ttc tct gca ctg acc gtg act gca atg tca tcc tgg gct cgg cgc        340
Ala Phe Ser Ala Leu Thr Val Thr Ala Met Ser Ser Trp Ala Arg Arg
-35                 -30                 -25                 -20
```

```
agg agt tcc tca agc cgt cgg att cct tct ctg ccg ggg agc ccc gtg      388
Arg Ser Ser Ser Ser Arg Arg Ile Pro Ser Leu Pro Gly Ser Pro Val
            -15             -10             -5 tgc tgg gcc tgg cca tgg tac ccg gac acc aca tcg ttt cca ttg agg      436
Cys Trp Ala Trp Pro Trp Tyr Pro Asp Thr Thr Ser Phe Pro Leu Arg
        1               5                   10 tgc aga ggg aga gtc tgaccgggcc tccgtatctc tgaccacgat ggcgcttacc      491
Cys Arg Gly Arg Val
        15 tttcagactt cattaaactt atgaccaaaa aaaaaaaaa                            531

<210> SEQ ID NO 67
<211> LENGTH: 783
<212> TYPE: DNA
<213> ORGANISM: Homo sapiens
<220> FEATURE:
<221> NAME/KEY: sig_peptide
<222> LOCATION: 381..629
<223> OTHER INFORMATION: Von Heijne matrix
      score 8.60000038146973
      seq LELLTSCSPPASA/SQ
<221> NAME/KEY: polyA_signal
<222> LOCATION: 736..741
<221> NAME/KEY: polyA_site
<222> LOCATION: 770..783
<221> NAME/KEY: misc_feature
<222> LOCATION: 207..263
<223> OTHER INFORMATION: homology
      id :AA357230
      est

<400> SEQUENCE: 67
agggacttcc ggcctcgctg gcgtggacgt ttgtggtggg gcgtgttggt ccgcgctctc     60
agaactgtgc tgggaaggat ggtagggcga ctggggctca cctccgcacc gttgtaggac    120
ccggggtagg gttttgagcc cgtgggagct gccccacgcg gcctcgtcct gccaacggtc    180
ggatggcgga gacgaaggac gcagcgcaga tgttggtgac cttcaaggat gtggctgtga    240
cctttacccg ggaggagtgg agacagctgg acctggccca gaggaccctg taccgagagg    300
tgatcgggtt cccaaaccag agttggtcca cctgctagag catgggcagg agctgtggat    360
agtgaagaga ggcctctcac atg cta cct gtg cag agt ttc act ctt gtt gcc    413
                        Met Leu Pro Val Gln Ser Phe Thr Leu Val Ala
                            -80                 -75 cag gct gga gtg cag tgg cgc cat ctc agc tca ctg caa ctt ctg cct      461
Gln Ala Gly Val Gln Trp Arg His Leu Ser Ser Leu Gln Leu Leu Pro
        -70                 -65                 -60 ccc gag ttc aag gga ttc tcc tgc ctc agc ctc ccg agt agc tgg gat      509
Pro Glu Phe Lys Gly Phe Ser Cys Leu Ser Leu Pro Ser Ser Trp Asp
    -55                 -50                 -45 tac agg cgc cca cca cca tgc ccg gct ggt ttt ttt gta ttt tta gta      557
Tyr Arg Arg Pro Pro Pro Cys Pro Ala Gly Phe Phe Val Phe Leu Val
-40                 -35                 -30                 -25 gag acg ggg ctt cac cat gtt ggc cag gct ggt ctt gaa ctc ttg acc      605
Glu Thr Gly Leu His His Val Gly Gln Ala Gly Leu Glu Leu Leu Thr
                -20                 -15                 -10 tca tgt agt cca ccc gcc tct gcc tcc caa agt gct gcg att aca ggc      653
Ser Cys Ser Pro Pro Ala Ser Ala Ser Gln Ser Ala Ala Ile Thr Gly
            -5                  1                   5 gtg agc cac gtg ccc ggc aaa aaa aaa ctg ctt aag gtt gaa aag aaa      701
Val Ser His Val Pro Gly Lys Lys Lys Leu Leu Lys Val Glu Lys Lys
        10                  15                  20 aat tta aga aaw ttg ctg acg gra ata aaa acy taataaaact accacccgaa    754
Asn Leu Arg Xaa Leu Leu Thr Xaa Ile Lys Thr
```

```
                  25                  30                  35 ggaatgaaaa aaccaaaaaa aaaaaaaaa                                       783
```

<210> SEQ ID NO 68
<211> LENGTH: 996
<212> TYPE: DNA
<213> ORGANISM: Homo sapiens
<220> FEATURE:
<221> NAME/KEY: sig_peptide
<222> LOCATION: 140..205
<223> OTHER INFORMATION: Von Heijne matrix
      score 5.90000009536743
      seq IILGCLALFLLLQ/RK
<221> NAME/KEY: polyA_signal
<222> LOCATION: 965..970
<221> NAME/KEY: polyA_site
<222> LOCATION: 984..996
<221> NAME/KEY: misc_feature
<222> LOCATION: 676..959
<223> OTHER INFORMATION: homology
      id :AA399103
      est
<221> NAME/KEY: misc_feature
<222> LOCATION: 609..679
<223> OTHER INFORMATION: homology
      id :AA399103
      est
<221> NAME/KEY: misc_feature
<222> LOCATION: 225..433
<223> OTHER INFORMATION: homology
      id :AA398040
      est
<221> NAME/KEY: misc_feature
<222> LOCATION: 433..563
<223> OTHER INFORMATION: homology
      id :AA398040
      est

<400> SEQUENCE: 68

```
aacagttacg aaggagagct gcaaaagttg cagcagaaag gttgggagtc ccgacaggtt       60
ccgtagccca cagaaaagaa gcaagggacg gcaggactgt ttcacactt tctgcttctg      120 gaaggtgctg gacaaaaac atg gaa cta att tcc cca aca gtg att ata atc      172
                        Met Glu Leu Ile Ser Pro Thr Val Ile Ile Ile
                                         -20                  -15 ctg ggt tgc ctt gct ctg ttc tta ctc ctt cag cgg aag aat ttg cgc      220
Leu Gly Cys Leu Ala Leu Phe Leu Leu Leu Gln Arg Lys Asn Leu Arg
   -10                   -5                    1                5 aga ccc ccg tgc atc aag ggc tgg att cct tgg att gga gtt gga ttt      268
Arg Pro Pro Cys Ile Lys Gly Trp Ile Pro Trp Ile Gly Val Gly Phe
                10                  15                  20 gak ttt ggg aaa gcc cct cta gaa ttt ata gag aaa gca aga atc aag      316
Xaa Phe Gly Lys Ala Pro Leu Glu Phe Ile Glu Lys Ala Arg Ile Lys
             25                  30                  35 gta tgt ggt cgt ggc ava cgg ggt ctc cag agg aga caa tgc ttt ctt      364
Val Cys Gly Arg Gly Xaa Arg Gly Leu Gln Arg Arg Gln Cys Phe Leu
         40                  45                  50 ttt taaactttct ttcattgact cttaagtgca gggctagaac acggggaaca            417
Phe tacctgcttg cctcaaacta aaggatctag tcmtytctga aktcctctac tsacrrttra     477
caacaatatc ctgtgcaaaa ttttgcgaaa gaaatgaaat acaattgcmg cgtgcatcga     537
cattttggaa gtagagatt aacyyttcgt atttttactt cmtcgaagtt aagttccaaa     597
tgtgtatgtg ttaagtaaat gttttcagta aytgggaaag ataaagtgta atccaattta     657
agtttgtgaa aatgagtaat tccgtatcca aaytggagtt aacaccaaag tattgtacaa     717
```

-continued

```
attgcttgca cagttggtcc gtacacaata dacaggctyt gtattttag ctgacgttgt     777 tatttgatga tgatgtactc cattttcamt acggcccgaa gagamtagta atcctccttg     837
tagtagatgt ttttgtcttg aaagtatctt ttaaatgtyt gagcactta aggaacagac     897 ccttattaat gtyttttaag ttttattcaa tttccagtca caaatatttt atggtatttg     957
attgtytaat aaatttgtat gatattaaaa aaaaaaaa                             996

<210> SEQ ID NO 69
<211> LENGTH: 657
<212> TYPE: DNA
<213> ORGANISM: Homo sapiens
<220> FEATURE:
<221> NAME/KEY: sig_peptide
<222> LOCATION: 183..338
<223> OTHER INFORMATION: Von Heijne matrix
      score 3.79999995231628
      seq VMLETCGLLVSLG/QS
<221> NAME/KEY: polyA_signal
<222> LOCATION: 620..625
<221> NAME/KEY: polyA_site
<222> LOCATION: 644..657
<221> NAME/KEY: misc_feature
<222> LOCATION: 207..263
<223> OTHER INFORMATION: homology
      id :AA357230
      est

<400> SEQUENCE: 69
agggacttcc ggcctcgctg gcgtggacgt ttgtggtggg gcgtgttggt ccgcgctctc       60
agaactgtgc tgggaaggat ggtagggcga ctggggctca cctccgcacc gttgtaggac      120
ccggggtagg gttttgagcc cgtgggagct gccccacgcg gcctcgtcct gccaacggtc      180 gg atg gcg gag acg aag gac gca gcg cag atg ttg gtg acc ttc aag        227
   Met Ala Glu Thr Lys Asp Ala Ala Gln Met Leu Val Thr Phe Lys
       -50              -45                  -40 gat gtg gct gtg acc ttt acc cgg gag gag tgg aga cag ctg gac ctg        275
Asp Val Ala Val Thr Phe Thr Arg Glu Glu Trp Arg Gln Leu Asp Leu
    -35                  -30                  -25 gcc cag agg acc ctg tac cga gag gtg atg ctg gag acc tgt ggg ctt        323
Ala Gln Arg Thr Leu Tyr Arg Glu Val Met Leu Glu Thr Cys Gly Leu
    -20                  -15                  -10 ctg gtt tca cta ggg caa agc att tgg ctg cat ata aca gaa aac cag        371
Leu Val Ser Leu Gly Gln Ser Ile Trp Leu His Ile Thr Glu Asn Gln
-5                   1                    5                   10 atc aaa ctg gct tca cct gga agg aaa ttc act aac tcg cct gat gag        419
Ile Lys Leu Ala Ser Pro Gly Arg Lys Phe Thr Asn Ser Pro Asp Glu
             15                   20                   25 aag cct gag gtg tgg ttg gct cca ggc ctg ttc ggt gcc gca gcc cag        467
Lys Pro Glu Val Trp Leu Ala Pro Gly Leu Phe Gly Ala Ala Ala Gln
         30                   35                   40 tgacgccatc aaggatgtct tggttctctg ttccttcttc ttggttcagg cttctggatt      527
gtcctcaggc tggctcctca tagggatgct gggtgctgca gccttgactg gggcagcagg      587
cccccatggt tcaatccatc ctcccacctt ggaataaatg ctttcttttc acaatgagaa      647
aaaaaaaaaa                                                             657

<210> SEQ ID NO 70
<211> LENGTH: 416
<212> TYPE: DNA
<213> ORGANISM: Homo sapiens
<220> FEATURE:
<221> NAME/KEY: sig_peptide
<222> LOCATION: 140..205
```

```
<223> OTHER INFORMATION: Von Heijne matrix
      score 5.90000009536743
      seq IILGCLALFLLLQ/RK
<221> NAME/KEY: polyA_signal
<222> LOCATION: 383..388
<221> NAME/KEY: polyA_site
<222> LOCATION: 405..416
<221> NAME/KEY: misc_feature
<222> LOCATION: 225..316
<223> OTHER INFORMATION: homology
      id :AA398040
      est

<400> SEQUENCE: 70
aacagttacg aaggagagct gcaaaagttg cagcagaaag gttgggagtc ccgacaggtt    60
ccgtagccca cagaaaagaa gcaagggacg gcaggactgt ttcacacttt tctgcttctg   120
gaaggtgctg gacaaaaac atg gaa cta att tcc cca aca gtg att ata atc    172
                    Met Glu Leu Ile Ser Pro Thr Val Ile Ile Ile
                         -20                 -15 ctg ggt tgc ctt gct ctg ttc tta ctc ctt cag cgg aag aat ttg cgc    220
Leu Gly Cys Leu Ala Leu Phe Leu Leu Leu Gln Arg Lys Asn Leu Arg
    -10                  -5                 1                 5 aga ccc ccg tgc atc aag ggc tgg att cct tgg att gga gtt gga ttt    268
Arg Pro Pro Cys Ile Lys Gly Trp Ile Pro Trp Ile Gly Val Gly Phe
                 10                 15                 20 gag ttt ggg aaa gcc cct cta gaa ttt ata gag aaa gca aga atc aag    316
Glu Phe Gly Lys Ala Pro Leu Glu Phe Ile Glu Lys Ala Arg Ile Lys
             25                 30                 35 tat gga cca ata ttt aca gtc ttt gct atg gga aac cga atg acc ttt    364
Tyr Gly Pro Ile Phe Thr Val Phe Ala Met Gly Asn Arg Met Thr Phe
         40                 45                 50 gtt act gaa gaa gga agg aat taatgtgttt ctaaaatcca aaaaaaaaa a      416
Val Thr Glu Glu Gly Arg Asn
     55                 60

<210> SEQ ID NO 71
<211> LENGTH: 543
<212> TYPE: DNA
<213> ORGANISM: Homo sapiens
<220> FEATURE:
<221> NAME/KEY: sig_peptide
<222> LOCATION: 129..176
<223> OTHER INFORMATION: Von Heijne matrix
      score 4.80000019073486
      seq SLFIYIFLTCSNT/SP
<221> NAME/KEY: polyA_signal
<222> LOCATION: 513..518
<221> NAME/KEY: polyA_site
<222> LOCATION: 530..543
<221> NAME/KEY: misc_feature
<222> LOCATION: 264..500
<223> OTHER INFORMATION: homology
      id :AA534039
      est
<221> NAME/KEY: misc_feature
<222> LOCATION: 205..315
<223> OTHER INFORMATION: homology
      id :T82645
      est
<221> NAME/KEY: misc_feature
<222> LOCATION: 295..382
<223> OTHER INFORMATION: homology
      id :T82645
      est
<221> NAME/KEY: misc_feature
<222> LOCATION: 375..405
<223> OTHER INFORMATION: homology
      id :T82645
      est
<221> NAME/KEY: misc_feature
```

```
<222> LOCATION: 50
<223> OTHER INFORMATION: n=a, g, c or t

<400> SEQUENCE: 71
actgtcccat tcctccccct acaacacaca cacctttcag gcagggasgn gatgagcttc      60
cagccccaag agtggaggct gccacatcct aacatasgta tctattgaaa aggaagcagt    120 gtgtatct atg att ata tct ctg ttc atc tat ata ttt ttg aca tgt agc    170
         Met Ile Ile Ser Leu Phe Ile Tyr Ile Phe Leu Thr Cys Ser
             -15                 -10                  -5 aac acc tct cca tct tat caa gga act caa ctc ggt ctg ggt ctc ccc     218
Asn Thr Ser Pro Ser Tyr Gln Gly Thr Gln Leu Gly Leu Gly Leu Pro
 1               5                   10 agt gcc cag tgg tgg cct ttg aca ggt agg agg atg cag tgc tgc agg     266
Ser Ala Gln Trp Trp Pro Leu Thr Gly Arg Arg Met Gln Cys Cys Arg
15                  20                  25                  30 cta ttt tgt ttt ttg tta caa aac tgt ctt ttc cct ttt ccc ctc cac     314
Leu Phe Cys Phe Leu Leu Gln Asn Cys Leu Phe Pro Phe Pro Leu His
                 35                  40                  45 ctg att cag cat gat ccc tgt gag ctg gtt ctc aca atc tcc tgg gac     362
Leu Ile Gln His Asp Pro Cys Glu Leu Val Leu Thr Ile Ser Trp Asp
             50                  55                  60 tgg gct gag gca ggg gct tcg ctc tat tct ccc taaccatact gtcttccttt   415
Trp Ala Glu Ala Gly Ala Ser Leu Tyr Ser Pro
         65                  70 ccccccttgcc acttagcagt tatcccccca gctatgcctt ctccctccct cccttgccct   475
ggcatatatt gtgccttatt tatgctgcaa atataacatt aaactatcaa gtgaaaaaaa   535
aaaaaaaa                                                              543

<210> SEQ ID NO 72
<211> LENGTH: 605
<212> TYPE: DNA
<213> ORGANISM: Homo sapiens
<220> FEATURE:
<221> NAME/KEY: sig_peptide
<222> LOCATION: 285..341
<223> OTHER INFORMATION: Von Heijne matrix
      score 5.59999990463257
      seq PTLCVSSSPALWA/AS
<221> NAME/KEY: polyA_signal
<222> LOCATION: 575..580
<221> NAME/KEY: polyA_site
<222> LOCATION: 592..605
<221> NAME/KEY: misc_feature
<222> LOCATION: 53..296
<223> OTHER INFORMATION: homology
      id :W07033
      est
<221> NAME/KEY: misc_feature
<222> LOCATION: 348..432
<223> OTHER INFORMATION: homology
      id :W07033
      est
<221> NAME/KEY: misc_feature
<222> LOCATION: 435..497
<223> OTHER INFORMATION: homology
      id :W07033
      est
<221> NAME/KEY: misc_feature
<222> LOCATION: 293..337
<223> OTHER INFORMATION: homology
      id :W07033
      est
<221> NAME/KEY: misc_feature
<222> LOCATION: 521..560
<223> OTHER INFORMATION: homology
      id :W07033
      est
```

```
<221> NAME/KEY: misc_feature
<222> LOCATION: 489..520
<223> OTHER INFORMATION: homology
      id :W07033
      est
<221> NAME/KEY: misc_feature
<222> LOCATION: 15..337
<223> OTHER INFORMATION: homology
      id :AA151004
      est
<221> NAME/KEY: misc_feature
<222> LOCATION: 348..412
<223> OTHER INFORMATION: homology
      id :AA151004
      est
<221> NAME/KEY: misc_feature
<222> LOCATION: 434..485
<223> OTHER INFORMATION: homology
      id :AA151004
      est
<221> NAME/KEY: misc_feature
<222> LOCATION: 83..324
<223> OTHER INFORMATION: homology
      id :AA476506
      est
<221> NAME/KEY: misc_feature
<222> LOCATION: 347..560
<223> OTHER INFORMATION: homology
      id :AA476506
      est
<221> NAME/KEY: misc_feature
<222> LOCATION: 16..347
<223> OTHER INFORMATION: homology
      id :W56567
      est
<221> NAME/KEY: misc_feature
<222> LOCATION: 350..405
<223> OTHER INFORMATION: homology
      id :W56567
      est
<221> NAME/KEY: misc_feature
<222> LOCATION: 433..470
<223> OTHER INFORMATION: homology
      id :W56567
      est
<221> NAME/KEY: misc_feature
<222> LOCATION: 15..296
<223> OTHER INFORMATION: homology
      id :AA147584
      est
<221> NAME/KEY: misc_feature
<222> LOCATION: 348..421
<223> OTHER INFORMATION: homology
      id :AA147584
      est
<221> NAME/KEY: misc_feature
<222> LOCATION: 293..337
<223> OTHER INFORMATION: homology
      id :AA147584
      est
<221> NAME/KEY: misc_feature
<222> LOCATION: 419..453
<223> OTHER INFORMATION: homology
      id :AA147584
      est
<221> NAME/KEY: misc_feature
<222> LOCATION: 2..338
<223> OTHER INFORMATION: homology
      id :AA281959
      est
<221> NAME/KEY: misc_feature
<222> LOCATION: 350..432
<223> OTHER INFORMATION: homology
      id :AA281959
      est

<400> SEQUENCE: 72
aacgcctwta agacagcgga actaagaaaa gaagaggcct gtggacagaa caatcatgtc     60
```

```
tgactccctg gtggtgtgcg aggtagaccc agagctaaca gaaaagctga kgaaattccg      120
cttccgaaaa gagacagaca atgcagccat cataatgaag gtggacaaag accggcagat      180
ggtggtgctg gaggaagaat tcagaacat ttccccagag gagctcaaaa tggagttgcc       240
```

```
tgactccctg gtggtgtgcg aggtagaccc agagctaaca gaaaagctga kgaaattccg      120
cttccgaaaa gagacagaca atgcagccat cataatgaag gtggacaaag accggcagat      180
ggtggtgctg gaggaagaat tcagaacat  ttccccagag gagctcaaaa tggagttgcc      240
ggagagacag cccaggttcg tggtttacag ctacaagtac gtgc atg acg atg gcc       296
                                                 Met Thr Met Ala gag tgt cct acc ctt tgt gtt tca tct tct cca gcc ctg tgg gct gca        344
Glu Cys Pro Thr Leu Cys Val Ser Ser Ser Pro Ala Leu Trp Ala Ala
-15          Thr    -10              -5                      1 agc gaa aca aca gat gat gta tgc agg gag taaaaacagg ctggtgcaga          394
Ser Glu Thr Thr Asp Asp Val Cys Arg Glu
             5                   10 cagcagagct cacaaaggtg ttcgaaatcc gcaccactga tgacctcact gaggcctggc      454
tccaagaaaa gttgtctttc tttcgttgat ctctgggctg gggactgaat tcctgatgtc      514
tgagtcctca aggtgactgg ggacttggaa ccccctaggac ctgaacaacc aaggactta     574 aataaatttt aaaatgcaaa aaaaaaaaa a                                      605
```

```
<210> SEQ ID NO 73
<211> LENGTH: 864
<212> TYPE: DNA
<213> ORGANISM: Homo sapiens
<220> FEATURE:
<221> NAME/KEY: sig_peptide
<222> LOCATION: 136..444
<223> OTHER INFORMATION: Von Heijne matrix
      score 4.90000009536743
      seq VYAFLGLTAPSGS/KE
<221> NAME/KEY: polyA_signal
<222> LOCATION: 835..840
<221> NAME/KEY: polyA_site
<222> LOCATION: 851..864
<221> NAME/KEY: misc_feature
<222> LOCATION: 222..456
<223> OTHER INFORMATION: homology
      id :AA136758
      est
<221> NAME/KEY: misc_feature
<222> LOCATION: 557..648
<223> OTHER INFORMATION: homology
      id :AA136758
      est
<221> NAME/KEY: misc_feature
<222> LOCATION: 501..571
<223> OTHER INFORMATION: homology
      id :AA136758
      est
<221> NAME/KEY: misc_feature
<222> LOCATION: 130..456
<223> OTHER INFORMATION: homology
      id :AA393612
      est
<221> NAME/KEY: misc_feature
<222> LOCATION: 88..130
<223> OTHER INFORMATION: homology
      id :AA393612
      est
<221> NAME/KEY: misc_feature
<222> LOCATION: 501..538
<223> OTHER INFORMATION: homology
      id :AA393612
      est
<221> NAME/KEY: misc_feature
<222> LOCATION: 130..458
<223> OTHER INFORMATION: homology
      id :R59039
      est
<221> NAME/KEY: misc_feature
<222> LOCATION: 71..130
<223> OTHER INFORMATION: homology
```

```
        id :R59039
        est
<221> NAME/KEY: misc_feature
<222> LOCATION: 557..716
<223> OTHER INFORMATION: homology
        id :W48624
        est
<221> NAME/KEY: misc_feature
<222> LOCATION: 365..456
<223> OTHER INFORMATION: homology
        id :W48624
        est
<221> NAME/KEY: misc_feature
<222> LOCATION: 501..571
<223> OTHER INFORMATION: homology
        id :W48624
        est
<221> NAME/KEY: misc_feature
<222> LOCATION: 716..751
<223> OTHER INFORMATION: homology
        id :W48624
        est
<221> NAME/KEY: misc_feature
<222> LOCATION: 222..458
<223> OTHER INFORMATION: homology
        id :AA136810
        est
<221> NAME/KEY: misc_feature
<222> LOCATION: 501..581
<223> OTHER INFORMATION: homology
        id :AA136810
        est
<221> NAME/KEY: misc_feature
<222> LOCATION: 587..668
<223> OTHER INFORMATION: homology
        id :AA136810
        est
<221> NAME/KEY: misc_feature
<222> LOCATION: 130..419
<223> OTHER INFORMATION: homology
        id :T35647
        est
<221> NAME/KEY: misc_feature
<222> LOCATION: 59..130
<223> OTHER INFORMATION: homology
        id :T35647
        est
<221> NAME/KEY: misc_feature
<222> LOCATION: 557..852
<223> OTHER INFORMATION: homology
        id :HUM093F06A
        est
<221> NAME/KEY: misc_feature
<222> LOCATION: 501..571
<223> OTHER INFORMATION: homology
        id :HUM093F06A
        est
<221> NAME/KEY: misc_feature
<222> LOCATION: 130..384
<223> OTHER INFORMATION: homology
        id :T35666
        est

<400> SEQUENCE: 73
aaagttctcc ttccaccttc ccccacccct ctctgccaac cgctgtttca gcccctagct        60
ggattccagc cattgctgca gctgctccac agccctttc aggacccaaa caaccgcagc       120
cgctgttccc caggr atg gtg atc cgt gta tat att gca tct tcc tct ggc       171
              Met Val Ile Arg Val Tyr Ile Ala Ser Ser Ser Gly
                  -100                  -95 tct aca gcg att aag aag aaa caa caa gat gtg ctt ggt ttc cta gaa        219
Ser Thr Ala Ile Lys Lys Lys Gln Gln Asp Val Leu Gly Phe Leu Glu
    -90                 -85                 -80 gcc aac aaa ata gga ttt gaa gaa aaa gat att gca gcc aat gaa gag        267
Ala Asn Lys Ile Gly Phe Glu Glu Lys Asp Ile Ala Ala Asn Glu Glu
```

```
         -75                  -70                  -65                  -60
aat cgg aag tgg atg aga gaa aat gta cct gaa aat agt cga cca gcc            315
Asn Arg Lys Trp Met Arg Glu Asn Val Pro Glu Asn Ser Arg Pro Ala
                    -55                  -50                  -45 aca ggt aac ccc ctg cca cct cag att ttc aat gaa agc cag tat cgc            363
Thr Gly Asn Pro Leu Pro Pro Gln Ile Phe Asn Glu Ser Gln Tyr Arg
            -40                  -35                  -30 ggg gac tat gat gcc ttc ttt gaa gcc aga gaa aat aat gca gtg tat            411
Gly Asp Tyr Asp Ala Phe Phe Glu Ala Arg Glu Asn Asn Ala Val Tyr
        -25                  -20                  -15 gcc ttc tta ggc ttg aca gcc cca tct ggt tca aag gaa gca gga agg            459
Ala Phe Leu Gly Leu Thr Ala Pro Ser Gly Ser Lys Glu Ala Gly Arg
    -10                  -5                    1                    5 tgc aag caa agc agc aag cca tgaaccttga gcactgtgct tttaagcatc               510
Cys Lys Gln Ser Ser Lys Pro
                10 ctgaaaaatg agtctccatt gcttttataa aatagcagaa ttagctttgc sttcaaaaga         570 aataggstta atgttgaaat aatagattag ttgggttttc acatgcaaac amtcaaaatg         630 aatacaaaat taaatttga acattatggt gattatggtg aggagaatgg gatattaaca          690 taaaattata ttaataagta gatatygtag aaatagtgtt gttacctgcc aagccatcct         750 gtatacacca atgatttac aaagaaaaca cccttccctc cttytgccat tamtatggca          810 acctaagtgt atytgcagct ttacattaaa aaggagaaag agaaaaaaaa aaaa                864

<210> SEQ ID NO 74
<211> LENGTH: 1033
<212> TYPE: DNA
<213> ORGANISM: Homo sapiens
<220> FEATURE:
<221> NAME/KEY: sig_peptide
<222> LOCATION: 200..427
<223> OTHER INFORMATION: Von Heijne matrix
      score 4.69999980926514
      seq LIVYLWVVSFIAS/SS
<221> NAME/KEY: polyA_signal
<222> LOCATION: 1001..1006
<221> NAME/KEY: polyA_site
<222> LOCATION: 1022..1033
<221> NAME/KEY: misc_feature
<222> LOCATION: 55..406
<223> OTHER INFORMATION: homology
      id :AA056667
      est
<221> NAME/KEY: misc_feature
<222> LOCATION: 397..487
<223> OTHER INFORMATION: homology
      id :AA056667
      est
<221> NAME/KEY: misc_feature
<222> LOCATION: 527..584
<223> OTHER INFORMATION: homology
      id :AA056667
      est
<221> NAME/KEY: misc_feature
<222> LOCATION: 482..531
<223> OTHER INFORMATION: homology
      id :AA056667
      est
<221> NAME/KEY: misc_feature
<222> LOCATION: 581..634
<223> OTHER INFORMATION: homology
      id :AA056667
      est
<221> NAME/KEY: misc_feature
<222> LOCATION: 397..700
<223> OTHER INFORMATION: homology
      id :AA044187
      est
```

```
<221> NAME/KEY: misc_feature
<222> LOCATION: 222..406
<223> OTHER INFORMATION: homology
      id :AA044187
      est
<221> NAME/KEY: misc_feature
<222> LOCATION: 693..748
<223> OTHER INFORMATION: homology
      id :AA044187
      est
<221> NAME/KEY: misc_feature
<222> LOCATION: 68..406
<223> OTHER INFORMATION: homology
      id :AA131958
      est
<221> NAME/KEY: misc_feature
<222> LOCATION: 397..517
<223> OTHER INFORMATION: homology
      id :AA131958
      est
<221> NAME/KEY: misc_feature
<222> LOCATION: 510..558
<223> OTHER INFORMATION: homology
      id :AA131958
      est
<221> NAME/KEY: misc_feature
<222> LOCATION: 77..531
<223> OTHER INFORMATION: homology
      id :W95957
      est
<221> NAME/KEY: misc_feature
<222> LOCATION: 527..558
<223> OTHER INFORMATION: homology
      id :W95957
      est
<221> NAME/KEY: misc_feature
<222> LOCATION: 397..586
<223> OTHER INFORMATION: homology
      id :AA041216
      est
<221> NAME/KEY: misc_feature
<222> LOCATION: 286..406
<223> OTHER INFORMATION: homology
      id :AA041216
      est
<221> NAME/KEY: misc_feature
<222> LOCATION: 582..700
<223> OTHER INFORMATION: homology
      id :AA041216
      est
<221> NAME/KEY: misc_feature
<222> LOCATION: 77..406
<223> OTHER INFORMATION: homology
      id :W95790
      est
<221> NAME/KEY: misc_feature
<222> LOCATION: 397..539
<223> OTHER INFORMATION: homology
      id :W95790
      est
<221> NAME/KEY: misc_feature
<222> LOCATION: 474..760
<223> OTHER INFORMATION: homology
      id :AA461134
      est
<221> NAME/KEY: misc_feature
<222> LOCATION: 788..940
<223> OTHER INFORMATION: homology
      id :AA461134
      est

<400> SEQUENCE: 74
aagacgaggt catgaatcat gtgacggtgg cttgaggagg aacctgtctt taaagctgtc    60
cctgaagtga cagcggagag aaccaggcag cccagaaacc ccaggcgtgg agattgatcc   120
tgcgagagaa gggggttcat catggcggat gacctaaagc gattccttgta taaaaagtta   180
```

-continued

| | |
|---|---|
| ccaagtgttg aagggctcc atg cca ttg ttg tgt cag ata gag atg gag tac<br>                             Met Pro Leu Leu Cys Gln Ile Glu Met Glu Tyr<br>                                -75                        -70 | 232 |
| ctg tta tta aag tgg caa atg aca atg ctc cag agc atg ctt tgc gac<br>Leu Leu Leu Lys Trp Gln Met Thr Met Leu Gln Ser Met Leu Cys Asp<br>-65               -60                   -55                   -50 | 280 |
| ctg gtt tct tat cca ctt ttg ccc ttg caa cag acc aag gaa gca aac<br>Leu Val Ser Tyr Pro Leu Leu Pro Leu Gln Gln Thr Lys Glu Ala Asn<br>           -45                   -40                   -35 | 328 |
| ttg gac ttt cca aaa ata aaa gta tca tct gtt act ata aca cct acc<br>Leu Asp Phe Pro Lys Ile Lys Val Ser Ser Val Thr Ile Thr Pro Thr<br>-30                -25                   -20 | 376 |
| agg tgg ttc aat tta atc gtt tac ctt tgg gtg gtg agt ttc ata gcc<br>Arg Trp Phe Asn Leu Ile Val Tyr Leu Trp Val Val Ser Phe Ile Ala<br>   -15               -10                   -5 | 424 |
| agc agc agt gcc aat aca gga cta att gtc agc cta gaa aag gaa ctt<br>Ser Ser Ser Ala Asn Thr Gly Leu Ile Val Ser Leu Glu Lys Glu Leu<br>1                5                   10                  15 | 472 |
| gct cca ttg ttt gaa gaa ctg aga caa gtt gtg gaa gtt tct<br>Ala Pro Leu Phe Glu Glu Leu Arg Gln Val Val Glu Val Ser<br>        20                   25 | 514 |
| taatctgaca gtggtttcag tgtgtacctt atcttcatta taacaacaca atatcaatcc | 574 |
| agcaatcttt agactacaat aatactttta tccatgtgct caagaaaggg ccccttttttc | 634 |
| caacttatac taaagagcta gcatatagat gtaatttata gatagatcag ttgctatatt | 694 |
| ttctggtgta gggtctttct tatttagtga gatctaggga taccacagaa atggttcagt | 754 |
| ctatcaacag ctcccatgga gttagtctgg tcacagatat ggatgagaga ttytattcag | 814 |
| tggatcagaa tcaaactggt acattgatcc acttgagccg ttaagtgctg ccaattgtac | 874 |
| aatatgccca ggcttgcaga ataaagccaa ctttttattg tgaataataa taaggacata | 934 |
| ttttttyttca gattatgttt tatttyttttg cattgagtga ggaacataaa atggcttggt | 994 |
| aaaagtaata aaatcagtac aatcactaaa aaaaaaaa | 1033 |

<210> SEQ ID NO 75
<211> LENGTH: 499
<212> TYPE: DNA
<213> ORGANISM: Homo sapiens
<220> FEATURE:
<221> NAME/KEY: sig_peptide
<222> LOCATION: 68..133
<223> OTHER INFORMATION: Von Heijne matrix
    score 9.80000019073486
    seq LVVFCLALQLVPG/SP
<221> NAME/KEY: polyA_signal
<222> LOCATION: 472..477
<221> NAME/KEY: polyA_site
<222> LOCATION: 490..499

<400> SEQUENCE: 75

| | |
|---|---|
| aaacagcagt gcctggtcaa acccagcaac ccttggccag aacttactca cccatcccac | 60 |
| tgacacc atg aag cct gtg ctg cct ctc cag ttc ctg gtg gtg ttc tgc<br>       Met Lys Pro Val Leu Pro Leu Gln Phe Leu Val Val Phe Cys<br>              -20                   -15                 -10 | 109 |
| cta gca ctg cag ctg gtg cct ggg agt ccc aag cag cgt gtt ctg aag<br>Leu Ala Leu Gln Leu Val Pro Gly Ser Pro Lys Gln Arg Val Leu Lys<br>   -5                       1                       5 | 157 |
| tat atc ttg gaa cct cca ccc tgc ata tca gca cct gaa aac tgt act<br>Tyr Ile Leu Glu Pro Pro Pro Cys Ile Ser Ala Pro Glu Asn Cys Thr<br>    10                  15                   20 | 205 |
| cac ctg tgt aca atg cag gaa gat tgc gag aaa gga ttt cag tgc tgt | 253 |

| | | | | | | | | | | | | | |
|---|---|---|---|---|---|---|---|---|---|---|---|---|---|
|His|Leu|Cys|Thr|Met|Gln|Glu|Asp|Cys|Glu|Lys|Gly|Phe|Gln Cys Cys|
|25| | | |30| | | |35| | | |40| |

```
tcc tcc ttc tgt ggg ata gtc tgt tca tca gaa aca ttt caa aag cgc       301
Ser Ser Phe Cys Gly Ile Val Cys Ser Ser Glu Thr Phe Gln Lys Arg
            45                  50                  55 aac aga atc aaa cac aag ggc tca gaa gtc atc atg cct gcc aac           346
Asn Arg Ile Lys His Lys Gly Ser Glu Val Ile Met Pro Ala Asn
        60                  65                  70 tgaggcatat ttcctagatc attttgcctc tacgatgttt tttcttggtc cacctttagg     406
aaggtattga gaagcaagaa actggaggcc caatatctaa cctgcaaatc gttttttgagt    466 ttggcaataa aggctaatct accaaaaaaa aaa                                  499
```

<210> SEQ ID NO 76
<211> LENGTH: 978
<212> TYPE: DNA
<213> ORGANISM: Homo sapiens
<220> FEATURE:
<221> NAME/KEY: sig_peptide
<222> LOCATION: 274..399
<223> OTHER INFORMATION: Von Heijne matrix
      score 5.19999980926514
      seq LLFDLVCHEFCQS/DD
<221> NAME/KEY: polyA_signal
<222> LOCATION: 943..948
<221> NAME/KEY: polyA_site
<222> LOCATION: 966..978
<221> NAME/KEY: misc_feature
<222> LOCATION: 335..518
<223> OTHER INFORMATION: homology
      id :AA206225
      est
<221> NAME/KEY: misc_feature
<222> LOCATION: 225..274
<223> OTHER INFORMATION: homology
      id :AA206225
      est
<221> NAME/KEY: misc_feature
<222> LOCATION: 812..861
<223> OTHER INFORMATION: homology
      id :AA206225
      est
<221> NAME/KEY: misc_feature
<222> LOCATION: 186..224
<223> OTHER INFORMATION: homology
      id :AA206225
      est
<221> NAME/KEY: misc_feature
<222> LOCATION: 708..748
<223> OTHER INFORMATION: homology
      id :AA206225
      est
<221> NAME/KEY: misc_feature
<222> LOCATION: 276..314
<223> OTHER INFORMATION: homology
      id :AA206225
      est
<221> NAME/KEY: misc_feature
<222> LOCATION: 146..176
<223> OTHER INFORMATION: homology
      id :AA206225
      est
<221> NAME/KEY: misc_feature
<222> LOCATION: 879..909
<223> OTHER INFORMATION: homology
      id :AA206225
      est
<221> NAME/KEY: misc_feature
<222> LOCATION: 182..518
<223> OTHER INFORMATION: homology
      id :C15003
      est
<221> NAME/KEY: misc_feature
<222> LOCATION: 708..748

```
<223> OTHER INFORMATION: homology
      id :C15003
      est
<221> NAME/KEY: misc_feature
<222> LOCATION: 182..517
<223> OTHER INFORMATION: homology
      id :HUM407E11B
      est
<221> NAME/KEY: misc_feature
<222> LOCATION: 170..202
<223> OTHER INFORMATION: homology
      id :AA544037
      est
<221> NAME/KEY: misc_feature
<222> LOCATION: 517..595
<223> OTHER INFORMATION: homology
      id :HUM00TW170
      est
<221> NAME/KEY: misc_feature
<222> LOCATION: 596..665
<223> OTHER INFORMATION: homology
      id :HUM00TW170
      est
<221> NAME/KEY: misc_feature
<222> LOCATION: 697..748
<223> OTHER INFORMATION: homology
      id :HUM00TW170
      est
<221> NAME/KEY: misc_feature
<222> LOCATION: 805..861
<223> OTHER INFORMATION: homology
      id :HUM00TW170
      est
<221> NAME/KEY: misc_feature
<222> LOCATION: 212..369
<223> OTHER INFORMATION: homology
      id :HUM169E08B
      est
<221> NAME/KEY: misc_feature
<222> LOCATION: 406..493
<223> OTHER INFORMATION: homology
      id :HUM169E08B
      est
<221> NAME/KEY: misc_feature
<222> LOCATION: 542..595
<223> OTHER INFORMATION: homology
      id :HUM00TW112
      est
<221> NAME/KEY: misc_feature
<222> LOCATION: 697..748
<223> OTHER INFORMATION: homology
      id :HUM00TW112
      est

<400> SEQUENCE: 76
accaggaaca tccagctatt tatgatagca tttgcttcat tatgtcaagt tcaacaaatg      60
ttgacttgct ggtgaaggtg ggggaggttg tggacaagct ctttgatttg gatgagaaac    120
taatgttaag aatgggtcag aaatggggct gctcagcctc tggaccaacc ccaggaagag    180
tctgaagagc agccagtgtt tcggcttgtg ccctgtatac ttgaagctgc caaacaagta    240
cgttctgaaa atccagaatg gcttgatgtt tac atg cac att tta caa ctg ctt    294
                                   Met His Ile Leu Gln Leu Leu
                                                          -40 act aca gtg gat gat gga att caa gca att gta cat tgt cct gac act      342
Thr Thr Val Asp Asp Gly Ile Gln Ala Ile Val His Cys Pro Asp Thr
-35                 -30                 -25                 -20 gga aaa gac att tgg aat tta ctt ttt gac ctg gtc tgc cat gaa ttc      390
Gly Lys Asp Ile Trp Asn Leu Leu Phe Asp Leu Val Cys His Glu Phe
            -15                 -10                 -5 tgc cag tct gat gat cca gcc atc att ctt caa gaa cag aaa aca gtg    438
Cys Gln Ser Asp Asp Pro Ala Ile Ile Leu Gln Glu Gln Lys Thr Val
        1               5                   10
```

```
cta gcc tct gtt ttt tca gtg ttg tct gcc atc tat gcc tca cag act       486
Leu Ala Ser Val Phe Ser Val Leu Ser Ala Ile Tyr Ala Ser Gln Thr
    15                  20                  25 gag caa gag tat cta aag ata gaa aaa gta gat ctt cct cta att gac       534
Glu Gln Glu Tyr Leu Lys Ile Glu Lys Val Asp Leu Pro Leu Ile Asp
30                  35                  40                  45 agc ctc att cgg gtc tta caa aat atg gaa cag tgt cag aaa aaa cca       582
Ser Leu Ile Arg Val Leu Gln Asn Met Glu Gln Cys Gln Lys Lys Pro
                50                  55                  60 gag aac tcg gca gga gtc taacacagag gaaactaaaa ggactgattt              630
Glu Asn Ser Ala Gly Val
                65 aacccaagat gatttccact tgaaaatctt aaaaggatat tgttatggtg aagtttctgt     690 ctaataattt ttcaggcatt aacaaggag acggtggctc agggagtaaa ggaaggccgt      750 tgagcaaaca gaagtgttcc tctgcaattt caaaarcctt cttctttcta tagcccctgt    810 gggtggaaga ttttattaaa atcctacgtg aagttgataa ggcgcttgct kgatgacttg    870 gaaaaaaamc ttcccaagtt tgaaggttca gaastaaaaa rscktgaatg ggaattactt    930 sstgtbcaag aaaataaact ttattttttct cactgaaaaa aaaaaaaa                978

<210> SEQ ID NO 77
<211> LENGTH: 587
<212> TYPE: DNA
<213> ORGANISM: Homo sapiens
<220> FEATURE:
<221> NAME/KEY: sig_peptide
<222> LOCATION: 421..465
<223> OTHER INFORMATION: Von Heijne matrix
      score 3.90000009536743
      seq LVPLGQSFPLSEP/RC
<221> NAME/KEY: polyA_signal
<222> LOCATION: 553..558
<221> NAME/KEY: polyA_site
<222> LOCATION: 575..587
<221> NAME/KEY: misc_feature
<222> LOCATION: 182..322
<223> OTHER INFORMATION: homology
      id :T35951
      est
<221> NAME/KEY: misc_feature
<222> LOCATION: 32..132
<223> OTHER INFORMATION: homology
      id :T35951
      est
<221> NAME/KEY: misc_feature
<222> LOCATION: 136..193
<223> OTHER INFORMATION: homology
      id :T35951
      est
<221> NAME/KEY: misc_feature
<222> LOCATION: 182..322
<223> OTHER INFORMATION: homology
      id :T35949
      est
<221> NAME/KEY: misc_feature
<222> LOCATION: 32..132
<223> OTHER INFORMATION: homology
      id :T35949
      est
<221> NAME/KEY: misc_feature
<222> LOCATION: 136..193
<223> OTHER INFORMATION: homology
      id :T35949
      est
<221> NAME/KEY: misc_feature
<222> LOCATION: 136..299
<223> OTHER INFORMATION: homology
      id :AA381111
      est
```

```
<221> NAME/KEY: misc_feature
<222> LOCATION: 32..132
<223> OTHER INFORMATION: homology
      id :AA381111
      est
<221> NAME/KEY: misc_feature
<222> LOCATION: 136..322
<223> OTHER INFORMATION: homology
      id :AA381001
      est
<221> NAME/KEY: misc_feature
<222> LOCATION: 85..132
<223> OTHER INFORMATION: homology
      id :AA381001
      est
<221> NAME/KEY: misc_feature
<222> LOCATION: 182..322
<223> OTHER INFORMATION: homology
      id :HSCZQE041
      est
<221> NAME/KEY: misc_feature
<222> LOCATION: 136..193
<223> OTHER INFORMATION: homology
      id :HSCZQE041
      est
<221> NAME/KEY: misc_feature
<222> LOCATION: 82..132
<223> OTHER INFORMATION: homology
      id :HSCZQE041
      est
<221> NAME/KEY: misc_feature
<222> LOCATION: 316..428
<223> OTHER INFORMATION: homology
      id :AA477628
      est
<221> NAME/KEY: misc_feature
<222> LOCATION: 475..554
<223> OTHER INFORMATION: homology
      id :AA477628
      est
<221> NAME/KEY: misc_feature
<222> LOCATION: 182..322
<223> OTHER INFORMATION: homology
      id :HSC34G011
      est
<221> NAME/KEY: misc_feature
<222> LOCATION: 136..192
<223> OTHER INFORMATION: homology
      id :HSC34G011
      est
<221> NAME/KEY: misc_feature
<222> LOCATION: 41..119
<223> OTHER INFORMATION: homology
      id :AA090647
      est
<221> NAME/KEY: misc_feature
<222> LOCATION: 136..184
<223> OTHER INFORMATION: homology
      id :AA090647
      est
<221> NAME/KEY: misc_feature
<222> LOCATION: 316..426
<223> OTHER INFORMATION: homology
      id :AA505962
      est

<400> SEQUENCE: 77
aattcatttt tcactcctcc ctcctaggtc acacttttca gaaaagaat  ctgcatcctg      60 gaaaccagaa gaaaaatatg agacggggaa tcatcgtgtg atgtgtgtgc tgcctttggc     120
tkwgtgtgtk gaagtycckg ctcaggtgtt aggtacagtg tgtttgatcg tggtggcttg     180
aggggaaccc gctgttcaga gctgtgactg cggctgcact cagagaagct gcccttggct     240
gctcgtagcg ccgggccttc tctcctcgtc atcatccaga gcagccagtg tccgggaggc     300
agaagatgcc ccactccagc ctctggactg ggggctctct tcagtggctg aatgtccagc     360
```

```
agagctattt ccttccacag ggggccttgc agggaagggt ccaggacttg acatcttaag        420 atg cgt ctt gtc ccc ttg ggc cag tca ttt ccc ctc tct gag cct cgg        468
Met Arg Leu Val Pro Leu Gly Gln Ser Phe Pro Leu Ser Glu Pro Arg
-15             -10                 -5                  1 tgt ctt caa cct gtg aaa tgg gat cat aat cac tgc ctt acc tcc ctc        516
Cys Leu Gln Pro Val Lys Trp Asp His Asn His Cys Leu Thr Ser Leu
        5                   10                  15 acg gtt gtt gtg agg act gag tgt gtg gaa gtt ttt cat aaa ctt tgg        564
Thr Val Val Val Arg Thr Glu Cys Val Glu Val Phe His Lys Leu Trp
            20                  25                  30 atg cta gtg taaaaaaaaa aaaa                                              587
Met Leu Val
    35

<210> SEQ ID NO 78
<211> LENGTH: 400
<212> TYPE: DNA
<213> ORGANISM: Homo sapiens
<220> FEATURE:
<221> NAME/KEY: sig_peptide
<222> LOCATION: 198..278
<223> OTHER INFORMATION: Von Heijne matrix
      score 4.90000009536743
      seq CLLSYIALGAIHA/KI
<221> NAME/KEY: polyA_signal
<222> LOCATION: 364..369
<221> NAME/KEY: polyA_site
<222> LOCATION: 387..400

<400> SEQUENCE: 78
aactttgcct gggtgtcttg cgttctgcac attccggagg accagcttcc ccatcagaag        60
tctgactcca tggaaaccag atggggcaac ggggtggttc tagtgcagac tgtagctgca       120
gctcctctcc acctctagcc tgctcattc cagctcagaa attctactaa tggcgttttt        180
tcttcctgaa aaggaa atg aac agg gtc cct gct gat tct cca aat atg           230
               Met Asn Arg Val Pro Ala Asp Ser Pro Asn Met
               -25                 -20 tgt cta atc tgt tta ctg agt tac ata gca ctt gga gcc atc cat gca        278
Cys Leu Ile Cys Leu Leu Ser Tyr Ile Ala Leu Gly Ala Ile His Ala
-15                 -10                 -5 aaa atc tgt aga aga gca ttc cag gaa gag gga aga gca aat gca aag        326
Lys Ile Cys Arg Arg Ala Phe Gln Glu Glu Gly Arg Ala Asn Ala Lys
1               5                   10                  15 acg ggc gtg aga gct tgg tgc ata cag cca tgg gcc aaa taagtttcc          375
Thr Gly Val Arg Ala Trp Cys Ile Gln Pro Trp Ala Lys
            20                  25 ttggaatagc caaaaaaaaa aaaaa                                             400

<210> SEQ ID NO 79
<211> LENGTH: 1166
<212> TYPE: DNA
<213> ORGANISM: Homo sapiens
<220> FEATURE:
<221> NAME/KEY: sig_peptide
<222> LOCATION: 167..229
<223> OTHER INFORMATION: Von Heijne matrix
      score 5.59999990463257
      seq LVLSLQFLLLSYD/LF
<221> NAME/KEY: polyA_signal
<222> LOCATION: 1133..1138
<221> NAME/KEY: polyA_site
<222> LOCATION: 1154..1166
<221> NAME/KEY: misc_feature
<222> LOCATION: 22..377
<223> OTHER INFORMATION: homology
```

```
        id :AA306911
        est
<221> NAME/KEY: misc_feature
<222> LOCATION: 424..540
<223> OTHER INFORMATION: homology
        id :AA306911
        est
<221> NAME/KEY: misc_feature
<222> LOCATION: 376..424
<223> OTHER INFORMATION: homology
        id :AA306911
        est
<221> NAME/KEY: misc_feature
<222> LOCATION: 4..458
<223> OTHER INFORMATION: homology
        id :AA417777
        est
<221> NAME/KEY: misc_feature
<222> LOCATION: 10..447
<223> OTHER INFORMATION: homology
        id :AA236327
        est
<221> NAME/KEY: misc_feature
<222> LOCATION: 279..714
<223> OTHER INFORMATION: homology
        id :AA410332
        est
<221> NAME/KEY: misc_feature
<222> LOCATION: 680..893
<223> OTHER INFORMATION: homology
        id :N32991
        est
<221> NAME/KEY: misc_feature
<222> LOCATION: 881..1023
<223> OTHER INFORMATION: homology
        id :N32991
        est
<221> NAME/KEY: misc_feature
<222> LOCATION: 1056..1109
<223> OTHER INFORMATION: homology
        id :N32991
        est
<221> NAME/KEY: misc_feature
<222> LOCATION: 1122..1153
<223> OTHER INFORMATION: homology
        id :N32991
        est
<221> NAME/KEY: misc_feature
<222> LOCATION: 1024..1054
<223> OTHER INFORMATION: homology
        id :N32991
        est
<221> NAME/KEY: misc_feature
<222> LOCATION: 703..893
<223> OTHER INFORMATION: homology
        id :N24951
        est
<221> NAME/KEY: misc_feature
<222> LOCATION: 881..1023
<223> OTHER INFORMATION: homology
        id :N24951
        est
<221> NAME/KEY: misc_feature
<222> LOCATION: 1056..1109
<223> OTHER INFORMATION: homology
        id :N24951
        est
<221> NAME/KEY: misc_feature
<222> LOCATION: 1122..1153
<223> OTHER INFORMATION: homology
        id :N24951
        est
<221> NAME/KEY: misc_feature
<222> LOCATION: 1024..1054
<223> OTHER INFORMATION: homology
        id :N24951
        est
<221> NAME/KEY: misc_feature
<222> LOCATION: 225..563
```

```
<223> OTHER INFORMATION: homology
      id :AA455215
      est
<221> NAME/KEY: misc_feature
<222> LOCATION: 544..631
<223> OTHER INFORMATION: homology
      id :AA455215
      est
<221> NAME/KEY: misc_feature
<222> LOCATION: 629..660
<223> OTHER INFORMATION: homology
      id :AA455215
      est
<221> NAME/KEY: misc_feature
<222> LOCATION: 680..793
<223> OTHER INFORMATION: homology
      id :N66437
      est
<221> NAME/KEY: misc_feature
<222> LOCATION: 1055
<223> OTHER INFORMATION: n=a, g, c or t

<400> SEQUENCE: 79
aatgacaacc gacgttggag tttggaggtg cttgccttag agcaagggaa acagctctca    60
ttcaaaggaa ctagaagcct ctccctcagt ggtagggaga cagccaggag cggttttctg   120
ggaactgtgg gatgtgccct tgggggcccg agaaaacaga aggaag atg ctc cag       175
                                                 Met Leu Gln
                                                     -20 acc agt aac tac agc ctg gtg ctc tct ctg cag ttc ctg ctg ctg tcc     223
Thr Ser Asn Tyr Ser Leu Val Leu Ser Leu Gln Phe Leu Leu Leu Ser
        -15                 -10                 -5 tat gac ctc ttt gtc aat tcc ttc tca gaa ctg ctc caa aag act cct     271
Tyr Asp Leu Phe Val Asn Ser Phe Ser Glu Leu Leu Gln Lys Thr Pro
    1               5                   10 gtc atc cag ctt gtg ctc ttc atc atc cag gat att gca gtc ctc ttc     319
Val Ile Gln Leu Val Leu Phe Ile Ile Gln Asp Ile Ala Val Leu Phe
15                  20                  25                  30 aac atc atc atc att ttc ctc atg ttc ttc aac acc tcc gtc ttc cag     367
Asn Ile Ile Ile Ile Phe Leu Met Phe Phe Asn Thr Ser Val Phe Gln
                35                  40                  45 gct ggc ctg gtc aac ctc cta ttc cat aag ttc aaa ggg acc atc atc     415
Ala Gly Leu Val Asn Leu Leu Phe His Lys Phe Lys Gly Thr Ile Ile
            50                  55                  60 ctg aca gct gtg tac ttt gcc ctc agc atc tcc ctt cat gtc tgg gtc     463
Leu Thr Ala Val Tyr Phe Ala Leu Ser Ile Ser Leu His Val Trp Val
        65                  70                  75 atg aac tta cgc tgg aaa aac tcc aac agc ttc ata tgg aca gat gga     511
Met Asn Leu Arg Trp Lys Asn Ser Asn Ser Phe Ile Trp Thr Asp Gly
    80                  85                  90 ctt caa atg ctg ttt gta ttc cag aga cta gca gca gtg ttg tac tgc     559
Leu Gln Met Leu Phe Val Phe Gln Arg Leu Ala Ala Val Leu Tyr Cys
95                  100                 105                 110 tac ttc tat aaa cgg aca gcc gta aga cta ggc gat cct cac ttc tac     607
Tyr Phe Tyr Lys Arg Thr Ala Val Arg Leu Gly Asp Pro His Phe Tyr
                115                 120                 125 cag gac tct ttg tgg ctg cgc aag gag ttc atg caa gtt cga agg         652
Gln Asp Ser Leu Trp Leu Arg Lys Glu Phe Met Gln Val Arg Arg
            130                 135                 140 tgacctcttg tcacactgat ggatactttt ccttcctgat agaagccaca tttgctgctt   712
tgcagggaga gttggcccta tgcatgggca aacagctgga cttccaagg aaggttcaga    772 ctagctgtgt tcagcattca agaaggaaga tccccctct tgcacaatta gagtgtcccc    832
atcggtctcc agtgcggcat cccttccttg ccttctacct ctgttccacc cccttccttc   892
```

```
ctctcctctc tgtaccattc attctccctg accggccttt cttgccgagg gttctgtggc    952 tcttacccttt gtgaagcttt tcctttagcc tgggacagaa ggacctcccg gcccccaaag  1012
gatctcccag wtgaccaaag gatgcgaaga gtgatagtta cgntgctcct gactgatcac  1072
accgcagaca tttagatttt tatacccaag gcactttaaa aaaatgtttt ataaatagag  1132
aataaattga attyttgttc caaaaaaaaa aaaa                               1166
```

```
<210> SEQ ID NO 80
<211> LENGTH: 754
<212> TYPE: DNA
<213> ORGANISM: Homo sapiens
<220> FEATURE:
<221> NAME/KEY: sig_peptide
<222> LOCATION: 180..383
<223> OTHER INFORMATION: Von Heijne matrix
      score 4.59999990463257
      seq LPFSLVSMLVTQG/LV
<221> NAME/KEY: polyA_signal
<222> LOCATION: 722..727
<221> NAME/KEY: polyA_site
<222> LOCATION: 743..754
<221> NAME/KEY: misc_feature
<222> LOCATION: 116..450
<223> OTHER INFORMATION: homology
      id :W68799
      est
<221> NAME/KEY: misc_feature
<222> LOCATION: 593..710
<223> OTHER INFORMATION: homology
      id :W68799
      est
<221> NAME/KEY: misc_feature
<222> LOCATION: 18..117
<223> OTHER INFORMATION: homology
      id :W68799
      est
<221> NAME/KEY: misc_feature
<222> LOCATION: 561..598
<223> OTHER INFORMATION: homology
      id :W68799
      est
<221> NAME/KEY: misc_feature
<222> LOCATION: 48..511
<223> OTHER INFORMATION: homology
      id :AA149518
      est
<221> NAME/KEY: misc_feature
<222> LOCATION: 593..673
<223> OTHER INFORMATION: homology
      id :AA149518
      est
<221> NAME/KEY: misc_feature
<222> LOCATION: 535..710
<223> OTHER INFORMATION: homology
      id :W80356
      est
<221> NAME/KEY: misc_feature
<222> LOCATION: 256..405
<223> OTHER INFORMATION: homology
      id :W80356
      est
<221> NAME/KEY: misc_feature
<222> LOCATION: 432..511
<223> OTHER INFORMATION: homology
      id :W80356
      est
<221> NAME/KEY: misc_feature
<222> LOCATION: 392..437
<223> OTHER INFORMATION: homology
      id :W80356
      est
<221> NAME/KEY: misc_feature
<222> LOCATION: 535..710
<223> OTHER INFORMATION: homology
```

-continued

```
      id :W80631
      est
<221> NAME/KEY: misc_feature
<222> LOCATION: 289..437
<223> OTHER INFORMATION: homology
      id :W80631
      est
<221> NAME/KEY: misc_feature
<222> LOCATION: 432..511
<223> OTHER INFORMATION: homology
      id :W80631
      est
<221> NAME/KEY: misc_feature
<222> LOCATION: 343..511
<223> OTHER INFORMATION: homology
      id :AA142865
      est
<221> NAME/KEY: misc_feature
<222> LOCATION: 535..710
<223> OTHER INFORMATION: homology
      id :AA142865
      est
<221> NAME/KEY: misc_feature
<222> LOCATION: 256..341
<223> OTHER INFORMATION: homology
      id :AA142865
      est
<221> NAME/KEY: misc_feature
<222> LOCATION: 248..511
<223> OTHER INFORMATION: homology
      id :AA405876
      est
<221> NAME/KEY: misc_feature
<222> LOCATION: 21..271
<223> OTHER INFORMATION: homology
      id :AA405876
      est
<221> NAME/KEY: misc_feature
<222> LOCATION: 121..450
<223> OTHER INFORMATION: homology
      id :W68728
      est
<221> NAME/KEY: misc_feature
<222> LOCATION: 592..710
<223> OTHER INFORMATION: homology
      id :W68728
      est
<221> NAME/KEY: misc_feature
<222> LOCATION: 725
<223> OTHER INFORMATION: n=a, g, c or t

<400> SEQUENCE: 80
aagacaggtg gggtactcgg gaagctggag cgggccggcg gtgcagtcac gggggagcga      60
ggcctgctgg gcttggcaac gagggactcg gcctcgagg cgacccagac cacacagaca     120
ctgggtcaag gagtaagcag aggataaaca actggaagga gagcaagcac aaagtcatc     179 atg gct tca gcg tct gct cgt gga aac caa gat aaa gat gcc cat ttt      227
Met Ala Ser Ala Ser Ala Arg Gly Asn Gln Asp Lys Asp Ala His Phe
        -65                 -60                 -55 cca cca cca agc aag cag agc ctg ttg ttt tgt cca aaa tca aaa ctg      275
Pro Pro Pro Ser Lys Gln Ser Leu Leu Phe Cys Pro Lys Ser Lys Leu
    -50                 -45                 -40 cac atc cac aga gca gag atc tca aag att atg cga gaa tgt cag gaa      323
His Ile His Arg Ala Glu Ile Ser Lys Ile Met Arg Glu Cys Gln Glu
-35                 -30                 -25 gaa agt ttc tgg aag aga gct ctg cct ttt tct ctt gta agc atg ctt      371
Glu Ser Phe Trp Lys Arg Ala Leu Pro Phe Ser Leu Val Ser Met Leu
-20                 -15                 -10                  -5 gtc acc cag gga cta gtc tac caa ggt tat ttg gca gct aat tct aga      419
Val Thr Gln Gly Leu Val Tyr Gln Gly Tyr Leu Ala Ala Asn Ser Arg
                  1               5                  10
```

```
ttt gga tca ttg ccc aaa gtt gca ctt gct ggt ctc ttg gga ttt ggc      467
Phe Gly Ser Leu Pro Lys Val Ala Leu Ala Gly Leu Leu Gly Phe Gly
            15                  20                  25 ctt gga aag gta tca tac ata gga gta tgc cag agt aaa ttc cat ttt      515
Leu Gly Lys Val Ser Tyr Ile Gly Val Cys Gln Ser Lys Phe His Phe
        30                  35                  40 ttt gaa gat cag ctc cgt ggg gct ggt ttt ggt ccw aca gca              557
Phe Glu Asp Gln Leu Arg Gly Ala Gly Phe Gly Pro Thr Ala
45                  50                  55 taacaggcac tgcctcctta cctgtgagga atgcaaaata aagcatggat taagtgagaa     617
gggagactct cagccttcag cttcctaaat tctgtgtctg tgactttcga agtttttaa      677 acctctgaat ttgtacacat ttaaaatttc aaggtgtact ttaaaatnaa aatacttcta     737
atgtvaaaaa aaaaaaa                                                    754

<210> SEQ ID NO 81
<211> LENGTH: 709
<212> TYPE: DNA
<213> ORGANISM: Homo sapiens
<220> FEATURE:
<221> NAME/KEY: sig_peptide
<222> LOCATION: 179..298
<223> OTHER INFORMATION: Von Heijne matrix
      score 4.30000019073486
      seq ITLVSAAPGKVIC/EM
<221> NAME/KEY: polyA_signal
<222> LOCATION: 680..685
<221> NAME/KEY: polyA_site
<222> LOCATION: 697..708
<221> NAME/KEY: misc_feature
<222> LOCATION: 137..291
<223> OTHER INFORMATION: homology
      id :AA121372
      est
<221> NAME/KEY: misc_feature
<222> LOCATION: 6..91
<223> OTHER INFORMATION: homology
      id :AA121372
      est
<221> NAME/KEY: misc_feature
<222> LOCATION: 318..397
<223> OTHER INFORMATION: homology
      id :AA121372
      est
<221> NAME/KEY: misc_feature
<222> LOCATION: 95..132
<223> OTHER INFORMATION: homology
      id :AA121372
      est
<221> NAME/KEY: misc_feature
<222> LOCATION: 460..501
<223> OTHER INFORMATION: homology
      id :AA121372
      est
<221> NAME/KEY: misc_feature
<222> LOCATION: 432..465
<223> OTHER INFORMATION: homology
      id :AA121372
      est
<221> NAME/KEY: misc_feature
<222> LOCATION: 284..313
<223> OTHER INFORMATION: homology
      id :AA121372
      est
<221> NAME/KEY: misc_feature
<222> LOCATION: 254..670
<223> OTHER INFORMATION: homology
      id :AA614605
      est
<221> NAME/KEY: misc_feature
<222> LOCATION: 392..658
<223> OTHER INFORMATION: homology
      id :T55234
```

```
          est
<221> NAME/KEY: misc_feature
<222> LOCATION: 271..327
<223> OTHER INFORMATION: homology
      id :T55234
      est
<221> NAME/KEY: misc_feature
<222> LOCATION: 358..670
<223> OTHER INFORMATION: homology
      id :AA121362
      est
<221> NAME/KEY: misc_feature
<222> LOCATION: 312..344
<223> OTHER INFORMATION: homology
      id :AA121362
      est
<221> NAME/KEY: misc_feature
<222> LOCATION: 2..102
<223> OTHER INFORMATION: homology
      id :T53974
      est
<221> NAME/KEY: misc_feature
<222> LOCATION: 150..258
<223> OTHER INFORMATION: homology
      id :T53974
      est
<221> NAME/KEY: misc_feature
<222> LOCATION: 95..171
<223> OTHER INFORMATION: homology
      id :T53974
      est
<221> NAME/KEY: misc_feature
<222> LOCATION: 322..628
<223> OTHER INFORMATION: homology
      id :HSPD02295
      est
<221> NAME/KEY: misc_feature
<222> LOCATION: 445..670
<223> OTHER INFORMATION: homology
      id :AA454502
      est
<221> NAME/KEY: misc_feature
<222> LOCATION: 2..102
<223> OTHER INFORMATION: homology
      id :R09314
      est
<221> NAME/KEY: misc_feature
<222> LOCATION: 95..171
<223> OTHER INFORMATION: homology
      id :R09314
      est
<221> NAME/KEY: misc_feature
<222> LOCATION: 150..222
<223> OTHER INFORMATION: homology
      id :R09314
      est

<400> SEQUENCE: 81
aaaatcgcgg accaccgggg ctgccakctc gcctgactcc cggcctcttg cgctcctagg     60
ggcggagaag ggtgcgggct cttcgcccct tgtgtccttc tttcactaac ttctggactt    120
tccagctctt ccgaagttcg ttcttgcgca agcccaaag gctggaaaac cgtccacg      178 atg acc agc atg act cag tct ctg cgg gag gtg ata aag gcc atg acc     226
Met Thr Ser Met Thr Gln Ser Leu Arg Glu Val Ile Lys Ala Met Thr
-40             -35                 -30                 -25 aag gct cgc aat ttt gag aga gtt ttg gga aag att act ctt gtc tct     274
Lys Ala Arg Asn Phe Glu Arg Val Leu Gly Lys Ile Thr Leu Val Ser
                -20                 -15                 -10 gct gct cct ggg aaa gtg att tgt gaa atg aaa gta gaa gaa gag cat     322
Ala Ala Pro Gly Lys Val Ile Cys Glu Met Lys Val Glu Glu Glu His
            -5                   1                   5 acc aat gca ata ggc act ctc cac ggc ggt ttg aca gcc acg tta gta     370
Thr Asn Ala Ile Gly Thr Leu His Gly Gly Leu Thr Ala Thr Leu Val
```

```
                   10              15              20
gat aac ata tca aca atg gct ctg cta tgc acg gaa agg gga gca ccc    418
Asp Asn Ile Ser Thr Met Ala Leu Leu Cys Thr Glu Arg Gly Ala Pro
 25              30              35              40 gga gtc agt gtc gat atg aac ata acg tac atg tca cct gca aaa tta    466
Gly Val Ser Val Asp Met Asn Ile Thr Tyr Met Ser Pro Ala Lys Leu
                 45              50              55 gga gag gat ata gtg att aca gca cat gtt ctg aag caa gga aaa aca    514
Gly Glu Asp Ile Val Ile Thr Ala His Val Leu Lys Gln Gly Lys Thr
                 60              65              70 ctt gca ttt acc tct gtg ggt ctg acc aac aag gcc aca gga aaa tta    562
Leu Ala Phe Thr Ser Val Gly Leu Thr Asn Lys Ala Thr Gly Lys Leu
                 75              80              85 ata gca caa gga aga cac aca aaa cac ctg gga aac tgagagaaca         608
Ile Ala Gln Gly Arg His Thr Lys His Leu Gly Asn
 90              95             100 gcagaatgac ctaaagaaac ccaacaatga atatcaagta tagatttgac tcaaacaatt    668 gtaattttg aaataaacta gcaaaaccaa aaaaaaaaa g                          709

<210> SEQ ID NO 82
<211> LENGTH: 243
<212> TYPE: DNA
<213> ORGANISM: Homo sapiens
<220> FEATURE:
<221> NAME/KEY: sig_peptide
<222> LOCATION: 100..171
<223> OTHER INFORMATION: Von Heijne matrix
      score 3.70000004768372
      seq ILFNLLIFLCGFT/NY
<221> NAME/KEY: polyA_signal
<222> LOCATION: 211..216
<221> NAME/KEY: polyA_site
<222> LOCATION: 230..243
<221> NAME/KEY: misc_feature
<222> LOCATION: 2..164
<223> OTHER INFORMATION: homology
      id :H64488
      est
<221> NAME/KEY: misc_feature
<222> LOCATION: 2..164
<223> OTHER INFORMATION: homology
      id :AA131065
      est
<221> NAME/KEY: misc_feature
<222> LOCATION: 5..164
<223> OTHER INFORMATION: homology
      id :AA224847
      est
<221> NAME/KEY: misc_feature
<222> LOCATION: 10..164
<223> OTHER INFORMATION: homology
      id :AA161042
      est
<221> NAME/KEY: misc_feature
<222> LOCATION: 2..84
<223> OTHER INFORMATION: homology
      id :AA088770
      est
<221> NAME/KEY: misc_feature
<222> LOCATION: 104..164
<223> OTHER INFORMATION: homology
      id :AA088770
      est
<221> NAME/KEY: misc_feature
<222> LOCATION: 10..164
<223> OTHER INFORMATION: homology
      id :AA100852
      est
<221> NAME/KEY: misc_feature
<222> LOCATION: 79..164
<223> OTHER INFORMATION: homology
```

```
         id :AA146774
         est
<221> NAME/KEY: misc_feature
<222> LOCATION: 79..164
<223> OTHER INFORMATION: homology
         id :AA146605
         est
<221> NAME/KEY: misc_feature
<222> LOCATION: 109..164
<223> OTHER INFORMATION: homology
         id :AA299239
         est
<221> NAME/KEY: misc_feature
<222> LOCATION: 158..207
<223> OTHER INFORMATION: homology
         id :AA037885
         est
<221> NAME/KEY: misc_feature
<222> LOCATION: 160..207
<223> OTHER INFORMATION: homology
         id :AA480512
         est
<221> NAME/KEY: misc_feature
<222> LOCATION: 160..207
<223> OTHER INFORMATION: homology
         id :AA468030
         est
<221> NAME/KEY: misc_feature
<222> LOCATION: 160..207
<223> OTHER INFORMATION: homology
         id :AA420727
         est
<221> NAME/KEY: misc_feature
<222> LOCATION: 160..207
<223> OTHER INFORMATION: homology
         id :AA574382
         est
<221> NAME/KEY: misc_feature
<222> LOCATION: 160..207
<223> OTHER INFORMATION: homology
         id :AA133048
         est
<221> NAME/KEY: misc_feature
<222> LOCATION: 200..229
<223> OTHER INFORMATION: homology
         id :AA469266
         est
<221> NAME/KEY: misc_feature
<222> LOCATION: 200..229
<223> OTHER INFORMATION: homology
         id :AA550735
         est
<221> NAME/KEY: misc_feature
<222> LOCATION: 200..229
<223> OTHER INFORMATION: homology
         id :AA601071
         est
<221> NAME/KEY: misc_feature
<222> LOCATION: 200..229
<223> OTHER INFORMATION: homology
         id :AA225190
         est

<400> SEQUENCE: 82
aactcagtgg caacacccgg gagctgtttt gtcctttgtg gagcctcagc agttccctct      60
ttcagaactc actgccaaga gccctgaaca ggagccacc atg cag tgc ttc agc       114
                                            Met Gln Cys Phe Ser
                                                            -20 ttc att aag acc atg atg atc ctc ttc aat ttg ctc atc ttt ctg tgt      162
Phe Ile Lys Thr Met Met Ile Leu Phe Asn Leu Leu Ile Phe Leu Cys
            -15                 -10                  -5 ggc ttc acc aac tat acg gat ttt gag gac tca ccc tac ttc aaa atg      210
Gly Phe Thr Asn Tyr Thr Asp Phe Glu Asp Ser Pro Tyr Phe Lys Met
  1               5                  10
```

```
cat aaa cct gtt aca atg taaaaaaaaa aaaaa                                    243
His Lys Pro Val Thr Met
    15
```

```
<210> SEQ ID NO 83
<211> LENGTH: 829
<212> TYPE: DNA
<213> ORGANISM: Homo sapiens
<220> FEATURE:
<221> NAME/KEY: sig_peptide
<222> LOCATION: 346..408
<223> OTHER INFORMATION: Von Heijne matrix
      score 5.5
      seq SFLPSALVIWTSA/AF
<221> NAME/KEY: polyA_signal
<222> LOCATION: 792..797
<221> NAME/KEY: polyA_site
<222> LOCATION: 817..829
<221> NAME/KEY: misc_feature
<222> LOCATION: 260..464
<223> OTHER INFORMATION: homology
      id :H57434
      est
<221> NAME/KEY: misc_feature
<222> LOCATION: 118..184
<223> OTHER INFORMATION: homology
      id :H57434
      est
<221> NAME/KEY: misc_feature
<222> LOCATION: 56..113
<223> OTHER INFORMATION: homology
      id :H57434
      est
<221> NAME/KEY: misc_feature
<222> LOCATION: 454..485
<223> OTHER INFORMATION: homology
      id :H57434
      est
<221> NAME/KEY: misc_feature
<222> LOCATION: 118..545
<223> OTHER INFORMATION: homology
      id :N27248
      est
<221> NAME/KEY: misc_feature
<222> LOCATION: 65..369
<223> OTHER INFORMATION: homology
      id :H94779
      est
<221> NAME/KEY: misc_feature
<222> LOCATION: 471..519
<223> OTHER INFORMATION: homology
      id :H94779
      est
<221> NAME/KEY: misc_feature
<222> LOCATION: 61..399
<223> OTHER INFORMATION: homology
      id :H09880
      est
<221> NAME/KEY: misc_feature
<222> LOCATION: 408..452
<223> OTHER INFORMATION: homology
      id :H09880
      est
<221> NAME/KEY: misc_feature
<222> LOCATION: 60..399
<223> OTHER INFORMATION: homology
      id :H29351
      est
<221> NAME/KEY: misc_feature
<222> LOCATION: 393..432
<223> OTHER INFORMATION: homology
      id :H29351
      est
<221> NAME/KEY: misc_feature
<222> LOCATION: 260..444
<223> OTHER INFORMATION: homology
      id :AA459511
      est
```

```
<221> NAME/KEY: misc_feature
<222> LOCATION: 449..545
<223> OTHER INFORMATION: homology
      id :AA459511
      est
<221> NAME/KEY: misc_feature
<222> LOCATION: 117..184
<223> OTHER INFORMATION: homology
      id :AA459511
      est
<221> NAME/KEY: misc_feature
<222> LOCATION: 122..399
<223> OTHER INFORMATION: homology
      id :T74091
      est
<221> NAME/KEY: misc_feature
<222> LOCATION: 393..434
<223> OTHER INFORMATION: homology
      id :T74091
      est
<221> NAME/KEY: misc_feature
<222> LOCATION: 61..378
<223> OTHER INFORMATION: homology
      id :HSC3CB081
      est
<221> NAME/KEY: misc_feature
<222> LOCATION: 118..399
<223> OTHER INFORMATION: homology
      id :T82010
      est
<221> NAME/KEY: misc_feature
<222> LOCATION: 268..545
<223> OTHER INFORMATION: homology
      id :W02860
      est
<221> NAME/KEY: misc_feature
<222> LOCATION: 268..545
<223> OTHER INFORMATION: homology
      id :N44490
      est
<221> NAME/KEY: misc_feature
<222> LOCATION: 115
<223> OTHER INFORMATION: n=a, g, c or t

<400> SEQUENCE: 83 actccttta  gcatagggc  ttcggcgcca  gcggccagcg  ctagtcggtc  tggtaagtgc      60
ctgatgccga  gttccgtctc  tcgcgtcttt  tcctggtccc  aggcaaagcg  gasgnagatc    120
ctcaaacggc  ctagtgcttc  gcgcttccgg  agaaaatcag  cggtctaatt  aattcctctg   180
gtttgttgaa  gcagttacca  agaatcttca  acccttccc   acaaaagcta  attgagtaca   240
cgttcctgtt  gagtacacgt  tcctgttgat  ttacaaaagg  tgcaggtatg  agcaggtctg   300
aagactaaca  ttttgtgaag  ttgtaaaaca  gaaaacctgt  tagaa atg tgg tgg ttt    357
                                              Met Trp Trp Phe
                                                  -20 cag caa ggc ctc agt ttc ctt cct tca gcc ctt gta att tgg aca tct          405
Gln Gln Gly Leu Ser Phe Leu Pro Ser Ala Leu Val Ile Trp Thr Ser
        -15                 -10                  -5 gct gct ttc ata ttt tca tac att act gca gta aca ctc cac cat ata          453
Ala Ala Phe Ile Phe Ser Tyr Ile Thr Ala Val Thr Leu His His Ile
 1               5                  10                      15 gac ccg gct tta cct tat atc agt gac act ggt aca gta gct cca gaa          501
Asp Pro Ala Leu Pro Tyr Ile Ser Asp Thr Gly Thr Val Ala Pro Glu
            20                  25                  30 aaa tgc tta ttt ggg gca atg cta aat att gcg gca gtc tta tgt caa          549
Lys Cys Leu Phe Gly Ala Met Leu Asn Ile Ala Ala Val Leu Cys Gln
        35                  40                  45 aaa tagaaatcag gaagataatt caacttaaag aagttcattt catgaccaaa                602
Lys
```

```
ctcttcagaa acatgtcttt acaagcatat ctcttgtatt gctttctaca ctgttgaatt      662
gtctggcaat atttctgcag tggaaaattt gatttagcta gttcttgact tggataaata      722
tggtaaggtg ggcttttccc cctgtgtaat tggctacsac gtcttacttg agccaagttg      782
gtaagttgaa ataaaatgat watgagagtg acacavaaaa aaaaaaa                   829

<210> SEQ ID NO 84
<211> LENGTH: 674
<212> TYPE: DNA
<213> ORGANISM: Homo sapiens
<220> FEATURE:
<221> NAME/KEY: sig_peptide
<222> LOCATION: 177..233
<223> OTHER INFORMATION: Von Heijne matrix
      score 6.09999990463257
      seq LALLWSLPASDLG/RS
<221> NAME/KEY: polyA_signal
<222> LOCATION: 644..649
<221> NAME/KEY: polyA_site
<222> LOCATION: 663..674
<221> NAME/KEY: misc_feature
<222> LOCATION: 194..592
<223> OTHER INFORMATION: homology
      id :AA496246
      est
<221> NAME/KEY: misc_feature
<222> LOCATION: 1..100
<223> OTHER INFORMATION: homology
      id :AA496246
      est
<221> NAME/KEY: misc_feature
<222> LOCATION: 99..202
<223> OTHER INFORMATION: homology
      id :AA496246
      est
<221> NAME/KEY: misc_feature
<222> LOCATION: 187..592
<223> OTHER INFORMATION: homology
      id :AA476481
      est
<221> NAME/KEY: misc_feature
<222> LOCATION: 594..661
<223> OTHER INFORMATION: homology
      id :AA476481
      est
<221> NAME/KEY: misc_feature
<222> LOCATION: 188..592
<223> OTHER INFORMATION: homology
      id :AA496245
      est
<221> NAME/KEY: misc_feature
<222> LOCATION: 594..661
<223> OTHER INFORMATION: homology
      id :AA496245
      est
<221> NAME/KEY: misc_feature
<222> LOCATION: 194..444
<223> OTHER INFORMATION: homology
      id :AA476480
      est
<221> NAME/KEY: misc_feature
<222> LOCATION: 1..102
<223> OTHER INFORMATION: homology
      id :AA476480
      est
<221> NAME/KEY: misc_feature
<222> LOCATION: 99..187
<223> OTHER INFORMATION: homology
      id :AA476480
      est
<221> NAME/KEY: misc_feature
<222> LOCATION: 437..592
<223> OTHER INFORMATION: homology
      id :AA505488
      est
<221> NAME/KEY: misc_feature
```

```
<222> LOCATION: 594..661
<223> OTHER INFORMATION: homology
      id :AA505488
      est
<221> NAME/KEY: misc_feature
<222> LOCATION: 441..592
<223> OTHER INFORMATION: homology
      id :AA554685
      est
<221> NAME/KEY: misc_feature
<222> LOCATION: 594..661
<223> OTHER INFORMATION: homology
      id :AA554685
      est
<221> NAME/KEY: misc_feature
<222> LOCATION: 414..503
<223> OTHER INFORMATION: homology
      id :AA215595
      est
<221> NAME/KEY: misc_feature
<222> LOCATION: 510..539
<223> OTHER INFORMATION: homology
      id :AA215595
      est

<400> SEQUENCE: 84
ataagtgaac cagaccaccc tgatggcatc cacagtgatg tcaaggttgg ggctggccag    60
gggtgggtgg actagaagca tttgggagta gtggccaggg gccctggacg ctagccacgg   120
agctgctgca cagagcctgg tgtccacaag cttccaggtt ggggttggag cctggg atg   179
                                                                Met agc ccc ggc agc gcc ttg gcc ctt ctg tgg tcc ctg cca gcc tct gac    227
Ser Pro Gly Ser Ala Leu Ala Leu Leu Trp Ser Leu Pro Ala Ser Asp
        -15                 -10                 -5 ctg ggc cgg tca gtc att gct gga ctc tgg cca cac act ggc gtt ctc    275
Leu Gly Arg Ser Val Ile Ala Gly Leu Trp Pro His Thr Gly Val Leu
  1               5                  10 atc cac ttg gaa aca agc cag tct ttt ctg caa ggt cag ttg acc aag    323
Ile His Leu Glu Thr Ser Gln Ser Phe Leu Gln Gly Gln Leu Thr Lys
 15                  20                  25                  30 agc ata ttt ccc ctc tgt tgt aca tcg ttg ttt tgt gtt tgt gtt gta    371
Ser Ile Phe Pro Leu Cys Cys Thr Ser Leu Phe Cys Val Cys Val Val
                 35                  40                  45 aca gtg ggt gga ggg agg gtg ggg tct aca ttt gtt gca tgagtcgatg    420
Thr Val Gly Gly Gly Arg Val Gly Ser Thr Phe Val Ala
                 50                  55 ggtcagaact ttagtatacg catgcgtcct ctgagtgaca gggcattttg tcgaaaataa   480
gcaccttggt aactaaaccc ctctaatagc tataaaggct ttagttctgt attgattaag   540
ttactgtaaa agcttgggtt tattttgta ggacttaatg gctaagaatt agggaacata    600 gcaaggggc tcctctgttg gagtaatgta aattgtaatt ataaataaac atgcaaacct    660
ttaaaaaaaa aaaa                                                     674

<210> SEQ ID NO 85
<211> LENGTH: 478
<212> TYPE: DNA
<213> ORGANISM: Homo sapiens
<220> FEATURE:
<221> NAME/KEY: sig_peptide
<222> LOCATION: 179..319
<223> OTHER INFORMATION: Von Heijne matrix
      score 5.5
      seq SALLFFARPCVFC/FK
<221> NAME/KEY: polyA_signal
<222> LOCATION: 461..466
<221> NAME/KEY: polyA_site
<222> LOCATION: 465..478
```

```
<221> NAME/KEY: misc_feature
<222> LOCATION: 2..464
<223> OTHER INFORMATION: homology
       id :AA310996
       est
<221> NAME/KEY: misc_feature
<222> LOCATION: 8..464
<223> OTHER INFORMATION: homology
       id :AA312901
       est
<221> NAME/KEY: misc_feature
<222> LOCATION: 2..416
<223> OTHER INFORMATION: homology
       id :AA401411
       est
<221> NAME/KEY: misc_feature
<222> LOCATION: 2..349
<223> OTHER INFORMATION: homology
       id :R64030
       est
<221> NAME/KEY: misc_feature
<222> LOCATION: 56..464
<223> OTHER INFORMATION: homology
       id :AA400108
       est
<221> NAME/KEY: misc_feature
<222> LOCATION: 126..273
<223> OTHER INFORMATION: homology
       id :AA010825
       est
<221> NAME/KEY: misc_feature
<222> LOCATION: 2..147
<223> OTHER INFORMATION: homology
       id :AA010825
       est
<221> NAME/KEY: misc_feature
<222> LOCATION: 358..435
<223> OTHER INFORMATION: homology
       id :AA010825
       est
<221> NAME/KEY: misc_feature
<222> LOCATION: 78..464
<223> OTHER INFORMATION: homology
       id :AA504732
       est
<221> NAME/KEY: misc_feature
<222> LOCATION: 90..441
<223> OTHER INFORMATION: homology
       id :H60506
       est
<221> NAME/KEY: misc_feature
<222> LOCATION: 59..349
<223> OTHER INFORMATION: homology
       id :AA346780
       est
<221> NAME/KEY: misc_feature
<222> LOCATION: 2..331
<223> OTHER INFORMATION: homology
       id :AA281167
       est
<221> NAME/KEY: misc_feature
<222> LOCATION: 6..236
<223> OTHER INFORMATION: homology
       id :R35805
       est
<221> NAME/KEY: misc_feature
<222> LOCATION: 232..284
<223> OTHER INFORMATION: homology
       id :R35805
       est
<221> NAME/KEY: misc_feature
<222> LOCATION: 41..307
<223> OTHER INFORMATION: homology
       id :H13784
       est
<221> NAME/KEY: misc_feature
<222> LOCATION: 2..40
<223> OTHER INFORMATION: homology
       id :H13784
```

```
       est
<221> NAME/KEY: misc_feature
<222> LOCATION: 64..280
<223> OTHER INFORMATION: homology
      id :AA128122
      est
<221> NAME/KEY: misc_feature
<222> LOCATION: 293..349
<223> OTHER INFORMATION: homology
      id :AA128122
      est
<221> NAME/KEY: misc_feature
<222> LOCATION: 332..385
<223> OTHER INFORMATION: homology
      id :AA128122
      est
<221> NAME/KEY: misc_feature
<222> LOCATION: 163..420
<223> OTHER INFORMATION: homology
      id :AA555127
      est

<400> SEQUENCE: 85
aagtccttcg cgccctcctc gccctcccca ccgacatcat gctccagttc ctgcttggat      60
ttacactggg caacgtggtt ggaatgtatc tggctcagaa ctatgatata ccaaacctgg     120
ctaaaaaact tgaagaaatt aaaaaggact tggatgccaa gaagaaaccc cctagtgc      178 atg aga ctg cct cca gca ctg cct tca gga tat act gat tct act gct      226
Met Arg Leu Pro Pro Ala Leu Pro Ser Gly Tyr Thr Asp Ser Thr Ala
    -45                 -40                 -35 ctt gag ggc ctc gtt tac tat ctg aac caa aag ctt ttg ttt tcg tct      274
Leu Glu Gly Leu Val Tyr Tyr Leu Asn Gln Lys Leu Leu Phe Ser Ser
    -30                 -25                 -20 cca gcc tca gca ctt ctc ttc ttt gct aga ccc tgt gtt ttt tgc ttt      322
Pro Ala Ser Ala Leu Leu Phe Phe Ala Arg Pro Cys Val Phe Cys Phe
    -15                 -10                  -5                  1 aaa gca agc aaa atg ggg ccc caa ttt gag aac tac cca aca ttt cca      370
Lys Ala Ser Lys Met Gly Pro Gln Phe Glu Asn Tyr Pro Thr Phe Pro
                  5                  10                 15 aca tac tca cct ctt ccc ata atc cct ttc caa ctg cat ggg agg ttc      418
Thr Tyr Ser Pro Leu Pro Ile Ile Pro Phe Gln Leu His Gly Arg Phe
            20                  25                  30 taagactgga attattggtgc tagattagta aacatgactt ttaatgaaaa aaaaacaaaa    478

<210> SEQ ID NO 86
<211> LENGTH: 952
<212> TYPE: DNA
<213> ORGANISM: Homo sapiens
<220> FEATURE:
<221> NAME/KEY: sig_peptide
<222> LOCATION: 112..237
<223> OTHER INFORMATION: Von Heijne matrix
      score 7.19999980926514
      seq ILFSLSFLLVIIT/FP
<221> NAME/KEY: polyA_signal
<222> LOCATION: 910..915
<221> NAME/KEY: polyA_site
<222> LOCATION: 940..952

<400> SEQUENCE: 86
aatactttct cctctcccct ctcccaagca catctgagtt gctgcctgtt cttcacactt      60
agctccaaac ccatgaaaaa ttgccaagta taaagcttc tcaagaatga g atg gat      117
                                                        Met Asp
tct agg gtg tct tca cct gag aag caa gat aaa gag aat ttc gtg ggt      165
Ser Arg Val Ser Ser Pro Glu Lys Gln Asp Lys Glu Asn Phe Val Gly
-40                 -35                 -30                 -25 gtc aac aat aaa cgg ctt ggt gta tgt ggc tgg atc ctg ttt tcc ctc      213
```

```
Val Asn Asn Lys Arg Leu Gly Val Cys Gly Trp Ile Leu Phe Ser Leu
            -20             -15                     -10 tct ttc ctg ttg gtg atc att acc ttc ccc atc tcc ata tgg atg tgc    261
Ser Phe Leu Leu Val Ile Ile Thr Phe Pro Ile Ser Ile Trp Met Cys
             -5                   1                   5 ttg aag att tgatcctggt cctgccatgc ataratgtgt ttgtcaaagt            310
Leu Lys Ile
    10 tgacctccga acagttactt gcaacattcc tccacaagag atcctcacca rgagactccg   370 taactactca ggtagatgga gttgtctatt acagaatcta tagtgctgtc tcagcagtgg   430 ctaakgtcaa cgatgtccat caagcaacat ttctgctggc tcaaaccact ctgagaaatg   490 tcktagggac acaggacctt gtccccagat cttaggctgg acgagaagag atcgcccata   550 agcatccaga ctktacttga tgatgccacc gaactggtgg gggatccggg tggcccgagt   610 ggaaatcaaa gatgttcgga ttcccgtgca gttgcagaga tccatggcag ccgaggstga   670 ggccacccgg gaagsgagag ccaaggtcct tgcagctgaa ggagaaatga atgsttccaa   730 atccctgaag tcagcctcca tggtgstggs tgagtytccc atagctytcc agstgsgsta   790 cctgcagacc ttgagcacgg tagccaccga aagaatttt acgattgtgt ttcctbtgcc   850 catgaatata ctagagggca ttggtggcgt cagstatgat aaccacaaga agsttbscaa   910 ataaagcctg aggtcybctt gcggtagtca aaaaaaaaaa aa                     952
```

<210> SEQ ID NO 87
<211> LENGTH: 131
<212> TYPE: PRT
<213> ORGANISM: Homo sapiens
<220> FEATURE:
<221> NAME/KEY: SIGNAL
<222> LOCATION: -13..-1

<400> SEQUENCE: 87

```
Met Leu Ala Val Ser Leu Thr Val Pro Leu Leu Gly Ala Met Met Leu
            -10                 -5                  1

Leu Glu Ser Pro Ile Asp Pro Gln Pro Leu Ser Phe Lys Glu Pro Pro
    5                   10                  15

Leu Leu Leu Gly Val Leu His Pro Asn Thr Lys Leu Arg Gln Ala Glu
20                  25                  30                  35

Arg Leu Phe Glu Asn Gln Leu Val Gly Pro Glu Ser Ile Ala His Ile
                40                  45                  50

Gly Asp Val Met Phe Thr Gly Thr Ala Asp Gly Arg Val Val Lys Leu
                55                  60                  65

Glu Asn Gly Glu Ile Glu Thr Ile Ala Arg Phe Gly Ser Gly Pro Cys
            70                  75                  80

Lys Thr Arg Gly Asp Glu Pro Val Cys Gly Arg Pro Leu Gly Ile Arg
    85                  90                  95

Gly Arg Ala Gln Trp Asp Ser Leu Cys Gly Arg Cys Ile Gln Arg Asp
100                 105                 110                 115

Tyr Leu Lys
```

<210> SEQ ID NO 88
<211> LENGTH: 63
<212> TYPE: PRT
<213> ORGANISM: Homo sapiens
<220> FEATURE:
<221> NAME/KEY: SIGNAL
<222> LOCATION: -35..-1

```
<400> SEQUENCE: 88

Met Leu Thr Val Asn Asp Val Arg Phe Tyr Arg Asn Val Arg Ser Asn
-35             -30             -25             -20

His Phe Pro Phe Val Arg Leu Cys Gly Leu Leu His Leu Trp Leu Lys
            -15             -10                     -5

Val Phe Ser Leu Lys Gln Leu Lys Lys Lys Ser Trp Ser Lys Tyr Leu
         1               5                  10

Phe Glu Ser Cys Cys Tyr Arg Ser Leu Tyr Val Cys Val Phe Ile
     15             20                  25

<210> SEQ ID NO 89
<211> LENGTH: 163
<212> TYPE: PRT
<213> ORGANISM: Homo sapiens
<220> FEATURE:
<221> NAME/KEY: SIGNAL
<222> LOCATION: -31..-1
<221> NAME/KEY: UNSURE
<222> LOCATION: 91,108,109,112,124
<223> OTHER INFORMATION: Xaa = any one of the twenty amino acids

<400> SEQUENCE: 89

Met Ser Pro Ala Phe Arg Ala Met Asp Val Glu Pro Arg Ala Lys Gly
    -30             -25             -20

Ser Phe Trp Ser Pro Leu Ser Thr Arg Ser Gly Gly Thr His Ala Cys
-15             -10              -5                          1

Ser Ala Ser Met Arg Gln Pro Trp Ala Ser Pro Trp Ser Gln Gly Asn
             5               10                  15

Ile Ser Ser Thr Arg Pro Ser Leu Leu Arg Cys Ala Asn Ser Leu Pro
             20              25                  30

Ser Thr Lys Asp Lys Ala Lys Gly Pro Leu Leu Ala Gly His Pro Cys
     35              40                  45

Pro Ile Phe Ser Pro Gly Pro Phe Pro Cys Gly His Arg Glu Val Trp
50              55                  60                      65

Pro Glu Tyr Pro Thr Pro Ala Pro Leu His Pro Glu Leu Gly Ala Thr
             70                  75                  80

Ser Glu Val Ser Ser Leu Ser Glu His Xaa Phe Pro Cys Ser Ser Arg
             85                  90                  95

Gly Leu Ser Arg Leu Ser Asp Ala Gly Ala Xaa Xaa Pro Glu Xaa Lys
         100             105                 110

Gly Val Gln Pro Val Val Cys Lys Ala Leu Xaa Gly Thr Ala Glu Thr
         115             120                 125

Pro Pro Pro
130

<210> SEQ ID NO 90
<211> LENGTH: 52
<212> TYPE: PRT
<213> ORGANISM: Homo sapiens
<220> FEATURE:
<221> NAME/KEY: SIGNAL
<222> LOCATION: -32..-1

<400> SEQUENCE: 90

Met Leu Gly Thr Thr Gly Leu Gly Thr Gln Gly Pro Ser Gln Gln Ala
         -30             -25             -20

Leu Gly Phe Phe Ser Phe Met Leu Leu Gly Met Gly Gly Cys Leu Pro
         -15             -10              -5

Gly Phe Leu Leu Gln Pro Pro Asn Arg Ser Pro Thr Leu Pro Ala Ser
```

-continued

```
1               5               10              15
Thr Phe Ala His
                20

<210> SEQ ID NO 91
<211> LENGTH: 124
<212> TYPE: PRT
<213> ORGANISM: Homo sapiens
<220> FEATURE:
<221> NAME/KEY: SIGNAL
<222> LOCATION: -97..-1

<400> SEQUENCE: 91

Met Ala Asp Asp Leu Lys Arg Phe Leu Tyr Lys Lys Leu Pro Ser Val
        -95                 -90                 -85

Glu Gly Leu His Ala Ile Val Val Ser Asp Arg Asp Gly Val Pro Val
        -80                 -75                 -70

Ile Lys Val Ala Asn Asp Asn Ala Pro Glu His Ala Leu Arg Pro Gly
-65                 -60                 -55                 -50

Phe Leu Ser Thr Phe Ala Leu Ala Thr Asp Gln Gly Ser Lys Leu Gly
                -45                 -40                 -35

Leu Ser Lys Asn Lys Ser Ile Ile Cys Tyr Tyr Asn Thr Tyr Gln Val
                -30                 -25                 -20

Val Gln Phe Asn Arg Leu Pro Leu Val Val Ser Phe Ile Ala Ser Ser
        -15                 -10                 -5

Ser Ala Asn Thr Gly Leu Ile Val Ser Leu Glu Lys Glu Leu Ala Pro
        1                   5                   10                  15

Leu Phe Glu Glu Leu Arg Gln Val Val Glu Ile Ser
                20                  25

<210> SEQ ID NO 92
<211> LENGTH: 230
<212> TYPE: PRT
<213> ORGANISM: Homo sapiens
<220> FEATURE:
<221> NAME/KEY: SIGNAL
<222> LOCATION: -24..-1
<221> NAME/KEY: UNSURE
<222> LOCATION: 54,79
<223> OTHER INFORMATION: Xaa = any one of the twenty amino acids

<400> SEQUENCE: 92

Met Ala Ser Leu Gly Leu Gln Leu Val Gly Tyr Ile Leu Gly Leu Leu
                -20                 -15                 -10

Gly Leu Leu Gly Thr Leu Val Ala Met Leu Leu Pro Ser Trp Lys Thr
        -5                  1                   5

Ser Ser Tyr Val Gly Ala Ser Ile Val Thr Ala Val Gly Phe Ser Lys
        10                  15                  20

Gly Leu Trp Met Glu Cys Ala Thr His Ser Thr Gly Ile Thr Gln Cys
25                  30                  35                  40

Asp Ile Tyr Ser Thr Leu Leu Gly Leu Pro Ala Asp Ile Xaa Ala Ala
                45                  50                  55

Gln Ala Met Met Val Thr Ser Ser Ala Ile Ser Ser Leu Ala Cys Ile
                60                  65                  70

Ile Ser Val Val Gly Met Xaa Cys Thr Val Phe Cys Gln Glu Ser Arg
        75                  80                  85

Ala Lys Asp Arg Val Ala Val Ala Gly Gly Val Phe Phe Ile Leu Gly
        90                  95                  100

Gly Leu Leu Gly Phe Ile Pro Val Ala Trp Asn Leu His Gly Ile Leu
```

-continued

```
        105                 110                 115                 120
Arg Asp Phe Tyr Ser Pro Leu Val Pro Asp Ser Met Lys Phe Glu Ile
                125                 130                 135
Gly Glu Ala Leu Tyr Leu Gly Ile Ile Ser Ser Leu Phe Ser Leu Ile
            140                 145                 150
Ala Gly Ile Ile Leu Cys Phe Ser Cys Ser Ser Gln Arg Asn Arg Ser
            155                 160                 165
Asn Tyr Tyr Asp Ala Tyr Gln Ala Gln Pro Leu Ala Thr Arg Ser Ser
        170                 175                 180
Pro Arg Pro Gly Gln Pro Lys Val Lys Ser Glu Phe Asn Ser Tyr
185                 190                 195                 200
Ser Leu Thr Gly Tyr Val
                205

<210> SEQ ID NO 93
<211> LENGTH: 72
<212> TYPE: PRT
<213> ORGANISM: Homo sapiens
<220> FEATURE:
<221> NAME/KEY: SIGNAL
<222> LOCATION: -32..-1

<400> SEQUENCE: 93

Met Phe Ala Pro Ala Val Met Arg Ala Phe Arg Lys Asn Lys Thr Leu
        -30                 -25                 -20
Gly Tyr Gly Val Pro Met Leu Leu Leu Ile Val Gly Gly Ser Phe Gly
        -15                 -10                 -5
Leu Arg Glu Phe Ser Gln Ile Arg Tyr Asp Ala Val Lys Ser Lys Met
1               5                   10                  15
Asp Pro Glu Leu Glu Lys Lys Pro Lys Glu Asn Lys Ile Ser Leu Glu
            20                  25                  30
Ser Glu Tyr Glu Gly Ser Ile Cys
            35                  40

<210> SEQ ID NO 94
<211> LENGTH: 91
<212> TYPE: PRT
<213> ORGANISM: Homo sapiens
<220> FEATURE:
<221> NAME/KEY: SIGNAL
<222> LOCATION: -36..-1

<400> SEQUENCE: 94

Met Asn Thr Phe Glu Pro Asp Ser Leu Ala Val Ile Ala Phe Phe Leu
    -35                 -30                 -25
Pro Ile Trp Thr Phe Ser Ala Leu Thr Phe Leu Phe Leu His Leu Pro
-20                 -15                 -10                 -5
Pro Ser Thr Ser Leu Phe Ile Asn Leu Ala Arg Gly Gln Ile Lys Gly
                1                   5                   10
Pro Leu Gly Leu Ile Leu Leu Ser Phe Cys Gly Gly Tyr Thr Lys
            15                  20                  25
Cys Asp Phe Ala Leu Ser Tyr Leu Glu Ile Pro Asn Arg Ile Glu Phe
        30                  35                  40
Ser Ile Met Asp Pro Lys Arg Lys Thr Lys Cys
45                  50                  55

<210> SEQ ID NO 95
<211> LENGTH: 106
<212> TYPE: PRT
```

```
<213> ORGANISM: Homo sapiens
<220> FEATURE:
<221> NAME/KEY: SIGNAL
<222> LOCATION: -32..-1

<400> SEQUENCE: 95

Met Phe Ala Pro Ala Val Met Arg Ala Phe Arg Lys Asn Lys Thr Leu
        -30                 -25                 -20

Gly Tyr Gly Val Pro Met Leu Leu Leu Ile Val Gly Gly Ser Phe Gly
        -15                 -10                  -5

Leu Arg Glu Phe Ser Gln Ile Arg Tyr Asp Ala Val Lys Gly Lys Met
  1               5                  10                  15

Asp Pro Glu Leu Glu Lys Lys Leu Lys Glu Asn Lys Ile Ser Leu Glu
                 20                  25                  30

Ser Glu Tyr Glu Lys Ile Lys Asp Ser Lys Phe Asp Asp Trp Lys Asn
                 35                  40                  45

Ile Arg Gly Pro Arg Pro Trp Glu Asp Pro Asp Leu Leu Gln Gly Arg
                 50                  55                  60

Asn Pro Glu Ser Leu Lys Thr Lys Thr Thr
 65                  70

<210> SEQ ID NO 96
<211> LENGTH: 172
<212> TYPE: PRT
<213> ORGANISM: Homo sapiens
<220> FEATURE:
<221> NAME/KEY: SIGNAL
<222> LOCATION: -21..-1

<400> SEQUENCE: 96

Met Trp Trp Phe Gln Gln Gly Leu Ser Phe Leu Pro Ser Ala Leu Val
        -20                 -15                 -10

Ile Trp Thr Ser Ala Ala Phe Ile Phe Ser Tyr Ile Thr Ala Val Thr
 -5                   1                   5                  10

Leu His His Ile Asp Pro Ala Leu Pro Tyr Ile Ser Asp Thr Gly Thr
                 15                  20                  25

Val Ala Pro Glu Lys Cys Leu Phe Gly Ala Met Leu Asn Ile Ala Ala
                 30                  35                  40

Val Leu Cys Ile Ala Thr Ile Tyr Val Arg Tyr Lys Gln Val His Ala
 45                  50                  55

Leu Ser Pro Glu Glu Asn Val Ile Ile Lys Leu Asn Lys Ala Gly Leu
 60                  65                  70                  75

Val Leu Gly Ile Leu Ser Cys Leu Gly Leu Ser Ile Val Ala Asn Phe
                 80                  85                  90

Gln Glu Asn Asn Pro Phe Cys Cys Thr Cys Lys Trp Ser Cys Ala Tyr
                 95                 100                 105

Leu Trp Tyr Gly Leu Ile Ile Tyr Val Cys Ser Asp His Pro Phe Leu
                110                 115                 120

Pro Lys Cys Ser Pro Lys Ser Asn Gly Lys Thr Ser Leu Leu Asp Gln
                125                 130                 135

Thr Val Val Gly Tyr Leu Val Trp Ser Lys Cys Thr
140                 145                 150

<210> SEQ ID NO 97
<211> LENGTH: 56
<212> TYPE: PRT
<213> ORGANISM: Homo sapiens
<220> FEATURE:
<221> NAME/KEY: SIGNAL
```

```
<222> LOCATION: -42..-1

<400> SEQUENCE: 97

Met Cys Phe Pro Glu His Arg Arg Gln Met Tyr Ile Gln Asp Arg Leu
        -40                 -35                 -30

Asp Ser Val Thr Arg Arg Ala Arg Gln Gly Arg Ile Cys Ala Ile Leu
        -25                 -20                 -15

Leu Leu Gln Ser Gln Cys Ala Tyr Trp Ala Leu Pro Glu Pro Arg Thr
-10                  -5                   1                   5

Leu Asp Gly Gly His Leu Met Gln
                10

<210> SEQ ID NO 98
<211> LENGTH: 46
<212> TYPE: PRT
<213> ORGANISM: Homo sapiens
<220> FEATURE:
<221> NAME/KEY: SIGNAL
<222> LOCATION: -22..-1

<400> SEQUENCE: 98

Met Gln Asn His Leu Gln Thr Arg Pro Leu Phe Leu Thr Cys Leu Phe
        -20                 -15                 -10

Trp Pro Leu Ala Ala Leu Asn Val Asn Ser Thr Phe Glu Cys Leu Ile
-5                   1                   5                   10

Leu Gln Cys Ser Val Phe Ser Phe Ala Phe Phe Ala Leu Trp
                15                  20

<210> SEQ ID NO 99
<211> LENGTH: 251
<212> TYPE: PRT
<213> ORGANISM: Homo sapiens
<220> FEATURE:
<221> NAME/KEY: SIGNAL
<222> LOCATION: -28..-1
<221> NAME/KEY: UNSURE
<222> LOCATION: 54,131,132,140,179,194,213,221
<223> OTHER INFORMATION: Xaa = any one of the twenty amino acids

<400> SEQUENCE: 99

Met Trp Arg Leu Leu Ala Arg Ala Ser Ala Pro Leu Leu Arg Val Pro
            -25                 -20                 -15

Leu Ser Asp Ser Trp Ala Leu Leu Pro Ala Ser Ala Gly Val Lys Thr
        -10                  -5                   1

Leu Leu Pro Val Pro Ser Phe Glu Asp Val Ser Ile Pro Glu Lys Pro
5                   10                  15                  20

Lys Leu Arg Phe Ile Glu Arg Ala Pro Leu Val Pro Lys Val Arg Arg
                25                  30                  35

Glu Pro Lys Asn Leu Ser Asp Ile Arg Gly Pro Ser Thr Glu Ala Thr
            40                  45                  50

Glu Xaa Thr Glu Gly Asn Phe Ala Ile Leu Ala Leu Gly Gly Gly Tyr
        55                  60                  65

Leu His Trp Gly His Phe Glu Met Met Arg Leu Thr Ile Asn Arg Ser
    70                  75                  80

Met Asp Pro Lys Asn Met Phe Ala Ile Trp Arg Val Pro Ala Pro Phe
85                  90                  95                  100

Lys Pro Ile Thr Arg Lys Ser Val Gly His Arg Met Gly Gly Gly Lys
                105                 110                 115

Gly Ala Ile Asp His Tyr Val Thr Pro Val Lys Ala Gly Arg Xaa Xaa
            120                 125                 130
```

-continued

Val Glu Met Gly Gly Arg Cys Xaa Phe Glu Val Gln Gly Phe Leu
          135                 140                 145

Asp Gln Val Ala His Lys Leu Pro Phe Ala Ala Lys Ala Val Ser Arg
        150                 155                 160

Gly Thr Leu Glu Lys Met Arg Lys Asp Gln Glu Arg Glu Xaa Asn
165                 170                 175                 180

Asn Gln Asn Pro Trp Thr Phe Glu Arg Ile Ala Thr Ala Xaa Met Leu
                185                 190                 195

Gly Ile Arg Lys Val Leu Ser Pro Tyr Asp Leu Thr His Lys Gly Lys
            200                 205                 210

Xaa Trp Gly Lys Phe Tyr Met Pro Xaa Arg Val
        215                 220

<210> SEQ ID NO 100
<211> LENGTH: 77
<212> TYPE: PRT
<213> ORGANISM: Homo sapiens
<220> FEATURE:
<221> NAME/KEY: SIGNAL
<222> LOCATION: -30..-1

<400> SEQUENCE: 100

Met Leu Arg Leu Asp Ile Ile Asn Ser Leu Val Thr Thr Val Phe Met
-30                 -25                 -20                 -15

Leu Ile Val Ser Val Leu Ala Leu Ile Pro Glu Thr Thr Thr Leu Thr
            -10                 -5                  1

Val Gly Gly Gly Val Phe Ala Leu Val Thr Ala Val Cys Cys Leu Ala
        5                   10                  15

Asp Gly Ala Leu Ile Tyr Arg Lys Leu Leu Phe Asn Pro Ser Gly Pro
    20                  25                  30

Tyr Gln Lys Lys Pro Val His Glu Lys Lys Glu Val Leu
35                  40                  45

<210> SEQ ID NO 101
<211> LENGTH: 81
<212> TYPE: PRT
<213> ORGANISM: Homo sapiens
<220> FEATURE:
<221> NAME/KEY: SIGNAL
<222> LOCATION: -31..-1

<400> SEQUENCE: 101

Met Ser Asn Thr His Thr Val Leu Val Ser Leu Pro His Pro His Pro
        -30                 -25                 -20

Ala Leu Thr Cys Cys His Leu Gly Leu Pro His Pro Val Arg Ala Pro
-15                 -10                 -5                  1

Arg Pro Leu Pro Arg Val Glu Pro Trp Asp Pro Arg Trp Gln Asp Ser
            5                   10                  15

Glu Leu Arg Tyr Pro Gln Ala Met Asn Ser Phe Leu Asn Glu Arg Ser
        20                  25                  30

Ser Pro Cys Arg Thr Leu Arg Gln Glu Ala Ser Ala Asp Arg Cys Asp
    35                  40                  45

Leu
50

<210> SEQ ID NO 102
<211> LENGTH: 126
<212> TYPE: PRT
<213> ORGANISM: Homo sapiens

```
<220> FEATURE:
<221> NAME/KEY: SIGNAL
<222> LOCATION: -20..-1

<400> SEQUENCE: 102

Met Lys Val His Met His Thr Lys Phe Cys Leu Ile Cys Leu Leu Thr
-20              -15                 -10                  -5

Phe Ile Phe His His Cys Asn His Cys His Glu Glu His Asp His Gly
                  1              5                   10

Pro Glu Ala Leu His Arg Gln His Arg Gly Met Thr Glu Leu Glu Pro
            15                  20                  25

Ser Lys Phe Ser Lys Gln Ala Ala Glu Asn Glu Lys Lys Tyr Tyr Ile
            30                  35                  40

Glu Lys Leu Phe Glu Arg Tyr Gly Glu Asn Gly Arg Leu Ser Phe Phe
45                  50                  55                  60

Gly Leu Glu Lys Leu Leu Thr Asn Leu Gly Leu Gly Glu Arg Lys Val
                65                  70                  75

Val Glu Ile Asn His Glu Asp Leu Gly His Asp His Val Ser His Leu
                80                  85                  90

Arg Tyr Phe Gly Ser Ser Arg Gly Lys Ala Phe Ser Leu Thr
                95                  100                 105

<210> SEQ ID NO 103
<211> LENGTH: 273
<212> TYPE: PRT
<213> ORGANISM: Homo sapiens
<220> FEATURE:
<221> NAME/KEY: SIGNAL
<222> LOCATION: -45..-1
<221> NAME/KEY: UNSURE
<222> LOCATION: 181,187,193,196,198,199,203,212,214
<223> OTHER INFORMATION: Xaa = any one of the twenty amino acids

<400> SEQUENCE: 103

Met Asn Trp Ser Ile Phe Glu Gly Leu Leu Ser Gly Val Asn Lys Tyr
-45                 -40                 -35                 -30

Ser Thr Ala Phe Gly Arg Ile Trp Leu Ser Leu Val Phe Ile Phe Arg
                -25                 -20                 -15

Val Leu Val Tyr Leu Val Thr Ala Glu Arg Val Trp Ser Asp His
            -10                 -5                  1

Lys Asp Phe Asp Cys Asn Thr Arg Gln Pro Gly Cys Ser Asn Val Cys
    5                   10                  15

Phe Asp Glu Phe Phe Pro Val Ser His Val Arg Leu Trp Ala Leu Gln
20                  25                  30                  35

Leu Ile Leu Val Thr Cys Pro Ser Leu Leu Val Val Met His Val Ala
                40                  45                  50

Tyr Arg Glu Val Gln Glu Lys Arg His Arg Glu Ala His Gly Glu Asn
                55                  60                  65

Ser Gly Arg Leu Tyr Leu Asn Pro Gly Lys Lys Arg Gly Gly Leu Trp
            70                  75                  80

Trp Thr Tyr Val Cys Ser Leu Val Phe Lys Ala Ser Val Asp Ile Ala
            85                  90                  95

Phe Leu Tyr Val Phe His Ser Phe Tyr Pro Lys Tyr Ile Leu Pro Pro
100                 105                 110                 115

Val Val Lys Cys His Ala Asp Pro Cys Pro Asn Ile Val Asp Cys Phe
                120                 125                 130

Ile Ser Lys Pro Ser Glu Lys Asn Ile Phe Thr Leu Phe Met Val Ala
            135                 140                 145
```

```
Thr Ala Ala Ile Cys Ile Leu Leu Asn Leu Val Glu Leu Ile Tyr Leu
            150                 155                 160

Val Ser Lys Arg Cys His Glu Cys Leu Ala Ala Arg Lys Ala Gln Ala
        165                 170                 175

Met Xaa Thr Gly His His Pro Xaa Asp Thr Thr Phe Ser Xaa Lys Gln
180                 185                 190                 195

Xaa Asp Xaa Xaa Ser Gly Asp Xaa Ile Phe Leu Gly Ser Asp Ser His
                200                 205                 210

Xaa Pro Xaa Leu Pro Asp Arg Pro Arg Asp His Val Lys Lys Thr Ile
            215                 220                 225

Leu

<210> SEQ ID NO 104
<211> LENGTH: 158
<212> TYPE: PRT
<213> ORGANISM: Homo sapiens
<220> FEATURE:
<221> NAME/KEY: SIGNAL
<222> LOCATION: -37..-1

<400> SEQUENCE: 104

Met Ala Ser Lys Ile Leu Leu Asn Val Gln Glu Glu Val Thr Cys Pro
        -35                 -30                 -25

Ile Cys Leu Glu Leu Leu Thr Glu Pro Leu Ser Leu Asp Cys Gly His
        -20                 -15                 -10

Ser Leu Cys Arg Ala Cys Ile Thr Val Ser Asn Lys Glu Ala Val Thr
-5                   1                   5                  10

Ser Met Gly Gly Lys Ser Ser Cys Pro Val Cys Gly Ile Ser Tyr Ser
            15                  20                  25

Phe Glu His Leu Gln Ala Asn Gln His Arg Ala Asn Ile Val Glu Arg
            30                  35                  40

Leu Lys Glu Val Lys Leu Ser Pro Asp Asn Gly Lys Lys Arg Asp Leu
        45                  50                  55

Cys Asp His His Gly Glu Lys Leu Leu Leu Phe Cys Lys Glu Asp Arg
60                  65                  70                  75

Lys Val Ile Cys Trp Leu Cys Glu Arg Ser Gln Glu His Arg Gly His
            80                  85                  90

His Thr Gly Pro His Gly Gly Ser Ile Gln Gly Met Ser Gly Glu Thr
            95                 100                 105

Pro Gly Ser Pro Gln Glu Ala Glu Glu Gly Arg Gly Gly Ser
        110                 115                 120

<210> SEQ ID NO 105
<211> LENGTH: 51
<212> TYPE: PRT
<213> ORGANISM: Homo sapiens
<220> FEATURE:
<221> NAME/KEY: SIGNAL
<222> LOCATION: -19..-1
<221> NAME/KEY: UNSURE
<222> LOCATION: 8
<223> OTHER INFORMATION: Xaa = any one of the twenty amino acids

<400> SEQUENCE: 105

Met Arg Thr Leu Phe Asn Leu Leu Trp Leu Ala Leu Ala Cys Ser Pro
                -15                 -10                 -5

Val His Thr Thr Leu Ser Lys Ser Asp Ala Xaa Lys Pro Pro Gln Arg
        1                   5                  10
```

-continued

Arg Cys Trp Arg Arg Val Ser Phe Gln Ile Ser Arg Cys Lys Thr Gly
        15                  20                  25

Val Trp Trp
 30

<210> SEQ ID NO 106
<211> LENGTH: 359
<212> TYPE: PRT
<213> ORGANISM: Homo sapiens
<220> FEATURE:
<221> NAME/KEY: SIGNAL
<222> LOCATION: -34..-1
<221> NAME/KEY: UNSURE
<222> LOCATION: 20,64,65,130,156,282,288,289,294,296,300,302,310
<223> OTHER INFORMATION: Xaa = any one of the twenty amino acids

<400> SEQUENCE: 106

Met Leu Leu Ser Ile Gly Met Leu Met Leu Ser Ala Thr Gln Val Tyr
                -30                 -25                 -20

Thr Ile Leu Thr Val Gln Leu Phe Ala Phe Leu Asn Leu Leu Pro Val
                -15                 -10                 -5

Glu Ala Asp Ile Leu Ala Tyr Asn Phe Glu Asn Ala Ser Gln Thr Phe
 1               5                   10

Asp Asp Leu Pro Ala Xaa Phe Gly Tyr Arg Leu Pro Ala Glu Gly Leu
 15              20                  25                      30

Lys Gly Phe Leu Ile Asn Ser Lys Pro Glu Asn Ala Cys Glu Pro Ile
                 35                  40                      45

Val Pro Pro Val Lys Asp Asn Ser Ser Gly Thr Phe Ile Val Leu
                 50                  55                  60

Ile Xaa Xaa Leu Asp Cys Asn Phe Asp Ile Lys Val Leu Asn Ala Gln
     65                      70                  75

Arg Ala Gly Tyr Lys Ala Ala Ile Val His Asn Val Asp Ser Asp Asp
 80                  85                      90

Leu Ile Ser Met Gly Ser Asn Asp Ile Glu Val Leu Lys Lys Ile Asp
 95                  100                 105                 110

Ile Pro Ser Val Phe Ile Gly Glu Ser Ser Ala Ser Ser Leu Lys Asp
                 115                 120                 125

Glu Phe Thr Xaa Glu Lys Gly Gly His Leu Ile Leu Val Pro Glu Phe
             130                 135                 140

Ser Leu Pro Leu Glu Tyr Tyr Leu Ile Pro Phe Leu Ile Xaa Val Gly
             145                 150                 155

Ile Cys Leu Ile Leu Ile Val Ile Phe Met Ile Thr Lys Leu Ser Arg
             160                 165                 170

Asp Arg His Arg Ala Arg Arg Asn Arg Leu Arg Lys Asp Gln Leu Lys
175                 180                 185                 190

Lys Leu Pro Val His Lys Phe Lys Lys Gly Asp Glu Tyr Asp Val Cys
                 195                 200                 205

Ala Ile Cys Leu Asp Glu Tyr Glu Asp Gly Asp Lys Leu Arg Ile Leu
             210                 215                 220

Pro Cys Ser His Ala Tyr His Cys Lys Cys Val Asp Pro Trp Leu Thr
             225                 230                 235

Lys Thr Lys Lys Thr Cys Pro Val Cys Arg Gln Lys Val Val Pro Ser
240                 245                 250

Gln Gly Asp Ser Asp Ser Asp Thr Asp Ser Ser Gln Glu Glu Asn Glu
255                 260                 265                 270

Val Thr Glu His Thr Pro Leu Leu Arg Pro Leu Xaa Phe Cys Gln Cys
                 275                 280                 285

```
Pro Xaa Xaa Phe Gly Ala Leu Xaa Gly Xaa Pro Ala His Xaa Gln Xaa
        290                 295                 300

His Asp Arg Ile Ile Gln Thr Xaa Glu Glu Asp Asp Asn Glu Asp Thr
        305                 310                 315

Asp Ser Ser Asp Ala Glu Glu
        320             325

<210> SEQ ID NO 107
<211> LENGTH: 291
<212> TYPE: PRT
<213> ORGANISM: Homo sapiens
<220> FEATURE:
<221> NAME/KEY: SIGNAL
<222> LOCATION: -42..-1

<400> SEQUENCE: 107

Met Asp Ser Arg Val Ser Ser Pro Glu Lys Gln Asp Lys Glu Asn Phe
        -40                 -35                 -30

Val Gly Val Asn Asn Lys Arg Leu Gly Val Cys Gly Trp Ile Leu Phe
        -25                 -20                 -15

Ser Leu Ser Phe Leu Leu Val Ile Ile Thr Phe Pro Ile Ser Ile Trp
-10                  -5                  1                   5

Met Cys Leu Lys Ile Ile Lys Glu Tyr Glu Arg Ala Val Val Phe Arg
            10                  15                  20

Leu Gly Arg Ile Gln Ala Asp Lys Ala Lys Gly Pro Gly Leu Ile Leu
            25                  30                  35

Val Leu Pro Cys Ile Asp Val Phe Val Lys Val Asp Leu Arg Thr Val
            40                  45                  50

Thr Cys Asn Ile Pro Pro Gln Glu Ile Leu Thr Arg Asp Ser Val Thr
55                  60                  65                  70

Thr Gln Val Asp Gly Val Val Tyr Tyr Arg Ile Tyr Ser Ala Val Ser
                75                  80                  85

Ala Val Ala Asn Val Asn Asp Val His Gln Ala Thr Phe Leu Leu Ala
                90                  95                  100

Gln Thr Thr Leu Arg Asn Val Leu Gly Thr Gln Thr Leu Ser Gln Ile
            105                 110                 115

Leu Ala Gly Arg Glu Glu Ile Ala His Ser Ile Gln Thr Leu Leu Asp
            120                 125                 130

Asp Ala Thr Glu Leu Trp Gly Ile Arg Val Ala Arg Val Glu Ile Lys
135                 140                 145                 150

Asp Val Arg Ile Pro Val Gln Leu Gln Arg Ser Met Ala Ala Glu Ala
                155                 160                 165

Glu Ala Thr Arg Glu Ala Arg Ala Lys Val Leu Ala Ala Glu Gly Glu
            170                 175                 180

Met Ser Ala Ser Lys Ser Leu Lys Ser Ala Ser Met Val Leu Ala Glu
            185                 190                 195

Ser Pro Ile Ala Leu Gln Leu Arg Tyr Leu Gln Thr Leu Ser Thr Val
            200                 205                 210

Ala Thr Glu Lys Asn Ser Thr Ile Val Phe Pro Leu Pro Met Asn Ile
215                 220                 225                 230

Leu Glu Gly Ile Gly Gly Val Ser Tyr Asp Asn His Lys Lys Leu Pro
                235                 240                 245

Asn Lys Ala

<210> SEQ ID NO 108
```

-continued

```
<211> LENGTH: 67
<212> TYPE: PRT
<213> ORGANISM: Homo sapiens
<220> FEATURE:
<221> NAME/KEY: SIGNAL
<222> LOCATION: -26..-1

<400> SEQUENCE: 108

Met Ser Thr Trp Leu Leu Leu Ile Ala Leu Lys Thr Leu Ile Thr Trp
    -25                 -20                 -15
Val Ser Leu Phe Ile Asp Cys Val Met Thr Arg Lys Leu Thr Asn Cys
-10                  -5                   1                   5
Asn Ala Arg Glu Thr Ile Lys Gly Ile Gln Lys Arg Glu Ala Ser Asn
             10                  15                  20
Cys Phe Ala Ile Arg His Phe Glu Asn Lys Phe Ala Val Glu Thr Leu
         25                  30                  35
Ile Cys Ser
    40

<210> SEQ ID NO 109
<211> LENGTH: 127
<212> TYPE: PRT
<213> ORGANISM: Homo sapiens
<220> FEATURE:
<221> NAME/KEY: SIGNAL
<222> LOCATION: -63..-1

<400> SEQUENCE: 109

Met Ser Ala Ala Gly Ala Arg Gly Leu Arg Ala Thr Tyr His Arg Leu
            -60                 -55                 -50
Leu Asp Lys Val Glu Leu Met Leu Pro Glu Lys Leu Arg Pro Leu Tyr
        -45                 -40                 -35
Asn His Pro Ala Gly Pro Arg Thr Val Phe Phe Trp Ala Pro Ile Met
    -30                 -25                 -20
Lys Trp Gly Leu Val Cys Ala Gly Leu Ala Asp Met Ala Arg Pro Ala
-15                 -10                  -5                   1
Glu Lys Leu Ser Thr Ala Gln Ser Ala Val Leu Met Ala Thr Gly Phe
             5                  10                  15
Ile Trp Ser Arg Tyr Ser Leu Val Ile Ile Pro Lys Asn Trp Ser Leu
        20                  25                  30
Phe Ala Val Asn Phe Val Gly Ala Ala Gly Ala Ser Gln Leu Phe
    35                  40                  45
Arg Ile Trp Arg Tyr Asn Gln Glu Leu Lys Ala Lys Ala His Lys
50                  55                  60

<210> SEQ ID NO 110
<211> LENGTH: 97
<212> TYPE: PRT
<213> ORGANISM: Homo sapiens
<220> FEATURE:
<221> NAME/KEY: SIGNAL
<222> LOCATION: -20..-1
<221> NAME/KEY: UNSURE
<222> LOCATION: 53
<223> OTHER INFORMATION: Xaa = any one of the twenty amino acids

<400> SEQUENCE: 110

Met Lys Gly Trp Gly Trp Leu Ala Leu Leu Gly Ala Leu Leu Gly
-20                 -15                 -10                  -5
Thr Ala Trp Ala Arg Arg Ser Arg Asp Leu His Cys Gly Ala Cys Arg
             1                   5                  10
```

-continued

```
Ala Leu Val Asp Glu Leu Glu Trp Glu Ile Ala Gln Val Asp Pro Lys
         15                  20                  25

Lys Thr Ile Gln Met Gly Ser Phe Arg Ile Asn Pro Asp Gly Ser Gln
         30                  35                  40

Ser Val Val Glu Val Thr Val Thr Xaa Ser Pro Lys Thr Lys Val Ala
45                   50                  55                  60

His Ser Gly Phe Trp Met Lys Ile Arg Leu Leu Lys Lys Gly Pro Trp
                 65                  70                  75

Ser

<210> SEQ ID NO 111
<211> LENGTH: 86
<212> TYPE: PRT
<213> ORGANISM: Homo sapiens
<220> FEATURE:
<221> NAME/KEY: SIGNAL
<222> LOCATION: -20..-1

<400> SEQUENCE: 111

Met Lys Gly Trp Gly Trp Leu Ala Leu Leu Gly Ala Leu Leu Gly
-20                 -15                 -10                 -5

Thr Ala Trp Ala Arg Arg Ser Gln Asp Leu His Cys Gly Ala Cys Arg
                 1                   5                   10

Ala Leu Val Asp Glu Thr Arg Met Gly Asn Cys Pro Gly Gly Pro Gln
         15                  20                  25

Glu Asp His Ser Asp Gly Ile Phe Pro Asp Gln Ser Arg Trp Gln Pro
         30                  35                  40

Val Ser Gly Gly Gly Ala Leu Cys Pro Leu Arg Gly Pro Pro His Arg
45                   50                  55                  60

Ala Ala Gly Gly Asp Met
                 65

<210> SEQ ID NO 112
<211> LENGTH: 71
<212> TYPE: PRT
<213> ORGANISM: Homo sapiens
<220> FEATURE:
<221> NAME/KEY: SIGNAL
<222> LOCATION: -25..-1

<400> SEQUENCE: 112

Met Pro Ala Gly Val Pro Met Ser Thr Tyr Leu Lys Met Phe Ala Ala
-25                 -20                 -15                 -10

Ser Leu Leu Ala Met Cys Ala Gly Ala Glu Val Val His Arg Tyr Tyr
                 -5                  1                   5

Arg Pro Asp Leu Thr Ile Pro Glu Ile Pro Pro Lys Arg Gly Glu Leu
         10                  15                  20

Lys Thr Glu Leu Leu Gly Leu Glu Arg Lys His Lys Pro Gln Val
         25                  30                  35

Ser Gln Gln Glu Glu Leu Lys
40                  45

<210> SEQ ID NO 113
<211> LENGTH: 60
<212> TYPE: PRT
<213> ORGANISM: Homo sapiens
<220> FEATURE:
<221> NAME/KEY: SIGNAL
<222> LOCATION: -42..-1

<400> SEQUENCE: 113
```

```
Met Asp Gly His Trp Ser Ala Ala Phe Ser Ala Leu Thr Val Thr Ala
        -40                 -35                 -30

Met Ser Ser Trp Ala Arg Arg Arg Ser Ser Ser Arg Arg Ile Pro
    -25                 -20                 -15

Ser Leu Pro Gly Ser Pro Val Cys Trp Ala Trp Pro Trp Tyr Pro Asp
-10                  -5                   1                   5

Thr Thr Ser Phe Pro Leu Arg Cys Arg Gly Arg Val
            10                  15
```

<210> SEQ ID NO 114
<211> LENGTH: 118
<212> TYPE: PRT
<213> ORGANISM: Homo sapiens
<220> FEATURE:
<221> NAME/KEY: SIGNAL
<222> LOCATION: -83..-1
<221> NAME/KEY: UNSURE
<222> LOCATION: 28,32
<223> OTHER INFORMATION: Xaa = any one of the twenty amino acids

<400> SEQUENCE: 114

```
Met Leu Pro Val Gln Ser Phe Thr Leu Val Ala Gln Ala Gly Val Gln
            -80                 -75                 -70

Trp Arg His Leu Ser Ser Leu Gln Leu Leu Pro Pro Glu Phe Lys Gly
        -65                 -60                 -55

Phe Ser Cys Leu Ser Leu Pro Ser Ser Trp Asp Tyr Arg Arg Pro Pro
        -50                 -45                 -40

Pro Cys Pro Ala Gly Phe Phe Val Phe Leu Val Glu Thr Gly Leu His
-35                 -30                 -25                 -20

His Val Gly Gln Ala Gly Leu Glu Leu Leu Thr Ser Cys Ser Pro Pro
                -15                 -10                 -5

Ala Ser Ala Ser Gln Ser Ala Ala Ile Thr Gly Val Ser His Val Pro
        1                   5                   10

Gly Lys Lys Lys Leu Leu Lys Val Glu Lys Lys Asn Leu Arg Xaa Leu
    15                  20                  25

Leu Thr Xaa Ile Lys Thr
30                  35
```

<210> SEQ ID NO 115
<211> LENGTH: 76
<212> TYPE: PRT
<213> ORGANISM: Homo sapiens
<220> FEATURE:
<221> NAME/KEY: SIGNAL
<222> LOCATION: -22..-1
<221> NAME/KEY: UNSURE
<222> LOCATION: 22,43
<223> OTHER INFORMATION: Xaa = any one of the twenty amino acids

<400> SEQUENCE: 115

```
Met Glu Leu Ile Ser Pro Thr Val Ile Ile Leu Gly Cys Leu Ala
        -20                 -15                 -10

Leu Phe Leu Leu Leu Gln Arg Lys Asn Leu Arg Arg Pro Pro Cys Ile
    -5                  1                   5                   10

Lys Gly Trp Ile Pro Trp Ile Gly Val Gly Phe Xaa Phe Gly Lys Ala
                15                  20                  25

Pro Leu Glu Phe Ile Glu Lys Ala Arg Ile Lys Val Cys Gly Arg Gly
                30                  35                  40

Xaa Arg Gly Leu Gln Arg Arg Gln Cys Phe Leu Phe
    45                  50
```

```
<210> SEQ ID NO 116
<211> LENGTH: 95
<212> TYPE: PRT
<213> ORGANISM: Homo sapiens
<220> FEATURE:
<221> NAME/KEY: SIGNAL
<222> LOCATION: -52..-1

<400> SEQUENCE: 116

Met Ala Glu Thr Lys Asp Ala Ala Gln Met Leu Val Thr Phe Lys Asp
        -50                 -45                 -40
Val Ala Val Thr Phe Thr Arg Glu Glu Trp Arg Gln Leu Asp Leu Ala
    -35                 -30                 -25
Gln Arg Thr Leu Tyr Arg Glu Val Met Leu Glu Thr Cys Gly Leu Leu
-20                 -15                 -10                  -5
Val Ser Leu Gly Gln Ser Ile Trp Leu His Ile Thr Glu Asn Gln Ile
                  1                 5                  10
Lys Leu Ala Ser Pro Gly Arg Lys Phe Thr Asn Ser Pro Asp Glu Lys
              15                  20                  25
Pro Glu Val Trp Leu Ala Pro Gly Leu Phe Gly Ala Ala Gln
          30                  35                  40

<210> SEQ ID NO 117
<211> LENGTH: 82
<212> TYPE: PRT
<213> ORGANISM: Homo sapiens
<220> FEATURE:
<221> NAME/KEY: SIGNAL
<222> LOCATION: -22..-1

<400> SEQUENCE: 117

Met Glu Leu Ile Ser Pro Thr Val Ile Ile Leu Gly Cys Leu Ala
        -20                 -15                 -10
Leu Phe Leu Leu Leu Gln Arg Lys Asn Leu Arg Arg Pro Pro Cys Ile
    -5                  1                  5                  10
Lys Gly Trp Ile Pro Trp Ile Gly Val Gly Phe Glu Phe Gly Lys Ala
              15                  20                  25
Pro Leu Glu Phe Ile Glu Lys Ala Arg Ile Lys Tyr Gly Pro Ile Phe
              30                  35                  40
Thr Val Phe Ala Met Gly Asn Arg Met Thr Phe Val Thr Glu Glu Gly
              45                  50                  55
Arg Asn
    60

<210> SEQ ID NO 118
<211> LENGTH: 89
<212> TYPE: PRT
<213> ORGANISM: Homo sapiens
<220> FEATURE:
<221> NAME/KEY: SIGNAL
<222> LOCATION: -16..-1

<400> SEQUENCE: 118

Met Ile Ile Ser Leu Phe Ile Tyr Ile Phe Leu Thr Cys Ser Asn Thr
        -15                 -10                  -5
Ser Pro Ser Tyr Gln Gly Thr Gln Leu Gly Leu Gly Leu Pro Ser Ala
1                   5                  10                  15
Gln Trp Trp Pro Leu Thr Gly Arg Arg Met Gln Cys Cys Arg Leu Phe
              20                  25                  30
```

```
Cys Phe Leu Leu Gln Asn Cys Leu Phe Pro Phe Pro Leu His Leu Ile
        35                  40                  45

Gln His Asp Pro Cys Glu Leu Val Leu Thr Ile Ser Trp Asp Trp Ala
    50                  55                  60

Glu Ala Gly Ala Ser Leu Tyr Ser Pro
65                  70
```

<210> SEQ ID NO 119
<211> LENGTH: 30
<212> TYPE: PRT
<213> ORGANISM: Homo sapiens
<220> FEATURE:
<221> NAME/KEY: SIGNAL
<222> LOCATION: -19..-1

<400> SEQUENCE: 119

```
Met Thr Met Ala Glu Cys Pro Thr Leu Cys Val Ser Ser Pro Ala
            -15                 -10                 -5

Leu Trp Ala Ala Ser Glu Thr Thr Asp Asp Val Cys Arg Glu
                1               5                   10
```

<210> SEQ ID NO 120
<211> LENGTH: 115
<212> TYPE: PRT
<213> ORGANISM: Homo sapiens
<220> FEATURE:
<221> NAME/KEY: SIGNAL
<222> LOCATION: -103..-1

<400> SEQUENCE: 120

```
Met Val Ile Arg Val Tyr Ile Ala Ser Ser Gly Ser Thr Ala Ile
            -100                -95                 -90

Lys Lys Lys Gln Gln Asp Val Leu Gly Phe Leu Glu Ala Asn Lys Ile
        -85                 -80                 -75

Gly Phe Glu Glu Lys Asp Ile Ala Ala Asn Glu Glu Asn Arg Lys Trp
    -70                 -65                 -60

Met Arg Glu Asn Val Pro Glu Asn Ser Arg Pro Ala Thr Gly Asn Pro
-55                 -50                 -45                 -40

Leu Pro Pro Gln Ile Phe Asn Glu Ser Gln Tyr Arg Gly Asp Tyr Asp
            -35                 -30                 -25

Ala Phe Phe Glu Ala Arg Glu Asn Asn Ala Val Tyr Ala Phe Leu Gly
            -20                 -15                 -10

Leu Thr Ala Pro Ser Gly Ser Lys Glu Ala Gly Arg Cys Lys Gln Ser
        -5                  1                   5

Ser Lys Pro
10
```

<210> SEQ ID NO 121
<211> LENGTH: 105
<212> TYPE: PRT
<213> ORGANISM: Homo sapiens
<220> FEATURE:
<221> NAME/KEY: SIGNAL
<222> LOCATION: -76..-1

<400> SEQUENCE: 121

```
Met Pro Leu Leu Cys Gln Ile Glu Met Glu Tyr Leu Leu Leu Lys Trp
        -75                 -70                 -65

Gln Met Thr Met Leu Gln Ser Met Leu Cys Asp Leu Val Ser Tyr Pro
-60                 -55                 -50                 -45

Leu Leu Pro Leu Gln Gln Thr Lys Glu Ala Asn Leu Asp Phe Pro Lys
```

-continued

```
                    -40                 -35                 -30
Ile Lys Val Ser Ser Val Thr Ile Thr Pro Thr Arg Trp Phe Asn Leu
            -25                 -20                 -15

Ile Val Tyr Leu Trp Val Val Ser Phe Ile Ala Ser Ser Ser Ala Asn
        -10                  -5                   1

Thr Gly Leu Ile Val Ser Leu Glu Lys Glu Leu Ala Pro Leu Phe Glu
 5               10                  15                  20

Glu Leu Arg Gln Val Val Glu Val Ser
            25
```

<210> SEQ ID NO 122
<211> LENGTH: 93
<212> TYPE: PRT
<213> ORGANISM: Homo sapiens
<220> FEATURE:
<221> NAME/KEY: SIGNAL
<222> LOCATION: -22..-1

<400> SEQUENCE: 122

```
Met Lys Pro Val Leu Pro Leu Gln Phe Leu Val Val Phe Cys Leu Ala
            -20                 -15                 -10

Leu Gln Leu Val Pro Gly Ser Pro Lys Gln Arg Val Leu Lys Tyr Ile
     -5                   1                   5                  10

Leu Glu Pro Pro Pro Cys Ile Ser Ala Pro Glu Asn Cys Thr His Leu
                15                  20                  25

Cys Thr Met Gln Glu Asp Cys Gly Lys Gly Phe Gln Cys Cys Ser Ser
            30                  35                  40

Phe Cys Gly Ile Val Cys Ser Ser Glu Thr Phe Gln Lys Arg Asn Arg
            45                  50                  55

Ile Lys His Lys Gly Ser Glu Val Ile Met Pro Ala Asn
            60                  65                  70
```

<210> SEQ ID NO 123
<211> LENGTH: 109
<212> TYPE: PRT
<213> ORGANISM: Homo sapiens
<220> FEATURE:
<221> NAME/KEY: SIGNAL
<222> LOCATION: -42..-1

<400> SEQUENCE: 123

```
Met His Ile Leu Gln Leu Leu Thr Thr Val Asp Asp Gly Ile Gln Ala
            -40                 -35                 -30

Ile Val His Cys Pro Asp Thr Gly Lys Asp Ile Trp Asn Leu Leu Phe
        -25                 -20                 -15

Asp Leu Val Cys His Glu Phe Cys Gln Ser Asp Asp Pro Ala Ile Ile
-10                  -5                   1                   5

Leu Gln Glu Gln Lys Thr Val Leu Ala Ser Val Phe Ser Val Leu Ser
            10                  15                  20

Ala Ile Tyr Ala Ser Gln Thr Glu Gln Glu Tyr Leu Lys Ile Glu Lys
            25                  30                  35

Val Asp Leu Pro Leu Ile Asp Ser Leu Ile Arg Val Leu Gln Asn Met
     40                  45                  50

Glu Gln Cys Gln Lys Lys Pro Glu Asn Ser Ala Gly Val
55                  60                  65
```

<210> SEQ ID NO 124
<211> LENGTH: 51
<212> TYPE: PRT

```
<213> ORGANISM: Homo sapiens
<220> FEATURE:
<221> NAME/KEY: SIGNAL
<222> LOCATION: -15..-1

<400> SEQUENCE: 124

Met Arg Leu Val Pro Leu Gly Gln Ser Phe Pro Leu Ser Glu Pro Arg
-15                 -10                  -5                   1

Cys Leu Gln Pro Val Lys Trp Asp His Asn His Cys Leu Thr Ser Leu
             5                  10                  15

Thr Val Val Val Arg Thr Glu Cys Val Glu Val Phe His Lys Leu Trp
        20                  25                  30

Met Leu Val
    35

<210> SEQ ID NO 125
<211> LENGTH: 56
<212> TYPE: PRT
<213> ORGANISM: Homo sapiens
<220> FEATURE:
<221> NAME/KEY: SIGNAL
<222> LOCATION: -27..-1

<400> SEQUENCE: 125

Met Asn Arg Val Pro Ala Asp Ser Pro Asn Met Cys Leu Ile Cys Leu
            -25                 -20                 -15

Leu Ser Tyr Ile Ala Leu Gly Ala Ile His Ala Lys Ile Cys Arg Arg
        -10                 -5                   1                   5

Ala Phe Gln Glu Glu Gly Arg Ala Asn Ala Lys Thr Gly Val Arg Ala
                10                  15                  20

Trp Cys Ile Gln Pro Trp Ala Lys
                25

<210> SEQ ID NO 126
<211> LENGTH: 162
<212> TYPE: PRT
<213> ORGANISM: Homo sapiens
<220> FEATURE:
<221> NAME/KEY: SIGNAL
<222> LOCATION: -21..-1

<400> SEQUENCE: 126

Met Leu Gln Thr Ser Asn Tyr Ser Leu Val Leu Ser Leu Gln Phe Leu
    -20                 -15                 -10

Leu Leu Ser Tyr Asp Leu Phe Val Asn Ser Phe Ser Glu Leu Leu Gln
-5                   1                   5                  10

Lys Thr Pro Val Ile Gln Leu Val Leu Phe Ile Ile Gln Asp Ile Ala
                15                  20                  25

Val Leu Phe Asn Ile Ile Ile Ile Phe Leu Met Phe Phe Asn Thr Ser
                30                  35                  40

Val Phe Gln Ala Gly Leu Val Asn Leu Leu Phe His Lys Phe Lys Gly
    45                  50                  55

Thr Ile Ile Leu Thr Ala Val Tyr Phe Ala Leu Ser Ile Ser Leu His
60                  65                  70                  75

Val Trp Val Met Asn Leu Arg Trp Lys Asn Ser Asn Ser Phe Ile Trp
                80                  85                  90

Thr Asp Gly Leu Gln Met Leu Phe Val Phe Gln Arg Leu Ala Ala Val
                95                 100                 105

Leu Tyr Cys Tyr Phe Tyr Lys Arg Thr Ala Val Arg Leu Gly Asp Pro
        110                 115                 120
```

```
His Phe Tyr Gln Asp Ser Leu Trp Leu Arg Lys Glu Phe Met Gln Val
        125                 130                 135

Arg Arg
140

<210> SEQ ID NO 127
<211> LENGTH: 126
<212> TYPE: PRT
<213> ORGANISM: Homo sapiens
<220> FEATURE:
<221> NAME/KEY: SIGNAL
<222> LOCATION: -68..-1

<400> SEQUENCE: 127

Met Ala Ser Ala Ser Ala Arg Gly Asn Gln Asp Lys Asp Ala His Phe
            -65                 -60                 -55

Pro Pro Pro Ser Lys Gln Ser Leu Leu Phe Cys Pro Lys Ser Lys Leu
        -50                 -45                 -40

His Ile His Arg Ala Glu Ile Ser Lys Ile Met Arg Glu Cys Gln Glu
        -35                 -30                 -25

Glu Ser Phe Trp Lys Arg Ala Leu Pro Phe Ser Leu Val Ser Met Leu
-20                 -15                 -10                  -5

Val Thr Gln Gly Leu Val Tyr Gln Gly Tyr Leu Ala Ala Asn Ser Arg
                 1                   5                  10

Phe Gly Ser Leu Pro Lys Val Ala Leu Ala Gly Leu Leu Gly Phe Gly
        15                  20                  25

Leu Gly Lys Val Ser Tyr Ile Gly Val Cys Gln Ser Lys Phe His Phe
        30                  35                  40

Phe Glu Asp Gln Leu Arg Gly Ala Gly Phe Gly Pro Thr Ala
45                  50                  55

<210> SEQ ID NO 128
<211> LENGTH: 140
<212> TYPE: PRT
<213> ORGANISM: Homo sapiens
<220> FEATURE:
<221> NAME/KEY: SIGNAL
<222> LOCATION: -40..-1

<400> SEQUENCE: 128

Met Thr Ser Met Thr Gln Ser Leu Arg Glu Val Ile Lys Ala Met Thr
-40                 -35                 -30                 -25

Lys Ala Arg Asn Phe Glu Arg Val Leu Gly Lys Ile Thr Leu Val Ser
                -20                 -15                 -10

Ala Ala Pro Gly Lys Val Ile Cys Glu Met Lys Val Glu Glu Glu His
             -5                   1                   5

Thr Asn Ala Ile Gly Thr Leu His Gly Leu Thr Ala Thr Leu Val
        10                  15                  20

Asp Asn Ile Ser Thr Met Ala Leu Leu Cys Thr Glu Arg Gly Ala Pro
25                  30                  35                  40

Gly Val Ser Val Asp Met Asn Ile Thr Tyr Met Ser Pro Ala Lys Leu
                45                  50                  55

Gly Glu Asp Ile Val Ile Thr Ala His Val Leu Lys Gln Gly Lys Thr
            60                  65                  70

Leu Ala Phe Thr Ser Val Gly Leu Thr Asn Lys Ala Thr Gly Lys Leu
        75                  80                  85

Ile Ala Gln Gly Arg His Thr Lys His Leu Gly Asn
        90                  95                 100
```

```
<210> SEQ ID NO 129
<211> LENGTH: 43
<212> TYPE: PRT
<213> ORGANISM: Homo sapiens
<220> FEATURE:
<221> NAME/KEY: SIGNAL
<222> LOCATION: -24..-1

<400> SEQUENCE: 129
```

Met Gln Cys Phe Ser Phe Ile Lys Thr Met Met Ile Leu Phe Asn Leu
            -20                 -15                 -10

Leu Ile Phe Leu Cys Gly Phe Thr Asn Tyr Thr Asp Phe Glu Asp Ser
         -5                   1                   5

Pro Tyr Phe Lys Met His Lys Pro Val Thr Met
     10                  15

```
<210> SEQ ID NO 130
<211> LENGTH: 69
<212> TYPE: PRT
<213> ORGANISM: Homo sapiens
<220> FEATURE:
<221> NAME/KEY: SIGNAL
<222> LOCATION: -21..-1

<400> SEQUENCE: 130
```

Met Trp Trp Phe Gln Gln Gly Leu Ser Phe Leu Pro Ser Ala Leu Val
     -20                 -15                 -10

Ile Trp Thr Ser Ala Ala Phe Ile Phe Ser Tyr Ile Thr Ala Val Thr
 -5                   1                   5                  10

Leu His His Ile Asp Pro Ala Leu Pro Tyr Ile Ser Asp Thr Gly Thr
             15                  20                  25

Val Ala Pro Glu Lys Cys Leu Phe Gly Ala Met Leu Asn Ile Ala Ala
             30                  35                  40

Val Leu Cys Gln Lys
         45

```
<210> SEQ ID NO 131
<211> LENGTH: 78
<212> TYPE: PRT
<213> ORGANISM: Homo sapiens
<220> FEATURE:
<221> NAME/KEY: SIGNAL
<222> LOCATION: -19..-1

<400> SEQUENCE: 131
```

Met Ser Pro Gly Ser Ala Leu Ala Leu Leu Trp Ser Leu Pro Ala Ser
             -15                 -10                  -5

Asp Leu Gly Arg Ser Val Ile Ala Gly Leu Trp Pro His Thr Gly Val
             1                   5                  10

Leu Ile His Leu Glu Thr Ser Gln Ser Phe Leu Gln Gly Gln Leu Thr
     15                  20                  25

Lys Ser Ile Phe Pro Leu Cys Cys Thr Ser Leu Phe Cys Val Cys Val
 30                  35                  40                  45

Val Thr Val Gly Gly Gly Arg Val Gly Ser Thr Phe Val Ala
                 50                  55

```
<210> SEQ ID NO 132
<211> LENGTH: 80
<212> TYPE: PRT
<213> ORGANISM: Homo sapiens
<220> FEATURE:
```

```
<221> NAME/KEY: SIGNAL
<222> LOCATION: -47..-1

<400> SEQUENCE: 132

Met Arg Leu Pro Pro Ala Leu Pro Ser Gly Tyr Thr Asp Ser Thr Ala
        -45             -40             -35

Leu Glu Gly Leu Val Tyr Tyr Leu Asn Gln Lys Leu Leu Phe Ser Ser
        -30             -25             -20

Pro Ala Ser Ala Leu Leu Phe Phe Ala Arg Pro Cys Val Phe Cys Phe
-15             -10              -5                          1

Lys Ala Ser Lys Met Gly Pro Gln Phe Glu Asn Tyr Pro Thr Phe Pro
             5              10              15

Thr Tyr Ser Pro Leu Pro Ile Ile Pro Phe Gln Leu His Gly Arg Phe
         20              25              30

<210> SEQ ID NO 133
<211> LENGTH: 53
<212> TYPE: PRT
<213> ORGANISM: Homo sapiens
<220> FEATURE:
<221> NAME/KEY: SIGNAL
<222> LOCATION: -42..-1

<400> SEQUENCE: 133

Met Asp Ser Arg Val Ser Ser Pro Glu Lys Gln Asp Lys Glu Asn Phe
        -40             -35             -30

Val Gly Val Asn Asn Lys Arg Leu Gly Val Cys Gly Trp Ile Leu Phe
    -25             -20             -15

Ser Leu Ser Phe Leu Leu Val Ile Ile Thr Phe Pro Ile Ser Ile Trp
-10              -5                1               5

Met Cys Leu Lys Ile
             10

<210> SEQ ID NO 134
<211> LENGTH: 1053
<212> TYPE: DNA
<213> ORGANISM: Homo sapiens
<220> FEATURE:
<221> NAME/KEY: sig_peptide
<222> LOCATION: 131..169
<223> OTHER INFORMATION: Von Heijne matrix
      score 4.19999980926514
      seq MLAVSLTVPLLGA/MM
<221> NAME/KEY: polyA_site
<222> LOCATION: 1042..1053

<400> SEQUENCE: 134
gagcgagtcg acgggctgc gacagcgccg gccctgcgg ccgcaggtcg tcacagacga    60
tgatggccag gccccggagg ctaaggacgg cagctccttt agcggcagag ttttccgagt   120
gaccttcttg atg ctg gct gtt tct ctc acc gtt ccc ctg ctt gga gcc    169
            Met Leu Ala Val Ser Leu Thr Val Pro Leu Leu Gly Ala
                -10                 -5 atg atg ctg ctg gaa tct cct ata gat cca cag cct ctc agc ttc aaa    217
Met Met Leu Leu Glu Ser Pro Ile Asp Pro Gln Pro Leu Ser Phe Lys
1               5                  10                  15 gaa ccc ccg ctc ttg ctt ggt gtt ctg cat cca aat acg aag ctg cga    265
Glu Pro Pro Leu Leu Leu Gly Val Leu His Pro Asn Thr Lys Leu Arg
            20                  25                  30 cag gca gaa agg ctg ttt gaa aat caa ctt gtt gga ccg gag tcc ata    313
Gln Ala Glu Arg Leu Phe Glu Asn Gln Leu Val Gly Pro Glu Ser Ile
        35                  40                  45
```

| | | | | | | | | | | | | | | | | |
|---|---|---|---|---|---|---|---|---|---|---|---|---|---|---|---|---|
| gca | cat | att | ggg | gat | gtg | atg | ttt | act | ggg | aca | gca | gat | ggc | cgg | gtc | 361 |
| Ala | His | Ile | Gly | Asp | Val | Met | Phe | Thr | Gly | Thr | Ala | Asp | Gly | Arg | Val | |
| | | 50 | | | | 55 | | | | 60 | | | | | | |

| | | | | | | | | | | | | | | | | |
|---|---|---|---|---|---|---|---|---|---|---|---|---|---|---|---|---|
| gta | aaa | ctt | gaa | aat | ggt | gaa | ata | gag | acc | att | gcc | cgg | ttt | ggt | tcg | 409 |
| Val | Lys | Leu | Glu | Asn | Gly | Glu | Ile | Glu | Thr | Ile | Ala | Arg | Phe | Gly | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | cct | tgc | aaa | acc | cga | ggt | gat | gag | cct | gtg | tgt | ggg | aga | ccc | ctg | 457 |
| Gly | Pro | Cys | Lys | Thr | Arg | Gly | Asp | Glu | Pro | Val | Cys | Gly | Arg | Pro | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | atc | cgt | gca | ggg | ccc | aat | ggg | act | ctc | ttt | gtg | gcc | gat | gca | tac | 505 |
| Gly | Ile | Arg | Ala | Gly | Pro | Asn | Gly | Thr | Leu | Phe | Val | Ala | Asp | Ala | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | gga | cta | ttt | gaa | gta | aat | ccc | tgg | aaa | cgt | gaa | gtg | aaa | ctg | ctg | 553 |
| Lys | Gly | Leu | Phe | Glu | Val | Asn | Pro | Trp | Lys | Arg | Glu | Val | Lys | Leu | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| ctg | tcc | tcc | gag | aca | ccc | att | gag | ggg | aag | aac | atg | tcc | ttt | gtg | aat | 601 |
| Leu | Ser | Ser | Glu | Thr | Pro | Ile | Glu | Gly | Lys | Asn | Met | Ser | Phe | Val | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| gat | ctt | aca | gtc | act | cag | gat | ggg | agg | aag | att | tat | ttc | acc | gat | tct | 649 |
| Asp | Leu | Thr | Val | Thr | Gln | Asp | Gly | Arg | Lys | Ile | Tyr | Phe | Thr | Asp | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agc | agc | aaa | tgg | caa | aga | cga | gac | tac | ctg | ctt | ctg | gtg | atg | gag | ggc | 697 |
| Ser | Ser | Lys | Trp | Gln | Arg | Arg | Asp | Tyr | Leu | Leu | Leu | Val | Met | Glu | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| aca | gat | gac | ggg | cgc | ctg | ctg | gag | tat | gat | act | gtg | acc | agg | gaa | gta | 745 |
| Thr | Asp | Asp | Gly | Arg | Leu | Leu | Glu | Tyr | Asp | Thr | Val | Thr | Arg | Glu | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | gtt | tta | ttg | gac | cag | ctg | cgg | ttc | ccg | aat | gga | gtc | cag | ctg | tct | 793 |
| Lys | Val | Leu | Leu | Asp | Gln | Leu | Arg | Phe | Pro | Asn | Gly | Val | Gln | Leu | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| cct | gca | gaa | gac | ttt | gtc | ctg | gtg | gca | gaa | aca | acc | atg | gcc | agg | ata | 841 |
| Pro | Ala | Glu | Asp | Phe | Val | Leu | Val | Ala | Glu | Thr | Thr | Met | Ala | Arg | Ile | |
| | 210 | | | | | 215 | | | | | 220 | | | | | |

| | | | | | | | | | | | | | | | | |
|---|---|---|---|---|---|---|---|---|---|---|---|---|---|---|---|---|
| cga | aga | gtc | tac | gtt | tct | ggc | ctg | atg | aag | ggc | ggg | gct | gat | ctg | ttt | 889 |
| Arg | Arg | Val | Tyr | Val | Ser | Gly | Leu | Met | Lys | Gly | Gly | Ala | Asp | Leu | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtg | gag | aac | atg | cct | gga | ttt | cca | gac | aac | atc | cgg | ccc | agc | agc | tct | 937 |
| Val | Glu | Asn | Met | Pro | Gly | Phe | Pro | Asp | Asn | Ile | Arg | Pro | Ser | Ser | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| ggg | ggg | tac | tgg | gtg | ggc | atg | tcg | acc | atc | cgc | cct | aac | cct | ggg | ttt | 985 |
| Gly | Gly | Tyr | Trp | Val | Gly | Met | Ser | Thr | Ile | Arg | Pro | Asn | Pro | Gly | Phe | |
| | | | 260 | | | | | 265 | | | | | 270 | | | |

| | | | | | | | | | | | | | | | | |
|---|---|---|---|---|---|---|---|---|---|---|---|---|---|---|---|---|
| tcc | atg | ctg | gat | ttc | tta | tct | gag | aga | ccc | tgg | att | aaa | agg | atg | att | 1033 |
| Ser | Met | Leu | Asp | Phe | Leu | Ser | Glu | Arg | Pro | Trp | Ile | Lys | Arg | Met | Ile | |
| | | 275 | | | | | 280 | | | | | 285 | | | | |

| | | | | |
|---|---|---|---|---|
| ttt | aag | gta | aaaaaaaaa | a | 1053 |
| Phe | Lys | Val | | |
| | 290 | | | |

<210> SEQ ID NO 135
<211> LENGTH: 675
<212> TYPE: DNA
<213> ORGANISM: Homo sapiens
<220> FEATURE:
<221> NAME/KEY: polyA_signal
<222> LOCATION: 638..643
<221> NAME/KEY: polyA_site
<222> LOCATION: 662..675

<400> SEQUENCE: 135
accgaacagg aacagcacaa cctgggaccc agacatgcag tacctctacg caaagtaaaa    60

```
gtagcagtgg ttcagcacac tttggtatgt tgactgtta atg atg tac gtt tct          114
                                            Met Met Tyr Val Ser
                                              1               5 ata gaa atg tca ggt cca acc att tcc cat ttg ttc gac tat gtg gtc         162
Ile Glu Met Ser Gly Pro Thr Ile Ser His Leu Phe Asp Tyr Val Val
             10                  15                  20 tgt tac att tat ggc tta aag tcc ttt tct ctt aaa cag tta aaa aaa         210
Cys Tyr Ile Tyr Gly Leu Lys Ser Phe Ser Leu Lys Gln Leu Lys Lys
         25                  30                  35 aaa tct tgg tct aag tat tta ttt gaa tcc tgt tgc tat agg agt ttg         258
Lys Ser Trp Ser Lys Tyr Leu Phe Glu Ser Cys Cys Tyr Arg Ser Leu
         40                  45                  50 tat gtg tgt gtc ttc att taaacatacc tgcatacaaa gatggtttat               306
Tyr Val Cys Val Phe Ile
             55 ttctatttaa tatgtgacat ttgtttcctg gatatagtcc gtgaaccaca agatttatca      366 tattttttcaa taatatgaga agaaaatggg ccgtaaattg ttaaccattt tatgttcaga     426 tatttctcta gttttttacct agtttgcttt aacatagaga ccagcaagtg aatatatatg    486 cataaccttaa tatgttgaca caataattca gaataatttg ttaaagataa actaattttt   546 cagagaagaa catttaaagg gttaatattt ttgaaacgtt ttcagataat atctatttga    606 ttattgtggc ttctatttga aatgtgtcta aataaaatgc tgtttattta aaatgaaaaa    666 aaaaaaaaa                                                              675

<210> SEQ ID NO 136
<211> LENGTH: 1112
<212> TYPE: DNA
<213> ORGANISM: Homo sapiens
<220> FEATURE:
<221> NAME/KEY: sig_peptide
<222> LOCATION: 111..194
<223> OTHER INFORMATION: Von Heijne matrix
      score 4.80000019073486
      seq GVLLEPFVHQVGG/HS
<221> NAME/KEY: polyA_signal
<222> LOCATION: 1080..1085
<221> NAME/KEY: polyA_site
<222> LOCATION: 1101..1112

<400> SEQUENCE: 136
ccgagagaga ctacacggta ctgggacaca cggacaaaca acagacagaa gacgtactgg      60
ccgctggact ccgctgcctc ccccatctcc ccgccatctg cgcccggagg atg agc        116
                                                        Met Ser cca gcc ttc agg gcc atg gat gtg gag ccc cgc gcc aaa ggc gtc ctt       164
Pro Ala Phe Arg Ala Met Asp Val Glu Pro Arg Ala Lys Gly Val Leu
    -25                 -20                 -15 ctg gag ccc ttt gtc cac cag gtc ggg ggg cac tca tgc gtg ctc cgc       212
Leu Glu Pro Phe Val His Gln Val Gly Gly His Ser Cys Val Leu Arg
-10                  -5                   1               5 ttc aat gag aca acc ctg tgc aag ccc ctg gtc cca agg gaa cat cag       260
Phe Asn Glu Thr Thr Leu Cys Lys Pro Leu Val Pro Arg Glu His Gln
             10                  15                  20 ttc tac gag acc ctc cct gct gag atg cgc aaa ttc tct ccc cag tac       308
Phe Tyr Glu Thr Leu Pro Ala Glu Met Arg Lys Phe Ser Pro Gln Tyr
         25                  30                  35 aaa gga caa agc caa agg ccc ctt gtt agc tgg cca tcc ctg ccc cat       356
Lys Gly Gln Ser Gln Arg Pro Leu Val Ser Trp Pro Ser Leu Pro His
         40                  45                  50 ttt ttc ccc tgg tcc ttt ccc ctg tgg cca cag gga agt gtg gcc           401
Phe Phe Pro Trp Ser Phe Pro Leu Trp Pro Gln Gly Ser Val Ala
```

-continued

```
          55                  60                  65
tgaataccccc acccccggctc ctctgcaccc agagctgggg gccacctcag aagtgtcatc    461
tctctctgag cacgcattcc cctgcagcag tcgaggactg agcagattga gtgatgctgg    521
ggcagagagg cctgagagga aggtgttca gccagtcgtt tgtaaggcgc tcgtcggcac     581
ctgctgaaac gcccccacct gacagcccca tcctcaaaga ctgtcttaat tactcatggc    641
aggttctaga gacttaaggg gaaaagctgc tttcaaggcc accacatgtc tgtgctcccc    701
aaccagctct atctgccttg tgttcatttt gttattttgt gacgtgagac agcaaagacc    761
aataaaaaca tattttataa gaacaaaagg cctgggtgcc tacccgtgtg ggggcactgt    821
gggaagcctt tgctagggtg tcttgtgctg tgtggtttgt tttgttttgcc cctttatttt   881 gctttgctta cccagtcttc ccttactctt ggatgcttct taaccctcag gcaaacctgt    941 gttcccctg tattcaggct ctgctttaaa gcaagccatg aggctgttgg agtttctgtt    1001
tagggcatta aaaattcccg caaactataa agagcaatgt tttcagtctt ttaggattag   1061
aagaattaca taaaaattaa taaacatttt caatgatgga aaaaaaaaa a             1112
```

<210> SEQ ID NO 137
<211> LENGTH: 547
<212> TYPE: DNA
<213> ORGANISM: Homo sapiens
<220> FEATURE:
<221> NAME/KEY: sig_peptide
<222> LOCATION: 359..454
<223> OTHER INFORMATION: Von Heijne matrix
    score 4
    seq FSFMLLGMGGCLP/GF
<221> NAME/KEY: polyA_site
<222> LOCATION: 536..547

<400> SEQUENCE: 137

```
ctggggagcc ctgcctaaga tcatgctac aagaagttaa ataagtttcc cgaagtcaca      60
cagctagcct ctcatccctt ttctactgag aggaagtgga atgcactccg acaaggataa    120
ggttttattg tgagctggcc ttggaattaa accaccacca acacactttt ggattatcag    180
aaggtggaag gagtgcaaaa atgtcattcc catgcttgtc tgccaggcaa cctggtgtcc    240
attctttatg acgcctttcc tgaatcacag gtgcattggg gtgcttcctc ctccccagga    300
ctcccaccca actttgtgaa cacaacccac ttagaggagt tatctcagca cattatga     358 atg ttg ggg acc acg ggc ctc ggg aca cag ggt cct tcc cag cag gct       406
Met Leu Gly Thr Thr Gly Leu Gly Thr Gln Gly Pro Ser Gln Gln Ala
    -30                 -25                 -20 ctg ggc ttt ttc tcc ttt atg tta ctt gga atg ggc ggg tgc ctg cct       454
Leu Gly Phe Phe Ser Phe Met Leu Leu Gly Met Gly Gly Cys Leu Pro
    -15                 -10                 -5 gga ttc ctg cta cag cct ccc aat cga tct cct act ttg cct gca tcc       502
Gly Phe Leu Leu Gln Pro Pro Asn Arg Ser Pro Thr Leu Pro Ala Ser
  1                   5                  10                  15 acc ttt gcc cat taaagtcaat tctccaccca taaaaaaaaa aaa                  547
Thr Phe Ala His
              20
```

<210> SEQ ID NO 138
<211> LENGTH: 1198
<212> TYPE: DNA
<213> ORGANISM: Homo sapiens
<220> FEATURE:
<221> NAME/KEY: sig_peptide
<222> LOCATION: 26..316
<223> OTHER INFORMATION: Von Heijne matrix

```
        score 4
        seq RLPLVVSFIASSS/AN
<221> NAME/KEY: polyA_signal
<222> LOCATION: 1164..1169
<221> NAME/KEY: polyA_site
<222> LOCATION: 1187..1198

<400> SEQUENCE: 138
atcctgcgaa agaaggggggt tcatc atg gcg gat gac cta aag cga ttc ttg         52
                             Met Ala Asp Asp Leu Lys Arg Phe Leu
                                 -95                 -90 tat aaa aag tta cca agt gtt gaa ggg ctc cat gcc att gtt gtg tca        100
Tyr Lys Lys Leu Pro Ser Val Glu Gly Leu His Ala Ile Val Val Ser
            -85                 -80                 -75 gat aga gat gga gta cct gtt gtt aaa gtg gca aat gac aat gct cca        148
Asp Arg Asp Gly Val Pro Val Val Lys Val Ala Asn Asp Asn Ala Pro
        -70                 -65                 -60 gag cat gct ttg cga cct ggt ttc tta tcc act ttt gcc ctt gca aca        196
Glu His Ala Leu Arg Pro Gly Phe Leu Ser Thr Phe Ala Leu Ala Thr
    -55                 -50                 -45 gac caa gga agc aaa ctt gga ctt tcc aaa aat aaa agt atc atc tgt        244
Asp Gln Gly Ser Lys Leu Gly Leu Ser Lys Asn Lys Ser Ile Ile Cys
-40                 -35                 -30                 -25 tac tat aac acc tac cag gtg gtt caa ttt aat cgt tta cct ttg gtg        292
Tyr Tyr Asn Thr Tyr Gln Val Val Gln Phe Asn Arg Leu Pro Leu Val
                -20                 -15                 -10 gtg agt ttc ata gcc agc agc agt gcc aat aca gga cta att gtc agc        340
Val Ser Phe Ile Ala Ser Ser Ser Ala Asn Thr Gly Leu Ile Val Ser
             -5                   1                   5 cta gaa aag gag ctt gct cca ttg ttt gaa gaa ctg aga caa gtt gtg        388
Leu Glu Lys Glu Leu Ala Pro Leu Phe Glu Glu Leu Arg Gln Val Val
         10                  15                  20 gaa gtt tct taatctgaca gtggtttcag tgtgtacctt atcttcatta               437
Glu Val Ser
 25 taacaacaca atatcaatcc agcaatcttt agactacaat aatgctttta tccatgtgct     497 caagaaaggg cccctttttc caacttatac taaagagcta gcatatagat gtaatttata     557 gatagatcag ttgctatatt ttctggtgta gggtctttct tatttagtga gatctaggga    617 taccacagaa atggttcagt ctatcacagc tcccatggag ttagtctggt caccagatat    677 ggatgagaga ttctattcag tggattagaa tcaaactggt acattgatcc acttgagccg    737 ttaagtgctg ccaattgtac aatatgccca ggcttgcaga ataaagccaa ctttttattg    797 tgaataataa taaggacata tttttcttca gattatgttt tatttctttg cattgagtga    857 ggtacataaa atggcttggt aaaagtaata aaatcagtac aatcactaac tttcctttgt    917 acatattatt ttgcagtata gatgaatatt actaatcagt ttgattattc tcagagggtg    977 ctgctctttta atgaaaatga aaattatagc taatgttttt tcctcaaact ctgctttctg   1037 taaccaatca gtgttttaat gtttgtgtgt tcttcataaa atttaaatac aattcgttat   1097 tctgtttcca atgttagtat gtatgtaaac atgatagtac agccatttt ttcatatgtg    1157 agtaaaaata aaatagtatt tttaaaagta aaaaaaaaaa a                         1198

<210> SEQ ID NO 139
<211> LENGTH: 1400
<212> TYPE: DNA
<213> ORGANISM: Homo sapiens
<220> FEATURE:
<221> NAME/KEY: sig_peptide
<222> LOCATION: 36..107
```

```
<223> OTHER INFORMATION: Von Heijne matrix
      score 5.69999980926514
      seq ILGLLGLLGTLVA/ML
<221> NAME/KEY: polyA_signal
<222> LOCATION: 1302..1307
<221> NAME/KEY: polyA_site
<222> LOCATION: 1389..1400

<400> SEQUENCE: 139
```

| | | | | | | | | |
|---|---|---|---|---|---|---|---|---|
| cagtccctga agacgcttct actgagaggt ctgcc atg gcc tct ctt ggc ctc | | | | | | | | 53 |
| | | | | | Met | Ala Ser Leu Gly Leu | | |
| | | | | | | −20 | | |
| caa ctt gtg ggc tac atc cta ggc ctt ctg ggg ctt ttg ggc aca ctg | | | | | | | | 101 |
| Gln Leu Val Gly Tyr Ile Leu Gly Leu Leu Gly Leu Leu Gly Thr Leu | | | | | | | | |
| −15 | | | −10 | | | −5 | | |
| gtt gcc atg ctg ctc ccc agc tgg aaa aca agt tct tat gtc ggt gcc | | | | | | | | 149 |
| Val Ala Met Leu Leu Pro Ser Trp Lys Thr Ser Ser Tyr Val Gly Ala | | | | | | | | |
| 1 | | | 5 | | | 10 | | |
| agc att gtg aca gca gtt ggc ttc tcc aag ggc ctc tgg atg gaa tgt | | | | | | | | 197 |
| Ser Ile Val Thr Ala Val Gly Phe Ser Lys Gly Leu Trp Met Glu Cys | | | | | | | | |
| 15 | | 20 | | | 25 | | 30 | |
| gcc aca cac agc aca ggc atc acc cag tgt gac atc tat agc acc ctt | | | | | | | | 245 |
| Ala Thr His Ser Thr Gly Ile Thr Gln Cys Asp Ile Tyr Ser Thr Leu | | | | | | | | |
| | | 35 | | | 40 | | 45 | |
| ctg ggc ctg ccc gct gac atc cag gct gcc cag gcc atg atg gtg aca | | | | | | | | 293 |
| Leu Gly Leu Pro Ala Asp Ile Gln Ala Ala Gln Ala Met Met Val Thr | | | | | | | | |
| | 50 | | | 55 | | | 60 | |
| tcc agt gca atc tcc tcc ctg gcc tgc att atc tct gtg gtg ggc atg | | | | | | | | 341 |
| Ser Ser Ala Ile Ser Ser Leu Ala Cys Ile Ile Ser Val Val Gly Met | | | | | | | | |
| | 65 | | | 70 | | 75 | | |
| aga tgc aca gtc ttc tgc cag gaa tcc cga gcc aaa gac aga gtg gcg | | | | | | | | 389 |
| Arg Cys Thr Val Phe Cys Gln Glu Ser Arg Ala Lys Asp Arg Val Ala | | | | | | | | |
| 80 | | | 85 | | | 90 | | |
| gta gca ggt gga gtc ttt ttc atc ctt gga ggc ctc ctg gga ttc att | | | | | | | | 437 |
| Val Ala Gly Gly Val Phe Phe Ile Leu Gly Gly Leu Leu Gly Phe Ile | | | | | | | | |
| 95 | | | 100 | | | 105 | | 110 |
| cct gtt gcc tgg aat ctt cat ggg atc cta cgg gac ttc tac tca cca | | | | | | | | 485 |
| Pro Val Ala Trp Asn Leu His Gly Ile Leu Arg Asp Phe Tyr Ser Pro | | | | | | | | |
| | | 115 | | | 120 | | 125 | |
| ctg gtg cct gac agc atg aaa ttt gag att gga gag gct ctt tac ttg | | | | | | | | 533 |
| Leu Val Pro Asp Ser Met Lys Phe Glu Ile Gly Glu Ala Leu Tyr Leu | | | | | | | | |
| | 130 | | | 135 | | | 140 | |
| ggc att att tct tcc ctg ttc tcc ctg ata gct gga atc atc ctc tgc | | | | | | | | 581 |
| Gly Ile Ile Ser Ser Leu Phe Ser Leu Ile Ala Gly Ile Ile Leu Cys | | | | | | | | |
| | 145 | | | 150 | | | 155 | |
| ttt tcc tgc tca tcc cag aga aat cgc tcc aac tac tac gat gcc tac | | | | | | | | 629 |
| Phe Ser Cys Ser Ser Gln Arg Asn Arg Ser Asn Tyr Tyr Asp Ala Tyr | | | | | | | | |
| 160 | | | 165 | | | 170 | | |
| caa gcc caa cct ctt gcc aca agg agc tct cca agg cct ggt caa cct | | | | | | | | 677 |
| Gln Ala Gln Pro Leu Ala Thr Arg Ser Ser Pro Arg Pro Gly Gln Pro | | | | | | | | |
| 175 | | | 180 | | | 185 | | 190 |
| ccc aaa gtc aag agt gag ttc aat tcc tac agc ctg aca ggg tat gtg | | | | | | | | 725 |
| Pro Lys Val Lys Ser Glu Phe Asn Ser Tyr Ser Leu Thr Gly Tyr Val | | | | | | | | |
| | | 195 | | | 200 | | 205 | |
| tgaagaacca ggggccagag ctgggggtg gctggtctg tgaaaaacag tggacagcac | | | | | | | | 785 |
| cccgagggcc acaggtgagg gacactacca ctggatcgtg tcagaaggtg ctgctgaggg | | | | | | | | 845 |
| tagactgact ttggccattg gattgagcaa aggcagaaat gggggctagt gtaacagcat | | | | | | | | 905 |
| gcaggttgaa ttgccaagga tgctcgccat gccagccttt ctgttttcct caccttgctg | | | | | | | | 965 |
| ctccccctgcc ctaagtcccc aaccctcaac ttgaaacccc attcccttaa gccaggactc | | | | | | | | 1025 |

```
agaggatccc tttgccctct ggtttacctg ggactccatc cccaaaccca ctaatcacat    1085
cccactgact gaccctctgt gatcaaagac cctccctctg gctgaggttg gctcttagct    1145
cattgctggg gatgggaagg agaagcagtg gcttttgtgg gcattgctct aacctacttc    1205
tcaagcttcc ctccaaagaa actgattggc cctggaacct ccatcccact cttgttatga    1265
ctccacagtg tccagactaa tttgtgcatg aactgaaata aaaccatcct acggtatcca    1325
gggaacagaa agcaggatgc aggatgggag gacaggaagg cagcctggga catttaaaaa    1385
aataaaaaaa aaaaa                                                    1400

<210> SEQ ID NO 140
<211> LENGTH: 538
<212> TYPE: DNA
<213> ORGANISM: Homo sapiens
<220> FEATURE:
<221> NAME/KEY: sig_peptide
<222> LOCATION: 35..130
<223> OTHER INFORMATION: Von Heijne matrix
      score 8
      seq VPMLLLIAGGSFG/LR
<221> NAME/KEY: polyA_signal
<222> LOCATION: 505..510
<221> NAME/KEY: polyA_site
<222> LOCATION: 526..538

<400> SEQUENCE: 140
gcttggagtt ctgagccgat ggaggagttc actc atg ttt gca ctc gcg gtg atg     55
                                    Met Phe Ala Leu Ala Val Met
                                                             -30 cgt gct ttt cgc aag aac aag act ctc ggc tat gga gtc ccc atg ttg    103
Arg Ala Phe Arg Lys Asn Lys Thr Leu Gly Tyr Gly Val Pro Met Leu
-25                 -20                 -15                 -10 ttg ctg att gct gga ggt tct ttt ggt ctt cgt gag ttt tct caa atc    151
Leu Leu Ile Ala Gly Gly Ser Phe Gly Leu Arg Glu Phe Ser Gln Ile
            -5                   1               5 cga tat gat gct gtg aag agt aaa atg gat cct gag ctt gaa aaa aaa    199
Arg Tyr Asp Ala Val Lys Ser Lys Met Asp Pro Glu Leu Glu Lys Lys
         10                  15                  20 ccg aaa gag aat aaa ata tct tta gag tcg gaa tat gag gga agt atc    247
Pro Lys Glu Asn Lys Ile Ser Leu Glu Ser Glu Tyr Glu Gly Ser Ile
 25                  30                  35 tgt tgaagggcta ctatctttcc ttggcccttc tcccttgttg ggactcaatc          300
Cys
 40 tccagactat ctccccagag aatcttgtca aggcttggct ttaagctttg ttgggaaaat   360 caaagactcc aagtttgatg actggaagaa tattcgagga cccaggcctt gggaagatcc   420 tgacctcctc caaggaagaa atccagaaag ccttaagact aagacaactt gactctgctg   480 attctttttt ccttttttttt tttaaataaa aatactatta actggaaaaa aaaaaaa     538

<210> SEQ ID NO 141
<211> LENGTH: 1167
<212> TYPE: DNA
<213> ORGANISM: Homo sapiens
<220> FEATURE:
<221> NAME/KEY: sig_peptide
<222> LOCATION: 169..267
<223> OTHER INFORMATION: Von Heijne matrix
      score 7.80000019073486
      seq LTFLFLHLPPSTS/LF
<221> NAME/KEY: polyA_signal
<222> LOCATION: 1132..1137
<221> NAME/KEY: polyA_site
```

<222> LOCATION: 1155..1167

<400> SEQUENCE: 141

| | | | |
|---|---|---|---|
| gtaggaacta ctgtcccaga gctgaggcaa ggggatttct caggtcattt ggagaacaag | | | 60 |
| tgctttagta gtagtttaaa gtagtaactg ctactgtatt tagtggggtg gaattcagaa | | | 120 |
| gaaatttgaa gaccagatca tgggtggtct gcatgtgaat gaacagga atg agc cag | | | 177 |
| | | Met Ser Gln | |
| aca gcc tgg ctg tca ttg ctt tct tcc tcc cca ttt gga ccc ttc tct | | | 225 |
| Thr Ala Trp Leu Ser Leu Leu Ser Ser Ser Pro Phe Gly Pro Phe Ser | | | |
| -30 | -25 | -20 | -15 |
| gcc ctt aca ttt ttg ttt ctc cat cta cca cca tcc acc agt cta ttt | | | 273 |
| Ala Leu Thr Phe Leu Phe Leu His Leu Pro Pro Ser Thr Ser Leu Phe | | | |
| | -10 | -5 | 1 |
| att aac tta gca aga gga caa ata aag ggc cct ctt ggc ttg att ttg | | | 321 |
| Ile Asn Leu Ala Arg Gly Gln Ile Lys Gly Pro Leu Gly Leu Ile Leu | | | |
| 5 | | 10 | 15 |
| ctt ctt tct ttc tgt gga gga tat act aag tgc gac ttt gcc cta tcc | | | 369 |
| Leu Leu Ser Phe Cys Gly Gly Tyr Thr Lys Cys Asp Phe Ala Leu Ser | | | |
| 20 | | 25 | 30 |
| tat ttg gaa atc cct aac aga att gag ttt tct att atg gat cca aaa | | | 417 |
| Tyr Leu Glu Ile Pro Asn Arg Ile Glu Phe Ser Ile Met Asp Pro Lys | | | |
| 35 | 40 | 45 | 50 |
| aga aaa aca aaa tgc taatgaagcc atcagtcaag ggtcacatgc caataaacaa | | | 472 |
| Arg Lys Thr Lys Cys | | | |
| 55 | | | |
| taaattttcc agaagaaatg aaatccaact agacaaataa agtagagctt atgaaatggt | | | 532 |
| tcagtaagga tgagcttgtt gttttttgtt ttgttttgtt ttgttttttt aaagacggag | | | 592 |
| tctcgctctg tcactcaggc tggagtgcag tggtatgatc ttggctcact gtaacctccg | | | 652 |
| cctcccgggt tcaagccatt ctcctgcctc agtctcctga gtagctggga ttgcaggtgc | | | 712 |
| gtgccaccat gcctggctaa ttttttgtgtt tttggtagag acagggtttc accacgttgg | | | 772 |
| tcgggctggt ctcgggctcc tgacctcttg atccgcctgc cttggcctcc caaagtgatg | | | 832 |
| ggattacaga tgtgagccac cgtgcctagc caaggatgag atttttaaag tatgttccag | | | 892 |
| ttctgtgtca tggttggaag acagagtagg aaggatatgg aaaaggtcat ggggaagcag | | | 952 |
| aggtgattca tggctctgtg aatttgaggt gaatggttcc ttattgtcta ggccacttgt | | | 1012 |
| gaagaatatg agtcagttat tgccagcctt ggaatttact tctctagctt acaatggacc | | | 1072 |
| ttttgaactg ggaaacacct tgtctgcatt cactttaaaa tgtcaaaact aattttttata | | | 1132 |
| ataaatgttt attttcacat cgaaaaaaaa aaaaa | | | 1167 |

<210> SEQ ID NO 142
<211> LENGTH: 730
<212> TYPE: DNA
<213> ORGANISM: Homo sapiens
<220> FEATURE:
<221> NAME/KEY: sig_peptide
<222> LOCATION: 143..238
<223> OTHER INFORMATION: Von Heijne matrix
      score 8.80000019073486
      seq VPMLLLIVGGSFG/LR
<221> NAME/KEY: polyA_signal
<222> LOCATION: 697..702
<221> NAME/KEY: polyA_site
<222> LOCATION: 721..730
<221> NAME/KEY: misc_feature
<222> LOCATION: 1,14,28,52
<223> OTHER INFORMATION: n=a, g, c or t

<400> SEQUENCE: 142

```
nctttgcctt tctntccaca ggtgtccnct cccaggtcca actgcagact tngaattcgt    60
cttggtgaga gcgtgagctg ctgagatttg ggagtctgcg ctaggcccgc ttggagttct   120
gagccgatgg aagagttcac tc atg ttt gca ccc gcg gtg acg cgt gct ttt   172
                         Met Phe Ala Pro Ala Val Thr Arg Ala Phe
                             -30                 -25 cgc aag aac aag act ctc ggc tat gga gtc ccc atg ttg ttg ctg att    220
Arg Lys Asn Lys Thr Leu Gly Tyr Gly Val Pro Met Leu Leu Leu Ile
        -20                 -15                 -10 gtt gga ggt tct ttt ggt ctt cgt gag ttt tct caa atc cga tat gat    268
Val Gly Gly Ser Phe Gly Leu Arg Glu Phe Ser Gln Ile Arg Tyr Asp
 -5              1                   5                       10 gct gtg aag agt aaa atg gat cct gag ctt gaa aaa aaa ctg aaa gag    316
Ala Val Lys Ser Lys Met Asp Pro Glu Leu Glu Lys Lys Leu Lys Glu
                 15              20                  25 aat aaa ata tct tta gag tcg gaa tat gag aaa atc aaa gac tcc aag    364
Asn Lys Ile Ser Leu Glu Ser Glu Tyr Glu Lys Ile Lys Asp Ser Lys
             30                  35                  40 ttt gat gac tgg aag aat att cga gga ccc agg cct tgg gaa gat cct    412
Phe Asp Asp Trp Lys Asn Ile Arg Gly Pro Arg Pro Trp Glu Asp Pro
         45                  50                  55 gac ctc ctc caa gga aga aat cca gaa agc ctt aag act aag aca act    460
Asp Leu Leu Gln Gly Arg Asn Pro Glu Ser Leu Lys Thr Lys Thr Thr
 60                  65                  70 tgactctgct gattctcttt tccttttttt ttttaaataa aaatactatt aactggactt    520
cctaatatat acttctatca agtggaaagg aaattccagg cccatggaaa cttggatatg    580
ggtaatttga tgacaaataa tcttcactaa aggtcatgta caggttttta tacttcccag    640
ctattccatc tgtggatgaa agtaacaatg ttggccacgt atattttaca cctcgaaata    700
aaaaatgtga atactgctcc aaaaaaaaaa                                     730

<210> SEQ ID NO 143
<211> LENGTH: 1174
<212> TYPE: DNA
<213> ORGANISM: Homo sapiens
<220> FEATURE:
<221> NAME/KEY: sig_peptide
<222> LOCATION: 108..170
<223> OTHER INFORMATION: Von Heijne matrix
      score 5.5
      seq SFLPSALVIWTSA/AF
<221> NAME/KEY: polyA_signal
<222> LOCATION: 1141..1146
<221> NAME/KEY: polyA_site
<222> LOCATION: 1161..1174

<400> SEQUENCE: 143
cacgttcctg ttgagtacac gttcctgttg atttacaaaa ggtgcaggta tgagcaggtc     60
tgaagactaa cattttgtga agttgtaaaa cagaaaacct gttagaa atg tgg tgg    116
                                                    Met Trp Trp
                                                        -20 ttt cag caa ggc ctc agt ttc ctt cct tca gcc ctt gta att tgg aca    164
Phe Gln Gln Gly Leu Ser Phe Leu Pro Ser Ala Leu Val Ile Trp Thr
        -15                 -10                  -5 tct gct gct ttc ata ttt tca tac att act gca gta aca ctc cac cat    212
Ser Ala Ala Phe Ile Phe Ser Tyr Ile Thr Ala Val Thr Leu His His
 1               5                  10 ata gac ccg gct tta cct tat atc agt gac act ggt aca gta gct cca    260
Ile Asp Pro Ala Leu Pro Tyr Ile Ser Asp Thr Gly Thr Val Ala Pro
15                  20                  25                  30
```

```
gaa aaa tgc tta ttt ggg gca atg cta aat att gcg gca gtt tta tgc    308
Glu Lys Cys Leu Phe Gly Ala Met Leu Asn Ile Ala Ala Val Leu Cys
             35                  40                  45 att gct acc att tat gtt cgt tat aag caa gtt cat gct ctg agt cct    356
Ile Ala Thr Ile Tyr Val Arg Tyr Lys Gln Val His Ala Leu Ser Pro
             50                  55                  60 gaa gag aac gtt atc atc aaa tta aac aag gct ggc ctt gta ctt gga    404
Glu Glu Asn Val Ile Ile Lys Leu Asn Lys Ala Gly Leu Val Leu Gly
             65                  70                  75 ata ctg agt tgt tta gga ctt tct att gtg gca aac ttc cag aaa aca    452
Ile Leu Ser Cys Leu Gly Leu Ser Ile Val Ala Asn Phe Gln Lys Thr
         80                  85                  90 acc ctt ttt gct gca cat gta agt gga gct gtg ctt acc ttt ggt atg    500
Thr Leu Phe Ala Ala His Val Ser Gly Ala Val Leu Thr Phe Gly Met
 95                 100                 105                 110 ggc tca tta tat atg ttt gtt cag acc atc ctt tcc tac caa atg cag    548
Gly Ser Leu Tyr Met Phe Val Gln Thr Ile Leu Ser Tyr Gln Met Gln
                115                 120                 125 ccc aaa atc cat ggc aaa caa gtc ttc tgg atc aga ctg ttg ttg gtt    596
Pro Lys Ile His Gly Lys Gln Val Phe Trp Ile Arg Leu Leu Leu Val
            130                 135                 140 atc tgg tgt gga gta agt gca ctt agc atg ctg act tgc tca tca gtt    644
Ile Trp Cys Gly Val Ser Ala Leu Ser Met Leu Thr Cys Ser Ser Val
            145                 150                 155 ttg cac agt ggc aat ttt ggg act gat tta gaa cag aaa ctc cat tgg    692
Leu His Ser Gly Asn Phe Gly Thr Asp Leu Glu Gln Lys Leu His Trp
        160                 165                 170 aac ccc gag gac aaa ggt tat gcg ctt cac atg atc act act gca gca    740
Asn Pro Glu Asp Lys Gly Tyr Ala Leu His Met Ile Thr Thr Ala Ala
175                 180                 185                 190 gaa tgg tct atg tca ttt tcc ttc ttt ggt ttt ttc ctg act tac att    788
Glu Trp Ser Met Ser Phe Ser Phe Phe Gly Phe Phe Leu Thr Tyr Ile
                195                 200                 205 cgt gat ttt cag aaa att tcc tta cgg gtg gaa gcc aac tta cat gga    836
Arg Asp Phe Gln Lys Ile Ser Leu Arg Val Glu Ala Asn Leu His Gly
            210                 215                 220 tta acc ctc tat gac act gca cct tgc cct att aac aat gaa cga aca    884
Leu Thr Leu Tyr Asp Thr Ala Pro Cys Pro Ile Asn Asn Glu Arg Thr
            225                 230                 235 cgg cta ctt tcc aga gat att aga tgaaaggata aatatttct gtaatgatta    938
Arg Leu Leu Ser Arg Asp Ile Arg
        240                 245 tgattctcag ggattgggga aaggttcaca gaagttgctt attcttctct gaaattttca    998
accacttaat caaggctgac agtaacactg atgaatgctg ataatcagga aacatgaaag   1058
aagccatttg atagattatt ctaaaggata tcatcaagaa gactattaaa aacacctatg   1118
cctatacttt tttatctcag aaaataaagt caaaagacta tgaaaaaaaa aaaaaa       1174

<210> SEQ ID NO 144
<211> LENGTH: 1158
<212> TYPE: DNA
<213> ORGANISM: Homo sapiens
<220> FEATURE:
<221> NAME/KEY: polyA_signal
<222> LOCATION: 1133..1138
<221> NAME/KEY: polyA_site
<222> LOCATION: 1146..1158
<221> NAME/KEY: misc_feature
<222> LOCATION: 652
<223> OTHER INFORMATION: n=a, g, c or t
```

<400> SEQUENCE: 144

```
aarttgagct tggggactgc agctgtgggg agatttcagt gcattgcctc ccctgggtgc      60
tcttcatctt ggatttgaaa gttgagagca gcatgttttg cccactgaaa ctcatcctgs     120
tgrsagtgta mtggattatt ccttgggcct gaatgacttg aatgtttccc cgcctgagct     180
aacagtccat gtgggtgatt cagctctg atg gga tgt gtt ttc cag agc aca        232
                                Met Gly Cys Val Phe Gln Ser Thr
                                  1               5 gaa gac aaa tgt ata ttc aag ata gac tgg act ctg tca cca gga gag       280
Glu Asp Lys Cys Ile Phe Lys Ile Asp Trp Thr Leu Ser Pro Gly Glu
         10                  15                  20 cac gcc aag gac gaa tat gtg cta tac tat tac tcc aat ctc agt gtg       328
His Ala Lys Asp Glu Tyr Val Leu Tyr Tyr Tyr Ser Asn Leu Ser Val
 25                  30                  35                  40 cct att ggg cgc ttc cag aac cgc gta cac ttg atg ggg gac atc tta       376
Pro Ile Gly Arg Phe Gln Asn Arg Val His Leu Met Gly Asp Ile Leu
                 45                  50                  55 tgc aat gat ggc tct ctc ctg ctc caa gat gtg caa gag gct gac cag       424
Cys Asn Asp Gly Ser Leu Leu Leu Gln Asp Val Gln Glu Ala Asp Gln
             60                  65                  70 gga acc tat atc tgt gaa atc cgc ctc aaa ggg gag agc cag gtg ttc       472
Gly Thr Tyr Ile Cys Glu Ile Arg Leu Lys Gly Glu Ser Gln Val Phe
         75                  80                  85 aag aag gcg gta gta ctg cat gtg ctt cca gag gag ccc aaa ggt acg       520
Lys Lys Ala Val Val Leu His Val Leu Pro Glu Glu Pro Lys Gly Thr
     90                  95                 100 caa atg ctt act taaagagggg ccaaggggca agagctttca tgtgcaagag           572
Gln Met Leu Thr
105 gcaaggaaac tgattatctt gagtaaatgc agcctttgg gctaagtact taccacagag      632 tgaatcttca aagaaatgan tcattaaatt atttcagrtc agaataaaaa takgagttat     692 tttagttaak aataaaatat tgataattat tgtattatta ctttaaacac acttccccct     752 cacaaaagcc ctgtgaagga tgttttgttc acatataatg tccaaatatg ttttggacac    812 atatttatta aatggaataa atagtamttg aaccctggca ccthtgacaa caaagtcyat    872 gttyttttta ctatgcccta atacctttsa tcagttatcc acattgatgc tacatytgta    932 ttttataggt acccctatgtt aggtgttttg ggggatagaa aagaaataag cagkycaggc   992 tcagtggctc atgcctgtaa tcctagcatt ttgggaggct gaggcagcag aamtgcctga  1052 gccccagggt tcaagactgc agtgagctat gawggcacca ctgcattyta gcctgggwga  1112 cagagcaaga ctytgtttaa aataaaaaaa gagaaaaaaa aaaaaa                 1158
```

<210> SEQ ID NO 145
<211> LENGTH: 754
<212> TYPE: DNA
<213> ORGANISM: Homo sapiens
<220> FEATURE:
<221> NAME/KEY: sig_peptide
<222> LOCATION: 5..142
<223> OTHER INFORMATION: Von Heijne matrix
    score 6.59999990463257
    seq VCCYLFWLIAILA/QL
<221> NAME/KEY: polyA_signal
<222> LOCATION: 716..721
<221> NAME/KEY: polyA_site
<222> LOCATION: 742..754

<400> SEQUENCE: 145

```
tgtg atg agc gtg ttc tgg ggc ttc gtc ggc ttc ttg gtg cct tgg ttc       49
```

```
              Met Ser Val Phe Trp Gly Phe Val Gly Phe Leu Val Pro Trp Phe
                  -45                 -40                 -35 atc ccc aag ggt cct aac cgg gga gtt atc att acc atg ttg gtg acc           97
Ile Pro Lys Gly Pro Asn Arg Gly Val Ile Ile Thr Met Leu Val Thr
        -30                 -25                 -20 tgt tca gtt tgc tgc tat ctc ttt tgg ctg att gca att ctg gcc caa          145
Cys Ser Val Cys Cys Tyr Leu Phe Trp Leu Ile Ala Ile Leu Ala Gln
-15                 -10                 -5                  1 ctc aac cct ctc ttt gga ccg caa ttg aaa aat gaa acc atc tgg tat          193
Leu Asn Pro Leu Phe Gly Pro Gln Leu Lys Asn Glu Thr Ile Trp Tyr
            5                   10                  15 ctg aag tat cat tgg cct tgaggaagaa gacatgctct acagtgctca                 241
Leu Lys Tyr His Trp Pro
        20 gtctttgagg tcacgagaag agaatgcctt ctagatgcaa atcacctct  aaaccagacc        301 acttttcttg acttgcctgt tttggccatt agctgcctta acgttaaca  gcacatttga        361 atgccttatt ctacaatgca gcgtgttttc ctttgccttt tttgcacttt ggtgaattac        421 gtgcctccat aacctgaact gtgccgactc acaaaacga  ttatgtactc ttctgagata        481 gaagatgctg ttcttctgag agatacgtta ctctctcctt ggaatctgtg gatttgaaga        541 tggctcctgc cttctcacgt gggaatcagt gaagtgttta gaaactgctg caagacaaac        601 aagactccag tggggtggtc agtaggagag cacgttcaga gggaagagcc atctcaacag        661 aatcgcacca aactatactt tcaggatgaa tttcttcttt ctgccatctt ttggaataaa        721 tattttcctc ctttctatgt aaaaaaaaaa aaa                                     754

<210> SEQ ID NO 146
<211> LENGTH: 1073
<212> TYPE: DNA
<213> ORGANISM: Homo sapiens
<220> FEATURE:
<221> NAME/KEY: sig_peptide
<222> LOCATION: 98..181
<223> OTHER INFORMATION: Von Heijne matrix
      score 3.59999990463257
      seq PLSDSWALLPASA/GV
<221> NAME/KEY: polyA_signal
<222> LOCATION: 1035..1040
<221> NAME/KEY: polyA_site
<222> LOCATION: 1060..1073

<400> SEQUENCE: 146
ccgattacag ctaggtagtg gagcgccgct gcttacctgg gtgcaggaga cagccggagt         60
cgctggggga gctccgcgcc gccggacgcc cgtgacc atg tgg agg ctg ctg gct        115
                                        Met Trp Arg Leu Leu Ala
                                                        -25 cgc gct agt gcg ccg ctc ctg cgg gtg ccc ttg tca gat tcc tgg gca         163
Arg Ala Ser Ala Pro Leu Leu Arg Val Pro Leu Ser Asp Ser Trp Ala
        -20                 -15                 -10 ctc ctc ccc gcc agt gct ggc gta aag aca ctg ctc cca gta cca agt         211
Leu Leu Pro Ala Ser Ala Gly Val Lys Thr Leu Leu Pro Val Pro Ser
        -5                  1                   5                   10 ttt gaa gat gtt tcc att cct gaa aaa ccc aag ctt aga ttt att gaa         259
Phe Glu Asp Val Ser Ile Pro Glu Lys Pro Lys Leu Arg Phe Ile Glu
                    15                  20                  25 agg gca cca ctt gtg cca aaa gta aga aga gaa cct aaa aat tta agt         307
Arg Ala Pro Leu Val Pro Lys Val Arg Arg Glu Pro Lys Asn Leu Ser
            30                  35                  40 gac ata cgg gga cct tcc act gaa gct acg gag ttt aca gaa ggc aat         355
Asp Ile Arg Gly Pro Ser Thr Glu Ala Thr Glu Phe Thr Glu Gly Asn
```

```
                    45                  50                  55
ttt gca atc ttg gca ttg ggt ggt ggc tac ctg cat tgg ggc cac ttt        403
Phe Ala Ile Leu Ala Leu Gly Gly Gly Tyr Leu His Trp Gly His Phe
     60                  65                  70 gaa atg atg cgc ctg aca atc aac cgc tct atg gac ccc aag aac atg        451
Glu Met Met Arg Leu Thr Ile Asn Arg Ser Met Asp Pro Lys Asn Met
 75                  80                  85                  90 ttt gcc ata tgg cga gta cca gcc cct ttc aag ccc atc act cgc aaa        499
Phe Ala Ile Trp Arg Val Pro Ala Pro Phe Lys Pro Ile Thr Arg Lys
                 95                 100                 105 agt gtt ggg cat cgc atg ggg gga ggc aaa ggt gct att gac cac tac        547
Ser Val Gly His Arg Met Gly Gly Gly Lys Gly Ala Ile Asp His Tyr
                110                 115                 120 gtg aca cct gtg aag gct ggc cgc ctt gtt gta gag atg ggt ggg cgt        595
Val Thr Pro Val Lys Ala Gly Arg Leu Val Val Glu Met Gly Gly Arg
            125                 130                 135 tgt gaa ttt gaa gaa gtg caa ggt ttc ctt gac cag gtt gcc cac aag        643
Cys Glu Phe Glu Glu Val Gln Gly Phe Leu Asp Gln Val Ala His Lys
        140                 145                 150 ttg ccc ttc gca gca aag gct gtg agc cgc ggg act cta gag aag atg        691
Leu Pro Phe Ala Ala Lys Ala Val Ser Arg Gly Thr Leu Glu Lys Met
155                 160                 165                 170 cga aaa gat caa gag gaa aga gaa cgt aac aac cag aac ccc tgg aca        739
Arg Lys Asp Gln Glu Glu Arg Glu Arg Asn Asn Gln Asn Pro Trp Thr
                175                 180                 185 ttt gag cga ata gcc act gcc aac atg ctg ggc ata cgg aaa gta ctg        787
Phe Glu Arg Ile Ala Thr Ala Asn Met Leu Gly Ile Arg Lys Val Leu
            190                 195                 200 agc cca tat gac ttg acc cac aag ggg aaa tac tgg ggc aag ttc tac        835
Ser Pro Tyr Asp Leu Thr His Lys Gly Lys Tyr Trp Gly Lys Phe Tyr
        205                 210                 215 atg ccc aaa cgt gtg tagtgagtgt aggagataac tgtatatagg ctactgaaag        890
Met Pro Lys Arg Val
        220 aaggattctg catttctatt cccctcagcc tacccactga agtctttggg tagctcttaa       950 gccataacta aggagcagca tttgagtaga tttctgaaaa acgatgttat tgttgatttt      1010 aaaaagaaaa ctgtattttt attaaataaa atttaaacat cacttcagga aaaaaaaaa       1070 aaa                                                                    1073

<210> SEQ ID NO 147
<211> LENGTH: 413
<212> TYPE: DNA
<213> ORGANISM: Homo sapiens
<220> FEATURE:
<221> NAME/KEY: sig_peptide
<222> LOCATION: 46..189
<223> OTHER INFORMATION: Von Heijne matrix
      score 4.09999990463257
      seq VFMLIVSVLALIP/ET
<221> NAME/KEY: polyA_signal
<222> LOCATION: 377..382
<221> NAME/KEY: polyA_site
<222> LOCATION: 402..413

<400> SEQUENCE: 147
tgagaagagt tgagggaaag tgctgctgct gggtctgcag acgcg atg gat aac gtg       57
                                                 Met Asp Asn Val
                                                         -45 cag ccg aaa ata aaa cat cgc ccc ttc tgc ttc agt gtg aaa ggc cac        105
Gln Pro Lys Ile Lys His Arg Pro Phe Cys Phe Ser Val Lys Gly His
            -40                 -35                 -30
```

```
gtg aag atg ctg cgg ctg gat att atc aac tca ctg gta aca aca gta      153
Val Lys Met Leu Arg Leu Asp Ile Ile Asn Ser Leu Val Thr Thr Val
            -25                 -20                 -15 ttc atg ctc atc gta tct gtg ttg gca ctg ata cca gaa acc aca aca      201
Phe Met Leu Ile Val Ser Val Leu Ala Leu Ile Pro Glu Thr Thr Thr
            -10                  -5                   1 ttg aca gtt ggt gga ggg gtg ttt gca ctt gtg aca gca gta tgc tgc      249
Leu Thr Val Gly Gly Gly Val Phe Ala Leu Val Thr Ala Val Cys Cys
  5              10                  15                  20 ctt gcc gac ggg gcc ctt att tac cgg aag ctt ctg ttc aat ccc agc      297
Leu Ala Asp Gly Ala Leu Ile Tyr Arg Lys Leu Leu Phe Asn Pro Ser
                 25                  30                  35 ggt cct tac cag aaa aag cct gtg cat gaa aaa aaa gaa gtt ttg          342
Gly Pro Tyr Gln Lys Lys Pro Val His Glu Lys Lys Glu Val Leu
             40                  45                  50 taatttata ttacttttta gtttgatact aagtattaaa catatttctg tattcttcca     402
aaaaaaaaaa a                                                         413

<210> SEQ ID NO 148
<211> LENGTH: 609
<212> TYPE: DNA
<213> ORGANISM: Homo sapiens
<220> FEATURE:
<221> NAME/KEY: sig_peptide
<222> LOCATION: 139..231
<223> OTHER INFORMATION: Von Heijne matrix
      score 4.40000009536743
      seq TCCHLGLPHPVRA/PR
<221> NAME/KEY: polyA_signal
<222> LOCATION: 579..584
<221> NAME/KEY: polyA_site
<222> LOCATION: 598..609

<400> SEQUENCE: 148
tgtcggagtt ggaaagggac gcctggtttc cccccaagcg aaccgggatg ggaagtgact     60
tcaatgagat tgaacttcag ctggattgaa agagaggcta aagttccgc ttgccagcag     120 cctccttagt agagcgga atg agt aat acc cac acg gtg ctt gtc tca ctt      171
                    Met Ser Asn Thr His Thr Val Leu Val Ser Leu
                        -30                 -25 ccc cat ccg cac ccg gcc ctc acc tgc tgt cac ctc ggc ctc cca cac      219
Pro His Pro His Pro Ala Leu Thr Cys Cys His Leu Gly Leu Pro His
-20              -15                 -10                  -5 ccg gtc cgc gct ccc cgc cct ctt cct cgc gta gaa ccg tgg gat cct      267
Pro Val Arg Ala Pro Arg Pro Leu Pro Arg Val Glu Pro Trp Asp Pro
                  1               5                   10 agg tgg cag gac tca gag cta agg tat cca cag gcc atg aat tcc ttc      315
Arg Trp Gln Asp Ser Glu Leu Arg Tyr Pro Gln Ala Met Asn Ser Phe
         15                  20                  25 cta aat gag cgg tca tcg ccg tgc agg acc tta agg caa gaa gca tcg      363
Leu Asn Glu Arg Ser Ser Pro Cys Arg Thr Leu Arg Gln Glu Ala Ser
 30                  35                  40 gct gac aga tgt gat ctc tgaacctgat agattgctga ttttatctta              411
Ala Asp Arg Cys Asp Leu
 45                  50 ttttatcctt gacttggtac aagttttggg atttctgaaa agaccataca gataaccaca    471
aatatcaaga aagtcgtctt cagtattaag tagaatttag atttaggttt ccttcctgct    531
tcccacctcc ttcgaataag gaaacgtctt tgggaccaac tttatggaat aaataagctg    591
agctgcaaaa aaaaaaaa                                                  609
```

<210> SEQ ID NO 149
<211> LENGTH: 522
<212> TYPE: DNA
<213> ORGANISM: Homo sapiens
<220> FEATURE:
<221> NAME/KEY: polyA_site
<222> LOCATION: 512..522
<221> NAME/KEY: misc_feature
<222> LOCATION: 11
<223> OTHER INFORMATION: n=a, g, c or t

<400> SEQUENCE: 149

```
ccaactgcag nttcgaattt accgagcgga gaggagatgc acacggcact cgagtgtgag      60
gaaaaataga a atg aag gta cat atg cac aca aaa ttt tgc ctc att tgt      110
            Met Lys Val His Met His Thr Lys Phe Cys Leu Ile Cys
            1               5                   10 ttg ctg aca ttt att ttt cat cat tgc aac cat tgc cat gaa gaa cat      158
Leu Leu Thr Phe Ile Phe His His Cys Asn His Cys His Glu Glu His
    15                  20                  25 gac cat ggc cct gaa gcg ctt cac aga cag cat cgt gga atg aca gaa      206
Asp His Gly Pro Glu Ala Leu His Arg Gln His Arg Gly Met Thr Glu
30              35                  40                  45 ttg gag cca agc aaa ttt tca aag caa gct gct gaa aat gaa aaa aaa      254
Leu Glu Pro Ser Lys Phe Ser Lys Gln Ala Ala Glu Asn Glu Lys Lys
                50                  55                  60 tac tat att gaa aaa ctt ttt gag cgt tat ggt gaa aat gga aga tta      302
Tyr Tyr Ile Glu Lys Leu Phe Glu Arg Tyr Gly Glu Asn Gly Arg Leu
            65                  70                  75 tcc ttt ttt ggt ttg gag aaa ctt tta aca aac ttg ggc ctt gga gag      350
Ser Phe Phe Gly Leu Glu Lys Leu Leu Thr Asn Leu Gly Leu Gly Glu
        80                  85                  90 aga aaa gta gtt gag att aat cat gag gat ctt ggc cac gat cat gtt      398
Arg Lys Val Val Glu Ile Asn His Glu Asp Leu Gly His Asp His Val
95                  100                 105 tct cat tta ggt att ttg gca gtt caa gag gga aag cat ttt cac tca      446
Ser His Leu Gly Ile Leu Ala Val Gln Glu Gly Lys His Phe His Ser
110                 115                 120                 125 cat aac cac cag cat tcc cat aat cat tta aat tca gaa aat caa act      494
His Asn His Gln His Ser His Asn His Leu Asn Ser Glu Asn Gln Thr
                130                 135                 140 gtg acc agt gta tcc aca aaaaaaaaaa                                    522
Val Thr Ser Val Ser Thr
                145
```

<210> SEQ ID NO 150
<211> LENGTH: 1322
<212> TYPE: DNA
<213> ORGANISM: Homo sapiens
<220> FEATURE:
<221> NAME/KEY: sig_peptide
<222> LOCATION: 126..260
<223> OTHER INFORMATION: Von Heijne matrix
      score 4.59999990463257
      seq VLVYLVTAERVWS/DD
<221> NAME/KEY: polyA_signal
<222> LOCATION: 1283..1288
<221> NAME/KEY: polyA_site
<222> LOCATION: 1309..1322

<400> SEQUENCE: 150

```
ccgaaaacct tccccgcttc tggatatgaa attcaagctg cttgctgagt cctattgccg      60
gctgctggga gccaggagag ccctgaggag tagtcactca gtagcagctg acgcgtgggt     120 ccacc atg aac tgg agt atc ttt gag gga ctc ctg agt ggg gtc aac aag     170
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     | Met | Asn | Trp | Ser | Ile | Phe | Glu | Gly | Leu | Leu | Ser | Gly | Val | Asn | Lys |     |
|     | -45 |     |     |     | -40 |     |     |     |     | -35 |     |     |     |     |     |     |

```
tac tcc aca gcc ttt ggg cgc atc tgg ctg tct ctg gtc ttc atc ttc       218
Tyr Ser Thr Ala Phe Gly Arg Ile Trp Leu Ser Leu Val Phe Ile Phe
-30             -25                 -20                 -15 cgc gtg ctg gtg tac ctg gtg acg gcc gag cgt gtg tgg agt gat gac       266
Arg Val Leu Val Tyr Leu Val Thr Ala Glu Arg Val Trp Ser Asp Asp
                -10                 -5                   1 cac aag gac ttc gac tgc aat act cgc cag ccc ggc tgc tcc aac gtc       314
His Lys Asp Phe Asp Cys Asn Thr Arg Gln Pro Gly Cys Ser Asn Val
     5                  10                  15 tgc ttt gat gag ttc ttc cct gtg tcc cat gtg cgc ctc tgg gcc ctg       362
Cys Phe Asp Glu Phe Phe Pro Val Ser His Val Arg Leu Trp Ala Leu
 20                  25                  30 cag ctt atc ctg gtg aca tgc ccc tca ctg ctc gtg gtc atg cac gtg       410
Gln Leu Ile Leu Val Thr Cys Pro Ser Leu Leu Val Val Met His Val
35                  40                  45                  50 gcc tac cgg gag gtt cag gag aag agg cac cga gaa gcc cat ggg gag       458
Ala Tyr Arg Glu Val Gln Glu Lys Arg His Arg Glu Ala His Gly Glu
                 55                  60                  65 aac agt ggg cgc ctc tac ctg aac ccc ggc aag aag cgg ggt ggg ctc       506
Asn Ser Gly Arg Leu Tyr Leu Asn Pro Gly Lys Lys Arg Gly Gly Leu
             70                  75                  80 tgg tgg aca tat gtc tgc agc cta gtg ttc aag gcg agc gtg gac atc       554
Trp Trp Thr Tyr Val Cys Ser Leu Val Phe Lys Ala Ser Val Asp Ile
         85                  90                  95 gcc ttt ctc tat gtg ttc cac tca ttc tac ccc aaa tat atc ctc cct       602
Ala Phe Leu Tyr Val Phe His Ser Phe Tyr Pro Lys Tyr Ile Leu Pro
     100                 105                 110 cct gtg gtc aag tgc cac gca gat cca tgt ccc aat ata gtg gac tgc       650
Pro Val Val Lys Cys His Ala Asp Pro Cys Pro Asn Ile Val Asp Cys
115                 120                 125                 130 ttc atc tcc aag ccc tca gag aag aac att ttc acc ctc ttc atg gtg       698
Phe Ile Ser Lys Pro Ser Glu Lys Asn Ile Phe Thr Leu Phe Met Val
                135                 140                 145 gcc aca gct gcc atc tgc atc ctg ctc aac ctc gtg gag ctc atc tac       746
Ala Thr Ala Ala Ile Cys Ile Leu Leu Asn Leu Val Glu Leu Ile Tyr
            150                 155                 160 ctg gtg agc aag aga tgc cac gag tgc ctg gca gca agg aaa gct caa       794
Leu Val Ser Lys Arg Cys His Glu Cys Leu Ala Ala Arg Lys Ala Gln
        165                 170                 175 gcc atg tgc aca ggt cat cac ccc cac gat acc acc tct tcc tgc aaa       842
Ala Met Cys Thr Gly His His Pro His Asp Thr Thr Ser Ser Cys Lys
    180                 185                 190 caa gac gac ctc ctt tcg ggt gac ctc atc ttt ctg ggc tca gac agt       890
Gln Asp Asp Leu Leu Ser Gly Asp Leu Ile Phe Leu Gly Ser Asp Ser
195                 200                 205                 210 cat cct cct ctc tta cca gac cgc ccc cga gac cat gtg aag aaa acc       938
His Pro Pro Leu Leu Pro Asp Arg Pro Arg Asp His Val Lys Lys Thr
                215                 220                 225 atc ttg tgaggggctg cctggactgg tctggcaggt tgggcctgga tggggaggct        994
Ile Leu ctagcatctc tcataggtgc aacctgagag tgggggagct aagccatgag gtaggggcag    1054
gcaagagaga ggattcagac gctctgggag ccagttccta gtcctcaact ccagccacct    1114
gccccagctc gacggcactg ggccagttcc cctctgctc tgcagctcgg tttccttttc     1174
tagaatggaa atagtgaggg ccaatgccca gggttggagg gaggagggcg ttcatagaag    1234
aacacacatg cgggcacctt catcgtgtgt ggcccactgt cagaacttaa taaagtcaa     1294
```

-continued

```
ctcatttgct ggttaaaaaa aaaaaaaa                                          1322

<210> SEQ ID NO 151
<211> LENGTH: 1290
<212> TYPE: DNA
<213> ORGANISM: Homo sapiens
<220> FEATURE:
<221> NAME/KEY: sig_peptide
<222> LOCATION: 50..160
<223> OTHER INFORMATION: Von Heijne matrix
      score 4
      seq PLSLDCGHSLCRA/CI
<221> NAME/KEY: polyA_site
<222> LOCATION: 1280..1290

<400> SEQUENCE: 151
gaggagagcc tcaggagtta ggaccagaag aagccaggga agcagtgca atg gct tca     58
                                                     Met Ala Ser
                                                         -35 aaa atc ttg ctt aac gta caa gag gag gtg acc tgt ccc atc tgc ctg      106
Lys Ile Leu Leu Asn Val Gln Glu Glu Val Thr Cys Pro Ile Cys Leu
            -30                 -25                 -20 gag ctg ttg aca gaa ccc ttg agt cta gac tgt ggc cac agc ctc tgc      154
Glu Leu Leu Thr Glu Pro Leu Ser Leu Asp Cys Gly His Ser Leu Cys
        -15                 -10                  -5 cga gcc tgc atc act gtg agc aac aag gag gca gtg acc agc atg gga      202
Arg Ala Cys Ile Thr Val Ser Asn Lys Glu Ala Val Thr Ser Met Gly
  1               5                  10 gga aaa agc agc tgt cct gtg tgt ggt atc agt tac tca ttt gaa cat      250
Gly Lys Ser Ser Cys Pro Val Cys Gly Ile Ser Tyr Ser Phe Glu His
15              20                  25                  30 cta cag gct aat cag cat ctg gcc aac ata gtg gag aga ctc aag gag      298
Leu Gln Ala Asn Gln His Leu Ala Asn Ile Val Glu Arg Leu Lys Glu
                35                  40                  45 gtc aag ttg agc cca gac aat ggg aag aag aga gat ctc tgt gat cat      346
Val Lys Leu Ser Pro Asp Asn Gly Lys Lys Arg Asp Leu Cys Asp His
            50                  55                  60 cat gga gag aaa ctc cta ctc ttc tgt aag gag gat agg aaa gtc att      394
His Gly Glu Lys Leu Leu Leu Phe Cys Lys Glu Asp Arg Lys Val Ile
        65                  70                  75 tgc tgg ctt tgt gag cgg tct cag gag cac cgt ggt cac cac aca gtc      442
Cys Trp Leu Cys Glu Arg Ser Gln Glu His Arg Gly His His Thr Val
    80                  85                  90 ctc acg gag gaa gta ttc aag gaa tgt cag gag aaa ctc cag gca gtc      490
Leu Thr Glu Glu Val Phe Lys Glu Cys Gln Glu Lys Leu Gln Ala Val
95                  100                 105                 110 ctc aag agg ctg aag aag gaa gag gag gaa gct gag aag ctg gaa gct      538
Leu Lys Arg Leu Lys Lys Glu Glu Glu Glu Ala Glu Lys Leu Glu Ala
                115                 120                 125 gac atc aga gaa gag aaa act tcc tgg aag tat cag gta caa act gag      586
Asp Ile Arg Glu Glu Lys Thr Ser Trp Lys Tyr Gln Val Gln Thr Glu
            130                 135                 140 aga caa agg ata caa aca gaa ttt gat cag ctt aga agc atc cta aat      634
Arg Gln Arg Ile Gln Thr Glu Phe Asp Gln Leu Arg Ser Ile Leu Asn
        145                 150                 155 aat gag gag cag aga gag ctg caa aga ttg gaa gaa gaa aag aag          682
Asn Glu Glu Gln Arg Glu Leu Gln Arg Leu Glu Glu Glu Lys Lys
    160                 165                 170 acg ctg gat aag ttt gca gag gct gag gat gag cta gtt cag cag aag      730
Thr Leu Asp Lys Phe Ala Glu Ala Glu Asp Glu Leu Val Gln Gln Lys
175                 180                 185                 190
```

```
                    -continued cag ttg gtg aga gag ctc atc tca gat gtg gag tgt cgg agt cag tgg    778
Gln Leu Val Arg Glu Leu Ile Ser Asp Val Glu Cys Arg Ser Gln Trp
            195                 200                 205 tca aca atg gag ctg ctg cag gac atg agt gga atc atg aaa tgg agt    826
Ser Thr Met Glu Leu Leu Gln Asp Met Ser Gly Ile Met Lys Trp Ser
        210                 215                 220 gag atc tgg agg ctg aaa aag cca aaa atg gtt tcc aag aaa ctg aag    874
Glu Ile Trp Arg Leu Lys Lys Pro Lys Met Val Ser Lys Lys Leu Lys
    225                 230                 235 act gta ttc cat gct cca gat ctg agt agg atg ctg caa atg ttt aga    922
Thr Val Phe His Ala Pro Asp Leu Ser Arg Met Leu Gln Met Phe Arg
240                 245                 250 gaa ctg aca gct gtc cgg tgc tac tgg gtg gat gtc aca ctg aat tca    970
Glu Leu Thr Ala Val Arg Cys Tyr Trp Val Asp Val Thr Leu Asn Ser
255                 260                 265                 270 gtc aac cta aat ttg aat ctt gtc ctt tca gaa gat cag aga caa gtg   1018
Val Asn Leu Asn Leu Asn Leu Val Leu Ser Glu Asp Gln Arg Gln Val
                275                 280                 285 ata tct gtg cca att tgg cct ttt cag tgt tat aat tat ggt gtc ttg   1066
Ile Ser Val Pro Ile Trp Pro Phe Gln Cys Tyr Asn Tyr Gly Val Leu
            290                 295                 300 gga tcc caa tat ttc tcc tct ggg aaa cat tac tgg gaa gtg gac gtg   1114
Gly Ser Gln Tyr Phe Ser Ser Gly Lys His Tyr Trp Glu Val Asp Val
        305                 310                 315 tcc aag aaa act gcc tgg atc ctg ggg gta tac tgt aga aca tat tcc   1162
Ser Lys Lys Thr Ala Trp Ile Leu Gly Val Tyr Cys Arg Thr Tyr Ser
    320                 325                 330 cgc cat atg aag tat gtt gtt aga aga tgt gca aat cgt caa aat ctt   1210
Arg His Met Lys Tyr Val Val Arg Arg Cys Ala Asn Arg Gln Asn Leu
335                 340                 345                 350 tac acc aaa tac aga cct cta ttt ggc tac tgg gtt ata ggg tta cag   1258
Tyr Thr Lys Tyr Arg Pro Leu Phe Gly Tyr Trp Val Ile Gly Leu Gln
                355                 360                 365 aat aaa tgt aag tat ggt gcc aaaaaaaaa a                           1290
Asn Lys Cys Lys Tyr Gly Ala
            370

<210> SEQ ID NO 152
<211> LENGTH: 1364
<212> TYPE: DNA
<213> ORGANISM: Homo sapiens
<220> FEATURE:
<221> NAME/KEY: sig_peptide
<222> LOCATION: 83..139
<223> OTHER INFORMATION: Von Heijne matrix
      score 8.60000038146973
      seq LLWLALACSPVHT/TL
<221> NAME/KEY: polyA_site
<222> LOCATION: 1356..1354

<400> SEQUENCE: 152
gcctgggagc tgaggcagcc accgtctcag cctggccagc cctctggacc ccgaggttgg     60
accctactgt gacacaccta cc atg cgg aca ctc ttc aac ctc ctc tgg ctt    112
                          Met Arg Thr Leu Phe Asn Leu Leu Trp Leu
                                      -15                 -10 gcc ctg gcc tgc agc cct gtt cac act acc ctg tca aag tca gat gcc    160
Ala Leu Ala Cys Ser Pro Val His Thr Thr Leu Ser Lys Ser Asp Ala
            -5                  1               5 aaa aaa gcc gcc tca aag acg ctg ctg gag aag agt cag ttt tca gat    208
Lys Lys Ala Ala Ser Lys Thr Leu Leu Glu Lys Ser Gln Phe Ser Asp
        10                  15                  20 aag ccg gtg caa gac cgg ggt ttg gtg gtg acg gac ctc aaa gct gag    256
```

-continued

```
                Lys Pro Val Gln Asp Arg Gly Leu Val Val Thr Asp Leu Lys Ala Glu
                 25                  30                  35 agt gtg gtt ctt gag cat cgc agc tac tgc tcg gca aag gcc cgg gac        304
Ser Val Val Leu Glu His Arg Ser Tyr Cys Ser Ala Lys Ala Arg Asp
 40                  45                  50                  55 aga cac ttt gct ggg gat gta ctg ggc tat gtc act cca tgg aac agc        352
Arg His Phe Ala Gly Asp Val Leu Gly Tyr Val Thr Pro Trp Asn Ser
                     60                  65                  70 cat ggc tac gat gtc acc aag gtc ttt ggg agc aag ttc aca cag atc        400
His Gly Tyr Asp Val Thr Lys Val Phe Gly Ser Lys Phe Thr Gln Ile
                 75                  80                  85 tca ccc gtc tgg ctg cag ttg aag aga cgt ggc cgt gag atg ttt gag        448
Ser Pro Val Trp Leu Gln Leu Lys Arg Arg Gly Arg Glu Met Phe Glu
             90                  95                 100 gtc acg ggc ctc cac gac gtg gac caa ggg tgg atg cga gct gtc agg        496
Val Thr Gly Leu His Asp Val Asp Gln Gly Trp Met Arg Ala Val Arg
        105                 110                 115 aag cat gcc aag ggc ctg cac ata gtg cct cgg ctc ctg ttt gag gac        544
Lys His Ala Lys Gly Leu His Ile Val Pro Arg Leu Leu Phe Glu Asp
120                 125                 130                 135 tgg act tac gat gat ttc cgg aac gtc tta gac agt gag gat gag ata        592
Trp Thr Tyr Asp Asp Phe Arg Asn Val Leu Asp Ser Glu Asp Glu Ile
                    140                 145                 150 gag gag ctg agc aag acc gtg gtc cag gtg gca aag aac cag cat ttc        640
Glu Glu Leu Ser Lys Thr Val Val Gln Val Ala Lys Asn Gln His Phe
                155                 160                 165 gat ggc ttc gtg gtg gag gtc tgg aac cag ctg cta agc cag aag cgc        688
Asp Gly Phe Val Val Glu Val Trp Asn Gln Leu Leu Ser Gln Lys Arg
            170                 175                 180 gtg ggc ctc atc cac atg ctc acc cac ttg gcc gag gcc ctg cac cag        736
Val Gly Leu Ile His Met Leu Thr His Leu Ala Glu Ala Leu His Gln
        185                 190                 195 gcc cgg ctg ctg gcc ctc ctg gtc atc ccg cct gcc atc acc ccc ggg        784
Ala Arg Leu Leu Ala Leu Leu Val Ile Pro Pro Ala Ile Thr Pro Gly
200                 205                 210                 215 acc gac cag ctg ggc atg ttc acg cac aag gag ttt gag cag ctg gcc        832
Thr Asp Gln Leu Gly Met Phe Thr His Lys Glu Phe Glu Gln Leu Ala
                    220                 225                 230 ccc gtg ctg gat ggt ttc agc ctc atg acc tac gac tac tct aca gcg        880
Pro Val Leu Asp Gly Phe Ser Leu Met Thr Tyr Asp Tyr Ser Thr Ala
                235                 240                 245 cat cag cct ggc cct aat gca ccc ctg tcc tgg gtt cga gcc tgc gtc        928
His Gln Pro Gly Pro Asn Ala Pro Leu Ser Trp Val Arg Ala Cys Val
            250                 255                 260 cag gtc ctg gac ccg aag tcc aag tgg cga agc aaa atc ctc ctg ggg        976
Gln Val Leu Asp Pro Lys Ser Lys Trp Arg Ser Lys Ile Leu Leu Gly
265                 270                 275 ctc aac ttc tat ggt atg gac tac gcg acc tcc aag gat gcc cgt gag       1024
Leu Asn Phe Tyr Gly Met Asp Tyr Ala Thr Ser Lys Asp Ala Arg Glu
280                 285                 290                 295 cct gtt gtc ggg gcc agg tac atc cag aca ctg aag gac cac agg ccc       1072
Pro Val Val Gly Ala Arg Tyr Ile Gln Thr Leu Lys Asp His Arg Pro
                    300                 305                 310 cgg atg gtg tgg gac agc cag gcc tca gag cac ttc ttc gag tac aag       1120
Arg Met Val Trp Asp Ser Gln Ala Ser Glu His Phe Phe Glu Tyr Lys
                315                 320                 325 aag agc cgc agt ggg agg cac gtc gtc ttc tac cca acc ctg aag tcc       1168
Lys Ser Arg Ser Gly Arg His Val Val Phe Tyr Pro Thr Leu Lys Ser
            330                 335                 340
```

```
ctg cag gtg cgg ctg gag ctg gcc cgg gag ctg ggc gtt ggg gtc tct    1216
Leu Gln Val Arg Leu Glu Leu Ala Arg Glu Leu Gly Val Gly Val Ser
    345                 350                 355 atc tgg gag ctg ggc cag ggc ctg gac tac ttc tac gac ctg ctc        1261
Ile Trp Glu Leu Gly Gln Gly Leu Asp Tyr Phe Tyr Asp Leu Leu
360                 365                 370 taggtgggca ttgcggcctc cgcggtggac gtgttctttt ctaagccatg gagtgagtga  1321
gcaggtgtga aatacaggcc tccactccgt ttgcaaaaaa aaa                    1364

<210> SEQ ID NO 153
<211> LENGTH: 1470
<212> TYPE: DNA
<213> ORGANISM: Homo sapiens
<220> FEATURE:
<221> NAME/KEY: sig_peptide
<222> LOCATION: 57..95
<223> OTHER INFORMATION: Von Heijne matrix
      score 3.90000009536743
      seq MLLSIGMLMLSAT/QV
<221> NAME/KEY: polyA_signal
<222> LOCATION: 1438..1443
<221> NAME/KEY: polyA_site
<222> LOCATION: 1458..1470

<400> SEQUENCE: 153
gctggcaaga ctgtttgtgt tgcgggggcc ggacttcaag gtgattttac aacgag atg   59
                                                               Met ctg ctc tcc ata ggg atg ctc atg ctg tca gcc aca caa gtc tac acc    107
Leu Leu Ser Ile Gly Met Leu Met Leu Ser Ala Thr Gln Val Tyr Thr
        -10                  -5                   1 gtc ttg act gtc cag ctc ttt gca ttc tta aac cca ctg cct gta gaa    155
Val Leu Thr Val Gln Leu Phe Ala Phe Leu Asn Pro Leu Pro Val Glu
  5                  10                  15                  20 gca gac att tta gca tat aac ttt gaa aat gca tct cag aca ttt gat    203
Ala Asp Ile Leu Ala Tyr Asn Phe Glu Asn Ala Ser Gln Thr Phe Asp
                 25                  30                  35 gac ctc cct gca aga ttt ggt tat aga ctt cca gct gaa ggt tta aag    251
Asp Leu Pro Ala Arg Phe Gly Tyr Arg Leu Pro Ala Glu Gly Leu Lys
            40                  45                  50 ggt ttt tta att aac tca aaa cca gag aat gcc tgt gaa ccc ata gtg    299
Gly Phe Leu Ile Asn Ser Lys Pro Glu Asn Ala Cys Glu Pro Ile Val
        55                  60                  65 cct cca cca gta aaa gac aat tca tct ggc act ttc atc gtg tta att    347
Pro Pro Pro Val Lys Asp Asn Ser Ser Gly Thr Phe Ile Val Leu Ile
70                  75                  80 aga aga ctt gat tgt aat ttt gat ata aag gtt tta aat gca cag aga    395
Arg Arg Leu Asp Cys Asn Phe Asp Ile Lys Val Leu Asn Ala Gln Arg
85                  90                  95                 100 gca gga tac aag gca gcc ata gtt cac aat gtt gat tct gat gac ctc    443
Ala Gly Tyr Lys Ala Ala Ile Val His Asn Val Asp Ser Asp Asp Leu
                105                 110                 115 att agc atg gga tcc aac gac att gag gta cta aag aaa att gac att    491
Ile Ser Met Gly Ser Asn Asp Ile Glu Val Leu Lys Lys Ile Asp Ile
            120                 125                 130 cca tct gtc ttt att ggt gaa tca tca gct agt tct ctg aaa gat gaa    539
Pro Ser Val Phe Ile Gly Glu Ser Ser Ala Ser Ser Leu Lys Asp Glu
        135                 140                 145 ttc aca tat gaa aaa ggg ggc cac ctt atc tta gtt cca gaa ttt agt    587
Phe Thr Tyr Glu Lys Gly Gly His Leu Ile Leu Val Pro Glu Phe Ser
    150                 155                 160 ctt cct ttg gaa tac tac cta att ccc ttc ctt atc ata gtg ggc atc    635
Leu Pro Leu Glu Tyr Tyr Leu Ile Pro Phe Leu Ile Ile Val Gly Ile
```

|  |  |  |
|---|---|---|
| tgt ctc atc ttg ata gtc att ttc atg atc aca aaa ttt gtc cag gat<br>Cys Leu Ile Leu Ile Val Ile Phe Met Ile Thr Lys Phe Val Gln Asp<br>                  185                 190                 195 | 683 |
| aga cat aga gct aga aga aac aga ctt cgt aaa gat caa ctt aag aaa<br>Arg His Arg Ala Arg Arg Asn Arg Leu Arg Lys Asp Gln Leu Lys Lys<br>                  200                 205                 210 | 731 |
| ctt cct gta cat aaa ttc aag aaa gga gat gag tat gat gta tgt gcc<br>Leu Pro Val His Lys Phe Lys Lys Gly Asp Glu Tyr Asp Val Cys Ala<br>                  215                 220                 225 | 779 |
| att tgt ttg gat gag tat gaa gat gga gac aaa ctc aga atc ctt ccc<br>Ile Cys Leu Asp Glu Tyr Glu Asp Gly Asp Lys Leu Arg Ile Leu Pro<br>                  230                 235                 240 | 827 |
| tgt tcc cat gct tat cat tgc aag tgt gta gac cct tgg cta act aaa<br>Cys Ser His Ala Tyr His Cys Lys Cys Val Asp Pro Trp Leu Thr Lys<br>245                  250                 255                 260 | 875 |
| acc aaa aaa acc tgt cca gtg tgc agg caa aaa gtt gtt cct tct caa<br>Thr Lys Lys Thr Cys Pro Val Cys Arg Gln Lys Val Val Pro Ser Gln<br>                  265                 270                 275 | 923 |
| ggc gat tca gac tct gac aca gac agt agt caa gaa gaa aat gaa gtg<br>Gly Asp Ser Asp Ser Asp Thr Asp Ser Ser Gln Glu Glu Asn Glu Val<br>                  280                 285                 290 | 971 |
| aca gaa cat acc cct tta ctg aga cct tta gct tct gtc agt gcc cag<br>Thr Glu His Thr Pro Leu Leu Arg Pro Leu Ala Ser Val Ser Ala Gln<br>                  295                 300                 305 | 1019 |
| tca ttt ggg gct tta tcg gaa tcc cgc tca cat cag aac atg aca gaa<br>Ser Phe Gly Ala Leu Ser Glu Ser Arg Ser His Gln Asn Met Thr Glu<br>                  310                 315                 320 | 1067 |
| tct tca gac tat gag gaa gac gac aat gaa gat act gac agt agt gat<br>Ser Ser Asp Tyr Glu Glu Asp Asp Asn Glu Asp Thr Asp Ser Ser Asp<br>325                  330                 335                 340 | 1115 |
| gca gaa aat gaa att aat gaa cat gat gtc gtg gtc cag ttg cag cct<br>Ala Glu Asn Glu Ile Asn Glu His Asp Val Val Val Gln Leu Gln Pro<br>                  345                 350                 355 | 1163 |
| aat ggt gaa cgg gat tac aac ata gca aat act gtt tgactttcag<br>Asn Gly Glu Arg Asp Tyr Asn Ile Ala Asn Thr Val<br>                  360                 365 | 1209 |
| aagatgattg gtttatttcc ctttaaaatg attaggtata tactgtaatt tgatttttg | 1269 |
| ctcccttaaa agatttctgt agaaataact tattttttag tactctacag tttaatcaaa | 1329 |
| ttactgaaac aggacttttg atctggtatt tatctgccaa gaatatactt cattcactaa | 1389 |
| taatagactg gtgctgtaac tcaagcatca attcagctct tcttttggaa tgaaagtata | 1449 |
| gccaaaacaa aaaaaaaaa a | 1470 |

<210> SEQ ID NO 154
<211> LENGTH: 982
<212> TYPE: DNA
<213> ORGANISM: Homo sapiens
<220> FEATURE:
<221> NAME/KEY: sig_peptide
<222> LOCATION: 72..197
<223> OTHER INFORMATION: Von Heijne matrix
      score 7.19999980926514
      seq ILFSLSFLLVIIT/FP
<221> NAME/KEY: polyA_site
<222> LOCATION: 970..982

<400> SEQUENCE: 154

| | |
|---|---|
| gctgcctgtt cttcacactt agctccaaac ccatgaaaaa ttgccaagta taaagcttc | 60 |
| tcaagaatga g atg gat tct agg gtg tct tca cct gag aag caa gat aaa | 110 |

```
            Met Asp Ser Arg Val Ser Ser Pro Glu Lys Gln Asp Lys
                -40                  -35                  -30 gag aat ttc gtg ggt gtc aac aat aaa cgg ctt ggt gta tgt ggc tgg         158
Glu Asn Phe Val Gly Val Asn Asn Lys Arg Leu Gly Val Cys Gly Trp
            -25                  -20                  -15 atc ctg ttt tcc ctc tct ttc ctg ttg gtg atc att acc ttc ccc atc         206
Ile Leu Phe Ser Leu Ser Phe Leu Leu Val Ile Ile Thr Phe Pro Ile
            -10                   -5                    1 tcc ata tgg atg tgc ttg aag atc att agg gag tat gaa cgt gct gtt         254
Ser Ile Trp Met Cys Leu Lys Ile Ile Arg Glu Tyr Glu Arg Ala Val
     5                   10                   15 gta ttc cgt ctg gga cgc atc caa gct gac aaa gcc aag ggg cca ggt         302
Val Phe Arg Leu Gly Arg Ile Gln Ala Asp Lys Ala Lys Gly Pro Gly
 20                   25                   30                   35 ttg atc ctg gtc ctg cca tgc ata gat gtg ttt gtc aag gtt gac ctc         350
Leu Ile Leu Val Leu Pro Cys Ile Asp Val Phe Val Lys Val Asp Leu
                 40                   45                   50 cga aca gtt act tgc aac att cct cca caa gag atc ctc acc aga gac         398
Arg Thr Val Thr Cys Asn Ile Pro Pro Gln Glu Ile Leu Thr Arg Asp
             55                   60                   65 tcc gta act act cag gta gat gga gtt gtc tat tac aga atc tat agt         446
Ser Val Thr Thr Gln Val Asp Gly Val Val Tyr Tyr Arg Ile Tyr Ser
             70                   75                   80 gct gtc tca gca gtg gct aat gtc aac gat gtc cat caa gca aca ttt         494
Ala Val Ser Ala Val Ala Asn Val Asn Asp Val His Gln Ala Thr Phe
 85                   90                   95 ctg ctg gct caa acc act ctg aga aat gtc tta ggg aca cag acc ttg         542
Leu Leu Ala Gln Thr Thr Leu Arg Asn Val Leu Gly Thr Gln Thr Leu
100                  105                  110                  115 tcc cag atc tta gct gga cga gaa gag atc gcc cat agc atc cag act         590
Ser Gln Ile Leu Ala Gly Arg Glu Glu Ile Ala His Ser Ile Gln Thr
                 120                  125                  130 tta ctt gat gat gcc acc gaa ctg tgg ggg atc cgg gtg gcc cga gtg         638
Leu Leu Asp Asp Ala Thr Glu Leu Trp Gly Ile Arg Val Ala Arg Val
             135                  140                  145 gaa atc aaa gat gtt cgg att ccc gtg cag ttg cag aga tcc atg gca         686
Glu Ile Lys Asp Val Arg Ile Pro Val Gln Leu Gln Arg Ser Met Ala
             150                  155                  160 gcc gag gct gag gcc acc cgg gaa gcg aga gcc aag gtc ctt gca gct         734
Ala Glu Ala Glu Ala Thr Arg Glu Ala Arg Ala Lys Val Leu Ala Ala
 165                  170                  175 gaa gga gaa atg agt gct tcc aaa tcc ctg aag tca gcc tcc atg gtg         782
Glu Gly Glu Met Ser Ala Ser Lys Ser Leu Lys Ser Ala Ser Met Val
180                  185                  190                  195 ctg gct gag tct ccc ata gct ctc cag ctg cgc tac ctg cag acc ttg         830
Leu Ala Glu Ser Pro Ile Ala Leu Gln Leu Arg Tyr Leu Gln Thr Leu
                 200                  205                  210 agc acg gta gcc acc gag aag aat tct acg att gtg ttt cct ctg ccc         878
Ser Thr Val Ala Thr Glu Lys Asn Ser Thr Ile Val Phe Pro Leu Pro
             215                  220                  225 atg aat ata cta gag ggc att ggt ggc gtc agc tat gat aac cac aag         926
Met Asn Ile Leu Glu Gly Ile Gly Gly Val Ser Tyr Asp Asn His Lys
             230                  235                  240 aag ctt cca aat aaa gcc tgaggtcctc ttgcggtagt cagctaaaaa aaaaaaaa      982
Lys Leu Pro Asn Lys Ala
             245

<210> SEQ ID NO 155
<211> LENGTH: 455
<212> TYPE: DNA
```

```
<213> ORGANISM: Homo sapiens
<220> FEATURE:
<221> NAME/KEY: polyA_signal
<222> LOCATION: 425..430
<221> NAME/KEY: polyA_site
<222> LOCATION: 443..455

<400> SEQUENCE: 155 gtt atg cca ccc aga aac cta ctg gag tta ctt att aac atc aag gct      48
    Met Pro Pro Arg Asn Leu Leu Glu Leu Leu Ile Asn Ile Lys Ala
    1               5                   10                  15 gga acc tat ttg cct cag tcc tat ctg att cat gag cac atg gtt att      96
Gly Thr Tyr Leu Pro Gln Ser Tyr Leu Ile His Glu His Met Val Ile
                20                  25                  30 act gat cgc atc gaa aac att gat cac ctg ggt ttc ttt att tat cga     144
Thr Asp Arg Ile Glu Asn Ile Asp His Leu Gly Phe Phe Ile Tyr Arg
                35                  40                  45 ctg tgt cat gac aag gaa act tac aaa ctg caa cgc aga gaa act att     192
Leu Cys His Asp Lys Glu Thr Tyr Lys Leu Gln Arg Arg Glu Thr Ile
            50                  55                  60 aaa ggt att cag aaa cgt gaa gcc agc aat tgt ttc gca att cgg cat     240
Lys Gly Ile Gln Lys Arg Glu Ala Ser Asn Cys Phe Ala Ile Arg His
65                  70                  75 ttt gaa aac aaa ttt gcc gtg gaa act tta att tgt tct tgaacagtca      289
Phe Glu Asn Lys Phe Ala Val Glu Thr Leu Ile Cys Ser
80                  85                  90 agaaaaacat tattgaggaa aattaatatc acagcataac cccaccttt acattttgtg   349 cagtgattat tttttaaagt cttctttcat gtaagtagca aacagggctt tactatcttt   409
tcatctcatt aattcaatta aaaccattac cccaaaaaaa aaaaaa                  455

<210> SEQ ID NO 156
<211> LENGTH: 738
<212> TYPE: DNA
<213> ORGANISM: Homo sapiens
<220> FEATURE:
<221> NAME/KEY: sig_peptide
<222> LOCATION: 90..278
<223> OTHER INFORMATION: Von Heijne matrix
      score 3.5
      seq GLVCAGLADMARP/AE
<221> NAME/KEY: polyA_signal
<222> LOCATION: 704..709
<221> NAME/KEY: polyA_site
<222> LOCATION: 724..738

<400> SEQUENCE: 156
gggaaaagtg actagctccc cttcgttgtc agccagggac gagaacacag ccacgctccc    60
acccggctgc aacgatccc tcggcggcg atg tcg gcc gcc ggt gcc cga ggc     113
                                Met Ser Ala Ala Gly Ala Arg Gly
                                                -60 ctg cgg gcc acc tac cac cgg ctc ccc gat aaa gtg gag ctg atg ctg    161
Leu Arg Ala Thr Tyr His Arg Leu Pro Asp Lys Val Glu Leu Met Leu
-55                 -50                 -45                 -40 ccc gag aaa ttg agg ccg ttg tac aac cat cca gca ggt ccc aga aca    209
Pro Glu Lys Leu Arg Pro Leu Tyr Asn His Pro Ala Gly Pro Arg Thr
                -35                 -30                 -25 gtt ttc ttc tgg gct cca att atg aaa tgg ggg ttg gtg tgt gct gga    257
Val Phe Phe Trp Ala Pro Ile Met Lys Trp Gly Leu Val Cys Ala Gly
            -20                 -15                 -10 ttg gct gat atg gcc aga cct gca gaa aaa ctt agc aca gct caa tct    305
Leu Ala Asp Met Ala Arg Pro Ala Glu Lys Leu Ser Thr Ala Gln Ser
        -5                   1                   5
```

-continued

```
gct gtt ttg atg gct aca ggg ttt att tgg tca aga tac tca ctt gta       353
Ala Val Leu Met Ala Thr Gly Phe Ile Trp Ser Arg Tyr Ser Leu Val
 10              15                  20                  25 att att ccg aaa aat tgg agt ctg ttt gct gtt aat ttc ttt gtg ggg       401
Ile Ile Pro Lys Asn Trp Ser Leu Phe Ala Val Asn Phe Phe Val Gly
                 30                  35                  40 gca gca gga gcc tct cag ctt ttt cgt att tgg aga tat aac caa gaa       449
Ala Ala Gly Ala Ser Gln Leu Phe Arg Ile Trp Arg Tyr Asn Gln Glu
             45                  50                  55 cta aaa gct aaa gca cac aaa taaaagagtt cctgatcacc tgaacaatct          500
Leu Lys Ala Lys Ala His Lys
             60 agatgtggac aaaaccattg ggacctagtt tattatttgg ttattgataa agcaaagcta     560 actgtgtgtt tagaaggcac tgtaactggt agctagttct tgattcaata gaaaaatgca     620 gcaaactttt aataacagtc tctctacatg acttaaggaa cttatctatg gatattagta    680 acattttct accatttgtc cgtaataaac catacttgct cgtaaaaaaa aaaaaaaa       738

<210> SEQ ID NO 157
<211> LENGTH: 649
<212> TYPE: DNA
<213> ORGANISM: Homo sapiens
<220> FEATURE:
<221> NAME/KEY: sig_peptide
<222> LOCATION: 88..147
<223> OTHER INFORMATION: Von Heijne matrix
      score 12.3999996185303
      seq ALLLGALLGTAWA/RR
<221> NAME/KEY: polyA_signal
<222> LOCATION: 619..624
<221> NAME/KEY: polyA_site
<222> LOCATION: 637..649

<400> SEQUENCE: 157
ccaaagtgag agtccagcgg tcttccagcg cttgggccac ggcggcggcc ctgggagcag     60
aggaggagcg acccccattac gctaaag atg aaa ggc tgg ggt tgg ctg gcc ctg   114
                                 Met Lys Gly Trp Gly Trp Leu Ala Leu
                                 -20                 -15 ctt ctg ggg gcc ctg ctg gga acc gcc tgg gct cgg agg agc cag gat      162
Leu Leu Gly Ala Leu Leu Gly Thr Ala Trp Ala Arg Arg Ser Gln Asp
   -10                  -5                   1                   5 ctc cac tgt gga gca tgc agg gct ctg gtg gat gaa cta gaa tgg gaa      210
Leu His Cys Gly Ala Cys Arg Ala Leu Val Asp Glu Leu Glu Trp Glu
                 10                  15                  20 att gcc cag gtg gac ccc aag aag acc att cag atg gga tcc ttc cgg      258
Ile Ala Gln Val Asp Pro Lys Lys Thr Ile Gln Met Gly Ser Phe Arg
             25                  30                  35 atc aat cca gat ggc agc cag tca gtg gtg gag gta act gtt act gtt      306
Ile Asn Pro Asp Gly Ser Gln Ser Val Val Glu Val Thr Val Thr Val
         40                  45                  50 ccc cca aac aaa gta gct cac tct ggc ttt gga tgaaattcga ctgcttaaaa    359
Pro Pro Asn Lys Val Ala His Ser Gly Phe Gly
     55                  60 aggaccttgg tctaatagaa atgaagaaaa cagactcaga aaaagatttt ggctctgtct    419
catttggaag aagctgcagg cttattcccc atgcacttgc ttcctggctg caaaccttaa    479
tactttgttt ctgctgtaga atttgttagc aaacaggag tcctgatcag cacccttctc    539
cacatccaca tgactggttt ttaatgtagc actgtggtat acatgcaaac atccgttcaa    599
aatctgagtc ggagctaaaa ataaaaaatg aaaaacaaa aaaaaaaaa                  649
```

```
<210> SEQ ID NO 158
<211> LENGTH: 714
<212> TYPE: DNA
<213> ORGANISM: Homo sapiens
<220> FEATURE:
<221> NAME/KEY: sig_peptide
<222> LOCATION: 33..92
<223> OTHER INFORMATION: Von Heijne matrix
      score 12.3999996185303
      seq ALLLGALLGTAWA/RR
<221> NAME/KEY: polyA_site
<222> LOCATION: 703..714

<400> SEQUENCE: 158
```

| | | |
|---|---|---|
| agcagaggtg gagcgacccc attacgctaa ag atg aaa ggc tgg ggt tgg ctg<br>                                                     Met Lys Gly Trp Gly Trp Leu<br>                                                     -20                 -15 | 53 |

```
gcc ctg ctt ctg ggg gcc ctg ctg gga acc gcc tgg gct cgg agg agc      101
Ala Leu Leu Leu Gly Ala Leu Leu Gly Thr Ala Trp Ala Arg Arg Ser
            -10                  -5                   1 cag gat ctc cac tgt gga gca tgc agg gct ctg gtg gat gaa cta gaa      149
Gln Asp Leu His Cys Gly Ala Cys Arg Ala Leu Val Asp Glu Leu Glu
      5                   10                  15 tgg gaa att gcc cag gtg gac ccc aag aag acc att cag atg gga tct      197
Trp Glu Ile Ala Gln Val Asp Pro Lys Lys Thr Ile Gln Met Gly Ser
 20                  25                  30                  35 ttc cgg atc aat cca gat ggc agc cag tca gtg gtg gag gtg cct tat      245
Phe Arg Ile Asn Pro Asp Gly Ser Gln Ser Val Val Glu Val Pro Tyr
                40                  45                  50 gcc cgc tca gag gcc cac ctc aca gag ctg ctg gag gag ata tgt gac      293
Ala Arg Ser Glu Ala His Leu Thr Glu Leu Leu Glu Glu Ile Cys Asp
        55                  60                  65 cgg atg aag gag tat ggg gaa cag att gat cct tcc acc cat cgc aag      341
Arg Met Lys Glu Tyr Gly Glu Gln Ile Asp Pro Ser Thr His Arg Lys
    70                  75                  80 aac tac gta cgt gta gtg ggc cgg aat gga gaa tcc agt gaa ctg gac      389
Asn Tyr Val Arg Val Val Gly Arg Asn Gly Glu Ser Ser Glu Leu Asp
85                  90                  95 cta caa ggc atc cga atc gac tca gat att agc ggc acc ctc aag ttt      437
Leu Gln Gly Ile Arg Ile Asp Ser Asp Ile Ser Gly Thr Leu Lys Phe
100                 105                 110                 115 gcg tgt ggg agc att gtg gag gaa tac gag gat gaa ctc att gaa ttc      485
Ala Cys Gly Ser Ile Val Glu Glu Tyr Glu Asp Glu Leu Ile Glu Phe
                120                 125                 130 ttt tcc cga gag gct gac aat gtt aaa gac aaa ctt tgc agt aag cga      533
Phe Ser Arg Glu Ala Asp Asn Val Lys Asp Lys Leu Cys Ser Lys Arg
            135                 140                 145 aca gat ctt tgt gac cat gcc ctg cac ata tcg cat gat gag cta          578
Thr Asp Leu Cys Asp His Ala Leu His Ile Ser His Asp Glu Leu
        150                 155                 160 tgaaccactg gagcagccca cactggcttg atggatcacc cccaggaggg gaaaatggtg    638
gcaatgcctt ttatatatta tgttttact gaaattaact gaaaaaatat gaaaccaaaa    698
gtacaaaaaa aaaaaa                                                    714

<210> SEQ ID NO 159
<211> LENGTH: 596
<212> TYPE: DNA
<213> ORGANISM: Homo sapiens
<220> FEATURE:
<221> NAME/KEY: sig_peptide
<222> LOCATION: 33..107
<223> OTHER INFORMATION: Von Heijne matrix
      score 5
```

```
        seq MFAASLLAMCAGA/EV
<221> NAME/KEY: polyA_signal
<222> LOCATION: 546..551
<221> NAME/KEY: polyA_site
<222> LOCATION: 584..596

<400> SEQUENCE: 159
cacagttcct ctcctcctag agcctgccga cc atg ccc gcg ggc gtg ccc atg         53
                                   Met Pro Ala Gly Val Pro Met
                                   -25                 -20 tcc acc tac ctg aaa atg ttc gca gcc agt ctc ctg gcc atg tgc gca        101
Ser Thr Tyr Leu Lys Met Phe Ala Ala Ser Leu Leu Ala Met Cys Ala
            -15             -10                  -5 ggg gca gaa gtg gtg cac agg tac tac cga ccg gac ctg aca ata cct        149
Gly Ala Glu Val Val His Arg Tyr Tyr Arg Pro Asp Leu Thr Ile Pro
    1               5                   10 gaa att cca cca aag cgt gga gaa ctc aaa acg gag ctt ttg gga ctg        197
Glu Ile Pro Pro Lys Arg Gly Glu Leu Lys Thr Glu Leu Leu Gly Leu
15              20                  25                  30 aaa gaa aga aaa cac aaa cct caa gtt tct caa cag gag gaa ctt aaa        245
Lys Glu Arg Lys His Lys Pro Gln Val Ser Gln Gln Glu Glu Leu Lys
                35                  40                  45 taactatgcc aagaattctg tgaataatat aagtcttaaa tatgtatttc ttaatttatt      305
gcatcaaact acttgtcctt aagcacttag tctaatgcta actgcaagag gaggtgctca      365
gtggatgttt agccgatacg ttgaaattta attacggttt gattgatatt tcttgaaaac      425
tgccaaagca catatcatca aaccatttca tgaatatggt ttggaagatg tttagtcttg      485
aatataacgc gaaatagaat atttgtaagt ctactatatg ggttgtcttt atttcatata      545
aattaagaaa ttatttaaaa ctatgaacta gtttcattaa aaaaaaaga a                596

<210> SEQ ID NO 160
<211> LENGTH: 403
<212> TYPE: DNA
<213> ORGANISM: Homo sapiens
<220> FEATURE:
<221> NAME/KEY: polyA_signal
<222> LOCATION: 375..380
<221> NAME/KEY: polyA_site
<222> LOCATION: 390..403

<400> SEQUENCE: 160
tgaagagaat ggctgttgca gtcggcgtca gagcagctcc agtgccgggg attcggacgg       60
agagcgcgag gactcggcgg ctgagcgcgc ccgacagcag ctagaggcgc tgctcaacaa      120 gact atg cgc att cgc atg aca gat gga cgg aca ctg gtc ggc tgc ttt      169
     Met Arg Ile Arg Met Thr Asp Gly Arg Thr Leu Val Gly Cys Phe
     1               5                   10                  15 ctc tgc act gac cgt gac tgc aat gtc atc ctg ggc tcg gcg cag gag      217
Leu Cys Thr Asp Arg Asp Cys Asn Val Ile Leu Gly Ser Ala Gln Glu
            20                  25                  30 ttc ctc aag ccg tcg gat tcc ttc tct gcc ggg gag ccc cgt gtg ctg      265
Phe Leu Lys Pro Ser Asp Ser Phe Ser Ala Gly Glu Pro Arg Val Leu
                35                  40                  45 ggc ctg gcc atg gta ccc gga cac cac atc gtt tcc att gag gtg cag      313
Gly Leu Ala Met Val Pro Gly His His Ile Val Ser Ile Glu Val Gln
50                  55                  60 agg gag agt ctg acc ggg cct ccg tat ctc tgaccacgat ggcgcttacc         363
Arg Glu Ser Leu Thr Gly Pro Pro Tyr Leu
    65                  70 tttcagactt cattaaactt atgaccaaaa aaaaaaaaa                            403
```

<210> SEQ ID NO 161
<211> LENGTH: 727
<212> TYPE: DNA
<213> ORGANISM: Homo sapiens
<220> FEATURE:
<221> NAME/KEY: sig_peptide
<222> LOCATION: 126..575
<223> OTHER INFORMATION: Von Heijne matrix
      score 8.60000038146973
      seq LELLTSCSPPASA/SQ
<221> NAME/KEY: polyA_signal
<222> LOCATION: 670..675
<221> NAME/KEY: polyA_site
<222> LOCATION: 721..727
<221> NAME/KEY: misc_feature
<222> LOCATION: 257,376..377
<223> OTHER INFORMATION: n=a, g, c or t

<400> SEQUENCE: 161

```
ctcagaactg tgctgggaag gatggtaggg cgactggggc tcacctccgc accgttgtag      60
gacccggggt agggttttga gcccgtggga gctgccccac gcggcctcgt cctgccaacg     120 gtcgg atg gcg gag acg aag gac aca gcg cag atg ttg gtg acc ttc aag    170
      Met Ala Glu Thr Lys Asp Thr Ala Gln Met Leu Val Thr Phe Lys
         -150            -145                -140 gat gtg gct gtg acc ttt acc cgg gag gag tgg aga cag ctg gac ctg     218
Asp Val Ala Val Thr Phe Thr Arg Glu Glu Trp Arg Gln Leu Asp Leu
-135            -130                -125                -120 gcc cag agg acc ctg tac cga gag ggc atc ggg ttc ccn aaa cca gag     266
Ala Gln Arg Thr Leu Tyr Arg Glu Gly Ile Gly Phe Pro Lys Pro Glu
                -115                -110                -105 ttg gtc cac ctg cta gag cat ggg cag gag ctg tgg ata gtg aag aga     314
Leu Val His Leu Leu Glu His Gly Gln Glu Leu Trp Ile Val Lys Arg
            -100                 -95                 -90 ggc ctc tca cat gct acc tgt gca gag ttt cac tct tgt tgc cca ggc     362
Gly Leu Ser His Ala Thr Cys Ala Glu Phe His Ser Cys Cys Pro Gly
         -85                 -80                 -75 tgg agt gca gtg gnn cgc cat ctc agc tca ctg caa ctt ctg cct ccc     410
Trp Ser Ala Val Xaa Arg His Leu Ser Ser Leu Gln Leu Leu Pro Pro
     -70                 -65                 -60 gag ttc aag gga ttc tcc tgc ctc agc ctc ccg agt agc tgg gat tac     458
Glu Phe Lys Gly Phe Ser Cys Leu Ser Leu Pro Ser Ser Trp Asp Tyr
-55                 -50                 -45                 -40 agg cgc cca cca cca tgc ccg gct ggt ttt ttt gta ttt tta gta gag     506
Arg Arg Pro Pro Pro Cys Pro Ala Gly Phe Phe Val Phe Leu Val Glu
                -35                 -30                 -25 acg ggg ctt cac cat gtt ggc cag gct ggt ctt gaa ctc ttg acc tca     554
Thr Gly Leu His His Val Gly Gln Ala Gly Leu Glu Leu Leu Thr Ser
            -20                 -15                 -10 tgt agt cca ccc gcc tct gcc tcc caa agt gct gcg att aca ggc gtg     602
Cys Ser Pro Pro Ala Ser Ala Ser Gln Ser Ala Ala Ile Thr Gly Val
         -5                   1                   5 agc cac cgt gcc cgg cag aga aaa act gct taaggttgaa aagagaaatt        652
Ser His Arg Ala Arg Gln Arg Lys Thr Ala
 10                  15 taagaaattg ctgacggaat aaaaacataa tagaactaca acaccgaagg aaatgaaaga    712
agcaaaaaaa aaaaa                                                      727
```

<210> SEQ ID NO 162
<211> LENGTH: 944
<212> TYPE: DNA
<213> ORGANISM: Homo sapiens
<220> FEATURE:

```
<221> NAME/KEY: sig_peptide
<222> LOCATION: 90..155
<223> OTHER INFORMATION: Von Heijne matrix
      score 5.90000009536743
      seq IILGCLALFLLLQ/RK
<221> NAME/KEY: polyA_signal
<222> LOCATION: 913..918
<221> NAME/KEY: polyA_site
<222> LOCATION: 932..944

<400> SEQUENCE: 162
```

| | | |
|---|---|---|
| gaatcaggtt ccgtagccca cagaaaagaa gcaagggacg gcaggactgt ttcacacttt | 60 | |
| tctgcttctg gaaggtgctg gacaaaaac atg gaa cta att tcc cca aca gtg<br>           Met Glu Leu Ile Ser Pro Thr Val<br>             -20         -15 | 113 | |
| att ata atc ctg ggt tgc ctt gct ctg ttc tta ctc ctt cag cgg aag<br>Ile Ile Ile Leu Gly Cys Leu Ala Leu Phe Leu Leu Leu Gln Arg Lys<br>    -10        -5           1 | 161 | |
| aat ttg cgt aga ccc ccg tgc atc aag ggc tgg att cct tgg att gga<br>Asn Leu Arg Arg Pro Pro Cys Ile Lys Gly Trp Ile Pro Trp Ile Gly<br>   5         10         15 | 209 | |
| gtt gga ttt gag ttt ggg aaa gcc cct cta gaa ttt ata gag aaa gca<br>Val Gly Phe Glu Phe Gly Lys Ala Pro Leu Glu Phe Ile Glu Lys Ala<br>  20         25        30 | 257 | |
| aga atc aag gta tgt ggt cgt ggc aga cgg ggt ctc cag agg aga caa<br>Arg Ile Lys Val Cys Gly Arg Gly Arg Arg Gly Leu Gln Arg Arg Gln<br>35        40        45        50 | 305 | |
| tgc ttt ctt ttt taaactttct ttcattgact cttaagtgca gggctagaac<br>Cys Phe Leu Phe | 357 | |
| acggggaaca tacctgcttg cctcaactaa aggatctagt catttctgaa ttcctctact | 417 | |
| aacaattaac aacaatatcc tgtgcaaaat tttgcgaaag aaatgaaata caattgcagc | 477 | |
| gtgcatcgac attttttggaa gtagagatta acttttcgta tttttacttc atcgaagtta | 537 | |
| agttccaaat gtgtatgtgt taagtaaatg ttttcagtaa ttgggaaaga taaagtgtaa | 597 | |
| tccaatttaa gtttgtgaaa atgagtaatt cgtatccaaa ttggagttaa caccaaagta | 657 | |
| ttgtacaaat tgcttgcaca gttggtccgt acacaataga caggctctgt atttttagct | 717 | |
| gacgttgtta tttgatgatg atgtactcca ttttcactac ggcccgaaga gactagtaat | 777 | |
| cctccttgta gtagatgttt ttgtcttgaa agtatctttt aaatgtctga gcactttaag | 837 | |
| gaacagaccc ttattaatgt cttttaagtt ttattcaatt tccagtcaca aatattttat | 897 | |
| ggtatttgat tgtctaataa atttgtatga tattaaaaaa aaaaaaa | 944 | |

```
<210> SEQ ID NO 163
<211> LENGTH: 598
<212> TYPE: DNA
<213> ORGANISM: Homo sapiens
<220> FEATURE:
<221> NAME/KEY: sig_peptide
<222> LOCATION: 126..287
<223> OTHER INFORMATION: Von Heijne matrix
      score 3.90000009536743
      seq LETCGLLVSLVES/IW
<221> NAME/KEY: polyA_signal
<222> LOCATION: 561..566
<221> NAME/KEY: polyA_site
<222> LOCATION: 587..598

<400> SEQUENCE: 163
```

| | | |
|---|---|---|
| ctcagaactg tgctgggaag gatggtaggg cgactggggc tcacctccgc accgttgtag | 60 | |
| gacccggggt agggttttga gcccgtggga gctgccccac gcggcctcgt cctgccaacg | 120 | |

-continued

```
gtcgg atg gcg gag acg aag gac gca gcg cag atg ttg gtg acc ttc aag    170
      Met Ala Glu Thr Lys Asp Ala Ala Gln Met Leu Val Thr Phe Lys
              -50                 -45                 -40 gat gtg gct gtg acc ttt acc cgg gag gag tgg aga cag ctg gac ctg       218
Asp Val Ala Val Thr Phe Thr Arg Glu Glu Trp Arg Gln Leu Asp Leu
            -35                 -30                 -25 gcc cag agg acc ctg tac cga gag gtg atg ctg gag acc tgt ggg ctt       266
Ala Gln Arg Thr Leu Tyr Arg Glu Val Met Leu Glu Thr Cys Gly Leu
        -20                 -15                 -10 ctg gtt tca cta gtg gaa agc att tgg ctg cat ata aca gaa aac cag       314
Leu Val Ser Leu Val Glu Ser Ile Trp Leu His Ile Thr Glu Asn Gln
    -5                   1                   5 atc aaa ctg gct tca cct gga agg aaa ttc act aac tcg cct gat gag       362
Ile Lys Leu Ala Ser Pro Gly Arg Lys Phe Thr Asn Ser Pro Asp Glu
10                  15                  20                  25 aag cct gag gtg tgg ttg gct cca ggc ctg ttc ggt gcc gca gcc cag       410
Lys Pro Glu Val Trp Leu Ala Pro Gly Leu Phe Gly Ala Ala Ala Gln
                30                  35                  40 tgacgccatc aaggatgtct tggttctctg ttccttcttc ttggttcagg cttctgattg     470
tcctcaggct ggctcctcat agggatgctg ggtgctgcag ccttgactgg ggcagcaggc     530
ccccatgttc aatccatcct cccaccttgg aataaatgct ttcttttcac aatgagaaaa     590
aaaaaaaa                                                              598

<210> SEQ ID NO 164
<211> LENGTH: 360
<212> TYPE: DNA
<213> ORGANISM: Homo sapiens
<220> FEATURE:
<221> NAME/KEY: sig_peptide
<222> LOCATION: 85..150
<223> OTHER INFORMATION: Von Heijne matrix
      score 5.90000009536743
      seq IILGCLALFLLLQ/RK
<221> NAME/KEY: polyA_site
<222> LOCATION: 349..360

<400> SEQUENCE: 164
caggttccgt agccacagaa aagaagcaag ggacggcagg actgtttcac acttttctgc     60
ttctggaagg tgctggacaa aaac atg gaa cta att tcc cca aca gtg att       111
                            Met Glu Leu Ile Ser Pro Thr Val Ile
                            -20                 -15 ata atc ctg ggt tgc ctt gct ctg ttc tta ctc ctt cag cgg aag aat       159
Ile Ile Leu Gly Cys Leu Ala Leu Phe Leu Leu Leu Gln Arg Lys Asn
        -10                 -5                   1 ttg cgt aga ccc ccg tgc atc aag ggc tgg att cct tgg att gga gtt       207
Leu Arg Arg Pro Pro Cys Ile Lys Gly Trp Ile Pro Trp Ile Gly Val
    5                   10                  15 gga ttt gag ttt ggg aaa gcc cct cta gaa ttt ata gag aaa gca aga       255
Gly Phe Glu Phe Gly Lys Ala Pro Leu Glu Phe Ile Glu Lys Ala Arg
20                  25                  30                  35 atc aag tat gga cca ata ttt aca gtc ttt gct atg gga aac cga atg       303
Ile Lys Tyr Gly Pro Ile Phe Thr Val Phe Ala Met Gly Asn Arg Met
                40                  45                  50 acc ttt gtt act gaa gaa gaa gga att aat gtg ttt cta aaa tcc           348
Thr Phe Val Thr Glu Glu Glu Gly Ile Asn Val Phe Leu Lys Ser
        55                  60                  65 aaaaaaaaaa aa                                                         360

<210> SEQ ID NO 165
<211> LENGTH: 490
```

```
<212> TYPE: DNA
<213> ORGANISM: Homo sapiens
<220> FEATURE:
<221> NAME/KEY: sig_peptide
<222> LOCATION: 77..124
<223> OTHER INFORMATION: Von Heijne matrix
      score 4.80000019073486
      seq SLFIYIFLTCSNT/SP
<221> NAME/KEY: polyA_signal
<222> LOCATION: 461..466
<221> NAME/KEY: polyA_site
<222> LOCATION: 477..490

<400> SEQUENCE: 165
atgagcttcc agccccaaga gtggaggctg ccacatccca acatagtatc tattgaaaag      60
gaagcagtgt gtatct atg att ata tct ctg ttc atc tat ata ttt ttg aca    112
               Met Ile Ile Ser Leu Phe Ile Tyr Ile Phe Leu Thr
                -15             -10                 -5 tgt agc aac acc tct cca tct tat caa gga act caa ctc ggt ctg ggt      160
Cys Ser Asn Thr Ser Pro Ser Tyr Gln Gly Thr Gln Leu Gly Leu Gly
             1               5                  10 ctc ccc agt gcc cag tgg tgg cct ttg aca ggt agg agg atg cag tgc      208
Leu Pro Ser Ala Gln Trp Trp Pro Leu Thr Gly Arg Arg Met Gln Cys
         15                  20                  25 tgc agg cta ttt tgt ttt ttg tta caa aac tgt ctt ttc cct ttt ccc      256
Cys Arg Leu Phe Cys Phe Leu Leu Gln Asn Cys Leu Phe Pro Phe Pro
     30                  35                  40 ctc cac ctg att cag cat gat ccc tgt gag ctg gtt ctc aca atc tcc      304
Leu His Leu Ile Gln His Asp Pro Cys Glu Leu Val Leu Thr Ile Ser
 45                  50                  55                  60 tgg gac tgg gct gag gca ggg gct tcg ctc tat tct ccc taaccatact       353
Trp Asp Trp Ala Glu Ala Gly Ala Ser Leu Tyr Ser Pro
                 65                  70 gtcttccttt cccccttgcc acttagcagt tatcccccca gctatgcctt ctccctccct    413
cccttgccct ggcatatatt gtgccttatt tatgctgcaa ataacatt aaactatcaa     473 gtgaaaaaaa aaaaaaa                                                  490

<210> SEQ ID NO 166
<211> LENGTH: 488
<212> TYPE: DNA
<213> ORGANISM: Homo sapiens
<220> FEATURE:
<221> NAME/KEY: polyA_signal
<222> LOCATION: 458..463
<221> NAME/KEY: polyA_site
<222> LOCATION: 475..488

<400> SEQUENCE: 166
ccgcttccga aaagagacag acaatgcagc catcata atg aag gtg gac aaa gac     55
                                            Met Lys Val Asp Lys Asp
                                             1               5 cgg cag atg gtg gtg ctg gag gaa gaa ttt cgg aac att tcc cca gag     103
Arg Gln Met Val Val Leu Glu Glu Glu Phe Arg Asn Ile Ser Pro Glu
             10                  15                  20 gag ctc aaa atg gag ttg ccg gag aga cag ccc agg ttc gtg gtt tac     151
Glu Leu Lys Met Glu Leu Pro Glu Arg Gln Pro Arg Phe Val Val Tyr
         25                  30                  35 agc tac aag tac gtg cgt gac gat ggc cga gtg tcc tac cct ttg tgt     199
Ser Tyr Lys Tyr Val Arg Asp Asp Gly Arg Val Ser Tyr Pro Leu Cys
     40                  45                  50 ttc atc ttc tcc agc cct gtg ggc tgc aag ccg gaa caa cag atg atg     247
Phe Ile Phe Ser Ser Pro Val Gly Cys Lys Pro Glu Gln Gln Met Met
 55                  60                  65                  70
```

```
tat gca ggg agt aaa aac agg ctg gtg cag aca gca gag ctc aca aag      295
Tyr Ala Gly Ser Lys Asn Arg Leu Val Gln Thr Ala Glu Leu Thr Lys
                75                  80                  85 gtg ttc gaa atc cgc acc act gat gac ctc act gag gcc tgg ctc caa      343
Val Phe Glu Ile Arg Thr Thr Asp Asp Leu Thr Glu Ala Trp Leu Gln
        90                  95                 100 gaa aag ttg tct ttc ttt cgt tgatctctgg gctggggact gaattcctga         394
Glu Lys Leu Ser Phe Phe Arg
            105 tgtctgagtc ctcaaggtga ctggggactt ggaaccccta ggacctgaac aaccaagact    454 ttaaataaat tttaaaatgc aaaaaaaaaa aaaa                                488

<210> SEQ ID NO 167
<211> LENGTH: 771
<212> TYPE: DNA
<213> ORGANISM: Homo sapiens
<220> FEATURE:
<221> NAME/KEY: sig_peptide
<222> LOCATION: 48..356
<223> OTHER INFORMATION: Von Heijne matrix
      score 4.90000009536743
      seq VYAFLGLTAPSGS/KE
<221> NAME/KEY: polyA_signal
<222> LOCATION: 742..747
<221> NAME/KEY: polyA_site
<222> LOCATION: 760..771

<400> SEQUENCE: 167
ccacagccct tttcaggacc caaacaaccg cagccgctgt tcccagg atg gtg atc       56
                                                    Met Val Ile cgt gta tat att gca tct tcc tct ggc tct aca gcg att aag aag aaa     104
Arg Val Tyr Ile Ala Ser Ser Ser Gly Ser Thr Ala Ile Lys Lys Lys
-100                -95                 -90                 -85 caa caa gat gtg ctt ggt ttc cta gaa gcc aac aaa ata gga ttt gaa     152
Gln Gln Asp Val Leu Gly Phe Leu Glu Ala Asn Lys Ile Gly Phe Glu
                -80                 -75                 -70 gaa aaa gat att gca gcc aat gaa gag aat cgg aag tgg atg aga gaa     200
Glu Lys Asp Ile Ala Ala Asn Glu Glu Asn Arg Lys Trp Met Arg Glu
            -65                 -60                 -55 aat gta cct gag aat agt cga cca gcc aca ggt aac ccc ctg cca cct     248
Asn Val Pro Glu Asn Ser Arg Pro Ala Thr Gly Asn Pro Leu Pro Pro
        -50                 -45                 -40 cag att ttc aat gaa agc cag tat cgc ggg gac tat gat gcc ttc ttt     296
Gln Ile Phe Asn Glu Ser Gln Tyr Arg Gly Asp Tyr Asp Ala Phe Phe
    -35                 -30                 -25 gaa gcc aga gaa aat aat gca gtg tat gcc ttc tta ggc ttg aca gcc     344
Glu Ala Arg Glu Asn Asn Ala Val Tyr Ala Phe Leu Gly Leu Thr Ala
-20                 -15                 -10                  -5 cca tct ggt tca aag gaa gca gaa gtg caa gca aag cag caa gca         389
Pro Ser Gly Ser Lys Glu Ala Glu Val Gln Ala Lys Gln Gln Ala
                 1               5                  10 tgaaccttga gcactgtgct ttaagcatcc tgaaaaatga gtctccattg cttttataaa    449
atagcagaat tagctttgct tcaaaagaaa taggcttaat gttgaaataa tagattagtt    509
gggttttcac atgcaaacac tcaaaatgaa tacaaaatta aaatttgaac attatggtga    569
ttatggtgag gagaatggga tattaacata aaattatatt aataagtaga tatcgtagaa    629
atagtgttgt tacctgccaa gccatcctgt atacaccaat gattttacaa agaaaacacc    689
cttccctcct tctgccatta ctatggcaac ctaagtgtat ctgcagctct acattaaaaa    749
ggagaaagag aaaaaaaaaa aa                                             771
```

<210> SEQ ID NO 168
<211> LENGTH: 959
<212> TYPE: DNA
<213> ORGANISM: Homo sapiens
<220> FEATURE:
<221> NAME/KEY: sig_peptide
<222> LOCATION: 69..359
<223> OTHER INFORMATION: Von Heijne matrix
score 4
seq RLPLVVSFIASSS/AN
<221> NAME/KEY: polyA_signal
<222> LOCATION: 927..932
<221> NAME/KEY: polyA_site
<222> LOCATION: 947..959

<400> SEQUENCE: 168

```
cggagagaac caggcagccc agaaacccca ggcgtggaga ttgatcctgc gagagaaggg       60 ggttcatc atg gcg gat gac cta aag cga ttc ttg tat aaa aag tta cca      110
         Met Ala Asp Asp Leu Lys Arg Phe Leu Tyr Lys Lys Leu Pro
             -95             -90                 -85 agt gtt gaa ggg ctc cat gcc att gtt gtg tca gat aga gat gga gta      158
Ser Val Glu Gly Leu His Ala Ile Val Val Ser Asp Arg Asp Gly Val
        -80             -75                 -70 cct gtt att aaa gtg gca aat gac aat gct cca gag cat gct ttg cga      206
Pro Val Ile Lys Val Ala Asn Asp Asn Ala Pro Glu His Ala Leu Arg
    -65             -60                 -55 cct ggt ttc tta tcc act ttt gcc ctt gca aca gac caa gga agc aaa      254
Pro Gly Phe Leu Ser Thr Phe Ala Leu Ala Thr Asp Gln Gly Ser Lys
    -50             -45                 -40 ctt gga ctt tcc aaa aat aaa agt atc atc tgt tac tat aac acc tac      302
Leu Gly Leu Ser Lys Asn Lys Ser Ile Ile Cys Tyr Tyr Asn Thr Tyr
-35             -30                 -25                 -20 cag gtg gtt caa ttt aat cgt tta cct ttg gtg gtg agt ttc ata gcc      350
Gln Val Val Gln Phe Asn Arg Leu Pro Leu Val Val Ser Phe Ile Ala
            -15                 -10                 -5 agc agc agt gcc aat aca gga cta att gtc agc cta gaa aag gaa ctt      398
Ser Ser Ser Ala Asn Thr Gly Leu Ile Val Ser Leu Glu Lys Glu Leu
                1               5                   10 gct cca ttg ttt gaa gaa ctg aga caa gtt gtg gaa gtt tct              440
Ala Pro Leu Phe Glu Glu Leu Arg Gln Val Val Glu Val Ser
    15                  20                  25 taatctgaca gtggtttcag tgtgtacctt atcttcatta taacaacaca atatcaatcc     500
agcaatcttt agactacaat aatactttta tccatgtgct caagaagggg cccctttttc     560
caacttatac taaagagcta gcatatagat gtaatttata gatagatcag ttgctatatt     620
ttctggtgta gggtctttct tatttagtga gatctaggga taccacagaa atggttcagt     680
ctatcacagc tcccatggag ttagtctggt caccagatat ggatgagaga ttctattcag     740
tggatcagaa tcaaactggt acattgatcc acttgagccg ttaagtgctg ccaattgtac     800
aatatgccca ggcttgcaga ataaagccaa ctttttattg tgaataataa taaggacata     860
tttttcttca gattatgttt tatttctttg cattgagtga ggaacataaa atggcttggt     920
aaaagtaata aaatcagtac aatcactaaa aaaaaaaa                            959
```

<210> SEQ ID NO 169
<211> LENGTH: 464
<212> TYPE: DNA
<213> ORGANISM: Homo sapiens
<220> FEATURE:
<221> NAME/KEY: sig_peptide
<222> LOCATION: 33..98

```
<223> OTHER INFORMATION: Von Heijne matrix
      score 9.80000019073486
      seq LVVFCLALQLVPG/SP
<221> NAME/KEY: polyA_signal
<222> LOCATION: 437..442
<221> NAME/KEY: polyA_site
<222> LOCATION: 455..464

<400> SEQUENCE: 169
gccagaactt actcacccat cccactgaca cc atg aag cct gtg ctg cct ctc         53
                                    Met Lys Pro Val Leu Pro Leu
                                        -20 cag ttc ctg gtg gtg ttc tgc cta gca ctg cag ctg gtg cct ggg agt        101
Gln Phe Leu Val Val Phe Cys Leu Ala Leu Gln Leu Val Pro Gly Ser
-15             -10              -5                          1 ccc aag cag cgt gtt ctg aag tat atc ttg gaa cct cca ccc tgc ata        149
Pro Lys Gln Arg Val Leu Lys Tyr Ile Leu Glu Pro Pro Pro Cys Ile
            5                10                  15 tca gca cct gaa aac tgt act cac ctg tgt aca atg cag gaa gat tgc        197
Ser Ala Pro Glu Asn Cys Thr His Leu Cys Thr Met Gln Glu Asp Cys
        20                  25                  30 gag aaa gga ttt cag tgc tgt tcc tcc ttc tgt ggg ata gtc tgt tca        245
Glu Lys Gly Phe Gln Cys Cys Ser Ser Phe Cys Gly Ile Val Cys Ser
    35                  40                  45 tca gaa aca ttt caa aag cgc aac aga atc aaa cac aag ggc tca gaa        293
Ser Glu Thr Phe Gln Lys Arg Asn Arg Ile Lys His Lys Gly Ser Glu
50                  55                  60                  65 gtc atc atg cct gcc aac tgaggcatat ttcctagatc attttgcctc               341
Val Ile Met Pro Ala Asn
                70 tacgatgttt tttcttggtc cacctttagg aagtattga gaagcaagaa actggaggcc       401 caatatctaa cctgcaaatc gtttttgagt ttggcaataa aggctaatct accaaaaaaa      461 aaa                                                                    464

<210> SEQ ID NO 170
<211> LENGTH: 799
<212> TYPE: DNA
<213> ORGANISM: Homo sapiens
<220> FEATURE:
<221> NAME/KEY: sig_peptide
<222> LOCATION: 110..235
<223> OTHER INFORMATION: Von Heijne matrix
      score 5.19999980926514
      seq LLFDLVCHEFCQS/DD
<221> NAME/KEY: polyA_signal
<222> LOCATION: 764..769
<221> NAME/KEY: polyA_site
<222> LOCATION: 787..799

<400> SEQUENCE: 170
ccaaccccag gaagagtctg aagagcagcc agtgtttcgg cttgtgccct gtatacttga       60
agctgccaaa caagtacgtt ctgaaaatcc agaatggctt gatgtttac atg cac att      118
                                                     Met His Ile
                                                             -40 tta caa ctg ctt act aca gtg gat gat gga att caa gca att gta cat        166
Leu Gln Leu Leu Thr Thr Val Asp Asp Gly Ile Gln Ala Ile Val His
            -35                 -30                 -25 tgt cct gac act gga aaa gac att tgg aat cta ctt ttt gac ctg gtc        214
Cys Pro Asp Thr Gly Lys Asp Ile Trp Asn Leu Leu Phe Asp Leu Val
        -20                 -15                 -10 tgc cat gaa ttc tgc cag tct gat gat cca ccc atc att ctt caa gaa        262
Cys His Glu Phe Cys Gln Ser Asp Asp Pro Pro Ile Ile Leu Gln Glu
        -5                   1                   5
```

```
cag aaa aca gtg cta gcc tct gtt ttt tca gtg ttg tct gcc atc tat      310
Gln Lys Thr Val Leu Ala Ser Val Phe Ser Val Leu Ser Ala Ile Tyr
 10              15                  20                  25 gcc tca cag act gag caa gag tat cta aag ata gaa aaa gta gat ctt      358
Ala Ser Gln Thr Glu Gln Glu Tyr Leu Lys Ile Glu Lys Val Asp Leu
             30                  35                  40 cct cta att gac agc ctc att cgg gtc tta caa aat atg gaa cag tgt      406
Pro Leu Ile Asp Ser Leu Ile Arg Val Leu Gln Asn Met Glu Gln Cys
                 45                  50                  55 cag aaa aaa cca gag aac tcg gca gag tct aac aca gag gaa act aaa      454
Gln Lys Lys Pro Glu Asn Ser Ala Glu Ser Asn Thr Glu Glu Thr Lys
             60                  65                  70 agg act gat tta acc caa gat gat ttc cac ttg aaa atc tta aag gat      502
Arg Thr Asp Leu Thr Gln Asp Asp Phe His Leu Lys Ile Leu Lys Asp
 75                  80                  85 att tta tgt gaa ttt ctt tct aat att ttt cag gca tta aca aag gag      550
Ile Leu Cys Glu Phe Leu Ser Asn Ile Phe Gln Ala Leu Thr Lys Glu
 90                  95                 100                 105 acg gtg gct cag gga gta aag gaa ggc cag ttg agc aaa cag aag tgt      598
Thr Val Ala Gln Gly Val Lys Glu Gly Gln Leu Ser Lys Gln Lys Cys
                110                 115                 120 tcc tct gca ttt caa aac ctt ctt cct ttc tat agc cct gtg gtg gaa      646
Ser Ser Ala Phe Gln Asn Leu Leu Pro Phe Tyr Ser Pro Val Val Glu
            125                 130                 135 gat ttt att aaa atc cta cgt gaa gtt gat aag gcg ctt gct gat gac      694
Asp Phe Ile Lys Ile Leu Arg Glu Val Asp Lys Ala Leu Ala Asp Asp
            140                 145                 150 ttg gaa aaa aac ttc cca agt ttg aag gtt cag act taaaacctga           740
Leu Glu Lys Asn Phe Pro Ser Leu Lys Val Gln Thr
            155                 160                 165 attggaatta cttctgtaca agaaataaac tttattttc tcactgaaaa aaaaaaaaa      799

<210> SEQ ID NO 171
<211> LENGTH: 320
<212> TYPE: DNA
<213> ORGANISM: Homo sapiens
<220> FEATURE:
<221> NAME/KEY: polyA_site
<222> LOCATION: 308..320

<400> SEQUENCE: 171
tcatcatcca gagcagccag tgtccgggag gcagaag atg ccc cac tcc aag cct     55
                                        Met Pro His Ser Lys Pro
                                         1               5 ctg gac tgg ggg ctc tct tca gtg gct gaa tgt cca gca gag cta ttt     103
Leu Asp Trp Gly Leu Ser Ser Val Ala Glu Cys Pro Ala Glu Leu Phe
             10                  15                  20 cct tcc aca ggg ggc ctt gca ggg aag ggt cca gga ctt gac atc tta     151
Pro Ser Thr Gly Gly Leu Ala Gly Lys Gly Pro Gly Leu Asp Ile Leu
         25                  30                  35 aga tgc gtc ttg tcc cct tgg gcc agt cat ttc ccc tct ctg agc ctc     199
Arg Cys Val Leu Ser Pro Trp Ala Ser His Phe Pro Ser Leu Ser Leu
 40                  45                  50 ggt gtc ttc aac ctg tgaaatggga tcataatcac tgccttacct ccctcacggt     254
Gly Val Phe Asn Leu
 55 tgttgtgagg actgagtgtg tggaagtttt tcataaactt tggatgctag tgtaaaaaaa     314 aaaaaa                                                               320
```

```
<210> SEQ ID NO 172
<211> LENGTH: 331
<212> TYPE: DNA
<213> ORGANISM: Homo sapiens
<220> FEATURE:
<221> NAME/KEY: sig_peptide
<222> LOCATION: 129..209
<223> OTHER INFORMATION: Von Heijne matrix
      score 4.90000009536743
      seq CLLSYIALGAIHA/KI
<221> NAME/KEY: polyA_site
<222> LOCATION: 318..331

<400> SEQUENCE: 172
atggaaacca gatggggcaa cggggtggtt ctagtgcaga ctgtagctgc agctcctctc      60
cacctctagc ctgctcattt ccagctcaga aattctacta atggcgtttt ttcttcctga     120 aaaaggaa atg aac agg gtc cct gct gat tct cca aat atg tgt cta atc     170
         Met Asn Arg Val Pro Ala Asp Ser Pro Asn Met Cys Leu Ile
             -25             -20                 -15 tgt tta ctg agt tac ata gca ctt gga gcc atc cat gca aaa atc tgt     218
Cys Leu Leu Ser Tyr Ile Ala Leu Gly Ala Ile His Ala Lys Ile Cys
        -10                 -5                  1 agg aga gca ttc cag gaa gag gga aga gca aat gca aag acg ggc gtg     266
Arg Arg Ala Phe Gln Glu Glu Gly Arg Ala Asn Ala Lys Thr Gly Val
  5               10                  15 aga gct tgg tgc ata cag cca tgg gcc aaa taaagtttcc ttggaatagc      316
Arg Ala Trp Cys Ile Gln Pro Trp Ala Lys
 20              25 caaaaaaaaa aaaaa                                                       331

<210> SEQ ID NO 173
<211> LENGTH: 1075
<212> TYPE: DNA
<213> ORGANISM: Homo sapiens
<220> FEATURE:
<221> NAME/KEY: sig_peptide
<222> LOCATION: 78..359
<223> OTHER INFORMATION: Von Heijne matrix
      score 4.19999980926514
      seq IILTAVYFALSIS/LH
<221> NAME/KEY: polyA_signal
<222> LOCATION: 1042..1047
<221> NAME/KEY: polyA_site
<222> LOCATION: 1063..1075

<400> SEQUENCE: 173
gtggtaggga gcagccagga gcggttttct gggaactgtg ggatgtgccc ttggggggcc      60
gagaaaacag aaggaag atg ctc cag acc agt aac tac agc ctg gtg ctc     110
                   Met Leu Gln Thr Ser Asn Tyr Ser Leu Val Leu
                              -90                 -85 tct ctg cag ttc ctg ctg ctg tcc tat gac ctc ttt gtc aat tcc ttc     158
Ser Leu Gln Phe Leu Leu Leu Ser Tyr Asp Leu Phe Val Asn Ser Phe
        -80                 -75                 -70 tca gaa ctg ctc caa aag act cct gtc atc cag ctt gtg ctc ttc atc     206
Ser Glu Leu Leu Gln Lys Thr Pro Val Ile Gln Leu Val Leu Phe Ile
    -65                 -60                 -55 atc cag gat att gca gtc ctc ttc aac atc atc atc ttc ctc atg     254
Ile Gln Asp Ile Ala Val Leu Phe Asn Ile Ile Ile Phe Leu Met
  -50                 -45                 -40 ttc ttc aac acc ttc gtc ttc cag gct ggc ctg gtc aac ctc cta ttc     302
Phe Phe Asn Thr Phe Val Phe Gln Ala Gly Leu Val Asn Leu Leu Phe
-35                 -30                 -25                 -20 cat aag ttc aaa ggg acc atc atc ctg aca gct gtg tac ttt gcc ctc     350
His Lys Phe Lys Gly Thr Ile Ile Leu Thr Ala Val Tyr Phe Ala Leu
```

```
                -15              -10             -5
agc atc tcc ctt cat gtc tgg gtc atg aac tta cgc tgg aaa aac tcc    398
Ser Ile Ser Leu His Val Trp Val Met Asn Leu Arg Trp Lys Asn Ser
         1               5                  10 aac agc ttc ata tgg aca gat gga ctt caa atg ctg ttt gta ttc cag    446
Asn Ser Phe Ile Trp Thr Asp Gly Leu Gln Met Leu Phe Val Phe Gln
     15              20                  25 aga cta gca gca gtg ttg tac tgc tac ttc tat aaa cgg aca gcc gta    494
Arg Leu Ala Ala Val Leu Tyr Cys Tyr Phe Tyr Lys Arg Thr Ala Val
 30              35                  40                  45 aga cta ggc gat cct cac ttc tac cag gac tct ttg tgg ctg cgc aag    542
Arg Leu Gly Asp Pro His Phe Tyr Gln Asp Ser Leu Trp Leu Arg Lys
                 50                  55                  60 gag ttc atg caa gtt cga agg tgacctcttg tcacactgat ggatactttt       593
Glu Phe Met Gln Val Arg Arg
                 65 ccttcctgat agaagccaca tttgctgctt tgcagggaga gttggcccta tgcatgggca  653 aacagctgga ctttccaagg aaggttcaga ctagctgtgt tcagcattca agaaggaaga  713 tccccctct tgcacaatta gagtgtcccc atcggtctcc agtgcggcat cccttccttg   773 ccttctacct ctgttccacc cccttccttc ctctcctctc tgtaccattc attctccctg  833 accggccttt cttgccgagg gttctgtggc tcttacccttt gtgaagcttt tcctttagcc  893 tgggacagaa ggacctcccg gcccccaaag gatctcccag tgaccaaagg atgcgaagag  953 tgatagttac gtgctcctga ctgatcacac cgcagacatt tagattttta tacccaaggc  1013 actttaaaaa aatgttttat aaatagagaa taaattgaat tcttgttcca aaaaaaaaaa  1073 aa                                                                1075

<210> SEQ ID NO 174
<211> LENGTH: 632
<212> TYPE: DNA
<213> ORGANISM: Homo sapiens
<220> FEATURE:
<221> NAME/KEY: sig_peptide
<222> LOCATION: 62..265
<223> OTHER INFORMATION: Von Heijne matrix
      score 4.59999990463257
      seq LPFSLVSMLVTQG/LV
<221> NAME/KEY: polyA_signal
<222> LOCATION: 602..607
<221> NAME/KEY: polyA_site
<222> LOCATION: 621..632

<400> SEQUENCE: 174
cactgggtca aggagtaagc agaggataaa caactggaag gagagcaagc acaaagtcat    60 c atg gct tca gcg tct gct cgt gga aac caa gat aaa gat gcc cat ttt   109
  Met Ala Ser Ala Ser Ala Arg Gly Asn Gln Asp Lys Asp Ala His Phe
              -65                 -60                 -55 cca cca cca agc aag cag agc ctg ttg ttt tgt cca aaa tca aaa ctg     157
Pro Pro Pro Ser Lys Gln Ser Leu Leu Phe Cys Pro Lys Ser Lys Leu
         -50                 -45                 -40 cac atc cac aga gca gag atc tca aag att atg cga gaa tgt cag gaa     205
His Ile His Arg Ala Glu Ile Ser Lys Ile Met Arg Glu Cys Gln Glu
     -35                 -30                 -25 gaa agt ttc tgg aag aga gct ctg cct ttt tct ctt gta agc atg ctt     253
Glu Ser Phe Trp Lys Arg Ala Leu Pro Phe Ser Leu Val Ser Met Leu
-20              -15                 -10                 -5 gtc acc cag gga cta gtc tac caa ggt tat ttg gca gct aat tct aga     301
Val Thr Gln Gly Leu Val Tyr Gln Gly Tyr Leu Ala Ala Asn Ser Arg
             1               5                  10
```

```
ttt gga tca ttg ccc aaa gtt gca ctt gct ggt ctc ttg gga ttt ggc      349
Phe Gly Ser Leu Pro Lys Val Ala Leu Ala Gly Leu Leu Gly Phe Gly
            15                  20                  25 ctt gga aag gta tca tac ata gga gta tgc cag agt aaa ttc cat ttt      397
Leu Gly Lys Val Ser Tyr Ile Gly Val Cys Gln Ser Lys Phe His Phe
        30                  35                  40 ttt gaa gat cag ctc cgt ggg gct ggt ttt ggt cca cag cat aac agg      445
Phe Glu Asp Gln Leu Arg Gly Ala Gly Phe Gly Pro Gln His Asn Arg
45                  50                  55                  60 cac tgc ctc ctt acc tgt gag gaa tgc aaa ata aag cat gga tta agt      493
His Cys Leu Leu Thr Cys Glu Glu Cys Lys Ile Lys His Gly Leu Ser
                65                  70                  75 gag aag gga gac tct cag cct tca gct tcc taaattctgt gtctgtgact        543
Glu Lys Gly Asp Ser Gln Pro Ser Ala Ser
                80                  85 ttcgaagttt tttaaacctc tgaatttgta cacatttaaa atttcaagtg tactttaaaa    603
taaaatactt ctaatgtaaa aaaaaaaaa                                      632

<210> SEQ ID NO 175
<211> LENGTH: 430
<212> TYPE: DNA
<213> ORGANISM: Homo sapiens
<220> FEATURE:
<221> NAME/KEY: polyA_signal
<222> LOCATION: 402..407
<221> NAME/KEY: polyA_site
<222> LOCATION: 419..430

<400> SEQUENCE: 175
gtattgggaa agtgatttgt gaa atg aaa gta gaa gaa gag cat acc aat gca    53
                         Met Lys Val Glu Glu Glu His Thr Asn Ala
                           1               5                  10 ata ggc act ctc cac ggc ggt ttg aca gcc acg tta gta gat aac ata      101
Ile Gly Thr Leu His Gly Gly Leu Thr Ala Thr Leu Val Asp Asn Ile
                15                  20                  25 tca aca atg gct ctg cta tgc acg gaa agg gga gca ccc gga gtc agt      149
Ser Thr Met Ala Leu Leu Cys Thr Glu Arg Gly Ala Pro Gly Val Ser
        30                  35                  40 gtc gat atg aac ata acg tac atg tca cct gca aaa tta gga gag gat      197
Val Asp Met Asn Ile Thr Tyr Met Ser Pro Ala Lys Leu Gly Glu Asp
    45                  50                  55 ata gtg att aca gca cat gtt ctg aag caa gga aaa aca ctt gca ttt      245
Ile Val Ile Thr Ala His Val Leu Lys Gln Gly Lys Thr Leu Ala Phe
60                  65                  70 acc tct gtg ggt ctg acc aac aag gcc aca gga aaa tta ata gca caa      293
Thr Ser Val Gly Leu Thr Asn Lys Ala Thr Gly Lys Leu Ile Ala Gln
75                  80                  85                  90 gga aga cac aca aaa cac ctg gga aac tgagagaaca gcagaatgac            340
Gly Arg His Thr Lys His Leu Gly Asn
                95 ctaaagaaac ccaacaatga atatcaagta tagatttgac tcaaacaatt gtaatttttg    400 aaataaacta gcaaaaccaa aaaaaaaaaa                                     430

<210> SEQ ID NO 176
<211> LENGTH: 185
<212> TYPE: DNA
<213> ORGANISM: Homo sapiens
<220> FEATURE:
<221> NAME/KEY: sig_peptide
<222> LOCATION: 42..113
<223> OTHER INFORMATION: Von Heijne matrix
```

```
        score 3.70000004768372
        seq ILFNLLIFLCGFT/NY
<221> NAME/KEY: polyA_site
<222> LOCATION: 172..185

<400> SEQUENCE: 176
ctttcagaac tcactgccaa gagccctgaa caggagccac c atg cag tgc ttc agc      56
                                              Met Gln Cys Phe Ser
                                                              -20 ttc att aag acc atg atg atc ctc ttc aat ttg ctc atc ttt ctg tgt      104
Phe Ile Lys Thr Met Met Ile Leu Phe Asn Leu Leu Ile Phe Leu Cys
                -15                 -10                  -5 ggc ttc acc aac tat acg gat ttt gag gac tca ccc tac ttc aaa atg      152
Gly Phe Thr Asn Tyr Thr Asp Phe Glu Asp Ser Pro Tyr Phe Lys Met
             1               5                  10 cat aaa cct gtt aca atg taaaaaaaaa aaaaa                              185
His Lys Pro Val Thr Met
     15

<210> SEQ ID NO 177
<211> LENGTH: 585
<212> TYPE: DNA
<213> ORGANISM: Homo sapiens
<220> FEATURE:
<221> NAME/KEY: sig_peptide
<222> LOCATION: 108..170
<223> OTHER INFORMATION: Von Heijne matrix
        score 5.5
        seq SFLPSALVIWTSA/AF
<221> NAME/KEY: polyA_signal
<222> LOCATION: 550..555
<221> NAME/KEY: polyA_site
<222> LOCATION: 574..585

<400> SEQUENCE: 177
cacgttcctg ttgagtacac gttcctgttg atttacaaaa ggtgcaggta tgagcaggtc      60
tgaagactaa cattttgtga agttgtaaaa cagaaaacct gttagaa atg tgg tgg      116
                                                    Met Trp Trp
                                                              -20 ttt cag caa ggc ctc agt ttc ctt cct tca gcc ctt gta att tgg aca      164
Phe Gln Gln Gly Leu Ser Phe Leu Pro Ser Ala Leu Val Ile Trp Thr
                -15                 -10                  -5 tct gct gct ttc ata ttt tca tac att act gca gta aca ctc cac cat      212
Ser Ala Ala Phe Ile Phe Ser Tyr Ile Thr Ala Val Thr Leu His His
         1               5                  10 ata gac ccg gct tta cct tat atc agt gac act ggt aca gta gct cca      260
Ile Asp Pro Ala Leu Pro Tyr Ile Ser Asp Thr Gly Thr Val Ala Pro
 15              20                  25                  30 gaa aaa tgc tta ttt ggg gca atg cta aat att gcg gca gtc tta tgt      308
Glu Lys Cys Leu Phe Gly Ala Met Leu Asn Ile Ala Ala Val Leu Cys
                 35                  40                  45 caa aaa tagaaatcag gaagataatt caacttaaag aagttcattt catgaccaaa      364
Gln Lys ctcttcagaa acatgtcttt acaagcatat ctcttgtatt gctttctaca ctgttgaatt      424
gtctggcaat atttctgcag tggaaaattt gatttagcta gttcttgact gataaatatg      484
gtaaggtggg cttttccccc tgtgtaattg gctactatgt cttactgagc caagttgtaa      544
tttgaaataa aatgatatga gagtgacaca aaaaaaaaa a                           585

<210> SEQ ID NO 178
<211> LENGTH: 613
<212> TYPE: DNA
<213> ORGANISM: Homo sapiens
```

```
<220> FEATURE:
<221> NAME/KEY: sig_peptide
<222> LOCATION: 118..171
<223> OTHER INFORMATION: Von Heijne matrix
      score 5.90000009536743
      seq ALALLWSLPASDL/GR
<221> NAME/KEY: polyA_signal
<222> LOCATION: 583..588
<221> NAME/KEY: polyA_site
<222> LOCATION: 602..613

<400> SEQUENCE: 178
ggggtgggtg gactagaagc atttgggagt agtggccagg ggccctggac gctagccacg      60
gagctgccgc acagagcctg gtgtccacaa gcttccaggt tggggttgga gcctggg       117 atg agc ccc ggc agc gcc ttg gcc ctt ctg tgg tcc ctg cca gcc tct      165
Met Ser Pro Gly Ser Ala Leu Ala Leu Leu Trp Ser Leu Pro Ala Ser
        -15                 -10                 -5 gac ctg ggc cgg tca gtc att gct gga ctc tgg cca cac act ggc gtt      213
Asp Leu Gly Arg Ser Val Ile Ala Gly Leu Trp Pro His Thr Gly Val
  1               5                  10 ctc atc cac ttg gaa aca agc cag tct ttt ctg caa ggt cag ttg acc      261
Leu Ile His Leu Glu Thr Ser Gln Ser Phe Leu Gln Gly Gln Leu Thr
 15                 20                  25                  30 aag agc ata ttt ccc ctc tgt tgt aca tcg ttg ttt tgt gtt tgt gtt      309
Lys Ser Ile Phe Pro Leu Cys Cys Thr Ser Leu Phe Cys Val Cys Val
                35                  40                  45 gta aca gtg ggt gga ggg agg gtg ggg tct aca ttt gtt gca              351
Val Thr Val Gly Gly Gly Arg Val Gly Ser Thr Phe Val Ala
             50                  55                  60 tgagtcgatg ggtcagaact ttagtatacg catgcgtcct ctgagtgaca gggcattttg    411
tcgaaaataa gcaccttggt aactaaaccc ctctaatagc tataaaggct ttagttctgt    471
attgattaag ttactgtaaa gcttgggtt tatttttgta ggacttaatg gctaagaatt     531
agaacatagc aagggggctc ctctgttgga gtaatgtaaa ttgtaattat aaataaacat    591
gcaaaccttt aaaaaaaaaa aa                                            613

<210> SEQ ID NO 179
<211> LENGTH: 427
<212> TYPE: DNA
<213> ORGANISM: Homo sapiens
<220> FEATURE:
<221> NAME/KEY: sig_peptide
<222> LOCATION: 128..268
<223> OTHER INFORMATION: Von Heijne matrix
      score 5.5
      seq SALLFFARPCVFC/FK
<221> NAME/KEY: polyA_signal
<222> LOCATION: 410..415
<221> NAME/KEY: polyA_site
<222> LOCATION: 424..427

<400> SEQUENCE: 179
agcttggatt tacactgggc aacgtggttg gaatgtatct ggctcagaac tatgatatac      60
caaacctggc taaaaaactt gaagaaatta aaaaggactt ggatgccaag aagaaacccc    120 ctagtgc atg aga ctg cct cca gca ctg cct tca gga tat act gat tct     169
        Met Arg Leu Pro Pro Ala Leu Pro Ser Gly Tyr Thr Asp Ser
            -45                 -40                 -35 act gct ctt gag ggc ctc gtt tac tat ctg aac caa aag ctt ttg ttt      217
Thr Ala Leu Glu Gly Leu Val Tyr Tyr Leu Asn Gln Lys Leu Leu Phe
            -30                 -25                 -20 tcg tct cca gcc tca gca ctt ctc ttc ttt gct aga ccc tgt gtt ttt      265
Ser Ser Pro Ala Ser Ala Leu Leu Phe Phe Ala Arg Pro Cys Val Phe
```

|  |  |
|---|---:|
| tgc ttt aaa gca agc aaa atg ggg ccc caa ttt gag aac tac cca aca<br>Cys Phe Lys Ala Ser Lys Met Gly Pro Gln Phe Glu Asn Tyr Pro Thr<br>1                       5                      10                 15 | 313 |
| ttt cca aca tac tca cct ctt ccc ata atc cct ttc caa ctg cat ggg<br>Phe Pro Thr Tyr Ser Pro Leu Pro Ile Ile Pro Phe Gln Leu His Gly<br>                   20                      25                     30 | 361 |
| agg ttc taagactgga attatggtgc tagattagta aacatgactt ttaatgaaaa<br>Arg Phe | 417 |
| aaaaacaaaa | 427 |

<210> SEQ ID NO 180
<211> LENGTH: 905
<212> TYPE: DNA
<213> ORGANISM: Homo sapiens
<220> FEATURE:
<221> NAME/KEY: sig_peptide
<222> LOCATION: 149..457
<223> OTHER INFORMATION: Von Heijne matrix
score 4.90000009536743
seq FLLAQTTLRNVLG/TQ
<221> NAME/KEY: polyA_site
<222> LOCATION: 893..912

<400> SEQUENCE: 180

|  |  |
|---|---:|
| gctgcctgtt cttcacactt agctccaaac ccatgaaaaa ttgccaagta taaaagcttc | 60 |
| tcaagaatga gatggattct agggtgtctt cacctgagaa gcaagataaa gagaatttcg | 120 |
| tgggtgtcaa caataaacgg cttggtgt atg tgg ctg gat cct gtt ttc cct<br>                                       Met Trp Leu Asp Pro Val Phe Pro<br>                                                  -100 | 172 |
| ctc ttt cct gtt ggt gat cat tac ctt ccc cat ctc cat atg gat gtg<br>Leu Phe Pro Val Gly Asp His Tyr Leu Pro His Leu His Met Asp Val<br>-95                 -90                     -85                     -80 | 220 |
| ctt gaa ggt ttg atc ctg gtc ctg cca tgc ata gat gtg ttt gtc aaa<br>Leu Glu Gly Leu Ile Leu Val Leu Pro Cys Ile Asp Val Phe Val Lys<br>                 -75                     -70                     -65 | 268 |
| gtt gac ctc cga aca gtt act tgc aac att cct cca caa gag atc ctc<br>Val Asp Leu Arg Thr Val Thr Cys Asn Ile Pro Pro Gln Glu Ile Leu<br>                 -60                     -55                     -50 | 316 |
| acc aga gac tcc gta act act cag gta gat gga gtt gtc tat tac aga<br>Thr Arg Asp Ser Val Thr Thr Gln Val Asp Gly Val Val Tyr Tyr Arg<br>       -45                     -40                     -35 | 364 |
| atc tat agt gct gtc tca gca gtg gct aat gtc aac gat gtc cat caa<br>Ile Tyr Ser Ala Val Ser Ala Val Ala Asn Val Asn Asp Val His Gln<br>       -30                     -25                     -20 | 412 |
| gca aca ttt ctg ctg gct caa acc act ctg aga aat gtc tta ggg aca<br>Ala Thr Phe Leu Leu Ala Gln Thr Thr Leu Arg Asn Val Leu Gly Thr<br>-15                 -10                     -5                      1 | 460 |
| cag acc ttg tcc cag atc tta gct gga cga gaa gag atc gcc cat agc<br>Gln Thr Leu Ser Gln Ile Leu Ala Gly Arg Glu Glu Ile Ala His Ser<br>                   5                      10                     15 | 508 |
| atc cag act tta ctt gat gat gcc acc gaa ctg tgg ggg atc cgg gtg<br>Ile Gln Thr Leu Leu Asp Asp Ala Thr Glu Leu Trp Gly Ile Arg Val<br>             20                     25                     30 | 556 |
| gcc cga gtg gaa atc aaa gat gtt cgg att ccc gtg cag ttg cag aga<br>Ala Arg Val Glu Ile Lys Asp Val Arg Ile Pro Val Gln Leu Gln Arg<br>             35                     40                     45 | 604 |
| tcc atg gca gcc gag gct gag gcc acc cgg gaa gcg aga gcc aag gtc<br>Ser Met Ala Ala Glu Ala Glu Ala Thr Arg Glu Ala Arg Ala Lys Val<br>50                       55                      60                     65 | 652 |

-continued

| | |
|---|---|
| ctt gca gct gaa gga gaa atg aat gct tcc aaa tcc ctg aag tca gcc<br>Leu Ala Ala Glu Gly Glu Met Asn Ala Ser Lys Ser Leu Lys Ser Ala<br>              70                      75                      80 | 700 |
| tcc atg gtg ctg gct gag tct ccc ata gct ctc cag ctg cgc tac ctg<br>Ser Met Val Leu Ala Glu Ser Pro Ile Ala Leu Gln Leu Arg Tyr Leu<br>        85                      90                      95 | 748 |
| cag acc ttg agc acg gta gcc acc gag aag aat tct acg att gtg ttt<br>Gln Thr Leu Ser Thr Val Ala Thr Glu Lys Asn Ser Thr Ile Val Phe<br>            100                   105               110 | 796 |
| cct ctg ccc atg aat ata cta gag ggc att ggt ggc gtc agc tat gat<br>Pro Leu Pro Met Asn Ile Leu Glu Gly Ile Gly Gly Val Ser Tyr Asp<br>115                    120                   125 | 844 |
| aac cac aag aag ctt cca aat aaa gcc tgaggtcctc ttgcggtagt<br>Asn His Lys Lys Leu Pro Asn Lys Ala<br>130                    135 | 891 |
| caaaaaaaaa aaaa | 905 |

<210> SEQ ID NO 181
<211> LENGTH: 307
<212> TYPE: PRT
<213> ORGANISM: Homo sapiens
<220> FEATURE:
<221> NAME/KEY: SIGNAL
<222> LOCATION: -13..-1

<400> SEQUENCE: 181

Met Leu Ala Val Ser Leu Thr Val Pro Leu Leu Gly Ala Met Met Leu
            -10                   -5                    1

Leu Glu Ser Pro Ile Asp Pro Gln Pro Leu Ser Phe Lys Glu Pro Pro
    5                   10               15

Leu Leu Leu Gly Val Leu His Pro Asn Thr Lys Leu Arg Gln Ala Glu
20                 25                 30                 35

Arg Leu Phe Glu Asn Gln Leu Val Gly Pro Glu Ser Ile Ala His Ile
            40                   45                 50

Gly Asp Val Met Phe Thr Gly Thr Ala Asp Gly Arg Val Val Lys Leu
              55                  60                 65

Glu Asn Gly Glu Ile Glu Thr Ile Ala Arg Phe Gly Ser Gly Pro Cys
            70                   75                 80

Lys Thr Arg Gly Asp Glu Pro Val Cys Gly Arg Pro Leu Gly Ile Arg
85                 90                 95

Ala Gly Pro Asn Gly Thr Leu Phe Val Ala Asp Ala Tyr Lys Gly Leu
100                 105               110             115

Phe Glu Val Asn Pro Trp Lys Arg Glu Val Lys Leu Leu Leu Ser Ser
            120                 125              130

Glu Thr Pro Ile Glu Gly Lys Asn Met Ser Phe Val Asn Asp Leu Thr
              135               140             145

Val Thr Gln Asp Gly Arg Lys Ile Tyr Phe Thr Asp Ser Ser Ser Lys
            150                 155             160

Trp Gln Arg Arg Asp Tyr Leu Leu Leu Val Met Glu Gly Thr Asp Asp
        165                 170               175

Gly Arg Leu Leu Glu Tyr Asp Thr Val Thr Arg Glu Val Lys Val Leu
180                 185               190             195

Leu Asp Gln Leu Arg Phe Pro Asn Gly Val Gln Leu Ser Pro Ala Glu
            200                 205             210

Asp Phe Val Leu Val Ala Glu Thr Thr Met Ala Arg Ile Arg Arg Val
            215                 220             225

Tyr Val Ser Gly Leu Met Lys Gly Gly Ala Asp Leu Phe Val Glu Asn

-continued

```
                230                 235                 240
Met Pro Gly Phe Pro Asp Asn Ile Arg Pro Ser Ser Ser Gly Gly Tyr
            245                 250                 255

Trp Val Gly Met Ser Thr Ile Arg Pro Asn Pro Gly Phe Ser Met Leu
260                 265                 270                 275

Asp Phe Leu Ser Glu Arg Pro Trp Ile Lys Arg Met Ile Phe Lys Val
                280                 285                 290

Lys Lys Lys

<210> SEQ ID NO 182
<211> LENGTH: 59
<212> TYPE: PRT
<213> ORGANISM: Homo sapiens

<400> SEQUENCE: 182

Met Met Tyr Val Ser Ile Glu Met Ser Gly Pro Thr Ile Ser His Leu
1               5                   10                  15

Phe Asp Tyr Val Val Cys Tyr Ile Tyr Gly Leu Lys Ser Phe Ser Leu
                20                  25                  30

Lys Gln Leu Lys Lys Lys Ser Trp Ser Lys Tyr Leu Phe Glu Ser Cys
            35                  40                  45

Cys Tyr Arg Ser Leu Tyr Val Cys Val Phe Ile
        50                  55

<210> SEQ ID NO 183
<211> LENGTH: 97
<212> TYPE: PRT
<213> ORGANISM: Homo sapiens
<220> FEATURE:
<221> NAME/KEY: SIGNAL
<222> LOCATION: -28...-1

<400> SEQUENCE: 183

Met Ser Pro Ala Phe Arg Ala Met Asp Val Glu Pro Arg Ala Lys Gly
                -25                 -20                 -15

Val Leu Leu Glu Pro Phe Val His Gln Val Gly Gly His Ser Cys Val
            -10                 -5                  1

Leu Arg Phe Asn Glu Thr Thr Leu Cys Lys Pro Leu Val Pro Arg Glu
5                   10                  15                  20

His Gln Phe Tyr Glu Thr Leu Pro Ala Glu Met Arg Lys Phe Ser Pro
                25                  30                  35

Gln Tyr Lys Gly Gln Ser Gln Arg Pro Leu Val Ser Trp Pro Ser Leu
            40                  45                  50

Pro His Phe Phe Pro Trp Ser Phe Pro Leu Trp Pro Gln Gly Ser Val
        55                  60                  65

Ala

<210> SEQ ID NO 184
<211> LENGTH: 52
<212> TYPE: PRT
<213> ORGANISM: Homo sapiens
<220> FEATURE:
<221> NAME/KEY: SIGNAL
<222> LOCATION: -32...-1

<400> SEQUENCE: 184

Met Leu Gly Thr Thr Gly Leu Gly Thr Gln Gly Pro Ser Gln Gln Ala
        -30                 -25                 -20

Leu Gly Phe Phe Ser Phe Met Leu Leu Gly Met Gly Gly Cys Leu Pro
```

```
              -15              -10              -5
Gly Phe Leu Leu Gln Pro Pro Asn Arg Ser Pro Thr Leu Pro Ala Ser
1                5               10              15

Thr Phe Ala His
            20
```

<210> SEQ ID NO 185
<211> LENGTH: 124
<212> TYPE: PRT
<213> ORGANISM: Homo sapiens
<220> FEATURE:
<221> NAME/KEY: SIGNAL
<222> LOCATION: -97..-1

<400> SEQUENCE: 185

```
Met Ala Asp Asp Leu Lys Arg Phe Leu Tyr Lys Lys Leu Pro Ser Val
        -95              -90             -85

Glu Gly Leu His Ala Ile Val Val Ser Asp Arg Asp Gly Val Pro Val
    -80              -75             -70

Val Lys Val Ala Asn Asp Asn Ala Pro Glu His Ala Leu Arg Pro Gly
-65              -60             -55                     -50

Phe Leu Ser Thr Phe Ala Leu Ala Thr Asp Gln Gly Ser Lys Leu Gly
            -45             -40                     -35

Leu Ser Lys Asn Lys Ser Ile Ile Cys Tyr Tyr Asn Thr Tyr Gln Val
            -30             -25             -20

Val Gln Phe Asn Arg Leu Pro Leu Val Val Ser Phe Ile Ala Ser Ser
        -15              -10              -5

Ser Ala Asn Thr Gly Leu Ile Val Ser Leu Glu Lys Glu Leu Ala Pro
1                5               10              15

Leu Phe Glu Glu Leu Arg Gln Val Val Glu Val Ser
                20              25
```

<210> SEQ ID NO 186
<211> LENGTH: 230
<212> TYPE: PRT
<213> ORGANISM: Homo sapiens
<220> FEATURE:
<221> NAME/KEY: SIGNAL
<222> LOCATION: -24..-1

<400> SEQUENCE: 186

```
Met Ala Ser Leu Gly Leu Gln Leu Val Gly Tyr Ile Leu Gly Leu Leu
            -20              -15             -10

Gly Leu Leu Gly Thr Leu Val Ala Met Leu Leu Pro Ser Trp Lys Thr
         -5              1                5

Ser Ser Tyr Val Gly Ala Ser Ile Val Thr Ala Val Gly Phe Ser Lys
        10              15              20

Gly Leu Trp Met Glu Cys Ala Thr His Ser Thr Gly Ile Thr Gln Cys
25              30              35                      40

Asp Ile Tyr Ser Thr Leu Leu Gly Leu Pro Ala Asp Ile Gln Ala Ala
            45              50                      55

Gln Ala Met Met Val Thr Ser Ser Ala Ile Ser Ser Leu Ala Cys Ile
            60              65                      70

Ile Ser Val Val Gly Met Arg Cys Thr Val Phe Cys Gln Glu Ser Arg
        75              80              85

Ala Lys Asp Arg Val Ala Val Ala Gly Gly Val Phe Phe Ile Leu Gly
        90              95              100

Gly Leu Leu Gly Phe Ile Pro Val Ala Trp Asn Leu His Gly Ile Leu
```

```
                    105                 110                 115                 120
Arg Asp Phe Tyr Ser Pro Leu Val Pro Asp Ser Met Lys Phe Glu Ile
                125                 130                 135

Gly Glu Ala Leu Tyr Leu Gly Ile Ile Ser Ser Leu Phe Ser Leu Ile
            140                 145                 150

Ala Gly Ile Ile Leu Cys Phe Ser Cys Ser Ser Gln Arg Asn Arg Ser
            155                 160                 165

Asn Tyr Tyr Asp Ala Tyr Gln Ala Gln Pro Leu Ala Thr Arg Ser Ser
        170                 175                 180

Pro Arg Pro Gly Gln Pro Lys Val Lys Ser Glu Phe Asn Ser Tyr
185                 190                 195                 200

Ser Leu Thr Gly Tyr Val
                205

<210> SEQ ID NO 187
<211> LENGTH: 72
<212> TYPE: PRT
<213> ORGANISM: Homo sapiens
<220> FEATURE:
<221> NAME/KEY: SIGNAL
<222> LOCATION: -32..-1

<400> SEQUENCE: 187

Met Phe Ala Leu Ala Val Met Arg Ala Phe Arg Lys Asn Lys Thr Leu
        -30                 -25                 -20

Gly Tyr Gly Val Pro Met Leu Leu Ile Ala Gly Gly Ser Phe Gly
    -15                 -10                 -5

Leu Arg Glu Phe Ser Gln Ile Arg Tyr Asp Ala Val Lys Ser Lys Met
1               5                   10                  15

Asp Pro Glu Leu Glu Lys Lys Pro Lys Glu Asn Lys Ile Ser Leu Glu
            20                  25                  30

Ser Glu Tyr Glu Gly Ser Ile Cys
            35                  40

<210> SEQ ID NO 188
<211> LENGTH: 88
<212> TYPE: PRT
<213> ORGANISM: Homo sapiens
<220> FEATURE:
<221> NAME/KEY: SIGNAL
<222> LOCATION: -33..-1

<400> SEQUENCE: 188

Met Ser Gln Thr Ala Trp Leu Ser Leu Leu Ser Ser Ser Pro Phe Gly
            -30                 -25                 -20

Pro Phe Ser Ala Leu Thr Phe Leu Phe Leu His Leu Pro Pro Ser Thr
        -15                 -10                 -5

Ser Leu Phe Ile Asn Leu Ala Arg Gly Gln Ile Lys Gly Pro Leu Gly
1               5                   10                  15

Leu Ile Leu Leu Leu Ser Phe Cys Gly Gly Tyr Thr Lys Cys Asp Phe
                20                  25                  30

Ala Leu Ser Tyr Leu Glu Ile Pro Asn Arg Ile Glu Phe Ser Ile Met
            35                  40                  45

Asp Pro Lys Arg Lys Thr Lys Cys
            50                  55

<210> SEQ ID NO 189
<211> LENGTH: 106
<212> TYPE: PRT
```

```
<213> ORGANISM: Homo sapiens
<220> FEATURE:
<221> NAME/KEY: SIGNAL
<222> LOCATION: -32..-1

<400> SEQUENCE: 189

Met Phe Ala Pro Ala Val Thr Arg Ala Phe Arg Lys Asn Lys Thr Leu
    -30                 -25                 -20

Gly Tyr Gly Val Pro Met Leu Leu Leu Ile Val Gly Gly Ser Phe Gly
    -15                 -10                  -5

Leu Arg Glu Phe Ser Gln Ile Arg Tyr Asp Ala Val Lys Ser Lys Met
  1               5                  10                  15

Asp Pro Glu Leu Glu Lys Lys Leu Lys Glu Asn Lys Ile Ser Leu Glu
                 20                  25                  30

Ser Glu Tyr Glu Lys Ile Lys Asp Ser Lys Phe Asp Asp Trp Lys Asn
                 35                  40                  45

Ile Arg Gly Pro Arg Pro Trp Glu Asp Pro Asp Leu Leu Gln Gly Arg
     50                  55                  60

Asn Pro Glu Ser Leu Lys Thr Lys Thr Thr
 65                  70

<210> SEQ ID NO 190
<211> LENGTH: 267
<212> TYPE: PRT
<213> ORGANISM: Homo sapiens
<220> FEATURE:
<221> NAME/KEY: SIGNAL
<222> LOCATION: -21..-1

<400> SEQUENCE: 190

Met Trp Trp Phe Gln Gln Gly Leu Ser Phe Leu Pro Ser Ala Leu Val
    -20                 -15                 -10

Ile Trp Thr Ser Ala Ala Phe Ile Phe Ser Tyr Ile Thr Ala Val Thr
 -5                   1                   5                  10

Leu His His Ile Asp Pro Ala Leu Pro Tyr Ile Ser Asp Thr Gly Thr
                 15                  20                  25

Val Ala Pro Glu Lys Cys Leu Phe Gly Ala Met Leu Asn Ile Ala Ala
                 30                  35                  40

Val Leu Cys Ile Ala Thr Ile Tyr Val Arg Tyr Lys Gln Val His Ala
     45                  50                  55

Leu Ser Pro Glu Glu Asn Val Ile Ile Lys Leu Asn Lys Ala Gly Leu
 60                  65                  70                  75

Val Leu Gly Ile Leu Ser Cys Leu Gly Leu Ser Ile Val Ala Asn Phe
                 80                  85                  90

Gln Lys Thr Thr Leu Phe Ala Ala His Val Ser Gly Ala Val Leu Thr
                 95                 100                 105

Phe Gly Met Gly Ser Leu Tyr Met Phe Val Gln Thr Ile Leu Ser Tyr
                110                 115                 120

Gln Met Gln Pro Lys Ile His Gly Lys Gln Val Phe Trp Ile Arg Leu
                125                 130                 135

Leu Leu Val Ile Trp Cys Gly Val Ser Ala Leu Ser Met Leu Thr Cys
140                 145                 150                 155

Ser Ser Val Leu His Ser Gly Asn Phe Gly Thr Asp Leu Glu Gln Lys
                160                 165                 170

Leu His Trp Asn Pro Glu Asp Lys Gly Tyr Ala Leu His Met Ile Thr
                175                 180                 185

Thr Ala Ala Glu Trp Ser Met Ser Phe Ser Phe Phe Gly Phe Phe Leu
```

```
                    190                 195                 200
Thr Tyr Ile Arg Asp Phe Gln Lys Ile Ser Leu Arg Val Glu Ala Asn
            205                 210                 215

Leu His Gly Leu Thr Leu Tyr Asp Thr Ala Pro Cys Pro Ile Asn Asn
220                 225                 230                 235

Glu Arg Thr Arg Leu Leu Ser Arg Asp Ile Arg
                240                 245

<210> SEQ ID NO 191
<211> LENGTH: 108
<212> TYPE: PRT
<213> ORGANISM: Homo sapiens

<400> SEQUENCE: 191

Met Gly Cys Val Phe Gln Ser Thr Glu Asp Lys Cys Ile Phe Lys Ile
1               5                   10                  15

Asp Trp Thr Leu Ser Pro Gly Glu His Ala Lys Asp Glu Tyr Val Leu
            20                  25                  30

Tyr Tyr Tyr Ser Asn Leu Ser Val Pro Ile Gly Arg Phe Gln Asn Arg
        35                  40                  45

Val His Leu Met Gly Asp Ile Leu Cys Asn Asp Gly Ser Leu Leu Leu
    50                  55                  60

Gln Asp Val Gln Glu Ala Asp Gln Gly Thr Tyr Ile Cys Glu Ile Arg
65                  70                  75                  80

Leu Lys Gly Glu Ser Gln Val Phe Lys Lys Ala Val Val Leu His Val
                85                  90                  95

Leu Pro Glu Glu Pro Lys Gly Thr Gln Met Leu Thr
            100                 105

<210> SEQ ID NO 192
<211> LENGTH: 69
<212> TYPE: PRT
<213> ORGANISM: Homo sapiens
<220> FEATURE:
<221> NAME/KEY: SIGNAL
<222> LOCATION: -46..-1

<400> SEQUENCE: 192

Met Ser Val Phe Trp Gly Phe Val Gly Phe Leu Val Pro Trp Phe Ile
    -45                 -40                 -35

Pro Lys Gly Pro Asn Arg Gly Val Ile Ile Thr Met Leu Val Thr Cys
-30                 -25                 -20                 -15

Ser Val Cys Cys Tyr Leu Phe Trp Leu Ile Ala Ile Leu Ala Gln Leu
                -10                 -5                  1

Asn Pro Leu Phe Gly Pro Gln Leu Lys Asn Glu Thr Ile Trp Tyr Leu
        5                   10                  15

Lys Tyr His Trp Pro
    20

<210> SEQ ID NO 193
<211> LENGTH: 251
<212> TYPE: PRT
<213> ORGANISM: Homo sapiens
<220> FEATURE:
<221> NAME/KEY: SIGNAL
<222> LOCATION: -28..-1

<400> SEQUENCE: 193

Met Trp Arg Leu Leu Ala Arg Ala Ser Ala Pro Leu Leu Arg Val Pro
            -25                 -20                 -15
```

-continued

```
Leu Ser Asp Ser Trp Ala Leu Leu Pro Ala Ser Ala Gly Val Lys Thr
        -10                  -5                    1
Leu Leu Pro Val Pro Ser Phe Glu Asp Val Ser Ile Pro Glu Lys Pro
 5                   10                  15                  20
Lys Leu Arg Phe Ile Glu Arg Ala Pro Leu Val Pro Lys Val Arg Arg
                 25                  30                  35
Glu Pro Lys Asn Leu Ser Asp Ile Arg Gly Pro Ser Thr Glu Ala Thr
             40                  45                  50
Glu Phe Thr Glu Gly Asn Phe Ala Ile Leu Ala Leu Gly Gly Gly Tyr
             55                  60                  65
Leu His Trp Gly His Phe Glu Met Met Arg Leu Thr Ile Asn Arg Ser
     70                  75                  80
Met Asp Pro Lys Asn Met Phe Ala Ile Trp Arg Val Pro Ala Pro Phe
 85                  90                  95                 100
Lys Pro Ile Thr Arg Lys Ser Val Gly His Arg Met Gly Gly Gly Lys
                105                 110                 115
Gly Ala Ile Asp His Tyr Val Thr Pro Val Lys Ala Gly Arg Leu Val
                120                 125                 130
Val Glu Met Gly Gly Arg Cys Glu Phe Glu Glu Val Gln Gly Phe Leu
            135                 140                 145
Asp Gln Val Ala His Lys Leu Pro Phe Ala Ala Lys Ala Val Ser Arg
        150                 155                 160
Gly Thr Leu Glu Lys Met Arg Lys Asp Gln Glu Glu Arg Glu Arg Asn
165                 170                 175                 180
Asn Gln Asn Pro Trp Thr Phe Glu Arg Ile Ala Thr Ala Asn Met Leu
                185                 190                 195
Gly Ile Arg Lys Val Leu Ser Pro Tyr Asp Leu Thr His Lys Gly Lys
                200                 205                 210
Tyr Trp Gly Lys Phe Tyr Met Pro Lys Arg Val
                215                 220

<210> SEQ ID NO 194
<211> LENGTH: 99
<212> TYPE: PRT
<213> ORGANISM: Homo sapiens
<220> FEATURE:
<221> NAME/KEY: SIGNAL
<222> LOCATION: -48...-1

<400> SEQUENCE: 194

Met Asp Asn Val Gln Pro Lys Ile Lys His Arg Pro Phe Cys Phe Ser
                -45                 -40                 -35
Val Lys Gly His Val Lys Met Leu Arg Leu Asp Ile Ile Asn Ser Leu
            -30                 -25                 -20
Val Thr Thr Val Phe Met Leu Ile Val Ser Val Leu Ala Leu Ile Pro
        -15                 -10                  -5
Glu Thr Thr Thr Leu Thr Val Gly Gly Val Phe Ala Leu Val Thr
 1                   5                  10                  15
Ala Val Cys Cys Leu Ala Asp Gly Ala Leu Ile Tyr Arg Lys Leu Leu
                 20                  25                  30
Phe Asn Pro Ser Gly Pro Tyr Gln Lys Lys Pro Val His Glu Lys Lys
                 35                  40                  45
Glu Val Leu
     50
```

```
<210> SEQ ID NO 195
<211> LENGTH: 81
<212> TYPE: PRT
<213> ORGANISM: Homo sapiens
<220> FEATURE:
<221> NAME/KEY: SIGNAL
<222> LOCATION: -31..-1

<400> SEQUENCE: 195

Met Ser Asn Thr His Thr Val Leu Val Ser Leu Pro His Pro
    -30                 -25                 -20

Ala Leu Thr Cys Cys His Leu Gly Leu Pro His Pro Val Arg Ala Pro
-15                 -10                  -5                   1

Arg Pro Leu Pro Arg Val Glu Pro Trp Asp Pro Arg Trp Gln Asp Ser
            5                  10                  15

Glu Leu Arg Tyr Pro Gln Ala Met Asn Ser Phe Leu Asn Glu Arg Ser
         20                  25                  30

Ser Pro Cys Arg Thr Leu Arg Gln Glu Ala Ser Ala Asp Arg Cys Asp
     35                  40                  45

Leu
50

<210> SEQ ID NO 196
<211> LENGTH: 150
<212> TYPE: PRT
<213> ORGANISM: Homo sapiens

<400> SEQUENCE: 196

Met Lys Val His Met His Thr Lys Phe Cys Leu Ile Cys Leu Leu Thr
1               5                   10                  15

Phe Ile Phe His His Cys Asn His Cys His Glu Glu His Asp His Gly
                20                  25                  30

Pro Glu Ala Leu His Arg Gln His Arg Gly Met Thr Glu Leu Glu Pro
             35                  40                  45

Ser Lys Phe Ser Lys Gln Ala Ala Glu Asn Glu Lys Lys Tyr Tyr Ile
         50                  55                  60

Glu Lys Leu Phe Glu Arg Tyr Gly Glu Asn Gly Arg Leu Ser Phe Phe
65                  70                  75                  80

Gly Leu Glu Lys Leu Leu Thr Asn Leu Gly Leu Gly Glu Arg Lys Val
                85                  90                  95

Val Glu Ile Asn His Glu Asp Leu Gly His Asp His Val Ser His Leu
            100                 105                 110

Gly Ile Leu Ala Val Gln Glu Gly Lys His Phe His Ser His Asn His
            115                 120                 125

Gln His Ser His Asn His Leu Asn Ser Glu Asn Gln Thr Val Thr Ser
    130                 135                 140

Val Ser Thr Lys Lys Lys
145             150

<210> SEQ ID NO 197
<211> LENGTH: 273
<212> TYPE: PRT
<213> ORGANISM: Homo sapiens
<220> FEATURE:
<221> NAME/KEY: SIGNAL
<222> LOCATION: -45..-1

<400> SEQUENCE: 197

Met Asn Trp Ser Ile Phe Glu Gly Leu Leu Ser Gly Val Asn Lys Tyr
-45                 -40                 -35                 -30
```

-continued

```
Ser Thr Ala Phe Gly Arg Ile Trp Leu Ser Leu Val Phe Ile Phe Arg
            -25              -20              -15

Val Leu Val Tyr Leu Val Thr Ala Glu Arg Val Trp Ser Asp Asp His
            -10               -5                        1

Lys Asp Phe Asp Cys Asn Thr Arg Gln Pro Gly Cys Ser Asn Val Cys
 5               10                       15

Phe Asp Glu Phe Phe Pro Val Ser His Val Arg Leu Trp Ala Leu Gln
 20              25                  30                       35

Leu Ile Leu Val Thr Cys Pro Ser Leu Leu Val Val Met His Val Ala
             40                  45                   50

Tyr Arg Glu Val Gln Glu Lys Arg His Arg Glu Ala His Gly Glu Asn
             55                  60                   65

Ser Gly Arg Leu Tyr Leu Asn Pro Gly Lys Arg Gly Gly Leu Trp
 70                      75                   80

Trp Thr Tyr Val Cys Ser Leu Val Phe Lys Ala Ser Val Asp Ile Ala
 85                  90                   95

Phe Leu Tyr Val Phe His Ser Phe Tyr Pro Lys Tyr Ile Leu Pro Pro
100                     105                 110                 115

Val Val Lys Cys His Ala Asp Pro Cys Pro Asn Ile Val Asp Cys Phe
                120                 125                 130

Ile Ser Lys Pro Ser Glu Lys Asn Ile Phe Thr Leu Phe Met Val Ala
             135                 140                 145

Thr Ala Ala Ile Cys Ile Leu Leu Asn Leu Val Glu Leu Ile Tyr Leu
         150                 155                 160

Val Ser Lys Arg Cys His Glu Cys Leu Ala Ala Arg Lys Ala Gln Ala
         165                 170                 175

Met Cys Thr Gly His His Pro His Asp Thr Thr Ser Ser Cys Lys Gln
180                 185                 190                 195

Asp Asp Leu Leu Ser Gly Asp Leu Ile Phe Leu Gly Ser Asp Ser His
                 200                 205                 210

Pro Pro Leu Leu Pro Asp Arg Pro Arg Asp His Val Lys Lys Thr Ile
             215                 220                 225

Leu
```

<210> SEQ ID NO 198
<211> LENGTH: 413
<212> TYPE: PRT
<213> ORGANISM: Homo sapiens
<220> FEATURE:
<221> NAME/KEY: SIGNAL
<222> LOCATION: -37..-1

<400> SEQUENCE: 198

```
Met Ala Ser Lys Ile Leu Leu Asn Val Gln Glu Glu Val Thr Cys Pro
             -35                 -30                 -25

Ile Cys Leu Glu Leu Leu Thr Glu Pro Leu Ser Leu Asp Cys Gly His
 -20                 -15                 -10

Ser Leu Cys Arg Ala Cys Ile Thr Val Ser Asn Lys Glu Ala Val Thr
 -5               1                   5                    10

Ser Met Gly Gly Lys Ser Ser Cys Pro Val Cys Gly Ile Ser Tyr Ser
                 15                  20                  25

Phe Glu His Leu Gln Ala Asn Gln His Leu Ala Asn Ile Val Glu Arg
             30                  35                  40

Leu Lys Glu Val Lys Leu Ser Pro Asp Asn Gly Lys Lys Arg Asp Leu
             45                  50                  55
```

```
Cys Asp His His Gly Glu Lys Leu Leu Phe Cys Lys Glu Asp Arg
 60                  65                  70                  75

Lys Val Ile Cys Trp Leu Cys Glu Arg Ser Gln Glu His Arg Gly His
             80                  85                  90

His Thr Val Leu Thr Glu Glu Val Phe Lys Glu Cys Gln Glu Lys Leu
             95                 100                 105

Gln Ala Val Leu Lys Arg Leu Lys Lys Glu Glu Glu Ala Glu Lys
        110                 115                 120

Leu Glu Ala Asp Ile Arg Glu Glu Lys Thr Ser Trp Lys Tyr Gln Val
    125                 130                 135

Gln Thr Glu Arg Gln Arg Ile Gln Thr Glu Phe Asp Gln Leu Arg Ser
140                 145                 150                 155

Ile Leu Asn Asn Glu Glu Gln Arg Glu Leu Gln Arg Leu Glu Glu Glu
                160                 165                 170

Glu Lys Lys Thr Leu Asp Lys Phe Ala Glu Ala Glu Asp Glu Leu Val
            175                 180                 185

Gln Gln Lys Gln Leu Val Arg Glu Leu Ile Ser Asp Val Glu Cys Arg
        190                 195                 200

Ser Gln Trp Ser Thr Met Glu Leu Leu Gln Asp Met Ser Gly Ile Met
    205                 210                 215

Lys Trp Ser Glu Ile Trp Arg Leu Lys Lys Pro Lys Met Val Ser Lys
220                 225                 230                 235

Lys Leu Lys Thr Val Phe His Ala Pro Asp Leu Ser Arg Met Leu Gln
            240                 245                 250

Met Phe Arg Glu Leu Thr Ala Val Arg Cys Tyr Trp Val Asp Val Thr
        255                 260                 265

Leu Asn Ser Val Asn Leu Asn Leu Val Leu Ser Glu Asp Gln
    270                 275                 280

Arg Gln Val Ile Ser Val Pro Ile Trp Pro Phe Gln Cys Tyr Asn Tyr
    285                 290                 295

Gly Val Leu Gly Ser Gln Tyr Phe Ser Ser Gly Lys His Tyr Trp Glu
300                 305                 310                 315

Val Asp Val Ser Lys Lys Thr Ala Trp Ile Leu Gly Val Tyr Cys Arg
            320                 325                 330

Thr Tyr Ser Arg His Met Lys Tyr Val Val Arg Arg Cys Ala Asn Arg
            335                 340                 345

Gln Asn Leu Tyr Thr Lys Tyr Arg Pro Leu Phe Gly Tyr Trp Val Ile
        350                 355                 360

Gly Leu Gln Asn Lys Cys Lys Tyr Gly Ala Lys Lys Lys
    365                 370                 375

<210> SEQ ID NO 199
<211> LENGTH: 393
<212> TYPE: PRT
<213> ORGANISM: Homo sapiens
<220> FEATURE:
<221> NAME/KEY: SIGNAL
<222> LOCATION: -19..-1

<400> SEQUENCE: 199

Met Arg Thr Leu Phe Asn Leu Leu Trp Leu Ala Leu Ala Cys Ser Pro
                -15                 -10                  -5

Val His Thr Thr Leu Ser Lys Ser Asp Ala Lys Lys Ala Ala Ser Lys
              1                   5                  10

Thr Leu Leu Glu Lys Ser Gln Phe Ser Asp Lys Pro Val Gln Asp Arg
```

```
            15                  20                  25
Gly Leu Val Val Thr Asp Leu Lys Ala Glu Ser Val Leu Glu His
 30                  35                  40                  45

Arg Ser Tyr Cys Ser Ala Lys Ala Arg Asp Arg His Phe Ala Gly Asp
                 50                  55                  60

Val Leu Gly Tyr Val Thr Pro Trp Asn Ser His Gly Tyr Asp Val Thr
                 65                  70                  75

Lys Val Phe Gly Ser Lys Phe Thr Gln Ile Ser Pro Val Trp Leu Gln
                 80                  85                  90

Leu Lys Arg Arg Gly Arg Glu Met Phe Glu Val Thr Gly Leu His Asp
 95                 100                 105

Val Asp Gln Gly Trp Met Arg Ala Val Arg Lys His Ala Lys Gly Leu
110                 115                 120                 125

His Ile Val Pro Arg Leu Leu Phe Glu Asp Trp Thr Tyr Asp Asp Phe
                130                 135                 140

Arg Asn Val Leu Asp Ser Glu Asp Glu Ile Glu Glu Leu Ser Lys Thr
                145                 150                 155

Val Val Gln Val Ala Lys Asn Gln His Phe Asp Gly Phe Val Val Glu
                160                 165                 170

Val Trp Asn Gln Leu Leu Ser Gln Lys Arg Val Gly Leu Ile His Met
175                 180                 185

Leu Thr His Leu Ala Glu Ala Leu His Gln Ala Arg Leu Leu Ala Leu
190                 195                 200                 205

Leu Val Ile Pro Pro Ala Ile Thr Pro Gly Thr Asp Gln Leu Gly Met
                210                 215                 220

Phe Thr His Lys Glu Phe Glu Gln Leu Ala Pro Val Leu Asp Gly Phe
                225                 230                 235

Ser Leu Met Thr Tyr Asp Tyr Ser Thr Ala His Gln Pro Gly Pro Asn
                240                 245                 250

Ala Pro Leu Ser Trp Val Arg Ala Cys Val Gln Val Leu Asp Pro Lys
255                 260                 265

Ser Lys Trp Arg Ser Lys Ile Leu Leu Gly Leu Asn Phe Tyr Gly Met
270                 275                 280                 285

Asp Tyr Ala Thr Ser Lys Asp Ala Arg Glu Pro Val Val Gly Ala Arg
                290                 295                 300

Tyr Ile Gln Thr Leu Lys Asp His Arg Pro Arg Met Val Trp Asp Ser
                305                 310                 315

Gln Ala Ser Glu His Phe Phe Glu Tyr Lys Lys Ser Arg Ser Gly Arg
                320                 325                 330

His Val Val Phe Tyr Pro Thr Leu Lys Ser Leu Gln Val Arg Leu Glu
335                 340                 345

Leu Ala Arg Glu Leu Gly Val Gly Val Ser Ile Trp Glu Leu Gly Gln
350                 355                 360                 365

Gly Leu Asp Tyr Phe Tyr Asp Leu Leu
                370

<210> SEQ ID NO 200
<211> LENGTH: 381
<212> TYPE: PRT
<213> ORGANISM: Homo sapiens
<220> FEATURE:
<221> NAME/KEY: SIGNAL
<222> LOCATION: -13..-1

<400> SEQUENCE: 200
```

```
Met Leu Leu Ser Ile Gly Met Leu Met Leu Ser Ala Thr Gln Val Tyr
            -10                 -5                   1
Thr Val Leu Thr Val Gln Leu Phe Ala Phe Leu Asn Pro Leu Pro Val
         5                  10                  15
Glu Ala Asp Ile Leu Ala Tyr Asn Phe Glu Asn Ala Ser Gln Thr Phe
 20              25                  30                  35
Asp Asp Leu Pro Ala Arg Phe Gly Tyr Arg Leu Pro Ala Glu Gly Leu
             40                  45                  50
Lys Gly Phe Leu Ile Asn Ser Lys Pro Glu Asn Ala Cys Glu Pro Ile
             55                  60                  65
Val Pro Pro Val Lys Asp Asn Ser Ser Gly Thr Phe Ile Val Leu
             70                  75                  80
Ile Arg Arg Leu Asp Cys Asn Phe Asp Ile Lys Val Leu Asn Ala Gln
 85              90                  95
Arg Ala Gly Tyr Lys Ala Ala Ile Val His Asn Val Asp Ser Asp Asp
100             105                 110                 115
Leu Ile Ser Met Gly Ser Asn Asp Ile Glu Val Leu Lys Lys Ile Asp
                120                 125                 130
Ile Pro Ser Val Phe Ile Gly Glu Ser Ser Ala Ser Ser Leu Lys Asp
                135                 140                 145
Glu Phe Thr Tyr Glu Lys Gly Gly His Leu Ile Leu Val Pro Glu Phe
            150                 155                 160
Ser Leu Pro Leu Glu Tyr Tyr Leu Ile Pro Phe Leu Ile Ile Val Gly
            165                 170                 175
Ile Cys Leu Ile Leu Ile Val Ile Phe Met Ile Thr Lys Phe Val Gln
180             185                 190                 195
Asp Arg His Arg Ala Arg Arg Asn Arg Leu Arg Lys Asp Gln Leu Lys
                200                 205                 210
Lys Leu Pro Val His Lys Phe Lys Lys Gly Asp Glu Tyr Asp Val Cys
                215                 220                 225
Ala Ile Cys Leu Asp Glu Tyr Glu Asp Gly Asp Lys Leu Arg Ile Leu
                230                 235                 240
Pro Cys Ser His Ala Tyr His Cys Lys Cys Val Asp Pro Trp Leu Thr
245                 250                 255
Lys Thr Lys Lys Thr Cys Pro Val Cys Arg Gln Lys Val Val Pro Ser
260                 265                 270                 275
Gln Gly Asp Ser Asp Ser Asp Thr Asp Ser Ser Gln Glu Glu Asn Glu
                280                 285                 290
Val Thr Glu His Thr Pro Leu Leu Arg Pro Leu Ala Ser Val Ser Ala
                295                 300                 305
Gln Ser Phe Gly Ala Leu Ser Glu Ser Arg Ser His Gln Asn Met Thr
            310                 315                 320
Glu Ser Ser Asp Tyr Glu Glu Asp Asp Asn Glu Asp Thr Asp Ser Ser
            325                 330                 335
Asp Ala Glu Asn Glu Ile Asn Glu His Asp Val Val Gln Leu Gln
340                 345                 350                 355
Pro Asn Gly Glu Arg Asp Tyr Asn Ile Ala Asn Thr Val
            360                 365
```

<210> SEQ ID NO 201
<211> LENGTH: 291
<212> TYPE: PRT
<213> ORGANISM: Homo sapiens
<220> FEATURE:
<221> NAME/KEY: SIGNAL

<222> LOCATION: -42..-1

<400> SEQUENCE: 201

Met Asp Ser Arg Val Ser Pro Glu Lys Gln Asp Lys Glu Asn Phe
        -40                 -35                 -30
Val Gly Val Asn Asn Lys Arg Leu Gly Val Cys Gly Trp Ile Leu Phe
        -25                 -20                 -15
Ser Leu Ser Phe Leu Leu Val Ile Ile Thr Phe Pro Ile Ser Ile Trp
-10                 -5                  1                   5
Met Cys Leu Lys Ile Ile Arg Glu Tyr Glu Arg Ala Val Val Phe Arg
                10                  15                  20
Leu Gly Arg Ile Gln Ala Asp Lys Ala Lys Gly Pro Gly Leu Ile Leu
                25                  30                  35
Val Leu Pro Cys Ile Asp Val Phe Val Lys Val Asp Leu Arg Thr Val
        40                  45                  50
Thr Cys Asn Ile Pro Pro Gln Glu Ile Leu Thr Arg Asp Ser Val Thr
55                  60                  65                  70
Thr Gln Val Asp Gly Val Val Tyr Tyr Arg Ile Tyr Ser Ala Val Ser
                    75                  80                  85
Ala Val Ala Asn Val Asn Asp Val His Gln Ala Thr Phe Leu Leu Ala
                90                  95                  100
Gln Thr Thr Leu Arg Asn Val Leu Gly Thr Gln Thr Leu Ser Gln Ile
                105                 110                 115
Leu Ala Gly Arg Glu Glu Ile Ala His Ser Ile Gln Thr Leu Leu Asp
        120                 125                 130
Asp Ala Thr Glu Leu Trp Gly Ile Arg Val Ala Arg Val Glu Ile Lys
135                 140                 145                 150
Asp Val Arg Ile Pro Val Gln Leu Gln Arg Ser Met Ala Ala Glu Ala
                    155                 160                 165
Glu Ala Thr Arg Glu Ala Arg Ala Lys Val Leu Ala Ala Glu Gly Glu
                170                 175                 180
Met Ser Ala Ser Lys Ser Leu Lys Ser Ala Ser Met Val Leu Ala Glu
        185                 190                 195
Ser Pro Ile Ala Leu Gln Leu Arg Tyr Leu Gln Thr Leu Ser Thr Val
200                 205                 210
Ala Thr Glu Lys Asn Ser Thr Ile Val Phe Pro Leu Pro Met Asn Ile
215                 220                 225                 230
Leu Glu Gly Ile Gly Gly Val Ser Tyr Asp Asn His Lys Lys Leu Pro
                    235                 240                 245
Asn Lys Ala

<210> SEQ ID NO 202
<211> LENGTH: 92
<212> TYPE: PRT
<213> ORGANISM: Homo sapiens

<400> SEQUENCE: 202

Met Pro Pro Arg Asn Leu Leu Glu Leu Leu Ile Asn Ile Lys Ala Gly
1               5                   10                  15
Thr Tyr Leu Pro Gln Ser Tyr Leu Ile His Glu His Met Val Ile Thr
                20                  25                  30
Asp Arg Ile Glu Asn Ile Asp His Leu Gly Phe Phe Ile Tyr Arg Leu
                35                  40                  45
Cys His Asp Lys Glu Thr Tyr Lys Leu Gln Arg Arg Glu Thr Ile Lys
        50                  55                  60

```
Gly Ile Gln Lys Arg Glu Ala Ser Asn Cys Phe Ala Ile Arg His Phe
 65                  70                  75                  80

Glu Asn Lys Phe Ala Val Glu Thr Leu Ile Cys Ser
                 85                  90
```

<210> SEQ ID NO 203
<211> LENGTH: 127
<212> TYPE: PRT
<213> ORGANISM: Homo sapiens
<220> FEATURE:
<221> NAME/KEY: SIGNAL
<222> LOCATION: -63..-1

<400> SEQUENCE: 203

```
Met Ser Ala Ala Gly Ala Arg Gly Leu Arg Ala Thr Tyr His Arg Leu
            -60                 -55                 -50

Pro Asp Lys Val Glu Leu Met Leu Pro Glu Lys Leu Arg Pro Leu Tyr
                -45                 -40                 -35

Asn His Pro Ala Gly Pro Arg Thr Val Phe Phe Trp Ala Pro Ile Met
            -30                 -25                 -20

Lys Trp Gly Leu Val Cys Ala Gly Leu Ala Asp Met Ala Arg Pro Ala
-15                 -10                  -5                   1

Glu Lys Leu Ser Thr Ala Gln Ser Ala Val Leu Met Ala Thr Gly Phe
                  5                  10                  15

Ile Trp Ser Arg Tyr Ser Leu Val Ile Ile Pro Lys Asn Trp Ser Leu
                 20                  25                  30

Phe Ala Val Asn Phe Phe Val Gly Ala Ala Gly Ala Ser Gln Leu Phe
                 35                  40                  45

Arg Ile Trp Arg Tyr Asn Gln Glu Leu Lys Ala Lys Ala His Lys
 50                  55                  60
```

<210> SEQ ID NO 204
<211> LENGTH: 84
<212> TYPE: PRT
<213> ORGANISM: Homo sapiens
<220> FEATURE:
<221> NAME/KEY: SIGNAL
<222> LOCATION: -20..-1

<400> SEQUENCE: 204

```
Met Lys Gly Trp Gly Trp Leu Ala Leu Leu Gly Ala Leu Leu Gly
-20                 -15                 -10                  -5

Thr Ala Trp Ala Arg Arg Ser Gln Asp Leu His Cys Gly Ala Cys Arg
                  1                   5                  10

Ala Leu Val Asp Glu Leu Glu Trp Glu Ile Ala Gln Val Asp Pro Lys
                 15                  20                  25

Lys Thr Ile Gln Met Gly Ser Phe Arg Ile Asn Pro Asp Gly Ser Gln
                 30                  35                  40

Ser Val Val Glu Val Thr Val Thr Val Pro Pro Asn Lys Val Ala His
 45                  50                  55                  60

Ser Gly Phe Gly
```

<210> SEQ ID NO 205
<211> LENGTH: 182
<212> TYPE: PRT
<213> ORGANISM: Homo sapiens
<220> FEATURE:
<221> NAME/KEY: SIGNAL
<222> LOCATION: -20..-1

```
<400> SEQUENCE: 205

Met Lys Gly Trp Gly Trp Leu Ala Leu Leu Leu Gly Ala Leu Leu Gly
-20              -15                 -10                  -5

Thr Ala Trp Ala Arg Arg Ser Gln Asp Leu His Cys Gly Ala Cys Arg
             1               5                  10

Ala Leu Val Asp Glu Leu Glu Trp Glu Ile Ala Gln Val Asp Pro Lys
         15                  20                  25

Lys Thr Ile Gln Met Gly Ser Phe Arg Ile Asn Pro Asp Gly Ser Gln
         30                  35                  40

Ser Val Val Glu Val Pro Tyr Ala Arg Ser Glu Ala His Leu Thr Glu
45                   50                  55                  60

Leu Leu Glu Glu Ile Cys Asp Arg Met Lys Glu Tyr Gly Glu Gln Ile
                 65                  70                  75

Asp Pro Ser Thr His Arg Lys Asn Tyr Val Arg Val Gly Arg Asn
                 80                  85                  90

Gly Glu Ser Ser Glu Leu Asp Leu Gln Gly Ile Arg Ile Asp Ser Asp
                 95                  100                 105

Ile Ser Gly Thr Leu Lys Phe Ala Cys Gly Ser Ile Val Glu Glu Tyr
        110                 115                 120

Glu Asp Glu Leu Ile Glu Phe Phe Ser Arg Glu Ala Asp Asn Val Lys
125                 130                 135                 140

Asp Lys Leu Cys Ser Lys Arg Thr Asp Leu Cys Asp His Ala Leu His
                145                 150                 155

Ile Ser His Asp Glu Leu
            160

<210> SEQ ID NO 206
<211> LENGTH: 71
<212> TYPE: PRT
<213> ORGANISM: Homo sapiens
<220> FEATURE:
<221> NAME/KEY: SIGNAL
<222> LOCATION: -25..-1

<400> SEQUENCE: 206

Met Pro Ala Gly Val Pro Met Ser Thr Tyr Leu Lys Met Phe Ala Ala
-25                 -20                 -15                 -10

Ser Leu Leu Ala Met Cys Ala Gly Ala Glu Val Val His Arg Tyr Tyr
             -5                  1                   5

Arg Pro Asp Leu Thr Ile Pro Glu Ile Pro Pro Lys Arg Gly Glu Leu
         10                  15                  20

Lys Thr Glu Leu Leu Gly Leu Lys Glu Arg Lys His Lys Pro Gln Val
         25                  30                  35

Ser Gln Gln Glu Glu Leu Lys
40                  45

<210> SEQ ID NO 207
<211> LENGTH: 73
<212> TYPE: PRT
<213> ORGANISM: Homo sapiens

<400> SEQUENCE: 207

Met Arg Ile Arg Met Thr Asp Gly Arg Thr Leu Val Gly Cys Phe Leu
1               5                   10                  15

Cys Thr Asp Arg Asp Cys Asn Val Ile Leu Gly Ser Ala Gln Glu Phe
            20                  25                  30

Leu Lys Pro Ser Asp Ser Phe Ser Ala Gly Glu Pro Arg Val Leu Gly
```

```
                35                  40                  45
Leu Ala Met Val Pro Gly His His Ile Val Ser Ile Glu Val Gln Arg
     50                  55                  60

Glu Ser Leu Thr Gly Pro Pro Tyr Leu
 65                  70
```

<210> SEQ ID NO 208
<211> LENGTH: 169
<212> TYPE: PRT
<213> ORGANISM: Homo sapiens
<220> FEATURE:
<221> NAME/KEY: SIGNAL
<222> LOCATION: -150..-1
<221> NAME/KEY: UNSURE
<222> LOCATION: -67
<223> OTHER INFORMATION: Xaa = any one of the twenty amino acids

<400> SEQUENCE: 208

```
Met Ala Glu Thr Lys Asp Thr Ala Gln Met Leu Val Thr Phe Lys Asp
-150                -145                -140                -135

Val Ala Val Thr Phe Thr Arg Glu Glu Trp Arg Gln Leu Asp Leu Ala
                -130                -125                -120

Gln Arg Thr Leu Tyr Arg Glu Gly Ile Gly Phe Pro Lys Pro Glu Leu
                -115                -110                -105

Val His Leu Leu Glu His Gly Gln Glu Leu Trp Ile Val Lys Arg Gly
                -100                 -95                 -90

Leu Ser His Ala Thr Cys Ala Glu Phe His Ser Cys Cys Pro Gly Trp
     -85                 -80                 -75

Ser Ala Val Xaa Arg His Leu Ser Ser Leu Gln Leu Leu Pro Pro Glu
-70                  -65                 -60                 -55

Phe Lys Gly Phe Ser Cys Leu Ser Leu Pro Ser Ser Trp Asp Tyr Arg
                 -50                 -45                 -40

Arg Pro Pro Pro Cys Pro Ala Gly Phe Val Phe Leu Val Glu Thr
                 -35                 -30                 -25

Gly Leu His His Val Gly Gln Ala Gly Leu Glu Leu Leu Thr Ser Cys
     -20                 -15                 -10

Ser Pro Pro Ala Ser Ala Ser Gln Ser Ala Ala Ile Thr Gly Val Ser
 -5                   1                   5                  10

His Arg Ala Arg Gln Arg Lys Thr Ala
                 15
```

<210> SEQ ID NO 209
<211> LENGTH: 76
<212> TYPE: PRT
<213> ORGANISM: Homo sapiens
<220> FEATURE:
<221> NAME/KEY: SIGNAL
<222> LOCATION: -22..-1

<400> SEQUENCE: 209

```
Met Glu Leu Ile Ser Pro Thr Val Ile Ile Leu Gly Cys Leu Ala
         -20                 -15                 -10

Leu Phe Leu Leu Leu Gln Arg Lys Asn Leu Arg Pro Pro Cys Ile
     -5                   1                   5                  10

Lys Gly Trp Ile Pro Trp Ile Gly Val Gly Phe Glu Phe Gly Lys Ala
                 15                  20                  25

Pro Leu Glu Phe Ile Glu Lys Ala Arg Ile Lys Val Cys Gly Arg Gly
                 30                  35                  40

Arg Arg Gly Leu Gln Arg Gln Cys Phe Leu Phe
```

```
                   45                  50
```

<210> SEQ ID NO 210
<211> LENGTH: 95
<212> TYPE: PRT
<213> ORGANISM: Homo sapiens
<220> FEATURE:
<221> NAME/KEY: SIGNAL
<222> LOCATION: -54...-1

<400> SEQUENCE: 210

```
Met Ala Glu Thr Lys Asp Ala Ala Gln Met Leu Val Thr Phe Lys Asp
            -50                 -45                 -40

Val Ala Val Thr Phe Thr Arg Glu Glu Trp Arg Gln Leu Asp Leu Ala
        -35                 -30                 -25

Gln Arg Thr Leu Tyr Arg Glu Val Met Leu Glu Thr Cys Gly Leu Leu
    -20                 -15                 -10

Val Ser Leu Val Glu Ser Ile Trp Leu His Ile Thr Glu Asn Gln Ile
 -5                   1                   5                  10

Lys Leu Ala Ser Pro Gly Arg Lys Phe Thr Asn Ser Pro Asp Glu Lys
                15                  20                  25

Pro Glu Val Trp Leu Ala Pro Gly Leu Phe Gly Ala Ala Gln
            30                  35                  40
```

<210> SEQ ID NO 211
<211> LENGTH: 92
<212> TYPE: PRT
<213> ORGANISM: Homo sapiens
<220> FEATURE:
<221> NAME/KEY: SIGNAL
<222> LOCATION: -22...-1

<400> SEQUENCE: 211

```
Met Glu Leu Ile Ser Pro Thr Val Ile Ile Leu Gly Cys Leu Ala
            -20                 -15                 -10

Leu Phe Leu Leu Leu Gln Arg Lys Asn Leu Arg Arg Pro Pro Cys Ile
 -5                   1                   5                  10

Lys Gly Trp Ile Pro Trp Ile Gly Val Gly Phe Glu Phe Gly Lys Ala
                15                  20                  25

Pro Leu Glu Phe Ile Glu Lys Ala Arg Ile Lys Tyr Gly Pro Ile Phe
            30                  35                  40

Thr Val Phe Ala Met Gly Asn Arg Met Thr Phe Val Thr Glu Glu Glu
            45                  50                  55

Gly Ile Asn Val Phe Leu Lys Ser Lys Lys Lys
        60                  65                  70
```

<210> SEQ ID NO 212
<211> LENGTH: 89
<212> TYPE: PRT
<213> ORGANISM: Homo sapiens
<220> FEATURE:
<221> NAME/KEY: SIGNAL
<222> LOCATION: -16...-1

<400> SEQUENCE: 212

```
Met Ile Ile Ser Leu Phe Ile Tyr Ile Phe Leu Thr Cys Ser Asn Thr
        -15                 -10                  -5

Ser Pro Ser Tyr Gln Gly Thr Gln Leu Gly Leu Gly Leu Pro Ser Ala
 1                    5                  10                  15

Gln Trp Trp Pro Leu Thr Gly Arg Arg Met Gln Cys Cys Arg Leu Phe
            20                  25                  30
```

```
Cys Phe Leu Leu Gln Asn Cys Leu Phe Pro Phe Pro Leu His Leu Ile
         35                  40                  45

Gln His Asp Pro Cys Glu Leu Val Leu Thr Ile Ser Trp Asp Trp Ala
 50                  55                  60

Glu Ala Gly Ala Ser Leu Tyr Ser Pro
65               70
```

<210> SEQ ID NO 213
<211> LENGTH: 109
<212> TYPE: PRT
<213> ORGANISM: Homo sapiens

<400> SEQUENCE: 213

```
Met Lys Val Asp Lys Asp Arg Gln Met Val Val Leu Glu Glu Glu Phe
 1               5                  10                  15

Arg Asn Ile Ser Pro Glu Glu Leu Lys Met Glu Leu Pro Glu Arg Gln
             20                  25                  30

Pro Arg Phe Val Val Tyr Ser Tyr Lys Tyr Val Arg Asp Asp Gly Arg
         35                  40                  45

Val Ser Tyr Pro Leu Cys Phe Ile Phe Ser Ser Pro Val Gly Cys Lys
 50                  55                  60

Pro Glu Gln Gln Met Met Tyr Ala Gly Ser Lys Asn Arg Leu Val Gln
65                  70                  75                  80

Thr Ala Glu Leu Thr Lys Val Phe Glu Ile Arg Thr Thr Asp Asp Leu
                 85                  90                  95

Thr Glu Ala Trp Leu Gln Glu Lys Leu Ser Phe Phe Arg
            100                 105
```

<210> SEQ ID NO 214
<211> LENGTH: 114
<212> TYPE: PRT
<213> ORGANISM: Homo sapiens
<220> FEATURE:
<221> NAME/KEY: SIGNAL
<222> LOCATION: -103..-1

<400> SEQUENCE: 214

```
Met Val Ile Arg Val Tyr Ile Ala Ser Ser Gly Ser Thr Ala Ile
            -100                 -95                 -90

Lys Lys Lys Gln Gln Asp Val Leu Gly Phe Leu Glu Ala Asn Lys Ile
         -85                 -80                 -75

Gly Phe Glu Glu Lys Asp Ile Ala Ala Asn Glu Glu Asn Arg Lys Trp
         -70                 -65                 -60

Met Arg Glu Asn Val Pro Glu Asn Ser Arg Pro Ala Thr Gly Asn Pro
-55                 -50                 -45                 -40

Leu Pro Pro Gln Ile Phe Asn Glu Ser Gln Tyr Arg Gly Asp Tyr Asp
                 -35                 -30                 -25

Ala Phe Phe Glu Ala Arg Glu Asn Asn Ala Val Tyr Ala Phe Leu Gly
         -20                 -15                 -10

Leu Thr Ala Pro Ser Gly Ser Lys Glu Ala Glu Val Gln Ala Lys Gln
         -5                   1                   5

Gln Ala
 10
```

<210> SEQ ID NO 215
<211> LENGTH: 124
<212> TYPE: PRT
<213> ORGANISM: Homo sapiens

```
<220> FEATURE:
<221> NAME/KEY: SIGNAL
<222> LOCATION: -97..-1

<400> SEQUENCE: 215

Met Ala Asp Asp Leu Lys Arg Phe Leu Tyr Lys Lys Leu Pro Ser Val
        -95                 -90                 -85
Glu Gly Leu His Ala Ile Val Val Ser Asp Arg Asp Gly Val Pro Val
    -80                 -75                 -70
Ile Lys Val Ala Asn Asp Asn Ala Pro Glu His Ala Leu Arg Pro Gly
-65                 -60                 -55                 -50
Phe Leu Ser Thr Phe Ala Leu Ala Thr Asp Gln Gly Ser Lys Leu Gly
                -45                 -40                 -35
Leu Ser Lys Asn Lys Ser Ile Ile Cys Tyr Tyr Asn Thr Tyr Gln Val
            -30                 -25                 -20
Val Gln Phe Asn Arg Leu Pro Leu Val Val Ser Phe Ile Ala Ser Ser
        -15                 -10                  -5
Ser Ala Asn Thr Gly Leu Ile Val Ser Leu Glu Lys Glu Leu Ala Pro
  1                  5                  10                  15
Leu Phe Glu Glu Leu Arg Gln Val Val Glu Val Ser
                20                  25

<210> SEQ ID NO 216
<211> LENGTH: 93
<212> TYPE: PRT
<213> ORGANISM: Homo sapiens
<220> FEATURE:
<221> NAME/KEY: SIGNAL
<222> LOCATION: -22..-1

<400> SEQUENCE: 216

Met Lys Pro Val Leu Pro Leu Gln Phe Leu Val Val Phe Cys Leu Ala
        -20                 -15                 -10
Leu Gln Leu Val Pro Gly Ser Pro Lys Gln Arg Val Leu Lys Tyr Ile
     -5                   1                   5                  10
Leu Glu Pro Pro Pro Cys Ile Ser Ala Pro Glu Asn Cys Thr His Leu
                15                  20                  25
Cys Thr Met Gln Glu Asp Cys Gly Lys Gly Phe Gln Cys Cys Ser Ser
                30                  35                  40
Phe Cys Gly Ile Val Cys Ser Ser Glu Thr Phe Gln Lys Arg Asn Arg
            45                  50                  55
Ile Lys His Lys Gly Ser Glu Val Ile Met Pro Ala Asn
        60                  65                  70

<210> SEQ ID NO 217
<211> LENGTH: 207
<212> TYPE: PRT
<213> ORGANISM: Homo sapiens
<220> FEATURE:
<221> NAME/KEY: SIGNAL
<222> LOCATION: -42..-1

<400> SEQUENCE: 217

Met His Ile Leu Gln Leu Leu Thr Thr Val Asp Asp Gly Ile Gln Ala
        -40                 -35                 -30
Ile Val His Cys Pro Asp Thr Gly Lys Asp Ile Trp Asn Leu Leu Phe
    -25                 -20                 -15
Asp Leu Val Cys His Glu Phe Cys Gln Ser Asp Asp Pro Pro Ile Ile
-10                  -5                   1                   5
```

```
Leu Gln Glu Gln Lys Thr Val Leu Ala Ser Val Phe Ser Val Leu Ser
                10                  15                  20

Ala Ile Tyr Ala Ser Gln Thr Glu Gln Glu Tyr Leu Lys Ile Glu Lys
            25                  30                  35

Val Asp Leu Pro Leu Ile Asp Ser Leu Ile Arg Val Leu Gln Asn Met
        40                  45                  50

Glu Gln Cys Gln Lys Lys Pro Glu Asn Ser Ala Glu Ser Asn Thr Glu
55                  60                  65                  70

Glu Thr Lys Arg Thr Asp Leu Thr Gln Asp Asp Phe His Leu Lys Ile
                75                  80                  85

Leu Lys Asp Ile Leu Cys Glu Phe Leu Ser Asn Ile Phe Gln Ala Leu
            90                  95                  100

Thr Lys Glu Thr Val Ala Gln Gly Val Lys Glu Gly Gln Leu Ser Lys
        105                 110                 115

Gln Lys Cys Ser Ser Ala Phe Gln Asn Leu Leu Pro Phe Tyr Ser Pro
120                 125                 130

Val Val Glu Asp Phe Ile Lys Ile Leu Arg Glu Val Asp Lys Ala Leu
135                 140                 145                 150

Ala Asp Asp Leu Glu Lys Asn Phe Pro Ser Leu Lys Val Gln Thr
                155                 160                 165
```

<210> SEQ ID NO 218
<211> LENGTH: 59
<212> TYPE: PRT
<213> ORGANISM: Homo sapiens

<400> SEQUENCE: 218

```
Met Pro His Ser Lys Pro Leu Asp Trp Gly Leu Ser Ser Val Ala Glu
1               5                   10                  15

Cys Pro Ala Glu Leu Phe Pro Ser Thr Gly Gly Leu Ala Gly Lys Gly
            20                  25                  30

Pro Gly Leu Asp Ile Leu Arg Cys Val Leu Ser Pro Trp Ala Ser His
        35                  40                  45

Phe Pro Ser Leu Ser Leu Gly Val Phe Asn Leu
    50                  55
```

<210> SEQ ID NO 219
<211> LENGTH: 56
<212> TYPE: PRT
<213> ORGANISM: Homo sapiens
<220> FEATURE:
<221> NAME/KEY: SIGNAL
<222> LOCATION: -27..-1

<400> SEQUENCE: 219

```
Met Asn Arg Val Pro Ala Asp Ser Pro Asn Met Cys Leu Ile Cys Leu
        -25                 -20                 -15

Leu Ser Tyr Ile Ala Leu Gly Ala Ile His Ala Lys Ile Cys Arg Arg
    -10                 -5                  1                   5

Ala Phe Gln Glu Glu Gly Arg Ala Asn Ala Lys Thr Gly Val Arg Ala
                10                  15                  20

Trp Cys Ile Gln Pro Trp Ala Lys
            25
```

<210> SEQ ID NO 220
<211> LENGTH: 162
<212> TYPE: PRT
<213> ORGANISM: Homo sapiens
<220> FEATURE:

```
<221> NAME/KEY: SIGNAL
<222> LOCATION: -94..-1

<400> SEQUENCE: 220

Met Leu Gln Thr Ser Asn Tyr Ser Leu Val Leu Ser Leu Gln Phe Leu
                -90                 -85                 -80

Leu Leu Ser Tyr Asp Leu Phe Val Asn Ser Phe Ser Glu Leu Leu Gln
            -75                 -70                 -65

Lys Thr Pro Val Ile Gln Leu Val Leu Phe Ile Ile Gln Asp Ile Ala
        -60                 -55                 -50

Val Leu Phe Asn Ile Ile Ile Ile Phe Leu Met Phe Phe Asn Thr Phe
    -45                 -40                 -35

Val Phe Gln Ala Gly Leu Val Asn Leu Leu Phe His Lys Phe Lys Gly
-30                 -25                 -20                 -15

Thr Ile Ile Leu Thr Ala Val Tyr Phe Ala Leu Ser Ile Ser Leu His
                -10                  -5                   1

Val Trp Val Met Asn Leu Arg Trp Lys Asn Ser Asn Ser Phe Ile Trp
          5                  10                  15

Thr Asp Gly Leu Gln Met Leu Phe Val Phe Gln Arg Leu Ala Ala Val
         20                  25                  30

Leu Tyr Cys Tyr Phe Tyr Lys Arg Thr Ala Val Arg Leu Gly Asp Pro
 35                  40                  45                  50

His Phe Tyr Gln Asp Ser Leu Trp Leu Arg Lys Glu Phe Met Gln Val
                 55                  60                  65

Arg Arg

<210> SEQ ID NO 221
<211> LENGTH: 154
<212> TYPE: PRT
<213> ORGANISM: Homo sapiens
<220> FEATURE:
<221> NAME/KEY: SIGNAL
<222> LOCATION: -68..-1

<400> SEQUENCE: 221

Met Ala Ser Ala Ser Ala Arg Gly Asn Gln Asp Lys Asp Ala His Phe
                -65                 -60                 -55

Pro Pro Pro Ser Lys Gln Ser Leu Leu Phe Cys Pro Lys Ser Lys Leu
            -50                 -45                 -40

His Ile His Arg Ala Glu Ile Ser Lys Ile Met Arg Glu Cys Gln Glu
        -35                 -30                 -25

Glu Ser Phe Trp Lys Arg Ala Leu Pro Phe Ser Leu Val Ser Met Leu
-20                 -15                 -10                  -5

Val Thr Gln Gly Leu Val Tyr Gln Gly Tyr Leu Ala Ala Asn Ser Arg
                  1                   5                  10

Phe Gly Ser Leu Pro Lys Val Ala Leu Ala Gly Leu Leu Gly Phe Gly
         15                  20                  25

Leu Gly Lys Val Ser Tyr Ile Gly Val Cys Gln Ser Lys Phe His Phe
         30                  35                  40

Phe Glu Asp Gln Leu Arg Gly Ala Gly Phe Gly Pro Gln His Asn Arg
 45                  50                  55                  60

His Cys Leu Leu Thr Cys Glu Cys Lys Ile Lys His Gly Leu Ser
                 65                  70                  75

Glu Lys Gly Asp Ser Gln Pro Ser Ala Ser
             80                  85
```

-continued

```
<210> SEQ ID NO 222
<211> LENGTH: 99
<212> TYPE: PRT
<213> ORGANISM: Homo sapiens

<400> SEQUENCE: 222

Met Lys Val Glu Glu His Thr Asn Ala Ile Gly Thr Leu His Gly
1               5                  10                  15

Gly Leu Thr Ala Thr Leu Val Asp Asn Ile Ser Thr Met Ala Leu Leu
            20                  25                  30

Cys Thr Glu Arg Gly Ala Pro Gly Val Ser Val Asp Met Asn Ile Thr
            35                  40                  45

Tyr Met Ser Pro Ala Lys Leu Gly Glu Asp Ile Val Ile Thr Ala His
        50                  55                  60

Val Leu Lys Gln Gly Lys Thr Leu Ala Phe Thr Ser Val Gly Leu Thr
65                  70                  75                  80

Asn Lys Ala Thr Gly Lys Leu Ile Ala Gln Gly Arg His Thr Lys His
                85                  90                  95

Leu Gly Asn

<210> SEQ ID NO 223
<211> LENGTH: 43
<212> TYPE: PRT
<213> ORGANISM: Homo sapiens
<220> FEATURE:
<221> NAME/KEY: SIGNAL
<222> LOCATION: -24..-1

<400> SEQUENCE: 223

Met Gln Cys Phe Ser Phe Ile Lys Thr Met Met Ile Leu Phe Asn Leu
                -20                 -15                 -10

Leu Ile Phe Leu Cys Gly Phe Thr Asn Tyr Thr Asp Phe Glu Asp Ser
            -5                   1                   5

Pro Tyr Phe Lys Met His Lys Pro Val Thr Met
        10                  15

<210> SEQ ID NO 224
<211> LENGTH: 69
<212> TYPE: PRT
<213> ORGANISM: Homo sapiens
<220> FEATURE:
<221> NAME/KEY: SIGNAL
<222> LOCATION: -21..-1

<400> SEQUENCE: 224

Met Trp Trp Phe Gln Gln Gly Leu Ser Phe Leu Pro Ser Ala Leu Val
    -20                 -15                 -10

Ile Trp Thr Ser Ala Ala Phe Ile Phe Ser Tyr Ile Thr Ala Val Thr
-5                   1                   5                  10

Leu His His Ile Asp Pro Ala Leu Pro Tyr Ile Ser Asp Thr Gly Thr
                15                  20                  25

Val Ala Pro Glu Lys Cys Leu Phe Gly Ala Met Leu Asn Ile Ala Ala
            30                  35                  40

Val Leu Cys Gln Lys
    45

<210> SEQ ID NO 225
<211> LENGTH: 78
<212> TYPE: PRT
<213> ORGANISM: Homo sapiens
<220> FEATURE:
```

```
<221> NAME/KEY: SIGNAL
<222> LOCATION: -18..-1

<400> SEQUENCE: 225
```

Met Ser Pro Gly Ser Ala Leu Ala Leu Leu Trp Ser Leu Pro Ala Ser
              -15               -10                -5

Asp Leu Gly Arg Ser Val Ile Ala Gly Leu Trp Pro His Thr Gly Val
  1               5                  10

Leu Ile His Leu Glu Thr Ser Gln Ser Phe Leu Gln Gly Gln Leu Thr
 15              20                  25                      30

Lys Ser Ile Phe Pro Leu Cys Cys Thr Ser Leu Phe Cys Val Cys Val
             35                  40                  45

Val Thr Val Gly Gly Gly Arg Val Gly Ser Thr Phe Val Ala
             50                  55                  60

```
<210> SEQ ID NO 226
<211> LENGTH: 80
<212> TYPE: PRT
<213> ORGANISM: Homo sapiens
<220> FEATURE:
<221> NAME/KEY: SIGNAL
<222> LOCATION: -47..-1

<400> SEQUENCE: 226
```

Met Arg Leu Pro Pro Ala Leu Pro Ser Gly Tyr Thr Asp Ser Thr Ala
         -45              -40              -35

Leu Glu Gly Leu Val Tyr Tyr Leu Asn Gln Lys Leu Leu Phe Ser Ser
     -30              -25              -20

Pro Ala Ser Ala Leu Leu Phe Phe Ala Arg Pro Cys Val Phe Cys Phe
-15              -10               -5                        1

Lys Ala Ser Lys Met Gly Pro Gln Phe Glu Asn Tyr Pro Thr Phe Pro
         5                  10               15

Thr Tyr Ser Pro Leu Pro Ile Pro Phe Gln Leu His Gly Arg Phe
         20                  25                  30

```
<210> SEQ ID NO 227
<211> LENGTH: 241
<212> TYPE: PRT
<213> ORGANISM: Homo sapiens
<220> FEATURE:
<221> NAME/KEY: SIGNAL
<222> LOCATION: -103..-1

<400> SEQUENCE: 227
```

Met Trp Leu Asp Pro Val Phe Pro Leu Phe Pro Val Gly Asp His Tyr
         -100             -95              -90

Leu Pro His Leu His Met Asp Val Leu Glu Gly Leu Ile Leu Val Leu
         -85              -80              -75

Pro Cys Ile Asp Val Phe Val Lys Val Asp Leu Arg Thr Val Thr Cys
         -70              -65              -60

Asn Ile Pro Pro Gln Glu Ile Leu Thr Arg Asp Ser Val Thr Thr Gln
-55              -50                  -45                      -40

Val Asp Gly Val Val Tyr Tyr Arg Ile Tyr Ser Ala Val Ser Ala Val
             -35                  -30                  -25

Ala Asn Val Asn Asp Val His Gln Ala Thr Phe Leu Leu Ala Gln Thr
             -20                  -15                  -10

Thr Leu Arg Asn Val Leu Gly Thr Gln Thr Leu Ser Gln Ile Leu Ala
         -5                   1                   5

Gly Arg Glu Glu Ile Ala His Ser Ile Gln Thr Leu Leu Asp Asp Ala

```
              10                 15                 20                 25

Thr Glu Leu Trp Gly Ile Arg Val Ala Arg Val Glu Ile Lys Asp Val
                        30                  35                  40

Arg Ile Pro Val Gln Leu Gln Arg Ser Met Ala Ala Glu Ala Glu Ala
                        45                  50                  55

Thr Arg Glu Ala Arg Ala Lys Val Leu Ala Ala Glu Gly Glu Met Asn
                60                  65                  70

Ala Ser Lys Ser Leu Lys Ser Ala Ser Met Val Leu Ala Glu Ser Pro
        75                  80                  85

Ile Ala Leu Gln Leu Arg Tyr Leu Gln Thr Leu Ser Thr Val Ala Thr
        90                  95                 100                 105

Glu Lys Asn Ser Thr Ile Val Phe Pro Leu Pro Met Asn Ile Leu Glu
                       110                 115                 120

Gly Ile Gly Gly Val Ser Tyr Asp Asn His Lys Lys Leu Pro Asn Lys
                       125                 130                 135

Ala

<210> SEQ ID NO 228
<211> LENGTH: 560
<212> TYPE: DNA
<213> ORGANISM: Homo sapiens
<220> FEATURE:
<221> NAME/KEY: CDS
<222> LOCATION: (11)..(439)
<221> NAME/KEY: polyA_site
<222> LOCATION: (547)..(560)
<221> NAME/KEY: polyA_signal
<222> LOCATION: (530)..(535)

<400> SEQUENCE: 228
cagaacaatc atg tct gac tcc ctg gtg gtg tgc gag gta gac cca gag          49
           Met Ser Asp Ser Leu Val Val Cys Glu Val Asp Pro Glu
             1               5                  10 cta aca gaa aag ctg agg aaa ttc cgc ttc cga aaa gag aca gac aat         97
Leu Thr Glu Lys Leu Arg Lys Phe Arg Phe Arg Lys Glu Thr Asp Asn
 15                  20                  25 gca gcc atc ata atg aag gtg gac aaa gac cgg cag atg gtg gtg ctg        145
Ala Ala Ile Ile Met Lys Val Asp Lys Asp Arg Gln Met Val Val Leu
 30                  35                  40                  45 gag gaa gaa ttt cgg aac att tcc cca gag gag ctc aaa atg gag ttg        193
Glu Glu Glu Phe Arg Asn Ile Ser Pro Glu Glu Leu Lys Met Glu Leu
                 50                  55                  60 ccg gag aga cag ccc agg ttc gtg gtt tac agc tac aag tac gtg cgt        241
Pro Glu Arg Gln Pro Arg Phe Val Val Tyr Ser Tyr Lys Tyr Val Arg
             65                  70                  75 gac gat ggc cga gtg tcc tac cct ttg tgt ttc atc ttc tcc agc cct        289
Asp Asp Gly Arg Val Ser Tyr Pro Leu Cys Phe Ile Phe Ser Ser Pro
         80                  85                  90 gtg ggc tgc aag ccg gaa caa cag atg atg tat gca ggg agt aaa aac        337
Val Gly Cys Lys Pro Glu Gln Gln Met Met Tyr Ala Gly Ser Lys Asn
 95                 100                 105 agg ctg gtg cag aca gca gag ctc aca aag gtg ttc gaa atc cgc acc        385
Arg Leu Val Gln Thr Ala Glu Leu Thr Lys Val Phe Glu Ile Arg Thr
110                 115                 120                 125 act gat gac ctc act gag gcc tgg ctc caa gaa aag ttg tct ttc ttt        433
Thr Asp Asp Leu Thr Glu Ala Trp Leu Gln Glu Lys Leu Ser Phe Phe
                130                 135                 140 cgt tga tctctgggct ggggactgaa ttcctgatgt ctgagtcctc aaggtgactg         489
Arg
```

-continued

```
gggacttgga acccctagga cctgaacaac caagacttta aataaatttt aaaatgcaaa    549
aaaaaaaaaa a                                                        560
```

<210> SEQ ID NO 229
<211> LENGTH: 142
<212> TYPE: PRT
<213> ORGANISM: Homo sapiens

<400> SEQUENCE: 229

```
Met Ser Asp Ser Leu Val Val Cys Glu Val Asp Pro Glu Leu Thr Glu
1               5                   10                  15

Lys Leu Arg Lys Phe Arg Phe Arg Lys Glu Thr Asp Asn Ala Ala Ile
            20                  25                  30

Ile Met Lys Val Asp Lys Asp Arg Gln Met Val Val Leu Glu Glu Glu
        35                  40                  45

Phe Arg Asn Ile Ser Pro Glu Glu Leu Lys Met Glu Leu Pro Glu Arg
    50                  55                  60

Gln Pro Arg Phe Val Val Tyr Ser Tyr Lys Tyr Val Arg Asp Asp Gly
65                  70                  75                  80

Arg Val Ser Tyr Pro Leu Cys Phe Ile Phe Ser Ser Pro Val Gly Cys
                85                  90                  95

Lys Pro Glu Gln Gln Met Met Tyr Ala Gly Ser Lys Asn Arg Leu Val
            100                 105                 110

Gln Thr Ala Glu Leu Thr Lys Val Phe Glu Ile Arg Thr Thr Asp Asp
        115                 120                 125

Leu Thr Glu Ala Trp Leu Gln Glu Lys Leu Ser Phe Phe Arg
    130                 135                 140
```

CLAUDIN-50 PROTEIN

RELATED U.S. APPLICATION DATA

The present application is a continuation-in-part of U.S. application Ser. No. 09/191,997 filed Nov. 13, 1998 (now abandoned), and claims priority from U.S. Provisional Patent Application Ser. No. 60/066,677, filed Nov. 13, 1997, U.S. Provisional Patent Application Ser. No. 60/069,957, filed Dec. 17, 1997; U.S. Provisional Patent Application Ser. No. 60/074,121, filed Feb. 9, 1998; U.S. Provisional Patent Application Ser. No. 60/081,563, filed Apr. 13, 1998; U.S. Provisional Patent Application Ser. No. 60/096,116, filed Aug. 10, 1998; and U.S. Provisional Patent Application Ser. No. 60/099,273, filed Sep. 4, 1998, the entireties of which are hereby incoporated by reference.

BACKGROUND OF THE INVENTION

The estimated 50,000–100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized. Cloning vectors such as yeast artificial chromosomes (YACs) and bacterial artificial chromosomes (BACs) are able to accept DNA inserts ranging from 300 to 1000 kilobases (kb) or 100–400 kb in length respectively, thereby facilitating the manipulation and ordering of DNA sequences distributed over great distances on the human chromosomes. Automated DNA sequencing machines permit the rapid sequencing of human genes. Bioinformatics software enables the comparison of nucleic acid and protein sequences, thereby assisting in the characterization of human gene products.

Currently, two different approaches are being pursued for identifying and characterizing the genes distributed along the human genome. In one approach, large fragments of genomic DNA are isolated, cloned, and sequenced. Potential open reading frames in these genomic sequences are identified using bio-informatics software. However, this approach entails sequencing large stretches of human DNA which do not encode proteins in order to find the protein encoding sequences scattered throughout the genome. In addition to requiring extensive sequencing, the bio-informatics software may mischaracterize the genomic sequences obtained. Thus, the software may produce false positives in which non-coding DNA is mischaracterized as coding DNA or false negatives in which coding DNA is mislabeled as non-coding DNA.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding portions of the genome. Often, only short stretches of the cDNAs are sequenced to obtain sequences called expressed sequence tags (ESTs). The ESTs may then be used to isolate or purify extended cDNAs which include sequences adjacent to the EST sequences. The extended cDNAs may contain all of the sequence of the EST which was used to obtain them or only a portion of the sequence of the EST which was used to obtain them. In addition, the extended cDNAs may contain the full coding sequence of the gene from which the EST was derived or, alternatively, the extended cDNAs may include portions of the coding sequence of the gene from which the EST was derived. It will be appreciated that there may be several extended cDNAs which include the EST sequence as a result of alternate splicing or the activity of alternative promoters.

In the past, the short EST sequences which could be used to isolate or purify extended cDNAs were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs. (Adams et al., Nature 377:174, 1996, Hillier et al., Genome Res. 6:807–828, 1996).

In addition, in those reported instances where longer cDNA sequences have been obtained, the reported sequences typically correspond to coding sequences and do not include the full 5' untranslated region of the mRNA from which the cDNA is derived. Such incomplete sequences may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs which can be used to obtain extended cDNAs which may include the 5' sequences contained in the 5' ESTs.

While many sequences derived from human chromosomes have practical applications, approaches based on the identification and characterization of those chromosomal sequences which encode a protein product are particularly relevant to diagnostic and therapeutic uses. Of the 50,000–100,000 protein coding genes, those genes encoding proteins which are secreted from the cell in which they are synthesized, as well as the secreted proteins themselves, are particularly valuable as potential therapeutic agents. Such proteins are often involved in cell to cell communication and may be responsible for producing a clinically relevant response in their target cells.

In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy induced neutropenia and multiple sclerosis. For these reasons, extended cDNAs encoding secreted proteins or portions thereof represent a particularly valuable source of therapeutic agents. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. This may prove beneficial in gene therapy strategies in which it is desired to deliver a particular gene product to cells other than the cell in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' portions of the genes for secretory proteins which encode signal peptides.

Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross, S. H. et al., Purification of CpG Islands using a Methylated DNA Binding Column, Nature Genetics 6: 236–244 (1994)). The second consists of isolating human genomic DNA sequences containing SpeI binding sites by the use of SpeI binding protein. (Mortlock et al., Genome Res. 6:327–335, 1996). Both of these approaches have their limits due to a lack of specificity or of comprehensiveness.

5' ESTs and extended cDNAs obtainable therefrom may be used to efficiently identify and isolate upstream regulatory regions which control the location, developmental stage, rate, and quantity of protein synthesis, as well as the stability of the mRNA. Theil et al., BioFactors 4:87–93 (1993). Once identified and characterized, these regulatory regions may be utilized in gene therapy or protein purification schemes to obtain the desired amount and locations of protein synthesis or to inhibit, reduce, or prevent the synthesis of undesirable gene products.

In addition, ESTs containing the 5' ends of secretory protein genes or extended cDNAs which include sequences adjacent to the sequences of the ESTs may include sequences useful as probes for chromosome mapping and the identification of individuals. Thus, there is a need to identify and characterize the sequences upstream of the 5' coding sequences of genes encoding secretory proteins.

SUMMARY OF THE INVENTION

The present invention relates to purified, isolated, or recombinant cDNAs which encode secreted proteins or fragments thereof. Preferably, the purified, isolated or recombinant cDNAs contain the entire open reading frame of their corresponding mRNAs, including a start codon and a stop codon. For example, the cDNAs may include nucleic acids encoding the signal peptide as well as the mature protein. Such cDNAs will be referred herein as "full-length" cDNAs. Alternatively, the cDNAs may contain a fragment of the open reading frame. Such cDNAs will be referred herein as "ESTs" or "5' EST". In some embodiments, the fragment may encode only the sequence of the mature protein. Alternatively, the fragment may encode only a fragment of the mature protein. A further aspect of the present invention is a nucleic acid which encodes the signal peptide of a secreted protein.

The present extended cDNAs were obtained using ESTs which include sequences derived from the authentic 5' ends of their corresponding mRNAs. As used herein the terms "EST" or "5' EST" refer to the short cDNAs which were used to obtain the extended cDNAs of the present invention. As used herein, the term "extended cDNA" refers to the cDNAs which include sequences adjacent to the 5' EST used to obtain them. The extended cDNAs may contain all or a portion of the sequence of the EST which was used to obtain them. The term "corresponding mRNA" refers to the mRNA which was the template for the cDNA synthesis which produced the 5' EST. As used herein, the term "purified" does not require absolute purity; rather, it is intended as a relative definition. Individual extended cDNA clones isolated from a cDNA library have been conventionally purified to electrophoretic homogeneity. The sequences obtained from these clones could not be obtained directly either from the library or from total human DNA. The extended cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$–$10^6$ fold purification of the native message. Purification of starting material or natural material to at least one order of magnitude, preferably two or three orders, and more preferably four or five orders of magnitude is expressly contemplated.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

The term "isolated" requires that the material be removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. Specifically excluded from the definition of "isolated" are: naturally occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either in an vitro heterogeneous preparation or plated as a heterogeneous population of single colonies, and/or further wherein the polynucleotide of the present invention makes up less than 5% (or alternatively 1%, 2%, 3%, 4%, 10%, 25%, 50%, 75%, or 90% 95%, or 99%) of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as an in vitro preparation, still further excluded are the above chromosomes, libraries and preparations as a heterogeneous mixture separated by electrophoresis (including blot transfers of the same) wherein the polynucleotide of the invention have not been further separated from the heterologous polynucleotides in the electrophoresis transfer medium (e.g., further separating by excising a single band from a heterogeneous band population in an agarose gel or nylon blot). Likewise, heterogeneous mixtures of polypeptides separated by electrophoresis (including blot transfers of the same) wherein the polypeptides of the invention has not been further separated from the heterologous polypeptides in the electrophoresis transfer medium.

Thus, cDNAs encoding secreted polypeptides or fragments thereof which are present in cDNA libraries in which one or more cDNAs encoding secreted polypeptides or fragments thereof make up 5% or more of the number of nucleic acid inserts in the backbone molecules are "enriched recombinant cDNAs" as defined herein. Likewise, cDNAs encoding secreted polypeptides or fragments thereof which are in a population of plasmids in which one or more cDNAs of the present invention have been inserted such that they represent 5% or more of the number of inserts in the plasmid backbone are "enriched recombinant cDNAs" as defined herein. However, cDNAs encoding secreted polypeptides or fragments thereof which are in cDNA libraries in which the cDNAs encoding secreted polypeptides or fragments thereof constitute less than 5% of the number of nucleic acid inserts in the population of backbone molecules, such as libraries in which backbone molecules having a cDNA insert encoding a secreted polypeptide are extremely rare, are not "enriched recombinant cDNAs."

As used herein, the term "recombinant" means that the extended cDNA is adjacent to "backbone" nucleic acid to which it is not adjacent in its natural environment. Additionally, to be "enriched" the extended cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched extended cDNAs represent 15% or more of the number of nucleic acid inserts in the population of recombinant backbone molecules. More preferably, the enriched extended cDNAs represent 50% or more of the number of nucleic acid inserts in the population of recombinant backbone molecules. In a highly preferred embodiment, the enriched extended cDNAs represent 90% or more of the number of nucleic acid inserts in the population of recombinant backbone molecules. "Stringent", "moderate," and "low" hybridization conditions are as defined in Example 29.

The term "polypeptide" refers to a polymer of amino acids without regard to the length of the polymer; thus, "peptides," "oligopeptides", and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12, 1983; Seifter et al., Meth Enzymol 182:626–646, 1990; Rattan et al., Ann NY Acad Sci 663:48–62, 1992). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. The term "polypeptide" may also be used interchangeably with the term "protein".

As used interchangeably herein, the terms "nucleic acid molecule", "oligonucleontides", and "polynucleotides" include RNA or, DNA (either single or double stranded, coding, non-coding, complementary or antisense), or RNA/ DNA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications (a) an alternative linking group, (b) an analogous form of purine, (c) an analogous form of pyrimidine, or (d) an analogous sugar; for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid(v)ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. Nos. 5,610,289 or 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198.

In specific embodiments, the polynucleotides of the invention are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron, or any specified intron(s). In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 genomic flanking or overlapping gene(s) (or heterologous ORFs).

The polynucleotide sequences of the invention may be prepared by any known method, including synthetic, recombinant, ex vivo generation, or a combination thereof, as well as utilizing any purification methods known in the art.

The terms "comprising", "consisting of" and "consisting essentially of" may be interchanged for one another throughout the instant application". The term "having" has the same meaning as "comprising" and may be replaced with either the term "consisting of" or "consisting essentially of".

"Stringent", "moderate," and "low" hybridization conditions are as defined below.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., Biochemistry, $4^{th}$ edition, 1995).

The terms "complementary" or "complement thereof" are used herein to refer to the sequences of polynucleotides which are capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide," "complementary nucleic acid" and "complementary nucleotide sequence" . These terms are applied to pairs of polynucleotides based solely upon their sequences and not any particular set of conditions under which the two polynucleotides would actually bind. Preferably, a "complementary" sequence is a sequence which an A at each position where there is a T on the opposite strand, a T at each position where there is an A on the opposite strand, a G at each position where there is a C on the opposite strand and a C at each position where there is a G on the opposite strand.

The term "allele" is used herein to refer to variants of a nucleotide sequence. A biallelic polymorphism has two forms. Diploid organisms may be homozygous or heterozygous for an allelic form. Unless otherwise specified, the polynucleotides of the present invention encompass all allelic variants of the disclosed polynucleotides.

The term "upstream" is used herein to refer to a location that is toward the 5' end of the polynucleotide from a specific reference point.

As used herein, the term "non-human animal" refers to any non-human vertebrate animal, including insects, birds, rodents and more usually mammals. Preferred non-human animals include: primates; farm animals such as swine, goats, sheep, donkeys, cattle, horses, chickens, rabbits; and rodents, more preferably rats or mice. As used herein, the term "animal" is used to refer to any species in the animal kingdom, preferably vertebrates, including birds and fish, and more preferable a mammal. Both the terms "animal" and "mammal" expressly embrace human subjects unless preceded with the term "non-human".

The terms "vertebrate nucleic acid" and "vertebrate polypeptide" are used herein to refer to any nucleic acid or polypeptide respectively which are derived from a vertebrate species including birds and more usually mammals, preferably primates such as humans, farm animals such as swine, goats, sheep, donkeys, and horses, rabbits or rodents, more preferably rats or mice. As used herein, the term "vertebrate" is used to refer to any vertebrate, preferably a mammal. The term "vertebrate" expressly embraces human subjects unless preceded with the term "non-human".

"Stringent", "moderate," and "low" hybridization conditions are as defined below.

The term "capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo(dT) primers and hybridizing them to mRNA to subsequently prime the reverse transcription of said hybridized mRNA to generate a first cDNA strand are well known to those skilled in the art and are described in Current Protocols in Molecular Biology, John Wiley and Sons, Inc. 1997 and Sambrook et al., Molecular Cloning: A Laboratory Manual, Second Edition, Cold Spring Harbor Laboratory Press, 1989, the entire disclosures of which are incorporated herein by reference. Preferably, said oligo(dT) primers are present in a large excess in order to allow the hybridization of all mRNA 3' ends to at least one oligo(dT) molecule. The priming and reverse transcription step are preferably performed between 37° C. and 55° C. depending on the type of reverse transcriptase used.

Preferred oligo(dT) primers for priming reverse transcription of mRNAs are oligonucleotides containing a stretch of thymidine residues of sufficient length to hybridize specifically to the polyA tail of mRNAs, preferably of 12 to 18 thymidine residues in length. More preferably, such oligo(T) primers comprise an additional sequence upstream of the poly(dT) stretch in order to allow the addition of a given sequence to the 5' end of all first cDNA strands which may then be used to facilitate subsequent manipulation of the cDNA. Preferably, this added sequence is 8 to 60 residues in length. For instance, the addition of a restriction site in 5' of cDNAs facilitates subcloning of the obtained cDNA. Alternatively, such an added 5' end may also be used to design primers of PCR to specifically amplify cDNA clones of interest.

In particular, the some sequences of the present invention relate to cDNAs which were derived from genes encoding secreted proteins. As used herein, a "secreted" protein is one which, when expressed in a suitable host cell, is transported across or through a membrane, including transport as a result of signal peptides in its amino acid sequence. "Secreted" proteins include without limitation proteins secreted wholly (e.g. soluble proteins), or partially (e.g. receptors) from the cell in which they are expressed. "Secreted" proteins also include without limitation proteins which are transported across the membrane of the endoplasmic reticulum.

cDNAs encoding secreted proteins may include nucleic acid sequences, called signal sequences, which encode signal peptides which direct the extracellular secretion of the proteins encoded by the cDNAs. Generally, the signal peptides are located at the amino termini of secreted proteins. Polypeptides comprising these signal peptides (as delineated in the sequence listing), and polynucleotides encoding the same, are preferred embodiments of the present invention.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The cDNAs of the present invention have several important applications. For example, they may be used to express the entire secreted protein which they encode. Alternatively, they may be used to express fragments of the secreted protein. The fragments may comprise the signal peptides encoded by the cDNAs or the mature proteins encoded by the cDNAs (i.e. the proteins generated when the signal peptide is cleaved off). The cDNAs and fragments thereof also have important applications as polynucleotides. For example, the cDNAs of the sequence listing and fragments thereof, may be used to distinguish human tissues/cells from non-human tissues/cells and to distinguish between human tissues/cells that do and do not express the polynucleotides comprising the cDNAs. By knowing the tissue expression pattern of the cDNAs, either through routine experimentation or by using the instant disclosure, the polynucleotides of the present invention may be used in methods of determining the identity of an unknown tissue/cell sample. As part of determining the identity of an unknown tissue/cell sample, the polynucleotides of the present invention may be used to determine what the unknown tissue/cell sample is and what the unknown sample is not. For example, if a cDNA is expressed in a particular tissue/cell type, and the unknown tissue/cell sample does not express the cDNA, it may be inferred that the unknown tissue/cells are either not human or not the same human tissue/cell type as that which expresses the cDNA. These methods of determining tissue/cell identity are based on methods which detect the presence or absence of the mRNA (or corresponding cDNA) in a tissue/cell sample using methods well know in the art (e.g., hybridization or PCR based methods).

In other useful applications, fragments of the cDNAs encoding signal peptides as well as degenerate polynucleotides encoding the same, may be ligated to sequences encoding either the polypeptide from the same gene or to sequences encoding a heterologous polypeptide to facilitate secretion.

Antibodies which specifically recognize the entire secreted proteins encoded by the cDNAs or fragments thereof having at least 6 consecutive amino acids, 8 consecutive amino acids, 10 consecutive amino acids, at least 15 consecutive amino acids, at least 25 consecutive amino acids, or at least 40 consecutive amino acids may also be obtained as described below. Antibodies which specifically recognize the mature protein generated when the signal peptide is cleaved may also be obtained as described below. Similarly, antibodies which specifically recognize the signal peptides encoded by the cDNAs may also be obtained.

In some embodiments, the cDNAs include the signal sequence. In other embodiments, the cDNAs may include the full coding sequence for the mature protein (i.e. the protein generated when the signal polypeptide is cleaved off). In addition, the cDNAs may include regulatory regions upstream of the translation start site or downstream of the stop codon which control the amount, location, or developmental stage of gene expression. As discussed above, secreted proteins are therapeutically important. Thus, the proteins expressed from the cDNAs may be useful in treating or controlling a variety of human conditions. The cDNAs may also be used to obtain the corresponding genomic DNA. The term "corresponding genomic DNA" refers to the genomic DNA which encodes mRNA which includes the sequence of one of the strands of the cDNA in which thymidine residues in the sequence of the cDNA are replaced by uracil residues in the mRNA.

The cDNAs or genomic DNAs obtained therefrom may be used in forensic procedures to identify individuals or in diagnostic procedures to identify individuals having genetic diseases resulting from abnormal expression of the genes corresponding to the cDNAs. In addition, the present invention is useful for constructing a high resolution map of the human chromosomes.

The present invention also relates to secretion vectors capable of directing the secretion of a protein of interest. Such vectors may be used in gene therapy strategies in which it is desired to produce a gene product in one cell which is to be delivered to another location in the body. Secretion vectors may also facilitate the purification of desired proteins.

The present invention also relates to expression vectors capable of directing the expression of an inserted gene in a desired spatial or temporal manner or at a desired level. Such vectors may include sequences upstream of the cDNAs such as promoters or upstream regulatory sequences.

In addition, the present invention may also be used for gene therapy to control or treat genetic diseases. Signal peptides may also be fused to heterologous proteins to direct their extracellular secretion.

One embodiment of the present invention is a purified or isolated nucleic acid comprising the sequence of one of SEQ ID NOs: 134–180 or a sequence complementary thereto, allelic variants thereof, and degenerate variants thereof. In one aspect of this embodiment, the nucleic acid is recombinant.

Another embodiment of the present invention is a purified or isolated nucleic acid comprising at least 8 consecutive bases of the sequence of one of SEQ ID NOs: 134–180, 228 or one of the sequences complementary thereto, allelic variants thereof, and degenerate variants thereof. In one aspect of this embodiment, the nucleic acid comprises at least 10, 12, 15, 18, 20, 25, 28, 30, 35, 40, 50, 75, 100, 150, 200, 300, 400, 500, 1000 or 2000 consecutive bases of one of the sequences of SEQ ID NOs: 134–180, 228 or one of the sequences complementary thereto, allelic variants thereof, and degenerate variants thereof. The nucleic acid may be a recombinant nucleic acid. In addition to the above preferred nucleic acid sizes, further preferred sub-genuses of nucleic acids comprise at least 8 nucleotides, wherein "at least 8" is defined as any integer between 8 and the integer representing the 3' most nucleotide position as set forth in the sequence listing or elsewhere herein. Further included as preferred polynucleotides of the present invention are nucleic acid fragments at least 8 nucleotides in length, as described above, that are further specified in terms of their 5' and 3' position. The 5' and 3' positions are represented by the position numbers set forth in the sequence listing below. For allelic degenerate variants and cDNAs deposits, position 1 is defined as the 5' most nucleotide of the ORF, i.e., the nucleotide "A" of the start codon with the remaining nucleotides numbered consecutively. Therefore, every combination of a 5' and 3' nucleotide position that a polynucleotide fragment of the present invention, at least 8 contiguous nucleotides in length, could occupy is included in the invention as an individual specie. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 8, and where "y" equals an integer between 9 and the number of nucleotides of the polynucleotide sequence of the present invention; and where "x" is an integer smaller then "y" by at least 8.

The present invention also provides for the exclusion of any species of polynucleotide fragments of the present invention specified by 5' and 3' positions or sub-genuses of polynucleotides specified by size in nucleotides as described above. Any number of fragments specified by 5' and 3' positions or by size in nucleotides, as described above, may be excluded from the present invention.

Another embodiment of the present invention is a vertebrate purified or isolated nucleic acid of at least 15, 18, 20, 23, 25, 28, 30, 35, 40, 50, 75, 100, 200, 300, 500 or 1000 nucleotides in length which hybridizes under stringent conditions to the sequence of one of SEQ ID NOs: 134–180, 228 or a sequence complementary to one of the sequences of SEQ ID NOs: 134–180 on 228. In one aspect of this embodiment, the nucleic acid is recombinant.

Another embodiment of the present invention is a purified or isolated nucleic acid comprising the full coding sequences of one of SEQ ID NOs: 134–180, 228 or an allelic variant thereof, wherein the full coding sequence optionally comprises the sequence encoding signal peptide as well as the sequence encoding mature protein. In one aspect of this embodiment, the nucleic acid is recombinant.

A further embodiment of the present invention is a purified or isolated nucleic acid comprising the nucleotides of one of SEQ ID NOs: 134–180 or 228, or an allelic variant thereof which encode a mature protein. In one aspect of this embodiment, the nucleic acid is recombinant. In another aspect of this embodiment, the nucleic acid is an expression vector wherein said nucleotides of one of SEQ ID NOs: 134–180 or 228, or an allelic variant thereof which encode a mature protein, are operably linked to a promoter.

Yet another embodiment of the present invention is a purified or isolated nucleic acid comprising the nucleotides of one of SEQ ID NOs: 134–180 or 228, or an allelic variant thereof, which encode the signal peptide. In one aspect of this embodiment, the nucleic acid is recombinant. In another aspect of this embodiment, the nucleic acid is an fusion vector wherein said nucleotides of one of SEQ ID NOs: 134–180 or 228, or an allelic variant thereof which encode the signal peptide, are operably linked to a second nucleic acid encoding an heterologous polypeptide.

Another embodiment of the present invention is a purified or isolated nucleic acid encoding a polypeptide comprising the sequence of one of the sequences of SEQ ID NOs: 181–227 or 229, or allelic variant thereof. In one aspect of this embodiment, the nucleic acid is recombinant.

Another embodiment of the present invention is a purified or isolated nucleic acid encoding a polypeptide comprising the sequence of a mature protein included in one of the sequences of SEQ ID NOs: 181–227 or 229, or allelic variant thereof. In one aspect of this embodiment, the nucleic acid is recombinant.

Another embodiment of the present invention is a purified or isolated nucleic acid encoding a polypeptide comprising the sequence of a signal peptide included in one of the sequences of SEQ ID NOs: 181–227 or 229, or allelic variant thereof. In one aspect of this embodiment, the nucleic acid is recombinant. In another aspect it is present in a vector of the invention.

Further embodiments of the invention include isolated polynucleotides that comprise, a nucleotide sequence at least 70% identical, more preferably at least 75% identical, and still more preferably at least 80%, 85%, 90%, 95%, 96%, 97%, 98%, or 99% identical to any of the polynucleotides of the present invention. Methods of determining identity include those well known in the art and described herein.

Yet another embodiment of the present invention is a purified or isolated protein comprising the sequence of one of SEQ ID NOs: 181–227 or 229, or allelic variant thereof.

Another embodiment of the present invention is a purified or isolated polypeptide comprising at least 5 or 8 consecutive amino acids of one of the sequences of SEQ ID NOs: 181–227 or 229, In one aspect of this embodiment, the purified or isolated polypeptide comprises at least 10, 12, 15, 20, 25, 30, 35, 40, 50, 60, 75, 100, 150 or 200 consecutive amino acids of one of the sequences of SEQ ID NOs: 181–227 or 229.

In addition to the above polypeptide fragments, further preferred sub-genuses of polypeptides comprise at least 8 amino acids, wherein "at least 8" is defined as any integer between 8 and the integer representing the C-terminal amino acid of the polypeptide of the present invention including the polypeptide sequences of the sequence listing below. Further included are species of polypeptide fragments at least 8 amino acids in length, as described above, that are further specified in terms of their N-terminal and C-terminal positions. Preferred species of polypeptide fragments specified by their N-terminal and C-terminal positions include the signal peptides delineated in the sequence listing below. However, included in the present invention as individual species are all polypeptide fragments, at least 8 amino acids in length, as described above, and may be particularly specified by a N-terminal and C-terminal position. That is, every combination of a N-terminal and C-terminal position that a fragment at least 8 contiguous amino acid residues in length could occupy, on any given amino acid sequence of the sequence listing or of the present invention is included in the present invention.

The present invention also provides for the exclusion of any fragment species specified by N-terminal and C-terminal positions or of any fragment sub-genus specified by size in amino acid residues as described above. Any number of fragments specified by N-terminal and C-terminal positions or by size in amino acid residues as described above may be excluded as individual species.

The above polypeptide fragments of the present invention can be immediately envisaged using the above description and are therefore not individually listed solely for the purpose of not unnecessarily lengthening the specification. Moreover, the above fragments need not be active since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to detect the full length nature, and other forms in a biological sample or to distinguish between human and non-human cells and tissues or to determine whether cells or tissues in a biological sample are or are not of the same type which express the polypeptide of the present invention. Preferred polypeptide fragments of the present invention comprising a signal peptide may be used to facilitate secretion of either the polypeptide of the same gene or a heterologous polypeptide using methods well known in the art.

Another embodiment of the present invention is an isolated or purified polypeptide comprising a signal peptide of one of the polypeptides of SEQ ID NOs: 181–227 or 229.

Yet another embodiment of the present invention is an isolated or purified polypeptide comprising a mature protein of one of the polypeptides of SEQ ID NOs: 181–227 or 229.

Yet another embodiment of the present invention is an isolated or purified polypeptide comprising a full length polypeptide, mature protein, or signal peptide encoded by an allelic variant of the polynucleotides of the present invention.

A further embodiment of the present invention are polypeptides having an amino acid sequence with at least 70% similarity, and more preferably at least 75%, 80%, 85%, 90%, 95%, 96%, 97%, 98%, or 99% similarity to a polypeptide of the present invention, as well as polypeptides having an amino acid sequence at least 70% identical, more preferably at least 75% identical, and still more preferably 80%, 85%, 90%, 95%, 96%, 97%, 98%, or 99% identical to a polypeptide of the present invention. Further included in the invention are isolated nucleic acid molecules encoding such polypeptides. Methods for determining identity include those well known in the art and described herein.

A further embodiment of the present invention is a method of making a protein comprising one of the sequences of SEQ ID NO: 181–227 or 229, comprising the steps of obtaining a cDNA comprising one of the sequences of sequence of SEQ ID NO: 134–180 or 228, inserting the cDNA in an expression vector such that the cDNA is operably linked to a promoter, and introducing the expression vector into a host cell whereby the host cell produces the protein encoded by said cDNA. In one aspect of this embodiment, the method further comprises the step of isolating the protein.

Another embodiment of the present invention is a protein obtainable by the method described in the preceding paragraph.

Another embodiment of the present invention is a method of making a protein comprising the amino acid sequence of the mature protein contained in one of the sequences of SEQ ID NO: 181–227 or 229, comprising the steps of obtaining a cDNA comprising one of the nucleotides sequence of sequence of SEQ ID NO: 134–180 or 228 which encode for the mature protein, inserting the cDNA in an expression vector such that the cDNA is operably linked to a promoter, and introducing the expression vector into a host cell whereby the host cell produces the mature protein encoded by the cDNA. In one aspect of this embodiment, the method further comprises the step of isolating the protein.

Another embodiment of the present invention is a mature protein obtainable by the method described in the preceding paragraph.

Another embodiment of the present invention is a host cell containing the purified or isolated nucleic acids comprising the sequence of one of SEQ ID NOs: 134–180 or 228 or a sequence complementary thereto described herein.

Another embodiment of the present invention is a host cell containing the purified or isolated nucleic acids comprising the full coding sequences of one of SEQ ID NOs: 134–180 or 228, wherein the full coding sequence comprises the sequence encoding the signal peptide and the sequence encoding the mature protein described herein.

Another embodiment of the present invention is a host cell containing the purified or isolated nucleic acids comprising the nucleotides of one of SEQ ID NOs: 134–180 or 228 which encode a mature protein which are described herein.

Another embodiment of the present invention is a host cell containing the purified or isolated nucleic acids comprising the nucleotides of one of SEQ ID NOs: 134–180 or 228 which encode the signal peptide which are described herein.

Another embodiment of the present invention is a purified or isolated antibody capable of specifically binding to a protein comprising the sequence of one of SEQ ID NOs: 181–227 or 229. In one aspect of this embodiment, the antibody is capable of binding to a polypeptide comprising at least 6 consecutive amino acids, at least 8 consecutive amino acids, or at least 10 consecutive amino acids of the sequence of one of SEQ ID NOs: 181–227 or 229.

Another embodiment of the present invention is an array of cDNAs or fragments thereof of at least 15 nucleotides in length which includes at least one of the sequences of SEQ ID NOs: 134–180 or 228, or one of the sequences complementary to the sequences of SEQ ID NOs: 134–180 or 228, or a fragment thereof of at least 15 consecutive nucleotides. In one aspect of this embodiment, the array includes at least two of the sequences of SEQ ID NOs: 134–180 or 228, the sequences complementary to the sequences of SEQ ID NOs: 134–180 or 228, or fragments thereof of at least 15 consecutive nucleotides. In another aspect of this embodiment, the array includes at least five of the sequences of SEQ ID NOs: 134–180 or 228, the sequences complementary to the sequences of SEQ ID NOs: 134–180 or 228, or fragments thereof of at least 15 consecutive nucleotides.

A further embodiment of the invention encompasses purified polynucleotides comprising an insert from a clone deposited in ATCC accession No. 98619 or a fragment thereof comprising a contiguous span of at least 8, 10, 12, 15, 20, 25, 40, 60, 100, or 200 nucleotides of said insert. An additional embodiment of the invention encompasses purified polypeptides which comprise, consist of, or consist essentially of an amino acid sequence encoded by the insert from a clone deposited in ATCC accession No. 98619, as well as polypeptides which comprise a fragment of said amino acid sequence consisting of a signal peptide, a mature protein, or a contiguous span of at least 5, 8, 10, 12, 15, 20, 25, 40, 60, 100, or 200 amino acids encoded by said insert.

An additional embodiment of the invention encompasses purified polypeptides which comprise, consist of, or consist essentially of an amino acid sequence encoded by the insert from a clone deposited in an ATCC deposit, which contains the sequences of SEQ ID NOs. 2540 and 4246, having an accession No. 99061735 and named SignalTag 15061999 or deposited in an ATCC deposit having an accession No. 98121805 and named SignalTag 166-191, which contains SEQ ID NOs.: 47–73, as well as polypeptides which comprise a fragment of said amino acid sequence consisting of a signal peptide, a mature protein, or a contiguous span of at least 5, 8, 10, 12, 15, 20, 25, 30, 35, 40, 50, 60, 75, 100, 150 or 200 amino acids encoded by said insert.

An additional embodiment of the invention encompasses purified polypeptides which comprise a contiguous span of at least 5, 8, 10, 12, 15, 20, 25, 30, 35, 40, 50, 60, 75, 100, 150 or 200 amino acids of SEQ ID NOs: 181–227, wherein said contiguous span comprises at least one of the amino acid positions which was not shown to be identical to a public sequence in the instant application. Also encompassed by the invention are purified polynucleotides encoding said polypeptides.

Another embodiment of the present invention is a computer readable medium having stored thereon a sequence selected from the group consisting of a cDNA code of SEQ ID NOs. 134–180 or 228 and a polypeptide code of SEQ ID NOs. 181–227 or 229.

Another embodiment of the present invention is a computer system comprising a processor and a data storage device wherein the data storage device has stored thereon a sequence selected from the group consisting of a cDNA code of SEQ ID NOs. 134–180 or 228 and a polypeptide code of SEQ ID NOs. 181–227 or 229. In some embodiments the computer system further comprises a sequence comparer and a data storage device having reference sequences stored thereon. For example, the sequence comparer may comprise a computer program which indicates polymorphisms. In other aspects of the computer system, the system further comprises an identifier which identifies features in said sequence.

Another embodiment of the present invention is a method for comparing a first sequence to a reference sequence wherein the first sequence is selected from the group consisting of a cDNA code of SEQ ID NOs. 134–180 or 228 and a polypeptide code of SEQ ID NOs. 181–227 or 229 comprising the steps of reading the first sequence and the reference sequence through use of a computer program which compares sequences and determining differences between the first sequence and the reference sequence with the computer program. In some aspects of this embodiment, said step of determining differences between the first sequence and the reference sequence comprises identifying polymorphisms.

Another aspect of the present invention is a method for determining the level of identity between a first sequence and a reference sequence, wherein the first sequence is selected from the group consisting of a cDNA code of SEQ ID NOs. 134–180 or 228 and a polypeptide code of SEQ ID NOs. 181–227 or 229, comprising the steps of reading the first sequence and the reference sequence through the use of a computer program which determines identity levels and determining identity between the first sequence and the reference sequence with the computer program.

Another embodiment of the present invention is a method for identifying a feature in a sequence selected from the group consisting of a cDNA code of SEQ ID NOs. 134–180 or 228 and a polypeptide code of SEQ ID NOs. 181–227 or 229 comprising the steps of reading the sequence through the use of a computer program which identifies features in sequences and identifying features in the sequence with said computer program. In one aspect of this embodiment, the computer program comprises a computer program which identifies open reading frames. In a further embodiment, the computer program comprises a program that identifies linear or structural motifs in a polypeptide sequence.

BRIEF DESCRIPTION OF THE DRAWINGS

FIG. 2 is an analysis of the 43 amino terminal amino acids of all human SwissProt proteins to determine the frequency of false positives and false negatives using the techniques for signal peptide identification described herein.

FIG. 4 shows the distribution of 5' ESTs in each category and the number of 5' ESTs in each category having a given minimum von Heijne's score.

FIG. 5 shows the tissues from which the mRNAs corresponding to the 5' ESTs in each of the categories described herein were obtained.

FIG. 8 describes the transcription factor binding sites present in each of these promoters.

DETAILED DESCRIPTION OF THE PREFERRED EMBODIMENT

I. Obtaining 5' ESTs

Figure 1:
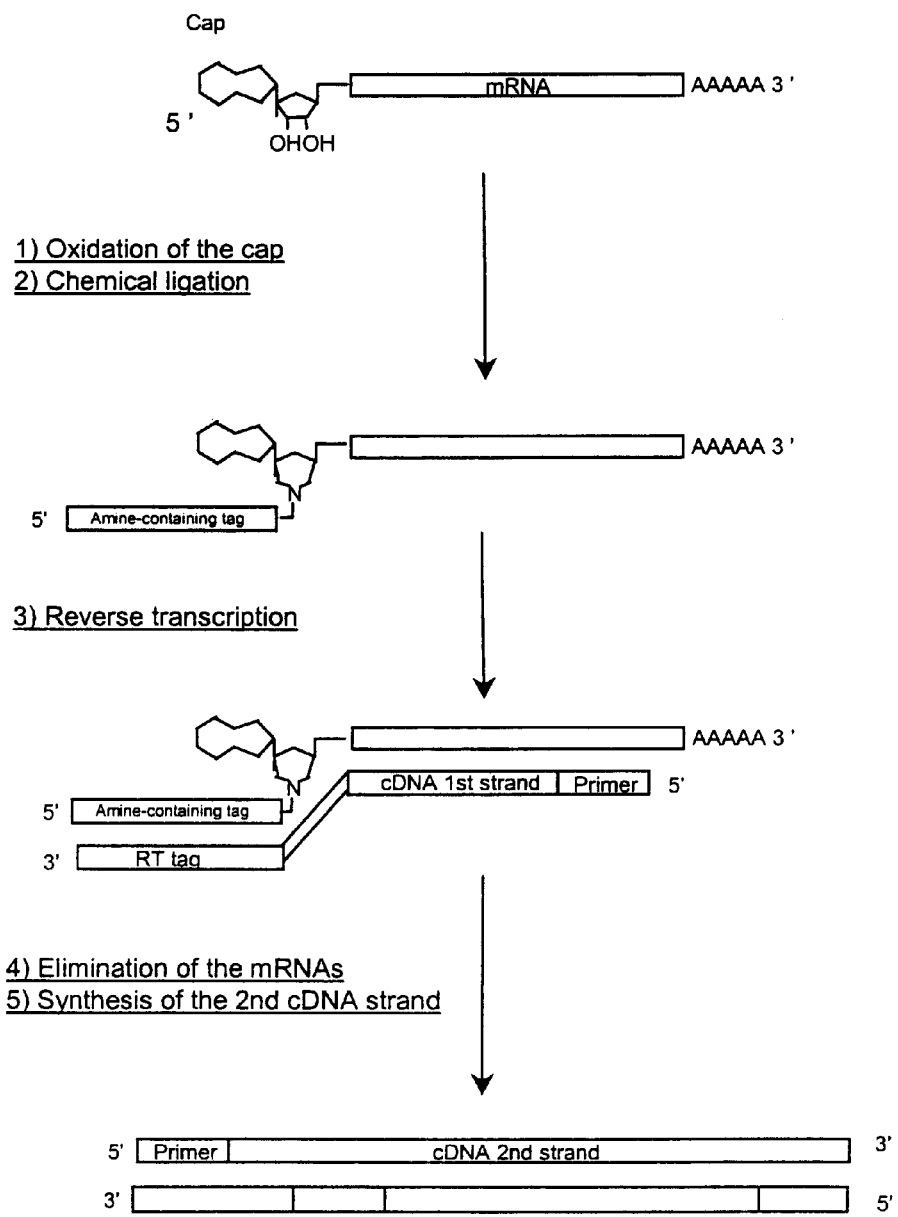
FIG. 1 is a summary of a procedure for obtaining cDNAs which have been selected to include the 5' ends of the mRNAs from which they are derived.

The present extended cDNAs were obtained using 5' ESTs which were isolated as described below.

A. Chemical Methods for Obtaining mRNAs Having Intact 5' Ends

In order to obtain the 5' ESTs used to obtain the extended cDNAs of the present invention, mRNAs having intact 5' ends must be obtained. Currently, there are two approaches for obtaining such mRNAs. One of these approaches is a chemical modification method involving derivatization of the 5' ends of the mRNAs and selection of the derivatized mRNAs. The 5' ends of eukaryotic mRNAs possess a structure referred to as a "cap" which comprises a guanosine methylated at the 7 position. The cap is joined to the first transcribed base of the mRNA by a 5',5'-triphosphate bond. In some instances, the 5' guanosine is methylated in both the 2 and 7 positions. Rarely, the 5' guanosine is trimethylated at the 2, 7 and 7 positions. In the chemical method for obtaining mRNAs having intact 5' ends, the 5' cap is specifically derivatized and coupled to a reactive group on an immobilizing substrate. This specific derivatization is based on the fact that only the ribose linked to the methylated guanosine at the 5' end of the mRNA and the ribose linked to the base at the 3' terminus of the mRNA, possess 2',3'-cis diols. Optionally, where the 3' terminal ribose has a 2',3'-cis diol, the 2',3'-cis diol at the 3' end may be chemically modified, substituted, converted, or eliminated, leaving only the ribose linked to the methylated guanosine at the 5' end of the mRNA with a 2',3'-cis diol. A variety of techniques are available for eliminating the 2',3'-cis diol on the 3' terminal ribose. For example, controlled alkaline hydrolysis may be used to generate mRNA fragments in which the 3' terminal ribose is a 3'-phosphate, 2'-phosphate or (2',3')-cyclophosphate. Thereafter, the fragment which includes the original 3' ribose may be eliminated from the mixture through chromatography on an oligo-dT column. Alternatively, a base which lacks the 2',3'-cis diol may be added to the 3' end of the mRNA using an RNA ligase such as T4 RNA ligase. Example 1 below describes a method for ligation of pCp to the 3' end of messenger RNA.

EXAMPLE 1

Ligation of the Nucleoside Diphosphate pCp to the 3' End of Messenger RNA

1 μg of RNA was incubated in a final reaction medium of 10 μl in the presence of 5 U of $T_4$ phage RNA ligase in the buffer provided by the manufacturer (Gibco-BRL), 40 U of the RNase inhibitor RNasin (Promega) and, 2 μl of $^{32}$pCp (Amersham #PB 10208). The incubation was performed at 37° C. for 2 hours or overnight at 7–8° C.

Following modification or elimination of the 2',3'-cis diol at the 3' ribose, the 2',3'-cis diol present at the 5' end of the mRNA may be oxidized using reagents such as $NaBH_4$, $NaBH_3CN$, or sodium periodate, thereby converting the 2',3'-cis diol to a dialdehyde. Example 2 describes the oxidation of the 2',3'-cis diol at the 5' end of the mRNA with sodium periodate.

EXAMPLE 2

Oxidation of 2',3'-cis Diol at the 5' End of the mRNA 0.1 OD unit of either a capped oligoribonucleotide of 47 nucleotides (including the cap) or an uncapped oligoribonucleotide of 46 nucleotides were treated as follows. The oligoribonucleotides were produced by in vitro transcription using the transcription kit "AmpliScribe T7" (Epicentre Technologies). As indicated below, the DNA template for the RNA transcript contained a single cytosine. To synthesize the uncapped RNA, all four NTPs were included in the in vitro transcription reaction. To obtain the capped RNA, GTP was replaced by an analogue of the cap, m7G(5')ppp (5')G. This compound, recognized by polymerase, was incorporated into the 5' end of the nascent transcript during the step of initiation of transcription but was not capable of incorporation during the extension step. Consequently, the resulting RNA contained a cap at its 5' end. The sequences of the oligoribonucleotides produced by the in vitro transcription reaction were:

+Cap:
5' m7GpppGCAUCCUACUCCCAUCCAAUUCCA CCCUAACUCCUCCCAUCUCCAC-3' (SEQ ID NO: 1)
−Cap:
5'-pppGCAUCCUACUCCCAUCCAAUUCCACCC AACUCCUCCCAUCUCCAC-3' (SEQ ID NO: 2)

The oligoribonucleotides were dissolved in 9 μl of acetate buffer (0.1 M sodium acetate, pH 5.2) and 3 μl of freshly prepared 0.1 M sodium periodate solution. The mixture was incubated for 1 hour in the dark at 4° C. or room temperature. Thereafter, the reaction was stopped by adding 4 μl of 10% ethylene glycol. The product was ethanol precipitated, resuspended in 10 μl or more of water or appropriate buffer and dialyzed against water.

The resulting aldehyde groups may then be coupled to molecules having a reactive amine group, such as hydrazine, carbazide, thiocarbazide or semicarbazide groups, in order to facilitate enrichment of the 5' ends of the mRNAs. Molecules having reactive amine groups which are suitable for use in selecting mRNAs having intact 5' ends include avidin, proteins, antibodies, vitamins, ligands capable of specifically binding to receptor molecules, or oligonucleotides. Example 3 below describes the coupling of the resulting dialdehyde to biotin.

EXAMPLE 3

Coupling of the Dialdehyde with Biotin

The oxidation product obtained in Example 2 was dissolved in 50 μl of sodium acetate at a pH of between 5 and 5.2 and 50 μl of freshly prepared 0.02 M solution of biotin hydrazide in a methoxyethanol/water mixture (1:1) of formula:

$$NH_2-NH-\overset{\bullet}{\underset{\parallel}{C}}-(CH_2)_{\overline{n}}-NH-\overset{\bullet}{\underset{\parallel}{C}}-(CH_2)_4-\underset{S}{\overset{H}{\underset{|}{N}}}\overset{\bullet}{=}NH$$

In the compound used in these experiments, n=5, and the solid black dots represent oxygen. However, it will be appreciated that other commercially available hydrazides may also be used, such as molecules of the formula above in which n varies from 0 to 5.

The mixture was then incubated for 2 hours at 37° C. Following the incubation, the mixture was precipitated with ethanol and dialyzed against distilled water.

Example 4 demonstrates the specificity of the biotinylation reaction.

EXAMPLE 4

Specificity of Biotinylation

The specificity of the biotinylation for capped mRNAs was evaluated by gel electrophoresis of the following samples:

Sample 1. The 46 nucleotide uncapped in vitro transcript prepared as in Example 2 and labeled with $^{32}$pCp as described in Example 1.

Sample 2. The 46 nucleotide uncapped in vitro transcript prepared as in Example 2, labeled with $^{32}$pCp as described in Example 1, treated with the oxidation reaction of Example 2, and subjected to the biotinylation conditions of Example 3.

Sample 3. The 47 nucleotide capped in vitro transcript prepared as in Example 2 and labeled with $^{32}$pCp as described in Example 1.

Sample 4. The 47 nucleotide capped in vitro transcript prepared as in Example 2, labeled with $^{32}$pCp as described in Example 1, treated with the oxidation reaction of Example 2, and subjected to the biotinylation conditions of Example 3.

Samples 1 and 2 had identical migration rates, demonstrating that the uncapped RNAs were not oxidized and biotinylated. Sample 3 migrated more slowly than Samples 1 and 2, while Sample 4 exhibited the slowest migration. The difference in migration of the RNAs in Samples 3 and 4 demonstrates that the capped RNAs were specifically biotinylated.

In some cases, mRNAs having intact 5' ends may be enriched by binding the molecule containing a reactive amine group to a suitable solid phase substrate such as the inside of the vessel containing the mRNAs, magnetic beads, chromatography matrices, or nylon or nitrocellulose membranes. For example, where the molecule having a reactive amine group is biotin, the solid phase substrate may be coupled to avidin or streptavidin. Alternatively, where the molecule having the reactive amine group is an antibody or receptor ligand, the solid phase substrate may be coupled to the cognate antigen or receptor. Finally, where the molecule having a reactive amine group comprises an oligonucleotide, the solid phase substrate may comprise a complementary oligonucleotide.

The mRNAs having intact 5' ends may be released from the solid phase following the enrichment procedure. For example, where the dialdehyde is coupled to biotin hydrazide and the solid phase comprises streptavidin, the mRNAs may be released from the solid phase by simply heating to 95 degrees Celsius in 2% SDS. In some methods, the molecule having a reactive amine group may also be cleaved from the mRNAs having intact 5' ends following enrichment. Example 5 describes the capture of biotinylated mRNAs with streptavidin coated beads and the release of the biotinylated mRNAs from the beads following enrichment.

EXAMPLE 5

Capture and Release of Biotinylated mRNAs Using Strepatividin Coated Beads

The streptavidin-coated magnetic beads were prepared according to the manufacturer's instructions (CPG Inc., USA). The biotinylated mRNAs were added to a hybridization buffer (1.5 M NaCl, pH 5–6). After incubating for 30 minutes, the unbound and nonbiotinylated material was removed. The beads were washed several times in water with 1% SDS. The beads obtained were incubated for 15 minutes at 95° C. in water containing 2% SDS.

Example 6 demonstrates the efficiency with which biotinylated mRNAs were recovered from the streptavidin coated beads.

EXAMPLE 6

Efficiency of Recovery of Biotinylated mRNAs

The efficiency of the recovery procedure was evaluated as follows. RNAs were labeled with $^{32}$pCp, oxidized, biotinylated and bound to streptavidin coated beads as described above. Subsequently, the bound RNAs were incubated for 5, 15 or 30 minutes at 95° C. in the presence of 2% SDS.

The products of the reaction were analyzed by electrophoresis on 12% polyacrylamide gels under denaturing conditions (7 M urea). The gels were subjected to autoradiography. During this manipulation, the hydrazone bonds were not reduced.

Increasing amounts of nucleic acids were recovered as incubation times in 2% SDS increased, demonstrating that biotinylated mRNAs were efficiently recovered.

In an alternative method for obtaining mRNAs having intact 5' ends, an oligonucleotide which has been derivatized to contain a reactive amine group is specifically coupled to mRNAs having an intact cap. Preferably, the 3' end of the mRNA is blocked prior to the step in which the aldehyde groups are joined to the derivatized oligonucleotide, as described above, so as to prevent the derivatized oligonucleotide from being joined to the 3' end of the mRNA. For example, pCp may be attached to the 3' end of the mRNA using T4 RNA ligase. However, as discussed above, blocking the 3' end of the mRNA is an optional step. Derivatized oligonucleotides may be prepared as described below in Example 7.

EXAMPLE 7

Derivatization of the Oligonucleotide

An oligonucleotide phosphorylated at its 3' end was converted to a 3' hydrazide in 3' by treatment with an aqueous solution of hydrazine or of dihydrazide of the formula $H_2N(R1)NH_2$ at about 1 to 3 M, and at pH 4.5, in the presence of a carbodiimide type agent soluble in water such as 1-ethyl-3-(3-dimethylaminopropyl)carbodiimide at a final concentration of 0.3 M at a temperature of 8° C. overnight.

The derivatized oligonucleotide was then separated from the other agents and products using a standard technique for isolating oligonucleotides.

As discussed above, the mRNAs to be enriched may be treated to eliminate the 3' OH groups which may be present thereon. This may be accomplished by enzymatic ligation of sequences lacking a 3' OH, such as pCp, as described above in Example 1. Alternatively, the 3' OH groups may be eliminated by alkaline hydrolysis as described in Example 8 below.

EXAMPLE 8

Alkaline Hydrolysis of mRNA

The mRNAs may be treated with alkaline hydrolysis as follows. In a total volume of 100μl of 0.1N sodium hydroxide, 1.5 μg mRNA is incubated for 40 to 60 minutes at 4° C. The solution is neutralized with acetic acid and precipitated with ethanol.

Following the optional elimination of the 3' OH groups, the diol groups at the 5' ends of the mRNAs are oxidized as described below in Example 9.

EXAMPLE 9

Oxidation of Diols

Up to 1 OD unit of RNA was dissolved in 9 μl of buffer (0.1 M sodium acetate, pH 6–7 or water) and 3 μl of freshly prepared 0.1 M sodium periodate solution. The reaction was incubated for 1 h in the dark at 4° C. or room temperature. Following the incubation, the reaction was stopped by adding 4 μl of 10% ethylene glycol. Thereafter the mixture was incubated at room temperature for 15 minutes. After ethanol precipitation, the product was resuspended in 10 μl or more of water or appropriate buffer and dialyzed against water.

Following oxidation of the diol groups at the 5' ends of the mRNAs, the derivatized oligonucleotide was joined to the resulting aldehydes as described in Example 10.

EXAMPLE 10

Reaction of Aldehydes with Derivatized Oligonucleotides

The oxidized mRNA was dissolved in an acidic medium such as 50 μl of sodium acetate pH 4–6. 50 μl of a solution of the derivatized oligonucleotide was added such that an mRNA:derivatized oligonucleotide ratio of 1:20 was obtained and mixture was reduced with a borohydride. The mixture was allowed to incubate for 2 h at 37° C. or overnight (14 h) at 10° C. The mixture was ethanol precipitated, resuspended in 10 μl or more of water or appropriate buffer and dialyzed against distilled water. If desired, the resulting product may be analyzed using acrylamide gel electrophoresis, HPLC analysis, or other conventional techniques.

Following the attachment of the derivatized oligonucleotide to the mRNAs, a reverse transcription reaction may be performed as described in Example 11 below.

EXAMPLE 11

Reverse Transcription of mRNAs

An oligodeoxyribonucleotide was derivatized as follows. 3 OD units of an oligodeoxyribonucleotide of sequence ATCAAGAATTCGCACGAGACCATTA (SEQ ID NO: 3) having 5'-OH and 3'-P ends were dissolved in 70 μl of a 1.5 M hydroxybenzotriazole solution, pH 5.3, prepared in dimethylformamide/water (75:25) containing 2 μg of 1-ethyl-3-(3-dimethylaminopropyl)carbodiimide. The mixture was incubated for 2 h 30 min at 22° C. The mixture was then precipitated twice in $LiClO_4$/acetone. The pellet was resuspended in 200 μl of 0.25 M hydrazine and incubated at 8° C. from 3 to 14 h. Following the hydrazine reaction, the mixture was precipitated twice in $LiClO_4$/acetone.

The messenger RNAs to be reverse transcribed were extracted from blocks of placenta having sides of 2 cm which had been stored at −80° C. The mRNA was extracted using conventional acidic phenol techniques. Oligo-dT chromatography was used to purify the mRNAs. The integrity of the mRNAs was checked by Northern-blotting.

The diol groups on 7 μg of the placental mRNAs were oxidized as described above in Example 9. The derivatized oligonucleotide was joined to the mRNAs as described in Example 10 above except that the precipitation step was replaced by an exclusion chromatography step to remove derivatized oligodeoxyribonucleotides which were not joined to mRNAs. Exclusion chromatography was performed as follows:

10 ml of AcA34 (BioSepra#230151) gel were equilibrated in 50 ml of a solution of 10 mM Tris pH 8.0, 300 mM NaCl, 1 mM EDTA, and 0.05% SDS. The mixture was allowed to sediment. The supernatant was eliminated and the gel was resuspended in 50 ml of buffer. This procedure was repeated 2 or 3 times.

A glass bead (diameter 3 mm) was introduced into a 2 ml disposable pipette (length 25 cm). The pipette was filled with the gel suspension until the height of the gel stabilized at 1 cm from the top of the pipette. The column was then equilibrated with 20 ml of equilibration buffer (10 mM Tris HCl pH 7.4, 20 mM NaCl).

10 μl of the mRNA which had been reacted with the derivatized oligonucleotide were mixed in 39 μl of 10 mM urea and 2 μl of blue-glycerol buffer, which had been prepared by dissolving 5 mg of bromophenol blue in 60% glycerol (v/v), and passing the mixture through a filter with a filter of diameter 0.45 mn.

The column was loaded. As soon as the sample had penetrated, equilibration buffer was added. 100 μl fractions were collected. Derivatized oligonucleotide which had not been attached to mRNA appeared in fraction 16 and later fractions. Fractions 3 to 15 were combined and precipitated with ethanol.

The mRNAs which had been reacted with the derivatized oligonucleotide were spotted on a nylon membrane and hybridized to a radioactive probe using conventional techniques. The radioactive probe used in these hybridizations was an oligodeoxyribonucleotide of sequence TAATGGTCTCGTGCGAATTCTTGAT (SEQ ID NO: 4) which was anticomplementary to the derivatized oligonucleotide and was labeled at its 5' end with $^{32}$P. 1/10th of the mRNAs which had been reacted with the derivatized oligonucleotide was spotted in two spots on the membrane and the membrane was visualized by autoradiography after hybridization of the probe. A signal was observed, indicating that the derivatized oligonucleotide had been joined to the mRNA.

The remaining 9/10 of the mRNAs which had been reacted with the derivatized oligonucleotide was reverse transcribed as follows. A reverse transcription reaction was carried out with reverse transcriptase following the manufacturer's instructions. To prime the reaction, 50 pmol of nonamers with random sequence were used.

A portion of the resulting cDNA was spotted on a positively charged nylon membrane using conventional methods. The cDNAs were spotted on the membrane after the cDNA:RNA heteroduplexes had been subjected to an alkaline hydrolysis in order to eliminate the RNAs. An oligonucleotide having a sequence identical to that of the derivatized oligonucleotide was labeled at its 5' end with $^{32}$P and hybridized to the cDNA blots using conventional techniques. Single-stranded cDNAs resulting from the reverse transcription reaction were spotted on the membrane. As controls, the blot contained 1 pmol, 100 fmol, 50 fmol, 10 fmol and 1 fmol respectively of a control oligodeoxyribonucleotide of sequence identical to that of the derivatized oligonucleotide. The signal observed in the spots containing the cDNA indicated that approximately 15 fmol of the derivatized oligonucleotide had been reverse transcribed.

These results demonstrate that the reverse transcription can be performed through the cap and, in particular, that reverse transcriptase crosses the 5'-P-P-P-5' bond of the cap of eukaryotic messenger RNAs.

The single stranded cDNAs obtained after the above first strand synthesis were used as template for PCR reactions. Two types of reactions were carried out. First, specific amplification of the mRNAs for the alpha globin, dehydrogenase, pp15 and elongation factor E4 were carried out using the following pairs of oligodeoxyribonucleotide primers.

alpha-globin
GLO-S: CCG ACA AGA CCA ACG TCA AGG CCG C (SEQ ID NO: 5)
GLO-As: TCA CCA GCA GGC AGT GGC TTA GGA G 3' (SEQ ID NO: 6)
dehydrogenase
3 DH-S: AGT GAT TCC TGC TAC TTT GGA TGG C (SEQ ID NO: 7)
3 DH-As: GCT TGG TCT TGT TCT GGA GTT TAG A (SEQ ID NO: 8)
pp15
PP15-S: TCC AGA ATG GGA GAC AAG CCA ATT T (SEQ ID NO: 9)
PP15-As: AGG GAG GAG GAA ACA GCG TGA GTC C (SEQ ID NO: 10)
Elongation factor E4
EFA1-S: ATG GGA AAG GAA AAG ACT CAT ATC A (SEQ ID NO: 11)
EFIA-As: AGC AGC AAC AAT CAG GAC AGC ACA G (SEQ ID NO: 12) Non-specific amplifications were also carried out with the antisense (_As) oligodeoxyribonucleotides of the pairs described above and a primer chosen from the sequence of the derivatized oligodeoxyribonucleotide (ATCAAGAATTCGCACGAGACCATTA) (SEQ ID NO: 13).

A 1.5% agarose gel containing the following samples corresponding to the PCR products of reverse transcription was stained with ethidium bromide. (1/20th of the products of reverse transcription were used for each PCR reaction).

Sample 1: The products of a PCR reaction using the globin primers of SEQ ID NOs 5 and 6 in the presence of cDNA.

Sample 2: The products of a PCR reaction using the globin primers of SEQ ID NOs 5 and 6 in the absence of added cDNA.

Sample 3: The products of a PCR reaction using the dehydrogenase primers of SEQ ID NOs 7 and 8 in the presence of cDNA.

Sample 4: The products of a PCR reaction using the dehydrogenase primers of SEQ ID NOs 7 and 8 in the absence of added cDNA.

Sample 5: The products of a PCR reaction using the pp15 primers of SEQ ID NOs 9 and 10 in the presence of cDNA.

Sample 6: The products of a PCR reaction using the pp15 primers of SEQ ID NOs 9 and 10 in the absence of added cDNA.

Sample 7: The products of a PCR reaction using the EIE4 primers of SEQ ID NOs 11 and 12 in the presence of added cDNA.

Sample 8: The products of a PCR reaction using the EIE4 primers of SEQ ID NOs 11 and 12 in the absence of added cDNA.

In Samples 1, 3, 5 and 7, a band of the size expected for the PCR product was observed, indicating the presence of the corresponding sequence in the cDNA population.

PCR reactions were also carried out with the antisense oligonucleotides of the globin and dehydrogenase primers (SEQ ID NOs 6 and 8) and an oligonucleotide whose sequence corresponds to that of the derivatized oligonucleotide. The presence of PCR products of the expected size in the samples corresponding to samples 1 and 3 above indicated that the derivatized oligonucleotide had been incorporated.

The above examples summarize the chemical procedure for enriching mRNAs for those having intact 5' ends. Further detail regarding the chemical approaches for obtaining mRNAs having intact 5' ends are disclosed in International Application No. WO96/34981, published Nov. 7, 1996.

Strategies based on the above chemical modifications to the 5' cap structure may be utilized to generate cDNAs which have been selected to include the 5' ends of the mRNAs from which they are derived. In one version of such procedures, the 5' ends of the mRNAs are modified as described above. Thereafter, a reverse transcription reaction is conducted to extend a primer complementary to the mRNA to the 5' end of the mRNA. Single stranded RNAs are eliminated to obtain a population of cDNA/mRNA heteroduplexes in which the mRNA includes an intact 5' end. The resulting heteroduplexes may be captured on a solid phase coated with a molecule capable of interacting with the molecule used to derivatize the 5' end of the mRNA. Thereafter, the strands of the heteroduplexes are separated to recover single stranded first cDNA strands which include the 5' end of the mRNA. Second strand cDNA synthesis may then proceed using conventional techniques. For example, the procedures disclosed in WO 96/34981 or in Caminci, P.

et al. High-Efficiency Full-Length cDNA Cloning by Biotinylated CAP Trapper. Genomics 37:327–336 (1996), may be employed to select cDNAs which include the sequence derived from the 5' end of the coding sequence of the mRNA.

Following ligation of the oligonucleotide tag to the 5' cap of the mRNA, a reverse transcription reaction is conducted to extend a primer complementary to the mRNA to the 5' end of the mRNA. Following elimination of the RNA component of the resulting heteroduplex using standard techniques, second strand cDNA synthesis is conducted with a primer complementary to the oligonucleotide tag.

FIG. 1 summarizes the above procedures for obtaining cDNAs which have been selected to include the 5' ends of the mRNAs from which they are derived.

B. Enzymatic Methods for Obtaining mRNAs Having Intact 5' Ends

Other techniques for selecting cDNAs extending to the 5' end of the mRNA from which they are derived are fully enzymatic. Some versions of these techniques are disclosed in Dumas Milne-Edwards J.B. (Doctoral Thesis of Paris VI University, Le clonage des ADNc complets: difficultes et perspectives nouvelles. Apports pour l'etude de la regulation de l'expression de la tryptophane hydroxylase de rat, Dec. 20, 1993), EP0 625572 and Kato et al. Construction of a Human Full-Length cDNA Bank. Gene 150:243–250 (1994).

Briefly, in such approaches, isolated mRNA is treated with alkaline phosphatase to remove the phosphate groups present on the 5' ends of uncapped incomplete mRNAs. Following this procedure, the cap present on full length mRNAs is enzymatically removed with a decapping enzyme such as T4 polynucleotide kinase or tobacco acid pyrophosphatase. An oligonucleotide, which may be either a DNA oligonucleotide or a DNA-RNA hybrid oligonucleotide having RNA at its 3' end, is then ligated to the phosphate present at the 5' end of the decapped mRNA using T4 RNA ligase. The oligonucleotide may include a restriction site to facilitate cloning of the cDNAs following their synthesis. Example 12 below describes one enzymatic method based on the doctoral thesis of Dumas.

EXAMPLE 12

Enzymatic Approach for Obtaining 5' ESTs

Twenty micrograms of PolyA+ RNA were dephosphorylated using Calf Intestinal Phosphatase (Biolabs). After a phenol chloroform extraction, the cap structure of mRNA was hydrolyzed using the Tobacco Acid Pyrophosphatase (purified as described by Shinshi et al., Biochemistry 15: 2185–2190, 1976) and a hemi 5' DNA/RNA-3' oligonucleotide having an unphosphorylated 5' end, a stretch of adenosine ribophosphate at the 3' end, and an EcoRI site near the 5' end was ligated to the 5' P ends of mRNA using the T4 RNA ligase (Biolabs). Oligonucleotides suitable for use in this procedure are preferably 30–50 bases in length. Oligonucleotides having an unphosphorylated 5' end may be synthesized by adding a fluorochrome at the 5' end. The inclusion of a stretch of adenosine ribophosphates at the 3' end of the oligonucleotide increases ligation efficiency. It will be appreciated that the oligonucleotide may contain cloning sites other than EcoRI.

Following ligation of the oligonucleotide to the phosphate present at the 5' end of the decapped mRNA, first and second strand cDNA synthesis may be carried out using conventional methods or those specified in EP0 625,572 and Kato et al. Construction of a Human Full-Length cDNA Bank. Gene 150:243–250 (1994), and Dumas Milne-Edwards, supra. The resulting cDNA may then be ligated into vectors such as those disclosed in Kato et al. Construction of a Human Full-Length cDNA Bank. Gene 150:243–250 (1994) or other nucleic acid vectors known to those skilled in the art using techniques such as those described in Sambrook et al., Molecular Cloning: A Laboratory Manual 2d Ed., Cold Spring Harbor Laboratory Press (1989).

II. Characterization of 5' ESTs

The above chemical and enzymatic approaches for enriching mRNAs having intact 5' ends were employed to obtain 5' ESTs. First, mRNAs were prepared as described in Example 13 below.

EXAMPLE 13

Preparation of mRNA

Total human RNAs or PolyA+ RNAs derived from 29 different tissues were respectively purchased from LABIMO and CLONTECH and used to generate 44 cDNA libraries as described below. The purchased RNA had been isolated from cells or tissues using acid guanidium thiocyanatephenol-chloroform extraction (Chomczyniski, P and Sacchi, N., Analytical Biochemistry 162:156–159, 1987). PolyA+ RNA was isolated from total RNA (LABIMO) by two passes of oligodT chromatography, as described by Aviv and Leder (Aviv, H. and Leder, P., Proc. Natl. Acad. Sci. USA 69:1408–1412, 1972) in order to eliminate ribosomal RNA.

The quality and the integrity of the poly A+ were checked. Northern blots hybridized with a globin probe were used to confirm that the mRNAs were not degraded. Contamination of the PolyA+ mRNAs by ribosomal sequences was checked using RNAs blots and a probe derived from the sequence of the 28S RNA. Preparations of mRNAs with less than 5% of ribosomal RNAs were used in library construction. To avoid constructing libraries with RNAs contaminated by exogenous sequences (prokaryotic or fungal), the presence of bacterial 16S ribosomal sequences or of two highly expressed mRNAs was examined using PCR.

Following preparation of the mRNAs, the above described chemical and/or the enzymatic procedures for enriching mRNAs having intact 5' ends discussed above were employed to obtain 5' ESTs from various tissues. In both approaches an oligonucleotide tag was attached to the cap at the 5' ends of the mRNAs. The oligonucleotide tag had an EcoRI site therein to facilitate later cloning procedures.

Following attachment of the oligonucleotide tag to the mRNA by either the chemical or enzymatic methods, the integrity of the mRNA was examined by performing a Northern blot with 200–500 ng of mRNA using a probe complementary to the oligonucleotide tag.

EXAMPLE 14 cDNA Synthesis Using mRNA Templates Having Intact 5' Ends

For the mRNAs joined to oligonucleotide tags using both the chemical and enzymatic methods, first strand cDNA synthesis was performed with reverse transcriptase using random nonamers as primers. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

For both the chemical and the enzymatic methods, synthesis of the second strand of the cDNA is conducted as follows. After removal of RNA by alkaline hydrolysis, the first strand of cDNA is precipitated using isopropanol in order to eliminate residual primers. The second strand of the cDNA was synthesized with Klenow using a primer corresponding to the 5' end of the ligated oligonucleotide described in Example 12. Preferably, the primer is 20–25 bases in length. Methylated dCTP was also used for second strand synthesis in order to protect internal EcoRI sites in the cDNA from digestion during the cloning process.

Following cDNA synthesis, the cDNAs were cloned into pBlueScript as described in Example 15 below.

EXAMPLE 15

Insertion of cDNAs Into BlueScript

Following second strand synthesis, the ends of the cDNA were blunted with T4 DNA polymerase (Biolabs) and the cDNA was digested with EcoRI. Since methylated dCTP was used during cDNA synthesis, the EcoRI site present in the tag was the only site which was hemi-methylated. Consequently, only the EcoRI site in the oligonucleotide tag was susceptible to EcoRI digestion. The cDNA was then size fractionated using exclusion chromatography (AcA, Biosepra). Fractions corresponding to cDNAs of more than 150 bp were pooled and ethanol precipitated. The cDNA was directionally cloned into the SmaI and EcoRI ends of the phagemid pBlueScript vector (Stratagene). The ligation mixture was electroporated into bacteria and propagated under appropriate antibiotic selection.

Clones containing the oligonucleotide tag attached were selected as described in Example 16 below.

EXAMPLE 16

Selection of Clones Having the Oligonucleotide Tag Attached Thereto

The plasmid DNAs containing 5' EST libraries made as described above were purified (Qiagen). A positive selection of the tagged clones was performed as follows. Briefly, in this selection procedure, the plasmid DNA was converted to single stranded DNA using gene II endonuclease of the phage F1 in combination with an exonuclease (Chang et al., Gene 127:95–8, (1993)) such as exonuclease III or T7 gene 6 exonuclease. The resulting single stranded DNA was then purified using paramagnetic beads as described by Fry et al., Biotechniques, 13: 124–131 (1992). In this procedure, the single stranded DNA was hybridized with a biotinylated oligonucleotide having a sequence corresponding to the 3' end of the oligonucleotide described in Example 13. Preferably, the primer has a length of 20–25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA was then electroporated into bacteria. The percentage of positive clones having the 5' tag oligonucleotide was estimated to typically rank between 90 and 98% using dot blot analysis.

Following electroporation, the libraries were ordered in 384-microtiter plates (MTP). A copy of the MTP was stored for future needs. Then the libraries were transferred into 96 MTP and sequenced as described below.

EXAMPLE 17

Sequencing of Insert in Selected Clones

Plasmid inserts were first amplified by PCR on PE 9600 thermocyclers (Perkin-Elmer), using standard SETA-A and SETA-B primers (Genset SA), AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer, Applied Biosystems Division, Foster City, Calif.). Sequencing reactions were performed using PE 9600 thermocyclers (Perkin Elmer) with standard dye-primer chemistry and ThermoSequenase (Amersham Life Science). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with EtOH, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data from the 44 cDNA libraries made as described above were transferred to a proprietary database, where quality control and validation steps were performed. A proprietary base-caller ("Trace"), working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the EST sequences. However, the resulting EST sequences may contain 1 to 5 bases belonging to the above mentioned sequences at their 5' end. If needed, these can easily be removed on a case by case basis.

Thereafter, the sequences were transferred to the proprietary NETGENE™ Database for further analysis as described below.

Following sequencing as described above, the sequences of the 5' ESTs were entered in a proprietary database called NETGENE™ for storage and manipulation. It will be appreciated by those skilled in the art that the data could be stored and manipulated on any medium which can be read and accessed by a computer. Computer readable media include magnetically readable media, optically readable media, or electronically readable media. For example, the computer readable media may be a hard disc, a floppy disc, a magnetic tape, CD-ROM, RAM, or ROM as well as other types of other media known to those skilled in the art.

In addition, the sequence data may be stored and manipulated in a variety of data processor programs in a variety of formats. For example, the sequence data may be stored as text in a word processing file, such as Microsoft WORD or WORDPERFECT or as an ASCII file in a variety of database programs familiar to those of skill in the art, such as DB2, SYBASE, or ORACLE.

The computer readable media on which the sequence information is stored may be in a personal computer, a network, a server or other computer systems known to those skilled in the art. The computer or other system preferably includes the storage media described above, and a processor for accessing and manipulating the sequence data.

Once the sequence data has been stored it may be manipulated and searched to locate those stored sequences which contain a desired nucleic acid sequence or which encode a protein having a particular functional domain. For example, the stored sequence information may be compared to other known sequences to identify homologies, motifs implicated in biological function, or structural motifs.

Programs which may be used to search or compare the stored sequences include the MacPattern (EMBL), BLAST, and BLAST2 program series (NCBI), basic local alignment search tool programs for nucleotide (BLASTN) and peptide (BLASTX) comparisons (Altschul et al, J. Mol. Biol. 215: 403 (1990)) and FASTA (Pearson and Lipman, Proc. Natl. Acad. Sci. USA, 85: 2444 (1988)). The BLAST programs then extend the alignments on the basis of defined match and mismatch criteria.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Before searching the cDNAs in the NETGENE™ database for sequence motifs of interest, cDNAs derived from mRNAs which were not of interest were identified and eliminated from further consideration as described in Example 18 below.

EXAMPLE 18

Elimination of Undesired Sequences From Further Consideration

5' ESTs in the NETGENE™ database which were derived from undesired sequences such as transfer RNAs, ribosomal RNAs, mitochondrial RNAs, procaryotic RNAs, fungal RNAs, Alu sequences, L1 sequences, or repeat sequences were identified using the FASTA and BLASTN programs with the parameters listed in Table I.

To eliminate 5' ESTs encoding tRNAs from further consideration, the 5' EST sequences were compared to the sequences of 1190 known tRNAs obtained from EMBL release 38, of which 100 were human. The comparison was performed using FASTA on both strands of the 5' ESTs. Sequences having more than 80% homology over more than 60 nucleotides were identified as tRNA. Of the 144,341 sequences screened, 26 were identified as tRNAs and eliminated from further consideration.

To eliminate 5' ESTs encoding rRNAs from further consideration, the 5' EST sequences were compared to the sequences of 2497 known rRNAs obtained from EMBL release 38, of which 73 were human. The comparison was performed using BLASTN on both strands of the 5' ESTs with the parameter S=108. Sequences having more than 80% homology over stretches longer than 40 nucleotides were identified as rRNAs. Of the 144,341 sequences screened, 3,312 were identified as rRNAs and eliminated from further consideration.

To eliminate 5' ESTs encoding mtRNAs from further consideration, the 5' EST sequences were compared to the sequences of the two known mitochondrial genomes for which the entire genomic sequences are available and all sequences transcribed from these mitochondrial genomes including tRNAs, rRNAs, and mRNAs for a total of 38 sequences. The comparison was performed using BLASTN on both strands of the 5' ESTs with the parameter S=108. Sequences having more than 80% homology over stretches longer than 40 nucleotides were identified as mtRNAs. Of the 144,341 sequences screened, 6,110 were identified as mtRNAs and eliminated from further consideration.

Sequences which might have resulted from exogenous contaminants were eliminated from further consideration by comparing the 5' EST sequences to release 46 of the EMBL bacterial and fungal divisions using BLASTN with the parameter S=144. All sequences having more than 90% homology over at least 40 nucleotides were identified as exogenous contaminants. Of the 42 cDNA libraries examined, the average percentages of procaryotic and fungal sequences contained therein were 0.2% and 0.5% respectively. Among these sequences, only one could be identified as a sequence specific to fungi. The others were either fungal or procaryotic sequences having homologies with vertebrate sequences or including repeat sequences which had not been masked during the electronic comparison.

In addition, the 5' ESTs were compared to 6093 Alu sequences and 1115 L1 sequences to mask 5' ESTs containing such repeat sequences from further consideration. 5' ESTs including THE and MER repeats, SSTR sequences or satellite, micro-satellite, or telomeric repeats were also eliminated from further consideration. On average, 11.5% of the sequences in the libraries contained repeat sequences. Of this 11.5%, 7% contained Alu repeats, 3.3% contained L1 repeats and the remaining 1.2% were derived from the other types of repetitive sequences which were screened. These percentages are consistent with those found in cDNA libraries prepared by other groups. For example, the cDNA libraries of Adams et al. contained between 0% and 7.4% Alu repeats depending on the source of the RNA which was used to prepare the cDNA library (Adams et al., Nature 377:174, 1996).

The sequences of those 5' ESTs remaining after the elimination of undesirable sequences were compared with the sequences of known human mRNAs to determine the accuracy of the sequencing procedures described above.

EXAMPLE 19

Measurement of Sequencing Accuracy by Comparison to Known Sequences

To further determine the accuracy of the sequencing procedure described above, the sequences of 5' ESTs derived from known sequences were identified and compared to the known sequences. First, a FASTA analysis with overhangs shorter than 5 bp on both ends was conducted on the 5' ESTs to identify those matching an entry in the public human mRNA database. The 6655 5' ESTs which matched a known human mRNA were then realigned with their cognate mRNA and dynamic programming was used to include substitutions, insertions, and deletions in the list of "errors" which would be recognized. Errors occurring in the last 10 bases of the 5' EST sequences were ignored to avoid the inclusion of spurious cloning sites in the analysis of sequencing accuracy.

This analysis revealed that the sequences incorporated in the NETGENE™ database had an accuracy of more than 99.5%.

To determine the efficiency with which the above selection procedures select cDNAs which include the 5' ends of their corresponding mRNAs, the following analysis was performed.

EXAMPLE 20

Determination of Efficiency of 5' EST Selection

To determine the efficiency at which the above selection procedures isolated 5' ESTs which included sequences close to the 5' end of the mRNAs from which they were derived, the sequences of the ends of the 5' ESTs which were derived from the elongation factor 1 subunit α and ferritin heavy chain genes were compared to the known cDNA sequences for these genes. Since the transcription start sites for the elongation factor 1 subunit α and ferritin heavy chain are well characterized, they may be used to determine the percentage of 5' ESTs derived from these genes which included the authentic transcription start sites.

For both genes, more than 95% of the cDNAs included sequences close to or upstream of the 5' end of the corresponding mRNAs.

To extend the analysis of the reliability of the procedures for isolating 5' ESTs from ESTs in the NETGENE™ database, a similar analysis was conducted using a database composed of human mRNA sequences extracted from GenBank database release 97 for comparison. For those 5' ESTs derived from mRNAs included in the GeneBank database, more than 85% had their 5' ends close to the 5' ends of the known sequence. As some of the mRNA sequences available in the GenBank database are deduced from genomic sequences, a 5' end matching with these sequences will be counted as an internal match. Thus, the method used here underestimates the yield of ESTs including the authentic 5' ends of their corresponding mRNAs.

The EST libraries made above included multiple 5' ESTs derived from the same mRNA. The sequences of such 5' ESTs were compared to one another and the longest 5' ESTs for each mRNA were identified. Overlapping cDNAs were assembled into continuous sequences (contigs). The resulting continuous sequences were then compared to public databases to gauge their similarity to known sequences, as described in Example 21 below.

EXAMPLE 21

Clustering of the 5' ESTs and Calculation of Novelty Indices for cDNA Libraries

For each sequenced EST library, the sequences were clustered by the 5' end. Each sequence in the library was compared to the others with BLASTN2 (direct strand, parameters S=107). ESTs with High Scoring Segment Pairs (HSPs) at least 25 bp long, having 95% identical bases and beginning closer than 10 bp from each EST 5' end were grouped. The longest sequence found in the cluster was used as representative of the cluster. A global clustering between libraries was then performed leading to the definition of super-contigs.

To assess the yield of new sequences within the EST libraries, a novelty rate (NR) was defined as: NR=100× (Number of new unique sequences found in the library/Total number of sequences from the library). Typically, novelty rating range between 10% and 41% depending on the tissue from which the EST library was obtained. For most of the libraries, the random sequencing of 5' EST libraries was pursued until the novelty rate reached 20%.

Following characterization as described above, the collection of 5' ESTs in NETGENE™ was screened to identify those 5' ESTs bearing potential signal sequences as described in Example 22 below.

EXAMPLE 22

Identification of Potential Signal Sequences in 5' ESTs

The 5' ESTs in the NETGENE™ database were screened to identify those having an uninterrupted open reading frame (ORF) longer than 45 nucleotides beginning with an ATG codon and extending to the end of the EST. Approximately half of the cDNA sequences in NETGENE™ contained such an ORF. The ORFs of these 5' ESTs were searched to identify potential signal motifs using slight modifications of the procedures disclosed in Von Heijne, G. A New Method for Predicting Signal Sequence Cleavage Sites. Nucleic Acids Res. 14:46834690 (1986). Those 5' EST sequences encoding a 15 amino acid long stretch with a score of at least 3.5 in the Von Heijne signal peptide identification matrix were considered to possess a signal sequence. Those 5' ESTs which matched a known human mRNA or EST sequence and had a 5' end more than 20 nucleotides downstream of the known 5' end were excluded from further analysis. The remaining cDNAs having signal sequences therein were included in a database called SIGNALTAG™.

To confirm the accuracy of the above method for identifying signal sequences, the analysis of Example 23 was performed.

EXAMPLE 23

Confirmation of Accuracy of Identification of Potential Signal Sequences in 5' ESTs The accuracy of the above procedure for identifying signal sequences encoding signal peptides was evaluated by applying the method to the 43 amino terminal amino acids of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Figure 3:
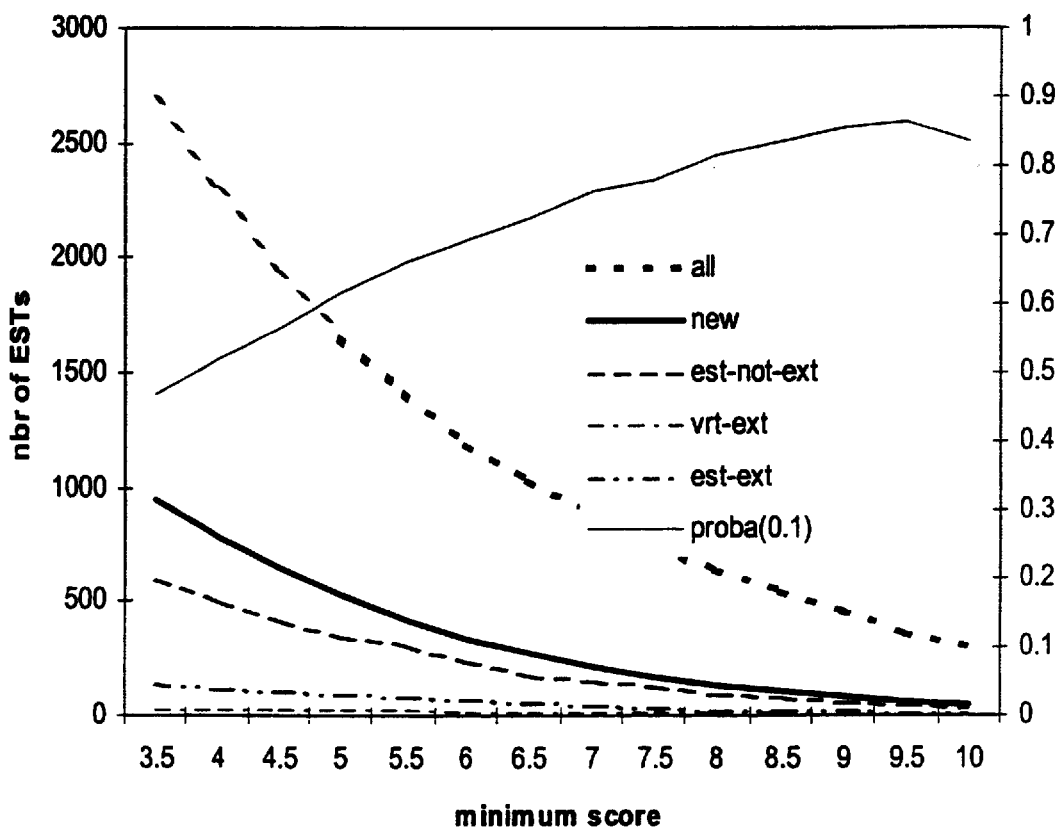
FIG. 3 shows the distribution of von Heijne scores for 5' ESTs in each of the categories described herein and the probability that these 5' ESTs encode a signal peptide.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIGS. 2 and 3.

Using the above method of identifying secretory proteins, 5' ESTs for human glucagon, gamma interferon induced monokine precursor, secreted cyclophilin-like protein, human pleiotropin, and human biotinidase precursor all of which are polypeptides which are known to be secreted, were obtained. Thus, the above method successfully identified those 5' ESTs which encode a signal peptide.

To confirm that the signal peptide encoded by the 5' ESTs actually functions as a signal peptide, the signal sequences from the 5' ESTs may be cloned into a vector designed for the identification of signal peptides. Some signal peptide identification vectors are designed to confer the ability to grow in selective medium on host cells which have a signal sequence operably inserted into the vector. For example, to confirm that a 5' EST encodes a genuine signal peptide, the signal sequence of the 5' EST may be inserted upstream and in frame with a non-secreted form of the yeast invertase gene in signal peptide selection vectors such as those described in U.S. Pat. No. 5,536,637. Growth of host cells containing signal sequence selection vectors having the signal sequence from the 5' EST inserted therein confirms that the 5' EST encodes a genuine signal peptide.

Alternatively, the presence of a signal peptide may be confirmed by cloning the extended cDNAs obtained using the ESTs into expression vectors such as pXT1 (as described below), or by constructing promoter-signal sequence-reporter gene vectors which encode fusion proteins between the signal peptide and an assayable reporter protein. After introduction of these vectors into a suitable host cell, such as COS cells or NIH 3T3 cells, the growth medium may be harvested and analyzed for the presence of the secreted protein. The medium from these cells is compared to the medium from cells containing vectors lacking the signal sequence or extended cDNA insert to identify vectors which encode a functional signal peptide or an authentic secreted protein.

Those 5' ESTs which encoded a signal peptide, as determined by the method of Example 22 above, were further grouped into four categories based on their homology to known sequences. The categorization of the 5' ESTs is described in Example 24 below.

EXAMPLE 24

Categorization of 5' ESTs Encoding a Signal Peptide

Those 5' ESTs having a sequence not matching any known vertebrate sequence nor any publicly available EST sequence were designated "new." Of the sequences in the SIGNALTAG™ database, 947 of the 5' ESTs having a Von Heijne's score of at least 3.5 fell into this category.

Those 5' ESTs having a sequence not matching any vertebrate sequence but matching a publicly known EST were designated "EST-ext", provided that the known EST sequence was extended by at least 40 nucleotides in the 5' direction. Of the sequences in the SIGNALTAG™ database, 150 of the 5' ESTs having a Von Heijne's score of at least 3.5 fell into this category.

Those ESTs not matching any vertebrate sequence but matching a publicly known EST without extending the known EST by at least 40 nucleotides in the 5' direction were designated "EST." Of the sequences in the SIGNALTAG™ database, 599 of the 5' ESTs having a Von Heijne's score of at least 3.5 fell into this category.

Those 5' ESTs matching a human mRNA sequence but extending the known sequence by at least 40 nucleotides in the 5' direction were designated "VERT-ext." Of the sequences in the SIGNALTAG™ database, 23 of the 5' ESTs having a Von Heijne's score of at least 3.5 fell into this category. Included in this category was a 5' EST which extended the known sequence of the human translocase mRNA by more than 200 bases in the 5' direction. A 5' EST which extended the sequence of a human tumor suppressor gene in the 5' direction was also identified.

FIG. 4 shows the distribution of 5' ESTs in each category and the number of 5' ESTs in each category having a given minimum von Heijne's score.

Each of the 5' ESTs was categorized based on the tissue from which its corresponding mRNA was obtained, as described below in Example 25.

EXAMPLE 25

Categorization of Expression Patterns

FIG. 5 shows the tissues from which the mRNAs corresponding to the 5' ESTs in each of the above described categories were obtained.

In addition to categorizing the 5' ESTs by the tissue from which the cDNA library in which they were first identified was obtained, the spatial and temporal expression patterns of the mRNAs corresponding to the 5' ESTs, as well as their expression levels, may be determined as described in Example 26 below. Characterization of the spatial and temporal expression patterns and expression levels of these mRNAs is useful for constructing expression vectors capable of producing a desired level of gene product in a desired spatial or temporal manner, as will be discussed in more detail below.

In addition, 5' ESTs whose corresponding mRNAs are associated with disease states may also be identified. For example, a particular disease may result from lack of expression, over expression, or under expression of an mRNA corresponding to a 5' EST. By comparing mRNA expression patterns and quantities in samples taken from healthy individuals with those from individuals suffering from a particular disease, 5' ESTs responsible for the disease may be identified.

It will be appreciated that the results of the above characterization procedures for 5' ESTs also apply to extended cDNAs (obtainable as described below) which contain sequences adjacent to the 5' ESTs. It will also be appreciated that if it is desired to defer characterization until extended cDNAs have been obtained rather than characterizing the ESTs themselves, the above characterization procedures can be applied to characterize the extended cDNAs after their isolation.

EXAMPLE 26

Evaluation of Expression Levels and Patterns of mRNAs Corresponding to 5' ESTs or Extended cDNAs Expression levels and patterns of mRNAs corresponding to 5' ESTs or extended cDNAs (obtainable as described below) may be analyzed by solution hybridization with long probes as described in International Patent Application No. WO 97/05277. Briefly, a 5' EST, extended cDNA, or fragment thereof corresponding to the gene encoding the mRNA to be characterized is inserted at a cloning site immediately downstream of a bacteriophage (T3, T7 or SP6) RNA polymerase promoter to produce antisense RNA. Preferably, the 5' EST or extended cDNA has 100 or more nucleotides. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The 5' ESTs, extended cDNAs, or fragments thereof may also be tagged with nucleotide sequences for the serial analysis of gene expression (SAGE) as disclosed in UK Patent Application No. 2,305,241 A. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a "tagging endonuclease" is ligated to the digested cDNAs in the first pool. Digestion with the second endonuclease produces short "tag" fragments from the cDNAs.

A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags." In some embodiments, the ditags are concatamerized to produce ligation products containing from 2 to 200 ditags. The tag sequences are then determined and compared to the sequences of the 5' ESTs or extended cDNAs to determine which 5' ESTs or extended cDNAs are expressed in the cell, tissue, organism, or other source of nucleic acids from which the tags were derived. In this way, the expression pattern of the 5' ESTs or extended cDNAs in the cell, tissue, organism, or other source of nucleic acids is obtained.

Quantitative analysis of gene expression may also be performed using arrays. As used herein, the term array means a one dimensional, two dimensional, or multidimensional arrangement of full length cDNAs (i.e. extended cDNAs which include the coding sequence for the signal peptide, the coding sequence for the mature protein, and a stop codon), extended cDNAs, 5' ESTs or fragments of the full length cDNAs, extended cDNAs, or 5' ESTs of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full length cDNAs, extended cDNAs, 5' ESTs, or fragments thereof in a complementary DNA microarray as described by Schena et al. Science 270:467470, 1995; Proc. Natl. Acad. Sci. U.S.A. 93:10614–10619 (1996). Full length cDNAs, extended cDNAs, 5' ESTs or fragments thereof are amplified by PCR and arrayed from 96-well microtiter plates onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C. Cell or tissue mRNA is isolated or commercially obtained and probes are prepared by a single round of reverse transcription. Probes are hybridized to 1 cm$^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with full length cDNAs, extended cDNAs, 5' ESTs, or fragments thereof in complementary DNA arrays as described by Pietu et al. Genome Research 6:492–503 (1996). The full length cDNAs, extended cDNAs, 5' ESTs or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the 5' ESTs or extended cDNAs can be done through high density nucleotide arrays as described by Lockhart et al. Nature Biotechnology 14: 1675–1680, 1996, and Sosnowsky et al. Proc. Natl. Acad. Sci. 94:1119–1123, 1997. Oligonucleotides of 15–50 nucleotides corresponding to sequences of the 5' ESTs or extended cDNAs are synthesized directly on the chip (Lockhart et al., supra) or synthesized and then addressed to the chip (Sosnowski et al., supra). Preferably, the oligonucleotides are about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94:1119–1123)., the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST or extended cDNA from which the oligonucleotide sequence has been designed.

III. Use of 5' ESTs to Clone Extended cDNAs and to Clone the Corresponding Genomic DNAs Once 5' ESTs which include the 5' end of the corresponding mRNAs have been selected using the procedures described above, they can be utilized to isolate extended cDNAs which contain sequences adjacent to the 5' ESTs. The extended cDNAs may include the entire coding sequence of the protein encoded by the corresponding mRNA, including the authentic translation start site, the signal sequence, and the sequence encoding the mature protein remaining after cleavage of the signal peptide. Such extended cDNAs are referred to herein as "full length cDNAs." Alternatively, the extended cDNAs may include only the sequence encoding the mature protein remaining after cleavage of the signal peptide, or only the sequence encoding the signal peptide.

Example 27 below describes a general method for obtaining extended cDNAs. Example 28 below describes the cloning and sequencing of several extended cDNAs, including extended cDNAs which include the entire coding sequence and authentic 5' end of the corresponding mRNA for several secreted proteins.

The methods of Examples 27, 28, and 29 can also be used to obtain extended cDNAs which encode less than the entire coding sequence of the secreted proteins encoded by the genes corresponding to the 5' ESTs. In some embodiments, the extended cDNAs isolated using these methods encode at least 10 amino acids of one of the proteins encoded by the sequences of SEQ ID NOs: 134–180. In further embodiments, the extended cDNAs encode at least 20 amino acids of the proteins encoded by the sequences of SEQ ID NOs: 134–180. In further embodiments, the extended cDNAs encode at least 30 amino acids of the sequences of SEQ ID NOs: 134–180. In a preferred embodiment, the extended cDNAs encode a full length protein sequence, which includes the protein coding sequences of SEQ ID NOs: 134–180.

EXAMPLE 27

General Method for Using 5' ESTs to Clone and Sequence Extended cDNAs Which Include the Entire Coding Region and the Authentic 5' End of the Corresponding mRNA The following general method has been used to quickly and efficiently isolate extended cDNAs including sequence adjacent to the sequences of the 5' ESTs used to obtain them. This method may be applied to obtain extended cDNAs for any 5' EST in the NetGene™ database, including those 5' ESTs encoding secreted proteins. The method is summarized in FIG. 6.

1. Obtaining Extended cDNA a) First Strand Synthesis

The method takes advantage of the known 5' sequence of the mRNA. A reverse transcription reaction is conducted on purified mRNA with a poly 14dT primer containing a 49 nucleotide sequence at its 5' end allowing the addition of a known sequence at the end of the cDNA which corresponds to the 3' end of the mRNA. For example, the primer may have the following sequence: 5'-ATC GTT GAG ACT CGT ACC AGC AGA GTC ACG AGA GAG ACT ACA CGG TAC TGG TTT TTT TTT TTT TTVN-3' (SEQ ID NO: 14). Those skilled in the art will appreciate that other sequences may also be added to the poly dT sequence and used to prime the first strand synthesis. Using this primer and a reverse transcriptase such as the Superscript II (Gibco BRL) or Rnase H Minus M-MLV (Promega) enzyme, a reverse transcript anchored at the 3' polyA site of the RNAs is generated.

After removal of the mRNA hybridized to the first cDNA strand by alkaline hydrolysis, the products of the alkaline hydrolysis and the residual poly dT primer are eliminated with an exclusion column such as an AcA34 (Biosepra) matrix as explained in Example 11.

b) Second Strand Synthesis

A pair of nested primers on each end is designed based on the known 5' sequence from the 5' EST and the known 3' end added by the poly dT primer used in the first strand synthesis. Softwares used to design primers are either based on GC content and melting temperatures of oligonucleotides, such as OSP (Illier and Green, PCR Meth. Appl. 1:124–128, 1991), or based on the octamer frequency disparity method (Griffais et al., Nucleic Acids Res. 19: 3887–3891, 1991 such as PC-Rare (http://bioinformatics.weizmann.ac.il/software/PC-Rare/doc/manuel.html).

Preferably, the nested primers at the 5' end are separated from one another by four to nine bases. The 5' primer sequences may be selected to have melting temperatures and specificities suitable for use in PCR.

Preferably, the nested primers at the 3' end are separated from one another by four to nine bases. For example, the nested 3' primers may have the following sequences: (5'-CCA GCA GAG TCA CGA GAG AGA CTA CAC GG-3' (SEQ ID NO: 15), and 5'-CAC GAG AGA GAC TAC ACG GTA CTG G-3' (SEQ ID NO: 16). These primers were selected because they have melting temperatures and specificities compatible with their use in PCR. However, those skilled in the art will appreciate that other sequences may also be used as primers.

The first PCR run of 25 cycles is performed using the Advantage Tth Polymerase Mix (Clontech) and the outer primer from each of the nested pairs. A second 20 cycle PCR using the same enzyme and the inner primer from each of the nested pairs is then performed on $\frac{1}{2500}$ of the first PCR product. Thereafter, the primers and nucleotides are removed.

2. Sequencing of Full Length Extended cDNAs or Fragment Thereof

Due to the lack of position constraints on the design of 5' nested primers compatible for PCR use using the OSP software, amplicons of two types are obtained. Preferably, the second 5' primer is located upstream of the translation initiation codon thus yielding a nested PCR product containing the whole coding sequence. Such a full length extended cDNA undergoes a direct cloning procedure as described in section a. However, in some cases, the second 5' primer is located downstream of the translation initiation codon, thereby yielding a PCR product containing only part of the ORF. Such incomplete PCR products are submitted to a modified procedure described in section b.

a) Nested PCR Products Containing Complete ORFs

When the resulting nested PCR product contains the complete coding sequence, as predicted from the 5' EST sequence, it is cloned in an appropriate vector such as pED6dpc2, as described in section 3.

b) Nested PCR Products Containing Incomplete ORFs

When the amplicon does not contain the complete coding sequence, intermediate steps are necessary to obtain both the complete coding sequence and a PCR product containing the full coding sequence. The complete coding sequence can be assembled from several partial sequences determined directly from different PCR products as described in the following section.

Figure 6:
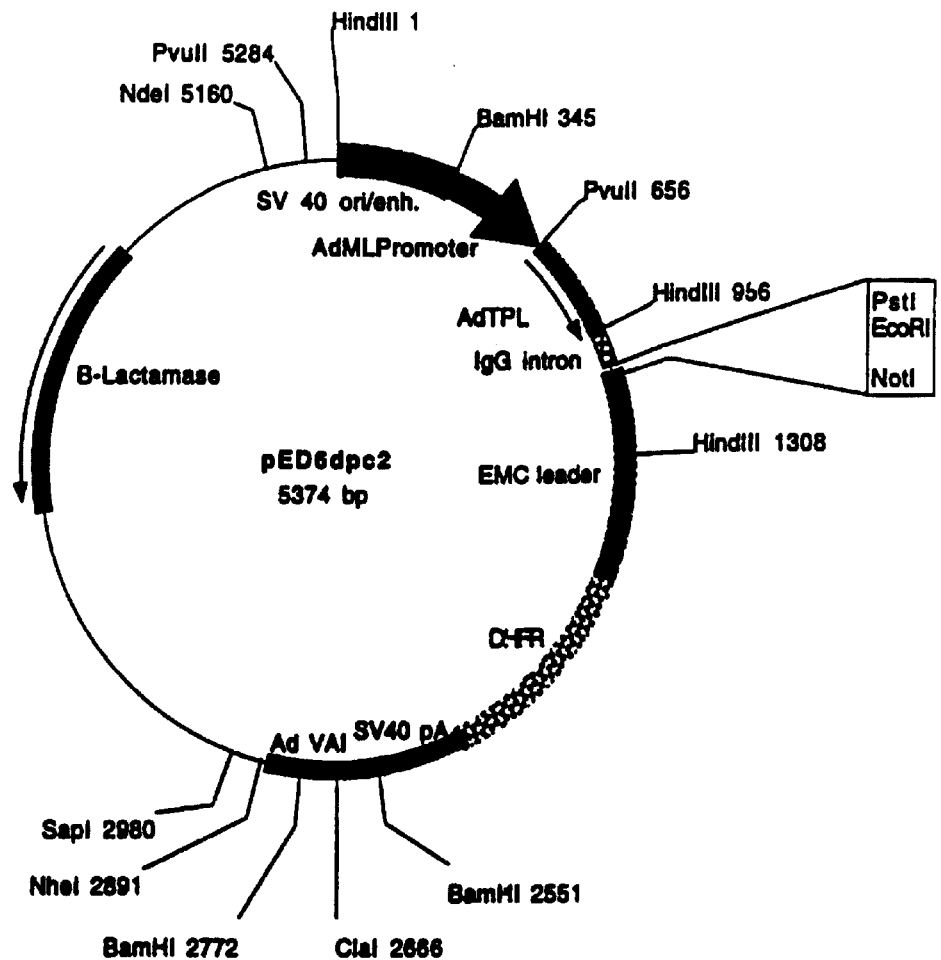
FIG. 6 is a map of pED6dpc2.

Once the full coding sequence has been completely determined, new primers compatible for PCR use are designed to obtain amplicons containing the whole coding region. However, in such cases, 3' primers compatible for PCR use are located inside the 3' UTR of the corresponding mRNA, thus yielding amplicons which lack part of this region, i.e. the polyA tract and sometimes the polyadenylation signal, as illustrated in FIG. 6. Such full length extended cDNAs are then cloned into an appropriate vector as described in section 3.

c) Sequencing Extended cDNAs

Sequencing of extended cDNAs is performed using a Die Terminator approach with the AmpliTaq DNA polymerase FS kit available from Perkin Elmer.

In order to sequence PCR fragments, primer walking is performed using software such as OSP to choose primers and automated computer software such as ASMG (Sutton et al., Genome Science Technol. 1: 9–19, 1995) to construct contigs of walking sequences including the initial 5' tag using minimum overlaps of 32 nucleotides. Preferably, primer walking is performed until the sequences of full length cDNAs are obtained.

Completion of the sequencing of a given extended cDNA fragment is assessed as follows. Since sequences located after a polyA tract are difficult to determine precisely in the case of uncloned products, sequencing and primer walking processes for PCR products are interrupted when a polyA tract is identified in extended cDNAs obtained as described in case b. The sequence length is compared to the size of the nested PCR product obtained as described above. Due to the limited accuracy of the determination of the PCR product size by gel electrophoresis, a sequence is considered complete if the size of the obtained sequence is at least 70% the size of the first nested PCR product. If the length of the sequence determined from the computer analysis is not at least 70% of the length of the nested PCR product, these PCR products are cloned and the sequence of the insertion is determined. When Northern blot data are available, the size of the mRNA detected for a given PCR product is used to finally assess that the sequence is complete. Sequences which do not fulfill the above criteria are discarded and will undergo a new isolation procedure.

Sequence data of all extended cDNAs are then transferred to a proprietary database, where quality controls and validation steps are carried out as described in example 15.

3. Cloning of Full Length Extended cDNAs

Figure 7:
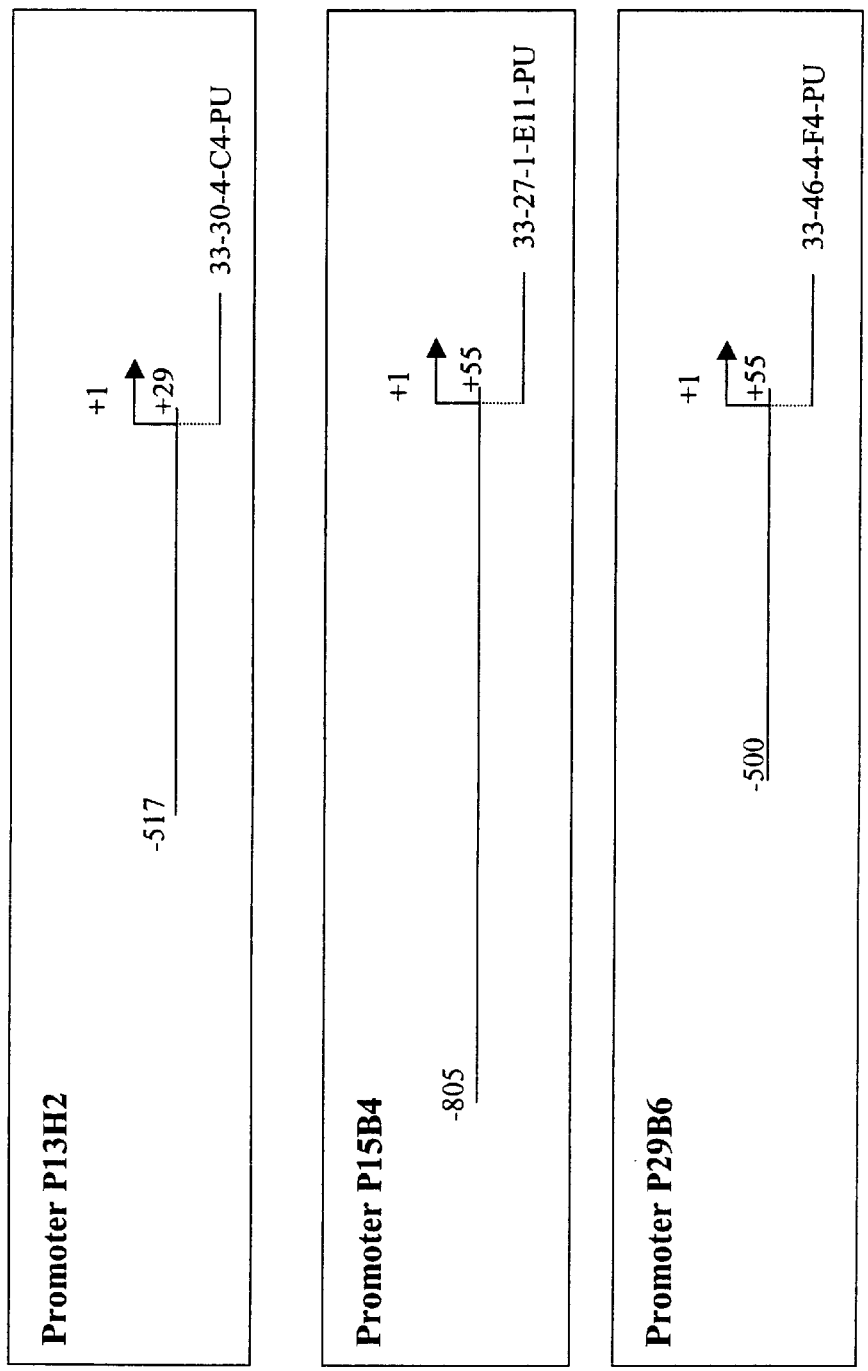
FIG. 7 provides a schematic description of the promoters isolated and the way they are assembled with the corresponding 5' tags.

The PCR product containing the full coding sequence is then cloned in an appropriate vector. For example, the extended cDNAs can be cloned into the expression vector pED6dpc2 (DiscoverEase, Genetics Institute, Cambridge, Mass.) as follows. The structure of pED6dpc2 is shown in FIG. 7. pED6dpc2 vector DNA is prepared with blunt ends by performing an EcoRI digestion followed by a fill in reaction. The blunt ended vector is dephosphorylated. After removal of PCR primers and ethanol precipitation, the PCR product containing the full coding sequence or the extended cDNA obtained as described above is phosphorylated with a kinase subsequently removed by phenol-Sevag extraction and precipitation. The double stranded extended cDNA is then ligated to the vector and the resulting expression plasmid introduced into appropriate host cells.

Since the PCR products obtained as described above are blunt ended molecules that can be cloned in either direction, the orientation of several clones for each PCR product is determined. Then, 4 to 10 clones are ordered in microtiter plates and subjected to a PCR reaction using a first primer located in the vector close to the cloning site and a second primer located in the portion of the extended cDNA corresponding to the 3' end of the mRNA. This second primer may be the antisense primer used in anchored PCR in the case of direct cloning (case a) or the antisense primer located inside the 3' UTR in the case of indirect cloning (case b). Clones in which the start codon of the extended cDNA is operably linked to the promoter in the vector so as to permit expression of the protein encoded by the extended cDNA are conserved and sequenced. In addition to the ends of cDNA inserts, approximately 50 bp of vector DNA on each side of the cDNA insert are also sequenced.

The cloned PCR products are then entirely sequenced according to the aforementioned procedure. In this case, contig assembly of long fragments is then performed on walking sequences that have already contigated for uncloned PCR products during primer walking. Sequencing of cloned amplicons is complete when the resulting contigs include the whole coding region as well as overlapping sequences with vector DNA on both ends.

4. Computer Analysis of Full Length Extended cDNA

Sequences of all full length extended cDNAs are then submitted to further analysis as described below and using the parameters found in Table I with the following modifications. For screening of miscellaneous subdivisions of Genbank, FASTA was used instead of BLASTN and 15 nucleotide of homology was the limit instead of 17. For Alu detection, BLASTN was used with the following parameters: S=72; identity=70%; and length=40 nucleotides. Polyadenylation signal and polyA tail which were not search for the 5' ESTs were searched. For polyadenylation signal detection the signal (AATAAA) was searched with one permissible mismatch in the last ten nucleotides preceding the 5' end of the polyA. For the polyA, a stretch of 8 amino acids in the last 20 nucleotides of the sequence was searched with BLAST2N in the sense strand with the following parameters (W=6, S=10, E=1000, and identity=90%). Finally, patented sequences and ORF homologies were searched using, respectively, BLASTN and BLASTP on GenSEQ (Derwent's database of patented nucleotide sequences) and SWISSPROT for ORFs with the following parameters (W=8 and B=10). Before examining the extended full length cDNAs for sequences of interest, extended cDNAs which are not of interest are searched as follows.

a) Elimination of Undesired Sequences

Although 5' ESTs were checked to remove contaminants sequences as described in Example 18, a last verification was carried out to identify extended cDNAs sequences derived from undesired sequences such as vector RNAs, transfer RNAs, ribosomal rRNAs, mitochondrial RNAs, prokaryotic RNAs and fungal RNAs using the FASTA and BLASTN programs on both strands of extended cDNAs as described below.

To identify the extended cDNAs encoding vector RNAs, extended cDNAs are compared to the known sequences of vector RNA using the FASTA program. Sequences of extended cDNAs with more than 90% homology over stretches of 15 nucleotides are identified as vector RNA.

To identify the extended cDNAs encoding tRNAs, extended cDNA sequences were compared to the sequences of 1190 known tRNAs obtained from EMBL release 38, of which 100 were human. Sequences of extended cDNAs having more than 80% homology over 60 nucleotides using FASTA were identified as tRNA.

To identify the extended cDNAs encoding rRNAs, extended cDNA sequences were compared to the sequences of 2497 known rRNAs obtained from EMBL release 38, of which 73 were human. Sequences of extended cDNAs having more than 80% homology over stretches longer than 40 nucleotides using BLASTN were identified as rRNAs.

To identify the extended cDNAs encoding mtRNAs, extended cDNA sequences were compared to the sequences of the two known mitochondrial genomes for which the entire genomic sequences are available and all sequences transcribed from these mitochondrial genomes including tRNAs, rRNAs, and mRNAs for a total of 38 sequences. Sequences of extended cDNAs having more than 80% homology over stretches longer than 40 nucleotides using BLASTN were identified as mtRNAs.

Sequences which might have resulted from other exogenous contaminants were identified by comparing extended cDNA sequences to release 105 of Genbank bacterial and fungal divisions. Sequences of extended cDNAs having more than 90% homology over 40 nucleotides using BLASTN were identified as exogenous prokaryotic or fungal contaminants.

In addition, extended cDNAs were searched for different repeat sequences, including Alu sequences, L1 sequences, THE and MER repeats, SSTR sequences or satellite, microsatellite, or telomeric repeats. Sequences of extended cDNAs with more than 70% homology over 40 nucleotide stretches using BLASTN were identified as repeat sequences and masked in further identification procedures. In addition, clones showing extensive homology to repeats, i.e., matches of either more than 50 nucleotides if the homology was at least 75% or more than 40 nucleotides if the homology was at least 85% or more than 30 nucleotides if the homology was at least 90%, were flagged.

b) Identification of Structural Features

Structural features, e.g. polyA tail and polyadenylation signal, of the sequences of full length extended cDNAs are subsequently determined as follows.

A polyA tail is defined as a homopolymeric stretch of at least 11 A with at most one alternative base within it. The polyA tail search is restricted to the last 20 nt of the sequence and limited to stretches of 11 consecutive A's because sequencing reactions are often not readable after such a polyA stretch. Stretches with 100% homology over 6 nucleotides are identified as polyA tails.

To search for a polyadenylation signal, the polyA tail is clipped from the full-length sequence. The 50 bp preceding the polyA tail are searched for the canonic polyadenylation AAUAAA signal allowing one mismatch to account for possible sequencing errors and known variation in the canonical sequence of the polyadenylation signal.

c) Identification of Functional Features

Functional features, e.g. ORFs and signal sequences, of the sequences of full length extended cDNAs were subsequently determined as follows.

The 3 upper strand frames of extended cDNAs are searched for ORFs defined as the maximum length fragments beginning with a translation initiation codon and ending with a stop codon. ORFs encoding at least 20 amino acids are preferred.

Each found ORF is then scanned for the presence of a signal peptide in the first 50 amino-acids or, where appropriate, within shorter regions down to 20 amino acids or less in the ORF, using the matrix method of von Heijne (Nuc. Acids Res. 14: 46834690 (1986)), the disclosure of which is incorporated herein by reference and the modification described in Example 22.

d) Homology to Either Nucleotidic or Proteic Sequences

Sequences of full length extended cDNAs are then compared to known sequences on a nucleotidic or proteic basis.

Sequences of full length extended cDNAs are compared to the following known nucleic acid sequences: vertebrate sequences (Genbank release #GB), EST sequences (Genbank release #GB), patented sequences (Genseqn release GSEQ) and recently identified sequences (Genbank daily release) available at the time of filing. Full length cDNA sequences are also compared to the sequences of a private database (Genset internal sequences) in order to find sequences that have already been identified by applicants. Sequences of full length extended cDNAs with more than 90% homology over 30 nucleotides using either BLASTN or BLAST2N as indicated in Table H are identified as sequences that have already been described. Matching vertebrate sequences are subsequently examined using FASTA; full length extended cDNAs with more than 70% homology over 30 nucleotides are identified as sequences that have already been described.

ORFs encoded by full length extended cDNAs as defined in section c) are subsequently compared to known amino acid sequences found in Swissprot release CHP, PIR release PIR# and Genpept release GPEPT public databases using BLASTP with the parameter W=8 and allowing a maximum of 10 matches. Sequences of full length extended cDNAs showing extensive homology to known protein sequences are recognized as already identified proteins.

In addition, the three-frame conceptual translation products of the top strand of full length extended cDNAs are compared to publicly known amino acid sequences of Swissprot using BLASTX with the parameter E=0.001. Sequences of full length extended cDNAs with more than 70% homology over 30 amino acid stretches are detected as already identified proteins. 5. Selection of Cloned Full Length Sequence of the Present Invention Cloned full length extended cDNA sequences that have already been characterized by the aforementioned computer analysis are then submitted to an automatic procedure in order to preselect full length extended cDNAs containing sequences of interest.

a) Automatic Sequence Preselection

All complete cloned full length extended cDNAs clipped for vector on both ends are considered. First, a negative selection is operated in order to eliminate unwanted cloned sequences resulting from either contaminants or PCR artifacts as follows. Sequences matching contaminant sequences such as vector RNA, tRNA, mtRNA, rRNA sequences are discarded as well as those encoding ORF sequences exhibiting extensive homology to repeats as defined in section 4 a). Sequences obtained by direct cloning using nested primers on 5' and 3' tags (section 1. case a) but lacking polyA tail are discarded. Only ORFs containing a signal peptide and ending either before the polyA tail (case a) or before the end of the cloned 3' UTR (case b) are kept. Then, ORFs containing unlikely mature proteins such as mature proteins which size is less than 20 amino acids or less than 25% of the immature protein size are eliminated.

In the selection of the OFR, priority was given to the ORF and the frame corresponding to the polypeptides described in SignalTag Patents (U.S. patent application Ser. Nos: 08/905,223; 08/905,135; 08/905,051; 08/905,144; 08/905,279; 08/904,468; 08/905,134; and 08/905,133). If the ORF was not found among the OFRs described in the SignalTag Patents, the ORF encoding the signal peptide with the highest score according to Von Heijne method as defined in Example 22 was chosen. If the scores were identical, then the longest ORF was chosen.

Sequences of full length extended cDNA clones are then compared pairwise with BLAST after masking of the repeat sequences. Sequences containing at least 90% homology over 30 nucleotides are clustered in the same class. Each cluster is then subjected to a cluster analysis that detects sequences resulting from internal priming or from alternative splicing, identical sequences or sequences with several frameshifts. This automatic analysis serves as a basis for manual selection of the sequences.

b) Manual Sequence Selection

Manual selection is carried out using automatically generated reports for each sequenced full length extended cDNA clone. During this manual procedures, a selection is operated between clones belonging to the same class as follows. ORF sequences encoded by clones belonging to the same class are aligned and compared. If the homology between nucleotidic sequences of clones belonging to the same class is more than 90% over 30 nucleotide stretches or if the homology between amino acid sequences of clones belonging to the same class is more than 80% over 20 amino acid stretches, than the clones are considered as being identical. The chosen ORF is the best one according to the criteria mentioned below. If the nucleotide and amino acid homologies are less than 90% and 80% respectively, the clones are said to encode distinct proteins which can be both selected if they contain sequences of interest.

Selection of full length extended cDNA clones encoding sequences of interest is performed using the following criteria. Structural parameters (initial tag, polyadenylation site and signal) are first checked. Then, homologies with known nucleic acids and proteins are examined in order to determine whether the clone sequence match a known nucleic/proteic sequence and, in the latter case, its covering rate and the date at which the sequence became public. If there is no extensive match with sequences other than ESTs or genomic DNA, or if the clone sequence brings substantial new information, such as encoding a protein resulting from alternative slicing of an mRNA coding for an already known protein, the sequence is kept. Examples of such cloned full length extended cDNAs containing sequences of interest are described in Example 28. Sequences resulting from chimera or double inserts as assessed by homology to other sequences are discarded during this procedure.

EXAMPLE 28

Cloning and Sequencing of Extended cDNAs

The procedure described in Example 27 above was used to obtain the extended cDNAs of the present invention. Using this approach, the full length cDNA of SEQ ID NO: 17 was obtained. This cDNA falls into the "EST-ext" category described above and encodes the signal peptide MKKVLLLITAILAVAVG (SEQ ID NO: 18) having a von Heijne score of 8.2.

The full length cDNA of SEQ ID NO: 49 was also obtained using this procedure. This cDNA falls into the "EST-ext" category described above and encodes the signal peptide MWWFQQGLSFLPSALVIWTSA (SEQ ID NO: 20) having a von Heijne score of 5.5.

Another full length cDNA obtained using the procedure described above has the sequence of SEQ ID NO: 21. This cDNA, falls into the "EST-ext" category described above and encodes the signal peptide MVLTTLPSANSANSPVN-MPTTGPNSLSYASSALSPCLT (SEQ ID NO: 22) having a von Heijne score of 5.9.

The above procedure was also used to obtain a full length cDNA having the sequence of SEQ ID NO: 23. This cDNA falls into the "EST-ext" category described above and encodes the signal peptide ILSTVTALTFAXA (SEQ ID NO: 24) having a von Heijne score of 5.5.

The full length cDNA of SEQ ID NO: 25 was also obtained using this procedure. This cDNA falls into the "new" category described above and encodes a signal peptide LVLTLCTLPLAVA (SEQ ID NO: 26) having a von Heijne score of 10.1.

The full length cDNA of SEQ ID NO: 27 was also obtained using this procedure. This cDNA falls into the "new" category described above and encodes a signal peptide LWLLFFLVTAIHA (SEQ ID NO: 28) having a von Heijne score of 10.7.

The above procedures were also used to obtain the extended cDNAs of the present invention. 5' ESTs expressed in a variety of tissues were obtained as described above. The appended sequence listing provides the tissues from which the extended cDNAs were obtained. It will be appreciated that the extended cDNAs may also be expressed in tissues other than the tissue listed in the sequence listing. 5' ESTs obtained as described above were used to obtain extended cDNAs having the sequences of SEQ ID NOs: 40–86. Table H provides the sequence identification numbers of the extended cDNAs of the present invention, the locations of the full coding sequences in SEQ ID NOs: 40–86 (i.e. the nucleotides encoding both the signal peptide and the mature protein, listed under the heading FCS location in Table H), the locations of the nucleotides in SEQ ID NOs: 40–86 which encode the signal peptides (listed under the heading SigPep Location in Table II), the locations of the nucleotides in SEQ ID NOs: 40–86 which encode the mature proteins generated by cleavage of the signal peptides (listed under the heading Mature Polypeptide Location in Table II), the locations in SEQ ID NOs: 40–86 of stop codons (listed under the heading Stop Codon Location in Table II), the locations in SEQ ID NOs: 40–86 of polyA signals (listed under the heading Poly A Signal Location in Table II) and the locations of polyA sites (listed under the heading Poly A Site Location in Table II).

The polypeptides encoded by the extended cDNAs were screened for the presence of known structural or functional motifs or for the presence of signatures, small amino acid sequences which are well conserved amongst the members of a protein family. The conserved regions have been used to derive consensus patterns or matrices included in the PROSITE data bank, in particular in the file prosite.dat (Release 13.0 of November 1995, located at http://expasy.hcuge.ch/sprot/prosite.html. Prosite_convert and prosite_scan programs (http://ulrec3.unil.ch/ftpserveur/prosite_scan) were used to find signatures on the extended cDNAs.

For each pattern obtained with the prosite_convert program from the prosite.dat file, the accuracy of the detection on a new protein sequence has been tested by evaluating the frequency of irrelevant hits on the population of human secreted proteins included in the data bank SWISSPROT. The ratio between the number of hits on shuffled proteins (with a window size of 20 amino acids) and the number of hits on native (unshuffled) proteins was used as an index. Every pattern for which the ration was greater than 20% (one hit on shuffled proteins for 5 hits on native proteins) was skipped during the search with prosite_scan. The program used to shuffle protein sequences (db_shuffled) and the program used to determine the statistics for each pattern in the protein data banks (prosite_statistics) are available on the ftp site http://ulrec3.unil.ch/ftpserveur/prosite_scan.

The results of the search are provided in Table III. The first column provides the ID number of the sequence. The second column indicates the beginning and end positions of the signature. The Prosite definition of the signature is indicated in the third column.

Table IV lists the sequence identification numbers of the polypeptides of SEQ ID NOs: 87–133, the locations of the amino acid residues of SEQ ID NOs: 87–133 in the full length polypeptide (second column), the locations of the amino acid residues of SEQ ID NOs: 87–133 in the signal peptides (third column), and the locations of the amino acid residues of SEQ ID NOs: 87–133 in the mature polypeptide created by cleaving the signal peptide from the full length polypeptide (fourth column). In Table IV, the first amino acid of the signal peptide is designated as amino acid number 1. In the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings.

The extended cDNAs of the present invention were categorized based on their homology to known sequences. Genebank release #103, division ESTs, and Geneseq release #28 were used to scan the extended cDNAs using Blast. For each extended cDNA ID, the covering rate of the sequence by another sequence was determined as follows. The length in nucleotides of the matching segment was calculated (even when gaps were present) and divided by the length in nucleotides of the extended cDNA sequence. When more than one covering rate was obtained for a given extended cDNA, the higher covering rate was used to classify the extended cDNA. The Geneseq sequences have been categorized as either ESTs or vertebrate, with ESTs being those sequences obtained by random sequencing of cDNA libraries and vertebrate sequences being those sequences containing sequences resembling known functional motifs.

The results of this categorization are provided in Table V. The first column lists the sequence identification number of the sequence being categorized. The second column indicates those sequences having no matches with the database scanned. The third column indicates those sequences having a covering rate of less than 30%. The fourth column indicates those sequences having a covering rate greater than 30%. The fifth column indicates sequences partially or totally covered by vertebrate sequences as described above.

The nucleotide sequences of the sequences of SEQ ID NOs: 40–86, 134–180 and 228, and the amino acid sequences encoded by SEQ ID NOs: 40–86, 134–180, 228 (i.e. amino acid sequences of SEQ ID NOs: 87–133 and 181–227) are provided in the appended sequence listing. In some instances, the sequences are preliminary and may include some incorrect or ambiguous sequences or amino acids. The sequences of SEQ ID NOs: 40–86, 134–180 and 228 can readily be screened for any errors therein and any sequence ambiguities can be resolved by resequencing a fragment containing such errors or ambiguities on both strands. Nucleic acid fragments for resolving sequencing errors or ambiguities may be obtained from the deposited clones or can be isolated using the techniques described herein. Resolution of any such ambiguities or errors may be facilitated by using primers which hybridize to sequences located close to the ambiguous or erroneous sequences. For example, the primers may hybridize to sequences within 50–75 bases of the ambiguity or error. Upon resolution of an error or ambiguity, the corresponding corrections can be made in the protein sequences encoded by the DNA containing the error or ambiguity. The amino acid sequence of the protein encoded by a particular clone can also be determined by expression of the clone in a suitable host cell, collecting the protein, and determining its sequence.

For each amino acid sequence, Applicants have identified what they have determined to be the reading frame best identifiable with sequence information available at the time of filing. Some of the amino acid sequences may contain "Xaa" designators. These "Xaa" designators indicate either (1) a residue which cannot be identified because of nucleotide sequence ambiguity or (2) a stop codon in the determined sequence where Applicants believe one should not exist (if the sequence were determined more accurately).

Cells containing the 47 extended cDNAs (SEQ ID NOs: 134–180) of the present invention in the vector pED6dpc2, are maintained in permanent deposit by the inventors at Genset, S.A., 24 Rue Royale, 75008 Paris, France.

A pool of the cells containing the 47 extended cDNAs (SEQ ID NOs: 134–180), from which the cells containing a particular polynucleotide is obtainable, will be deposited with the American Type Culture Collection. Each extended cDNA clone will be transfected into separate bacterial cells (E-coli) in this composite deposit. A pool of cells containing the 43 extended cDNAs (SEQ ID NOs: 134, 136–143, 145–162, 164–174, and 176–180), from which the cells containing a particular polynucleotide is obtainable, were deposited with the American Type Culture Collection on Dec. 16, 1997, under the name SignalTag 1-43, and ATCC accession No. 98619. A pool of cells comprising the 2 extended cDNAs (SEQ ID NOs: 144 and 163), from which the cells containing a particular polynucleotide is obtainable, were deposited with the American Type Culture Collection on Oct. 15, 1998, under the name SignalTag 44–66, and ATCC accession No. 98923. Each extended cDNA can be removed from the pED6dpc2 vector in which it was deposited by performing a NotI, PstI double digestion to produce the appropriate fragment for each clone. The proteins encoded by the extended cDNAs may also be expressed from the promoter in pED6dpc2.

Bacterial cells containing a particular clone can be obtained from the composite deposit as follows: An oligonucleotide probe or probes should be designed to the sequence that is known for that particular clone. This sequence can be derived from the sequences provided herein, or from a combination of those sequences. The design of the oligonucleotide probe should preferably follow these parameters:

(a) It should be designed to an area of the sequence which has the fewest ambiguous bases ("N's"), if any;

(b) Preferably, the probe is designed to have a $T_m$ of approx. 80° C. (assuming 2 degrees for each A or T and 4 degrees for each G or C). However, probes having melting temperatures between 40° C. and 80° C. may also be used provided that specificity is not lost.

The oligonucleotide should preferably be labeled with g-$^{32}$PATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantified by measurement in a scintillation counter. Preferably, specific activity of the resulting probe should be approximately $4 \times 10^6$ dpm/pmole.

The bacterial culture containing the pool of full-length clones should preferably be thawed and 100 µl of the stock used to inoculate a sterile culture flask containing 25 ml of sterile L-broth containing ampicillin at 100 µg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 µg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to 1×10⁶ dpm/mL. The filter is then preferably incubated at 65° C. with gentle agitation overnight. The filter is then preferably washed in 500 mL of 2×SSC/0.1% SDS at room temperature with gentle shaking for 15 minutes. A third wash with 0.1×SSC/ 0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

The plasmid DNA obtained using these procedures may then be manipulated using standard cloning techniques familiar to those skilled in the art. Alternatively, a PCR can be done with primers designed at both ends of the extended cDNA insertion. For example, a PCR reaction may be conducted using a primer having the sequence GGCCATACACTTGAGTGAC (SEQ ID NO: 38) and a primer having the sequence ATATAGACAAACGCACACC (SEQ. ID. NO: 39). The PCR product which corresponds to the extended cDNA can then be manipulated using standard cloning techniques familiar to those skilled in the art.

In addition to PCR based methods for obtaining extended cDNAs, traditional hybridization based methods may also be employed. These methods may also be used to obtain the genomic DNAs which encode the mRNAs from which the 5' ESTs were derived, mRNAs corresponding to the extended cDNAs, or nucleic acids which are homologous to extended cDNAs or 5' ESTs. Example 29 below provides an example of such methods.

EXAMPLE 29

Methods for Obtaining Extended cDNAs or Nucleic Acids Homologous to Extended cDNAs or 5' ESTs A full length cDNA library can be made using the strategies described in Examples 13, 14, 15, and 16 above by replacing the random nonamer used in Example 14 with an oligo-dT primer. For instance, the oligonucleotide of SEQ ID NO: 14 may be used.

Alternatively, a cDNA library or genomic DNA library may be obtained from a commercial source or made using techniques familiar to those skilled in the art. The library includes cDNAs which are derived from the mRNA corresponding to a 5' EST or which have homology to an extended cDNA or 5' EST. The cDNA library or genomic DNA library is hybridized to a detectable probe comprising at least 10 consecutive nucleotides from the 5' EST or extended cDNA using conventional techniques. Preferably, the probe comprises at least 12, 15, or 17 consecutive nucleotides from the 5' EST or extended cDNA. More preferably, the probe comprises at least 20–30 consecutive nucleotides from the 5' EST or extended cDNA. In some embodiments, the probe comprises more than 30 nucleotides from the 5' EST or extended cDNA.

Techniques for identifying cDNA clones in a cDNA library which hybridize to a given probe sequence are disclosed in Sambrook et al., Molecular Cloning: A Laboratory Manual 2d Ed., Cold Spring Harbor Laboratory Press, (1989). The same techniques may be used to isolate genomic DNAs.

Briefly, cDNA or genomic DNA clones which hybridize to the detectable probe are identified and isolated for further manipulation as follows. A probe comprising at least 10 consecutive nucleotides from the 5' EST or extended cDNA is labeled with a detectable label such as a radioisotope or a fluorescent molecule. Preferably, the probe comprises at least 12, 15, or 17 consecutive nucleotides from the 5' EST or extended cDNA. More preferably, the probe comprises 20–30 consecutive nucleotides from the 5' EST or extended cDNA. In some embodiments, the probe comprises more than 30 nucleotides from the 5' EST or extended cDNA.

Techniques for labeling the probe are well known and include phosphorylation with polynucleotide kinase, nick translation, in vitro transcription, and non-radioactive techniques. The cDNAs or genomic DNAs in the library are transferred to a nitrocellulose or nylon filter and denatured. After incubation of the filter with a blocking solution, the filter is contacted with the labeled probe and incubated for a sufficient amount of time for the probe to hybridize to cDNAs or genomic DNAs containing a sequence capable of hybridizing to the probe.

By varying the stringency of the hybridization conditions used to identify extended cDNAs or genomic DNAs which hybridize to the detectable probe, extended cDNAs having different levels of homology to the probe can be identified and isolated. To identify extended cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: Tm=81.5+16.6(log [Na+])+0.41(fraction G+C)–(600/N) where N is the length of the probe.

If the hybridization is carried out in a solution containing formamide, the melting temperature may be calculated using the equation Tm=81.5+16.6(log [Na+])+0.41 (fraction G+C)–(0.63% formamide)–(600/N) where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to extended cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 15–25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions. Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

Extended cDNAs, nucleic acids homologous to extended cDNAs or 5' ESTs, or genomic DNAs which have hybridized to the probe are identified by autoradiography or other conventional techniques.

The above procedure may be modified to identify extended cDNAs, nucleic acids homologous to extended cDNAs, or genomic DNAs having decreasing levels of homology to the probe sequence. For example, to obtain extended cDNAs, nucleic acids homologous to extended cDNAs, or genomic DNAs of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2xSSC, 0.5% SDS at the temperature of hybridization. These conditions are considered to be "moderate" conditions above 50° C. and "low" conditions below 50° C.

Alternatively, the hybridization may be carried out in buffers, such as 6xSSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6xSSC, 0.5% SDS at 50° C. These conditions are considered to be "moderate" conditions above 25% formamide and "low" conditions below 25% formamide.

Extended cDNAs, nucleic acids homologous to extended cDNAs, or genomic DNAs which have hybridized to the probe are identified by autoradiography.

If it is desired to obtain nucleic acids homologous to extended cDNAs, such as allelic variants thereof or nucleic acids encoding proteins related to the proteins encoded by the extended cDNAs, the level of homology between the hybridized nucleic acid and the extended cDNA or 5' EST used as the probe may readily be determined. To determine the level of homology between the hybridized nucleic acid and the extended cDNA or 5' EST from which the probe was derived, the nucleotide sequences of the hybridized nucleic acid and the extended cDNA or 5' EST from which the probe was derived are compared. For example, using the above methods, nucleic acids having at least 95% nucleic acid homology to the extended cDNA or 5' EST from which the probe was derived may be obtained and identified. Similarly, by using progressively less stringent hybridization conditions one can obtain and identify nucleic acids having at least 90%, at least 85%, at least 80% or at least 75% homology to the extended cDNA or 5' EST from which the probe was derived.

To determine whether a clone encodes a protein having a given amount of homology to the protein encoded by the extended cDNA or 5' EST, the amino acid sequence encoded by the extended cDNA or 5' EST is compared to the amino acid sequence encoded by the hybridizing nucleic acid. Homology is determined to exist when an amino acid sequence in the extended cDNA or 5' EST is closely related to an amino acid sequence in the hybridizing nucleic acid. A sequence is closely related when it is identical to that of the extended cDNA or 5' EST or when it contains one or more amino acid substitutions therein in which amino acids having similar characteristics have been substituted for one another. Using the above methods, one can obtain nucleic acids encoding proteins having at least 95%, at least 90%, at least 85%, at least 80% or at least 75% homology to the proteins encoded by the extended cDNA or 5' EST from which the probe was derived.

Alternatively, extended cDNAs may be prepared by obtaining mRNA from the tissue, cell, or organism of interest using mRNA preparation procedures utilizing poly A selection procedures or other techniques known to those skilled in the art. A first primer capable of hybridizing to the poly A tail of the mRNA is hybridized to the mRNA and a reverse transcription reaction is performed to generate a first cDNA strand.

The first cDNA strand is hybridized to a second primer containing at least 10 consecutive nucleotides of the sequences of the 5' EST for which an extended cDNA is desired. Preferably, the primer comprises at least 12, 15, or 17 consecutive nucleotides from the sequences of the 5' EST. More preferably, the primer comprises 20–30 consecutive nucleotides from the sequences of the 5' EST. In some embodiments, the primer comprises more than 30 nucleotides from the sequences of the 5' EST. If it is desired to obtain extended cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RTPCR may be performed as described above using primers from both ends of the cDNA to be obtained.

Extended cDNAs containing 5' fragments of the mRNA may be prepared by contacting an mRNA comprising the sequence of the 5' EST for which an extended cDNA is desired with a primer comprising at least 10 consecutive nucleotides of the sequences complementary to the 5' EST, hybridizing the primer to the mRNAs, and reverse transcribing the hybridized primer to make a first cDNA strand from the mRNAs. Preferably, the primer comprises at least 12, 15, or 17 consecutive nucleotides from the 5' EST. More preferably, the primer comprises 20–30 consecutive nucleotides from the 5' EST.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The double stranded extended cDNAs made using the methods described above are isolated and cloned. The extended cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in Current Protocols in Molecular Biology, John Wiley 503 Sons, Inc. (1997); and Sambrook et al. Molecular Cloning: A Laboratory Manual, Second Edition, Cold Spring Harbor Laboratory Press, (1989).

Alternatively, kits for obtaining full length cDNAs, such as the GeneTrapper (Cat. No. 10356-020, Gibco, BRL), may be used for obtaining full length cDNAs or extended cDNAs. In this approach, full length or extended cDNAs are prepared from mRNA and cloned into double stranded phagemids. The cDNA library in the double stranded phagemids is then rendered single stranded by treatment with an endonuclease, such as the Gene II product of the phage F1, and Exonuclease III as described in the manual accompanying the GeneTrapper kit. A biotinylated oligonucleotide comprising the sequence of a 5' EST, or a fragment containing at least 10 nucleotides thereof, is hybridized to the single stranded phagemids. Preferably, the fragment comprises at least 12, 15, or 17 consecutive nucleotides from the 5' EST. More preferably, the fragment comprises 20–30 consecutive nucleotides from the 5' EST. In some procedures, the fragment may comprise more than 30 consecutive nucleotides from the 5' EST.

Hybrids between the biotinylated oligonucleotide and phagemids having inserts containing the 5' EST sequence are isolated by incubating the hybrids with streptavidin coated paramagnetic beads and retrieving the beads with a magnet. Thereafter, the resulting phagemids containing the 5' EST sequence are released from the beads and converted into double stranded DNA using a primer specific for the 5' EST sequence. The resulting double stranded DNA is transformed into bacteria. Extended cDNAs containing the 5' EST sequence are identified by colony PCR or colony hybridization.

A plurality of extended cDNAs containing full length protein coding sequences or sequences encoding only the mature protein remaining after the signal peptide is cleaved may be provided as cDNA libraries for subsequent evaluation of the encoded proteins or use in diagnostic assays as described below.

IV. Expression of Proteins Encoded by Extended cDNAs Isolated Using 5' ESTs

Extended cDNAs containing the full protein coding sequences of their corresponding mRNAs or portions thereof, such as cDNAs encoding the mature protein, may be used to express the secreted proteins or portions thereof which they encode as described in Example 30 below. If desired, the extended cDNAs may contain the sequences encoding the signal peptide to facilitate secretion of the expressed protein. It will be appreciated that a plurality of extended cDNAs containing the full protein coding sequences or portions thereof may be simultaneously cloned into expression vectors to create an expression library for analysis of the encoded proteins as described below.

EXAMPLE 30

Expression of the Proteins Encoded by Extended cDNAs or Portions Thereof

To express the proteins encoded by the extended cDNAs or portions thereof, nucleic acids containing the coding sequence for the proteins or portions thereof to be expressed are obtained as described in Examples 27–29 and cloned into a suitable expression vector. If desired, the nucleic acids may contain the sequences encoding the signal peptide to facilitate secretion of the expressed protein. For example, the nucleic acid may comprise the sequence of one of SEQ ID NOs: 134–180 listed in Table VII and in the accompanying sequence listing. Alternatively, the nucleic acid may comprise those nucleotides which make up the full coding sequence of one of the sequences of SEQ ID NOs: 134–180 as defined in Table VII above.

It will be appreciated that should the extent of the full coding sequence (i.e. the sequence encoding the signal peptide and the mature protein resulting from cleavage of the signal peptide) differ from that listed in Table VII as a result of a sequencing error, reverse transcription or amplification error, mRNA splicing, post-translational modification of the encoded protein, enzymatic cleavage of the encoded protein, or other biological factors, one skilled in the art would be readily able to identify the extent of the full coding sequences in the sequences of SEQ ID NOs. 134–180. Accordingly, the scope of any claims herein relating to nucleic acids containing the full coding sequence of one of SEQ ID NOs. 134–180 is not to be construed as excluding any readily identifiable variations from or equivalents to the full coding sequences listed in Table VII. Similarly, should the extent of the full length polypeptides differ from those indicated in Table VIII as a result of any of the preceding factors, the scope of claims relating to polypeptides comprising the amino acid sequence of the full length polypeptides is not to be construed as excluding any readily identifiable variations from or equivalents to the sequences listed in Table VIII.

Alternatively, the nucleic acid used to express the protein or portion thereof may comprise those nucleotides which encode the mature protein (i.e. the protein created by cleaving the signal peptide off) encoded by one of the sequences of SEQ ID NOs: 134–180 as defined in Table VII.

It will be appreciated that should the extent of the sequence encoding the mature protein differ from that listed in Table VII as a result of a sequencing error, reverse transcription or amplification error, mRNA splicing, post-translational modification of the encoded protein, enzymatic cleavage of the encoded protein, or other biological factors, one skilled in the art would be readily able to identify the extent of the sequence encoding the mature protein in the sequences of SEQ ID NOs: 134–180. Accordingly, the scope of any claims herein relating to nucleic acids containing the sequence encoding the mature protein encoded by one of SEQ ID NOs: 134–180 is not to be construed as excluding any readily identifiable variations from or equivalents to the sequences listed in Table VII. Thus, claims relating to nucleic acids containing the sequence encoding the mature protein encompass equivalents to the sequences listed in Table VII, such as sequences encoding biologically active proteins resulting from post-translational modification, enzymatic cleavage, or other readily identifiable variations from or equivalents to the proteins in addition to cleavage of the signal peptide. Similarly, should the extent of the mature polypeptides differ from those indicated in Table VIII as a result of any of the preceding factors, the scope of claims relating to polypeptides comprising the sequence of a mature protein included in the sequence of one of SEQ ID NOs. 181–227 is not to be construed as excluding any readily identifiable variations from or equivalents to the sequences listed in Table VIII. Thus, claims relating to polypeptides comprising the sequence of the mature protein encompass equivalents to the sequences listed in Table VIII, such as biologically active proteins resulting from post-translational modification, enzymatic cleavage, or other readily identifiable variations from or equivalents to the proteins in addition to cleavage of the signal peptide. It will also be appreciated that should the biologically active form of the polypeptides included in the sequence of one of SEQ ID NOs. 181–227 or the nucleic acids encoding the biologically active form of the polypeptides differ from those identified as the mature polypeptide in Table VIII or the nucleotides encoding the mature polypeptide in Table VII as a result of a sequencing error, reverse transcription or amplification error, mRNA splicing, post-translational modification of the encoded protein, enzymatic cleavage of the encoded protein, or other biological factors, one skilled in the art would be readily able to identify the amino acids in the biologically active form of the polypeptides and the nucleic acids encoding the biologically active form of the polypeptides. In such instances, the claims relating to polypeptides comprising the mature protein included in one of SEQ ID NOs. 181–227 or nucleic acids comprising the nucleotides of one of SEQ ID NOs. 134–180 encoding the mature protein shall not be construed to exclude any readily identifiable variations from the sequences listed in Table VII and Table VIII.

In some embodiments, the nucleic acid used to express the protein or portion thereof may comprise those nucleotides which encode the signal peptide encoded by one of the sequences of SEQ ID NOs: 134–180 as defined in Table VII above.

It will be appreciated that should the extent of the sequence encoding the signal peptide differ from that listed in Table VII as a result of a sequencing error, reverse transcription or amplification error, mRNA splicing, post-translational modification of the encoded protein, enzymatic cleavage of the encoded protein, or other biological factors, one skilled in the art would be readily able to identify the extent of the sequence encoding the signal peptide in the sequences of SEQ ID NOs. 134–180. Accordingly, the scope of any claims herein relating to nucleic acids containing the sequence encoding the signal peptide encoded by one of SEQ ID NOs. 134–180 is not to be construed as excluding any readily identifiable variations from the sequences listed in Table VII. Similarly, should the extent of the signal peptides differ from those indicated in Table VIII as a result of any of the preceding factors, the scope of claims relating to polypeptides comprising the sequence of a signal peptide included in the sequence of one of SEQ ID NOs. 181–227 is not to be construed as excluding any readily identifiable variations from the sequences listed in Table VIII.

Alternatively, the nucleic acid may encode a polypeptide comprising at least 10 consecutive amino acids of one of the sequences of SEQ ID NOs: 181–227. In some embodiments, the nucleic acid may encode a polypeptide comprising at least 15 consecutive amino acids of one of the sequences of SEQ ID NOs: 181–227. In other embodiments, the nucleic acid may encode a polypeptide comprising at least 25 consecutive amino acids of one of the sequences of SEQ ID NOs: 181–227.

The nucleic acids inserted into the expression vectors may also contain sequences upstream of the sequences encoding the signal peptide, such as sequences which regulate expression levels or sequences which confer tissue specific expression.

The nucleic acid encoding the protein or polypeptide to be expressed is operably linked to a promoter in an expression vector using conventional cloning technology. The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767.

The following is provided as one exemplary method to express the proteins encoded by the extended cDNAs corresponding to the 5' ESTs or the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the extended cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The extended cDNA or portion thereof encoding the polypeptide to be expressed is obtained by PCR from the bacterial vector using oligonucleotide primers complementary to the extended cDNA or portion thereof and containing restriction endonuclease sequences for PstI incorporated into the 5' primer and BglII at the 5' end of the corresponding cDNA 3' primer, taking care to ensure that the extended cDNA is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Alternatively, the extended cDNAs may be cloned into pED6dpc2 as described above. The resulting pED6dpc2 constructs may be transfected into a suitable host cell, such as COS 1 cells. Methotrexate resistant cells are selected and expanded. Preferably, the protein expressed from the extended cDNA is released into the culture medium thereby facilitating purification.

Proteins in the culture medium are separated by gel electrophoresis. If desired, the proteins may be ammonium sulfate precipitated or separated based on size or charge prior to electrophoresis.

As a control, the expression vector lacking a cDNA insert is introduced into host cells or organisms and the proteins in the medium are harvested. The secreted proteins present in the medium are detected using techniques such as Coomassie or silver staining or using antibodies against the protein encoded by the extended cDNA. Coomassie and silver staining techniques are familiar to those skilled in the art.

Antibodies capable of specifically recognizing the protein of interest may be generated using synthetic 15-mer peptides having a sequence encoded by the appropriate 5' EST, extended cDNA, or portion thereof The synthetic peptides are injected into mice to generate antibody to the polypeptide encoded by the 5' EST, extended cDNA, or portion thereof.

Secreted proteins from the host cells or organisms containing an expression vector which contains the extended cDNA derived from a 5' EST or a portion thereof are compared to those from the control cells or organism. The presence of a band in the medium from the cells containing the expression vector which is absent in the medium from the control cells indicates that the extended cDNA encodes a secreted protein. Generally, the band corresponding to the protein encoded by the extended cDNA will have a mobility near that expected based on the number of amino acids in the open reading frame of the extended cDNA. However, the band may have a mobility different than that expected as a result of modifications such as glycosylation, ubiquitination, or enzymatic cleavage.

Alternatively, if the protein expressed from the above expression vectors does not contain sequences directing its secretion, the proteins expressed from host cells containing an expression vector containing an insert encoding a secreted protein or portion thereof can be compared to the proteins expressed in host cells containing the expression vector without an insert. The presence of a band in samples from cells containing the expression vector with an insert which is absent in samples from cells containing the expression vector without an insert indicates that the desired protein or portion thereof is being expressed. Generally, the band will have the mobility expected for the secreted protein or portion thereof. However, the band may have a mobility different than that expected as a result of modifications such as glycosylation, ubiquitination, or enzymatic cleavage.

The protein encoded by the extended cDNA may be purified using standard immunochromatography techniques. In such procedures, a solution containing the secreted protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is not possible, the extended cDNA sequence or portion thereof may be incorporated into expression vectors designed for use in purification schemes employing chimeric polypeptides. In such strategies the coding sequence of the extended cDNA or portion thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the extended cDNA or portion thereof. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the secreted proteins encoded by the 5' ESTs, extended cDNAs, or fragments thereof, the purified proteins may be tested for the ability to bind to the surface of various cell types as described in Example 31 below. It will be appreciated that a plurality of proteins expressed from these cDNAs may be included in a panel of proteins to be simultaneously evaluated for the activities specifically described below, as well as other biological roles for which assays for determining activity are available.

EXAMPLE 31

Analysis of Secreted Proteins to Determine Whether They Bind to the Cell Surface The proteins encoded by the 5' ESTs, extended cDNAs, or fragments thereof are cloned into expression vectors such as those described in Example 30. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto.

Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the cDNA binds specifically to the cell surface.

As discussed above, secreted proteins have been shown to have a number of important physiological effects and, consequently, represent a valuable therapeutic resource. The secreted proteins encoded by the extended cDNAs or portions thereof made according to Examples 27–29 may be evaluated to determine their physiological activities as described below.

EXAMPLE 32

Assaying the Proteins Expressed From Extended cDNAs or Portions Thereof for Cytokine, Cell Proliferation or Cell Differentiation Activity As discussed above, secreted proteins may act as cytokines or may affect cellular proliferation or differentiation. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7c and CMK. The proteins encoded by the above extended cDNAs or portions thereof may be evaluated for their ability to regulate T cell or thymocyte proliferation in assays such as those described above or in the following references: Current Protocols in Immunology, Ed. by J. E. Coligan et al., Greene Publishing Associates and Wiley-lnterscience; Takai et al. J. Immunol. 137:3494–3500 (1986); Bertagnolli et al. J. Immunol. 145:1706–1712 (1990); Bertagnolli et al., Cellular Immunology 133:327–341 (1991); Bertagnolli, et al. J. Immunol. 149:3778–3783 (1992); and Bowman et al., J. Immunol. 152:1756–1761 (1994).

In addition, numerous assays for cytokine production and/or the proliferation of spleen cells, lymph node cells and thymocytes are known. These include the techniques disclosed in Current Protocols in Immunology. J. E. Coligan et al. Eds., Vol 1 pp. 3.12.1–3.12.14 John Wiley and Sons, Toronto. (1994); and Schreiber, R. D. Current Protocols in Immunology., supra Vol 1 pp. 6.8.1–6.8.8, John Wiley and Sons, Toronto. (1994).

The proteins encoded by the cDNAs may also be assayed for the ability to regulate the proliferation and differentiation of hematopoietic or lymphopoietic cells. Many assays for such activity are familiar to those skilled in the art, including the assays in the following references: Bottomly, K., Davis, L. S. and Lipsky, P. E., Measurement of Human and Murine Interleukin 2 and Interleukin 4, Current Protocols in Immunology., J. E. Coligan et al. Eds. Vol 1 pp. 6.3.1–6.3.12, John Wiley and Sons, Toronto. (1991); deVries et al., J. Exp. Med. 173:1205–1211, 1991; Moreau et al., Nature 36:690–692, (1988); Greenberger et al., Proc. Natl. Acad. Sci. U.S.A. 80:2931–2938, (1983); Nordan, R., Measurement of Mouse and Human Interleukin 6. Current Protocols in Immunology. J. E. Coligan et al. Eds. Vol 1 pp. 6.6.1–6.6.5, John Wiley and Sons, Toronto. (1991); Smith et al., Proc. Natl. Acad. Sci. U.S.A. 83:1857–1861, 1986; Bennett, F., Giannotti, J., Clark, S. C. and Turner, K. J., Measurement of Human Interleukin 11. Current Protocols in Immunology. J. E. Coligan et al. Eds. Vol 1 pp. 6.15.1 John Wiley and Sons, Toronto. (1991); and Ciarletta, A., Giannotti, J., Clark, S. C. and Turner, K. J., Measurement of Mouse and Human Interleukin 9. Current Protocols in Immunology. J. E. Coligan et al., Eds. Vol 1 pp. 6.13.1, John Wiley and Sons, Toronto. (1991).

The proteins encoded by the cDNAs may also be assayed for their ability to regulate T-cell responses to antigens. Many assays for such activity are familiar to those skilled in the art, including the assays described in the following references: Chapter 3 (In Vitro Assays for Mouse Lymphocyte Function), Chapter 6 (Cytokines and Their Cellular Receptors) and Chapter 7, (Immunologic Studies in Humans) Current Protocols in Immunology, J. E. Coligan et al. Eds. Greene Publishing Associates and Wiley-Interscience; Weinberger et al., Proc. Natl. Acad. Sci. USA 77:6091–6095 (1980); Weinberger et al., Eur. J. Immun. 11:405411 (1981); Takai et al., J. Immunol. 137:3494–3500 (1986); and Takai et al., J. Immunol. 140:508–512 (1988).

Those proteins which exhibit cytokine, cell proliferation, or cell differentiation activity may then be formulated as pharmaceuticals and used to treat clinical conditions in which induction of cell proliferation or differentiation is beneficial. Alternatively, as described in more detail below, genes encoding these proteins or nucleic acids regulating the expression of these proteins may be introduced into appropriate host cells to increase or decrease the expression of the proteins as desired.

EXAMPLE 33

Assaying the Proteins Expressed From Extended cDNAs or Portions Thereof for Activity as Immune System Regulators The proteins encoded by the cDNAs may also be evaluated for their effects as immune regulators. For example, the proteins may be evaluated for their activity to influence thymocyte or splenocyte cytotoxicity. Numerous assays for such activity are familiar to those skilled in the art including the assays described in the following references: Chapter 3 (In Vitro Assays for Mouse Lymphocyte Function 3.1–3.19) and Chapter 7 (Immunologic studies in Humans) Current Protocols in Immunology, J. E. Coligan et al. Eds, Greene Publishing Associates and Wiley-Interscience; Herrmann et al., Proc. Natl. Acad. Sci. USA 78:2488–24921 (1981); Herrmann et al., J. Immunol. 128:1968–1974 (1982); Handa et al., J. Immunol. 135:1564–1572 (1985); Takai et al., J. Immunol. 137:3494–3500 (1986); Takai et al., J. Immunol. 140:508–512 (1988); Herrmann et al., Proc. Natl. Acad. Sci. USA 78:2488–2492 (1981); Herrmann et al J. Immunol. 128:1968–1974 (1982); Handa et al., J. Immunol. 135:1564–1572 (1985); Takai et al., J. Immunol. 137:3494–3500 (1986); Bowman et al., J. Virology 61:1992–1998; Takai et al., J. Immunol. 140:508–512 (1988); Bertagnolli et al., Cellular Immunology 133:327–341 (1991); and Brown et al., J. Immunol. 153:3079–3092 (1994).

The proteins encoded by the cDNAs may also be evaluated for their effects on T-cell dependent immunoglobulin responses and isotype switching. Numerous assays for such activity are familiar to those skilled in the art, including the assays disclosed in the following references: Maliszewski, J. Immunol. 144:3028–3033 (1990); and Mond, J. J. and Brunswick, M. Assays for B Cell Function: In vitro Antibody Production, Vol 1 pp. 3.8.1–3.8.16 Current Protocols in Immunology. J. E. Coligan et al Eds., John Wiley and Sons, Toronto. (1994).

The proteins encoded by the cDNAs may also be evaluated for their effect on immune effector cells, including their effect on Th1 cells and cytotoxic lymphocytes. Numerous assays for such activity are familiar to those skilled in the art, including the assays disclosed in the following references: Chapter 3 (In Vitro Assays for Mouse Lymphocyte Function 3.1–3.19) and Chapter 7 (Immunologic Studies in Humans) Current Protocols in Immunology, J. E. Coligan et al. Eds., Greene Publishing Associates and Wiley-Interscience; Takai et al., J. Immunol. 137:3494–3500 (1986); Takai et al.; J. Immunol. 140:508–512 (1988); and Bertagnolli et al., J. Immunol. 149:3778–3783 (1992).

The proteins encoded by the cDNAs may also be evaluated for their effect on dendritic cell mediated activation of naive T-cells. Numerous assays for such activity are familiar to those skilled in the art, including the assays disclosed in the following references: Guery et al., J. Immunol. 134:536–544 (1995); Inaba et al., Journal of Experimental Medicine 173:549–559 (1991); Macatonia et al., J. Immunol. 154:5071–5079 (1995); Porgador et al., Journal of Experimental Medicine 182:255–260 (1995); Nair et al., Journal of Virology 67:4062–4069 (1993); Huang et al., Science 264:961–965 (1994); Macatonia et al., Journal of Experimental Medicine 169:1255–1264 (1989); Bhardwaj et al., Journal of Clinical Investigation 94:797–807 (1994); and Inaba et al., Journal of Experimental Medicine 172:631–640 (1990).

The proteins encoded by the cDNAs may also be evaluated for their influence on the lifetime of lymphocytes. Numerous assays for such activity are familiar to those skilled in the art, including the assays disclosed in the following references: Darzynkiewicz et al., Cytometry 13:795–808 (1992); Gorczyca et al., Leukemia 7:659–670 (1993); Gorczyca et al., Cancer Research 53:1945–1951 (1993); Itoh et al., Cell 66:233–243 (1991); Zacharchuk et al., J. Immunol. 145:4037–4045 (1990); Zamai et al., Cytometry 14:891–897 (1993); and Gorczyca et al., International Journal of Oncology 1:639–648 (1992).

Assays for proteins that influence early steps of T-cell commitment and development include, without limitation, those described in: Antica et al., Blood 84:111–117 (1994); Fine et al., Cellular immunology 155:111–122 (1994); Galy et al., Blood 85:2770–2778 (1995); and Toki et al., Proc. Nat. Acad Sci. USA 88:7548–7551 (1991).

Those proteins which exhibit activity as immune system regulators activity may then be formulated as pharmaceuticals and used to treat clinical conditions in which regulation of immune activity is beneficial. For example, the protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses, in a number of ways. Down regulation may be in the form of inhibiting or blocking an immune response already in progress or may involve preventing the induction of an immune response. The functions of activated T-cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, (1989), pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor ligand interactions of B lymphocyte antigens can be used to inhibit T cell activation and prevent production of autoantibodies or T cell-derived cytokines which may be involved in the disease process.

Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/pr/pr mice or NZB hybrid mice, murine autoimmuno collagen arthritis, diabetes mellitus in OD mice and BB rats, and murine experimental myasthenia gravis (see Paul ed., Fundamental Immunology, Raven Press, New York, (1989), pp. 840–856). Upregulation of an antigen function (preferably a B lymphocyte antigen function), as a means of up regulating immune responses, may also be useful in therapy. Upregulation of immune responses may be in the form of enhancing an existing immune response or eliciting an initial immune response.

For example, enhancing an immune response through stimulating B lymphocyte antigen function may be useful in cases of viral infection. In addition, systemic viral diseases such as influenza, the common cold, and encephalitis might be alleviated by the administration of stimulatory form of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. The infected cells would now be capable of delivering a costimulatory signal to T cells in vivo, thereby activating the T cells.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acids encoding all or a portion of (e.g., a cytoplasmic-domain truncated portion) of an MHC class I α chain protein and $β_2$ macroglobulin protein or an MHC class II α chain protein and an MHC class II β chain protein to thereby express MHC class I or MHC class II proteins on the cell surface. Expression of the appropriate class II or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject. Alternatively, as described in more detail below, genes encoding these proteins or nucleic acids regulating the expression of these proteins may be introduced into appropriate host cells to increase or decrease the expression of the proteins as desired.

EXAMPLE 34

Assaying the Proteins Expressed From Extended cDNAs or Portions Thereof for Hematopoiesis Regulating Activity The proteins encoded by the extended cDNAs or portions thereof may also be evaluated for their hematopoiesis regulating activity. For example, the effect of the proteins on embryonic stem cell differentiation may be evaluated. Numerous assays for such activity are familiar to those skilled in the art, including the assays disclosed in the following references: Johansson et al. Cellular Biology 15:141–151 (1995); Keller et al., Molecular and Cellular Biology 13:473486 (1993); and McClanahan et al., Blood 81:2903–2915 (1993).

The proteins encoded by the extended cDNAs or portions thereof may also be evaluated for their influence on the lifetime of stem cells and stem cell differentiation. Numerous assays for such activity are familiar to those skilled in the art, including the assays disclosed in the following references: Freshney, M. G. Methylcellulose Colony Forming Assays, Culture of Hematopoietic Cells. R. I. Freshney, et al. Eds. pp. 265–268, Wiley-Liss, Inc., New York, N.Y. (1994); Hirayama et al., Proc. Natl. Acad. Sci. USA 89:5907–5911 (1992); McNiece, I. K. and Briddell, R. A. Primitive Hematopoietic Colony Forming Cells with High Proliferative Potential, Culture of Hematopoietic Cells. R. I. Freshney, et al. eds. Vol pp. 23–39, Wiley-Liss, Inc., New York, N.Y. (1994); Neben et al., Experimental Hematology 22:353–359 (1994); Ploemacher, R. E. Cobblestone Area Forming Cell Assay, Culture of Hematopoietic Cells. R. I. Freshney, et al. Eds. pp. 1–21, Wiley-Liss, Inc., New York, N.Y. (1994); Spooncer, E., Dexter, M. and Allen, T. Long Term Bone Marrow Cultures in the Presence of Stromal Cells, Culture of Hematopoietic Cells. R. I. Freshney, et al. Eds. pp. 163–179, Wiley-Liss, Inc., New York, N.Y. (1994); and Sutherland, H. J. Long Term Culture Initiating Cell Assay, Culture of Hematopoietic Cells. R. I. Freshney, et al. Eds. pp. 139–162, Wiley-Liss, Inc., New York, N.Y. (1994).

Those proteins which exhibit hematopoiesis regulatory activity may then be formulated as pharmaceuticals and used to treat clinical conditions in which regulation of hematopoeisis is beneficial. For example, a protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantion, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Alternatively, as described in more detail below, genes encoding these proteins or nucleic acids regulating the expression of these proteins may be introduced into appropriate host cells to increase or decrease the expression of the proteins as desired.

EXAMPLE 35

Assaying the Proteins Expressed From Extended cDNAs or Portions Thereof for Regulation of Tissue Growth The proteins encoded by the extended cDNAs or portions thereof may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491.

Assays for wound healing activity include, without limitation, those described in: Winter, Epidermal Wound Healing, pps. 71–112 (Maibach, HI and Rovee, D T, eds.), Year Book Medical Publishers, Inc., Chicago, as modified by Eaglstein and Mertz, J. Invest. Dermatol. 71:382–84 (1978).

Those proteins which are involved in the regulation of tissue growth may then be formulated as pharmaceuticals and used to treat clinical conditions in which regulation of tissue growth is beneficial. For example, a protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendonaigament formation. A protein of the present invention, which induces tendonIigament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendonaigament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e., for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium) muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to generate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokinc damage.

A protein of the present invention may also be useful for promoting or inhibiting differentiation of tissues described above from precursor tissues or cells; or for inhibiting the growth of tissues described above.

Alternatively, as described in more detail below, genes encoding these proteins or nucleic acids regulating the expression of these proteins may be introduced into appropriate host cells to increase or decrease the expression of the proteins as desired.

EXAMPLE 36

Assaying the Proteins Expressed from Extended cDNAs or Portions Thereof for Regulation of Reproductive Hormone or Cell Movement The proteins encoded by the extended cDNAs or portions thereof may also be evaluated for their ability to regulate reproductive hormones, such as follicle stimulating hormone. Numerous assays for such activity are familiar to those skilled in the art, including the assays disclosed in the following references: Vale et al., Endocrinology 91:562–572 (1972); Ling et al., Nature 321:779–782 (1986); Vale et al., Nature 321:776–779 (1986); Mason et al., Nature 318:659–663 (1985); Forage et al., Proc. Natl. Acad. Sci. USA 83:3091–3095 (1986). Chapter 6.12 (Measurement of Alpha and Beta Chemokincs) Current Protocols in Immunology, J. E. Coligan et al. Eds. Greene Publishing Associates and Wiley-Intersciece; Taub et al. J. Clin. Invest. 95:1370–1376 (1995); Lind et al. APMIS 103:140–146 (1995); Muller et al. Eur. J. Immunol. 25:1744–1748; Gruber et al. J. of Immunol. 152:5860–5867 (1994); and Johnston et al. J. of Immunol. 153:1762–1768 (1994).

Those proteins which exhibit activity as reproductive hormones or regulators of cell movement may then be formulated as pharmaceuticals and used to treat clinical conditions in which regulation of reproductive hormones or cell movement are beneficial. For example, a protein of the present invention may also exhibit activin- or inhibin-related activities. Inhibins are characterized by their ability to inhibit the release of follicle stimulating hormone (FSH), while activins are characterized by their ability to stimulate the release of folic stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-B group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

Alternatively, as described in more detail below, genes encoding these proteins or nucleic acids regulating the expression of these proteins may be introduced into appropriate host cells to increase or decrease the expression of the proteins as desired.

EXAMPLE 36A

Assaying the Proteins Expressed From Extended cDNAs or Portions Thereof for Chemotatic/chemokinetic Activity The proteins encoded by the extended cDNAs or portions thereof may also be evaluated for chemotactic/chemokinetic activity. For example, a protein of the present invention may have chemotactic or chemokinetic activity (e.g., act as a chemokine) for mammalian cells, including, for example, monocytes, fibroblasts, neutrophils, T-cells, mast cells, cosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhension of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokincs 6.12.1–6.12.28; Taub et al. J. Clin. Invest. 95:1370–1376 (1995); Lind et al. APMIS 103:140–146 (1995); Mueller et al. Eur. J. Immunol. 25:1744–1748; Gruber et al. J. of Immunol. 152:5860–5867 (1994); and Johnston et al. J. of Immunol. 153:1762–1768 (1994).

EXAMPLE 37

Assaying the Proteins Expressed From Extended cDNAs or Portions Thereof for Regulation of Blood Clotting The proteins encoded by the extended cDNAs or portions thereof may also be evaluated for their effects on blood clotting. Numerous assays for such activity are familiar to those skilled in the art, including the assays disclosed in the following references: Linet et al., J. Clin. Pharmacol. 26:131–140 (1986); Burdick et al., Thrombosis Res. 45:413–419 (1987); Humphrey et al., Fibrinolysis 5:71–79 (1991); and Schaub, Prostaglandins 35:467–474 (1988).

Those proteins which are involved in the regulation of blood clotting may then be formulated as pharmaceuticals and used to treat clinical conditions in which regulation of blood clotting is beneficial. For example, a protein of the invention may also exhibit hemostatic or thrombolytic activity. As a result, such a protein is expected to be useful in treatment of various coagulations disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke). Alternatively, as described in more detail below, genes encoding these proteins or nucleic acids regulating the expression of these proteins may be introduced into appropriate host cells to increase or decrease the expression of the proteins as desired.

EXAMPLE 38

Assaying the Proteins Expressed from Extended cDNAs or Portion Thereof for Involvement in Receptor/ligand Interactions The proteins encoded by the extended cDNAs or a portion thereof may also be evaluated for their involvement in receptor/ligand interactions. Numerous assays for such involvement are familiar to those skilled in the art, including the assays disclosed in the following references: Chapter 7.28 (Measurement of Cellular Adhesion under Static Conditions 7.28.1–7.28.22) Current Protocols in Immunology, J. E. Coligan et al. Eds. Greene Publishing Associates and Wiley-Interscience; Takai et al., Proc. Natl. Acad. Sci. USA 84:6864–6868 (1987); Bierer et al., J. Exp. Med. 168:1145–1156 (1988); Rosenstein et al., J. Exp. Med. 169:149–160 (1989); Stoltenborg et al., J. Immunol. Methods 175:59–68 (1994); Stitt et al., Cell 80:661–670 (1995); and Gyuris et al., Cell 75:791–803 (1993).

For example, the proteins of the present invention may also demonstrate activity as receptors, receptor ligands or inhibitors or agonists of receptor/ligand interactions. Examples of such receptors and ligands include, without limitation, cytokine receptors and their ligands, receptor linases and their ligands, receptor phosphatases and their ligands, receptors involved in cell-cell interactions and their ligands (including without limitation, cellular adhesion molecules (such as selections, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

EXAMPLE 38A

Assaying the Proteins Expressed From Extended cDNAs or Portions Thereof for Anti-inflammatory Activity The proteins encoded by the extended cDNAs or a portion thereof may also be evaluated for anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusioninury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

EXAMPLE 38B

Assaying the Proteins Expressed From Extended cDNA or Portions Thereof for Tumor Inhibition Activity The proteins encoded by the extended cDNAs or a portion thereof may also be evaluated for tumor inhibition activity. In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

EXAMPLE 39

Identification of Proteins Which Interact with Polypeptides Encoded by Extended cDNAs Proteins which interact with the polypeptides encoded by extended cDNAs or portions thereof, such as receptor proteins, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), the extended cDNAs or portions thereof, are inserted into an expression vector such that they are in frame with DNA encoding the DNA binding domain of the yeast transcriptional activator GAL4. cDNAs in a cDNA library which encode proteins which might interact with the polypeptides encoded by the extended cDNAs or portions thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the extended cDNAs or portions thereof.

Alternatively, the system described in Lustig et al., Methods in Enzymology 283: 83–99 (1997), may be used for identifying molecules which interact with the polypeptides encoded by extended cDNAs. In such systems, in vitro transcription reactions are performed on a pool of vectors containing extended cDNA inserts cloned downstream of a promoter which drives in vitro transcription. The resulting pools of mRNAs are introduced into *Xenopus laevis* oocytes. The oocytes are then assayed for a desired activity.

Alternatively, the pooled in vitro transcription products produced as described above may be translated in vitro. The pooled in vitro translation products can be assayed for a desired activity or for interaction with a known polypeptide.

Proteins or other molecules interacting with polypeptides encoded by extended cDNAs can be found by a variety of additional techniques. In one method, affinity columns containing the polypeptide encoded by the extended cDNA or a portion thereof can be constructed. In some versions, of this method the affinity column contains chimeric proteins in which the protein encoded by the extended cDNA or a portion thereof is fused to glutathione S-transferase. A mixture of cellular proteins or pool of expressed proteins as described above and is applied to the affinity column. Proteins interacting with the polypeptide attached to the column can then be isolated and analyzed on 2-D electrophoresis gel as described in Ramunsen et al. Electrophoresis 18:588–598 (1997). Alternatively, the proteins retained on the affinity column can be purified by electrophoresis based methods and sequenced. The same method can be used to isolate antibodies, to screen phage display products, or to screen phage display human antibodies.

Proteins interacting with polypeptides encoded by extended cDNAs or portions thereof can also be screened by using an Optical Biosensor as described in Edwards & Leatherbarrow, Analytical Biochemistry, 246:1–6 (1997). The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred manometers from the sensor surface). In these screening assays, the target molecule can be one of the polypeptides encoded by extended cDNAs or a portion thereof and the test sample can be a collection of proteins extracted from tissues or cells, a pool of expressed proteins, combinatorial peptide and/or chemical libraries, or phage displayed peptides. The tissues or cells from which the test proteins are extracted can originate from any species.

In other methods, a target protein is immobilized and the test population is a collection of unique polypeptides encoded by the extended cDNAs or portions thereof.

To study the interaction of the proteins encoded by the extended cDNAs or portions thereof with drugs, the microdialysis coupled to HPLC method described by Wang et al., Chromatographia 44:205–208(1997) or the affinity capillary electrophoresis method described by Busch et al., J. Chromatogr. 777:311–328 (1997).

The system described in U.S. Pat. No. 5,654,150, may also be used to identify molecules which interact with the polypeptides encoded by the extended cDNAs. In this system, pools of extended cDNAs are transcribed and translated in vitro and the reaction products are assayed for interaction with a known polypeptide or antibody.

It will be appreciated by those skilled in the art that the proteins expressed from the extended cDNAs or portions may be assayed for numerous activities in addition to those specifically enumerated above. For example, the expressed proteins may be evaluated for applications involving control and regulation of inflammation, tumor proliferation or metastasis, infection, or other clinical conditions. In addition, the proteins expressed from the extended cDNAs or portions thereof may be useful as nutritional agents or cosmetic agents.

The proteins expressed from the extended cDNAs or portions thereof may be used to generate antibodies capable of specifically binding to the expressed protein or fragments thereof as described in Example 40 below. The antibodies may capable of binding a full length protein encoded by one of the sequences of SEQ ID NOs. 134–180, a mature protein encoded by one of the sequences of SEQ ID NOs. 134–180, or a signal peptide encoded by one of the sequences of SEQ ID Nos. 134–180. Alternatively, the antibodies may be capable of binding fragments of the proteins expressed from the extended cDNAs which comprise at least 10 amino acids of the sequences of SEQ ID NOs: 181–227. In some embodiments, the antibodies may be capable of binding fragments of the proteins expressed from the extended cDNAs which comprise at least 15 amino acids of the sequences of SEQ ID NOs: 181–227. In other embodiments, the antibodies may be capable of binding fragments of the proteins expressed from the extended cDNAs which comprise at least 25 amino acids of the sequences of SEQ ID NOs: 181–227. In further embodiments, the antibodies may be capable of binding fragments of the proteins expressed from the extended cDNAs which comprise at least 40 amino acids of the sequences of SEQ ID NOs: 181–227.

EXAMPLE 40

Epitope and Antibody Fusions

A preferred embodiment of the present invention is directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:39984002. It is particularly noted that although a particular epitope may not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means. See, e.g., Houghten, R. A., Proc. Natl.

Acad. Sci. USA 82:5131–5135 (1985), further described in U.S. Pat. No. 4,631,211. Methods for determining the amino acids which make up an immunogenic epitope include x-ray crystallography, 2-dimensional nuclear magnetic resonance, and epitope mapping, e.g., the Pepscan method described by H. Mario Geysen et al. (1984); Proc. Natl. Acad. Sci. U.S.A. 81:3998–4002; PCT Publication No. WO 84/03564; and PCT Publication No. WO 84/03506. Another example is the algorithm of Jameson and Wolf, Comp. Appl. Biosci. 4:181–186 (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.).

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length sequence of the sequence listing. All combinations of sequences between the integers of 6 and the full-length sequence of a polypeptide of the present invention are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.;(1985) and Bittle, F. J. et al., (1985). A preferred immunogenic epitope includes the polypeptides of the sequence listing. The immunogenic epitopes may be presented together with a carrier protein, such as an albumin, to an animal system (such as rabbit or mouse) if necessary. Immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as—maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention including, but not limited to, polypeptides comprising an immunogenic or antigenic epitope can be fused to heterologous polypeptide sequences. For example, the polypeptides of the present invention may be fused with the constant region comprising portions of immunoglobulins (IgA, IgE, IgG, IgM), or portions of the constant region (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos.: 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies

The present invention further relates to antibodies and T-cell antigen receptors (TCR), which specifically bind the polypeptides, and more specifically, the epitopes of the polyepeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, eg., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. 1988); Hammerling, et al, 1981). (Said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene III protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab'F (ab)2 and F(ab')2 fragments can also be employed using methods known in the art such as those disclosed in WO 92/22324; Mullinax, R. L. et al. (1992); and Sawai, H. et al. (1995); and Better, M. et al. (1988).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. No. 5,530,101; and 5,585,089), veneering or resurfacing, (EP 0 592 106; EP 0 519 596; Padlan E. A., 1991; Studnicka G. M. et al., 1994; Roguska M. A. et al., 1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S.O. et al., 1992; Fell, H. P. et al., 1991).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989); and Nissinoff (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and thereby block its biological activity, The invention also concerns a purified or isolated antibody capable of specifically binding to a mutated full length or mature polypeptide of the present invention or to a fragment or variant thereof comprising an epitope of the mutated polypeptide. In another preferred embodiment, the present invention concerns an antibody capable of binding to a polypeptide comprising at least 10 consecutive amino acids of a polypeptide of the present invention and including at least one of the amino acids which can be encoded by the trait causing mutations.

Non-human animals or mammals, whether wild-type or transgenic, which express a different species of a polypeptide of the present invention than the one to which antibody binding is desired, and animals which do not express a polypeptide of the present invention (i.e. a knock out animal) are particularly useful for preparing antibodies. Gene knock out animals will recognize all or most of the exposed regions of a polypeptide of the present invention as foreign antigens, and therefore produce antibodies with a wider array of epitopes. Moreover, smaller polypeptides with only 10 to 30 amino acids may be useful in obtaining specific binding to any one of the polypeptides of the present invention. In addition, the humoral immune system of animals which produce a species of a polypeptide of the present invention that resembles the antigenic sequence will preferentially recognize the differences between the animal's native polypeptide species and the antigen sequence, and produce antibodies to these unique sites in the antigen sequence. Such a technique will be particularly useful in obtaining antibodies that specifically bind to any one of the polypeptides of the present invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a polypeptide of the present invention according to the invention in a biological sample, said method comprising the following steps:
  a) bringing into contact the biological sample with a polyclonal or monoclonal antibody that specifically binds a polypeptide of the present invention; and
  b) detecting the antigen-antibody complex formed.

The invention also concerns a diagnostic kit for detecting in vitro the presence of a polypeptide of the present invention in a biological sample, wherein said kit comprises:
  a) a polyclonal or monoclonal antibody that specifically binds a polypeptide of the present invention, optionally labeled;
  b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. *Bacic Methods in Molecular Biology* Elsevier, New York. Section 21-2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, 0. et al., Chap. 19 in: *Handhook of Experimental Immunology* D. Wier (ed) Blackwell (1973). Plateau concentration of antibody is usually in the range of 0.1 to 0.2 mg/ml of serum (about 12 □M). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

V. Use of cDNAs or Fragments Thereof as Reagents

The cDNAs of the present invention may be used as reagents in isolation procedures, diagnostic assays, and forensic procedures. For example, sequences from the cDNAs (or genomic DNAs obtainable therefrom) may be detectably labeled and used as probes to isolate other sequences capable of hybridizing to them. In addition, sequences from the cDNAs (or genomic DNAs obtainable therefrom) may be used to design PCR primers to be used in isolation, diagnostic, or forensic procedures.

EXAMPLE 41

Preparation of PCR Primers and Amplification of DNA

The extended cDNAs (or genomic DNAs obtainable therefrom) may be used to prepare PCR primers for a variety of applications, including isolation procedures for cloning nucleic acids capable of hybridizing to such sequences, diagnostic techniques and forensic techniques. The PCR primers are at least 10 bases, and preferably at least 12, 15, or 17 bases in length. More preferably, the PCR primers are at least 20–30 bases in length. In some embodiments, the PCR primers may be more than 30 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B.A. Ed. in Methods in Molecular Biology 67: Humana Press, Totowa (1997). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 42

Use of Extended cDNAs as Probes

Probes derived from extended cDNAs or portions thereof (or genomic DNAs obtainable therefrom) may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions. A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described in Example 30 above.

PCR primers made as described in Example 41 above may be used in forensic analyses, such as the DNA fingerprinting techniques described in Examples 43–47 below. Such analyses may utilize detectable probes or primers based on the sequences of the extended cDNAs isolated using the 5' ESTs (or genomic DNAs obtainable therefrom).

EXAMPLE 43

Forensic Matching by DNA Sequencing

In one exemplary method, DNA samples are isolated from forensic specimens of, for example, hair, semen, blood or skin cells by conventional methods. A panel of PCR primers based on a number of the extended cDNAs (or genomic DNAs obtainable therefrom), is then utilized in accordance with Example 41 to amplify DNA of approximately 100–200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 44

Positive Identification by DNA Sequencing

The technique outlined in the previous example may also be used on a larger scale to provide a unique fingerprint-type identification of any individual. In this technique, primers are prepared from a large number of sequences from Table II and the appended sequence listing. Preferably, 20 to 50 different primers are used. These primers are used to obtain a corresponding number of PCR-generated DNA segments from the individual in question in accordance with Example 41. Each of these DNA segments is sequenced, using the methods set forth in Example 43. The database of sequences generated through this procedure uniquely identifies the individual from whom the sequences were obtained. The same panel of primers may then be used at any later time to absolutely correlate tissue or other biological specimen with that individual.

EXAMPLE 45

Southern Blot Forensic Identification

The procedure of Example 44 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. Basic Methods in Molecular Biology, (1986), Elsevier Press. pp 62–65).

A panel of probes based on the sequences of the extended cDNAs (or genomic DNAs obtainable therefrom), or fragments thereof of at least 10 bases, are radioactively or calorimetrically labeled using methods known in the art, such as nick translation or end labeling, and hybridized to the Southern blot using techniques known in the art (Davis et al., supra). Preferably, the probe comprises at least 12, 15, or 17 consecutive nucleotides from the extended cDNA (or genomic DNAs obtainable therefrom). More preferably, the probe comprises at least 20–30 consecutive nucleotides from the extended cDNA (or genomic DNAs obtainable therefrom). In some embodiments, the probe comprises more than 30 nucleotides from the extended cDNA (or genomic DNAs obtainable therefrom).

Preferably, at least 5 to 10 of these labeled probes are used, and more preferably at least about 20 or 30 are used to provide a unique pattern. The resultant bands appearing from the hybridization of a large sample of extended cDNAs (or genomic DNAs obtainable therefrom) will be a unique identifier. Since the restriction enzyme cleavage will be different for every individual, the band pattern on the Southern blot will also be unique. Increasing the number of extended cDNA probes will provide a statistically higher level of confidence in the identification since there will be an increased number of sets of bands used for identification.

EXAMPLE 46

Dot Blot Identification Procedure

Another technique for identifying individuals using the extended cDNA sequences disclosed herein utilizes a dot blot hybridization technique.

Genomic DNA is isolated from nuclei of subject to be identified. Oligonucleotide probes of approximately 30 bp in length are synthesized that correspond to at least 10, preferably 50 sequences from the extended cDNAs or genomic DNAs obtainable therefrom. The probes are used to hybridize to the genomic DNA through conditions known to those in the art. The oligonucleotides are end labeled with $P^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments are sequentially hybridized with successively stringent conditions to detect minimal differences between the 30 bp sequence and the DNA. Tetramethylammonium chloride is useful for identifying clones containing small numbers of nucleotide mismatches (Wood et al., Proc. Natl. Acad. Sci. USA 82(6): 1585–1588 (1985)). A unique pattern of dots distinguishes one individual from another individual.

Extended cDNAs or oligonucleotides containing at least 10 consecutive bases from these sequences can be used as probes in the following alternative fingerprinting technique. Preferably, the probe comprises at least 12, 15, or 17 consecutive nucleotides from the extended cDNA (or genomic DNAs obtainable therefrom). More preferably, the probe comprises at least 20–30 consecutive nucleotides from the extended cDNA (or genomic DNAs obtainable therefrom). In some embodiments, the probe comprises more than 30 nucleotides from the extended cDNA (or genomic DNAs obtainable therefrom).

Preferably, a plurality of probes having sequences from different genes are used in the alternative fingerprinting technique. Example 47 below provides a representative alternative fingerprinting procedure in which the probes are derived from extended cDNAs.

EXAMPLE 47

Alternative "Fingerprint" Identification Technique 20-mer oligonucleotides are prepared from a large number, e.g. 50, 100, or 200, of extended cDNA sequences (or genomic DNAs obtainable therefrom) using commercially available oligonucleotide services such as Genset, Paris, France. Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

The antibodies generated in Examples 30 and 40 above may be used to identify the tissue type or cell species from which a sample is derived as described above.

EXAMPLE 48

Identification of Tissue Type or Cell Species by Means of Labeled Tissue Specific Antibodies Identification of specific tissues is accomplished by the visualization of tissue specific antigens by means of antibody preparations according to Examples 30 and 40 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

A. Immunohistochemical Techniques

Purified, high-titer antibodies, prepared as described above, are conjugated to a detectable marker, as described, for example, by Fudenberg, H., Chap. 26 in: Basic 503 Clinical Immunology, 3rd Ed. Lange, Los Altos, Calif. (1980) or Rose, N. et al., Chap. 12 in: Methods in Immunodiagnosis, 2d Ed. John Wiley 503 Sons, New York (1980).

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}$I, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 $\mu$m, unfixed) of the unknown tissue and known control, are mounted and each slide covered with different dilutions of the antibody preparation. Sections of known and unknown tissues should also be treated with preparations to provide a positive control, a negative control, for example, preimmune sera, and a control for non-specific staining, for example, buffer.

Treated sections are incubated in a humid chamber for 30 min at room temperature, rinsed, then washed in buffer for 30–45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: Basic Methods in Molecular Biology (P. Leder, ed), Elsevier, New York (1986), using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 $\mu$l, and containing from about 1 to 100 $\mu$g protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., (above) Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 30 and 40. In this procedure, as in procedure A above, appropriate positive and negative sample and reagent controls are run.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

The visualization of tissue specific antigen binding at levels above those seen in control tissues to one or more tissue specific antibodies, prepared from the gene sequences identified from extended cDNA sequences, can identify tissues of unknown origin, for example, forensic samples, or differentiated tumor tissue that has metastasized to foreign bodily sites.

In addition to their applications in forensics and identification, extended cDNAs (or genomic DNAs obtainable therefrom) may be mapped to their chromosomal locations. Example 49 below describes radiation hybrid (RH) mapping of human chromosomal regions using extended cDNAs. Example 50 below describes a representative procedure for mapping an extended cDNA (or a genomic DNA obtainable therefrom) to its location on a human chromosome. Example 51 below describes mapping of extended cDNAs (or genomic DNAs obtainable therefrom) on metaphase chromosomes by Fluorescence In Situ Hybridization (FISH).

EXAMPLE 49

Radiation Hybrid Mapping of Extended cDNAs to the Human Genome

Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. Genomics 4:509–517 (1989) and Cox et al., Science 250:245–250 (1990). The random and independent nature of the subclones permits efficient mapping of any human genome marker. Human DNA isolated from a panel of 80–100 cell lines provides a mapping reagent for ordering extended cDNAs (or genomic DNAs obtainable therefrom). In this approach, the frequency of breakage between markers is used to measure distance, allowing construction of fine resolution maps as has been done using conventional ESTs Schuler et al., Science 274:540–546 (1996).

RH mapping has been used to generate a high-resolution whole genome radiation hybrid map of human chromosome 17q22-q25.3 across the genes for growth hormone (GH) and thymidine kinase (TK) Foster et al., Genomics 33:185–192 (1996), the region surrounding the Gorlin syndrome gene (Obermayr et al., Eur. J. Hum. Genet. 4:242–245, 1996), 60 loci covering the entire short arm of chromosome 12 (Raeymaekers et al., Genomics 29:170–178, (1995)), the region of human chromosome 22 containing the neurofibromatosis type 2 locus (Frazer et al., Genomics 14:574–584 (1992)) and 13 loci on the long arm of chromosome 5 (Warrington et al., Genomics II1:701–708 (1991)).

EXAMPLE 50

Mapping of Extended cDNAs to Human Chromosomes Using PCR Techniques

Extended cDNAs (or genomic DNAs obtainable therefrom) may be assigned to human chromosomes using PCR based methodologies. In such approaches, oligonucleotide primer pairs are designed from the extended cDNA sequence (or the sequence of a genomic DNA obtainable therefrom) to minimize the chance of amplifying through an intron. Preferably, the oligonucleotide primers are 18–23 bp in length and are designed for PCR amplification. The creation of PCR primers from known sequences is well known to those with skill in the art. For a review of PCR technology see Erlich, H. A., PCR Technology; Principles and Applications for DNA Amplification. (1992). W.H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 $\mu$Cu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extion at 72° C. for 10 min. The amplified products are analyzed on a 6% polyacrylamide sequencing gel and visualized by autoradiography. If the length of the resulting PCR product is identical to the distance between the ends of the primer sequences in the extended cDNA from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given extended cDNA (or genomic DNA obtainable therefrom). DNA is isolated from the somatic hybrids and used as starting templates for PCR reactions using the primer pairs from the extended cDNAs (or genomic DNAs obtainable therefrom). Only those somatic cell hybrids with chromosomes containing the human gene corresponding to the extended cDNA (or genomic DNA obtainable therefrom) will yield an amplified fragment. The extended cDNAs (or genomic DNAs obtainable therefrom) are assigned to a chromosome by analysis of the segregation pattern of PCR products from the somatic hybrid DNA templates. The single human chromosome present in all cell hybrids that give rise to an amplified fragment is the chromosome containing that extended cDNA (or genomic DNA obtainable therefrom). For a review of techniques and analysis of results from somatic cell gene mapping experiments. (See Ledbetter et al., Genomics 6:475–481 (1990).)

Alternatively, the extended cDNAs (or genomic DNAs obtainable therefrom) may be mapped to individual chromosomes using FISH as described in Example 51 below.

EXAMPLE 51

Mapping of Extended 5' ESTs to Chromosomes Using Fluorescence In Situ Hybridization Fluorescence in situ hybridization allows the extended cDNA (or genomic DNA obtainable therefrom) to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of an extended cDNA (or genomic DNA obtainable therefrom) is obtained by FISH as described by Cherif et al. Proc. Natl. Acad. Sci. U.S.A., 87:6639–6643 (1990). Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 $\mu$M) is added for 17 h, followed by addition of 5-bromodeoxyuridine (5-BudR, 0.1 mM) for 6 h. Colcemid (1 $\mu$g/ml) is added for the last 15 min before harvesting the cells. Cells are collected, washed in RPMI, incubated with a hypotonic solution of KCl (75 mM) at 37° C. for 15 min and fixed in three changes of methanol:acetic acid (3:1). The cell suspension is dropped onto a glass slide and air dried. The extended cDNA (or genomic DNA obtainable therefrom) is labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 min.

Slides kept at −20° C. are treated for 1 h at 37° C. with RNase A (100 $\mu$g/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 $\mu$g/100 ml in 20 mM Tris-HCl, 2 mM CaCl$_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular extended cDNA (or genomic DNA obtainable therefrom) may be localized to a particular cytogenetic R-band on a given chromosome.

Once the extended cDNAs (or genomic DNAs obtainable therefrom) have been assigned to particular chromosomes using the techniques described in Examples 49–51 above, they may be utilized to construct a high resolution map of the chromosomes on which they are located or to identify the chromosomes in a sample.

EXAMPLE 52

Use of Extended cDNA to Construct or Expand Chromosome Maps

Chromosome mapping involves assigning a given unique sequence to a particular chromosome as described above.

Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the extended cDNAs (or genomic DNAs obtainable therefrom) are obtained. This approach is described in Ramaiah Nagaraja et al. Genome Research 7:210–222, (March, 1997). Briefly, in this approach each chromosome is broken into overlapping pieces which are inserted into the YAC vector. The YAC inserts are screened using PCR or other methods to determine whether they include the extended cDNA (or genomic DNA obtainable therefrom) whose position is to be determined. Once an insert has been found which includes the extended cDNA (or genomic DNA obtainable therefrom), the insert can be analyzed by PCR or other methods to determine whether the insert also contains other sequences known to be on the chromosome or in the region from which the extended cDNA (or genomic DNA obtainable therefrom) was derived. This process can be repeated for each insert in the YAC library to determine the location of each of the extended cDNAs (or genomic DNAs obtainable therefrom) relative to one another and to other known chromosomal markers. In this way, a high resolution map of the distribution of numerous unique markers along each of the organisms chromosomes may be obtained.

As described in Example 53 below extended cDNAs (or genomic DNAs obtainable therefrom) may also be used to identify genes associated with a particular phenotype, such as hereditary disease or drug response.

EXAMPLE 53

Identification of Genes Associated with Hereditary Diseases or Drug Response

This example illustrates an approach useful for the association of extended cDNAs (or genomic DNAs obtainable therefrom) with particular phenotypic characteristics. In this example, a particular extended cDNA (or genomic DNA obtainable therefrom) is used as a test probe to associate that extended cDNA (or genomic DNA obtainable therefrom) with a particular phenotypic characteristic.

Extended cDNAs (or genomic DNAs obtainable therefrom) are mapped to a particular location on a human chromosome using techniques such as those described in Examples 49 and 50 or other techniques known in the art. A search of Mendelian Inheritance in Man (V. McKusick, Mendelian Inheritance in Man (available on line through Johns Hopkins University Welch Medical Library) reveals the region of the human chromosome which contains the extended cDNA (or genomic DNA obtainable therefrom) to be a very gene rich region containing several known genes and several diseases or phenotypes for which genes have not been identified. The gene corresponding to this extended cDNA (or genomic DNA obtainable therefrom) thus becomes an immediate candidate for each of these genetic diseases.

Cells from patients with these diseases or phenotypes are isolated and expanded in culture. PCR primers from the extended cDNA (or genomic DNA obtainable therefrom) are used to screen genomic DNA, mRNA or cDNA obtained from the patients. Extended cDNAs (or genomic DNAs obtainable therefrom) that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the extended cDNA may be responsible for the genetic disease.

VI. Use of Extended cDNAs (or Genomic DNAs Obtainable Therefrom) to Construct Vectors The present extended cDNAs (or genomic DNAs obtainable therefrom) may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described in Example 54 below.

EXAMPLE 54

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegalovirus promoter, and other promoters familiar to those skilled in the art.

A signal sequence from an extended cDNA (or genomic DNA obtainable therefrom), such as one of the signal sequences in SEQ ID NOs: 134–180 as defined in Table VI above, is operably linked to the promoter such that the mRNA transcribed from the promoter will direct the translation of the signal peptide. The host cell, tissue, or organism may be any cell, tissue, or organism which recognizes the signal peptide encoded by the signal sequence in the extended cDNA (or genomic DNA obtainable therefrom). Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediated transfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and hplc. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

The extended cDNAs or 5' ESTs may also be used to clone sequences located upstream of the extended cDNAs or 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. Example 55 describes a method for cloning sequences upstream of the extended cDNAs or 5' ESTs.

EXAMPLE 55

Use of Extended cDNAs or 5' ESTs to Clone Upstream Sequences From Genomic DNA

Sequences derived from extended cDNAs or 5' ESTs may be used to isolate the promoters of the corresponding genes using chromosome walking techniques. In one chromosome walking technique, which utilizes the GenomeWalker™ kit available from Clontech, five complete genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions using an outer adaptor primer provided in the kit and an outer gene specific primer. The gene specific primer should be selected to be specific for the extended cDNA or 5' EST of interest and should have a melting temperature, length, and location in the extended cDNA or ' EST which is consistent with its use in PCR reactions. Each first PCR reaction contains 5 ng of genomic DNA, 5 µl of 10×Tth reaction buffer, 0.2 mM of each dNTP, 0.2 µM each of outer adaptor primer and outer gene specific primer, 1.1 mM of Mg(OAc)$_2$, and 1 µl of the Tth polymerase 50×mix in a total volume of 50 µl. The reaction cycle for the first PCR reaction is as follows: 1 min –94° C./2 sec –94° C., 3 min –72° C. (7 cycles)/2 sec –94° C., 3 min –67° C. (32 cycles)/5 min –67° C.

The product of the first PCR reaction is diluted and used as a template for a second PCR reaction according to the manufacturer's instructions using a pair of nested primers which are located internally on the amplicon resulting from the first PCR reaction. For example, 5 µl of the reaction product of the first PCR reaction mixture may be diluted 180 times. Reactions are made in a 50 µl volume having a composition identical to that of the first PCR reaction except the nested primers are used. The first nested primer is specific for the adaptor, and is provided with the GenomeWalker™ kit. The second nested primer is specific for the particular extended cDNA or 5' EST for which the promoter is to be cloned and should have a melting temperature, length, and location in the extended cDNA or 5' EST which is consistent with its use in PCR reactions. The reaction parameters of the second PCR reaction are as follows: 1 min –94° C./2 sec –94° C., 3 min –72° C. (6 cycles)/2 sec –94° C., 3 min –94° C. (25 cycles)/5 min –67° C.

The product of the second PCR reaction is purified, cloned, and sequenced using standard techniques. Alternatively, tow or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the extended cDNA or 5' EST sequence is hybridized to the single stranded DNA. Hybrids between the biotinylated oligonucleotide and the single stranded DNA containing the extended cDNA or EST sequence are isolated as described in Example 29 above. Thereafter, the single stranded DNA containing the extended cDNA or EST sequence is released from the beads and converted into double stranded DNA using a primer specific for the extended cDNA or 5' EST sequence or a primer corresponding to a sequence included in the cloning vector. The resulting double stranded DNA is transformed into bacteria. DNAs containing the 5' EST or extended cDNA sequences are identified by colony PCR or colony hybridization.

Once the upstream genomic sequences have been cloned and sequenced as described above, prospective promoters and transcription start sites within the upstream sequences may be identified by comparing the sequences upstream of the extended cDNAs or 5' ESTs with databases containing known transcription start sites, transcription factor binding sites, or promoter sequences.

In addition, promoters in the upstream sequences may be identified using promoter reporter vectors as described in Example 56.

EXAMPLE 56

Identification of Promoters in Cloned Upstream Sequences

The genomic sequences upstream of the extended cDNAs or 5' ESTs are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the extended cDNAs or 5' ESTs are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the extended cDNAs and ESTs. For example, if the expression pattern analysis indicates that the mRNA corresponding to a particular extended cDNA or 5' EST is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 57

Cloning and Identification of Promoters

Using the method described in Example 55 above with 5' ESTs, sequences upstream of several genes were obtained. Using the primer pairs GGG AAG ATG GAG ATA GTA TTG CCT G (SEQ ID NO: 29) and CTG CCA TGT ACA TGA TAG AGA GAT TC (SEQ ID NO: 30), the promoter having the internal designation P13H2 (SEQ ID NO: 31) was obtained.

Using the primer pairs GTA CCA GGGG ACT GTG ACC ATT GC (SEQ ID NO: 32) and CTG TGA CCA TTG CTC CCA AGA GAG (SEQ ID NO: 33), the promoter having the internal designation P15B4 (SEQ ID NO: 34) was obtained.

Using the primer pairs CTG GGA TGG AAG GCA CGG TA (SEQ ID NO: 35) and GAG ACC ACA CAG CTA GAC AA (SEQ ID NO: 36), the promoter having the internal designation P29B6 (SEQ ID NO: 37) was obtained.

FIG. 7 provides a schematic description of the promoters isolated and the way they are assembled with the corresponding 5' tags. The upstream sequences were screened for the presence of motifs resembling transcription factor binding sites or known transcription start sites using the computer program MatInspector release 2.0, August 1996.

FIG. 8 describes the transcription factor binding sites present in each of these promoters. The columns labeled matrices provides the name of the MatInspector matrix used. The column labeled position provides the 5' position of the promoter site. Numeration of the sequence starts from the transcription site as determined by matching the genomic sequence with the 5' EST sequence. The column labeled "orientation" indicates the DNA strand on which the site is found, with the + strand being the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

The promoters and other regulatory sequences located upstream of the extended cDNAs or 5' ESTs may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described in Example 26 above. For example, if a promoter which confers a high level of expression in muscle is desired, the promoter sequence upstream of an extended cDNA or 5' EST derived from an mRNA which is expressed at a high level in muscle, as determined by the method of Example 26, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Following the identification of promoter sequences using the procedures of Examples 55–57, proteins which interact with the promoter may be identified as described in Example 58 below.

EXAMPLE 58

Identification of Protein Which Internet with Promoter Sequences, Upstream Regulatory Sequences or mRNA Sequences within the promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art. Nucleic acids encoding proteins which interact with sequences in the promoter may be identified using one-hybrid systems such as those described in the manual accompanying the Matchmaker One-Hybrid System kit available from Clontech (Catalog No. K1603-1). Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VII. Use of Extended cDNAs (or Genomic DNAs Obtainable Therefrom) in Gene Therapy The present invention also comprises the use of extended cDNAs (or genomic DNAs obtainable therefrom) in gene therapy strategies, including antisense and triple helix strategies as described in Examples 57 and 58 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 59

Preparation and Use of Antisense Oligonucleotides

The antisense nucleic acid molecules to be used in gene therapy may be either DNA or RNA sequences. They may comprise a sequence complementary to the sequence of the extended cDNA (or genomic DNA obtainable therefrom). The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., Ann. Rev. Biochem. 55:569–597 (1986) and Izant and Weintraub, Cell 36:1007–1015 (1984).

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., Pharmacol. Ther. 50(2): 245–254 (1991).

Various types of antisense oligonucleotides complementary to the sequence of the extended cDNA (or genomic DNA obtainable therefrom) may be used. In one preferred embodiment, stable and semi-stable antisense oligonucleotides described in International Application No. PCT WO94/23026 are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, are used.

In yet another preferred embodiment, the covalently cross-linked antisense oligonucleotides described in International Application No. WO 96/31523, are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2 are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1 \times 10^{-10}$M to $1 \times 10^{-4}$M. Once the minimum concentration that can adequately control gene expression is identified, the optimized dose is translated into a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The extended cDNAs of the present invention (or genomic DNAs obtainable therefrom) may also be used in gene therapy approaches based on intracellular triple helix formation. Triple helix oligonucleotides are used to inhibit transcription from a genome. They are particularly useful for studying alterations in cell activity as it is associated with a particular gene. The extended cDNAs (or genomic DNAs obtainable therefrom) of the present invention or, more preferably, a portion of those sequences, can be used to inhibit gene expression in individuals having diseases associated with expression of a particular gene. Similarly, a portion of the extended cDNA (or genomic DNA obtainable therefrom) can be used to study the effect of inhibiting transcription of a particular gene within a cell. Traditionally, homopurine sequences were considered the most useful for triple helix strategies. However, homopyrimidine sequences can also inhibit gene expression. Such homopyrimidine oligonucleotides bind to the major groove at homopurine-:homopyrimidine sequences. Thus, both types of sequences from the extended cDNA or from the gene corresponding to the extended cDNA are contemplated within the scope of this invention.

EXAMPLE 60

Preparation and Use of Triple Helix Probes

The sequences of the extended cDNAs (or genomic DNAs obtainable therefrom) are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target gene corresponding to the extended cDNA from which the oligonucleotide was derived with known gene sequences that have been associated with a particular function. The cell functions can also be predicted based on the presence of abnormal physiologies within cells derived from individuals with a particular inherited disease, particularly when the extended cDNA is associated with the disease using techniques described in Example 53.

The oligonucleotides which are effective in inhibiting gene expression in tissue culture cells may then be introduced in vivo using the techniques described above and in Example 59 at a dosage calculated based on the in vitro results, as described in Example 59.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. Science 245:967–971 (1989).

EXAMPLE 61

Use of Extended cDNAs to Express an Encoded Protein in a Host Organism

The extended cDNAs of the present invention may also be used to express an encoded protein in a host organism to produce a beneficial effect. In such procedures, the encoded protein may be transiently expressed in the host organism or stably expressed in the host organism. The encoded protein may have any of the activities described above. The encoded protein may be a protein which the host organism lacks or, alternatively, the encoded protein may augment the existing levels of the protein in the host organism.

A full length extended cDNA encoding the signal peptide and the mature protein, or an extended cDNA encoding only the mature protein is introduced into the host organism. The extended cDNA may be introduced into the host organism using a variety of techniques known to those of skill in the art. For example, the extended cDNA may be injected into the host organism as naked DNA such that the encoded protein is expressed in the host organism, thereby producing a beneficial effect.

Alternatively, the extended cDNA may be cloned into an expression vector downstream of a promoter which is active in the host organism. The expression vector may be any of the expression vectors designed for use in gene therapy, including viral or retroviral vectors.

The expression vector may be directly introduced into the host organism such that the encoded protein is expressed in the host organism to produce a beneficial effect. In another approach, the expression vector may be introduced into cells in vitro. Cells containing the expression vector are thereafter selected and introduced into the host organism, where they express the encoded protein to produce a beneficial effect.

EXAMPLE 62

Use of Signal Peptides Encoded by 5' ESTs or Sequences Obtained Therefrom to Import Proteins Into Cells The short core hydrophobic region (h) of signal peptides encoded by the 5' ESTS or extended cDNAs derived from the 5' ESTs of the present invention may also be used as a carrier to import a peptide or a protein of interest, so-called cargo, into tissue culture cells (Lin et al., J. Biol. Chem., 270: 14225–14258 (1995); Du et al., J. Peptide Res., 51: 235–243 (1998); Rojas et al., Nature Biotech., 16: 370–375 (1998)).

When cell permeable peptides of limited size (approximately up to 25 amino acids) are to be translocated across cell membrane, chemical synthesis may be used in order to add the h region to either the C-terminus or the N-terminus to the cargo peptide of interest. Alternatively, when longer peptides or proteins are to be imported into cells, nucleic acids can be genetically engineered, using techniques familiar to those skilled in the art, in order to link the extended cDNA sequence encoding the h region to the 5' or the 3' end of a DNA sequence coding for a cargo polypeptide. Such genetically engineered nucleic acids are then translated either in vitro or in vivo after transfection into appropriate cells, using conventional techniques to produce the resulting cell permeable polypeptide. Suitable hosts cells are then simply incubated with the cell permeable polypeptide which is then translocated across the membrane.

This method may be applied to study diverse intracellular functions and cellular processes. For instance, it has been used to probe functionally relevant domains of intracellular proteins and to examine protein-protein interactions involved in signal transduction pathways (Lin et al., supra; Lin et al., J. Biol. Chem., 271: 5305–5308 (1996); Rojas et al., J. Biol. Chem., 271: 27456–27461 (1996); Liu et al., Proc. Natl. Acad. Sci. USA, 93: 11819–11824 (1996); Rojas et al., Bioch. Biophys. Res. Commun., 234: 675–680 (1997)).

Such techniques may be used in cellular therapy to import proteins producing therapeutic effects. For instance, cells isolated from a patient may be treated with imported therapeutic proteins and then re-introduced into the host organism.

Alternatively, the h region of signal peptides of the present invention could be used in combination with a nuclear localization signal to deliver nucleic acids into cell nucleus. Such oligonucleotides may be antisense oligonucleotides or oligonucleotides designed to form triple helixes, as described in examples 59 and 60 respectively, in order to inhibit processing and maturation of a target cellular RNA.

EXAMPLE 63

Reassembling & Reseqencing of Clones

Further study of the clones reported in SEQ ID NOs: 40 to 86 revealed a series of abnormalities. As a result, the clones were resequenced twice, reanalyzed and the open reading frames were reassigned. The corrected nucleotide sequences have been disclosed in SEQ ID NOs: 134 to 180 and 228 and the predicted amino acid sequences for the corresponding polypeptides have also been corrected and disclosed in SEQ ID NOs: 181 to 227 and 229. The corrected sequences have been placed in the Sequence Listing in the same order as the original sequences from which they were derived.

After this reanalysis process a few apparent abnormalities persisted. The sequences presented in SEQ ID NOs: 134, 149, 151, and 164 are apparently unlikely to be genuine full length cDNAs. These clones are missing a stop codon and are thus more probably 3' truncated cDNA sequences. Similarly, the sequences presented in SEQ ID NOs: 145, 155, and 166 may also not be genuine full length cDNAs based on homolgy studies with existing protein sequences. Although both of these sequences encode a potential start methionine each could represent of 5' truncated cDNA.

In addition, after the reassignment of open reading frames for the clones, new open reading frames were chosen in some instances. In case of SEQ ID NOs: 135, 149, 155, 160, 166, 171, and 175 the new open reading frames were no longer predicted to contain a signal peptide.

Table VI provides the sequence identification numbers of the extended cDNAs of the present invention, the locations of the full coding sequences in SEQ ID NOs: 134–180 (i.e. the nucleotides encoding both the signal peptide and the mature protein, listed under the heading FCS location in Table VII), the locations of the nucleotides in SEQ ID NOs: 134–180 which encode the signal peptides (listed under the heading SigPep Location in Table VII), the locations of the nucleotides in SEQ ID NOs: 134–180 which encode the mature proteins generated by cleavage of the signal peptides (listed under the heading Mature Polypeptide Location in Table VII), the locations in SEQ ID NOs: 134–180 of stop codons (listed under the heading Stop Codon Location in Table VII), the locations in SEQ ID NOs: 134–180 of polyA signals (listed under the heading PolyA Signal Location in Table VII) and the locations of polyA sites (listed under the heading PolyA Site Location in Table VII).

Table VIII lists the sequence identification numbers of the polypeptides of SEQ ID NOs: 181–227, the locations of the amino acid residues of SEQ ID NOs: 181–227 in the full length polypeptide (second column), the locations of the amino acid residues of SEQ ID NOs: 181–227 in the signal peptides (third column), and the locations of the amino acid residues of SEQ ID NOs: 181–227 in the mature polypeptide created by cleaving the signal peptide from the full length polypeptide (fourth column). In Table VIII, and in the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings.

EXAMPLE 64

Functional Analysis of Predicted Protein Sequences

It should be noted that the numbering of amino acids in the protein sequences discussed in FIGS. 9 to 16, and Table VI, the first methionine encountered is designated as amino acid number 1. In the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings.

Protein of SEQ ID NO: 181

The protein of SEQ ID NO: 181 is encoded by the extended cDNA SEQ ID NO: 134. The protein of SEQ ID NO: 181 is human strictosidine synthase. Strictodine synthase is a key enzyme in the production of, and therefore useful in making, the pharmaceutically important monoterpene indole alkaloids. Pathways for the production of monoterpene indole alkaloids can be reconstructed in various cell types, for example, insect cell cultures as described in Kutchan, T. M. et al. (1994) Phyochemistry 35(2): 353–360. Strictodine synthase can also be produced *E. coli* and its activity measuring using methods described in, for example, Roessner, C. A. et al. (1992) Protein Expr. Purif. 3(4): 295–300; Kutchan, T. M. (1989) FEBS Lett. 257(1): 127–130; Pennings, E. J. et al. (1989) Anal. Biochem. 176(2): 412415; Walton, N. J. (1987) Anal. Biochem. 163 (2): 482488. Preferred fragments of SEQ ID NO: 181 and the mature polypeptide encoded by the corresponding human cDNA of the deposited clone are those with strictodine synthase activity. Further preferred are fragments with not less then 100 fold less activity, not less than 10 fold activity, and not less than 5 fold activity when compared to mature protein.

Protein of SEQ ID NO: 183

The protein of SEQ ID NO: 183, encoded by the extended cDNA SEQ ID NO: 136, is human inositol hexakisphophate kinase-2. Inositol hexakisphophate kinase-2 phosphorylates inositol hexakisphosphate (InsP(6)) to diphosphoinositol pentakisphosphate/inositol heptakisphosphate (InsP(7)), a high energy regulator of cellular trafficking. Human inositol hexakisphophate kinase-2 also stimulates the uptake of inorganic phosphate and its products act as energy reserves. Therefore, hexakisphosphate kinase-2 is an ATP synthase, and its product, diphosphoinositol pentakisphosphate, acts as a high-energy phosphate donor. The human inositol hexakisphophate kinase-2 gene may be transfected into eukaryotic cells (preferably mammalian, yeast, and insect cells) and expressed to increase their growth, viability, and for more efficient secretions of polypeptides, including recombinant polypeptides. Preferred fragments of SEQ ID NO: 183 and the corresponding mature polypeptide encoded by the human cDNA of the deposited clone are those with inositol hexakisphophate kinase-2 activity. Further preferred are fragments with not less then 100 fold less activity, not less than 10 fold activity, and not less than 5 fold activity when compared to mature protein.

Protein of SEQ ID NO: 185 and 215:

The proteins of SEQ ID NOs: 185 and 215 encoded by the extended cDNA SEQ ID NOs: 138 and 168, respectively, are MEK binding partners. These proteins enhance enzymatic activation of mitogen-activated protein (MAP) kinase cascade. The MAP kinase pathway is one of the important enzymatic cascade that is conserved among all eukaryotes from yeast to human. This kind of pathway is involved in vital functions such as the regulation of growth, differentiation and apoptosis. These proteins are believed to act by facilitating the interaction of the two sequentially acting kinases MEK1 and ERK1 (Schaffer et al., Science, 281:1668–1671 (1998)).

Thus, the proteins of SEQ ID NO: 185 and 215 are involved in regulating protein-protein interaction in the signal transduction pathways. These proteins may be useful in diagnosing and/or treating several types of disorders including, but not limited to, cancer, neurodegenerative diseases, cardiovascular disorders, hypertension, renal injury and repair and septic shock. More specifically, over expression and mutant forms of this gene can serve as markers for cancer, such as ovarian cancer, using the nucleic acid as a probe or by using antibodies directed to the protein. Cells transfected with this gene have increased growth rate.

Protein of SEQ ID NO: 186

The protein of SEQ ID NO: 186, encoded by the extended cDNA SEQ ID NO: 139, is a new claudin named Claudin-50.

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions, spot desmosomes and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

The transmembrane component of tight junctions that has been the most studied is occluding. Occludin is believed to be directly involved in cell adhesion and the formation of tight junctions (Furuse et al., J. Cell Sci. 109:429435, 1996; Chen et al., J. 5 Cell Biol. 138:891–899, 1997). It has been proposed that occludin promotes cell adhesion through homophilic interactions (an occludin on the surface of one cell binds to an identical occludin on the surface of another cell). A detailed discussion of occludin structure and function is provided by Lampugnani and Dejana, Curr. Opin Cell Biol. 9:674–682, 1997.

More recently, a second family of tight junction components has been identified. Claudins are transmembrane proteins that appear to be directly involved in cell adhesion and the formation of tight junctions (Furuse et al., J. Cell Biology 141:1539–1550, 1998; Morita et al., Proc. Natl. Acad. Sci. USA 96:511–516, 1999). Other previously described proteins that appear to be members of the claudin family include RVP-1 (Briehl and Miesfeld, Molecular Endocrinology 5:1381–1388, 1991; Katahira et al., J. Biological Chemistry 272:26652–26656, 1997), the *Clostridium perfringens* enterotoxin receptor (CPE-R; see Katahira et al., J. Cell Biology 136:1239–1247, 1997; Katahira et al., J. Biological Chemistry 272:26652–26656, 1997) and TMVCF (transmembrane protein deleted in Velo-cardio-facial syndrome; Sirotkin et al., Genomics 42:245–51, 1997).

Based on hydrophobicity analysis, all claudins appear to be approximately 22 kD and contain four hydrophobic domains that transverse the plasma membrane. It has been proposed that claudins promote cell adhesion through homophilic interactions (a claudin on the surface of one cell binds to an identical claudin on the surface of another cell) or heterophilic interactions, possibly with occludin.

Although cell adhesion is required for certain normal physiological functions, there are situations in which the level of cell adhesion is undesirable. For example, many pathologies (such as autoimmune diseases and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Accordingly, there is a need in the art for compounds that modulate cell adhesion and improve drug delivery across permeability barriers without such disadvantages. The present invention fulfills this need and further provides other related advantages.

The present invention provides compounds and methods for modulating claudin-mediated cell adhesion and the formation of permeability barriers. Within certain aspects, the present invention provides cell adhesion modulating agents that inhibit or enhance claudin-mediated cell adhesion. Certain modulating agents comprise the claudin CAR sequence WKTSSTVG. Other modulating agents comprise at least five or seven consecutive amino acid residues of a claudin CAR sequence: Comprising the sequence TSSY, wherein each permutation is an individual specie of the present invention.

The present invention further provides for polypeptides comprising amino acid residues 32 to 35 of SEQ. ID NO: 186, wherein said sequence comprises an additional 1 to 31 consecutive residues of N-terminal sequence of SEQ. ID NO: 186 and an additional 1 to 193 consecutive C-terminal residues of SEQ. ID NO: 186. Further included are polypeptides comprising additional consecutive residues at both the N-terminal, C-terminal. Each permutation of the above polypeptides comprising additional N-terminal, C-terminal & N- and C terminal residues are included in the present invention as individual species.

The present invention further provides, within other aspects, polynucleotides encoding a modulating agent as provided above, expression vectors comprising such a polynucleotide, and host cells transformed or transfected with such an expression vector.

Within further aspects, the present invention provides modulating agents that comprise an antibody or antigen-binding fragment thereof that specifically binds to a claudin CAR sequence and modulates a claudin-mediated function.

The present invention further provides modulating agents comprising a mimetic of a claudin CAR sequence that comprises at least three or five consecutive amino acid residues of the claudin CAR sequence WKTSSYVG.

Within other aspects, modulating agents as described above may be linked to one or more of a drug, a detectable marker, a targeting agent and/or a support material. Alternatively, or in addition, modulating agents as described above may further comprise one or more of: (a) a cell adhesion recognition sequence that is bound by an adhesion molecule other than a claudin, wherein the cell adhesion recognition sequence is separated from any claudin CAR sequence(s) by a linker; and/or (b) an antibody or antigen-binding fragment thereof that specifically binds to a cell adhesion recognition sequence bound by an adhesion molecule other than a claudin. Such adhesion molecules may be selected from the group consisting of integrins, cadherins, occludin, N-CAM, JAM, PE-CAM, desmogleins, desmocollins, fibronectin, lammin and other extracellular matrix proteins.

Within other aspects, a modulating agent may comprise an antibody or antigen-binding fragment thereof that specifically binds to the claudin-50 CAR sequence WKTSSYVG.

The present invention further provides pharmaceutical compositions comprising a cell adhesion modulating agent as described above, in combination with a pharmaceutically acceptable carrier. Such compositions may further comprise a drug. In addition, or alternatively, such compositions may further comprise one or more of: (a) a peptide comprising a cell adhesion recognition sequence that is bound by an adhesion molecule other than a claudin; and/or (b) an antibody or antigen-binding fragment thereof that specifically binds to a cell adhesion recognition sequence bound by an adhesion molecule other than a claudin.

Within further aspects, methods are provided for modulating cell adhesion, comprising contacting a claudin-expressing cell with a cell adhesion modulating agent as described above.

Within one such aspect, the present invention provides methods for increasing vasopermeability in a mammal, comprising administering to a mammal a cell adhesion modulating agent as provided above, wherein the modulating agent inhibits claudin-mediated cell adhesion.

Within another aspect, methods are provided for reducing unwanted cellular adhesion in a mammal, comprising administering to a mammal a cell adhesion modulating agent as provided above, wherein the modulating agent inhibits claudin-mediated cell adhesion.

In yet another aspect, the present invention provides methods for enhancing the delivery of a drug through the skin of a mammal, comprising contacting epithelial cells of a mammal with a cell adhesion modulating agent as provided above and a drug, wherein the modulating agent inhibits claudin-mediated cell adhesion, and wherein the step of contacting is performed under conditions and for a time sufficient to allow passage of the drug across the epithelial cells.

The present invention further provides methods for enhancing the delivery of a drug to a tumor in a mammal, comprising administering to a mammal a cell adhesion modulating agent as provided above and a drug, wherein the modulating agent inhibits claudin-mediated cell adhesion.

Within further aspects, the present invention provides methods for treating cancer in a mammal, comprising administering to a mammal a cell adhesion modulating agent as provided above, wherein the modulating agent inhibits claudin-mediated cell adhesion.

The present invention further provides methods for inhibiting angiogenesis in a mammal, comprising administering to a mammal a cell adhesion modulating agent as provided above, wherein the modulating agent inhibits claudin mediated cell adhesion.

Within further aspects, the present invention provides methods for enhancing drug delivery to the central nervous system of a mammal, comprising administering to a mammal a cell adhesion modulating agent as provided above, wherein the modulating agent inhibits claudin-mediated cell adhesion.

The present invention further provides methods for enhancing wound healing in a mammal, comprising contacting a wound in a mammal with a cell adhesion modulating agent as provided above, wherein the modulating agent enhances claudin mediated cell adhesion.

Within a related aspect, the present invention provides methods for enhancing adhesion of foreign tissue implanted within a mammal, comprising contacting a site of implantation of foreign tissue in a mammal with a cell adhesion modulating agent as provided above, wherein the modulating agent enhances claudin mediated cell adhesion.

The present invention further provides methods for inducing apoptosis in a claudin-expressing cell, comprising contacting a claudin-expressing cell with a cell adhesion modulating agent as provided above, wherein the modulating agent inhibits claudin-mediated cell adhesion.

The present invention further provides methods for identifying an agent capable of modulating claudin-mediated cell adhesion. One such method comprises the steps of (a) culturing cells that express a claudin in the presence and absence of a candidate agent, under conditions and for a time sufficient to allow cell adhesion; and (b) visually evaluating the extent of cell adhesion among the cells.

Within another embodiment, such methods may comprise the steps of: (a) culturing normal rat kidney cells in the presence and absence of a candidate agent, under conditions and for a time sufficient to allow cell adhesion; and (b) comparing the level of cell surface claudin and E-cadhenn for cells cultured in the presence of candidate agent to the level for cells cultured in the absence of candidate agent.

Within a further embodiment, such methods may comprise the steps of: (a) culturing human aortic endothelial cells in the presence and absence of a candidate agent, under conditions and for a time sufficient to allow cell adhesion; and (b) comparing the level of cell surface claudin and N-cadherin for cells cultured in the presence of candidate agent to the level for cells cultured in the absence of candidate agent.

Within yet another embodiment, such methods comprise the steps of: (a) contacting an antibody that binds to a modulating agent comprising a claudin CAR sequence with a test compound; and (b) detecting the level of antibody that binds to the test compound.

The present invention further provides methods for detecting the presence of claudin-expressing cells in a sample, comprising: (a) contacting a sample with an antibody that binds to a claudin comprising a claudin CAR sequence under conditions and for a time sufficient to allow formation of an antibody-claudin complex; and (b) detecting the level of antibody-claudin complex, and there from detecting the presence of claudin-expressing cells in the sample.

Within further aspects, the present invention provides kits for detecting the presence of claudin-expressing cells in a sample, comprising: (a) an antibody that binds to a modulating agent comprising a claudin CAR sequence; and (b) a detection reagent.

The present invention further provides, within other aspects, kits for enhancing transdermal drug delivery, comprising: (a) a skin patch; and (b) a cell adhesion modulating agent, wherein the modulating agent comprises a claudin CAR sequence, and wherein the modulating agent inhibits claudin-mediated cell adhesion.

A detailed description of the above methods are described in PCT application WO 00/26360 (Blaschuck, O. W., et al.), incorporated herein in its entirety.

Further included in the present invention are methods of treating *Clostridium perfringens* or *Clostridium difficile* or *Clostridium botulinum* infections by targeting the enterotoxin, preferably *Clostridium perfringens* enterotoxin. Clostridium enterotoxin (CE) binds to Claudin-50. Purified Claudin-50 polypeptides can be used to absorb CE to prevent CE's cytotoxic effects on cells. Preferred CE binding Claudin-50 polypeptides include the full length and mature Claudin-50 polypeptide and fragments comprising the extracellular domains, amino acid residues 29 to 81 and 103 to 116. Further preferred CE binding Claudin-50 polypeptides include the extracellular domain 29 to 81 and fragments comprising the CAR sequence. CE binding Claudin-50 polypeptides may further be recombinantly fused or chemically coupled (covalently or non-covalently) to a heterologous polypeptide, molecule, or support. Means of administering CE binding Claudin-50 polypeptide compositions are those well known for administering biologically active polypeptides. Preferably, CE binding Claudin-50 polypeptide compositions are administered in at least equamolar concentration compared with CE. More preferably, CE binding Claudin-50 polypeptide compositions are administered in at least a 10 to 100 fold molar excess concentration compared with CE.

The above CE binding Claudin-50 polypeptides are also useful for affinity purification CE. For example, CE binding Claudin-50 polypeptides can be fixed or coupled to a solid support in a column and used to bind CE in a biological sample. CE can be released from the column for example, by using a salt gradient.

CE binding Claudin-50 polypeptide compositions are also useful in detecting and diagnosing *Clostridium perfringens* infection. The presence of CE indicates *Clostridium perfringens* infection. The level of CE is proportional to the level or degree of the disease or infection. Moreover, the degree of cellular disruption at tight junctions is also proportional to the level of CE. CE binding Claudin-50 polypeptides will preferentially bind endogenous claudins at the sites of tight junction disruptions. CE binding Claudin-50 polypeptides can therefore be used to detect or diagnose *Clostridium perfringens* infection by either binding CE or by binding sites of tight junction disruption. Biological samples including fluids and tissue samples can be assayed using methods well known in the art. *Clostridium perfringens* infections can further be localized in vivo using CE binding Claudin-50 polypeptides in in vivo imaging.

Protein of SEQ ID NO: 191

The protein of SEQ ID NO: 191 encoded by the extended cDNA SEQ ID NO: 144 and expressed in lymphocytes exhibits an extensive homology to a stretch of 91 amino acid of a human secreted protein expressed in peripheral blood mononucleocytes (Genpep accession number W36955 and Genseq accession number VOO433). The amino acid residues are identical except for the substitution of asparagine to isoleucine at positions 94, and the conservative substitutions at positions 108, 109 and 110 of the 110 amino acids long matched protein.

Protein of SEQ ID NO: 192

The protein of SEQ ID NO: 192 encoded by the extended cDNA SEQ ID NO: 145 exhibits extensive homologies to stretches of proteins encoding vacuolar proton-ATPase subunits M9.2 of either human (Genbank accession number Y15286) or bovine species (Genbank accession number Y15285). These two highly conserved proteins are extremely hydrophobic membrane proteins with two membrane-spanning helices and a potential metal-binding domain conserved in mammalian protein homologues (Ludwig et al., J. Biol. Chem., 273:10939–10947 (1998)). The amino acid residues are completely identical, the protein of SEQ ID NO: 192 is missing amino acids 1 to 92 from the Genbank sequences. The protein of SEQ ID NO: 192 contains the second putative transmembrane domain as well as the potential metal-binding site.

Taken together, these data suggest that the protein of SEQ ID NO: 192 may play a role in energy conservation, secondary active transport, acidification of intracellular compartments and/or cellular pH homeostasis. Preferred fragments of SEQ ID NO: 192 and the corresponding mature polypeptide encoded by the human cDNA of the deposited clone are those with inositol ATPase activity. Further preferred are fragments with not less then 100 fold less activity, not less than 10 fold activity, and not less than 5 fold activity when compared to mature protein.

Protein of SEQ ID NO: 193

The protein of SEQ ID NO: 193 encoded by the extended cDNA SEQ ID NO: 146 shows homology to short stretches of Drosophila, C. elegans and chloroplast proteins similar to E. coli ribosomal protein L16.

Taken together, these data suggest that the protein of SEQ ID NO: 193 may be a ribosomal protein.

Protein of SEQ ID NO: 194

The protein of SEQ ID NO: 194, encoded by the cDNA of SEQ ID NO: 147, is a chemokine. The protein can be used to attract and activate monocytes and lymphocytes, especially to a site of infection or tumor. The protein can also be used in in vivo imaging to identify/locate/diagnose sites of infection or tumors. Preferred fragments of SEQ ID NO: 194 and the corresponding mature polypeptide encoded by the human cDNA of the deposited clone are those with the above activities. Further preferred are fragments with not less then 100 fold less activity, not less than 10 fold activity, and not less than 5 fold activity when compared to mature protein.

Protein of SEQ ID NO: 197

The protein of SEQ ID NO: 197, encoded by the extended cDNA SEQ ID NO: 150, is human Connexin 31.1. Connexins are a family of integral membrane proteins that oligomerize into clusters of intercellular channels called gap junctions, which join cells in virtually all metazoans. These channels permit exchange of ions between neurons and between neurons and excitable cells such as myocardiocytes (for review, see Goodenough et al., Ann. Rev. Biochem., 65:475–502 (1996)). Human connexin 31.1 is expressed only in the skin, with Connexin 31.1 mRNA being 15–30 times more abundant in mature skin than in fetal skin. Within the skin layers, human Connexin 31.1 expression is localized to the keratinocyte layer. Human Connexin 31.1, is therefore useful as a marker for skin, particularly the keratinocyte layer, as well as keratinocytes, using either human Connexin 31.1 polynucleotides or antibodies made to human Connexin 31.1 polypeptides. Moreover, human Connexin 31.1 is useful as a marker for skin tumors because, whereas hyperplasia express Connexin 31.1, skin tumors at all stages do not. Hence, Connexin 31.1 polynucleotides and polypeptides are useful for differentiating between a skin hyperplasia and a tumor.

Human Connexin 31.1 is also useful in the methods for treating cancer, perferrably skin tumors, more preferably skin tumors involving keratinocytes. Preferred methods of using Human Connexin 31.1 for treating cancer includes the methods described in PCT application WO 97/28179 (Fick, J. R. et al.) incorporated herein in its entirety. Preferred fragments of SEQ ID NO: 197 and the corresponding mature polypeptide encoded by the human cDNA of the deposited clone are those with useful in the above methods, e.g., antigenic fragments and those fragments which form gap junctions.

Protein of SEQ ID NO: 198

The protein of SEQ ID NO: 198 encoded by the extended cDNA SEQ ID NO: 151 shows homologies with different DNA or RNA binding proteins such as the human Staf50 transcription factor (Genbank accession number X82200), the human Ro/SS-A ribonucleoprotein autoantigen (Swissprot accession number P19474) or the murine RPTI transcription factor (Swissprot accession number P15533). The protein of SEQ ID NO: 198 exhibits a putative signal peptide and also a PROSITE signature for a RING type zinc finger domain located from positions 15 to 59. Secreted proteins may have nucleic acid binding domain as shown by a nematode protein thought to regulate gene expression which exhibits zinc fingers as well as a functional signal peptide (Holst and Zipfel, J. Biol. Chem., 271:16275–16733 (1996)).

Taken together, these data suggest that the protein of SEQ ID NO: 198 may play a role in protein-protein interaction in intracellular signaling and eventually may directly or indirectly bind to DNA and/or RNA, hence regulating gene expression.

Protein of SEQ ID NO: 200

The protein of SEQ ID NO: 200 encoded by the extended cDNA SEQ ID NO: 153 exhibits extensive homologies to proteins encoding RING zinc finger proteins of the human chicken and rodent species, as well as an EGF-like domain. Two stretches of 341 and of 13 amino acids of the human RING zinc finger protein which might bind DNA (Genbank accession number AF037204). The amino acid residues are identical except for conservative substitutions at positions 18, 29, 156 and 282 of the 381 amino acid long human RING zinc finger. Such RING zinc finger proteins are thought to be involved in protein-protein interaction and are especially found in nucleic acid binding proteins. Secreted proteins may have nucleic acid binding domain as shown by a nematode protein thought to regulate gene expression which exhibits zinc fingers as well as a functional signal peptide (Holst and Zipfel, J. Biol. Chem., 271:16275–16733 (1996)).

Taken together, these data suggest that the protein of SEQ ID NO: 200 may play a role in protein-protein interaction or be a nucleic acid binding protein.

Protein of SEQ ID NO: 201 and 227

The proteins of SEQ ID NOs: 201 and 227 encoded by the extended cDNA SEQ ID NOs: 154 and 180, respectively, belong to the stomatin or band 7 family. The human stomatin is an integral membrane phosphoprotein thought to be involved to regulate the cation conductance by interacting with other proteins of the junctional complex of the membrane skeleton (Gallagher and Forget, J. Biol. Chem., 270:26358–26363 (1995)). The proteins of SEQ ID NOs: 201 and 227 exhibit the PROSITE signature typical for the band 7 family signature.

The proteins of SEQ ID NOs: 201 and 227 play a role in the regulation of ion transport, hence in the control of cellular volume. These proteins are useful in diagnosing and/or treating stomatocytosis and/or cryohydrocytosis by detecting a decreased level or absence of the proteins or alternatively by detecting a mutation or deletion affecting tertiary structure of the proteins.

Protein of SEQ ID NO: 213 and 229

The proteins of SEQ ID NO: 213 and 229, encoded by the cDNA of SEQ ID NO: 166 and 228, respectively, is human Glia Maturation Factor-gamma 2 (GMF-gamma 2). SEQ ID NO: 229 differs from SEQ ID NO: 213 in that SEQ ID NO: 229 has additional amino acids at the N-terminus. The following description applies equally to both SEQ ID NO: 213 and 229. A preferred use of GMF-gamma 2 is to stimulate neurite outgrowth or neurite re-sprouting. These methods include both 15 in vitro and in vivo uses, but preferred uses are those for treating neural injuries and cancer as disclosed in WO9739133 and WO9632959, incorporated herein in their entireties.

GMF-gamma 2 may also be used as a neurotrophic and as a neuroprotective agent against toxic insults, such as ethonal and other neurotoxic agents. GMF-gamma2 may be used as a neurotrophic or neuroprotective agent either in vitro or in vivo. A preferred target of GMF-gamma 2 as a neurotrophic or neuroprotective agent are primary neurons.

GMF-gamma 2 may further be used to stimulate the expression and secretion of NGF and BDNF in glial cells both in vitro and in vivo. Conditioned media from cells treated with GMF-gamma 2 is useful as a source of NGF and BDNF. GMF-gamma 2 may further be used to target cells directly or by recombinantly fusing GMF-gamma 2 to a heterologous protein, such as a ligand or antibody specific to the target cell (e.g., glial cells). Alternatively, GMF-gamma 2 may be fused or covalently or non-covalently coupled to a heterologous protein or other biological or non-biological molecule wherein the heterologous protein or molecule is used as this targeting reagent.

Preferred fragments of SEQ ID NOs: 213 and 229 and the corresponding polypeptide encoded by the human cDNAs of the deposited clones are those with the above activities. Further preferred are fragments with not less then 100 fold less activity, not less than 10 fold activity, and not less than 5 fold activity when compared to the protein of SEQ ID NO: 229 or the protein encoded by the corresponding human cDNA of the deposited clone.

Protein of SEQ ID NO: 214:

The protein of SEQ ID NO: 214 encoded by the extended cDNA SEQ ID NO: 167 isolated from brain shows extensive homology to a human SH3 binding domain glutamic acid-rich like protein or SH3BGRL (Egeo et al, Biochem. Biophys. Res. Commun., 247:302–306 (1998)) with Genbank accession number is AF042081. The amino acid residues are identical to SH3BGRL except for positions 63 and 101 in the 114 amino acid long matched sequence. This SH3BRGL protein is itself homologous to the middle proline-rich region of a protein containing an SH3 binding domain, the SH3BGR protein (Scartezzini et al., Hum. Genet., 99:387–392 (1997)). This proline-rich region is also highly conserved in mice. Both SH3BGR and SH3BGRL proteins are thought to be involved in the Down syndrome pathogenesis. The protein SEQ ID NO: 214 also contains the proline-rich SH3 binding domain (bold) and a potential RGD cell attachment sequence (underlined).

SH3 domains are small important functional modules found in several proteins from all eukaryotic organisms that are involved in a whole range of regulation of protein-protein interaction, e.g. in regulating enzymatic activities, recruiting specific substrates to the enzyme in signal transduction pathways, in interacting with viral proteins and they are also thought to play a role in determining the localization of proteins to the plasma membrane or the cytoskeleton (for a review, see Cohen et al, Cell, 80:237–248 (1995)).

The Arg-Gly-Asp (RGD) attachment site promote cell adhesion of a large number of adhesive extracellular matrix, blood and cell surface proteins to their integrin receptors which have been shown to regulate cell migration, growth, differentiation and apoptosis. This cell adhesion activity is also maintained in short RGD containing synthetic peptides which were shown to exhibit anti-thrombolytic and anti-metastatic activities and to inhibit bone degradation in vivo (for review, see Ruoslahti, Annu. Rev. Cell Dev. Biol., 12:697–715 (1996)).

Taken together, these data suggest that the protein of SEQ ID NO: 214 may be important in regulating protein-protein interaction in signal transduction pathways, and/or may play a role of localization of proteins to the plasma membrane or cytoskeleton, and/or may play a role in cell adhesion. Moreover, this protein or part therein, especially peptides containing the RGD motif, may be useful in diagnosing and treating cancer, thrombosis, osteoporosis and/or in diagnosing and treating disorders associated with the Down syndrome.

Protein of SEQ ID NO: 216

The protein of SEQ ID NO: 216 found in testis encoded by the extended cDNA SEQ ID NO: 169 shows homologies to protein domains with a 4-disulfide core signature found in either an extracellular proteinase inhibitor named chelonianin (Swissprot accession number P00993) or in rabbit and human proteins specifically expressed in epididymes (Genbank accession numbers U26725 and R13329). The matched domain in red sea turtle chelonianin is known to inhibit subtilisin, a serine protease (Kato and Tominaga, Fed. Proc., 38:832 (1979)). All cysteines of the 4 disulfide core signature thought to be crucial for biological activity are present in the protein of SEQ ID NO: 216. The 4 disulfide core signature is present except for a conservative substitution of asparagine to glutamine.

Taken together, these data suggest that the protein of SEQ ID NO: 216 may play a role in protein-protein interaction, act as a protease inhibitor and/or may also be related to male fertility.

Protein of SEQ ID NO: 223

The protein of SEQ ID NO: 223 encoded by the extended cDNA SEQ ID NO: 176 shows homology to short stretches of a human protein called Tspan-1 (Genbank accession number AF054838) which belongs to the 4 transmembrane superfamily of molecular facilitators called tetraspanin (Meakers et al., FASEB J., 11:428442 (1997)).

Taken together, these data suggest that the protein of SEQ ID NO: 223 may play a role in cell activation and proliferation, and/or adhesion and motility and/or differentiation and cancer.

As discussed above, the extended cDNAs of the present invention or portions thereof can be used for various purposes. The polynucleotides can be used to express recombinant protein for use for therapeutic use or research (not limited to research on the gene itself); as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support (e.g., microarrays), including for examination for expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation Molecular Cloning; A Laboratory Manual, 2d ed., Cole Spring Harbor Laboratory Press, Sambrook, J., E. F. Fritsch and T. Maniatis eds., (1989), and Methods in Enzymology; Guide to Molecular Cloning Techniques, Academic Press, Berger, S. L. and A. R. Kimmel eds., (1987).

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. Throughout this application, various publications, patents, and published patent applications are cited.

Some of the disclosures of the publications, patents, and published patent specifications referenced in this application may not have been incorporated into the present disclosure at the point of reference. Regardless of this, all of the disclosures of the publications, patents, and published patent specifications referenced in this application are hereby incorporated by reference in their entireties into the present disclosure to more fully describe the state of the art to which this invention pertains.

What is claimed is:

1. A purified and isolated Claudin polypeptide comprising an amino acid sequence of positions 1 to 206 of SEQ ID NO: 186.

2. The polypeptide of claim 1, wherein said polypeptide comprises an amino acid sequence of positions −24 to 206 of SEQ ID NO: 186.

3. A method of producing the polypeptide of claim 2, comprising the steps of:

(i) obtaining a host cell capable of expressing said polypeptide;

(ii) culturing said cell under conditions suitable for the expression of said polypeptide; and (iii) isolating said polypeptide from said host cell.

4. A method of producing the polypeptide of claim 1 comprising the steps of:

(i) obtaining a host cell capable of expressing said polypeptide;

(ii) culturing said cell under conditions suitable for the expression of said polypeptide; and (iii) isolating said polypeptide from said host cell.

* * * * *

UNITED STATES PATENT AND TRADEMARK OFFICE
CERTIFICATE OF CORRECTION

PATENT NO. : 6,573,068 B1
DATED : June 3, 2003
INVENTOR(S) : Jean-Baptiste Dumas Milne Edwards, Aymeric Duclert and Lydie Bougueleret It is certified that error appears in the above-identified patent and that said Letters Patent is hereby corrected as shown below:

Column 3,
Line 62, "as "ESTs" or "5' EST"." should read -- as "ESTs" or "5'ESTs".--.

Column 16,
Line 8, "NOs. 2540 and 4246" should read -- NOs. 25-40 and 42-46 --.

Column 18,
Line 62, "5'-pppGCAUCCUACUCCCAUCCAAUUCCACCCAACUCCUCCCAUCUCCAC-3'" should read --5'-pppGCAUCCUACUCCCAUCCAAUUCCACCCUAACUCCUCCCAUCUCCAC-3' --.

Column 22,
Line 61, "diameter 0.45 mn." should read -- diameter of 0.45 μm. --.

Column 24,
Line 67, "Caminci" should read -- Carninci --.

Column 28,
Line 8, "Insert" should read -- Inserts --.

Column 29,
Line 26, "helix-tum-helix" should read -- helix-turn-helix --.

Column 32,
Line 19, "14:46834690" should read -- 14:4683-4690 --.

Column 35,
Line 55, "270:467470" should read -- 270:467-470 --.

Column 41,
Line 43, "46834690" should read -- 4683-4690 --.

UNITED STATES PATENT AND TRADEMARK OFFICE
CERTIFICATE OF CORRECTION

PATENT NO. : 6,573,068 B1
DATED : June 3, 2003
INVENTOR(S) : Jean-Baptiste Dumas Milne Edwards, Aymeric Duclert and Lydie Bougueleret It is certified that error appears in the above-identified patent and that said Letters Patent is hereby corrected as shown below:

<u>Column 42,</u>
Line 13, "proteins. 5. Selection of" should read -- proteins.
5. Selection of Cloned Full Length Sequencesof the Present
Invention --.

<u>Column 44,</u>
Lines 2-3, "Table H" should read -- Table II --.
Line 7, "Table H" should read -- Table II --.

<u>Column 57,</u>
Line 50, "11:405411" should read -- 11:405-411 --.

<u>Column 62,</u>
Line 7, "13:473486" should read -- 13:473-486 --.

<u>Column 63,</u>
Line 59, "tendonaigament formation" should read -- tendon/ligament formation --.
Line 60, "tendonligament-like" should read -- tendon/ligament-like --.

<u>Column 64,</u>
Line 11, "tendonaigament cells" should read -- tendon/ligament cells --.

<u>Column 65,</u>
Line 9, "Chemokincs" should read -- Chemokines --.

<u>Column 70,</u>
Line 43, "Epitope" should read -- Epitopes --.

<u>Column 74,</u>
Lines 2-3, "5x $10^-_{15}$M, and" should read -- $5X10^{-15}$ M, and --.

<u>Column 78,</u>
Line 12, "*Bacic*" should read -- *Basic* --.

UNITED STATES PATENT AND TRADEMARK OFFICE
CERTIFICATE OF CORRECTION

PATENT NO. : 6,573,068 B1
DATED : June 3, 2003
INVENTOR(S) : Jean-Baptiste Dumas Milne Edwards, Aymeric Duclert and Lydie Bougueleret It is certified that error appears in the above-identified patent and that said Letters Patent is hereby corrected as shown below:

Column 80,
Line *61*, "calorimetrically" should read -- colorimetrically --.

Column 85,
Line 9, "Genomics I11:701-708" should read -- Genomics 11:701-708 --.

Column 86,
Line 63, "Extended cDNA" should read -- Extended cDNAs --.

Column 88,
Line 30, "Table VI" should read -- Table VII --.

Column 90,
Line 15, "3 min -94° C." should read -- 3 min -67° C. --.

Column 92,
Line 43, "Protein Which Internet" should read -- Proteins Which Intearct --.

Column 98,
Line 25, "Table Vl" should read --Table VII --.

Column 99,
Line 18, "412415" should read -- 412-415 --.
Line 19, "482488" should read -- 482-488 --.
Line 49, "Protein of" should read -- Proteins of --.

Column 100,
Line 35, "109:429435" should read -- 109:429-435 --.

Column 103,
Line 36, "E-cadhenn" should read -- E-cadherin -.

UNITED STATES PATENT AND TRADEMARK OFFICE
CERTIFICATE OF CORRECTION

PATENT NO. : 6,573,068 B1
DATED : June 3, 2003
INVENTOR(S) : Jean-Baptiste Dumas Milne Edwards, Aymeric Duclert and Lydie Bougueleret It is certified that error appears in the above-identified patent and that said Letters Patent is hereby corrected as shown below:

Column 107,
Line 12, "both 15 in vitro and" should read -- both in vitro and --.

Column 108,
Line 46, "11:428442" should read -- 11:428-442 --.

Signed and Sealed this

Sixth Day of April, 2004

JON W. DUDAS
*Acting Director of the United States Patent and Trademark Office*